(12) United States Patent
Ujjinamatada et al.

(10) Patent No.: US 10,336,697 B2
(45) Date of Patent: Jul. 2, 2019

(54) SPIRO[CYCLOBUTANE-1,3'-INDOLIN]-2'-ONE DERIVATIVES AS BROMODOMAIN INHIBITORS

(71) Applicant: Orion Corporation, Espoo (FI)

(72) Inventors: Ravi Kotrabasaiah Ujjinamatada, Anekal Taluk Bangalore (IN); Susanta Samajdar, Bangalore (IN); Chandrasekhar Abbineni, Hyderabad (IN); Subhendu Mukherjee, Hooghly W. Bengal (IN); Tero Linnanen, Turku (FI); Gerd Wohlfahrt, Helsinki (FI)

(73) Assignee: ORION CORPORATION (FI)

(*) Notice: Subject to any disclaimer, the term of this patent is extended or adjusted under 35 U.S.C. 154(b) by 0 days.

(21) Appl. No.: 15/736,450

(22) PCT Filed: Jun. 15, 2016

(86) PCT No.: PCT/FI2016/050431
§ 371 (c)(1),
(2) Date: Dec. 14, 2017

(87) PCT Pub. No.: WO2016/203112
PCT Pub. Date: Dec. 22, 2016

(65) Prior Publication Data
US 2018/0186739 A1    Jul. 5, 2018

(30) Foreign Application Priority Data
Jun. 16, 2015  (IN) .............. 660/KOL/2015

(51) Int. Cl.
| | | |
|---|---|---|
| C07D 401/04 | (2006.01) | |
| C07D 401/06 | (2006.01) | |
| C07D 401/12 | (2006.01) | |
| C07D 403/04 | (2006.01) | |
| C07D 405/12 | (2006.01) | |
| C07D 409/12 | (2006.01) | |
| C07D 417/06 | (2006.01) | |
| C07D 451/06 | (2006.01) | |
| C07D 453/02 | (2006.01) | |
| C07D 209/96 | (2006.01) | |
| A61P 37/02 | (2006.01) | |
| A61P 29/00 | (2006.01) | |
| A61P 35/00 | (2006.01) | |
| C07D 403/12 | (2006.01) | |
| C07D 413/12 | (2006.01) | |

(52) U.S. Cl.
CPC ............ C07D 209/96 (2013.01); A61P 29/00 (2018.01); A61P 35/00 (2018.01); A61P 37/02 (2018.01); C07D 401/04 (2013.01); C07D 401/06 (2013.01); C07D 401/12 (2013.01); C07D 403/04 (2013.01); C07D 403/12 (2013.01); C07D 405/12 (2013.01); C07D 409/12 (2013.01); C07D 413/12 (2013.01); C07D 417/06 (2013.01); C07D 451/06 (2013.01); C07D 453/02 (2013.01)

(58) Field of Classification Search
CPC .. C07D 401/04; C07D 401/06; C07D 401/12; C07D 403/04; C07D 405/12; C07D 409/12; C07D 417/06; C07D 451/06; C07D 453/02; C07D 209/96
See application file for complete search history.

(56) References Cited

U.S. PATENT DOCUMENTS

2014/0296229 A1   10/2014   Engelhardt et al.

FOREIGN PATENT DOCUMENTS

| WO | WO 2013/027168 A1 | 2/2013 |
| WO | WO 2015/092118 A1 | 6/2015 |
| WO | WO 2015049351 | * 9/2015 |

OTHER PUBLICATIONS

Daniel Gallenkamp et al., *Bromodomains and Their Pharmacological Inhibitors*, Chem Med Chem, vol. 9, No. 3, Mar. 4, 2014, pp. 438-464, XP055124420.
Wylie S. Palmer et al., *Structure-Guided Design of IACS-9571, a Selective High-Affinity Dual TRIM24-BRPF1 Bromodomain Inhibitor*, Journal of Medical Chemistry, vol. 59, No. 4, Jun. 10, 2015, pp. 1440-1454, XP055291579.
International Search Report, issued by the European Patent Office, dated Aug. 8, 2016, 3 pages.

* cited by examiner

*Primary Examiner* — Bruck Kifle
(74) *Attorney, Agent, or Firm* — Finnegan, Henderson, Farabow, Garrett & Dunner, L.L.P.

(57) ABSTRACT

The present invention provides novel spiro[cyclobutane-1, 3'-indolin]-2'-one derivatives of formula (I)

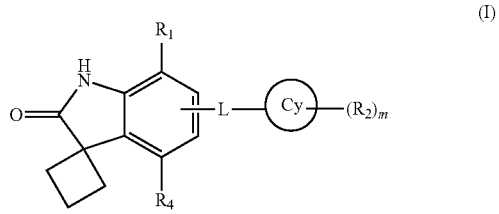

in which Cy, $R_1$, $R_2$, $R_4$, L, and m have the meaning given in the specification, and pharmaceutically acceptable salts thereof. The compounds of formula (I) are useful as bromodomain inhibitors in the treatment or prevention of diseases or disorders where bromodomain inhibition is desired.

30 Claims, No Drawings

SPIRO[CYCLOBUTANE-1,3'-INDOLIN]-2'-ONE DERIVATIVES AS BROMODOMAIN INHIBITORS

This is a National Stage Application under 35 U.S.C. § 371 of International Patent Application No. PCT/FI2016/050431, filed Jun. 15, 2016, which claims the benefit of Indian Patent Application No. 660/KOL/2015, filed Jun. 16, 2015, both of which are incorporated herein by reference.

TECHNICAL FIELD

The present invention relates to novel spiro[cyclobutane-1,3'-indolin]-2'-one derivatives of formula (I) which are useful as bromodomain inhibitors and to pharmaceutical compositions thereof.

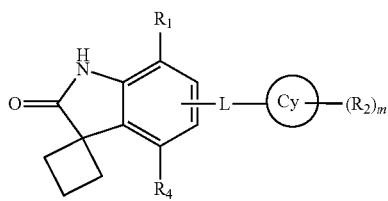

The invention relates also to the use of compounds of formula (I) for the treatment or prevention of diseases or disorders, in particular those where bromodomain inhibition is desired.

BACKGROUND OF THE INVENTION

The acetylation of histone lysine is central for providing the dynamic regulation of chromatin-based gene transcription. The bromodomain (BRD), which is the conserved structural module in chromatin-associated proteins and histone acetyl-tranferases, is the sole protein domain known to recognize acetyl-lysine residues on proteins.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. BRD2 and BRD3 are reported to associate with histones along actively transcribed genes and may be involved in facilitating transcriptional elongation (Leroy et al., Mol. Cell., 2008, 30(1):51-60), while BRD4 appears to be involved in the recruitment of the pTEF-[beta] complex to inducible genes, resulting in phosphorylation of RNA polymerase and increased transcriptional output (Hargreaves et al., Cell, 2009, 138(1): 129-145). It has also been reported that BRD4 or BRD3 may fuse with NUT (nuclear protein in testis) forming novel fusion oncogenes, BRD4-NUT or BRD3-NUT, in a highly malignant form of epithelial neoplasia (French et al., Cancer Research, 2003, 63, 304-307 and French et al., Journal of Clinical Oncology, 2004, 22 (20), 4135-4139). Data suggests that BRD-NUT fusion proteins contribute to carcinogenesis (Oncogene, 2008, 27, 2237-2242). BRD-t is uniquely expressed in the testes and ovary. All family members have been reported to have some function in controlling or executing aspects of the cell cycle, and have been shown to remain in complex with chromosomes during cell division suggesting a role in the maintenance of epigenetic memory. In addition some viruses make use of these proteins to tether their genomes to the host cell chromatin, as part of the process of viral replication (You et al., Cell, 2004, 1, 17(3), 349-60).

Japanese patent application JP 2008-156311 discloses a benzimidazole derivative which is said to be a BRD2 bromodomain binding agent which has utility with respect to virus infection/proliferation.

International patent application WO 2009/084693 discloses a series of thienotriazolodiazepiene derivatives that are said to inhibit the binding between an acetylated histone and a bromodomain containing protein and are said to be useful as anti-cancer agents.

International patent application WO 2011/054846 discloses a series of quinoline derivatives that inhibit the binding of BET family bromodomains with acetylated lysine residues.

Bromodomain and Extra-Terminal motif (BET) proteins BRD2, BRD3, BRD4, and BRDT consists of tandem bromodomains. These domains are frequently referred to as BD1 (first bromodomain) and BD2 (second bromodomain) respectively and they share a high sequence homology. Lack of availability of potent and selective inhibitors have hindered the progress of dissecting biology of such bromodomain selective BET inhibitors. Selective targeting of either of these BD domains might pose different therapeutic profile over the pan BET inhibitors.

There remains a need for potent bromodomain inhibitors with desirable selectivity and pharmaceutical properties. Certain spiro[cyclobutane-1,3'-indolin]-2'-one derivatives have been found according to the present invention which inhibit the binding of BET family bromodomains to acetylated lysine residues. Such compounds will hereafter be referred to as "bromodomain inhibitors".

SUMMARY OF THE INVENTION

The present invention provides new spiro[cyclobutane-1,3'-indolin]-2'-one derivatives which are able to inhibit the binding of BET family bromodomains to acetylated lysine residues. The compounds exhibit significant selectivity for BRD4 BD1 inhibition over BRD4 BD2 inhibition. The compounds of the present invention are represented by formula (I):

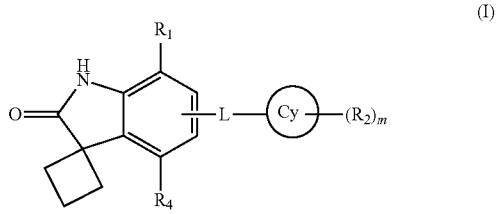

wherein

Cy is a 4-12 membered monocyclic or bicyclic ring containing 0-4 heteroatoms independently selected form N, O or S;

L is a linker selected from —N($R_{3a}$)S(O)$_2$—, —S(O)$_2$N($R_{3b}$)—, —C($R_{3c}$)(O$R_{3d}$)—, —NS(O)(CH$_3$)—, —N($R_{3e}$)C(O)—, —N($R_{3f}$)C(O)N($R_{3g}$)—, —N($R_{3h}$)C(O)CH($R_{3i}$)—, —N($R_{3j}$)C(O)CH($R_{3k}$)CH($R_{3l}$)— or —N($R_{3m}$)C(O)CHCH—;

$R_{3a}$, $R_{3b}$, $R_{3c}$, $R_{3d}$, $R_{3e}$, $R_{3f}$, $R_{3g}$, $R_{3h}$, $R_{3i}$, $R_{3j}$, $R_{3k}$, $R_{3l}$ and $R_{3m}$ are selected, independently, from hydrogen or $C_{1-7}$ alkyl;

$R_2$ is halogen, $C_{1-7}$ alkoxy, amino, cyano, oxo, —C(O)O—$C_{1-7}$ alkyl, optionally substituted aryl or optionally substituted heterocyclyl, wherein the optional substitution at each occurrence is, independently, selected from 1-3 substituents selected from halogen or $C_{1-7}$ alkoxy;

$R_4$ is hydrogen or halogen;

in case wherein

L is —S(O)$_2$N($R_{3b}$)—, —C($R_{3e}$)(O$R_{3d}$)—, —NS(O)(CH$_3$)—, —N($R_{3e}$)C(O)—, —N($R_{3f}$)C(O)N($R_{3g}$)—, —N($R_{3h}$)C(O)CH($R_{3i}$)—, —N($R_{3j}$)C(O)CH($R_{3k}$)CH($R_{3l}$)—, or —N($R_{3j}$)C(O)CHCH—;

then $R_1$ is hydrogen, $C_{1-7}$ alkyl, halogen, nitro, hydroxy $C_{1-7}$ alkyl, $C_{3-10}$ cycloalkyl, optionally substituted aryl, optionally substituted heterocyclyl, optionally substituted heterocyclyl $C_{1-7}$ alkyl, optionally substituted heterocyclyl $C_{2-7}$ alkenyl, optionally substituted aryl $C_{1-7}$ alkyl, optionally substituted aryl $C_{2-7}$ alkenyl, —NR$_a$R$_b$, —C(O)NR$_c$R$_d$, —C(O)OR$_e$, —C(O)R$_f$, —C(O$R_g$)-aryl, —C(OR$_h$)(R$_i$)-aryl, —OR$_j$ or —OC(O)R$_k$; wherein the optional substitution at each occurrence is, independently, selected from 1-3 substituents selected from halogen, hydroxy, $C_{1-7}$ alkyl or $C_{1-7}$ alkoxy; except that $R_1$ is not hydrogen when L is —S(O)$_2$NH— or —CH(OH)—, and $R_1$ is not hydrogen or halogen when L is —NHC(O)CH(CH$_3$)—;

in case wherein

L is —N($R_{3a}$)S(O)$_2$— then $R_1$ is —NR$_a$R$_b$, —C(O)NR$_c$R$_d$, —C(O)OR$_e$, —C(O)R$_f$, —C(OR$_g$)-aryl, —B(OH)$_2$, —C(OR$_h$)(R$_i$)-aryl, —OR$_n$ or —OC(O)R$_k$, —CH(CH$_3$)—aryl, hydroxy $C_{1-7}$ alkyl, aryl halo $C_{1-7}$ alkyl, optionally substituted heterocyclyl $C_{1-7}$ alkyl, optionally substituted heterocyclyl $C_{2-7}$ alkenyl, optionally substituted aryl, optionally substituted aryl $C_{2-7}$ alkenyl, optionally substituted 9-12 membered heterocyclic ring having 1-3 heteroatoms selected from N or O, pyridinyl having 1-2 substituents selected from halogen, hydroxy or $C_{1-7}$ alkoxy, 2-oxopiperidinyl, fluorophenyl $C_{1-7}$ alkyl, 1-methylpiperidinyl (when at least one of $R_2$ is halogen), piperidinyl (when at least two of $R_2$ is $C_{1-7}$ alkoxy), phenyl $C_{1-7}$ alkyl (when at least one of $R_2$ is halogen and at least one another of $R_2$ is $C_{1-7}$ alkoxy);

wherein the optional substitution at each occurrence is, independently, selected from 1-3 substituents selected from halogen, hydroxy, oxo, $C_{1-7}$ alkyl or $C_{1-7}$ alkoxy;

$R_a$, $R_b$, $R_c$ and $R_d$ are, independently, selected from hydrogen, $C_{1-7}$ alkyl, $C_{2-7}$ alkenyl, —C(O)—$C_{1-7}$ alkyl, optionally substituted heterocyclyl, optionally substituted $C_{3-10}$ cycloalkyl, optionally substituted heterocyclyl $C_{1-7}$ alkyl, optionally substituted aryl, optionally substituted aryl $C_{1-7}$ alkyl, optionally substituted $C_{3-10}$ cycloalkyl $C_{1-7}$ alkyl, optionally substituted —C(O)heterocyclyl; wherein the optional substitution at each occurrence is, independently, selected from 1-3 substituents selected from $C_{1-7}$ alkyl, —C(O)—$C_{1-7}$ alkyl, —C(O)O—$C_{1-7}$ alkyl, halogen, aryl $C_{1-7}$ alkyl, $C_{1-7}$ alkoxy, oxo or hydroxy $C_{1-7}$ alkyl;

$R_e$, $R_f$, $R_g$, $R_h$, $R_i$, and $R_j$ are, independently, selected from hydrogen, $C_{1-7}$ alkyl, halo $C_{1-7}$ alkyl, optionally substituted aryl, optionally substituted heterocyclyl, optionally substituted heterocyclyl $C_{1-7}$ alkyl or optionally substituted heterocyclyl $C_{3-7}$ cycloalkyl, wherein the optional substitution at each occurrence is, independently, selected from 1-3 substituents selected from $C_{1-7}$ alkyl or hydroxy $C_{1-7}$ alkyl;

$R_k$ is selected from optionally substituted aryl, optionally substituted hetero-cyclyl, optionally substituted heterocyclyl $C_{1-7}$ alkyl, wherein the optional substitution at each occurrence is, independently, selected from 1-3 substituents selected from $C_{1-7}$ alkyl or hydroxy $C_{1-7}$ alkyl;

$R_n$ is selected from optionally substituted aryl, halo $C_{1-7}$ alkyl, $C_{3-7}$ cycloalkyl substituted by 1-2 substituents selected from halogen, hydroxy or oxo, optionally substituted heterocyclyl, optionally substituted heterocyclyl $C_{1-7}$ alkyl, optionally substituted heterocyclyl $C_{3-7}$ cycloalkyl or —Z—NR$_{a1}$R$_{b1}$, wherein the optional substitution at each occurrence is, independently, selected from 1-3 substituents selected from hydroxy, $C_{1-7}$ alkyl, $C_{3-7}$ cycloalkyl, hydroxy $C_{1-7}$ alkyl, methylsulfonyl, halogen, amino, acetyl or oxo;

$R_{a1}$ and $R_{b1}$ are, independently, hydrogen, $C_{1-7}$ alkyl or $C_{3-7}$ cycloalkyl, Z is $C_{1-7}$ alkyl, $C_{3-7}$ cycloalkyl or $C_{3-7}$ cycloalkyl $C_{1-7}$ alkyl;

'm' is selected from 0, 1, 2 or 3;

or a pharmaceutically acceptable salt thereof.

In a further aspect, the present invention provides a pharmaceutical composition comprising spiro[cyclobutane-1,3'-indolin]-2'-one derivative of formula (I) or a pharmaceutically acceptable salt thereof.

In yet further aspect of the present invention, it provides spiro[cyclobutane-1,3'-indolin]-2'-one derivatives of formula (I) or a pharmaceutically acceptable thereof for use in the treatment or prevention of diseases or disorders where bromodomain inhibition is desired, in particular for the treatment or prevention of an autoimmune disease, inflammatory disease or cancer.

DETAILED DESCRIPTION OF THE INVENTION

An embodiment of the present application provides novel spiro[cyclobutane-1,3'-indolin]-2'-one derivatives of formula (I) or pharmaceutically acceptable salts thereof which are useful as bromodomain inhibitors.

One of the embodiments of the present invention provides a compound of formula (I):

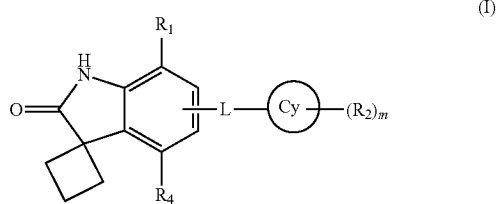

(I)

wherein

Cy is a 4-12 membered monocyclic or bicyclic ring containing 0-4 heteroatoms independently selected form N, O or S;

L is a linker selected from —N($R_{3a}$)S(O)$_2$—, —S(O)$_2$N($R_{3b}$)—, —C($R_{3c}$)(O$R_{3d}$)—, —NS(O)(CH$_3$)—, —N($R_{3e}$)C(O)—, —N($R_{3f}$)C(O)N($R_{3g}$)—, —N($R_{3h}$)C(O)CH($R_{3i}$)—, —N($R_{3j}$)C(O)CH($R_{3k}$)CH($R_{3l}$)— or —N($R_{3m}$)C(O)CHCH—;

$R_{3a}$, $R_{3b}$, $R_{3c}$, $R_{3d}$, $R_{3e}$, $R_{3f}$, $R_{3g}$, $R_{3h}$, $R_{3i}$, $R_{3j}$, $R_{3k}$, $R_{3l}$ and $R_{3m}$ are selected, independently, from hydrogen or $C_{1-7}$ alkyl;

$R_2$ is halogen, $C_{1-7}$ alkoxy, amino, cyano, oxo, —C(O)O—$C_{1-7}$ alkyl, optionally substituted aryl or optionally substituted heterocyclyl, wherein the optional substitution at each occurrence is, independently, selected from 1-3 substituents selected from halogen or $C_{1-7}$ alkoxy;

$R_4$ is hydrogen or halogen;
in case wherein
L is —S(O)$_2$N(R$_{3b}$)—, —C(R$_{3e}$)(OR$_{3d}$)—, —NS(O)(CH$_3$)—, —N(R$_{3e}$)C(O)—, —N(R$_{3f}$)C(O)N(R$_{3g}$)—, —N(R$_{3h}$)C(O)CH(R$_{3i}$)—, —N(R$_{3j}$)C(O)CH(R$_{3k}$)CH(R$_{3l}$)—, or —N(R$_{3j}$)C(O)CHCH—; then $R_1$ is hydrogen, $C_{1-7}$ alkyl, halogen, nitro, hydroxy $C_{1-7}$ alkyl, $C_{3-10}$ cycloalkyl, optionally substituted aryl, optionally substituted heterocyclyl, optionally substituted heterocyclyl $C_{1-7}$ alkyl, optionally substituted heterocyclyl $C_{2-7}$ alkenyl, optionally substituted aryl $C_{1-7}$ alkyl, optionally substituted aryl $C_{2-7}$ alkenyl, —NR$_a$R$_b$, —C(O)NR$_c$R$_d$, —C(O)OR$_e$, —C(O)R$_f$, —C(OR$_g$)-aryl, —C(OR$_h$)(R$_i$)-aryl, —OR$_j$ or —OC(O)R$_k$; wherein the optional substitution at each occurrence is, independently, selected from 1-3 substituents selected from halogen, hydroxy, $C_{1-7}$ alkyl or $C_{1-7}$ alkoxy; except that $R_1$ is not hydrogen when L is —S(O)$_2$NH— or —CH(OH)—, and $R_1$ is not hydrogen or halogen when L is —NHC(O)CH(CH$_3$)—;

in case wherein
L is —N(R$_{3a}$)S(O)$_2$—
then
$R_1$ is —NR$_a$R$_b$, —C(O)NR$_c$R$_d$, —C(O)OR$_e$, —C(O)R$_f$, —C(OR$_g$)-aryl, —B(OH)$_2$, —C(OR$_h$)(R$_i$)-aryl, —OR$_n$ or —OC(O)R$_k$, —CH(CH$_3$)—aryl, hydroxy $C_{1-7}$ alkyl, aryl halo $C_{1-7}$ alkyl, optionally substituted heterocyclyl $C_{1-7}$ alkyl, optionally substituted heterocyclyl $C_{2-7}$ alkenyl, optionally substituted aryl, optionally substituted aryl $C_{2-7}$ alkenyl, optionally substituted 9-12 membered heterocyclic ring having 1-3 heteroatoms selected from N or O, pyridinyl having 1-2 substituents selected from halogen, hydroxy or $C_{1-7}$ alkoxy, 2-oxopiperidinyl, fluorophenyl $C_{1-7}$ alkyl, 1-methylpiperidinyl (when at least one of $R_2$ is halogen), piperidinyl (when at least two of $R_2$ is $C_{1-7}$ alkoxy), phenyl $C_{1-7}$ alkyl (when at least one of $R_2$ is halogen and at least one another of $R_2$ is $C_{1-7}$ alkoxy); wherein the optional substitution at each occurrence is, independently, selected from 1-3 substituents selected from halogen, hydroxy, oxo, $C_{1-7}$ alkyl or $C_{1-7}$ alkoxy;

$R_a$, $R_b$, $R_c$ and $R_d$ are, independently, selected from hydrogen, $C_{1-7}$ alkyl, $C_{2-7}$ alkenyl, —C(O)—$C_{1-7}$ alkyl, optionally substituted heterocyclyl, optionally substituted $C_{3-10}$ cycloalkyl, optionally substituted heterocyclyl $C_{1-7}$ alkyl, optionally substituted aryl, optionally substituted aryl $C_{1-7}$ alkyl, optionally substituted $C_{3-10}$ cycloalkyl $C_{1-7}$ alkyl, optionally substituted —C(O)heterocyclyl; wherein the optional substitution at each occurrence is, independently, selected from 1-3 substituents selected from $C_{1-7}$ alkyl, —C(O)—$C_{1-7}$ alkyl, —C(O)O—$C_{1-7}$ alkyl, halogen, aryl $C_{1-7}$ alkyl, $C_{1-7}$ alkoxy, oxo or hydroxy $C_{1-7}$ alkyl;

$R_e$, $R_f$, $R_g$, $R_h$, $R_i$, and $R_j$ are, independently, selected from hydrogen, $C_{1-7}$ alkyl, halo $C_{1-7}$ alkyl, optionally substituted aryl, optionally substituted heterocyclyl, optionally substituted heterocyclyl $C_{1-7}$ alkyl or optionally substituted heterocyclyl $C_{3-7}$ cycloalkyl, wherein the optional substitution at each occurrence is, independently, selected from 1-3 substituents selected from $C_{1-7}$ alkyl or hydroxy $C_{1-7}$ alkyl;

$R_k$ is selected from optionally substituted aryl, optionally substituted heterocyclyl, optionally substituted heterocyclyl $C_{1-7}$ alkyl, wherein the optional substitution at each occurrence is, independently, selected from 1-3 substituents selected from $C_{1-7}$ alkyl or hydroxy $C_{1-7}$ alkyl;

$R_n$ is selected from optionally substituted aryl, halo $C_{1-7}$ alkyl, $C_{3-7}$ cycloalkyl substituted by 1-2 substituents selected from halogen, hydroxy or oxo, optionally substituted heterocyclyl, optionally substituted heterocyclyl $C_{1-7}$ alkyl, optionally substituted heterocyclyl $C_{3-7}$ cycloalkyl or —Z—NR$_{a1}$R$_{b1}$, wherein the optional substitution at each occurrence is, independently, selected from 1-3 substituents selected from hydroxy, $C_{1-7}$ alkyl, $C_{3-7}$ cycloalkyl, hydroxy $C_{1-7}$ alkyl, methylsulfonyl, halogen, amino, acetyl or oxo;

$R_{a1}$ and $R_{b1}$ are, independently, hydrogen, $C_{1-7}$ alkyl or $C_{3-7}$ cycloalkyl, Z is $C_{1-7}$ alkyl, $C_{3-7}$ cycloalkyl or $C_{3-7}$ cycloalkyl $C_{1-7}$ alkyl;

'm' is selected from 0, 1, 2 or 3;
or a pharmaceutically acceptable salt thereof.

It is to be understood that the left bond in each linker L is attached to the indolinone ring of formula (I).

The embodiments below are illustrative of the present invention and are not intended to limit the claims to the specific embodiments exemplified.

According to one embodiment is provided a compound of formula (I) wherein $R_4$ is hydrogen;

Cy is a 4-12 membered monocyclic or bicyclic ring containing 0-4 heteroatoms independently selected form N, O or S;

L is a linker selected from —N(R$_{3a}$)S(O)$_2$—, —S(O)$_2$N(R$_{3b}$)—, —C(R$_{3c}$)(OR$_{3d}$)—, —N(R$_{3e}$)C(O)—, —N(R$_{3f}$)C(O)N(R$_{3g}$)—, —N(R$_{3h}$)C(O)CH(R$_{3i}$)—, $R_{3a}$, $R_{3b}$, $R_{3c}$, $R_{3d}$, $R_{3e}$, $R_{3f}$, $R_{3g}$, $R_{3h}$ and $R_{3i}$ are selected, independently, from hydrogen or $C_{1-7}$ alkyl;

$R_2$ is halogen, $C_{1-7}$ alkoxy, amino, cyano, oxo, —C(O)O—$C_{1-7}$ alkyl, optionally substituted aryl or optionally substituted heterocyclyl, wherein the optional substitution at each occurrence is, independently, selected from 1-3 substituents selected from halogen or $C_{1-7}$ alkoxy;

in case wherein
L is —S(O)$_2$N(R$_{3b}$)—, —C(R$_{3e}$)(OR$_{3d}$)—, —N(R$_{3e}$)C(O)—, —N(R$_{3f}$)C(O)N(R$_{3g}$)— or —N(R$_{3h}$)C(O)CH(R$_{3i}$)—;
then $R_1$ is hydrogen, $C_{1-7}$ alkyl, halogen, hydroxy $C_{1-7}$ alkyl, $C_{3-10}$ cycloalkyl, optionally substituted aryl, optionally substituted heterocyclyl, optionally substituted heterocyclyl $C_{1-7}$ alkyl, optionally substituted aryl $C_{1-7}$ alkyl, optionally substituted aryl $C_{2-7}$ alkenyl, —NR$_a$R$_b$, —C(O)NR$_c$R$_d$, —C(O)OR$_e$, —C(O)R$_f$, —C(OR$_g$)-aryl, —C(OR$_h$)(R$_i$)-aryl or —OR$_j$; wherein the optional substitution at each occurrence is, independently, selected from 1-3 substituents selected from halogen, hydroxy, $C_{1-7}$ alkyl or $C_{1-7}$ alkoxy; except that $R_1$ is not hydrogen when L is —S(O)$_2$NH— or —CH(OH)—, and $R_1$ is not hydrogen or halogen when L is —NHC(O)CH(CH$_3$)—;

in case wherein
L is —N(R$_{3a}$)S(O)$_2$—
then
$R_1$ is —NR$_a$R$_b$, —C(O)NR$_c$R$_d$, —C(O)OR$_e$, —C(O)R$_f$, —C(OR$_g$)-aryl, —C(OR$_h$)(R$_i$)-aryl or —OR$_n$, —CH(CH$_3$)—aryl, hydroxy $C_{1-7}$ alkyl, aryl halo $C_{1-7}$ alkyl, optionally substituted heterocyclyl $C_{1-7}$ alkyl, optionally substituted aryl, optionally substituted aryl $C_{2-7}$ alkenyl, optionally substituted 9-12 membered heterocyclic ring having 1-3 heteroatoms selected from N or O, pyridinyl having 1-2 substituents selected from halogen, hydroxy or $C_{1-7}$ alkoxy, 2-oxopiperidinyl, fluorophenyl $C_{1-7}$ alkyl, 1-methylpiperidinyl (when at least one of $R_2$ is halogen), piperidinyl (when at least two of $R_2$ is $C_{1-7}$ alkoxy), phenyl $C_{1-7}$ alkyl (when at least one of $R_2$ is halogen and at least one another of $R_2$ is $C_{1-7}$ alkoxy); wherein the optional substitution at each occurrence is, independently, selected from 1-3 substituents selected from halogen, hydroxy, oxo, $C_{1-7}$ alkyl or $C_{1-7}$ alkoxy;

$R_a$, $R_b$, $R_c$ and $R_d$ are, independently, selected from hydrogen, $C_{1-7}$ alkyl, $C_{2-7}$ alkenyl, —C(O)—$C_{1-7}$ alkyl, optionally substituted heterocyclyl, optionally substituted $C_{3-10}$ cycloalkyl, optionally substituted heterocyclyl $C_{1-7}$ alkyl, optionally substituted aryl, optionally substituted aryl $C_{1-7}$ alkyl, optionally substituted $C_{3-10}$ cycloalkyl $C_{1-7}$ alkyl, optionally substituted —C(O)heterocyclyl; wherein the optional substitution at each occurrence is, independently, selected from 1-3 substituents selected from $C_{1-7}$ alkyl, —C(O)—$C_{1-7}$ alkyl, —C(O)O—$C_{1-7}$ alkyl, halogen, aryl $C_{1-7}$ alkyl, $C_{1-7}$ alkoxy, oxo or hydroxy $C_{1-7}$ alkyl;

$R_e$, $R_f$, $R_g$, $R_h$, $R_i$, and $R_j$ are, independently, selected from hydrogen, $C_{1-7}$ alkyl, optionally substituted aryl or optionally substituted heterocyclyl wherein the optional substitution at each occurrence is, independently, selected from 1-3 substituents selected from $C_{1-7}$ alkyl or hydroxy $C_{1-7}$ alkyl;

$R_n$ is selected from optionally substituted aryl or optionally substituted hetero-cyclyl wherein the optional substitution at each occurrence is, independently, selected from 1-3 substituents selected from $C_{1-7}$ alkyl or hydroxy $C_{1-7}$ alkyl; and 'm' is selected from 0, 1, 2 or 3;

or a pharmaceutically acceptable salt thereof.

According to one embodiment of the present invention, the compound of formula (I) is a compound of formula (IA)

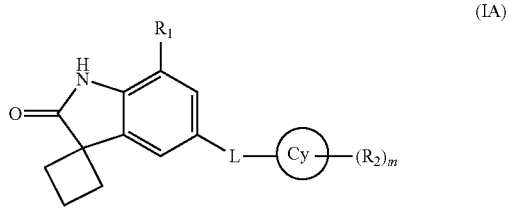

(IA)

wherein $R_1$, $R_2$, Cy, L and 'm' are same as defined in any of the above embodiments for formula (I), or a pharmaceutically acceptable salt thereof.

According to yet another embodiment of the present invention, the compound of formula (I) is a compound of formula (IB)

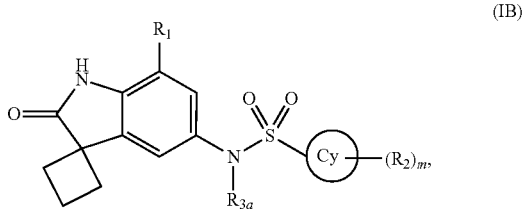

(IB)

wherein $R_1$, $R_2$, $R_{3a}$, Cy and 'm' are same as defined in any of the above embodiments for formula (I), or a pharmaceutically acceptable salt thereof.

According to yet another embodiment of the present invention, the compound of formula (I) is a compound of formula (IC)

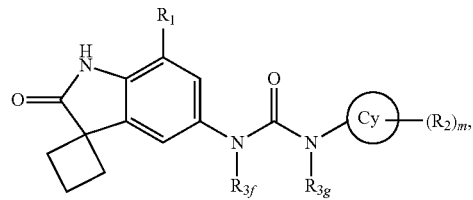

(IC)

wherein $R_1$, $R_2$, $R_{3f}$, $R_{3g}$, Cy and 'm' are same as defined in any of the above embodiments for formula (I), or a pharmaceutically acceptable salt thereof.

According to yet another embodiment of the present invention, the compound of formula (I) is a compound of formula (ID)

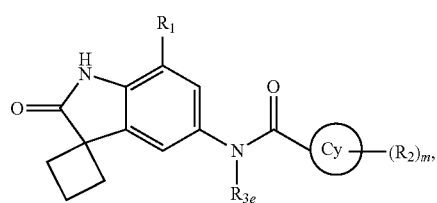

(ID)

wherein $R_1$, $R_2$, $R_{3e}$, Cy and 'm' are same as defined in any of the above embodiments for formula (I), or a pharmaceutically acceptable salt thereof.

According to one embodiment, specifically provided is a compound of formula (I) wherein Cy is phenyl, $C_{3-10}$ cycloalkyl or a 5-6 membered heterocyclic ring having 1-3 heteroatoms selected from N or O;

$R_4$ is hydrogen;

L is a linker selected from —N($R_{3a}$)S(O)$_2$—, —N($R_{3e}$)C(O)— or —N($R_{3f}$)C(O)N($R_{3g}$)—;

$R_{3a}$, $R_{3e}$, $R_{3f}$ and $R_{3g}$, are selected, independently, from hydrogen or $C_{1-7}$ alkyl;

$R_2$ is halogen, $C_{1-7}$ alkoxy, cyano, —C(O)O—$C_{1-7}$ alkyl or a 5-6 membered heterocyclic ring having 1-3 heteroatoms selected from N or O;

in case wherein

L is —N($R_{3e}$)C(O)— or —N($R_{3f}$)C(O)N($R_{3g}$)— then $R_1$ is hydrogen, $C_{1-7}$ alkyl, halogen, hydroxy $C_{1-7}$ alkyl, $C_{3-10}$ cycloalkyl, optionally substituted aryl, optionally substituted heterocyclyl, optionally substituted heterocyclyl $C_{1-7}$ alkyl, optionally substituted aryl $C_{1-7}$ alkyl, optionally substituted aryl $C_{2-7}$ alkenyl, —N$R_aR_b$, —C(O)N$R_cR_d$, —C(O)O$R_e$, —C(O)$R_f$, —C(O$R_g$)-aryl, —C(O$R_h$)($R_i$)-aryl or —O$R_j$; wherein the optional substitution at each occurrence is, independently, selected from 1-3 substituents selected from halogen, hydroxy, $C_{1-7}$ alkyl or $C_{1-7}$ alkoxy;

in case wherein

L is —N($R_{3a}$)S(O)$_2$— then $R_1$ is —N$R_aR_b$, —C(O)N$R_cR_d$, —C(O)O$R_e$, —C(O)$R_f$, —C(O$R_g$)-aryl, —C(O$R_h$)($R_i$)-aryl or —O$R_n$, —CH(CH$_3$)-aryl, hydroxy $C_{1-7}$ alkyl, aryl halo $C_{1-7}$ alkyl, optionally substituted heterocyclyl $C_{1-7}$ alkyl, optionally substituted aryl, optionally substituted aryl $C_{2-7}$ alkenyl, optionally substituted 9-12 membered heterocyclic ring having 1-3 heteroatoms selected from N or O, pyridinyl having 1-2 substituents selected from halogen, hydroxy or $C_{1-7}$ alkoxy, 2-oxopiperidinyl, fluorophenyl $C_{1-7}$ alkyl, 1-methylpiperidinyl (when at least one of $R_2$ is halogen), piperidinyl (when at least two of $R_2$ is $C_{1-7}$ alkoxy), phenyl $C_{1-7}$ alkyl (when at least one of $R_2$ is halogen and at least one another of $R_2$ is $C_{1-7}$ alkoxy); wherein the optional substitution at each occurrence is, independently, selected from 1-3 substituents selected from halogen, hydroxy, oxo, $C_{1-7}$ alkyl or $C_{1-7}$ alkoxy;

$R_a$, $R_b$, $R_c$ and $R_d$ are, independently, selected from hydrogen, $C_{1-7}$ alkyl, $C_{2-7}$ alkenyl, —C(O)—$C_{1-7}$ alkyl, optionally substituted heterocyclyl, optionally substituted $C_{3-10}$ cycloalkyl, optionally substituted heterocyclyl $C_{1-7}$ alkyl, optionally substituted aryl, optionally substituted aryl $C_{1-7}$ alkyl, optionally substituted $C_{3-10}$ cycloalkyl $C_{1-7}$ alkyl, optionally substituted —C(O)heterocyclyl; wherein the optional substitution at each occurrence is, independently, selected from 1-3 substituents selected from $C_{1-7}$ alkyl, —C(O)—$C_{1-7}$ alkyl, —C(O)O—$C_{1-7}$ alkyl, halogen, aryl $C_{1-7}$ alkyl, $C_{1-7}$ alkoxy, oxo or hydroxy $C_{1-7}$ alkyl;

$R_e$, $R_f$, $R_g$, $R_h$, $R_i$, and $R_j$ are, independently, selected from hydrogen, $C_{1-7}$ alkyl, optionally substituted aryl or optionally substituted heterocyclyl wherein the optional substitution at each occurrence is, independently, selected from 1-3 substituents selected from $C_{1-7}$ alkyl or hydroxy $C_{1-7}$ alkyl;

$R_n$ is selected from optionally substituted aryl or optionally substituted heterocyclyl wherein the optional substitution at each occurrence is, independently, selected from 1-3 substituents selected from $C_{1-7}$ alkyl or hydroxy $C_{1-7}$ alkyl; and 'm' is selected from 0, 1, 2 or 3;

or a pharmaceutically acceptable salt thereof.

According to one embodiment, specifically provided are compounds of formula (I), (IA), (IB), (IC) or (ID), wherein Cy is aromatic or non-aromatic cyclic ring with 5-10 ring atoms of which 0-4 are heteroatoms selected from a group consisting of N, O and S. In a subclass of the above embodiment are compounds wherein Cy is phenyl, $C_{3-10}$ cycloalkyl or a 5-6 membered heterocyclic ring having 1-3 heteroatoms selected from N or O. In yet another subclass of the above embodiment are compounds wherein Cy is phenyl, cyclohexyl or piperidinyl.

According to one embodiment, specifically provided are compounds of formula (I), (IA), (IB), (IC) or (ID), or according to any other embodiment or subclass referred to above, wherein L is a linker selected from —NHS(O)$_2$—, —NHC(O)— or —NHC(O)NH—. In a subclass of the above embodiment are compounds wherein L is —NHS(O)$_2$—.

According to yet one embodiment, specifically provided is a compound of formula (I), (IA) or (IB), wherein Cy is phenyl;
L is —NHS(O)$_2$—;
$R_4$ is hydrogen;
$R_2$ is halogen or $C_{1-7}$ alkoxy,
$R_1$ is —NHR$_a$, —C(O)NHR$_e$, —C(O)OR$_e$, —C(O)R$_f$, —C(OH)phenyl, —C(OH)($C_{1-7}$ alkyl)phenyl or —OR$_j$, —CH(CH$_3$)phenyl, hydroxy $C_{1-7}$ alkyl, aryl halo $C_{1-7}$ alkyl, optionally substituted heterocyclyl $C_{1-7}$ alkyl, optionally substituted phenyl, optionally substituted phenyl $C_{2-7}$ alkenyl, optionally substituted 9-12 membered heterocyclic ring having 1-3 heteroatoms selected from N or O, pyridinyl having 1-2 substituents selected from halogen, hydroxy or $C_{1-7}$ alkoxy, 2-oxopiperidinyl, fluoro-phenyl $C_{1-7}$ alkyl, 1-methylpiperidinyl (when at least one of $R_2$ is halogen), piperidinyl (when at least two of $R_2$ is $C_{1-7}$ alkoxy), phenyl $C_{1-7}$ alkyl (when at least one of $R_2$ is halogen and at least one another of $R_2$ is $C_{1-7}$ alkoxy); wherein the optional substitution at each occurrence is, independently, selected from 1-3 substituents selected from halogen, hydroxy, oxo, $C_{1-7}$ alkyl or $C_{1-7}$ alkoxy;

$R_a$ and $R_c$ are, independently, selected from hydrogen, $C_{1-7}$ alkyl, $C_{2-7}$ alkenyl, —C(O)—$C_{1-7}$ alkyl, optionally substituted $C_{3-10}$ cycloalkyl, optionally substituted heterocyclyl, optionally substituted heterocyclyl $C_{1-7}$ alkyl, optionally substituted $C_{3-10}$ cycloalkyl $C_{1-7}$ alkyl, optionally substituted —C(O)heterocyclyl; wherein the optional substitution at each occurrence is, independently, selected from 1-3 substituents selected from $C_{1-7}$ alkyl, —C(O)—$C_{1-7}$ alkyl, —C(O)O—$C_{1-7}$ alkyl, halogen, phenyl $C_{1-7}$ alkyl, $C_{1-7}$ alkoxy, oxo or hydroxy $C_{1-7}$ alkyl;

$R_e$ is hydrogen or $C_{1-7}$ alkyl;

$R_f$ and $R_j$ are independently optionally substituted phenyl or optionally substituted heterocyclyl wherein the optional substitution at each occurrence is, independently, selected from 1-3 substituents selected from $C_{1-7}$ alkyl or hydroxy $C_{1-7}$ alkyl;

wherein heterocyclyl at each occurrence is a 5-10 membered heterocyclic ring having 1-4 heteroatoms selected from O, N, or S; and 'm' is selected from 0, 1, 2 or 3;

or a pharmaceutically acceptable salt thereof.

In one subclass of any of the above embodiments are compounds of formula (I), (IA), (IB), (IC) or (ID), wherein Cy-($R_2$)$_m$ is selected from one of the following groups or tautomers thereof

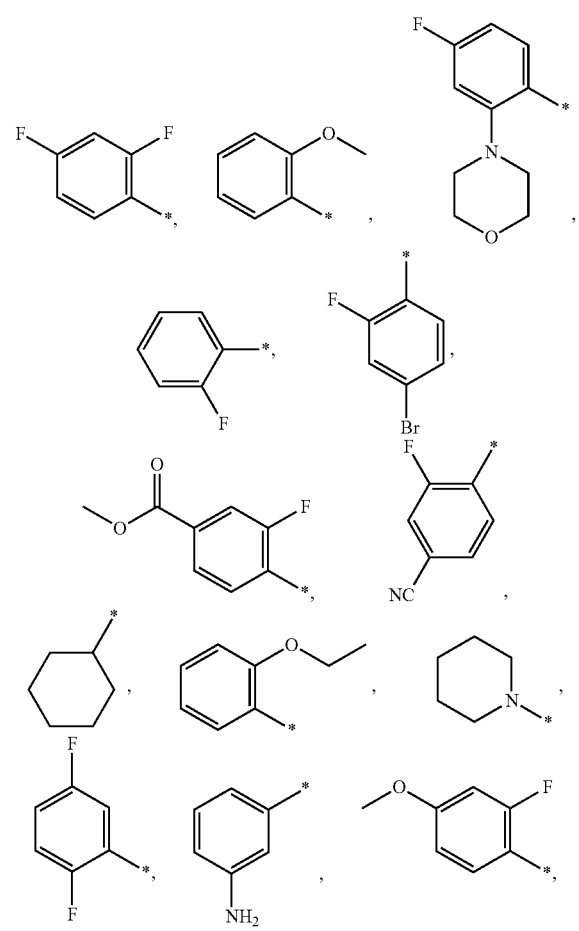

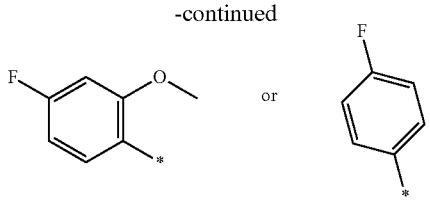

According to one embodiment, specifically provided are compounds of formula (I), (IA), (IB), (IC) or (ID) wherein $R_1$ is —$NR_aR_b$, —$C(O)NR_cR_d$, —$C(O)OR_e$, —$C(O)R_f$, —$C(OR_g)$-aryl, —$C(OR_h)(R_i)$-aryl or —$OR_n$, —$CH(CH_3)$-aryl, hydroxy $C_{1-7}$ alkyl, aryl halo $C_{1-7}$ alkyl, optionally substituted heterocyclyl $C_{1-7}$ alkyl, optionally substituted aryl, optionally substituted aryl $C_{2-7}$ alkenyl, optionally substituted 9-12 membered heterocyclic ring having 1-3 heteroatoms selected from N or O, pyridinyl having 1-2 substituents selected from halogen, hydroxy or $C_{1-7}$ alkoxy, 2-oxopiperidinyl, fluoro-phenyl $C_{1-7}$ alkyl, 1-methylpiperidinyl (when at least one of $R_2$ is halogen), piperidinyl (when at least two of $R_2$ is $C_{1-7}$ alkoxy), phenyl $C_{1-7}$ alkyl (when at least one of $R_2$ is halogen and at least one another of $R_2$ is $C_{1-7}$ alkoxy); and $R_n$ is selected from optionally substituted aryl or optionally substituted heterocyclyl wherein the optional substitution at each occurrence is, independently, selected from 1-3 substituents selected from $C_{1-7}$ alkyl or hydroxy $C_{1-7}$ alkyl; wherein the optional substitution at each occurrence is, independently, selected from 1-3 substituents selected from halogen, hydroxy, oxo, $C_{1-7}$ alkyl or $C_{1-7}$ alkoxy.

In one subclass of the above embodiment are compounds wherein $R_1$ is —$NR_aR_b$ or —$C(O)NR_cR_d$, and $R_a$, $R_b$, $R_c$ and $R_d$ are, independently, selected from hydrogen, optionally substituted heterocyclyl, optionally substituted heterocyclyl $C_{1-7}$ alkyl, optionally substituted $C_{3-10}$ cycloalkyl $C_{1-7}$ alkyl, wherein the optional substitution at each occurrence is, independently, selected from 1-3 substituents selected from $C_{1-7}$ alkyl, —$C(O)$—$C_{1-7}$ alkyl, —$C(O)O$—$C_{1-7}$ alkyl, halogen, aryl $C_{1-7}$ alkyl, $C_{1-7}$ alkoxy, oxo or hydroxy $C_{1-7}$ alkyl.

According to one embodiment are compounds of formula (I), (IA), (IB), (IC) or (ID), or according to any embodiment or subclass referred to above, wherein $R_1$ is optionally substituted heterocyclyl or optionally substituted heterocyclyl $C_{1-7}$ alkyl; in particular selected from one of the following groups or tautomers thereof

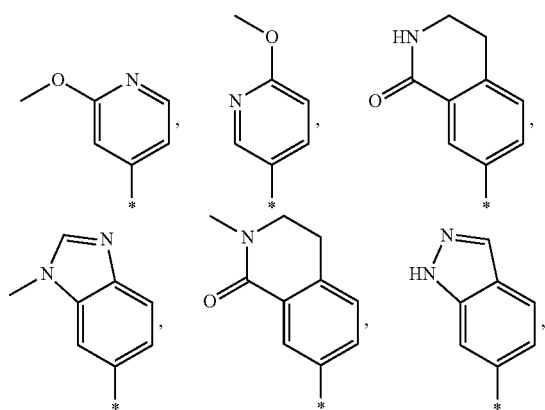

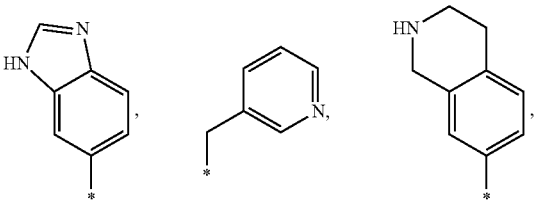

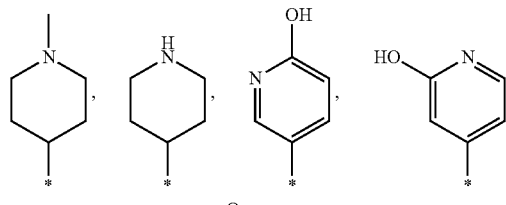

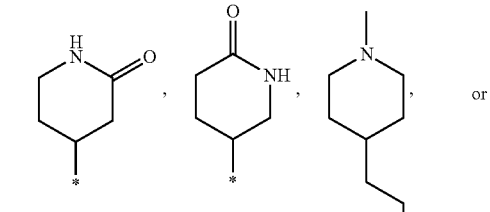

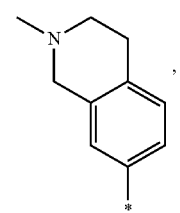

According to one embodiment, provided are compounds according to any embodiment or subclass referred to above, wherein $R_1$ is —$NR_aR_b$ or —$C(O)NR_cR_d$; in particular $R_a$, $R_b$, $R_c$ and $R_d$ being independently selected from hydrogen, $C_{1-7}$ alkyl (such as methyl), $C_{2-7}$ alkenyl (such as but-1-ene), —$C(O)$—$C_{1-7}$ alkyl (such as —$C(O)CH3$), or from one of the following groups or tautomers thereof

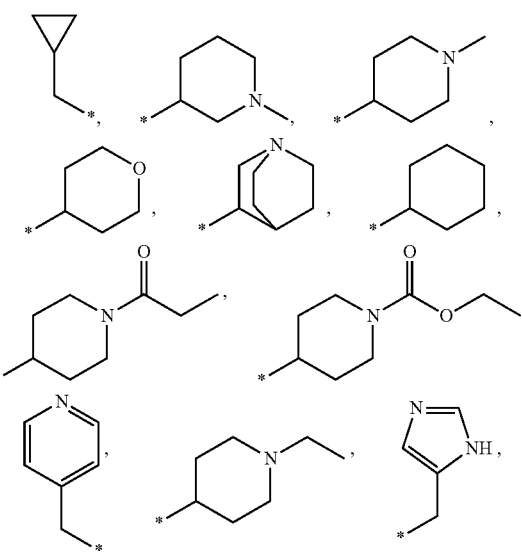

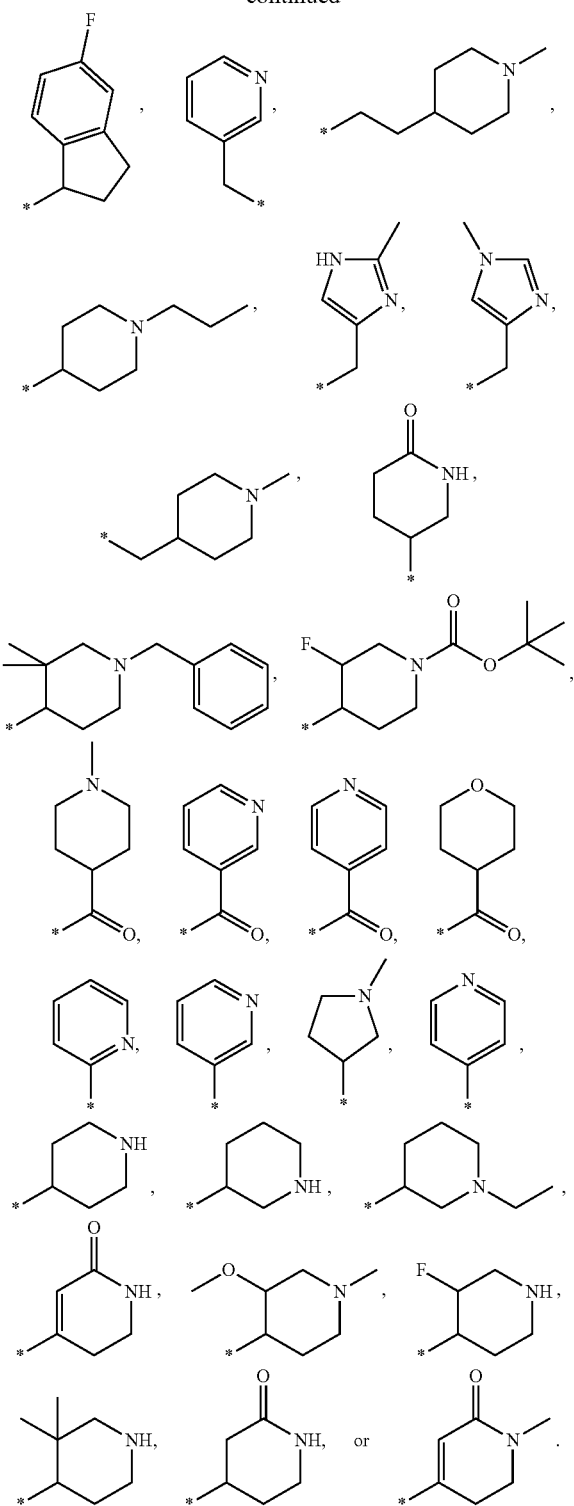

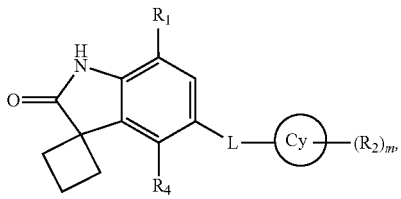

(IE)

wherein $R_1$, $R_2$, $R_4$, Cy, L and 'm' are as defined in any of the above embodiments for formula (I), or a pharmaceutically acceptable salt thereof.

According to one embodiment, provided is a compound of formula (I) or (IE), wherein Cy is a 4-12 membered monocyclic or bicyclic ring containing 0-4 heteroatoms independently selected form N, O or S;

L is a linker selected from —N($R_{3a}$)S(O)$_2$—, —NS(O)(CH$_3$)—, —N($R_{3e}$)C(O)—, —N($R_{3f}$)C(O)N($R_{3g}$)—, —N($R_{3j}$)C(O)CH($R_{3k}$)CH($R_{3l}$)— or —N($R_{3m}$)C(O)CHCH—;

$R_{3a}$, $R_{3e}$, $R_{3f}$, $R_{3g}$, $R_{3j}$, $R_{3k}$, $R_{3l}$ and $R_{3m}$ are selected, independently, from hydrogen or C$_{1-7}$ alkyl;

$R_2$ is halogen, C$_{1-7}$ alkoxy, amino, cyano, oxo, —C(O)O—C$_{1-7}$ alkyl, optionally substituted aryl or optionally substituted heterocyclyl, wherein the optional substitution at each occurrence is, independently, selected from 1-3 substituents selected from halogen or C$_{1-7}$ alkoxy;

$R_4$ is hydrogen or halogen;

in case wherein

L is —NS(O)(CH$_3$)—, —N($R_{3e}$)C(O)—, —N($R_{3f}$)C(O)N($R_{3g}$)—, —N($R_{3j}$)C(O)CH($R_{3k}$)CH($R_{3l}$)— or —N($R_{3j}$)C(O)CHCH—;

then $R_1$ is hydrogen, C$_{1-7}$ alkyl, halo C$_{1-7}$ alkyl, halogen, nitro, hydroxy C$_{1-7}$ alkyl, C$_{3-10}$ cycloalkyl, optionally substituted aryl, optionally substituted heterocyclyl, optionally substituted heterocyclyl C$_{1-7}$ alkyl, optionally substituted heterocyclyl C$_{2-7}$ alkenyl, optionally substituted aryl C$_{1-7}$ alkyl, optionally substituted aryl C$_{2-7}$ alkenyl, —NR$_a$R$_b$, —C(O)NR$_e$R$_d$, —C(O)OR$_e$, —C(O)R$_f$, —C(OR$_g$)-aryl, —C(OR$_h$)(R$_i$)-aryl, —OR$_j$ or —OC(O)R$_k$; wherein the optional substitution at each occurrence is, independently, selected from 1-3 substituents selected from halogen, hydroxy, C$_{1-7}$ alkyl or C$_{1-7}$ alkoxy;

in case wherein

L is —N($R_{3a}$)S(O)$_2$— then $R_1$ is —NR$_a$R$_b$, —C(O)NR$_e$R$_d$, —C(O)OR$_e$, —C(O)R$_f$, —C(OR$_g$)-aryl, —B(OH)$_2$, —C(OR$_h$)(R$_i$)-aryl, —OR$_n$ or —OC(O)R$_k$;

$R_a$, $R_b$, $R_c$ and $R_d$ are, independently, selected from hydrogen, C$_{1-7}$ alkyl, C$_{2-7}$ alkenyl, —C(O)—C$_{1-7}$ alkyl, optionally substituted heterocyclyl, optionally substituted C$_{3-10}$ cycloalkyl, optionally substituted heterocyclyl C$_{1-7}$ alkyl, optionally substituted aryl, optionally substituted aryl C$_{1-7}$ alkyl, optionally substituted C$_{3-10}$ cycloalkyl C$_{1-7}$ alkyl, optionally substituted —C(O)heterocyclyl; wherein the optional substitution at each occurrence is, independently, selected from 1-3 substituents selected from C$_{1-7}$ alkyl, —C(O)—C$_{1-7}$ alkyl, —C(O)O—C$_{1-7}$ alkyl, halogen, aryl C$_{1-7}$ alkyl, C$_{1-7}$ alkoxy, oxo or hydroxy C$_{1-7}$ alkyl;

$R_e$, $R_f$, $R_g$, $R_h$, $R_i$, and $R_j$ are, independently, selected from hydrogen, C$_{1-7}$ alkyl, optionally substituted aryl, optionally According to one embodiment, specifically provided are compounds according to any embodiment or subclass referred to above, wherein heterocyclyl at each occurrence is a 5-10 membered heterocyclic ring having 1-4 heteroatoms selected from O, N, or S.

According to one embodiment the compound of formula (I) is a compound represented by formula (IE):

substituted heterocyclyl, optionally substituted heterocyclyl C$_{1-7}$ alkyl, optionally substituted heterocyclyl C$_{3-7}$ cycloalkyl wherein the optional substitution at each occurrence is, independently, selected from 1-3 substituents selected from C$_{1-7}$ alkyl or hydroxy C$_{1-7}$ alkyl;

R$_k$ is selected from optionally substituted aryl, optionally substituted hetero-cyclyl, optionally substituted heterocyclyl C$_{1-7}$ alkyl, wherein the optional substitution at each occurrence is, independently, selected from 1-3 substituents selected from C$_{1-7}$ alkyl or hydroxy C$_{1-7}$ alkyl;

R$_n$ is selected from optionally substituted aryl, optionally substituted hetero-cyclyl, optionally substituted heterocyclyl C$_{1-7}$ alkyl, optionally substituted heterocyclyl C$_{3-7}$ cycloalkyl or —Z—NR$_{a1}$R$_{b1}$, wherein the optional substitution at each occurrence is, independently, selected from 1-3 substituents selected from hydroxy, C$_{1-7}$ alkyl, C$_{3-7}$ cycloalkyl, hydroxy C$_{1-7}$ alkyl, methylsulfonyl, halogen, amino, acetyl or oxo;

R$_{a1}$ and R$_{b1}$ are, independently, hydrogen, C$_{1-7}$ alkyl or C$_{3-7}$ cycloalkyl;

Z is C$_{1-7}$ alkyl, C$_{3-7}$ cycloalkyl or C$_{3-7}$ cycloalkyl C$_{1-7}$ alkyl;

'm' is selected from 0, 1, 2 or 3;

or a pharmaceutically acceptable salt thereof.

According to one embodiment, provided are compounds according to any embodiment or subclass referred to above, wherein Cy is aromatic or non-aromatic cyclic ring with 5-10 ring atoms of which 0-4 are heteroatoms selected from a group consisting of N, O and S.

According to one embodiment, provided are compounds according to any embodiment or subclass referred to above, wherein Cy is phenyl, C$_{3-10}$ cycloalkyl or a 5-6 membered heterocyclic ring having 1-3 heteroatoms selected from N or O.

According to one embodiment, provided are compounds according to any embodiment or subclass referred to above, wherein Cy is phenyl, cyclohexyl, piperidinyl or pyridyl.

According to one embodiment, provided are compounds according to any embodiment or subclass referred to above, wherein L is —N(R$_{3a}$)S(O)$_2$—.

According to one embodiment, provided are compounds according to any embodiment or subclass referred to above, wherein L is —NHS(O)$_2$—.

According to one embodiment, provided are compounds according to any embodiment or subclass referred to above, wherein R$_4$ is hydrogen.

According to one embodiment, provided are compounds according to any embodiment or subclass referred to above, wherein wherein R$_1$ is —OR$_n$ or —OC(O)R$_k$.

According to one embodiment, provided are compounds according to any embodiment or subclass referred to above, wherein R$_1$ is —OR$_n$.

According to one embodiment, provided are compounds according to any embodiment or subclass referred to above, R$_1$ is an optionally substituted heterocyclyl, optionally substituted heterocyclyl C$_{1-7}$ alkyl, optionally substituted heterocyclyl C$_{3-7}$ cycloalkyl or —Z—NR$_{a1}$R$_{b1}$, wherein the optional substitution at each occurrence is, independently, selected from 1-3 substituents selected from C$_{1-7}$ alkyl, C$_{3-7}$ cycloalkyl, halogen or oxo;

R$_{a1}$ and R$_{b1}$ are, independently, hydrogen, C$_{1-7}$ alkyl or C$_{3-7}$ cycloalkyl; and Z is C$_{1-7}$ alkyl, C$_{3-7}$ cycloalkyl or C$_{3-7}$ cycloalkyl C$_{1-7}$ alkyl;

wherein the heterocylyl, at each occurrence, is a 4-10 membered heterocyclic ring having 1-3 heteroatoms selected from N, O or S.

According to one embodiment, provided are compounds according to any embodiment or subclass referred to above, wherein R$_n$ is an optionally substituted heterocyclyl or optionally substituted heterocyclyl C$_{1-7}$ selected from one of the following groups or tautomers thereof:

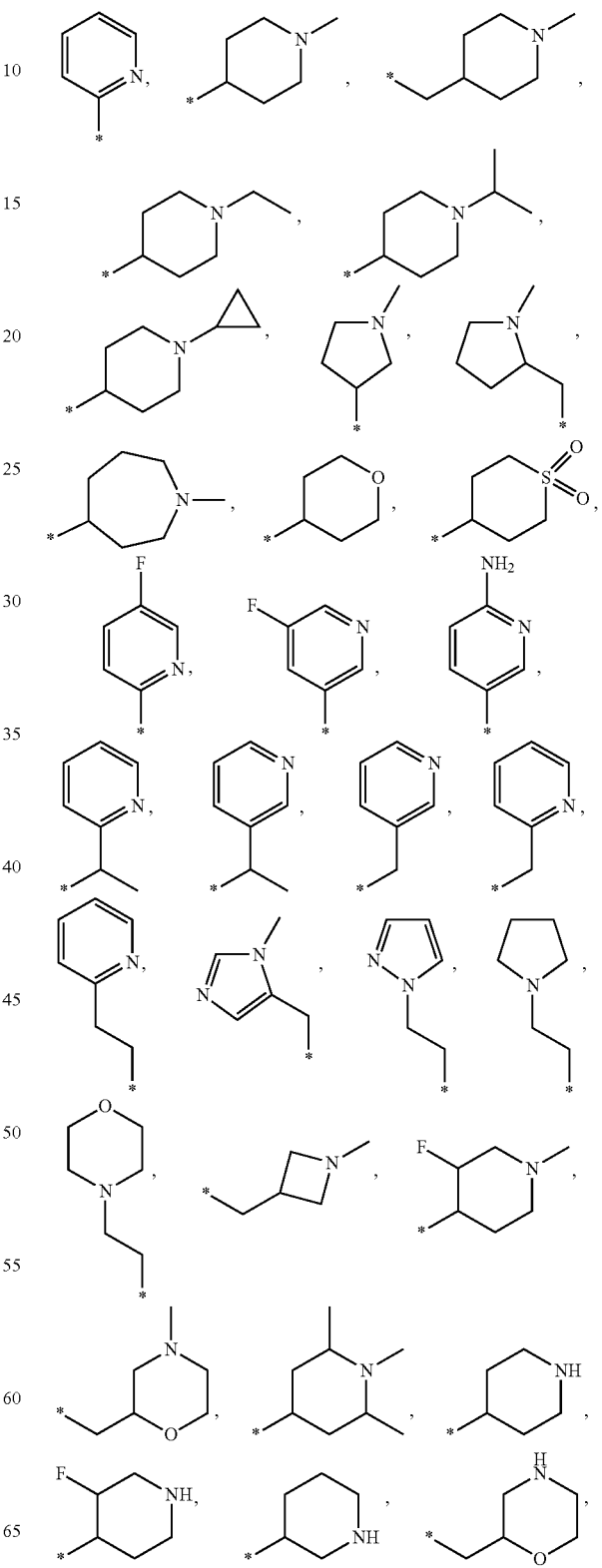

17
-continued

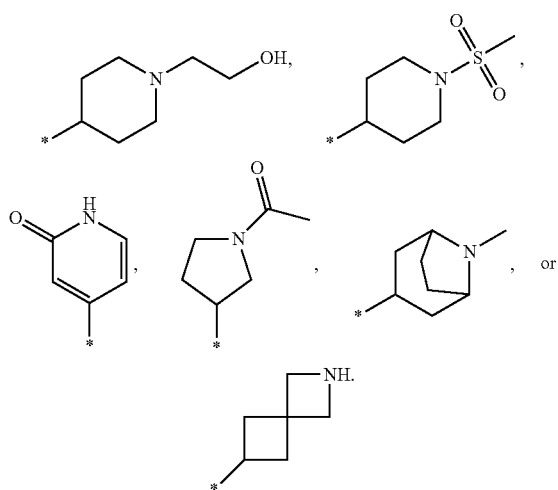

According to one embodiment, provided are compounds according to any embodiment or subclass referred to above, wherein Cy-(R$_2$)$_m$ is selected from one of the following groups or tautomers thereof 18
-continued

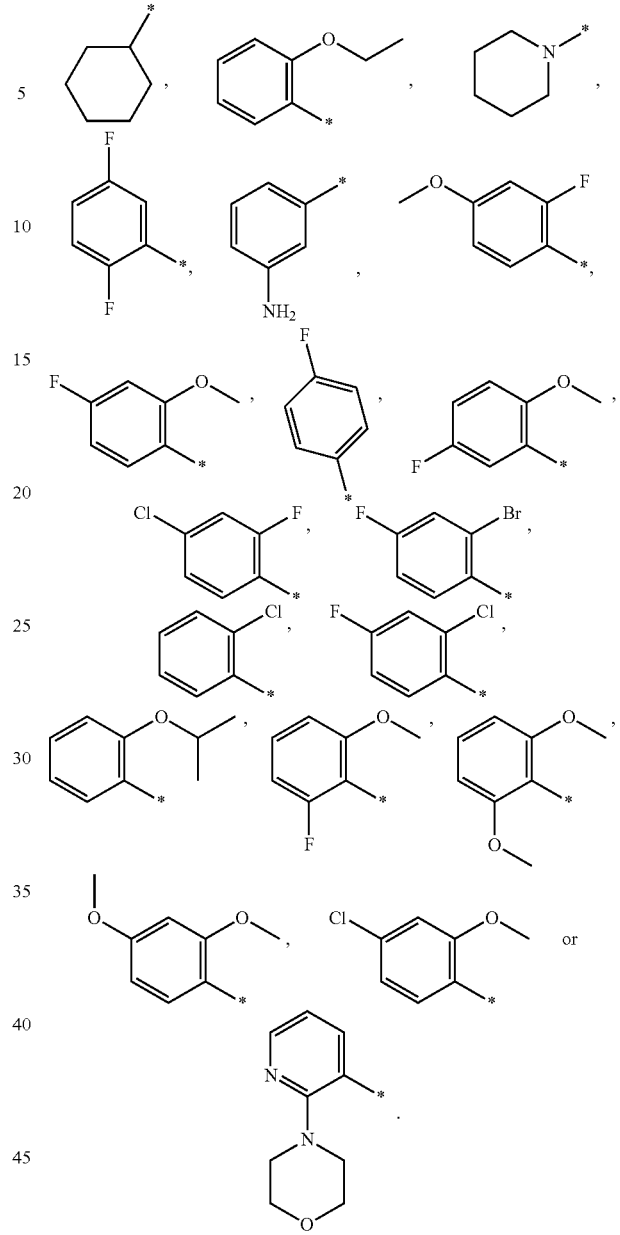

In yet another particular embodiment of the present invention, the compound of formula (I) is selected from the group consisting of:

| No. | Compound Name |
|---|---|
| 1. | 2,4-Difluoro-N-(7'-(3-hydroxyphenyl)-2'-oxospiro[cyclo butane-1,3'-indolin]-5'-yl)benzenesulfonamide; |
| 2. | 2,4-Difluoro-N-(7'-(2-methoxypyridin-4-yl)-2'-oxospiro [cyclobutane-1,3'-indolin]-5'-yl)benzenesulfonamide; |
| 3. | 2,4-Difluoro-N-(7'-(6-methoxypyridin-3-yl)-2'-oxospiro [cyclobutane-1,3'-indolin]-5'-yl)benzenesulfonamide; |
| 4. | 2,4-Difluoro-N-(2'-oxo-7'-(1-oxo-1,2,3,4-tetrahydro isoquinolin-7-yl)spiro-[cyclobutane-1,3'-indolin]-5'-yl)benzenesulfonamide; |
| 5. | 2,4-Difluoro-N-(7'-(1-methyl-1H-benzo[d]imidazol-6-yl)-2'-oxospiro[cyclobutane-1,3'-indolin]-5'-yl)benzene sulphonamide; |
| 6. | 2,4-Difluoro-N-(7'-(2-methyl-1-oxo-1,2,3,4-tetrahydro isoquinolin-7-yl)-2'-oxospiro[cyclobutane-1,3'-indolin]-5'-yl)benzenesulfonamide; |

| No. | Compound Name |
|---|---|
| 7. | N-(7'-(1H-indazol-6-yl)-2'-oxospiro[cyclobutane-1,3'-indolin]-5'-yl)-2,4-difluorobenzenesulfonamide; |
| 8. | N-(7'-(1H-benzo[d]imidazol-6-yl)-2'-oxospiro[cyclobutane-1,3'-indolin]-5'-yl)-2,4-difluorobenzenesulfonamide; |
| 9. | N-(7'-(2-fluorobenzyl)-2'-oxospiro[cyclobutane-1,3'-indolin]-5'-yl)-2-methoxybenzenesulfonamide; |
| 10. | N-(7'-(3-fluorobenzyl)-2'-oxospiro[cyclobutane-1,3'-indolin]-5'-yl)-2-methoxybenzenesulfonamide; |
| 11. | 2-Methoxy-N-(2'-oxo-7'-(1-phenylvinyl)spiro[cyclobutane-1,3'-indolin]-5'-yl)-benzenesulfonamide; |
| 12. | N-(7'-amino-2'-oxospiro[cyclobutane-1,3'-indolin]-5'-yl)-2-methoxybenzenesulfonamide; |
| 13. | N-(7'-((cyclopropylmethyl)amino)-2'-oxospiro[cyclobutane-1,3'-indolin]-5'-yl)-2-methoxybenzenesulfonamide; |
| 14. | N-(7'-(but-3-en-1-ylamino)-2'-oxospiro[cyclobutane-1,3'-indolin]-5'-yl)-2-methoxybenzenesulfonamide; |
| 15. | N-(7'-amino-2'-oxospiro[cyclobutane-1,3'-indolin]-5'-yl)-2,4-difluorobenzenesulfonamide; |
| 16. | 2,4-Difluoro-N-(7'-((1-methylpiperidin-3-yl)amino)-2'-oxo spiro[cyclobutane-1,3'-indolin]-5'-yl)benzenesulfonamide; |
| 17. | 2,4-Difluoro-N-(7'-((1-methylpiperidin-4-yl)amino)-2'-oxo spiro[cyclobutane-1,3'-indolin]-5'-yl)benzenesulfonamide; |
| 18. | 2,4-Difluoro-N-(2'-oxo-7'-((tetrahydro-2H-pyran-4-yl)amino) spiro[cyclobutane-1,3'-indolin]-5'-yl)benzenesulfonamide; |
| 19. | 2,4-Difluoro-N-(2'-oxo-7'-(quinuclidin-3-ylamino) spiro[cyclobutane-1,3'-indolin]-5'-yl)benzenesulfonamide; |
| 20. | N-(7'-(cyclohexylamino)-2'-oxospiro[cyclobutane-1,3'-indolin]-5'-yl)-2,4-difluorobenzenesulfonamide; |
| 21. | 2,4-Difluoro-N-(2'-oxo-7'-((1-propionylpiperidin-4-yl)amino)spiro[cyclobutane-1,3'-indolin]-5'-yl)benzenesulfonamide; |
| 22. | Ethyl 4-((5'-(2,4-difluorophenylsulfonamido)-2'-oxospiro [cyclobutane-1,3'-indolin]-7'-yl)amino)piperidine-1-carboxylate; |
| 23. | 2,4-Difluoro-N-(2'-oxo-7'-((pyridin-4-ylmethyl) amino)spiro[cyclobutane-1,3'-indolin]-5'-yl)benzenesulfonamide; |
| 24. | N-(7'-((1-ethylpiperidin-4-yl)amino)-2'-oxospiro[cyclo butane-1,3'-indolin]-5'-yl)-2,4-difluorobenzenesulfonamide; |
| 25. | N-(7'-(((1H-imidazol-5-yl)methyl)amino)-2'-oxospiro [cyclo butane-1,3'-indolin]-5'-yl)-2,4-difluorobenzene sulfonamide; |
| 26. | 2,4-Difluoro-N-(7'-((5-fluoro-2,3-dihydro-1H-inden-1-yl)amino)-2'-oxospiro-[cyclobutane-1,3'-indolin]-5'-yl)benzenesulfonamide; |
| 27. | 2,4-difluoro-N-(2'-oxo-7'-((pyridin-3-ylmethyl)amino) spiro[cyclobutane-1,3'-indolin]-5'-yl)benzenesulfonamide; |
| 28. | 2,4-Difluoro-N-(7'-((2-(1-methylpiperidin-4-yl)ethyl)amino)-2'-oxospiro[cyclobutane-1,3'-indolin]-5'-yl)benzenesulfonamide; |
| 29. | 2,4-Difluoro-N-(2'-oxo-7'-((1-propylpiperidin-4-yl)amino) spiro[cyclobutane-1,3'-indolin]-5'-yl)benzenesulfonamide; |
| 30. | 2,4-Difluoro-N-(7'-(((2-methyl-1H-imidazol-4-yl)methyl)amino)-2'-oxospiro-[cyclobutane-1,3'-indolin]-5'-yl)benzenesulfonamide; |
| 31. | 2,4-Difluoro-N-(7'-(((1-methyl-1H-imidazol-4-yl)methyl)amino)-2'-oxospiro-[cyclobutane-1,3'-indolin]-5'-yl)benzenesulfonamide; |
| 32. | 2,4-Difluoro-N-(7'-(((1-methylpiperidin-4-yl)methyl)amino)-2'-oxospiro[cyclobutane-1,3'-indolin]-5'-yl)benzenesulfonamide; |
| 33. | 2,4-Difluoro-N-(2'-oxo-7'-((6-oxopiperidin-3-yl)amino) spiro[cyclobutane-1,3'-indolin]-5'-yl)benzenesulfonamide; |
| 34. | 2,4-Difluoro-N-(7'-((1-methylpiperidin-3-yl)amino)-2'-oxospiro[cyclobutane-1,3'-indolin]-5'-yl)benzenesulfonamide; |
| 35. | 2,4-Difluoro-N-(7'-((1-methylpiperidin-3-yl)amino)-2'-oxospiro[cyclobutane-1,3'-indolin]-5'-yl)benzenesulfonamide; |
| 36. | N-(7'-((1-benzyl-3,3-dimethylpiperidin-4-yl)amino)-2'-oxospiro[cyclobutane-1,3'-indolin]-5'-yl)-2,4-difluorobenzenesulfonamide; |
| 37. | tert-Butyl 4-((5'-(2,4-difluorophenylsulfonamido)-2'-oxospiro[cyclobutane-1,3'-indolin]-7'-yl)amino)-3-fluoro piperidine-1-carboxylate; |
| 38. | 2-Methoxy-N-(7'-((1-methylpiperidin-3-yl)amino)-2'-oxo spiro[cyclobutane-1,3'-indolin]-5'-yl)benzenesulfonamide; |
| 39. | 2-Methoxy-N-(7'-((1-methylpiperidin-4-yl)amino)-2'-oxo spiro[cyclobutane-1,3'-indolin]-5'-yl)benzenesulfonamide; |
| 41. | Methyl 5'-(2,4-difluorophenylsulfonamido)-2'-oxospiro[cyclobutane-1,3'-indoline]-7'-carboxylate; |
| 42. | 5'-(2,4-Difluorophenylsulfonamido)-2'-oxospiro[cyclobutane-1,3'-indoline]-7'-carboxylic acid; |
| 43. | N-(5'-(2,4-difluorophenylsulfonamido)-2'-oxospiro[cyclo butane-1,3'-indolin]-7'-yl)-1-methylpiperidine-4-carboxamide; |
| 44. | N-(5'-(2,4-Difluorophenylsulfonamido)-2'-oxospiro[cyclobutane-1,3'-indolin]-7'-yl)nicotinamide; |
| 45. | N-(5'-(2,4-Difluorophenylsulfonamido)-2'-oxospiro[cyclobutane-1,3'-indolin]-7'-yl)isonicotinamide; |

| No. | Compound Name |
|---|---|
| 46. | N-(5'-(2,4-Difluorophenylsulfonamido)-2'-oxospiro[cyclo butane-1,3'-indolin]-7'-yl)tetrahydro-2H-pyran-4-carboxamide; |
| 47. | 2,4-Difluoro-N-(7'-(4-methylpiperazine-1-carbonyl)-2'-oxo spiro[cyclobutane-1,3'-indolin]-5'-yl)benzenesulfonamide; |
| 48. | 2,4-Difluoro-N-(7'-(morpholine-4-carbonyl)-2'-oxospiro [cyclobutane-1,3'-indolin]-5'-yl)benzenesulfonamide; |
| 49. | 5'-(2,4-Difluorophenylsulfonamido)-2'-oxo-N-(pyridin-2-yl)spiro[cyclobutane-1,3'-indoline]-7'-carboxamide; |
| 50. | 5'-(2,4-Difluorophenylsulfonamido)-2'-oxo-N-(tetrahydro-2H-pyran-4-yl)-spiro[cyclobutane-1,3'-indoline]-7'-carboxamide; |
| 51. | 5'-(2,4-Difluorophenylsulfonamido)-2'-oxo-N-(pyridin-3-yl)spiro[cyclobutane-1,3'-indoline]-7'-carboxamide; |
| 52. | 5'-(2,4-Difluorophenylsulfonamido)-N-(1-methylpyrrolidin-3-yl)-2'-oxospiro-[cyclobutane-1,3'-indoline]-7'-carboxamide; |
| 53. | 5'-(2,4-Difluorophenylsulfonamido)-N-methyl-N-(1-methyl piperidin-4-yl)-2'-oxospiro[cyclobutane-1,3'-indoline]-7'-carboxamide; |
| 54. | 5'-(2,4-Difluorophenylsulfonamido)-N-(1-ethylpiperidin-4-yl)-2'-oxospiro[cyclo-butane-1,3'-indoline]-7'-carboxamide; |
| 55. | N-cyclohexyl-5'-(2,4-difluorophenylsulfonamido)-2'-oxospiro[cyclobutane-1,3'-indoline]-7'-carboxamide; |
| 56. | 5'-(2,4-Difluorophenylsulfonamido)-N-(1-methylpiperidin-4-yl)-2'-oxospiro-[cyclobutane-1,3'-indoline]-7'-carboxamide; |
| 57. | 5'-(2,4-Difluorophenylsulfonamido)-2'-oxo-N-(pyridin-4-yl)spiro[cyclobutane-1,3'-indoline]-7'-carboxamide; |
| 58. | 5'-(2,4-Difluorophenylsulfonamido)-N-(1-methylpiperidin-3-yl)-2'-oxospiro-[cyclobutane-1,3'-indoline]-7'-carboxamide; |
| 59. | 2,4-Difluoro-N-(7'-(4-(2-hydroxypropan-2-yl)piperidine-1-carbonyl)-2'-oxo-spiro[cyclobutane-1,3'-indolin]-5'-yl)benzenesulfonamide; |
| 60. | 5'-(2-Methoxyphenylsulfonamido)-N-(1-methylpiperidin-4-yl)-2'-oxospiro-[cyclobutane-1,3'-indoline]-7'-carboxamide; |
| 61. | 4-Fluoro-N-(7'-(morpholine-4-carbonyl)-2'-oxospiro[cyclo butane-1,3'-indolin]-5'-yl)-2-morpholinobenzenesulfonamide; |
| 62. | 2,4-Difluoro-N-(2'-oxo-7'-(pyridin-4-ylamino)spiro [cyclobutane-1,3'-indolin]-5'-yl)benzenesulfonamide; |
| 63. | N-(5'-(2,4-difluorophenylsulfonamido)-2'-oxospiro[cyclobutane-1,3'-indolin]-7'-yl)acetamide; |
| 64. | 5'-(2-Methoxyphenylsulfonamido)-2'-oxo-N-(piperidin-4-yl)spiro[cyclobutane-1,3'-indoline]-7'-carboxamide; |
| 65. | 5'-(2,4-Difluorophenylsulfonamido)-2'-oxo-N-(piperidin-3-yl)spiro[cyclobutane-1,3'-indoline]-7'-carboxamide; |
| 66. | 5'-(2,4-Difluorophenylsulfonamido)-2'-oxo-N-(piperidin-4-yl)spiro[cyclobutane-1,3'-indoline]-7'-carboxamide; |
| 67. | 5'-(2,4-Difluorophenylsulfonamido)-2'-oxo-N-(piperidin-3-yl)spiro[cyclobutane-1,3'-indoline]-7'-carboxamide, isomer 2; |
| 68. | 5'-(2,4-Difluorophenylsulfonamido)-2'-oxo-N-(piperidin-3-yl)spiro[cyclobutane-1,3'-indoline]-7'-carboxamide, isomer 1; |
| 69. | 2,4-Difluoro-N-(7'-(hydroxymethyl)-2'-oxospiro[cyclobutane-1,3'-indolin]-5'-yl)benzenesulfonamide; |
| 70. | N-(7'-((1-ethylpiperidin-3-yl)amino)-2'-oxospiro[cyclobutane-1,3'-indolin]-5'-yl)-2,4-difluorobenzenesulfonamide; |
| 71. | 2,4-difluoro-N-(2'-oxo-7'-(piperidin-3-ylamino)spiro[cyclo butane-1,3'-indolin]-5'-yl)benzenesulfonamide hydrochloride; |
| 72. | 5'-(2,4-Difluoro-N-methylphenylsulfonamido)-N-(1-methyl piperidin-4-yl)-2'-oxospiro[cyclobutane-1,3'-indoline]-7'-carboxamide; |
| 73. | 5'-(2-Fluorophenylsulfonamido)-N-(1-methylpiperidin-4-yl)-2'-oxospiro[cyclo-butane-1,3'-indoline]-7'-carboxamide; |
| 74. | 5'-(4-bromo-2-fluorophenylsulfonamido)-N-(1-methyl piperidin-4-yl)-2'-oxo-spiro[cyclobutane-1,3'-indoline]-7'-carboxamide; |
| 75. | 5'-(2,4-Difluorobenzamido)-N-(1-methylpiperidin-4-yl)-2'-oxospiro[cyclobutane-1,3'-indoline]-7'-carboxamide; |
| 75a. | N-(7'-Cyclopropyl-2'-oxospiro[cyclobutane-1,3'-indolin]-5'-yl)-4-fluorobenzamide; |
| 76. | 2,4-Difluoro-N-(2'-oxo-7'-((6-oxo-1,2,3,6-tetrahydropyridin-4-yl)amino)-spiro[cyclobutane-1,3'-indolin]-5'-yl)benzenesulfonamide; |
| 77. | 2-Methoxy-N-(2'-oxo-7'-((6-oxo-1,2,3,6-tetrahydropyridin-4-yl)amino)spiro-[cyclobutane-1,3'-indolin]-5'-yl)benzenesulfonamide; |
| 78. | N-(7'-((3-fluoro-1-methylpiperidin-4-yl)amino)-2'-oxospiro [cyclobutane-1,3'-indolin]-5'-yl)-2-methoxy benzenesulfonamide; |
| 79. | 2-Methoxy-N-(7'-((3-methoxy-1-methylpiperidin-4-yl)amino) -2'-oxospiro-[cyclobutane-1,3'-indolin]-5'-yl)benzenesulfonamide; |
| 79a. | 2,4-Difluoro-N-(2'-oxo-7'-(piperidin-4-ylamino)spiro [cyclobutane-1,3'-indolin]-5'-yl)benzenesulfonamide; |
| 80. | Methyl 3-fluoro-4-(N-(7'-((1-methylpiperidin-4-yl) carbamoyl)-2'-oxospiro-[cyclobutane-1,3'-indolin]-5'-yl)sulfamoyl)benzoate; |
| 81. | 5'-(4-Cyano-2-fluorophenylsulfonamido)-N-(1-methyl piperidin-4-yl)-2'-oxo-spiro[cyclobutane-1,3'-indoline]-7'-carboxamide; |
| 83. | 5'-(Cyclohexanesulfonamido)-N-(1-methylpiperidin-4-yl)-2'-oxospiro[cyclo-butane-1,3'-indoline]-7'-carboxamide; |

| No. | Compound Name |
|---|---|
| 84. | 5'-(2-Ethoxyphenylsulfonamido)-N-(1-methylpiperidin-4-yl)-2'-oxospiro[cyclobutane-1,3'-indoline]-7'-carboxamide; |
| 85. | N-(1-methylpiperidin-4-yl)-2'-oxo-5'-(piperidine-1-sulfon amido)spiro[cyclobutane-1,3'-indoline]-7'-carboxamide; |
| 86. | 5'-(2,5-Difluorophenylsulfonamido)-N-(1-methylpiperidin-4-yl)-2'-oxospiro-[cyclobutane-1,3'-indoline]-7'-carboxamide; |
| 87. | 2-Methoxy-N-(2'-oxo-7'-(pyridin-3-ylmethyl) spiro[cyclobutane-1,3'-indolin]-5'-yl)benzenesulfonamide; |
| 88. | 2,4-Difluoro-N-(2'-oxo-7'-(1,2,3,4-tetrahydroisoquinolin-7-yl)spiro[cyclobutane-1,3'-indolin]-5'-yl)benzenesulfonamide; |
| 89. | 2,4-Difluoro-N-(7'-(1-methylpiperidin-4-yl)-2'-oxo spiro[cyclobutane-1,3'-indolin]-5'-yl)benzenesulfonamide; |
| 92. | 2,4-Dimethoxy-N-(2'-oxo-7'-(piperidin-4-yl)spiro[cyclobutane-1,3'-indolin]-5'-yl)benzenesulfonamide; |
| 93. | N-(7'-Benzyl-2'-oxospiro[cyclobutane-1,3'-indolin]-5'-yl)-2-fluoro-4-methoxybenzenesulfonamide; |
| 94. | N-(7'-Benzyl-2'-oxospiro[cyclobutane-1,3'-indolin]-5'-yl)-4-fluoro-2-methoxybenzenesulfonamide; |
| 95. | 2-Fluoro-N-(7'-(3-fluorobenzyl)-2'-oxospiro[cyclobutane-1,3'-indolin]-5'-yl)-4-methoxybenzenesulfonamide; |
| 96. | 4-Fluoro-N-(7'-(3-fluorobenzyl)-2'-oxospiro[cyclobutane-1,3'-indolin]-5'-yl)-2-methoxybenzenesulfonamide; |
| 97. | 2-Fluoro-N-(7'-(2-fluorobenzyl)-2'-oxospiro[cyclobutane-1,3'-indolin]-5'-yl)-4-methoxybenzenesulfonamide; |
| 98. | 2-Fluoro-4-methoxy-N-(7'-(1-methylpiperidin-4-yl)-2'-oxospiro[cyclobutane-1,3'-indolin]-5'-yl)benzenesulfonamide; |
| 99. | 2,4-Difluoro-N-(7'-(6-hydroxypyridin-3-yl)-2'-oxo spiro[cyclobutane-1,3'-indolin]-5'-yl)benzenesulfonamide; |
| 100. | 2,4-Difluoro-N-(7'-(2-hydroxypyridin-4-yl)-2'-oxo spiro[cyclobutane-1,3'-indolin]-5'-yl)benzenesulfonamide; |
| 102. | 2,4-Difluoro-N-(7'-((3-fluoropiperidin-4-yl)amino)-2'-oxo spiro[cyclobutane-1,3'-indolin]-5'-yl)benzenesulfonamide; |
| 103. | N-(7'-((3,3-dimethylpiperidin-4-yl)amino)-2'-oxospiro[cyclobutane-1,3'-indolin]-5'-yl)-2,4-difluorobenzenesulfonamide; |
| 104. | 2,4-Difluoro-N-(2'-oxo-7'-(2-oxopiperidin-4-yl)spiro [cyclobutane-1,3'-indolin]-5'-yl)benzenesulfonamide; |
| 105. | 2,4-Difluoro-N-(2'-oxo-7'-(6-oxopiperidin-3-yl)spiro [cyclobutane-1,3'-indolin]-5'-yl)benzenesulfonamide; |
| 106. | 2,4-Difluoro-N-(7'-(2-methyl-1,2,3,4-tetrahydroisoquinolin-7-yl)-2'-oxospiro-[cyclobutane-1,3'-indolin]-5'-yl)benzene sulfonamide; |
| 113. | 2-Methoxy-N-(2'-oxo-7'-(1-phenylethyl)spiro[cyclobutane-1,3'-indolin]-5'-yl)-benzenesulfonamide; |
| 114. | 2-Methoxy-N-(2'-oxo-7'-(1-phenylethyl)spiro[cyclobutane-1,3'-indolin]-5'-yl)-benzenesulfonamide, isomer 1; |
| 115. | 2-Methoxy-N-(2'-oxo-7'-(1-phenylethyl)spiro[cyclobutane-1,3'-indolin]-5'-yl)-benzenesulfonamide, isomer 2; |
| 116. | 2,4-Difluoro-N-(7'-(2-(1-methylpiperidin-4-yl)ethyl)-2'-oxo spiro[cyclobutane-1,3'-indolin]-5'-yl)benzenesulfonamide; |
| 117. | N-(7'-benzoyl-2'-oxospiro[cyclobutane-1,3'-indolin]-5'-yl)-2-methoxybenzenesulfonamide; |
| 118. | N-(7'-(hydroxy(phenyl)methyl)-2'-oxospiro[cyclobutane-1,3'-indolin]-5'-yl)-2-methoxybenzenesulfonamide; |
| 120. | N-(7'-(1-hydroxy-1-phenylethyl)-2'-oxospiro[cyclobutane-1,3'-indolin]-5'-yl)-2-methoxybenzenesulfonamide; |
| 121. | 1-(7'-Cyclopropyl-2'-oxospiro[cyclobutane-1,3'-indolin]-5'-yl)-3-(2-methoxyphenyl)urea, |
| 122. | 2-Methoxy-N-(2'-oxo-7'-(1-(pyridin-3-yl)ethyl)spiro[cyclobutane-1,3'-indolin]-5'-yl)benzenesulfonamide, |
| 123. | 2-Methoxy-N-(2'-oxo-7'-(1-(pyridin-2-yl)ethyl)spiro [cyclobutane-1,3'-indolin]-5'-yl)benzenesulfonamide, |
| 124. | 2-Methoxy-N-(2'-oxo-7'-(pyridin-2-yloxy)spiro[cyclobutane-1,3'-indolin]-5'-yl)-benzenesulfonamide |
| 125. | N-(7'-(fluoro(phenyl)methyl)-2'-oxospiro[cyclobutane-1,3'-indolin]-5'-yl)-2-methoxybenzenesulfonamide |
| 126. | 2,4-Difluoro-N-(2'-oxo-7'-(1-phenylethyl)spiro[cyclobutane-1,3'-indolin]-5'-yl)-benzenesulfonamide |
| 127. | 2-Methoxy-N-(7'-((1-methylpiperidin-4-yl)oxy)-2'-oxospiro[cyclobutane-1,3'-indolin]-5'-yl)benzenesulfonamide |
| 128. | 2-Fluoro-N-(7'-((1-methylpiperidin-4-yl)oxy)-2'-oxospiro[cyclobutane-1,3'-indolin]-5'-yl)benzenesulfonamide |
| 129. | 5-Fluoro-2-methoxy-N-(7'-((1-methylpiperidin-4-yl)oxy)-2'-oxospiro[cyclobutane-1,3'-indolin]-5'-yl)benzenesulfonamide |
| 130. | 4-Chloro-2-fluoro-N-(7'-((1-methylpiperidin-4-yl)oxy)-2'-oxospiro[cyclobutane-1,3'-indolin]-5'-yl)benzenesulfonamide |
| 131. | 4-Chloro-2-fluoro-N-(7'-((1-methylpiperidin-3-yl)oxy)-2'-oxospiro[cyclobutane-1,3'-indolin]-5'-yl)benzenesulfonamide |

-continued

| No. | Compound Name |
|---|---|
| 132. | 2-Bromo-4-fluoro-N-(7'-((1-methylpiperidin-4-yl)oxy)-2'-oxospiro[cyclobutane-1,3'-indolin]-5'-yl)benzenesulfonamide |
| 133. | 2-Chloro-N-(7'-((1-methylpiperidin-4-yl)oxy)-2'-oxospiro[cyclobutane-1,3'-indolin]-5'-yl)benzenesulfonamide |
| 134. | 2-Chloro-4-fluoro-N-(7'-((1-methylpiperidin-4-yl)oxy)-2'-oxospiro[cyclobutane-1,3'-indolin]-5'-yl)benzenesulfonamide |
| 135. | N-(7'-((1-ethylpiperidin-4-yl)oxy)-2'-oxospiro[cyclobutane-1,3'-indolin]-5'-yl)-2-methoxybenzenesulfonamide |
| 136. | N-(7'-((1-isopropylpiperidin-4-yl)oxy)-2'-oxospiro[cyclobutane-1,3'-indolin]-5'-yl)-2-methoxybenzenesulfonamide |
| 137. | N-(7'-((1-cyclopropylpiperidin-4-yl)oxy)-2'-oxospiro[cyclobutane-1,3'-indolin]-5'-yl)-2-methoxybenzenesulfonamide |
| 138. | 4-Chloro-2-fluoro-N-(7'-((1-methylpyrrolidin-3-yl)oxy)-2'-oxospiro[cyclobutane-1,3'-indolin]-5'-yl)benzenesulfonamide |
| 139. | (S)-2-methoxy-N-(7'-((1-methylpyrrolidin-2-yl)methoxy)-2'-oxospiro[cyclobutane-1,3'-indolin]-5'-yl)benzenesulfonamide |
| 140. | 2-Methoxy-N-(7'-((1-methylazepan-4-yl)oxy)-2'-oxospiro[cyclobutane-1,3'-indolin]-5'-yl)benzenesulfonamide |
| 141. | 2-Methoxy-N-(2'-oxo-7'-((tetrahydro-2H-pyran-4-yl)oxy)spiro[cyclobutane-1,3'-indolin]-5'-yl)benzenesulfonamide |
| 142. | 4-Chloro-2-fluoro-N-(2'-oxo-7'-((tetrahydro-2H-pyran-4-yl)oxy)spiro[cyclobutane-1,3'-indolin]-5'-yl)benzenesulfonamide |
| 143. | N-(7'-((1,1-dioxidotetrahydro-2H-thiopyran-4-yl)oxy)-2'-oxospiro[cyclobutane-1,3'-indolin]-5'-yl)-2-methoxybenzenesulfonamide |
| 144. | 4-Chloro-N-(7'-((1,1-dioxidotetrahydro-2H-thiopyran-4-yl)oxy)-2'-oxospiro-[cyclobutane-1,3'-indolin]-5'-yl)-2-fluorobenzenesulfonamide |
| 145. | N-(7'-((6-aminopyridin-3-yl)oxy)-2'-oxospiro[cyclobutane-1,3'-indolin]-5'-yl)-2-methoxybenzenesulfonamide |
| 146. | 2-Methoxy-N-(7'-((1-methylpiperidin-4-yl)methoxy)-2'-oxospiro[cyclobutane-1,3'-indolin]-5'-yl)benzenesulfonamide |
| 147. | 4-Chloro-2-fluoro-N-(7'-((5-fluoropyridin-2-yl)methoxy)-2'-oxospiro[cyclobutane-1,3'-indolin]-5'-yl)benzenesulfonamide |
| 148. | N-(7'-((5-fluoropyridin-2-yl)methoxy)-2'-oxospiro[cyclobutane-1,3'-indolin]-5'-yl)-2-methoxybenzenesulfonamide |
| 149. | N-(7'-((5-fluoropyridin-3-yl)methoxy)-2'-oxospiro[cyclobutane-1,3'-indolin]-5'-yl)-2-methoxybenzenesulfonamide |
| 150. | 2-Methoxy-N-(2'-oxo-7'-(1-(pyridin-2-yl)ethoxy)spiro[cyclobutane-1,3'-indolin]-5'-yl)benzenesulfonamide, Isomer I |
| 151. | 2-Methoxy-N-(2'-oxo-7'-(1-(pyridin-2-yl)ethoxy)spiro[cyclobutane-1,3'-indolin]-5'-yl)benzenesulfonamide, Isomer II |
| 152. | 2-methoxy-N-(2'-oxo-7'-(1-(pyridin-3-yl)ethoxy)spiro[cyclobutane-1,3'-indolin]-5'-yl)benzenesulfonamide, racemic |
| 153. | 2-methoxy-N-(2'-oxo-7'-(1-(pyridin-3-yl)ethoxy)spiro[cyclobutane-1,3'-indolin]-5'-yl)benzenesulfonamide, Isomer I |
| 154. | 2-methoxy-N-(2'-oxo-7'-(1-(pyridin-3-yl)ethoxy)spiro[cyclobutane-1,3'-indolin]-5'-yl)benzenesulfonamide, Isomer II |
| 155. | 4-Chloro-2-fluoro-N-(2'-oxo-7'-(1-(pyridin-2-yl)ethoxy)spiro[cyclobutane-1,3'-indolin]-5'-yl)benzenesulfonamide, Isomer I |
| 156. | 4-Chloro-2-fluoro-N-(2'-oxo-7'-(1-(pyridin-2-yl)ethoxy)spiro[cyclobutane-1,3'-indolin]-5'-yl)benzenesulfonamide, Isomer II |
| 157. | 2-Methoxy-N-(2'-oxo-7'-(pyridin-3-ylmethoxy)spiro[cyclobutane-1,3'-indolin]-5'-yl)benzenesulfonamide |
| 158. | 2-Methoxy-N-(2'-oxo-7'-(pyridin-2-ylmethoxy)spiro[cyclobutane-1,3'-indolin]-5'-yl)benzenesulfonamide |
| 159. | 4-Chloro-2-fluoro-N-(2'-oxo-7'-(2-(pyridin-2-yl)ethoxy)spiro[cyclobutane-1,3'-indolin]-5'-yl)benzenesulfonamide |
| 160. | 4-Chloro-2-fluoro-N-(7'-((1-methyl-1H-imidazol-5-yl)methoxy)-2'-oxospiro-[cyclobutane-1,3'-indolin]-5'-yl)benzenesulfonamide |
| 161. | N-(7'-(2-(1H-pyrazol-1-yl)ethoxy)-2'-oxospiro[cyclobutane-1,3'-indolin]-5'-yl)-4-chloro-2-fluorobenzenesulfonamide |
| 162. | N-(7'-(2-(dimethylamino)ethoxy)-2'-oxospiro[cyclobutane-1,3'-indolin]-5'-yl)-2-methoxybenzenesulfonamide |
| 163. | 4-Chloro-N-(7'-(2-(dimethylamino)ethoxy)-2'-oxospiro[cyclobutane-1,3'-indolin]-5'-yl)-2-fluorobenzenesulfonamide |
| 164. | N-(7'-(3-(dimethylamino)propoxy)-2'-oxospiro[cyclobutane-1,3'-indolin]-5'-yl)-2-methoxybenzenesulfonamide |
| 165. | N-(7'-(2-(diethylamino)ethoxy)-2'-oxospiro[cyclobutane-1,3'-indolin]-5'-yl)-2-methoxybenzenesulfonamide |
| 166. | N-(7'-((1-(dimethylamino)propan-2-yl)oxy)-2'-oxospiro[cyclobutane-1,3'-indolin]-5'-yl)-2-methoxybenzenesulfonamide |
| 167. | 2-Methoxy-N-(2'-oxo-7'-(2-(pyrrolidin-1-yl)ethoxy)spiro[cyclobutane-1,3'-indolin]-5'-yl)benzenesulfonamide |
| 168. | 2-Methoxy-N-(7'-(2-morpholinoethoxy)-2'-oxospiro[cyclobutane-1,3'-indolin]-5'-yl)benzenesulfonamide |
| 169. | 5'-((2-Methoxyphenyl)sulfonamido)-2'-oxospiro[cyclobutane-1,3'-indolin]-7'-yl 4-methylpiperazine-1-carboxylate |

-continued

| No. | Compound Name |
|---|---|
| 170. | 5'-((2-Methoxyphenyl)sulfonamido)-2'-oxospiro[cyclobutane-1,3'-indolin]-7'-yl morpholine-4-carboxylate |
| 171. | 2,4-Difluoro-N-(7'-((1-methylpiperidin-4-yl)oxy)-2'-oxospiro[cyclobutane-1,3'-indolin]-5'-yl)benzenesulfonamide |
| 172. | 2-Methoxy-N-(2'-oxo-7'-(1-(thiazol-2-yl)vinyl)spiro[cyclobutane-1,3'-indolin]-5'-yl)benzenesulfonamide |
| 173. | 2-Methoxy-N-(7'-(1-(1-methylpiperidin-3-yl)ethyl)-2'-oxospiro[cyclobutane-1,3'-indolin]-5'-yl)benzenesulfonamide, Isomer I |
| 174. | 2-Methoxy-N-(7'-(1-(1-methylpiperidin-3-yl)ethyl)-2'-oxospiro[cyclobutane-1,3'-indolin]-5'-yl)benzenesulfonamide, Isomer II |
| 175. | 4-Chloro-N-(7'-((4,4-difluorocyclohexyl)oxy)-2'-oxospiro[cyclobutane-1,3'-indolin]-5'-yl)-2-fluorobenzenesulfonamide |
| 176. | 4-Chloro-2-fluoro-N-(2'-oxo-7'-((4-oxocyclohexyl)oxy)spiro[cyclobutane-1,3'-indolin]-5'-yl)benzenesulfonamide |
| 177. | 2-Methoxy-N-(2'-oxo-7'-(1-(thiazol-2-yl)ethyl)spiro[cyclobutane-1,3'-indolin]-5'-yl)benzenesulfonamide |
| 178. | 2-Methoxy-N-methyl-N-(7'-((1-methylpiperidin-4-yl)oxy)-2'-oxospiro[cyclobutane-1,3'-indolin]-5'-yl)benzenesulfonamide |
| 179. | N-ethyl-2-methoxy-N-(7'-((1-methylpiperidin-4-yl)oxy)-2'-oxospiro[cyclobutane-1,3'-indolin]-5'-yl)benzenesulfonamide |
| 180. | 2,4-Difluoro-N-methyl-N-(7'-((1-methylpiperidin-4-yl)oxy)-2'-oxospiro[cyclobutane-1,3'-indolin]-5'-yl)benzenesulfonamide |
| 181. | 5'-(((2-Methoxyphenyl)(methyl)(oxo)-l6-sulfanylidene)amino)-7'-nitrospiro-[cyclobutane-1,3'-indolin]-2'-one |
| 182. | 7'-Amino-5'-(((2-methoxyphenyl)(methyl)(oxo)-l6-sulfanylidene)amino)spiro-[cyclobutane-1,3'-indolin]-2'-one |
| 183. | 5'-(((2-Methoxyphenyl)(methyl)(oxo)-l6-sulfanylidene)amino)-7'-((1-methyl-piperidin-4-yl)amino)spiro[cyclobutane-1,3'-indolin]-2'-one |
| 184. | 2-Isopropoxy-N-(7'-((1-methylpiperidin-4-yl)oxy)-2'-oxospiro[cyclobutane-1,3'-indolin]-5'-yl)benzenesulfonamide |
| 185. | 2-Fluoro-6-methoxy-N-(7'-((1-methylpiperidin-4-yl)oxy)-2'-oxospiro[cyclo-butane-1,3'-indolin]-5'-yl)benzenesulfonamide |
| 186. | 2,6-Dimethoxy-N-(7'-((1-methylpiperidin-4-yl)oxy)-2'-oxospiro[cyclobutane-1,3'-indolin]-5'-yl)benzenesulfonamide |
| 187. | 2,4-Dimethoxy-N-(7'-((1-methylpiperidin-4-yl)oxy)-2'-oxospiro[cyclobutane-1,3'-indolin]-5'-yl)benzenesulfonamide |
| 188. | 4-Chloro-2-methoxy-N-(7'-((1-methylpiperidin-4-yl)oxy)-2'-oxospiro[cyclo-butane-1,3'-indolin]-5'-yl)benzenesulfonamide |
| 189. | 4-Fluoro-2-methoxy-N-(7'-((1-methylpiperidin-4-yl)oxy)-2'-oxospiro[cyclo-butane-1,3'-indolin]-5'-yl)benzenesulfonamide |
| 190. | 2-Methoxy-N-(7'-((1-methylazetidin-3-yl)methoxy)-2'-oxospiro[cyclobutane-1,3'-indolin]-5'-yl)benzenesulfonamide |
| 191. | N-(7'-((3-fluoro-1-methylpiperidin-4-yl)oxy)-2'-oxospiro[cyclobutane-1,3'-indolin]-5'-yl)-2-methoxybenzenesulfonamide, Isomer I |
| 192. | N-(7'-((3-fluoro-1-methylpiperidin-4-yl)oxy)-2'-oxospiro[cyclobutane-1,3'-indolin]-5'-yl)-2-methoxybenzenesulfonamide, Isomer II |
| 193. | 4-Chloro-2-fluoro-N-(7'-((3-fluoro-1-methylpiperidin-4-yl)oxy)-2'-oxospiro-[cyclobutane-1,3'-indolin]-5'-yl)benzenesulfonamide |
| 194. | 4-Chloro-2-fluoro-N-(7'-((4-methylmorpholin-2-yl)methoxy)-2'-oxospiro[cyclo-butane-1,3'-indolin]-5'-yl)benzenesulfonamide |
| 195. | 4-Chloro-2-fluoro-N-(2'-oxo-7'-((1,2,6-trimethylpiperidin-4-yl)oxy)spiro-[cyclobutane-1,3'-indolin]-5'-yl)benzenesulfonamide |
| 196. | N-(7'-(2-(ethyl(methyl)amino)ethoxy)-2'-oxospiro[cyclobutane-1,3'-indolin]-5'-yl)-2-methoxybenzenesulfonamide |
| 197. | 4-Chloro-2-fluoro-N-(2'-oxo-7'-(piperidin-4-yloxy)spiro[cyclobutane-1,3'-indolin]-5'-yl)benzenesulfonamide |
| 198. | 4-Chloro-2-fluoro-N-(7'-((3-fluoropiperidin-4-yl)oxy)-2'-oxospiro[cyclobutane-1,3'-indolin]-5'-yl)benzenesulfonamide |
| 199. | 2-Methoxy-N-(2'-oxo-7'-(piperidin-4-yloxy)spiro[cyclobutane-1,3'-indolin]-5'-yl)benzenesulfonamide |
| 200. | 4-Chloro-2-fluoro-N-(2'-oxo-7'-(piperidin-3-yloxy)spiro[cyclobutane-1,3'-indolin]-5'-yl)benzenesulfonamide |
| 201. | 4-Chloro-N-(7'-((2,6-dimethylpiperidin-4-yl)oxy)-2'-oxospiro[cyclobutane-1,3'-indolin]-5'-yl)-2-fluorobenzenesulfonamide |
| 202. | 4-Chloro-2-fluoro-N-(7'-(morpholin-2-ylmethoxy)-2'-oxospiro[cyclobutane-1,3'-indolin]-5'-yl)benzenesulfonamide |
| 203. | 2-Methoxy-N-(7'-(morpholin-3-ylmethoxy)-2'-oxospiro[cyclobutane-1,3'-indolin]-5'-yl)benzenesulfonamide |
| 204. | 2-Methoxy-N-(7'-(2-(methylamino)ethoxy)-2'-oxospiro[cyclobutane-1,3'-indolin]-5'-yl)benzenesulfonamide |
| 205. | N-(7'-(2-(ethylamino)ethoxy)-2'-oxospiro[cyclobutane-1,3'-indolin]-5'-yl)-2-methoxybenzenesulfonamide |
| 206. | N-(7'-(2-(cyclopropylamino)ethoxy)-2'-oxospiro[cyclobutane-1,3'-indolin]-5'-yl)-2-methoxybenzenesulfonamide |
| 207. | N-(7'-((1-aminocyclopropyl)methoxy)-2'-oxospiro[cyclobutane-1,3'-indolin]-5'-yl)-4-chloro-2-fluorobenzenesulfonamide |

| No. | Compound Name |
|---|---|
| 208. | N-(7'-((4-hydroxycyclohexyl)oxy)-2'-oxospiro[cyclobutane-1,3'-indolin]-5'-yl)-2-methoxybenzenesulfonamide |
| 209. | N-(7'-((1-(2-hydroxyethyl)piperidin-4-yl)oxy)-2'-oxospiro[cyclobutane-1,3'-indolin]-5'-yl)-2-methoxybenzenesulfonamide |
| 210. | 4-Chloro-2-fluoro-N-(7'-((1-(methylsulfonyl)piperidin-4-yl)oxy)-2'-oxospiro-[cyclobutane-1,3'-indolin]-5'-yl)benzenesulfonamide |
| 211. | 5'-((4-Chloro-2-fluorophenyl)sulfonamido)-N-(1-methylpiperidin-4-yl)-2'-oxo-spiro[cyclobutane-1,3'-indoline]-7'-carboxamide |
| 212. | 4-Chloro-2-fluoro-N-(2'-oxo-7'-((2-oxo-1,2-dihydropyridin-4-yl)oxy)spiro-[cyclobutane-1,3'-indolin]-5'-yl)benzenesulfonamide |
| 213. | 2-Methoxy-N-(2'-oxo-7'-((2-oxo-1,2-dihydropyridin-4-yl)oxy)spiro[cyclobutane-1,3'-indolin]-5'-yl)benzenesulfonamide |
| 214. | Sodium ((2-methoxyphenyl)sulfonyl)(2'-oxo-7'-(1-phenylethyl)spiro[cyclo-butane-1,3'-indolin]-5'-yl)amide |
| 215. | N-(4'-chloro-7'-((1-methylpiperidin-4-yl)oxy)-2'-oxospiro[cyclobutane-1,3'-indolin]-5'-yl)-2-methoxybenzenesulfonamide |
| 216. | N-(4'-bromo-7'-((1-methylpiperidin-4-yl)oxy)-2'-oxospiro[cyclobutane-1,3'-indolin]-5'-yl)-2-methoxybenzenesulfonamide |
| 217. | (5'-((2-Methoxyphenyl)sulfonamido)-2'-oxospiro[cyclobutane-1,3'-indolin]-7'-yl)boronic acid |
| 218. | N-(7'-((1-methylpiperidin-4-yl)oxy)-2'-oxospiro[cyclobutane-1,3'-indolin]-5'-yl)-3-phenylpropanamide |
| 219. | N-(7'-((1-methylpiperidin-4-yl)oxy)-2'-oxospiro[cyclobutane-1,3'-indolin]-5'-yl)cinnamamide |
| 220. | N-(7'-((1-acetylpiperidin-4-yl)oxy)-2'-oxospiro[cyclobutane-1,3'-indolin]-5'-yl)-2-methoxybenzenesulfonamide |
| 221. | N-(7'-((1-acetylpyrrolidin-3-yl)oxy)-2'-oxospiro[cyclobutane-1,3'-indolin]-5'-yl)-4-chloro-2-fluorobenzenesulfonamide |
| 222. | N-(7'-bromo-2'-oxospiro[cyclobutane-1,3'-indolin]-5'-yl)-2-morpholinonicotin-amide |
| 223. | N-(7'-cyclopropyl-2'-oxospiro[cyclobutane-1,3'-indolin]-5'-yl)-2-morpholino-nicotinamide |
| 224. | 4-Chloro-2-fluoro-N-(7'-((1-methylpiperidin-4-yl)oxy)-2'-oxospiro[cyclobutane-1,3'-indolin]-5'-yl)benzamide |
| 225. | N-(7'-((1-methylpiperidin-4-yl)oxy)-2'-oxospiro[cyclobutane-1,3'-indolin]-5'-yl)-2-morpholinonicotinamide |
| 226. | 4-Fluoro-N-(2'-oxo-7'-((6-oxo-1,2,3,6-tetrahydropyridin-4-yl)amino)spiro-[cyclobutane-1,3'-indolin]-5'-yl)benzenesulfonamide |
| 227. | 2-Fluoro-N-(2'-oxo-7'-((6-oxo-1,2,3,6-tetrahydropyridin-4-yl)amino)spiro-[cyclobutane-1,3'-indolin]-5'-yl)benzenesulfonamide |
| 228. | 5'-(((2-Methoxyphenyl)(methyl)(oxo)-l6-sulfanylidene)amino)-7'-((1-methyl-piperidin-4-yl)oxy)spiro[cyclobutane-1,3'-indolin]-2'-one |
| 229. | 2-Methoxy-N-(7'-((1-methyl-6-oxo-1,2,3,6-tetrahydropyridin-4-yl)amino)-2'-oxospiro[cyclobutane-1,3'-indolin]-5'-yl)benzenesulfonamide | and pharmaceutically acceptable salts thereof.

In yet another embodiment according to the present patent application, it provides a pharmaceutical composition comprising a compound of formula (I), (IA), (IB), (IC), (ID) or (IE) of the present invention and at least one pharmaceutically acceptable excipient (such as a pharmaceutically acceptable carrier or diluent). Preferably, the pharmaceutical composition comprises a therapeutically effective amount of at least one compound described herein.

It should be understood that formulas (I), (IA), (IB), (IC), (ID), and (IE) encompass all stereoisomers, enantiomers, diastereomers and isotopes that may be contemplated from the chemical structure of the compounds according to above formulas.

The present compounds may also exist as tautomers or equilibrium mixtures thereof wherein a proton of a compound shifts from one atom to another. Examples of tautomers include, but are not limited to, amido-imido, keto-enol, phenol-keto, oxime-nitroso, nitro-aci, imine-enamine and the like. All tautomeric forms of the compounds are intended to be encompassed by their structural formula even though only one tautomeric form may be depicted.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "$C_{1-7}$ alkyl", as employed herein as such or as part of another group, refers to a straight or branched chain saturated hydrocarbon group having 1, 2, 3, 4, 5, 6 or 7 carbon atom(s). Representative examples of $C_{1-7}$ alkyl include, but are not limited to, methyl, ethyl, n-propyl, iso-propyl, n-butyl, iso-butyl, sec-butyl, tent-butyl, n-pentyl, iso-pentyl and n-hexyl. The term "$C_{1-3}$ alkyl" refers to an preferred embodiment of "$C_{1-7}$ alkyl" having 1, 2 or 3 carbon atoms.

The term "$C_{2-7}$ alkenyl", as employed herein as such or as part of another group, refers to an aliphatic hydrocarbon group having 2 to 7 carbon atoms and containing one or several double bonds. Representative examples include, but are not limited to, ethy-lene, prop-1-ene, but-1-ene, but-2-ene, pent-1-ene, pent-2-ene, hex-1-ene and hex-2-ene.

The term "$C_{3-10}$ cycloalkyl", as employed herein as such or as part of another group, refers to a saturated or partially saturated, monocyclic, bicyclic or polycyclic hydrocarbon ring system having 3 to 10 carbon atoms. Examples of $C_{3-10}$ cycloalkyl groups are include those where saturated 5 or 6 membered cycloalkyl ring is fused to a phenyl ring. The term "$C_{3-7}$ cycloalkyl", as employed herein as such or as part of another group, refers to a saturated or partially saturated monocyclic hydrocarbon ring containing 3, 4, 5, 6 or 7 carbon atoms. Representative examples of $C_{3-10}$ cycloalkyl include, but are not limited to, cyclopropyl, cyclobutyl, cyclopentyl and cyclohexyl.

The term "halo" or "halogen", as employed herein as such or as part of another group, refers to chlorine, bromine, fluorine or iodine.

The term "$C_{1-7}$ alkoxy", as employed herein as such or as part of another group, refers to $C_{1-7}$ alkyl, as defined herein, appended to the parent molecular moiety through an oxygen atom. Representative examples of $C_{1-7}$ alkoxy include, but are not limited to methoxy, ethoxy, propoxy, butoxy, isobutoxy, sec-butoxy and tent-butoxy.

The term "hydroxy", as employed herein as such or as part of another group, refers to an —OH group. The term "amino", as employed herein as such or as part of another group, refers to an —NH$_2$ group. The term "cyano", as employed herein as such or as part of another group, refers to a —CN group. The term "carboxy", as employed herein as such or as part of another group, refers to —COOH group. The term "carbonyl", as employed herein as such or as part of another group, refers to a carbon atom double-bonded to an oxygen atom (C=O). The term "oxo", as employed herein as such or as part of another group, refers to oxygen atom linked to another atom by a double bond (=O).

The term "hydroxy $C_{1-7}$ alkyl", as employed herein, refers to at least one hydroxy group, as defined herein, appended to the parent molecular moiety through a $C_{1-7}$ alkyl group, as defined herein. Representative examples of hydroxyl $C_{1-7}$ alkyl include, but are not limited to, hydroxymethyl, 2,2-dihydroxyethyl, 1-hydroxyethyl, 3-hydroxypropyl, 1-hydroxypropyl, 1-methyl-1-hydroxyethyl and 1-methyl-1-hydroxypropyl.

The term "halo $C_{1-7}$ alkyl", as employed herein, refers to at least one halogen, as defined herein, appended to the parent molecular moiety through a $C_{1-7}$ alkyl group, as defined herein. Representative examples of halo $C_{1-7}$ alkyl include, but are not limited to, fluoromethyl, difluoromethyl, trifluoromethyl, 2-chloroethyl and 3-bromopropyl.

The term "$C_{3-10}$ cycloalkyl $C_{1-7}$ alkyl", as employed herein refers to a $C_{3-10}$ cyclo-alkyl group, as defined herein, appended to the parent molecular moiety through a $C_{1-7}$ alkyl group, as defined herein.

The term "phenyl $C_{1-7}$ alkyl", as employed herein, refers to at least one phenyl group appended to the parent molecular moiety through a $C_{1-7}$ alkyl group, as defined herein. The term "halo phenyl $C_{1-7}$ alkyl", as employed herein, refers to at least one halo group appended to the parent molecular moiety through a phenyl $C_{1-7}$ alkyl group, as defined herein.

The term "aryl", as employed herein, refers to a monocyclic, bicyclic or polycyclic aromatic hydrocarbon ring system of 6 to 14 carbon atoms. Examples of aryl groups include, but are not limited to phenyl, naphthyl, biphenyl, anthryl, biphenylenyl, and acenaphthyl. Preferred aryl group is phenyl.

The term "aryl $C_{1-7}$ alkyl", as employed herein, refers to at least one aryl group appended to the parent molecular moiety through a $C_{1-7}$ alkyl group, as defined herein. Examples of aryl $C_{1-7}$ alkyl groups include, but are not limited to benzyl, benzhydryl, 1-phenylethyl, 2-phenylethyl, 3-phenylpropyl, 2-phenylpropyl, 1-naphthylmethyl and 2-naphthylmethyl. Preferred aryl $C_{1-7}$ alkyl group is phenyl $C_{1-7}$ alkyl. The term "aryl $C_{2-7}$ alkenyl", as employed herein, refers to an aryl group appended to the parent molecular moiety through a $C_{2-7}$ alkenyl group, as defined herein.

Examples of aryl $C_{1-7}$ alkenyl groups include, but are not limited to 1-phenylethenyl, 2-phenylethenyl and 2-phenyl-prop-1-enyl.

The term "aryl halo $C_{1-7}$ alkyl", as employed herein, refers to at least one aryl group, as defined herein, appended to the parent molecular moiety through a halo $C_{1-7}$ alkyl group, as defined herein. Examples of aryl halo $C_{1-7}$ alkyl groups include, but are not limited to phenyl fluoro methyl and 1-phenyl 2-chloro ethyl.

The term "monocyclic or bicyclic ring", as employed herein, refers to saturated, partially saturated or aromatic monocyclic or bicyclic ring system.

The term "heterocyclyl" includes the definitions of "heterocycloalkyl" and "heteroaryl".

The term "heterocycloalkyl" refers to a non-aromatic, saturated or partially saturated, monocyclic or polycyclic ring system with 3 to 10 ring atoms of which at least one, preferably 1-4, is a heteroatom selected from the group consisting of O, N, and S. One particular embodiment of "heterocycloalkyl" is a non-aromatic, saturated or partially saturated, monocyclic or polycyclic ring system with 5 to 10 ring atoms of which 1-4 are heteroatoms selected from the group consisting of N, O and S.

Examples of heterocycloalkyl groups include piperdinyl, piperazinyl, morpholinyl, thiomorpholinyl, 1,3-dioxolanyl and 1,4-dioxanyl.

The term "heteroaryl" refers to a monocyclic, bicyclic, or polycyclic aromatic ring system of 6-14 ring atoms containing at least one, preferably 1 to 4, heteroatom selected from the group consisting of N, O and S. One particular embodiment of "heteroaryl" is a monocyclic, bicyclic, or polycyclic aromatic ring with 5-10 ring atoms of which 1-4 are heteroatoms selected from the group consisting of N, O and S. Examples of 5-10 membered heteroaryl groups include furan, thiophene, indole, azaindole, oxazole, thiazole, thiadiazole, isoxazole, isothiazole, imidazole, 1H-indazole N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1,2,3,4-tetrahydroisoquinoline 1-methyltetrazole, benzoxazole, benzothiazole, benzofuran, benzisoxazole, benzimidazole, 3-quinuclidine, 3,4-dihydroisoquinolin-1(2H)-one, N-methylbenzimidazole, azabenzimidazole, indazole, quinazoline, quinoline, and isoquinoline. Examples of bicyclic heteroaryl groups include those where a phenyl, pyridine, pyrimidine or pyridazine ring is fused to a 5 or 6-membered monocyclic heterocyclyl ring having one or two nitrogen atoms in the ring, one nitrogen atom together with either one oxygen or one sulfur atom in the ring, or one O or S ring atom.

The term heterocyclyl $C_{1-7}$ alkyl refers to at least one heterocyclyl group, as defined herein, appended to the parent molecular moiety through a $C_{1-7}$ alkyl group.

The term heterocyclyl $C_{2-7}$ alkenyl refers to at least one heterocyclyl group, as defined herein, appended to the parent molecular moiety through a $C_{2-7}$ alkenyl group.

The term heterocyclyl $C_{3-7}$ cycloalkyl refers to at least one heterocyclyl group, as defined herein, appended to the parent molecular moiety through a $C_{3-7}$ cycloalkyl group, wherein the heterocyclyl group is attached to $C_{3-7}$ cycloalkyl group via spiro configuration or via single bond.

The term "4-12 membered monocyclic or bicyclic ring containing 0-4 hetero-atoms" refers to a 4-12 membered monocyclic or bicyclic aromatic or non-aromatic cyclic ring in which 0-4 of the ring carbon atoms have been independently replaced with N, O or S. Representative examples of such rings include, but are not limited to phenyl, pyridine, pyrimidine, morpholine, piperidine, piperazine, imidazole, pyrazole, pyrrole, thiophene, cyclopropyl, 2,3dihydrobenzo[b][1,4]dioxine, 1,2,3,4-tetrahydroisoquinoline, quinoline, indazole, [1,2,4]triazolo[4,3-a]pyridine and tetrahydroisoquinoline. A particular embodiment of "4-12 membered monocyclic or bicyclic ring containing 0-4 heteroatoms" are a monocyclic or bicyclic aromatic or non-aromatic cyclic ring with 5-10 ring atoms of which 0-4 are heteroatoms selected from a group consisting of N, O and S.

The term "4-10 membered heterocyclic ring having 1-4 heteroatoms selected from O, N, or S" refers to aromatic, saturated or partially saturated monocyclic, bicyclic or polycyclic ring which have 4 to 10 ring member atoms of which 1 to 4 are heteroatoms selected from a group consisting of O, N, and S.

The term "9-12 membered heterocyclic ring having 1-3 heteroatoms selected from N or O" refers to aromatic, saturated or partially saturated monocyclic, bicyclic or polycyclic ring which have 9 to 12 ring member atoms of which 1 to 3 are heteroatoms selected from a group consisting of N and O.

The term "optionally substituted or substituted", if not otherwise specified, means that at least one hydrogen atom of the optionally substituted group has been substituted with suitable groups as exemplified but not limited to halogen, nitro, cyano, hydroxy, oxo (=O), thio (=S), —N($C_{1-3}$ alkyl)C(O)($C_{1-7}$ alkyl), —NHC(O)($C_{1-7}$ alkyl), —NHC(O)(cycloalkyl), —NHC(O)(aryl), —NHC(O)(heterocyclyl), —NHC(O)(heteroaryl), —NHC(O)H, —C(O)NH$_2$, —C(O)NH($C_{1-7}$ alkyl), —C(O)NH(cycloalkyl), —C(O)NH(heterocyclyl), —C(O)NH(heteroaryl), —C(O)N($C_{1-7}$ alkyl)($C_{1-7}$ alkyl), —S(O)NH($C_{1-7}$ alkyl), —S(O)$_2$NH($C_{1-7}$ alkyl), —S(O)NH(cycloalkyl), —S(O)$_2$NH(cycloalkyl), carboxy, —C(O)O($C_{1-7}$ alkyl), —C(O)($C_{1-7}$ alkyl), =N—OH, alkyl, haloalkyl, alkoxy, haloalkoxy, alkenyl, alkynyl, aryl, arylalkyl, cycloalkyl, cycloalkenyl-alkyl, cycloalkenyl, amino, heteroaryl, heterocyclyl, heteroarylalkyl or heterocyclic ring.

One particular embodiment of "optionally substituted or substituted" is 1-3 substituents selected from the group consisting of $C_{1-7}$ alkyl, $C_{3-7}$ cycloalkyl, halogen, nitro, cyano, amino, hydroxy, halo $C_{1-7}$ alkyl, hydroxy $C_{1-7}$ alkyl, $C_{1-7}$ alkoxy and halo $C_{1-7}$ alkoxy substituents.

As used herein, the terms "treat", "treating" or "treatment" encompass either or both responsive and prophylaxis measures, e.g. measures designed to inhibit or delay the onset of the disease or disorder, achieve a full or partial reduction of the symptoms or disease state, and/or to alleviate, ameliorate, lessen, or cure the disease or disorder and/or its symptoms. The terms "treat," "treating" or "treatment", include, but are not limited to, prophylactic and/or therapeutic treatments.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and new-born subjects, whether male or female, are intended to be covered.

As used herein the term "therapeutically effective amount," refers to a sufficient amount of a compound or a composition being administered which will relieve to some extent one or more of the symptoms of the disease or condition being treated. The result can be reduction and/or alleviation of the signs, symptoms, or causes of a disease, or any other desired alteration of a biological system. The term "therapeutically effective amount" includes, for example, a prophylactically effective amount.

"Pharmaceutically acceptable" means that, which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salt" refers to the salts of the compounds, that is pharmaceutically acceptable and that possesses the desired pharmacological activity of the parent compound. Pharmaceutically acceptable salts of the compounds of this invention include those derived from suitable inorganic and organic acids and bases. Such salts include: acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclo-pentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methane sulfonic acid, ethane sulfonic acid, 1,2-ethane-disulfonic acid, 2-hydroxyethanesulfonic acid, benzene sulfonic acid, 4-chlorobenzenesulfonic acid, 2-naphthalenesulfonic acid, 4-toluene-sulfonic acid, camphor sulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxyl naphthoic acid, salicylic acid, stearic acid, muconic acid, and the like.

The term "stereoisomers" refers to any enantiomers, diastereomers, or geometrical isomers of the compounds of formula (I) wherever they are chiral or when they bear one or more double bond. When the compounds of the formula (I) and related formulae are chiral, they can exist in racemic or in optically active form. Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis. In the case of racemic amines, diastereomers are formed from the mixture by reaction with an optically active resolving agent. Examples of suitable resolving agents are optically active acids, such as the R and S forms of tartaric acid, diacetyl tartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritisnodosa, Behcet's disease, Kawasaki disease, Takayasu's Arteritis, vasculitis with organ involvement and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endo-toxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma and cardiac fibrosis.

Bromodomain inhibitors may be useful in the prevention and treatment of viral infections such as herpes virus, human papilloma virus, adenovirus and poxvirus and other DNA viruses.

Bromodomain inhibitors may be useful in the treatment of cancer, including hematological, epithelial including lung, breast and colon carcinomas, midline carcinomas, mesenchymal, hepatic, renal and neurological tumours.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac and gastro-intestinal injury and mortality.

In another embodiment the bromodomain inhibitor would be administered prior to surgical or other procedures associated with a high risk of sepsis, haemorrhage, extensive tissue damage, SIRS or MODS (multiple organ dysfunction syndrome).

In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns. In one embodiment the disease or condition for which a bromodomain inhibitor is indicated is selected from herpes simplex infections and reactivations, cold sores, herpes zoster infections and reactivations, chickenpox, shingles, human papilloma virus, cervical neoplasia, adenovirus infections, including acute respiratory disease, poxvirus infections such as cowpox and smallpox and African swine fever virus. In one particular embodiment a bromodomain inhibitor is indicated for the treatment of Human papilloma virus infections of skin or cervical epithelia.

The term "diseases or disorders where bromodomain inhibition is desired", is intended to include each of or all of the above disease states.

While it is possible that for use in therapy, a compound of formula (I) as well as pharmaceutically acceptable salts thereof may be administered as such, it is common to present the active ingredient as a pharmaceutical composition.

The compounds and pharmaceutically compositions of the present invention may be used in combination with other drugs that are used in the treatment/prevention/-suppression or amelioration of the diseases or conditions for which compounds of the present invention may be useful. Such other drugs may be administered, by a route and in an amount commonly used there for, simultaneously or sequentially with a compound of the present invention. When a compound of the present invention is used simultaneously with one or more other drugs, a pharmaceutical composition containing such other drugs in addition to the compound of the present invention may also be preferred. Accordingly, the pharmaceutical compositions of the present invention include those that also contain one or more other active ingredients, in addition to a compound of the present invention.

A pharmaceutical composition of the invention may be formulated as being compatible with its intended route of administration, which may preferably be an oral administration. For example the pharmaceutical compositions of the invention may be formulated for administration by inhalation, such as aerosols or dry powders; for oral administration, such in the form of tablets, capsules, gels, syrups, suspensions, emulsions, elixirs, solutions, powders or granules; for rectal or vaginal administration, such as suppositories; or for parenteral injection (including intravenous, subcutaneous, intramuscular, intravascular, or infusion) such as a sterile solution, suspension or emulsion.

The compounds of the present invention may also be entrapped in microcapsules prepared, for example, by coacervation techniques or by interfacial polymerization, for example, hydroxymethyl cellulose or gelatin-microcapsules and poly-(methylmeth-acylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, *Osol, A. Ed.* (1980).

The novel spiro[cyclobutane-1,3'-indolin]-2'-one derivatives of formula (I) according to the present invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimization procedures. The details of the processes according to the present invention are given in the example section mentioned below.

In a further aspect, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses.

Exemplary isotopes that can be incorporated in to compounds of the invention include isotopes of hydrogen, carbon, nitrogen, oxygen, phosphorous, sulfur, fluorine, chlorine and iodine, such as $^2H$ ("D"), $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically labeled compounds of the present inventions can generally be prepared by following procedures analogous to those disclosed in the Schemes and/or in the Examples herein below, by substituting an isotopically labeled reagent for a non-isotopically labeled reagent.

The abbreviations used in the entire specification may be summarized herein below with their particular meaning.

MeOH—Methanol, EtOH—Ethanol, DCM—Dichloromethane, DMF—N,N-Dimethyl formamide, DMSO—Dimethylsulfoxide, CDCl$_3$—Deuterated chloroform, EtOAc—Ethyl acetate, CH$_3$CN—Acetonitrile, THF—Tetrahydrofuran, TEA—Triethylamine, DIPEA—Diisopropylethylamine, TFA—Trifluoroacetic acid, AcOH—Acetic acid, AlCl$_3$—Aluminium chloride, NBS—N-bromosuccinimide, PyBOP—(Benzotriazol-1-yloxy) tripyrrolidino phosphonium hexafluorophosphate, HATU—(1-[Bis(dimethylamino)methylene]-1H-1,2,3-triazolo[4,5-b]pyridinium 3-oxid hexafluorophosphate), DMF.DMA—N,N-Dimethylformamide dimethyl acetal, NMO—N-methyl morpholine N-oxide, DCE—1,2-Dichloro ethane, CFL—Compact fluorescent lamp, KOAc—Potassium acetate, Na$_2$SO$_4$—Sodium sulphate, H$_2$SO$_4$—Sulfuric acid, HNO$_3$—Nitric acid, NaHCO$_3$—Sodiumbicarbonate, Na$_2$CO$_3$—Sodium carbonate, K$_2$CO$_3$—Potassium carbonate, Cs$_2$CO$_3$—Cesium carbonate, NaH—Sodium hydride, DAST—Diethyl amino sulfur trifluoride, NaBH$_4$—Sodiumborohydride, NaCNBH$_3$—Sodium cyanoborohydride, (BOC)$_2$O—Di-tert-butyl dicarbonate, EDC.HCl—1-Ethyl-3-(3-dimethylaminopropyl) carbodiimide hydrochloride, HOBt—1-hydroxybenzo-triazole, AcCl—Acetyl chloride, Ac$_2$O—Acetic anhydride, NH$_4$Cl—Ammonium chloride, H$_2$O—water, NaOMe—Sodium methoxide, NaOH—Sodium hydroxide, HCl—Hydrochloric acid, Pd (pph$_3$)$_4$—Tetrakis (triphenylphosphine) palladium (0), Pd (dppf)Cl$_2$—[1,1'-Bis(diphenyl phosphino)ferrocene]dichloropalladium(II), complex with dichloromethane, Pd(OAc)$_2$—Palladium (II) acetate, Pd/C—Palladium on activated carbon, TMSCl—Trimethyl silyl chloride, mCPBA—Meta chloro per benzoic acid, TFAA—Trifluoro acetic anhydride, TBSCl—tert-Butyl dimethyl silyl chloride, DMAP—N,N-dimethyl amino pyridine, $^t$BuXPhos—2-Di-tert-butylphosphino-2',4',6'-triisopropylbiphenyl, Pd2(dba)$_3$—Tris(dibenzylideneacetone)dipalladium(0), DIAD—Diisopropyl azodicarboxylate, IPA—Isopropyl alcohol, TBAF—Tetra butyl ammonium fluoride, NCS—N-chloro succinimide, TLC—Thin layer chromatography, RT—Room temperature, N—Normality, M—Molarity, s—Singlet, d—Doublet, t—Triplet, m—Multiplet, $^1$H NMR—Proton nuclear magnetic resonance, MS—Mass spectroscopy, HPLC—High-performance liquid chromatography, LC—Liquid chromatography, H—Proton, MHz—Mega hertz, Hz—Hertz, Ppm—Parts per million, Bs—Broad singlet, ES—Electro spray.

Although the invention has been illustrated by following examples, it is not to be construed as being limited thereby. Various modifications and embodiments can be made without departing from the spirit and scope thereof. The MS data provided in the examples described below were obtained as follows: Mass spectrum: LC/MS Agilent 6120 Quadrapole LC/MS. The NMR data provided in the examples described below were obtained as follows: $^1$H-NMR: Varian 400 MHz. The microwave chemistry was performed on a CEM Explorer.

The procedure for the compounds of formula (I) are detailed herein below stepwise including the general synthesis of various intermediates involved in process of synthesis of the compounds according to the present invention.

EXAMPLES

Intermediate-1: N-(7'-bromo-2'-oxospiro[cyclobutane-1,3'-indolin]-5'-yl)-2,4-difluoro-benzenesulfonamide

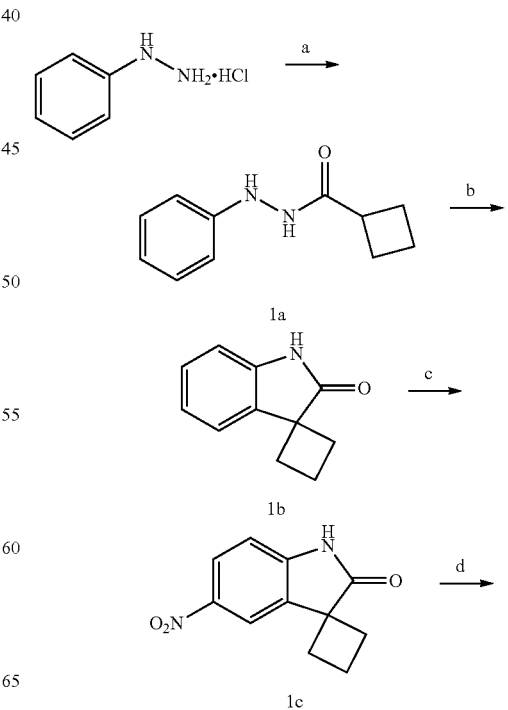

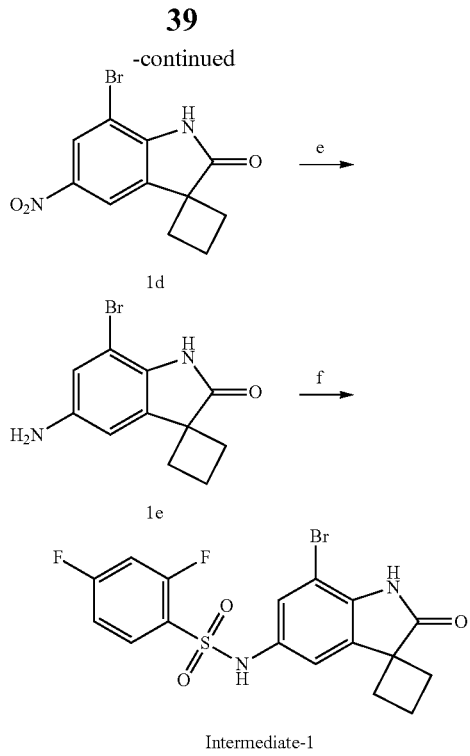

Intermediate-1

Step-a: N'-phenylcyclobutanecarbohydrazide (1a)

To a solution of phenyl hydrazine hydrochloride (60 g, 416.6 mmol) in DMF (200 mL) at −30° C. were added pyridine (100 mL, 1249.8 mmol) followed by cyclobutanecarbonylchloride (47.3 mL, 416.6 mmol) dropwise. The mixture was stirred at −30° C. for 2 h. The mixture was poured into ice cooled water and the solid formed was filtered off, washed with water and dried under reduced pressure to afford the title product as white solid. Yield 50.0 g (63%). $^1$H NMR (400 MHz, DMSO-$d_6$): δ 9.47 (s, 1H), 7.13-7.09 (m, 2H), 6.70-6.63 (m, 3H), 3.12-3.08 (m, 1H), 2.20-2.06 (m, 4H), 1.96-1.77 (m, 2H); LC-MS: m/z191.2 (M+H)$^+$.

Step-b: Spiro[cyclobutane-1,3'-indolin]-2'-one (1b)

To a solution of N'-phenylcyclobutanecarbohydrazide (15 g, 78.9 mmol) in quinoline (15 mL) was added calcium oxide (44.2 g, 789.0 mmol). The mixture was heated to 260° C. on pre-heated sand bath and stirred for 4 h. The mixture was cooled to RT and quenched with 6 N HCl dropwise. The mixture was extracted with EtOAc (250 ml×2). The combined organic layer was washed with water (200 mL), brine (200 mL), dried over sodium sulphate and concentrated under reduced pressure. The residue was purified on silica gel (60-120 mesh) to afford the title product as yellow solid 8.0 g (58%). $^1$H NMR (400 MHz, DMSO-$d_6$): δ 10.20 (s, 1H), 7.54 (d,J=7.4 Hz, 1H), 7.15 (t, J=7.3 Hz, 1H), 6.99 (t, J=7.4 Hz, 1H), 6.77 (d, J=7.8 Hz, 1H), 2.44-2.38 (m, 2H), 2.30-2.22 (m, 4H); LC-MS: m/z 174.1 (M+H)$^+$.

Step-c: 5'-Nitrospiro[cyclobutane-1,3'-indolin]-2'-one (1c)

To a stirring suspension of spiro[cyclobutane-1,3'-indolin]-2'-one (4.0 g, 23.12 mmol) in sulphuric acid (40 mL) at −20° C. was added potassium nitrate (2.3 g, 23.12 mmol) portion wise. The mixture was stirred at −20° C. for 30 min. The mixture was poured into ice cooled water and the solid formed was filtered off, washed with water and dried under reduced pressure and purified under column to afford title compound as yellow solid 2.0 g (40%). $^1$H NMR (400 MHz, DMSO-$d_6$): δ 10.95 (s, 1H), 8.44 (d, J=2.5 Hz, 1H), 8.15(dd, J=2.1 Hz & 8.5 Hz, 1H), 6.97 (d, J=8.3 Hz, 1H), 2.46-2.38 (m, 4H), 2.27-2.17 (m, 2H); LC-MS: m/z 217.1 (M−H)$^-$.

Step-d: 7'-Bromo-5'-nitrospiro[cyclobutane-1,3'-indolin]-2'-one (1d)

To a stirring suspension of 5'-nitrospiro[cyclobutane-1,3'-indolin]-2'-one (3.0 g, 13.76 mmol) in sulphuric acid (20 mL) at RT was added N-bromosuccinimide (2.9 g, 16.51 mmol) portion wise. The mixture was stirred at RT for 16 h. The mixture was poured into ice cooled water and the solid formed was filtered off, washed with water and dried under reduced pressure to afford title compound as pale brown solid 2.8 g (70%). $^1$H NMR (400 MHz, DMSO-$d_6$) δ 11.27 (s, 1H), 8.46 (d, J=2.1 Hz, 1H), 8.30 (d, J=1.9 Hz, 1H), 2.48-2.41 (m, 4H), 2.25-2.19 (m, 2H); LC-MS: m/z 297 (M+H)$^+$.

Step-e: 5'-Amino-7'-bromospiro[cyclobutane-1,3'-indolin]-2'-one (1e)

To a solution of 7'-bromo-5'-nitrospiro[cyclobutane-1,3'-indolin]-2'-one (2.8 g, 9.45 mmol) in EtOH (30 mL) and $H_2O$ (15 mL) were added iron powder (2.6 g, 47.25 mmol) and $NH_4Cl$ (2.5 g, 47.25 mmol). The mixture was heated to 100° C. for 3 h. The mixture was cooled to RT, filtered through celite and washed with EtOAc. The combined filtrate was concentrated. The residue was diluted with water, extracted with EtOAc (100 mL), washed with brine (100 mL), dried over sodium sulphate and concentrated under reduced pressure to afford the title compound as yellow solid 2.5 g (49%);$^1$H NMR (400 MHz, DMSO-$d_6$) δ 10.04 (s, 1H), 6.82 (d, J=2.0 Hz, 1H), 6.55 (d, J=2.0 Hz, 1H), 4.98 (s, 2H), 2.44-2.39 (m, 2H), 2.22-2.07 (m, 4H); LC-MS: m/z 267.5 (M+H)$^+$.

Step-f: N-(7'-bromo-2'-oxospiro[cyclobutane-1,3'-indolin]-5'-yl)-2,4-difluoro benzenesulfonamide (Intermediate 1)

To an ice cooled solution of 5'-amino-7'-bromospiro[cyclobutane-1,3'-indolin]-2'-one(2.3 g, 8.61 mmol) in DCM (30 mL) were added pyridine (4.2 mL, 51.66 mmol) followed by 2,4-difluorobenzenesulfonyl chloride (1.3 mL,9.47 mmol) dropwise. The mixture was stirred at RT for 2 h. The mixture was diluted with DCM (100 mL), washed with water (100 mL) and brine (100 mL), dried over sodium sulphate and concentrated under reduced pressure and column purified to afford the title compound as off white solid (1.8 g, 48%). $^1$H NMR (400 MHz, DMSO-$d_6$): δ 10.54 (s, 1H), 10.51 (s, 1H), 7.89-7.83 (m, 1H), 7.59-7.53 (m, 1H), 7.28-7.23 (m, 2H), 7.02 (d, J=1.5 Hz, 1H), 2.44-2.33 (m, 2H), 2.23-2.03 (m, 4H); LC-MS: m/z 445.0 (M+3H)$^{3+}$.

The below intermediates 2 and 3 were prepared according to the procedure depicted in step-f of intermediate-1 by using 5'-amino-7'-bromospiro[cyclobutane-1,3'-indolin]-2'-one as a starting compound and in presence of appropriate reactants, reagents, solvents and in appropriate conditions. The characterization data for the intermediates are detailed in below table.

| No | Structure | Characterization Data |
|---|---|---|
| 2 | 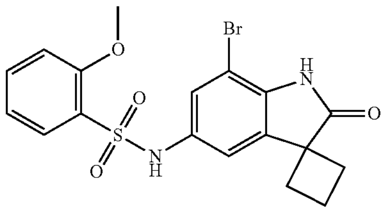 [SMILES: COc1ccccc1S(=O)(=O)Nc1cc(Br)c2c(c1)C1(CCC1)C(=O)N2] | $^1$H-NMR (400 MHz, DMSO-d$_6$) δ 10.45 (s, 1H), 9.88 (s, 1H), 7.73 (dd, J = 1.5 Hz, & 7.9 Hz, 1H), 7.59-7.55 (m, 1H), 7.23 (d, J = 1.9 Hz, 1H), 7.18 (d, J = 7.8 Hz, 1H), 7.04-7.01 (m, 2H), 3.90 (s, 3H), 2.50-2.37 (m, 2H), 2.22-2.07 (m, 4H); LC-MS: m/z 435.0 (M − H)$^-$. |
| 3 | 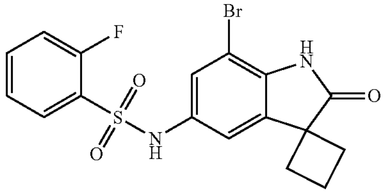 [SMILES: O=C1Nc2c(Br)cc(NS(=O)(=O)c3ccccc3F)cc2C12CCC2] | $^1$H NMR (400 MHz, DMSO-d$_6$): δ 10.52 (s, 1H), 10.47 (s, 1H), 7.82-7.77 (m, 1H), 7.73-7.67 (m, 1H), 7.47-7.42 (m, 1H), 7.38-7.34 (m, 1H), 7.25 (d, J = 1.5 Hz, 1H), 7.01 (d, J = 1..5 Hz, 1H), 2.42-2.32 (m, 2H), 2.21-2.02 (m, 4H); |

Intermediate-4: 2,4-Difluoro-N-(7'-nitro-2'-oxospiro[cyclobutane-1,3'-indolin]-5'-yl)benzenesulfonamide

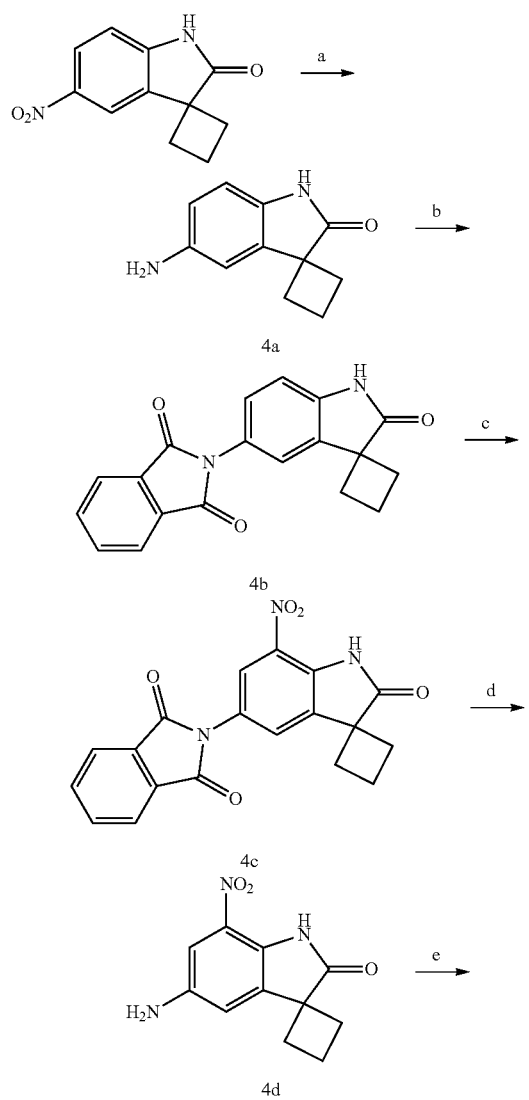

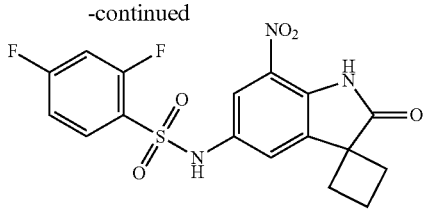

intermediate-4

Step-a: 5'-Aminospiro[cyclobutane-1,3'-indolin]-2'-one (4a)

The compound was prepared using the procedure of step-e of Intermediate-1. $^1$H NMR (400 MHz, DMSO-d$_6$): δ 9.77 (s, 1H), 6.82 (d, J=2.0 Hz, 1H), 6.47 (d, J=7.8 Hz, 1H), 6.39-6.36 (m, 1H), 4.69 (s, 2H), 2.44-2.37 (m, 2H), 2.20-2.00 (m, 4H); LC-MS: m/z 189.2 (M+1)$^+$.

Step-b: 2-(2'—Oxospiro[cyclobutane-1,3'-indolin]-5'-yl)isoindoline-1,3-dione (4b)

To a solution of 5'-aminospiro[cyclobutane-1,3'-indolin]-2'-one (3.6 g, 18.99 mmol) in AcOH (35 mL) was added pthalic anhydride (4.2 g, 20.48 mmol). The mixture was heated to 100° C. for 2 h. The mixture was poured into crushed ice and the solid formed was filtered off, washed with water and dried under reduced pressure to afford the title product as brown solid (4.5 g, 75%). $^1$H NMR (400 MHz, DMSO-d$_6$): δ 10.43 (s, 1H), 7.98-7.90 (m, 4H), 7.33 (d, J=1.9 Hz, 1H), 7.24-7.21 (m, 1H), 6.92 (d, J=8.3 Hz, 1H), 2.48-2.43 (m, 2H), 2.32-2.14 (m, 4H); LC-MS: m/z 319.1 (M+1)$^+$.

Step-c: 2-(7'-Nitro-2'-oxospiro[cyclobutane-1,3'-indolin]-5'-yl)isoindoline-1,3-dione (4c)

To a solution of 2-(2'-oxospiro[cyclobutane-1,3'-indolin]-5'-yl)isoindoline-1,3-dione (9.2 g, 28.93 mmol) in AcOH (100 mL) at RT was added nitric acid (9.0 mL) dropwise. The mixture was heated to 110° C. for 2 h. The mixture was poured into ice cooled water and the solid formed was filtered off, washed with water and dried under reduced pressure to afford title compound as brown solid (10.5 g). $^1$H NMR (400 MHz, DMSO-d$_6$): δ 10.19 (s, 1H), 8.15 (d, J=1.5 Hz, 1H), 8.13 (d, J=1.5 Hz, 1H), 8.02-7.93 (m, 4H), 2.51-2.48 (m, 2H), 2.39-2.37 (m, 4H); LC-MS: m/z 364.1 (M+1)$^+$.

Step-d: 5'-Amino-7'-nitrospiro[cyclobutane-1,3'-indolin]-2'-one (4d) To a solution of 2-(7'-nitro-2'-oxospiro[cyclobutane-1,3'-indolin]-5'-yl)iso-indoline-1,3-dione (10.5 g, 28.92 mmol) in EtOH (100 mL) was added hydrazine hydrate (21 mL) and then heated to 100° C. for 2h. Reaction mixture was poured into ice cooled water and the solid formed was filtered off, washed with water and dried under reduced pressure to afford the title compound (5.5 g). $^1$H NMR (400 MHz, DMSO-$d_6$): δ 10.52 (s, 1H), 7.30 (d, J=2.0 Hz, 1H), 7.11 (d, J=1.9 Hz, 1H), 5.38 (s, 2H), 2.54-2.48 (m, 2H), 2.48-2.14 (m, 4H); LC-MS: m/z234.1 (M+1)$^+$.

Step-e: 2,4-Difluoro-N-(7'-nitro-2'-oxospiro[cyclobutane-1,3'-indolin]-5'-yl)-benzenesulfonamide (Intermediate-4)

To an ice cooled solution of 5'-amino-7'-nitrospiro[cyclobutane-1,3'-indolin]-2'-one (2.0 g, 8.58 mmol) in DCM (20 mL) were added pyridine (1.4 mL, 17.16 mmol) followed by 2,4-difluorobenzenesulfonyl chloride (1.7 mL, 12.87 mmol) dropwise. The mixture was at RT for 3 h. The mixture was diluted with DCM (100 mL), washed with water (100 mL) and brine (100 mL), dried over sodium sulphate and concentrated under reduced pressure to afford the title compound as yellow solid (2.5 g, 89%.). $^1$H NMR (400 MHz, DMSO-$d_6$): δ 11.0 (s, 1H), 10.86 (s, 1H), 7.95-7.83 (m, 1H), 7.68 (d, J=1.5 Hz, 1H), 7.62 (d, J=1.5 Hz, 1H), 7.56 (t, J=8.8 Hz, 1H), 7.30-7.25 (m, 1H), 2.47-2.40 (m, 2H), 2.35-2.12 (m, 4H).

Intermediate-5: Methyl 5'-amino-2'-oxospiro[cyclobutane-1,3'-indoline]-7'-carboxylate:

Step-(a): Methyl 5'-nitro-2'-oxospiro[cyclobutane-1,3'-indoline]-7'-carboxylate

To a solution of 7'-bromo-5'-nitrospiro[cyclobutane-1,3'-indolin]-2'-one (1.0 g, 3.37 mmol) in triethyl amine (30 mL) were added xantphos (0.19 g, 0.337 mmol), palladium(ll) acetate (0.15 g, 0.674) and methanol (4 mL). The mixture was purged with carbon monoxide gas for 10 min and then heated to 80° C. for 16 h under carbon monoxide atmosphere. The mixture was diluted with EtOAc (100 mL) and washed with 1N HCl (100 mL), water (100 mL) and brine (100 mL), dried over sodium sulphate and concentrated under reduced pressure and column purified to afford the title compound as yellow solid (0.45 g, 48%.). $^1$H NMR (400 MHz, DMSO-$d_6$): δ 10.87 (s, 1H), 8.66 (d, J=2.4 Hz, 1H), 8.53(d, J=2.5 Hz, 1H), 3.90 (s, 3H), 2.45-2.32 (m, 4H), 2.28-2.16 (m, 2H); LC-MS: m/z 277.1 (M+H)$^+$.

Step-(b): Methyl 5'-amino-2'-oxospiro[cyclobutane-1,3'-indoline]-7'-carboxylate (Intermediate 5)

The compound was prepared using the procedure of step-e of Intermediate-1. $^1$H NMR (400 MHz, DMSO-$d_6$): δ 9.67 (s, 1H), 7.11 (d, J=2.5 Hz, 1H), 6.93(d, J=2.4 Hz, 1H), 5.03 (s, 2H), 3.80 (s, 3H), 2.46-2.40 (m, 2H), 2.26-2.12 (m, 4H); LC-MS: m/z 247.2 (M+H)$^+$.

Intermediate-6: 5'-Amino-N-(1-methylpiperidin-4-yl)-2'-oxospiro[cyclobutane-1,3'-indoline]-7'-carboxamide

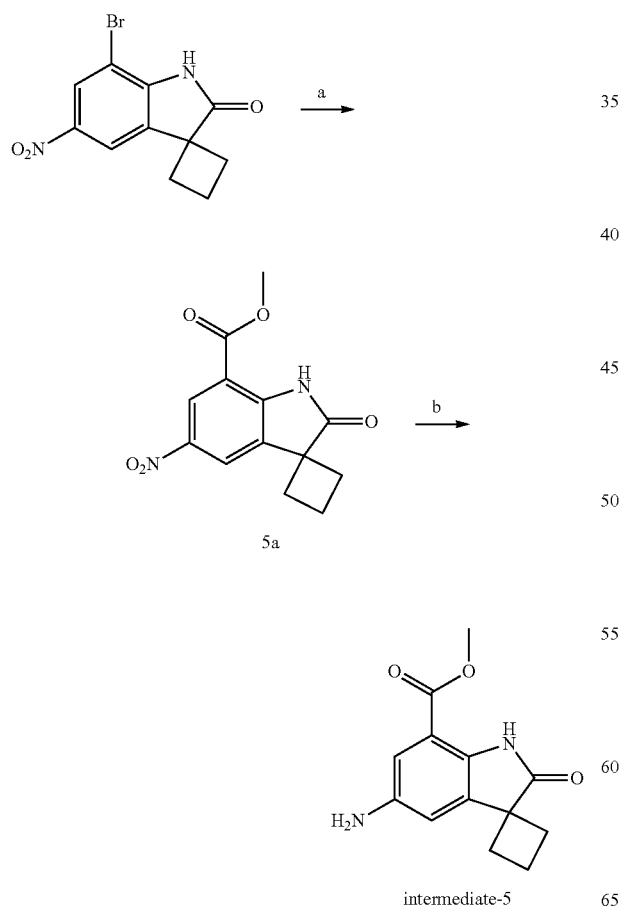

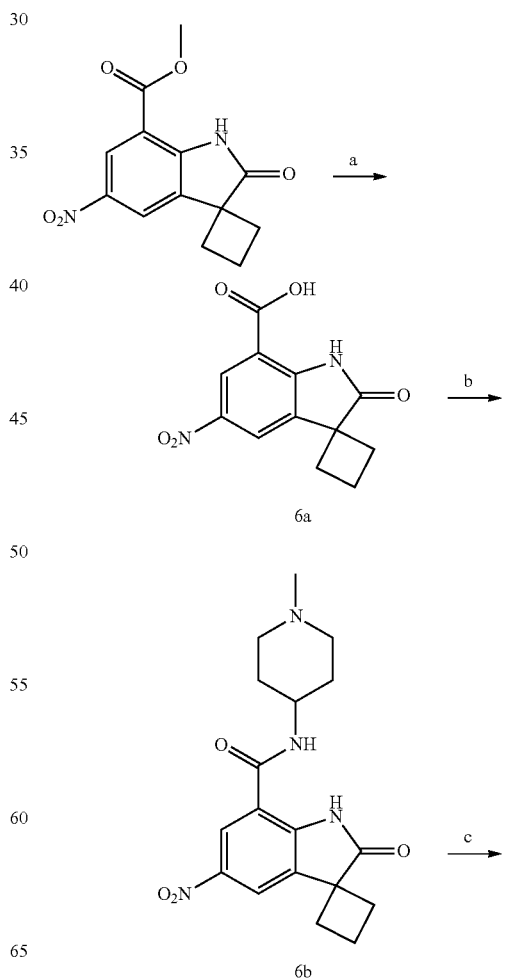

-continued

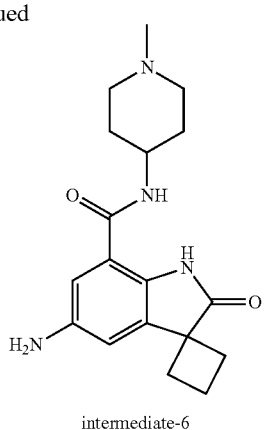

intermediate-6

Step a: 5'-Nitro-2'-oxospiro[cyclobutane-1,3'-indoline]-7'-carboxylic acid (6a)

To a solution of methyl 5'-nitro-2'-oxospiro[cyclobutane-1,3'-indoline]-7'-carboxylate (0.35 g, 1.27 mmol) in THF (4 mL) was added lithium hydroxide monohydrate (0.21 g, 5.08 mmol) in 2 mL of water. The mixture was stirred at RT for 16 h. The mixture was concentrated, diluted with water, acidified with 1N HCl and extracted with EtOAc (100 mL), washed with brine (100 mL), dried over sodium sulphate and concentrated under reduced pressure to afford the solid title compound (0.2 g, 60%). $^1$H NMR (400 MHz, DMSO-$d_6$): δ 13.80 (bs, 1H), 10.56 (s, 1H), 8.63 (d, J=2.4 Hz, 1H), 8.51 (d, J=2.4 Hz, 1H), 2.56-2.50 (m, 2H), 2.49-2.41 (m, 2H), 2.31-2.20 (m, 2H); LC-MS: m/z 263.1 (M+H)$^+$.

Step-b: N-(1-methylpiperidin-4-yl)-5'-nitro-2'-oxospiro[cyclobutane-1,3'-indoline]-7'-carboxamide (6b)

To a solution of 5'-nitro-2'-oxospiro[cyclobutane-1,3'-indoline]-7'-carboxylic acid (0.2 g, 0.76 mmol) in DCM (10 mL) were added 1-methylpiperidin-4-amine (0.14 mL, 1.14 mmol), HOBt (0.15 g, 1.14 mmol), EDC.HCl (0.22 g, 1.14 mmol) and diisopropyl ethylamine (0.4 mL, 2.29 mmol). The mixture was stirred at RT for 16 h. The mixture was poured into ice water and solids were filtered off. The mixture was then washed with water and dried under reduced pressure to afford the solid title compound (0.18 g, 66%). $^1$H NMR (400 MHz, DMSO-$d_6$): δ 10.19 (bs, 1H), 8.86 (bs, 1H), 8.65 (d, J=2.0 Hz, 1H), 8.54 (d, J=1.9 Hz, 1H), 3.81-3.70 (m, 1H), 2.86-2.82 (m, 2H), 2.47-2.42 (m, 4H), 2.38-2.24 (m, 2H), 2.23 (s, 3H), 2.18-2.03 (m, 2H), 1.83-1.80 (m, 2H), 1.66-1.55 (m, 2H); LC-MS: m/z 359.1 (M+H)$^+$.

Step-c: 5'-Amino-N-(1-methylpiperidin-4-yl)-2'-oxospiro[cyclobutane-1,3'-indoline]-7'-carboxamide (Intermediate-6)

The compound was prepared using the procedure of step-e of Intermediate-1. $^1$H NMR (400 MHz, DMSO-$d_6$): δ 9.23 (s, 1H), 8.17 (d, J=7.8 Hz, 1H), 7.01 (d, J=1.9 Hz, 1H), 6.78 (d, J=1.9 Hz, 1H), 4.95 (bs, 2H), 3.76-3.66 (m, 1H), 2.85-2.82 (m, 2H), 2.45-2.39 (m, 2H), 2.23 (s, 3H), 2.23-2.07 (m, 6H), 1.78-1.74 (m, 2H), 1.63-1.57 (m,2H); LC-MS: m/z 329.2 (M+H)$^+$.

Intermediate-7: 7'-Amino-5'-bromospiro[cyclobutane-1,3'-indolin]-2'-one

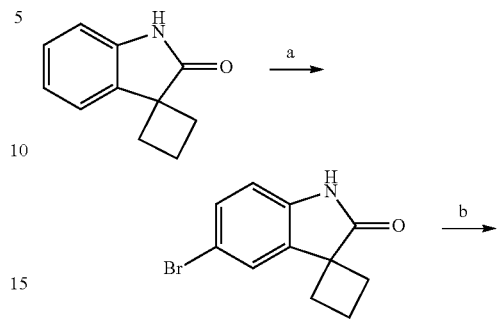

intermediate-7

Step-(a): 5'-Bromospiro[cyclobutane-1,3'-indolin]-2'-one (7a)

To a solution of spiro[cyclobutane-1,3'-indolin]-2'-one (5.0 g, 28.73 mmol) in acetonitrile (50 mL) at RT was added N-bromo succinimide (6.1 g, 34.47 mmol) portion wise. The mixture was stirred at RT for 2 h. The mixture was poured into crushed ice and the solid formed was filtered off. The mixture was washed with water and dried under reduced pressure to afford the title compound as off white solid (6.1 g). $^1$H NMR (400 MHz, DMSO-$d_6$): δ 10.34 (s, 1H), 7.75 (d, J=2.0 Hz, 1H), 7.33 (dd, $J_1$=2.0 Hz, $J_2$=8.3 Hz, 1H), 6.74 (d, J=8.1 Hz, 1H), 2.40-2.31 (m, 4H), 2.28-2.16 (m, 2H); LCMS: m/z 253.0 (M+H)$^+$.

Step-(b): 5'-Bromo-7'-nitrospiro[cyclobutane-1,3'-indolin]-2'-one (7b)

The compound was prepared using the procedure of step-c of Intermediate-1. $^1$H NMR (400 MHz, DMSO-$d_6$): δ 11.15 (s, 1H), 8.22 (d, J=1.4 Hz, 1H), 8.09 (d, J=1.9 Hz, 1H), 2.46-2.42 (m, 4H), 2.24-2.20 (m, 2H); LCMS: m/z 296.0 (M+H)$^+$.

Step-(c): 7'-Amino-5'-bromospiro[cyclobutane-1,3'-indolin]-2'-one (Intermediate-7)

The compound was prepared using the procedure of step-e of Intermediate-1. $^1$H NMR (400 MHz, DMSO-$d_6$): δ 9.81 (s, 1H), 6.96 (d, J=1.5 Hz, 1H), 6.68 (d, J=2.0 Hz, 1H), 5.08 (s, 2H), 2.41-2.35 (m, 2H), 2.28-2.22 (m, 2H), 2.19-2.11 (m, 2H); LCMS: 267.0 (M+H)$^+$.

Intermediate-8: 5'-Amino-7'-cyclopropylspiro[cyclobutane-1,3'-indolin]-2'-one

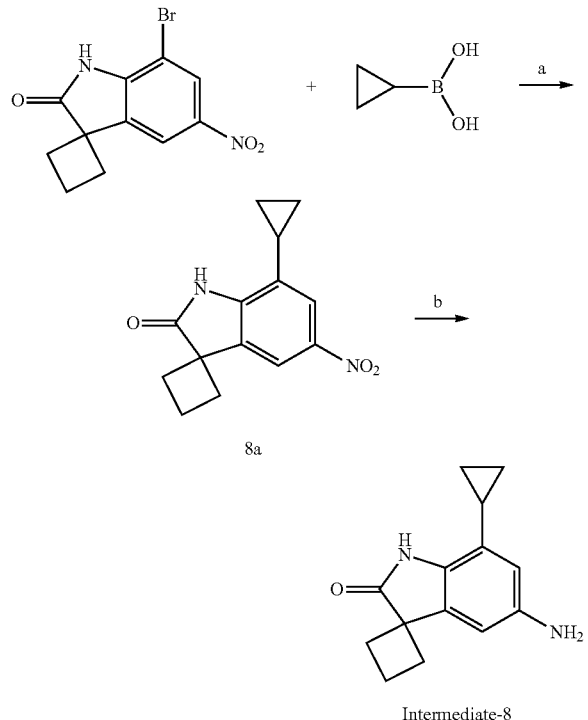

Intermediate-8

Step-a: 7'—Cyclopropyl-5'-nitrospiro[cyclobutane-1,3'-indolin]-2'-one (8a)

To a stirred solution of 7'-bromo-5'-nitrospiro[cyclobutane-1,3'-indolin]-2'-one (0.200 g, 0.673 mmol) in mixture of solvents 1,4-dioxane (10 mL): water (3 mL) was added potassium phosphate (0.285 g, 1.34 mmol), Pd(amphos)Cl$_2$ (0.047 g, 0.067 mmol) and cyclopropylboronic acid (0.069 g, 0.807 mmol). The mixture was purged with nitrogen gas for 10-15 min and heated to 100-110° C. for 12 h under nitrogen atmosphere or in a sealed tube. The mixture was poured into ice cold water (10 mL) and extracted with ethyl acetate. The combined extracts were washed with water, dried over MgSO4 and evaporated. The obtained crude product was purified by silica gel chromatography using a mixture of 70% ethyl acetate/hexane as an eluent to get the title compound as a pale yellow solid (0.120 g, 69.36%); LC-MS: 257.0

Step-b: 5'-Amino-7'-cyclopropylspiro[cyclobutane-1,3'-indolin]-2'-one (Intermediate-8)

The process of this step was adopted from step-c of Intermediate-7 (0.050 g, 51.55%); LC-MS: 229.1[M+H]$^+$.

Intermediate-9: 5'-Nitro-7'-(4,4,5,5-tetramethyl-1,3,2-dioxaborolan-2-yl)spiro[cyclobutane-1,3'-indolin]-2'-one

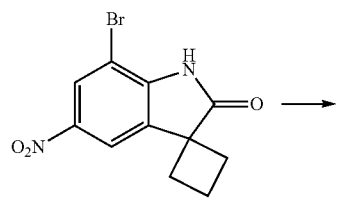

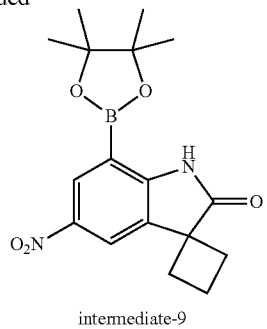

intermediate-9

To a solution of 7'-bromo-5'-nitrospiro[cyclobutane-1,3'-indolin]-2'-one (1.0 g, 3.38 mmol) and 4,4,4',4',5,5,5',5'-octamethyl-2,2'-bi(1,3,2-dioxaborolane) (1.76 g, 7.76 mmol) in 1,4-dioxane (20 mL) in sealed tube was added potassium acetate (1.0 g, 10.14 mmol). The reaction mixture was purged with nitrogen gas for 10 min and then Pd(dppf)$_2$Cl$_2$*DCM (0.28 g, 0.39 mmol) was added. The mixture was again purged with nitrogen gas for 5 min and then heated to 100° C. for 16 h. The mixture was diluted with EtOAc (150 mL) and washed with water (150 mL) and brine (150 mL), dried over sodium sulphate and concentrated under reduced pressure and purified by combi flash to afford the title compound as yellow solid (0.55 g, 47%). $^1$H NMR (400 MHz, DMSO-d$_6$): δ 9.79 (s, 1H), 8.54 (d, J=2.0 Hz, 1H), 8.24 (d, J=2.5 Hz, 1H), 2.48-2.40 (m, 4H), 2.33-2.19 (m, 2H), 1.17 (s, 12H); LCMS: m/z 345.2 (M+H)$^+$.

Intermediate-10: 1-(Pyridin-3-yl)vinyl Trifluoromethanesulfonate

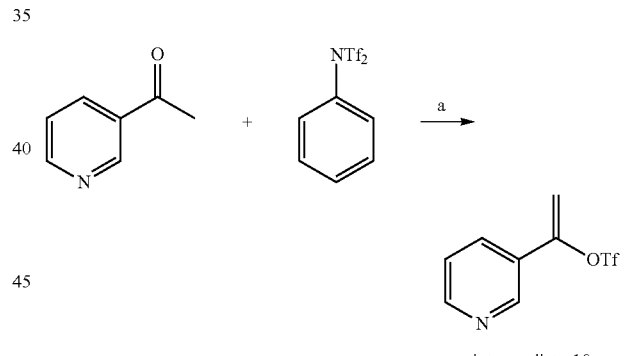

intermediate-10

To a solution of 1-(pyridin-3-yl)ethan-1-one (1.0 g, 8.26 mmol) in THF (20 mL) at −78° C. was added NaHMDS (sodium bis(trimethylsilyl)amide) 1.0 M in THF (12.3 mL, 12.39 mmol) over a period of 5 min. The mixture was slowly brought to −40° C. and stirred for 1 h. The mixture was again cooled to −78° C. and 1,1,1-trifluoro-N-phenyl-N-((trifluoromethyl)sulfonyl)methanesulfonamide (2.9 g, 8.26 mmol) in THF (5 mL) was added over a period of 5 min. The mixture was slowly brought to 0° C. followed by stirring for 4 h, cooling to −78° C. and quenching with 1 mL of MeOH in 10 mL of EtOAc. The mixture was slowly brought to RT and concentrated under reduced pressure. The residue was dissolved in 20 mL of diethyl ether and 20 mL of pentane was added. This organic layer was concentrated under reduced pressure and purified by combi flash to afford the title compound as colorless oil (1.20 g, 57%). $^1$H NMR (400 MHz, DMSO-d$_6$): δ 8.88 (d, J=1.9 Hz, 1H), 8.70-8.69 (m, 1H), 8.06-8.04 (m, 1H), 7.59-7.55 (m, 1H), 6.29 (d, J=4.9 Hz, 1H), 5.72 (d, J=4.9 Hz, 1H); LC-MS: m/z 254.1 (M+H)+.

Intermediate-11: -(Pyridin-2-yl)vinyl trifluoromethanesulfonate

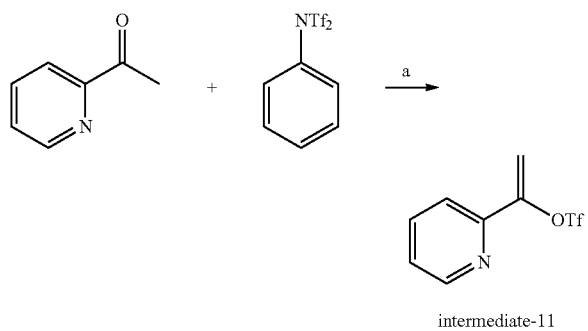

intermediate-11

The compound was prepared using the procedure of Intermediate-10. ¹H NMR (400 MHz, DMSO-d₆): δ 8.68 (d, J=4.4 Hz, 1H), 7.99-7.94 (m, 1H), 7.89-7.87 (m, 1H), 7.52-7.49 (m, 1H), 6.45 (d, J=4.4 Hz, 1H), 5.77 (d, J=4.4 Hz, 1H); LC-MS: m/z 254.1 (M+H)+.

Intermediate-12: tert-Butyl 3-fluoro-4-hydroxypiperidine-1-carboxylate

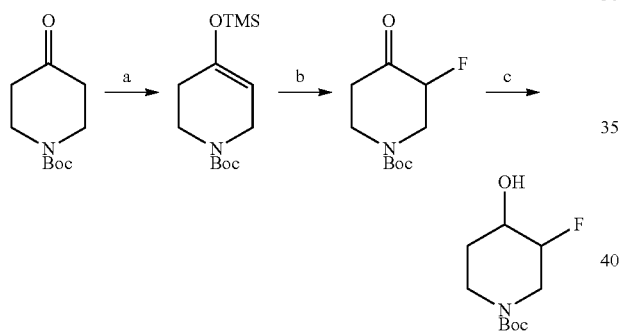

Step-a: tert-Butyl 4-((trimethylsilyl)oxy)-3,6-dihydropyridine-1(2H)-carboxylate To an ice cold solution of tert-butyl 4-oxopiperidine-1-carboxylate (5.0 g, 25.12 mmol) in DMF (30 mL) was added TMSCl (4.8 mL, 37.68 mmol) followed by triethyl amine (10.5 mL, 75.36 mmol) and heating to 80° C. for 16 h. The mixture was cooled to RT, diluted with water and extracted with EtOAc. The organic layer was washed with aqueous NaHCO₃, dried over sodium sulphate and concentrated under reduced pressure. The residue was purified by combi-flash to afford the title compound as pale yellow liquid (6.1 g, 90%). ¹H NMR (400 MHz, DMSO-d₆): δ 4.80 (s, 1H), 3.77 (s, 2H), 3.42 (t, J=5.9 Hz, 2H), 2.01 (t, J=5.4 Hz, 2H), 1.39 (s, 9H), 0.16 (s, 9H).

Step-b: tert-Butyl 3-fluoro-4-oxopiperidine-1-carboxylate

To an ice cold solution of tert-butyl 4-((trimethylsilyl)oxy)-3,6-dihydropyridine-1(2H)-carboxylate (6.1 g, 22.5 mmol) in acetonitrile (100 mL) was added SelectFluor (9.55 g, 27.0 mmol) followed by stirring at RT for 2 h. The mixture was diluted with water and extracted with EtOAc. The organic layer was dried over sodium sulphate and concentrated under reduced pressure. The residue was purified by combi-flash to afford the title compound as white solid (3.2 g, 63%). ¹H NMR (400 MHz, DMSO-d₆): δ 5.17-5.01 (m, 1H), 4.36-4.28 (m, 1H), 4.05-3.99 (m, 1H), 3.26-3.16 (m, 2H), 2.62-2.54 (m, 1H), 2.40-2.34 (m, 1H), 1.44 (s, 9H).

Step-c: tert-Butyl 3-fluoro-4-hydroxypiperidine-1-carboxylate

To an ice cold solution of tert-butyl 3-fluoro-4-oxopiperidine-1-carboxylate (2.0 g, 9.21 mmol) in MeOH (20 mL) was added sodium borohydride (0.7 g, 18.42 mmol) followed by stirring at RT for 6 h. The mixture was quenched with aqueous NH₄Cl and extracted with EtOAc. The organic layer was dried over sodium sulphate and concentrated under reduced pressure. The residue was purified by combi-flash to afford the title compound as white solid (diastereomers) (0.9 g, 45% and 0.6 g, 30%). ¹H NMR (400 MHz, DMSO-d₆): δ 5.27 (d, J=4.9 Hz, 1H), 4.36-4.15 (m, 1H), 3.69-3.67 (m, 2H), 3.50-3.28 (m, 1H), 3.22-3.18 (m, 2H), 1.77-1.74 (m, 1H), 1.40-1.38 (m, 10H).

Intermediate-13: Imino(2-methoxyphenyl)(methyl)-l6-sulfanone

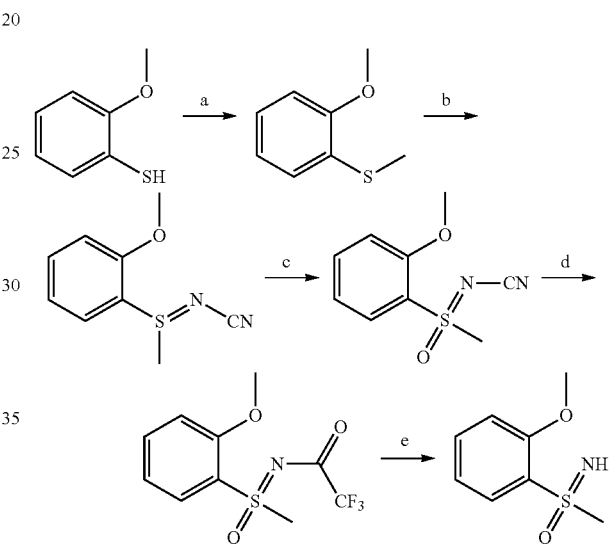

Step-a: (2-Methoxyphenyl)(methyl)sulfane

To an ice cold solution of 2-methoxybenzenethiol (2.0 g, 14.26 mmol) in DMF (20 mL) was added methyl iodide (1.8 mL, 28.52 mmol) followed by stirring for 5 min Then potassium carbonate (3.9 g, 25.52 mmol) was added portion wise followed by stirring at RT for 0.5 h. The mixture was diluted with water and extracted with EtOAc. The organic layer was dried over sodium sulphate and concentrated under reduced pressure. The residue was purified by combi-flash to afford the title compound as brown oil (2.0 g, 91%). ¹H NMR (400 MHz, DMSO-d₆): δ 7.15-7.11 (m, 2H), 6.98-6.94 (m, 2H), 3.81 (s, 3H), 2.37 (s, 3H).

Step-b: N-((2-methoxyphenyl)(methyl)-l4-sulfanylidene)cyanamide

To a solution of (2-methoxyphenyl)(methyl)sulfane (1.0 g, 6.49 mmol) in degassed MeOH (40 mL) was added cyanamide (0.35 g, 8.43 mmol), ᵗBuOK (0.87 g, 7.78 mmol) and NBS (1.7 g, 9.73 mmol). The mixture was stirred at RT for 4 h. The mixture was concentrated, diluted with EtOAc and washed with aqueous sodium thiosulfate. The organic layer was dried over sodium sulphate and concentrated under reduced pressure to afford the title compound as white solid (1.2 g, 95%). ¹H NMR (400 MHz, DMSO-d₆): δ 7.81 (dd, J=7.9 Hz & 1.5 Hz, 1H), 7.69-7.65 (m, 1H), 7.31-7.26 (m, 2H), 3.94 (s, 3H), 3.04 (s, 3H); LC-MS: m/z 195.1 (M+H)+.

Step-c: N-((2-methoxyphenyl)(methyl)(oxo)-l6-sulfanylidene)cyanamide

To a solution of N-((2-methoxyphenyl)(methyl)-l4-sulfanylidene)cyanamide (1.0 g, 5.15 mmol) in EtOH (50 mL) was added potassium carbonate (2.1 g, 15.45 mmol) followed by mCPBA (1.3 g, 7.72 mmol). The mixture was stirred at RT for 16 h. The mixture was quenched with aqueous sodium thiosulfate and extracted with EtOAc. The organic layer was washed with aqueous NaHCO₃, dried over sodium sulphate and concentrated under reduced pressure. The residue was purified by combi-flash to afford the title compound as white solid (0.25 g, 23%). ¹H NMR (400 MHz, DMSO-d₆): δ 7.90-7.84 (m, 2H), 7.44 (d, J=8.3 Hz, 1H), 7.31-7.27 (m, 1H), 4.00 (s, 3H), 3.68 (s, 3H); LC-MS: m/z 211.1 (M+H)⁺.

Step-d: 2,2,2-Trifluoro-N-((2-methoxyphenyl)(methyl)(oxo)-l6-sulfanyli-dene)acetamide To an ice cold solution of N-((2-methoxyphenyl)(methyl)(oxo)-l6-sulfanyli-dene)cyanamide (0.25 g, 1.19 mmol) in DCM (5 mL) was added TFAA (0.5 mL, 3.57 mmol) followed by stirring at RT for 2 h. The mixture was diluted with DCM and washed with water. The organic layer was dried over sodium sulphate and concentrated under reduced pressure to afford the title compound as white solid (0.25 g). ¹H NMR (400 MHz, DMSO-d₆): δ 7.90 (dd, J=7.9 Hz & 1.5 Hz, 1H), 7.83-7.78 (m, 1H), 7.37 (d, J=8.3 Hz, 1H), 7.30-7.26 (m, 1H), 3.94 (s, 3H), 3.67 (s, 3H); LC-MS: m/z 282.1 (M+H)⁺.

Step-e: Imino(2-methoxyphenyl)(methyl)-l6-sulfanone

To a solution of 2,2,2-trifluoro-N-((2-methoxyphenyl)(methyl)(oxo)-l6-sulfanyli-dene)acetamide (0.25 g, 0.89 mmol) in MeOH (5 mL) was added potassium carbonate (0.7 g, 5.33 mmol) followed by stirring at RT for 2 h. The mixture was filtered and concentrated under reduced pressure. The residue was purified by combi-flash to afford the title compound as off white solid (0.2 g). ¹H NMR (400 MHz, DMSO-d₆): δ 7.84 (dd, J=7.9 Hz & 2.0 Hz, 1H), 7.62-7.58 (m, 1H), 7.23 (d, J=8.3 Hz, 1H), 7.11 (t, J=7.3 Hz, 1H), 4.18 (bs, 1H), 3.92 (s, 3H), 3.14 (s, 3H); LC-MS: m/z 186.1 (M+H)⁺.

Intermediate-14: 7'-Nitro-5'-(4,4,5,5-tetramethyl-1,3,2-dioxaborolan-2-yl)spiro[-cyclobutane-1,3'-indolin]-2'-one

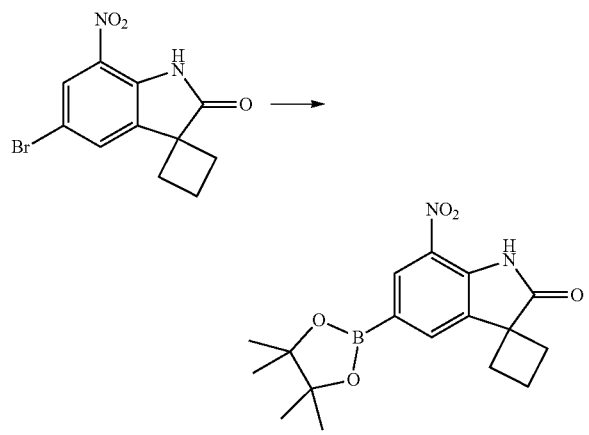

The compound was prepared using the procedure of Intermediate-9 and was obtained as pale yellow solid (0.8 g, 34%). ¹H NMR (400 MHz, DMSO-d₆): δ 11.17 (bs, 1H), 8.21 (s, 1H), 8.08 (s, 1H), 2.47-2.42 (m, 4H), 2.25-2.10 (m, 2H), 1.33 (s, 12H); LC-MS: m/z 345.2 (M+H)⁺.

Intermediate-15: (5-Fluoropyridin-2-yl)methyl methanesulfonate

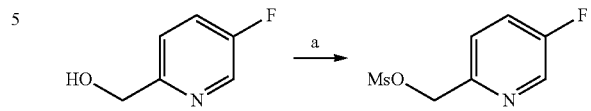

To an ice cold solution of (5-fluoropyridin-2-yl)methanol (0.25 g, 1.96 mmol) in DCM (10 mL) was added triethyl amine (0.8 mL, 5.90 mmol) followed by methane sulphonyl chloride (0.23 mL, 2.95 mmol). The mixture was stirred at RT for 2 h. The mixture was diluted with DCM and washed with water. The organic layer was dried over sodium sulphate and concentrated under reduced pressure to afford the title compound as brown gummy mass (0.3 g). LC-MS: m/z 206.1 (M+H)⁺.

Intermediate-16: 4-((tert-Butyldimethylsilyl)oxy)cyclohexan-1-ol

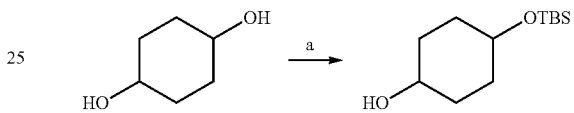

To an ice cold solution of cyclohexane-1,4-diol (3.0 g, 25.86 mmol) in DMF (50 mL) was added imidazole (5.3 g, 77.58 mmol) followed by TBS-Cl (4.7 g, 31.03 mmol). The mixture was stirred at RT for 2 h. The mixture was quenched with brine and extracted with EtOAc. The organic layer was dried over sodium sulphate and concentrated under reduced pressure to afford the title compound as colorless oily liquid (2.5 g, 42%). ES-MS: m/z 231.2 (M+H)⁺.

Intermediate-17: tert-Butyl 4-hydroxy-2,6-dimethylpiperidine-1-carboxylate

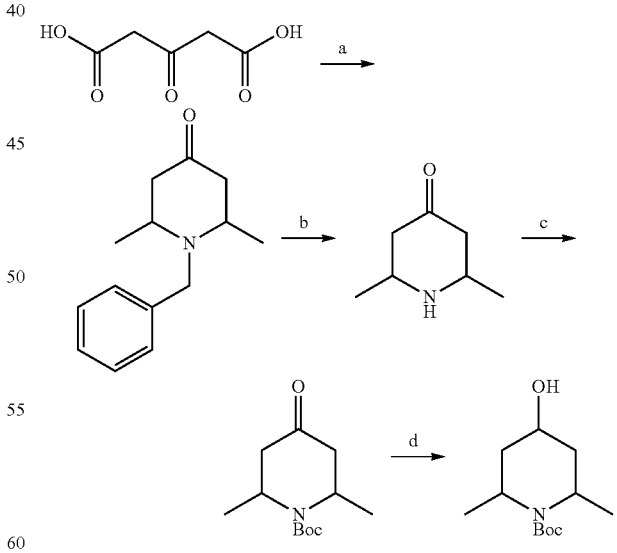

Step-a: 1-Benzyl-2,6-dimethylpiperidin-4-one

A solution of 3-oxopentanedioic acid (11.5 g, 78.76 mmol) and acetaldehyde (8.8 mL, 157.52 mmol) in water (25 mL) was stirred at RT for 10 min and then cooled to 0° C. Benzyl amine (8.2 mL, 78.76 mmol) was added dropwise over a period of 15 min (exothermic reaction) followed by stirring at RT for 3 days. The mixture was then stirred with 1 N HCl for 1 h followed by addition of aqueous NaHCO₃ to adjust pH to 8-10. The mixture was extracted with EtOAc Intermediate-18: 5'-Amino-1'-(4-methoxybenzyl)-7'-((1-methylpiperidin-4-yl)oxy)spiro [cyclobutane-1,3'-indolin]-2'-one

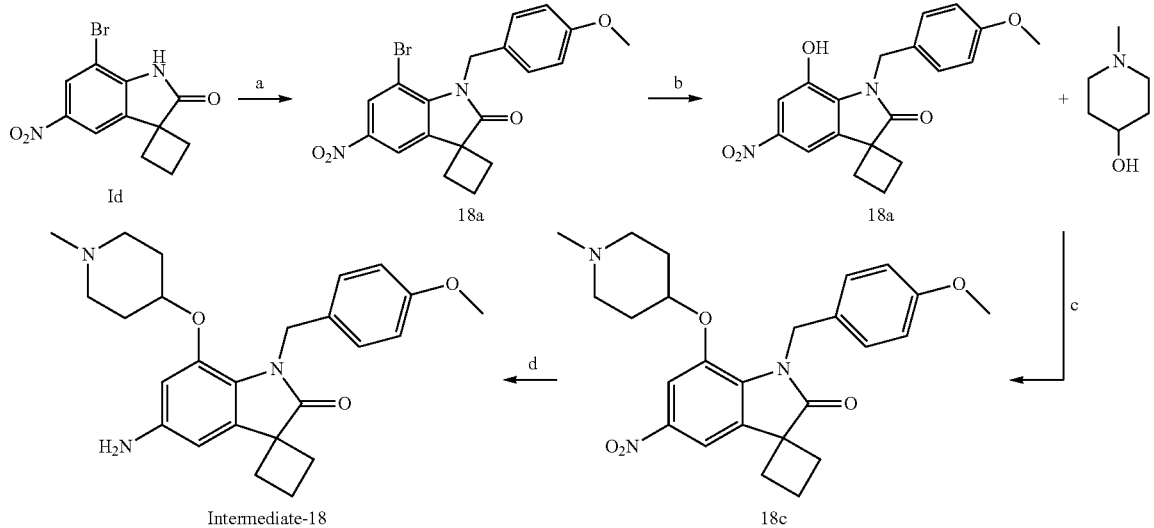

and the organic layer was washed with water and brine followed by drying over sodium sulphate and concentrating under reduced pressure. The residue was purified by combi-flash to afford the title compound as brown solid (5.0 g, 28%). ¹H NMR (400 MHz, DMSO-d₆): δ 7.42-7.21 (m, 5H), 3.85-3.79 (m, 1H), 3.68-3.65 (m, 1H), 3.22-3.17 (m, 2H), 2.44-2.40 (m, 2H), 2.14-2.08 (m, 2H), 1.02 (d, J=6.4 Hz, 6H); ES-MS: m/z 218.2 (M+H)⁺.

Step-b: 2,6-Dimethylpiperidin-4-one

To a solution of 1-benzyl-2,6-dimethylpiperidin-4-one (1.4 g, 6.45 mmol) in MeOH (15 mL) was added 10% Pd—C (0.7 g). The mixture was stirred at RT under hydrogen bladder pressure for 6 h. The mixture was filtered through celite pad and concentrated under reduced pressure to afford the title compound as brown oil (0.7 g). ¹H NMR (400 MHz, DMSO-d₆): δ 3.36-3.29 (m, 2H), 2.35-2.31 (m, 2H), 2.00-1.95 9m, 2H), 1.01 (d, J=6.8 Hz, 6H); LC-MS: m/z 128.2 (M+H)⁺.

Step-c: tert-Butyl 2,6-dimethyl-4-oxopiperidine-1-carboxylate

To a solution of 2,6-dimethylpiperidin-4-one (0.7 g, 5.51 mmol) in DCM (10 mL) were added triethyl amine (1.5 mL, 11.02 mmol), DMAP (0.07 g, 0.55 mmol) and (Boc)₂O (1.9 mL, 8.26 mmol) followed by stirring at RT for 16 h. The mixture was diluted with DCM and washed with water. The organic layer was dried over sodium sulphate and concentrated under reduced pressure. The residue was purified by combi-flash to afford the title compound as off white solid (0.34 g, 27%). ¹H NMR (400 MHz, DMSO-d₆): δ 4.23-4.20 (m, 2H), 2.95-2.89 (m, 2H), 2.28 (s, 1H), 2.24 (s, 1H), 1.43 (s, 9H), 1.16 (d, J=6.8 Hz, 6H); ES-MS: m/z 128.2 (M-Boc)⁻.

Step-d: Synthesis of tert-butyl 4-hydroxy-2,6-dimethylpiperidine-1-carboxylate

The compound was prepared using the procedure of step-c of Intermediate-12. ¹H NMR (400 MHz, DMSO-d₆): δ 4.66 (bs, 1H), 4.03-3.94 (m, 2H), 3.75-3.70 (m, 1H), 2.07-1.98 (m, 1H), 1.91-1.85 (m, 1H), 1.66-1.59 (m, 1H), 1.45-1.41 (m, 1H), 1.39 (s, 9H), 1.26 (d, J=6.8 Hz, 3H), 1.07 (d, J=6.9 Hz, 3H).

Step-a: 7'-Bromo-1'-(4-methoxybenzyl)-5'-nitrospiro[cyclobutane-1,3'-indolin]-2'-one (18a)

To an ice cold solution of 7'-bromo-5'-nitrospiro[cyclobutane-1,3'-indolin]-2'-one (13.0 g, 43.77 mmol) in DMF (130 mL) was added Cs₂CO₃ (28.5 g, 87.51 mmol) followed by 4-methoxybenzyl chloride (7.2 mL, 52.5 mmol) and stirring at RT for 3 h. The mixture was diluted with ice water and extracted with EtOAc. The organic layer was dried over sodium sulphate and concentrated. The residue was purified by combi-flash to afford the title compound as pale brown solid (12.0 g, 66%). ¹H NMR (400 MHz, DMSO-d₆) δ 8.56 (d, J=1.9 Hz, 1H), 8.26 (d, J=2.4 Hz, 1H), 7.06 (d, J=8.3 Hz, 2H), 6.87 (d, J=8.4 Hz, 2H), 5.26 (s, 2H), 3.71 (s, 3H), 2.63-2.53 (m, 2H), 2.51-2.24 (m, 4H).

Step-b: 7'-Hydroxy-1'-(4-methoxybenzyl)-5'-nitrospiro[cyclobutane-1,3'-indolin]-2'-one (18b)

To a solution of 7'-bromo-1'-(4-methoxybenzyl)-5'-nitrospiro[cyclobutane-1,3'-indolin]-2'-one (10.0 g, 23.96 mmol) in 1,4-dioxane (60 mL) and H₂O (40 mL) was added KOH(4.1 g, 71.89 mmol) followed by degassing with nitrogen purging for 20 min. Then ᵗBuXPhos (1.0 g, 2.39 mmol) and Pd₂(dba)₃ (2.20 g, 2.39 mmol) were added followed by degassing with nitrogen purging for 20 min. The mixture was then heated at 100° C. for 16 h and thereafter concentrated under reduced pressure. The residue was diluted with EtOAc (250 ml) and washed with water (250 mL) and brine (250 mL) followed by drying over sodium sulphate and concentring under reduced pressure. The product was purified by combi-flash to afford the title compound as pale brown solid (3.5 g, 42%). ¹H NMR (400 MHz, DMSO-d₆) δ 10.76 (s, 1H), 8.06 (d, J=2.5 Hz, 1H), 7.63 (d, J=2.0 Hz, 1H), 7.18 (d, J=8.8 Hz, 2H), 6.86 (d, J=8.8 Hz, 2H), 5.06 (s, 2H), 3.70 (s, 3H), 2.51-2.19 (m, 6H); LC-MS: m/z 355.1 (M+H)⁺.

Step-c: 1'-(4-Methoxybenzyl)-7'-((1-methylpiperidin-4-yl)oxy)-5'-nitrospiro [cyclobutane-1,3'-indolin]-2'-one (18c)

To a cold solution of 1-methylpiperidin-4-ol (6.5 g, 56.48 mmol) in THF (140 mL) was added triphenyl phosphine (14.8 g, 56.48 mmol) followed by DIAD (11.1 mL, 56.48 mmol). The mixture was stirred at 0° C. for 15 min followed by adding 7'-hydroxy-1'-(4-methoxybenzyl)-5'-nitrospiro[cyclobutane-1,3'-indolin]-2'-one (5.0 g, 14.12 mmol). The mixture was stirred at RT for 16 h and then diluted with EtOAc and washed with water. The organic layer was dried over sodium sulphate and concentrated under reduced pressure. The residue was purified by combi-flash to afford the title compound as yellow solid (7.5 g). $^1$H NMR (400 MHz, DMSO-d$_6$) δ 8.20 (d, J=1.4 Hz, 1H), 7.77 (d, J=1.5 Hz, 1H), 7.05 (d, J=8.8 Hz, 2H), 6.87 (d, J=8.8 Hz, 2H), 5.12 (s, 2H), 4.60-4.59 (m, 1H), 3.69 (s, 3H), 2.67-2.45 (m, 5H), 2.32-2.11 (m, 8H), 1.89-1.84 (m, 2H), 1.53-1.51 (m, 2H); LC-MS: m/z 452.1 (M+H)$^+$.

Step-d: 5'-Amino-1'-(4-methoxybenzyl)-7'-((1-methylpiperidin-4-yl)oxy)spiro[cyclobutane-1,3'-indolin]-2'-one (Intermediate 18)

To a solution of 1'-(4-methoxybenzyl)-7'-((1-methylpiperidin-4-yl)oxy)-5'-nitrospiro[cyclobutane-1,3'-indolin]-2'-one (15.0 g, 33.25 mmol) in EtOH (150 mL) and H$_2$O (30 mL) were added iron powder (9.3 g, 166.25 mmol) and NH$_4$Cl (8.81 g, 166.25 mmol) followed by heating to 100° C. for 2 h. The mixture was cooled to RT, filtered through celite and washed with EtOAc. The combined filtrate was concentrated and the residue was diluted with water, extracted with EtOAc (500 mL), washed with brine (500 mL), dried over sodium sulphate and concentrated under reduced pressure and purified by combi-flash to afford the title compound as a pale yellow solid (8.3 g). $^1$H NMR (400 MHz, DMSO-d$_6$) δ 7.05 (d, J=8.8 Hz, 2H), 6.86 (d, J=8.8 Hz, 2H), 6.51 (d, J=1.4 Hz, 1H), 6.19 (d, J=2.0 Hz, 1H), 4.95 (bs, 4H), 4.30-4.28 (m, 1H), 3.69 (s, 3H), 3.16-2.62 (m, 4H), 2.46-2.36 (m, 5H), 2.26-2.08 (m, 4H), 1.92-1.91 (m, 2H), 1.66-1.65 (m, 2H); LC-MS: m/z 422.1 (M+H)$^+$.

The below intermediates were prepared according to the protocol described in the synthesis of Intermediate-18 with appropriate variations in reactants, quantities of reagents, solvents and reaction conditions.

| No | Structure | Characterization Data |
|---|---|---|
| 19 | 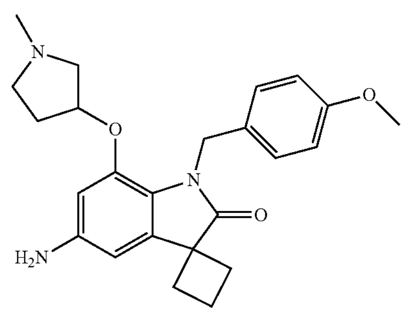 [SMILES: COc1ccc(CN2C(=O)C3(CCC3)c3cc(N)cc(OC4CCN(C)C4)c32)cc1] | $^1$H NMR (400 MHz, DMSO-d$_6$): δ 7.05 (d, J = 8.3 Hz, 2H), 6.86 (d, J = 8.8 Hz, 2H), 6.55 (s, 1H), 6.09 (s, 1H), 4.97-4.90 (m, 4H), 4.85-4.84 (m, 1H), 3.70 (s, 3H), 3.18-3.06 (m, 2H), 2.65-2.60 (m, 3H), 2.49-2.42 (m, 3H), 2.33-2.05 (m, 6H), 1.89-1.87 (m, 1H); LCMS: m/z 408.2 (M + H)$^+$. |
| 20 | 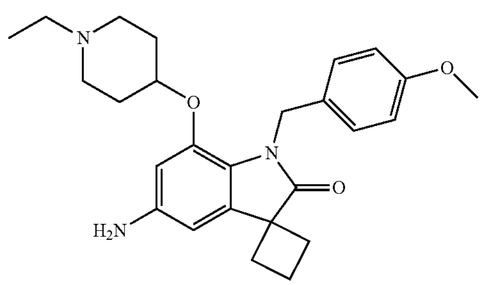 [SMILES: CCN1CCC(Oc2cc(N)cc3c2N(Cc2ccc(OC)cc2)C(=O)C32CCC2)CC1] | $^1$H NMR (400 MHz, DMSO-d$_6$): δ 7.18-7.15 (m, 2H), 6.87 (d, J = 8.3 Hz, 2H), 6.54 (s, 1H), 6.20 (s, 1H), 4.95 (s, 2H), 4.86 (s, 2H), 4.41-4.38 (m, 1H), 3.69 (s, 3H), 3.01-2.81 (m, 2H), 2.46-2.42 (m, 3H), 2.23-2.21 (m, 7H), 2.17-1.99 (m, 2H), 1.78-1.72 (m, 2H), 1.21-1.12 (m, 3H); LCMS: m/z 436.3 (M + H)$^+$. |
| 21 | 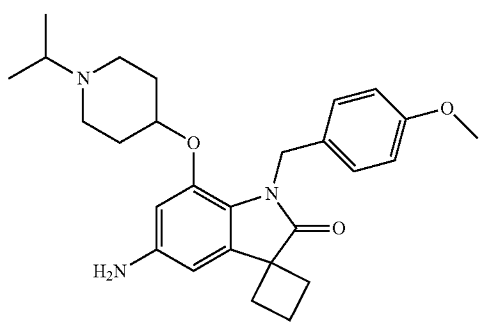 [SMILES: COc1ccc(CN2C(=O)C3(CCC3)c3cc(N)cc(OC4CCN(C(C)C)CC4)c32)cc1] | $^1$H NMR (400 MHz, DMSO-d$_6$): δ 7.18-7.06 (m, 2H), 6.85 (d, J = 7.8 Hz, 2H), 6.53 (s, 1H), 6.20 (s, 1H), 4.96-4.79 (m, 4H), 4.18-4.16 (m, 1H), 3.69 (s, 3H), 3.19-3.01 (m, 2H), 2.67-2.41 (m, 4H), 2.33-1.74 (m, 7H), 1.35-1.07 (m, 8H); LC-MS: m/z 450.3 (M + H)$^+$. |

| No | Structure | Characterization Data |
|---|---|---|
| 22 | 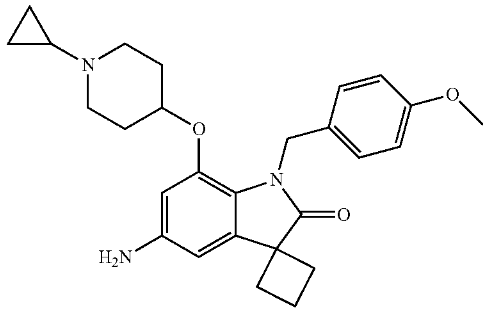 [SMILES: COc1ccc(CN2C(=O)C3(CCC3)c3cc(N)cc(OC4CCN(C5CC5)CC4)c32)cc1] | $^1$H NMR (400 MHz, DMSO-d$_6$): δ 7.05 (d, J = 8.8 Hz, 2H), 6.83 (d, J = 8.3 Hz, 2H), 6.49 (d, J = 1.5 Hz, 1H), 6.19 (d, J = 1.5 Hz, 1H), 4.94 (s, 2H), 4.80-4.78 (m, 2H), 4.18-4.16 (m, 1H), 3.84-3.82 (m, 1H), 3.68 (s, 3H), 2.91-2.89 (m, 2H), 2.68-2.62 (m, 2H), 2.44-2.13 (m, 6H), 1.79-1.76 (m, 2H), 1.45-1.42 (m, 2H), 0.39-0.38 (m, 2H), 0.28-0.24 (m, 2H); ES-MS: m/z 448.3 (M + H)$^+$. |
| 23 | 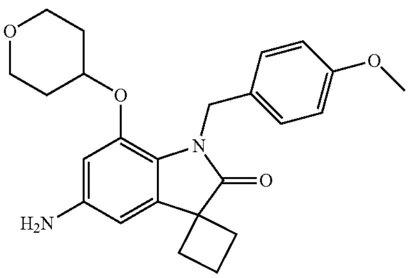 [SMILES: COc1ccc(CN2C(=O)C3(CCC3)c3cc(N)cc(OC4CCOCC4)c32)cc1] | $^1$H NMR (400 MHz, DMSO-d$_6$): δ 7.04 (d, J = 8.3 Hz, 2H), 6.84 (d, J = 8.3 Hz, 2H), 6.50 (d, J = 1.5 Hz, 1H), 6.21 (s, 1H), 4.94 (s, 2H), 4.82 (s, 2H), 4.36-4.31 (m, 1H), 3.74-3.69 (m, 5H), 3.38-3.36 (m, 2H), 2.45-2.42 (m, 2H), 2.24-2.08 (m, 4H), 1.84-1.81 (m, 2H), 1.41-1.34 (m, 2H); LCMS: m/z 409.2 (M + H)$^+$. |
| 24 | 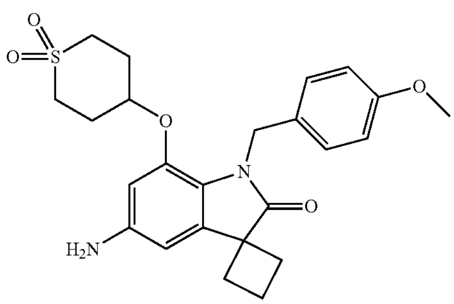 [SMILES: COc1ccc(CN2C(=O)C3(CCC3)c3cc(N)cc(OC4CCS(=O)(=O)CC4)c32)cc1] | $^1$H NMR (400 MHz, DMSO-d$_6$): δ 7.00 (d, J = 8.8, 2H), 6.83 (d, J = 8.8 Hz, 2H), 6.55 (d, J = 2.0 Hz, 1H), 6.19 (d, J = 2.0 Hz, 1H), 4.93 (s, 2H), 4.85 (bs, 2H), 4.47-4.45 (m, 1H), 3.70 (s, 3H), 3.09-2.90 (m, 2H), 2.89-2.88 (m, 2H), 2.67-2.43 (m, 4H), 2.32-2.20 (m, 2H), 2.09-2.07 (m, 3H), 1.92-1.91 (m, 1H); LC-MS: m/z 457.2 (M + H)$^+$. |
| 25 | 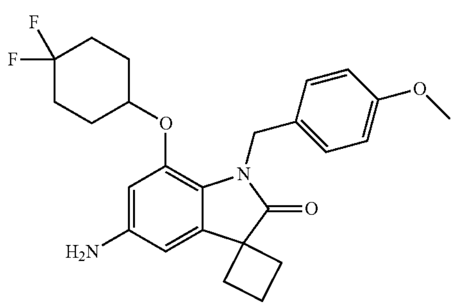 [SMILES: COc1ccc(CN2C(=O)C3(CCC3)c3cc(N)cc(OC4CCC(F)(F)CC4)c32)cc1] | $^1$H NMR (400 MHz, DMSO-d$_6$): δ 7.00 (d, J = 9.0 Hz, 2H), 6.83 (d, J = 8.8 Hz, 2H), 6.52 (d, J = 1.5 Hz, 1H), 6.21 (s, 1H), 4.93 (s, 2H), 4.84 (s, 2H), 4.36-4.34 (m, 1H), 3.68 (s, 3H), 2.49-2.40 (m, 2H), 2.29-2.10 (m, 4H), 1.88-1.78 (m, 6H), 1.59-1.51 (m, 2H); LCMS: m/z 443.3 (M + H)$^+$. |
| 26 | 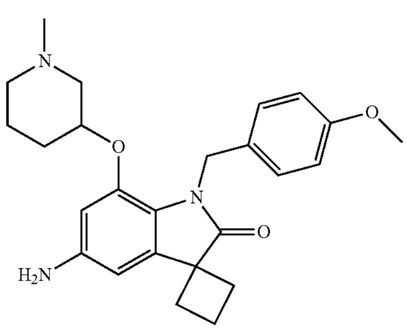 [SMILES: COc1ccc(CN2C(=O)C3(CCC3)c3cc(N)cc(OC4CCCN(C)C4)c32)cc1] | $^1$H NMR (400 MHz, DMSO-d$_6$): δ 7.06 (d, J = 8.4 Hz, 2H), 6.85 (d, J = 8.3 Hz, 2H), 6.58 (s, 1H), 6.23 (s, 1H), 4.98-4.88 (m, 4H), 4.22-4.20 (m, 1H), 3.88-3.86 (m, 1H), 3.69 (s, 3H), 3.35-3.31 (m, 1H), 3.15-2.95 (m, 1H), 2.67-2.44 (m, 6H), 2.25-2.10 (m, 4H), 2.08-1.80 (m, 3H), 1.58-1.56 (m, 1H); LCMS: m/z 422.3 (M + H)$^+$. |

| No | Structure | Characterization Data |
|---|---|---|
| 27 | 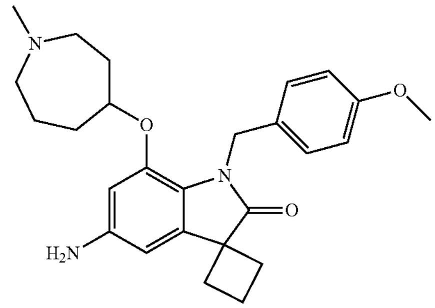 | LCMS: m/z 436.3 (M + H)⁺ |
| 28 | 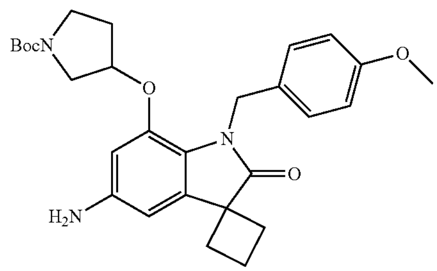 [SMILES: COc1ccc(CN2C(=O)C3(CCC3)c3cc(N)cc(OC4CCN(C(=O)OC(C)(C)C)C4)c32)cc1] | $^1$H NMR (400 MHz, DMSO-d$_6$): δ 7.01 (d, J = 8.3 Hz, 2H), 6.82-6.80 (m, 2H), 6.52 (d, J = 1.5 Hz, 1H), 6.14 (s, 1H), 4.91-4.82 (m, 3H), 3.69 (s, 3H), 3.47-3.17 (m, 4H), 2.52-2.40 (m, 4H), 2.22-1.80 (m, 6H), 1.40 (s, 9H). |
| 29 | 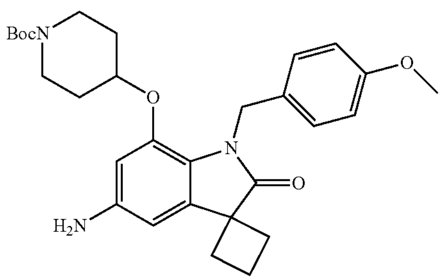 [SMILES: COc1ccc(CN2C(=O)C3(CCC3)c3cc(N)cc(OC4CCN(C(=O)OC(C)(C)C)CC4)c32)cc1] | $^1$H NMR (400 MHz, DMSO-d$_6$): δ 7.00 (d, J = 8.3 Hz, 2H), 6.81 (d, J = 8.8 Hz, 2H), 6.51 (d, J = 1.9 Hz, 1H), 6.19 (d, J = 1.4 Hz, 1H), 4.93 (s, 2H), 4.83 (s, 2H), 4.33-4.31 (m, 1H), 3.68 (s, 3H), 3.47-3.44 (m, 2H), 3.04-3.01 (m, 2H), 2.46-2.42 (m, 2H), 2.26-2.23 (m, 4H), 1.76-1.74 (m, 2H), 1.39 (s, 9H), 1.29-1.23 (m, 2H). |
| 30 | 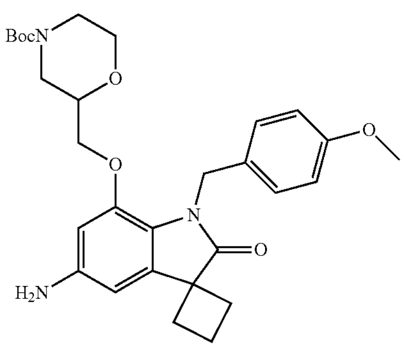 [SMILES: COc1ccc(CN2C(=O)C3(CCC3)c3cc(N)cc(OCC4CN(C(=O)OC(C)(C)C)CCO4)c32)cc1] | $^1$H NMR (400 MHz, DMSO-d$_6$): δ 7.12 (d, J = 8.3 Hz, 2H), 6.82 (d, J = 8.8 Hz, 2H), 6.54 (d, J = 1.4 Hz, 1H), 6.16 (d, J = 1.5 Hz, 1H), 4.91-4.89 (m, 4H), 4.09-4.00 (m, 1H), 3.89-3.82 (m, 4H), 3.70-3.69 (m, 1H), 3.69 (s, 3H), 3.50-3.33 (m, 2H), 2.85-2.80 (m, 1H), 2.49-2.43 (m, 2H), 2.21-2.06 (m, 4H), 1.40 (s, 9H); LC-MS: m/z 524.1 (M + H)⁺. |
| 31 | 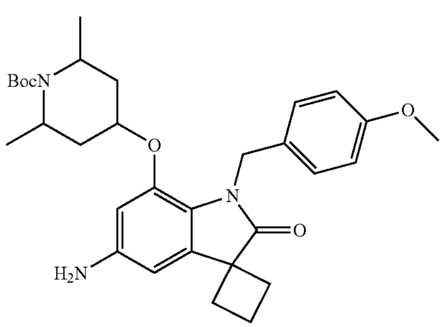 | $^1$H NMR (400 MHz, DMSO-d$_6$): δ 7.02 (d, J = 8.3 Hz, 2H), 6.82 (d, J = 8.3 Hz, 2H), 6.50 (s, 1H), 6.17 (s, 1H), 4.92 (s, 2H), 4.85 (bs, 2H), 4.60-4.51 (m, 1H), 4.17-4.13 (m, 1H), 3.76-3.73 (m, 1H), 3.68 (s, 3H), 2.55-2.45 (m, 2H), 2.43-2.17 (m, 6H), 1.85-1.79 (m, 1H), 1.57-1.51 (m, 1H), 1.39 (s, 9H), 1.13-1.07 (m, 6H). |

| No | Structure | Characterization Data |
|---|---|---|
| 32 | (TBSO-cyclohexyl-O-indolinone with H₂N, spirocyclobutane, N-PMB) | ¹H NMR (400 MHz, DMSO-d₆): δ 7.08 (d, J = 8.3 Hz, 1H), 7.03 (d, J = 8.8 Hz, 1H), 6.84-6.78 (m, 2H), 6.48-6.46 (m, 1H), 6.18-6.17 (m, 1H), 4.93-4.90 (m, 2H), 4.81 (bs, 2H), 4.17-4.15 (m, 1H), 3.84-3.82 (m, 1H), 3.71-3.68 (m, 3H), 2.43-2.40 (m, 2H), 2.20-2.08 (m, 4H), 1.83-1.80 (m, 1H), 1.71-1.65 (m, 4H), 1.52-1.51 (m, 3H), 0.87-0.84 (m, 9H), 0.03-0.02 (m, 6H); LC-MS: m/z 537.3 (M + H)⁺. |
| 33 | (2-chloropyridin-4-yl-O-indolinone with H₂N, spirocyclobutane, N-PMB) | ¹H NMR (400 MHz, DMSO-d₆): δ 8.17-8.11 (m, 1H), 6.89 (d, J = 1.9 Hz, 1H), 6.81 (d, J = 8.8 Hz, 2H), 6.74-6.73 (m, 1H), 6.62 (d, J = 2.3 Hz, 2H), 6.52 (d, J = 2.0 Hz, 1H), 6.04 (d, J = 1.5 Hz, 1H), 5.09 (s, 2H), 4.72 (s, 2H), 3.63 (s, 3H), 2.60-2.50 (m, 2H), 2.40-2.38 (m, 4H); LCMS: m/z 436.2 (M + H)⁺. |
| 34 | (1-methylpyrrolidin-2-yl-methoxy-indolinone with H₂N, spirocyclobutane, N-PMB) | ¹H NMR (400 MHz, DMSO-d₆): δ 7.09 (d, J = 8.3 Hz, 2H), 6.83 (d, J = 8.8 Hz, 2H), 6.51 (s, 1H), 6.20 (s, 1H), 4.92 (s, 2H), 4.88 (s, 2H), 3.87-3.85 (m, 1H), 3.69 (s, 3H), 3.64-3.61 (m, 1H), 2.98-2.94 (m 1H), 2.43-2.39 (m, 3H), 2.33-2.12 (m, 8H), 1.82-1.80 (m, 1H), 1.62-1.58 (m, 2H), 1.48-1.43 (m, 1H); LCMS: m/z 422.2 (M + H)⁺. |
| 35 | (1-methylpiperidin-4-yl-methoxy-indolinone with H₂N, spirocyclobutane, N-PMB) | LC-MS: m/z 436.1 (M + H)⁺. |
| 36 | (1-(pyridin-3-yl)ethoxy-indolinone with H₂N, spirocyclobutane, N-PMB) | ¹H NMR (400 MHz, DMSO-d₆): δ 8.42-8.41 (m, 1H), 8.34 (d, J = 0.9 Hz, 1H), 7.16-7.14 (m, 2H), 7.03 (d, J = 8.8 Hz, 2H), 6.87 (d, J = 8.4 Hz, 2H), 6.45 (d, J = Hz, 1H), 5.95 (d, J = 2 Hz, 1H) 5.33-5.32 (m, 1H), 5.09-4.94 (m, 2H), 4.78-4.76 (m, 2H), 3.72 (s, 3H), 2.47-2.42 (m, 2H), 2.24-2.18 (m, 4H), 1.40 (d, J = 6.3 Hz, 3H); LC-MS: m/z 430.2 (M + H)⁺. |

| No | Structure | Characterization Data |
|---|---|---|
| 37 | 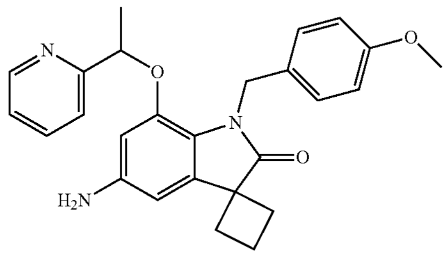 [SMILES: COc1ccc(CN2C(=O)C3(CCC3)c3cc(N)cc(OC(C)c4ccccn4)c32)cc1] | ¹H NMR (400 MHz, DMSO-d₆): δ 8.51 (d, J = 4.4 Hz, 1H), 7.52 (t, J = 7.3 Hz, 1H), 7.24-7.21 (m, 1H), 7.07 (d, J = 8.3 Hz, 2H), 6.87 (d, J = 8.3 Hz, 2H), 6.60 (d, J = 7.8 Hz, 1H), 6.45 (s, 1H), 5.87 (s, 1H), 5.25-5.20 (m, 1H), 5.14-4.93 (m, 2H), 4.76 (s, 2H), 3.71 (s, 3H), 2.46-2.43 (m, 2H), 2.32-2.07 (m, 4H), 1041 (d, J = 6.3 Hz, 3H); LC-MS: m/z 430.2 (M + H)⁺. |
| 38 | 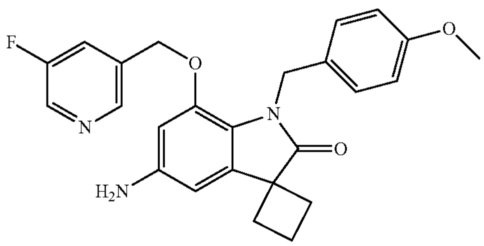 [SMILES: COc1ccc(CN2C(=O)C3(CCC3)c3cc(N)cc(OCc4cncc(F)c4)c32)cc1] | ¹H NMR (400 MHz, DMSO-d₆): δ 8.51 (d, J = 2 Hz, 1H), 8.35 (s, 1H), 7.28 (d, J = 9.3 Hz, 1H), 6.88 (d, J = 8.3 Hz, 2H), 6.75 (d, J = 8.8 Hz, 2H), 6.54 (s, 1H), 6.20 (s, 1H), 5.00 (s, 2H), 4.89 (s, 2H), 4.85 (s, 2H), 3.68 (s, 3H), 2.36-2.18 (m, 6H); LC-MS: m/z 434.2 (M + H)⁺. |
| 39 | 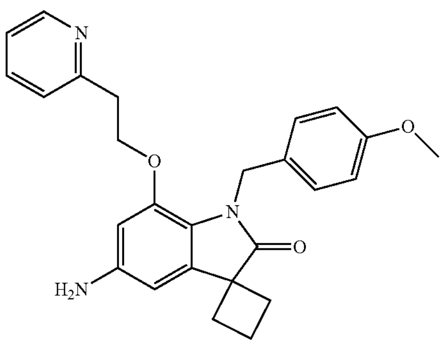 [SMILES: COc1ccc(CN2C(=O)C3(CCC3)c3cc(N)cc(OCCc4ccccn4)c32)cc1] | LC-MS: m/z 430.1 (M + H)⁺. |
| 40 | 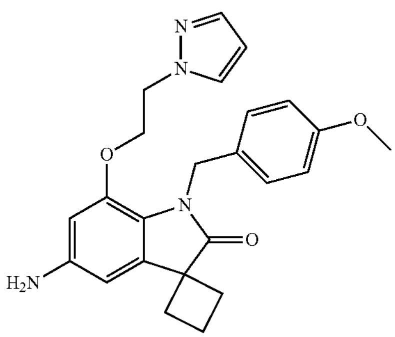 [SMILES: COc1ccc(CN2C(=O)C3(CCC3)c3cc(N)cc(OCCn4cccn4)c32)cc1] | ¹H NMR (400 MHz, DMSO-d₆): δ 7.65 (d, J = 2.0 Hz, 1H), 7.47 (d, J = 2.0 Hz, 1H), 7.02 (d, J = 8.8 Hz, 2H), 6.81 (d, J = 8.8 Hz, 2H), 6.50 (d, J = 2.0 Hz, 1H), 6.23-6.22 (m, 1H), 6.15 (d, J = 2.0 Hz, 1H), 4.89 (s, 2H), 4.73 (s, 2H), 4.36 (t, J = 5.3 Hz, 2H), 4.19 (t, J = 5.4 Hz, 2H), 3.69 (s, 3H), 2.42-2.21 (m, 2H), 2.19-2.17 (m, 4H); LC-MS: m/z 419.1 (M + H)⁺. |
| 41 | 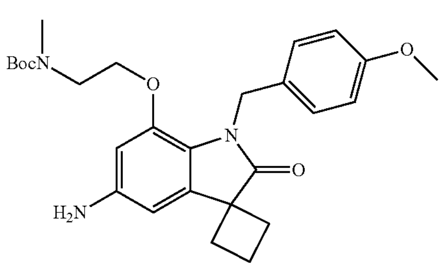 [SMILES: COc1ccc(CN2C(=O)C3(CCC3)c3cc(N)cc(OCCN(C)C(=O)OC(C)(C)C)c32)cc1] | ¹H NMR (400 MHz, DMSO-d₆): δ 7.12-7.08 (m, 2H), 6.83 (d, J = 8.3 Hz, 2H), 6.51 (s, 1H), 6.19 (s, 1H), 4.87 (s, 2H), 4.85 (s, 2H), 3.90-3.88 (m, 2H), 3.69 (s, 3H), 3.41-3.37 (m, 2H), 2.75 (s, 3H), 2.43-2.33 (m, 2H), 2.22-2.09 (m, 4H), 1.39-1.23 (m, 9H); LCMS: m/z 482.3 (M + H)⁺. |

| No | Structure | Characterization Data |
|---|---|---|
| 42 | 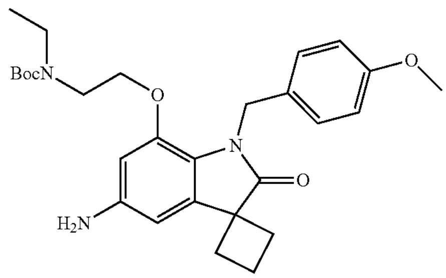 [SMILES: CCN(CCOc1cc(N)cc2c1N(Cc1ccc(OC)cc1)C(=O)C21CCC1)C(=O)OC(C)(C)C] | ¹H NMR (400 MHz, DMSO-d₆): δ 7.09-7.08 (m, 2H), 6.83 (d, J = 8.4 Hz, 2H), 6.51 (s, 1H), 6.18 (s, 1H), 4.88 (s, 2H), 4.85 (bs, 2H), 3.86 (t, J = 5.8 Hz, 2H), 3.68 (s, 3H), 3.40-3.35 (m, 2H), 3.11-3.09 (m, 2H), 2.46-2.32 (m, 2H), 2.21-2.09 (m, 4H), 1.35 (bs, 9H), 0.97 (t, J = 6.4 Hz, 3H); LC-MS: m/z 496.3 (M + H)⁺. |
| 43 | 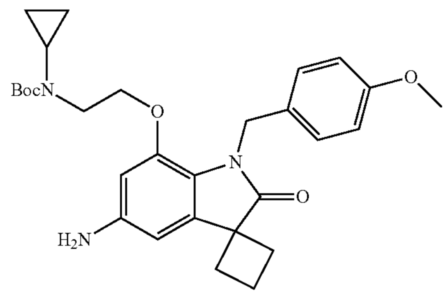 [SMILES: COc1ccc(CN2C(=O)C3(CCC3)c3cc(N)cc(OCCN(C(=O)OC(C)(C)C)C4CC4)c32)cc1] | ¹H NMR (400 MHz, DMSO-d₆): δ 7.10 (d, J = 8.3 Hz, 2H), 6.83 (t, J = 8.8 Hz, 2H), 6.65 (s, 1H), 6.19 (s, 1H), 4.88 (s, 2H), 4.85 (bs, 2H), 3.91 (t, J = 5.4 Hz, 2H), 3.69 (s, 3H), 3.40 (t, J = 5.3 Hz, 2H), 2.49-2.33 (m, 3H), 2.21-2.08 (m, 4H), 1.35 (s, 9H), 0.67-0.65 (m, 2H), 0.53-0.51 (m, 2H). |
| 44 | 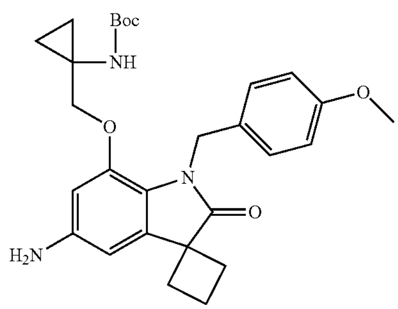 [SMILES: COc1ccc(CN2C(=O)C3(CCC3)c3cc(N)cc(OCC4(NC(=O)OC(C)(C)C)CC4)c32)cc1] | ¹H NMR (400 MHz, DMSO-d₆): δ 8.47 (bs, 1H), 7.17 (t, J = 8.8 Hz, 2H), 6.81 (d, J = 8.8 Hz, 2H), 6.47 (s, 1H), 6.09 (s, 1H), 4.98 (s, 2H), 4.81 (bs, 2H), 3.81 (s, 2H), 3.68 (s, 3H), 2.44-2.40 (m, 2H), 2.32-2.12 (m, 4H), 1.35 (s, 9H), 0.70-0.64 (m, 4H); LC-MS: m/z 494.1 (M + H)⁺. |
| 45 | 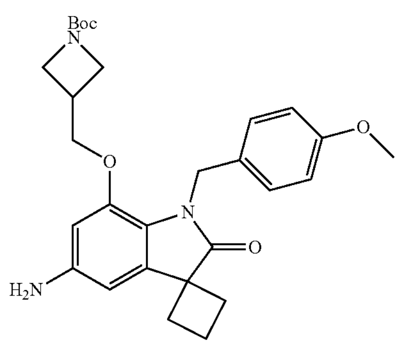 [SMILES: COc1ccc(CN2C(=O)C3(CCC3)c3cc(N)cc(OCC4CN(C(=O)OC(C)(C)C)C4)c32)cc1] | ¹H NMR (400 MHz, DMSO-d₆): δ 7.02 (d, J = 8.3 Hz, 2H), 6.83 (d, J = 8.8 Hz, 2H), 6.52 (d, J = 2.0 Hz, 1H), 6.18 (d, J = 2.0 Hz, 1H), 4.88-4.86 (m, 4H), 3.93 (d, J = 6.3 Hz, 2H), 3.83 (t, J = 8.3 Hz, 2H), 3.69 (s, 3H), 3.50-3.46 (m, 2H), 2.78-2.76 (m, 1H), 2.46-2.41 (m, 2H), 2.25-2.13 (m, 4H), 1.36 (s, 9H); ESMS: m/z 494.3 (M + H)⁺. |
| 46 | 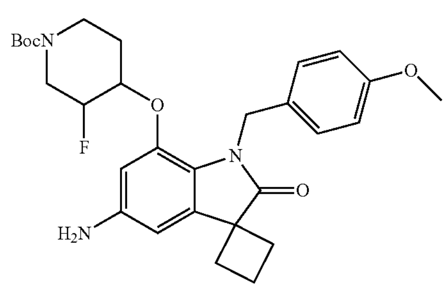 [SMILES: COc1ccc(CN2C(=O)C3(CCC3)c3cc(N)cc(OC4CCN(C(=O)OC(C)(C)C)CC4F)c32)cc1] | ¹H NMR (400 MHz, DMSO-d₆): δ 7.00 (d, J = 8.8 Hz, 1H), 6.82 (d, J = 8.8 Hz, 2H), 6.55 (d, J = 1.9 Hz, 1H), 6.24 (d, J = 1.4 Hz, 1H), 4.99-4.89 (m, 2H), 4.88 (s, 2H), 4.44-4.30 (m, 2H), 3.68 (s, 3H), 3.50-3.40 (m, 1H), 3.20-3.10 (m, 2H), 2.51-2.44 (m, 4H), 2.28-2.10 (m, 4H), 1.82-1.78 (m, 1H), 1.40 (s, 9H), 1.22-1.16 (m, 1H); LCMS: m/z 526.3 (M + H)⁺. |

-continued

| No | Structure | Characterization Data |
|---|---|---|
| 47 | 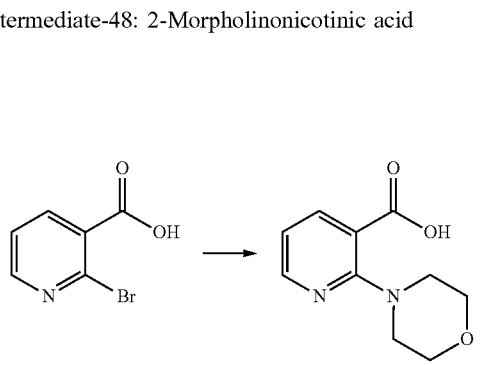 | $^1$H NMR (400 MHz, DMSO-d$_6$): δ 7.29-7.23 (m, 5H), 7.01 (t, J = 8.8 Hz, 2H), 6.81 (d, J = 8.8 Hz, 2H), 6.53 (d, J = 1.4 Hz, 1H), 6.22 (d, J = 2.0 Hz, 1H), 4.95-4.78 (m, 6H), 4.02-3.82 (m, 2H), 3.66 (s, 3H), 3.42-3.32 (m, 3H), 3.21-3.18 (m, 2H), 2.67-2.42 (m, 5H), 2.33-2.09 (m, 3H); LCMS: m/z 514.1 (M + H)$^+$. |

Intermediate-48: 2-Morpholinonicotinic acid

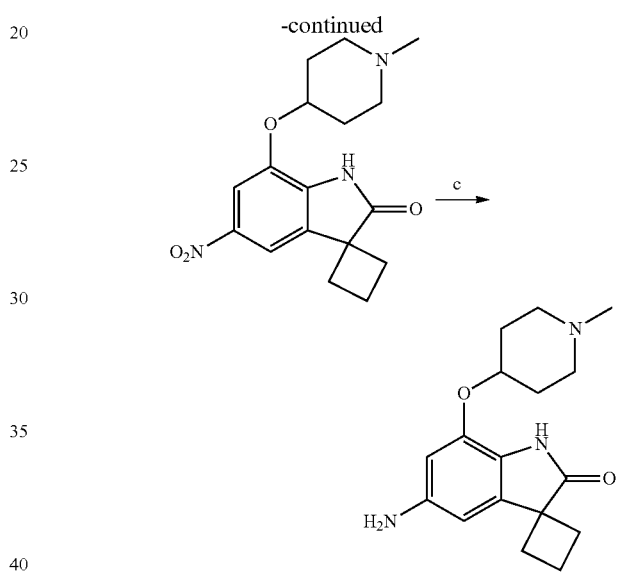

The compound was prepared using the procedure of Example-IX. $^1$H NMR (400 MHz, DMSO-d$_6$): δ 10.03 (s, 1H), 6.82 (s, 1H), 6.56 (s, 1H), 4.96 (s, 2H), 2.43-2.41 (m, 2H), 2.21-2.16 (m, 4H); LC-MS: m/z 269.1 (M+2H)$^{2+}$.

Intermediate-49: 5'-amino-7'-((1-methylpiperidin-4-yl)oxy) spiro[cyclobutane-1,3'-indolin]-2'-one:

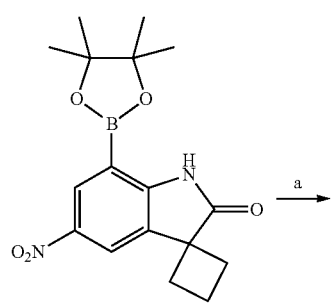

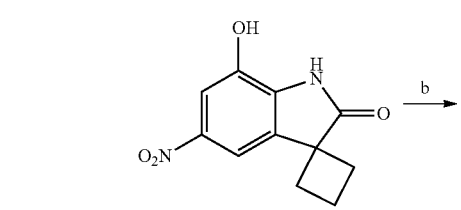

Step-a: 7'-Hydroxy-5'-nitrospiro[cyclobutane-1,3'-indolin]-2'-one

To a cold solution of 5'-nitro-7'-(4,4,5,5-tetramethyl-1,3,2-dioxaborolan-2-yl)-spiro[cyclobutane-1,3'-indolin]-2'-one (5.0 g, 14.53 mmol, Intermediate-9) in THF (30 mL) was added 30% of H$_2$O$_2$ (150 mL) followed by stirring at RT for 3 h. The mixture was diluted with water and extracted with EtOAc. The organic layer was dried over sodium sulphate and concentrated under reduced pressure. The residue was purified by combi-flash to afford the title compound as yellow solid (1.5 g, 44%). $^1$H NMR (400 MHz, DMSO-d$_6$): δ 10.78 (s, 1H), 10.54 (s, 1H), 8.01 (d, J=2.0 Hz, 1H), 7.62 (d, J=2.4 Hz, 1H), 2.43-2.41 (m, 4H), 2.24-2.18 (m, 2H); LCMS: m/z 235.1 (M+H)$^+$.

Step-b: 7'-((1-Methylpiperidin-4-yl)oxy)-5'-nitrospiro [cyclobutane-1,3'-indolin]-2'-one:

To a cold solution of 1-methylpiperidin-4-ol (2.2 g, 18.8 mmol) in THF (60 mL) was added triphenyl phosphine (4.9 g, 18.8 mmol) and DIAD (3.7 mL, 18.8 mmol) followed by stirring at 0° C. for 15 min. Then 7'-hydroxy-5'-nitrospiro [cyclobutane-1,3'-indolin]-2'-one (1.1 g, 4.70 mmol) was added followed by stirring at RT for 16 h. The mixture was diluted with EtOAc and washed with water. The organic layer was dried over sodium sulphate and concentrated under reduced pressure. The residue was purified by combiflash to afford the title compound as yellow solid (0.9 g, 58%). ¹H NMR (400 MHz, DMSO-d₆): δ 10.97 (s, 1H), 8.15 (d, J=2.0 Hz, 1H), 7.80 (d, J=2.0 Hz, 1H), 4.57-4.55 (m, 1H), 2.67-2.65 (m, 2H), 2.49-2.41 (m, 4H), 2.33-2.19 (m, 7H), 1.93-1.89 (m, 2H), 1.74-1.66 (m, 2H); LCMS: m/z 332.2 (M+H)⁺.

Step-c: 5'-Amino-7'-((1-methylpiperidin-4-yl)oxy)spiro[cyclobutane-1,3'-indolin]-2'-one To a solution of 7'-((1-methylpiperidin-4-yl)oxy)-5'-nitro-spiro[cyclobutane-1,3'-indolin]-2'-one (0.26 g, 0.78 mmol) in a mixture of MeOH (10 mL) and THF (3 mL) was added 10% Pd—C (0.1 g) followed by stirring under hydrogen bladder pressure at RT for 6 h. The mixture was filtered through celite bed and washed with EtOAc. The organic layer was concentrated under reduced pressure to afford the title compound as off white solid (0.21 g). ¹H NMR (400 MHz, DMSO-d₆): δ 9.74 (s, 1H), 6.45 (d, J=1.5 Hz, 1H), 6.17 (d, J=1.4 Hz, 1H), 4.70-4.68 (bs, 2H), 4.09-4.06 (m, 1H), 2.67-2.65 (m, 2H), 2.43-2.32 (m, 2H), 2.18 (s, 3H), 2.15-2.01 (m, 6H), 1.91-1.84 (m, 2H), 1.68-1.60 (m, 2H); LCMS: m/z 302.2 (M+H)⁺.

Intermediate-50: 5'-Amino-7'-(3-(dimethylamino)propoxy)-1'-(4-methoxybenzyl)spiro [cyclobutane-1,3'-indolin]-2'-one

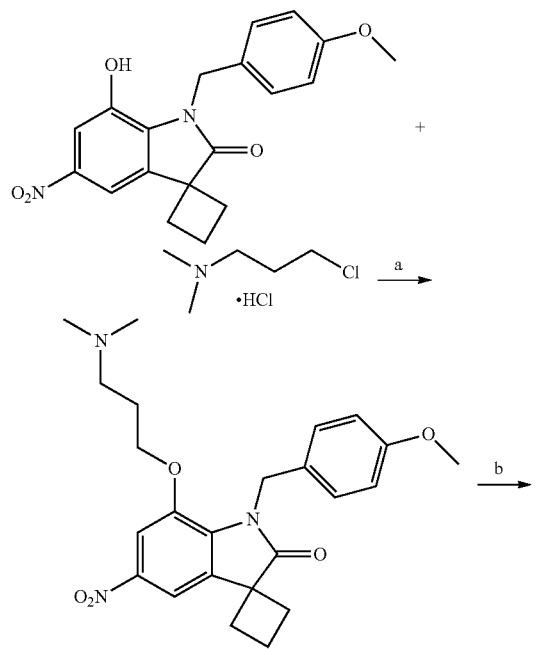

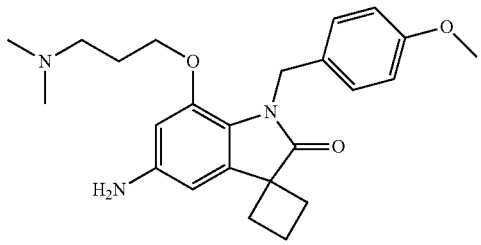

Step-a: 7'-(3-(Dimethylamino)propoxy)-1'-(4-methoxybenzyl)-5'-nitrospiro-[cyclobutane-1,3'-indolin]-2'-one In a sealed tube, to a solution of 7'-hydroxy-1'-(4-methoxybenzyl)-5'-nitro-spiro[cyclobutane-1,3'-indolin]-2'-one (0.25 g, 0.706 mmol) in DMF (5 mL) were added slowly potassium carbonate (0.29 g, 2.12 mmol) and NaI (0.012 g, 0.07 mmol) followed by stirring at RT for 5 min 3-Chloro—N,N-dimethylpropan-1-amine hydrochloride (0.22 g, 1.41 mmol) was added and the mixture was heated to 60° C. for 4 h. The mixture was cooled to RT, diluted with EtOAc and washed with water. The organic layer was dried over sodium sulphate and concentrated under reduced pressure. The residue was purified by combi-flash to afford the title compound as pale yellow solid (0.12 g, 38%). ¹H NMR (400 MHz, DMSO-d₆): δ 8.24 (s, 1H), 7.79 (s, 1H), 7.08 (d, J=8.4 H$_z$, 2H), 6.87 (d, J=8.3 Hz, 2H), 5.08 (s, 2H), 4.10 (t, J=5.9 Hz, 2H), 3.70 (s, 3H), 2.57-2.50 (m, 2H), 2.47-2.23 (m, 12H), 1.80-1.76 (m, 2H); LCMS: m/z 440.2 (M+H)⁺.

Step-b: 5'-Amino-7'-(3-(dimethylamino)propoxy)-1'-(4-methoxybenzyl) spiro-[cyclobutane-1,3'-indolin]-2'-one The compound was prepared according to the procedure of step-d of Intermediate-18. ¹H NMR (400 MHz, DMSO-d₆): δ 7.06 (d, J=8.3 Hz, 2H), 6.85 (d, J=8.3 Hz, 2H), 6.51 (s, 1H), 6.16 (s, 1H), 4.94-4.84 (m, 4H), 3.82 (t, J=5.9 Hz, 2H), 3.69 (s, 3H), 2.56-2.38 (m, 4H), 2.37-2.13 (m, 10H), 1.78-1.76 (m, 2H); LCMS: m/z 410.3 (M+H)⁺.

The below intermediates were prepared according to the protocol described in the synthesis of Intermediate-50 with appropriate variations in reactants, quantities of reagents, solvents and reaction conditions.

| No | Structure | Characterization Data |
|---|---|---|
| 51 | 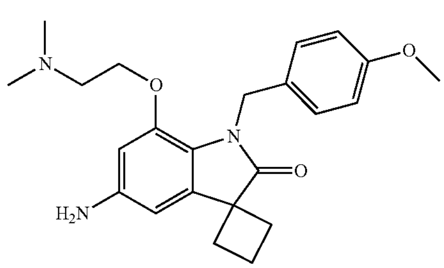 | ¹H NMR (400 MHz, DMSO-d₆): δ 7.13 (d, J = 8.8 Hz, 2H), 6.83 (d, J = 8.4 Hz, 2H), 6.50 (s, 1H), 6.18 (s, 1H), 4.91 (s, 2H), 4.84 (bs, 2H), 3.86 (t, J = 5.9 Hz, 2H), 3.69 (s, 3H), 2.46-2.41 (m, 4H), 2.21-2.11 (m, 10H); LC-MS: m/z 396.2 (M + H)⁺. |

-continued

| No | Structure | Characterization Data |
|---|---|---|
| 52 | 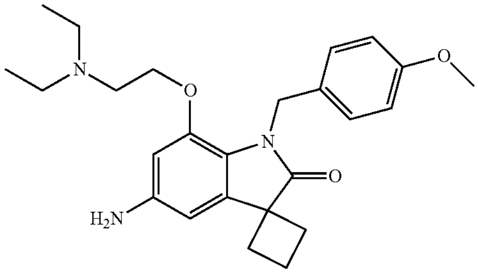 [SMILES: CCN(CC)CCOc1cc(N)cc2c1N(Cc1ccc(OC)cc1)C(=O)C21CCC1] | ¹H NMR (400 MHz, DMSO-d₆): δ 7.05 (d, J = 7.4 Hz, 2H), 6.86 (d, J = 7.8 Hz, 2H), 6.59 (s, 1H), 6.21 (s, 1H), 4.98-4.93 (m, 4H), 4.15-4.11 (m, 2H), 3.70 (s, 3H), 3.21-3.20 (m, 2H), 3.16-3.05 (m, 2H), 2.46-2.38 (m, 3H), 2.32-2.18 (m, 5H), 1.16-1.15 (m, 6H); LCMS: m/z 424.3 (M + H)⁺. |
| 53 | 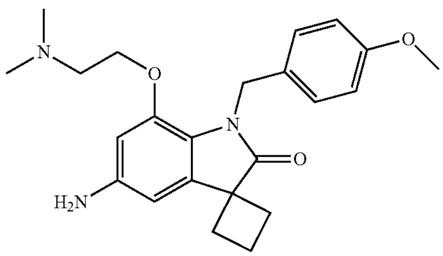 | ¹H NMR (400 MHz, DMSO-d₆): δ 7.06-7.03 (m, 2H), 6.85 (d, J = 8.3 Hz, 2H), 6.58-6.56 (m, 1H), 6.23 (s, 1H), 4.98-4.87 (m, 4H), 4.04-3.87 (m, 1H), 3.70 (s, 3H), 2.50-2.40 (m, 10H), 2.33-2.08 (m, 4H), 1.17-1.07 (m, 3H); LCMS: m/z 410.3 (M + H)⁺. |
| 54 | 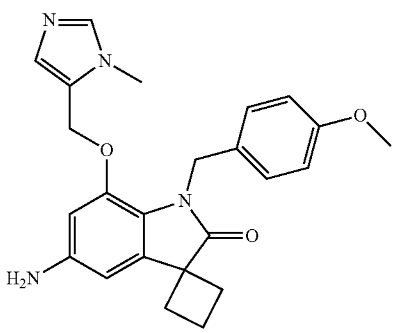 [SMILES: COc1ccc(CN2C(=O)C3(CCC3)c3cc(N)cc(OCc4cncn4C)c32)cc1] | LCMS: m/z 419.1 (M + H)⁺. |
| 55 | 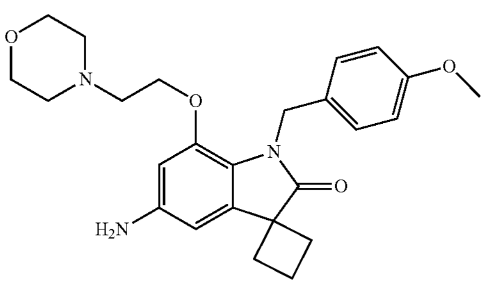 [SMILES: COc1ccc(CN2C(=O)C3(CCC3)c3cc(N)cc(OCCN4CCOCC4)c32)cc1] | ¹H NMR (400 MHz, DMSO-d₆): δ 7.13 (d, J = 8.3 Hz, 2H), 6.83 (d, J = 8.8 Hz, 2H), 6.50 (d, J = 1.5 Hz, 1H), 6.19 (d, J = 1.5 Hz, 1H), 4.94 (s, 2H), 4.86 (bs, 2H), 3.91 (t, J = 5.4 Hz, 2H), 3.69 (s, 3H), 3.53-3.51 (m, 4H), 2.50-2.49 (m, 2H), 2.43-2.25 (m, 6H), 2.23-2.08 (m, 4H); LC-MS: m/z 438.3 (M + H)⁺. |
| 56 | 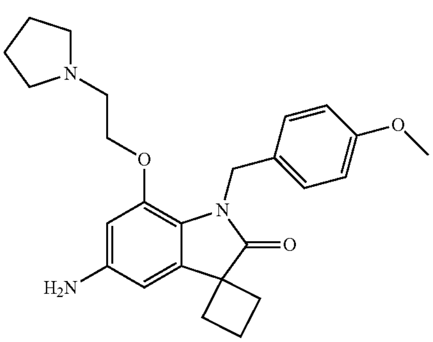 [SMILES: COc1ccc(CN2C(=O)C3(CCC3)c3cc(N)cc(OCCN4CCCC4)c32)cc1] | ¹H NMR (400 MHz, DMSO-d₆): δ 7.07 (d, J = 8.3 Hz, 2H), 6.85 (d, J = 8.8 Hz, 2H), 6.57 (s, 1H), 6.19 (d, J = 2.0 Hz, 1H), 4.95-4.93 (m, 4H), 4.04-4.02 (m, 2H), 3.69 (s, 3H), 2.85-2.78 (m, 2H), 2.51-2.43 (m, 6H), 2.25-2.08 (m, 4H), 1.85-1.75 (m, 4H); LC-MS: m/z 422.3 (M + H)⁺. |

Intermediate-57: 5'-Amino-7'-((2-chloropyridin-4-yl)oxy)-1'-(4-methoxybenzyl)-spiro[cyclobutane-1,3'-indolin]-2'-one

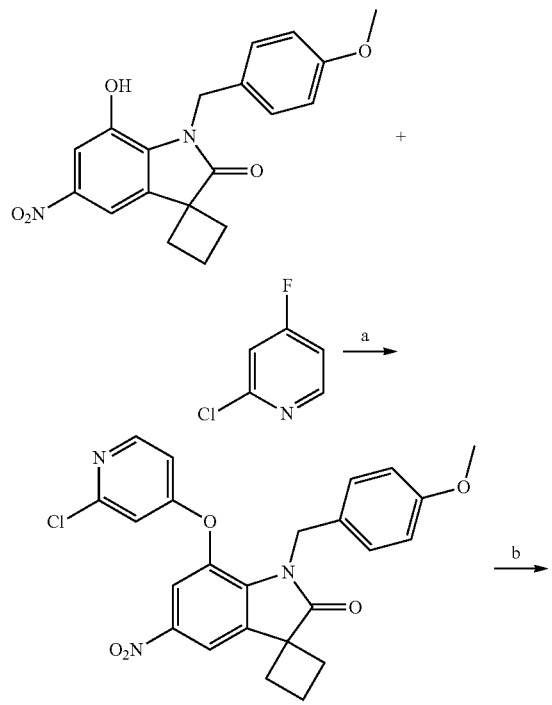

in DMF (10 mL) was added potassium carbonate (1.17 g, 8.46 mmol) and 2-chloro-4-fluoropyridine (1.5 g, 11.30 mmol) followed by heating to 100° C. for 16 h. The mixture was poured into water and extracted with EtOAc. The organic layer was dried over sodium sulphate and concentrated under reduced pressure. The residue was purified by combi-flash to afford the title compound as an off white solid (1.0 g, 76%). $^1$H NMR (400 MHz, DMSO-$d_6$): δ 8.53 (d, J=1.9 Hz, 1H), 8.18 (d, J=5.9 Hz, 1H), 7.94 (d, J=2.0 Hz, 1H), 6.89-6.84 (m, 3H), 6.78 (d, J=1.9 Hz, 1H),6.65 (d, J=8.8 Hz, 2H), 4.89 (s, 2H), 3.64 (s, 3H), 2.65-2.54 (m, 4H), 2.40-2.26 (m, 2H); LCMS: m/z 466.1 (M+H)$^+$.

Step-b: 5'-Amino-7'-((2-chloropyridin-4-yl)oxy)-1'-(4-methoxybenzyl)spiro [cyclobutane-1,3'-indolin]-2'-one The compound was prepared according to the procedure of step-d of Intermediate-18. $^1$H NMR (400 MHz, DMSO-$d_6$): δ 8.17-8.11 (m, 1H), 6.89 (d, J=1.9 Hz, 1H), 6.81 (d, J=8.8 Hz, 2H), 6.74-6.73 (m, 1H), 6.62 (d, J=2.3 Hz, 2H),6.52 (d, J=2.0 Hz, 1H), 6.04 (d, J=1.5 Hz, 1H), 5.09 (s, 2H), 4.72 (s, 2H), 3.63 (s, 3H), 2.60-2.50 (m, 2H), 2.40-2.38 (m, 4H); LCMS: m/z 436.2 (M+H)$^+$.

The below intermediate was prepared according to the protocol described in the synthesis of Intermediate-57 with appropriate variations in reactants, quantities of reagents, solvents and reaction conditions.

| No | Structure | Characterization Data |
|---|---|---|
| 58 | 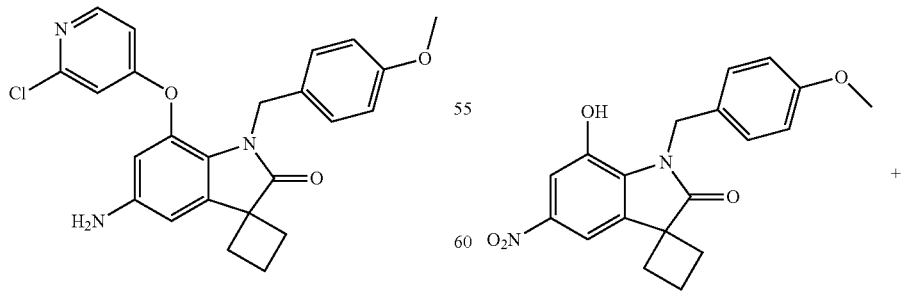 | $^1$H NMR (400 MHz, DMSO-$d_6$): δ 8.53-8.49 (m, 2H), 7.53 (d, J = 7.3 Hz, 1H), 7.35-7.32 (m, 1H), 6.86 (d, J = 8.4 Hz, 2H), 6.74 (d, J = 8.3 Hz, 2H), 6.53 (s, 1H), 6.25 (s, 1H), 4.96 (s, 2H), 4.91 (bs, 2H), 4.83 (s, 2H), 3.68 (s, 3H), 2.45-2.42 (m, 2H), 2.24-2.19 (m, 4H); LC-MS: m/z 416.2 (M + H)$^+$. |

-continued

Intermediate-59: 5'-Amino-7'-((6-aminopyridin-3-yl)oxy)-1'-(4-methoxybenzyl)spiro [cyclobutane-1,3'-indolin]-2'-one Step-a: 7'-((2-Chloropyridin-4-yl)oxy)-1'-(4-methoxybenzyl)-5'-nitrospiro [cyclobutane-1,3'-indolin]-2'-one To a solution of 7'-hydroxy-1'-(4-methoxybenzyl)-5'-nitrospiro[cyclobutane-1,3'-indolin]-2'-one (1.0 g, 2.82 mmol)

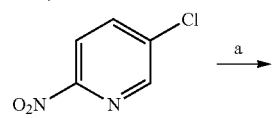

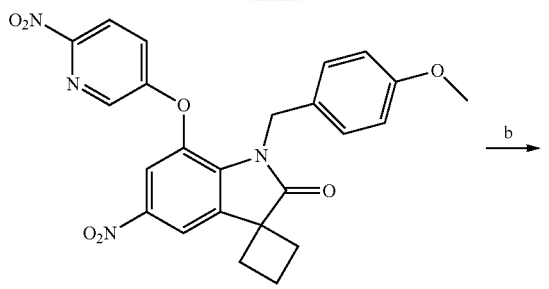

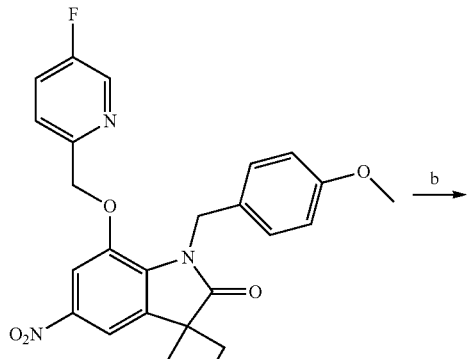

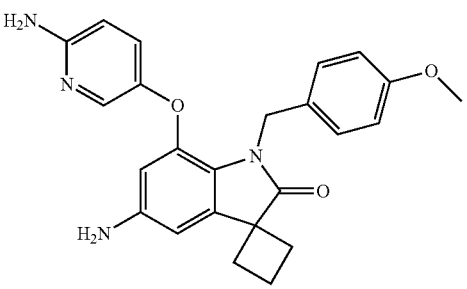

Step-a: 1'-(4-Methoxybenzyl)-5'-nitro-7'-((6-nitropyridin-3-yl)oxy)spiro[cyclobutane-1,3'-indolin]-2'-one The compound was prepared according to the procedure of step-a of Intermediate-50. $^1$H NMR (400 MHz, DMSO-$d_6$): δ 8.56 (d, J=2.0 Hz, 1H), 8.20 (d, J=2.4 Hz, 1H), 8.10 (d, J=8.8 Hz, 1H), 8.01 (d, J=1.4 Hz, 1H), 7.34-7.32 (m, 1H), 6.86 (d, J=8.3 Hz, 2H), 6.59 (d, J=8.3 Hz, 2H), 4.95 (s, 2H), 3.55 (s, 3H), 2.57-2.50 (m, 2H), 2.44-2.27 (m, 4H).

Step-b: 5'-Amino-7'-((6-aminopyridin-3-yl)oxy)-1'-(4-methoxybenzyl)spiro [cyclobutane-1,3'-indolin]-2'-one The compound was prepared according to the procedure of step-d of Intermediate-18. $^1$H NMR (400 MHz, DMSO-$d_6$): δ 7.43 (d, J=2.9 Hz, 1H), 7.05 (d, J=8.8 Hz, 2H), 6.85-6.80 (m, 3H), 6.58 (d, J=1.9 Hz, 1H), 6.39 (d, J=8.8 Hz, 1H), 5.83 (s, 2H), 5.76 (d, J=2.0 Hz, 1H), 4.89-4.87 (m, 4H), 3.69 (s, 3H), 2.55-2.51 (m, 2H), 2.28-2.09 (m, 4H); LC-MS: m/z 417.1 (M+H)$^+$.

Intermediate-60: 5'-Amino-7'-((5-fluoropyridin-2-yl)methoxy)-1'-(4-methoxybenzyl)-spiro[cyclobutane-1,3'-indolin]-2'-one

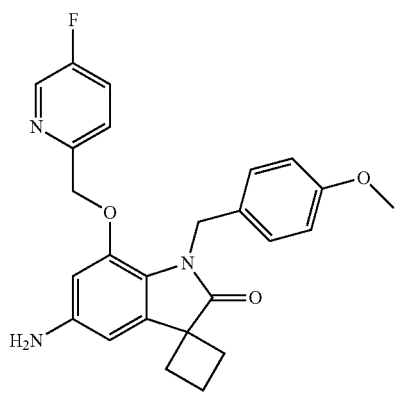

Step-a: 7'-((5-Fluoropyridin-2-yl)methoxy)-1'-(4-methoxybenzyl)-5'-nitrospiro[cyclobutane-1,3'-indolin]-2'-one To a solution of 7'-hydroxy-1'-(4-methoxybenzyl)-5'-nitrospiro[cyclobutane-1,3'-indolin]-2'-one (0.3 g, 0.84 mmol) in DMF (5 mL) was added potassium carbonate (0.35 g, 2.53 mmol) and (5-fluoropyridin-2-yl)methyl methane sulfonate (0.26 g, 1.26 mmol) followed by stirring at RT for 16 h. The mixture was poured into ice water and extracted with EtOAc. The organic layer was dried over sodium sulphate and concentrated under reduced pressure. The residue was purified by combi-flash to give the title compound as pale yellow solid (0.28 g, 71%). $^1$H NMR (400 MHz, DMSO-$d_6$): δ 8.60 (d, J=2.5 Hz, 1H), 8.23 (s, 1H), 7.89 (s, 1H), 7.72-7.67 (m, 1H), 7.31-7.28 (m, 1H), 6.96 (d, J=8.8 Hz, 2H), 6.77 (d, J=8.3 Hz, 2H), 5.30 (s, 2H), 5.04 (s, 2H), 3.68 (s, 3H), 2.56-2.43 (m, 4H), 2.34-2.20 (m, 2H); LC-MS: m/z 464.2 (M+H)$^+$.

Step-b: 5'-Amino-7'-((5-fluoropyridin-2-yl)methoxy)-1'-(4-methoxybenzyl) spiro[cyclobutane-1,3'-indolin]-2'-one The compound was prepared according to the procedure of step-d of Intermediate-18. $^1$H NMR (400 MHz, DMSO-$d_6$): δ 8.56 (d, J=2.4 Hz, 1H), 7.66-7.61 (m, 1H), 7.15-7.12 (m, 1H), 6.95 (d, J=8.4 Hz, 2H), 6.76 (d, J=8.3 Hz, 2H), 6.54 (s, 1H), 6.18 (s, 1H), 5.05 (bs, 2H), 4.99 (s, 2H), 4.89 (s, 2H), 3.68 (s, 3H), 2.46-2.43 (m, 2H), 2.25-2.12 (m, 4H); LC-MS: m/z 434.4 (M+H)$^+$.

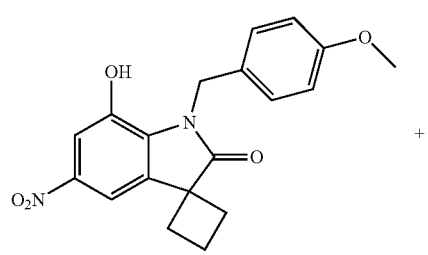

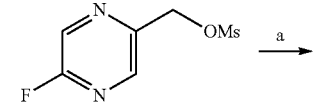

Intermediate-61: 5'-Amino-7'-(1-(thiazol-2-yl)vinyl)spiro[cyclobutane-1,3'-indolin]-2'-one

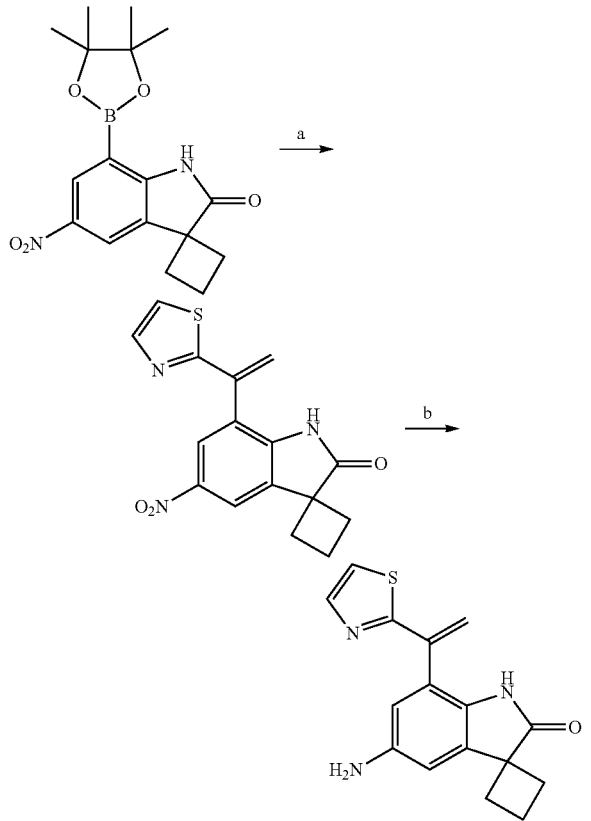

Step-a: 5'-Nitro-7'-(1-(thiazol-2-yl)vinyl)spiro[cyclobutane-1,3'-indolin]-2'-one To a solution of 5'-nitro-7'-(4,4,5,5-tetramethyl-1,3,2-dioxaborolan-2-yl)spiro-[cyclobutane-1,3'-indolin]-2'-one (0.3 g, 0.87 mmol, Intermediate-9) in 1,4-dioxane (10 mL) and H$_2$O (2 mL) were added 1-(thiazol-2-yl)vinyl trifluoro methane sulfonate (0.25 g, 0.96 mmol) and sodium carbonate (0.28 g, 2.61 mmol) followed by degassing with nitrogen purging for 20 min. Then Pd(PPh$_3$)$_4$ (0.1 g, 0.087 mmol) was added followed by heating at 100° C. for 16 h. The mixture was diluted with EtOAc (50 ml), washed with water (50 mL) and brine (50 mL), dried over sodium sulphate and concentrated under reduced pressure and purified by combi-flash to afford the title compound as pale yellow solid (0.25 g). $^1$H NMR (400 MHz, DMSO-d$_6$): δ 10.87 (s, 1H), 8.50 (d, J=2.4 Hz, 1H), 8.04 (d, J=2.0 Hz, 1H), 7.83 (d, J=2.5 Hz, 1H), 7.77 (d, J=3.5 Hz, 1H), 6.34 (s, 1H), 5.73 (s, 1H), 2.46-2.17 (m, 6H); LCMS: m/z 328.1 (M+H)$^+$.

Step-b: 5'-Amino-7'-(1-(thiazol-2-yl)vinyl)spiro[cyclobutane-1,3'-indolin]-2'-one To a solution of 5'-nitro-7'-(1-(thiazol-2-yl) vinyl) spiro [cyclobutane-1, 3'-indolin]-2'-one (0.25 g, 0.76 mmol) in EtOH (10 mL) and H$_2$O (3 mL) were added iron powder (0.21 g, 3.80 mmol) and NH$_4$Cl (0.21 g, 3.80 mmol) followed by heating to 100° C. for 2 h. The mixture was cooled to RT, filtered through celite and washed with EtOAc. The combined filtrate was concentrated, the residue was diluted with water and extracted with EtOAc (100 mL), washed with brine (100 mL), dried over sodium sulphate and concentrated under reduced pressure and purified by combi-flash to afford the title compound as pale yellow solid (0.1 g, 44%). $^1$H NMR (400 MHz, DMSO-d$_6$): δ 9.64 (s, 1H), 7.82 (d, J=3.4 Hz, 1H), 7.68 (d, J=2.9 Hz, 1H), 6.87 (d, J=2.5 Hz, 1H), 6.32 (d, J=2.0 Hz, 1H), 6.19 (s, 1H), 5.39 (s, 1H), 4.79 (s, 2H), 2.45-2.39 (m, 2H), 2.23-2.12 (m, 4H); LCMS: m/z 298.1 (M+H)$^+$.

Intermediate-62: 5'-Amino-7'-(1-(1-methylpiperidin-3-yl)ethyl)spiro[cyclobutane-1,3'-indolin]-2'-one

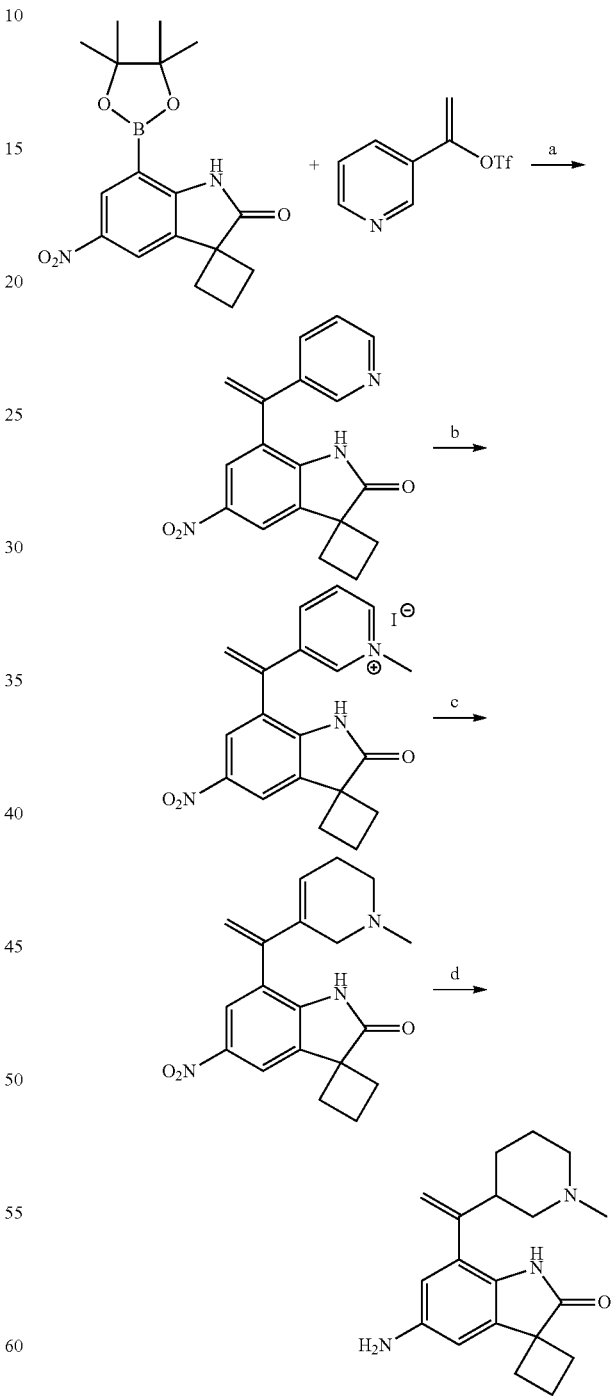

Step-a: 5'-Nitro-7'-(1-(pyridin-3-yl)vinyl)spiro[cyclobutane-1,3'-indolin]-2'-one To a solution of 5'-nitro-7'-(4,4,5,5-tetramethyl-1,3,2-dioxaborolan-2-yl)spiro-[cyclobutane-1,3'-indolin]-2'-one (0.5 g, 1.45 mmol, Intermediate-9) in 1,4-dioxane (10 mL) and H$_2$O (3 mL) in a sealed tube were added 1-(pyridin-3-yl)vinyl trifluoro-methanesulfonate (0.73 g, 2.90 mmol) and sodium carbonate (0.38 g, 3.62 mmol) followed by degassing with nitrogen purging for 20 min. Pd(PPh$_3$)$_4$ (0.17 g, 0.145 mmol) was added followed by heating at 100° C. for 16 h. The mixture was concentrated under reduced pressure and the residue was diluted with EtOAc (100 ml), washed with water (100 mL) and brine (100 mL), dried over sodium sulphate and concentrated under reduced pressure and purified by combi flash to afford the title compound as yellow solid (0.4 g). $^1$H NMR (400 MHz, DMSO-d$_6$): δ 10.72 (s, 1H), 8.57 (d, J=2.5 Hz, 1H), 8.54 (d, J=1.5 Hz, 1H), 8.53 (d, J=1.0 Hz, 1H), 7.90 (d, J=2.4 Hz, 1H), 7.68-7.53 (m, 1H), 7.40-7.36 (m, 1H), 6.10 (s, 1H), 5.56 (s, 1H), 2.48-2.41 (m, 4H), 2.28-2.22 (m, 2H). LCMS: m/z 322.2 (M+H)$^+$.

Step-b: 1-Methyl-3-(1-(5'-nitro-2'-oxospiro[cyclobutane-1,3'-indolin]-7'-yl)vinyl) pyridin-1-ium iodide To a solution of 5'-nitro-7'-(1-(pyridin-3-yl)vinyl)spiro[cyclobutane-1,3'-indolin]-2'-one (0.3 g, 0.93 mmol) in acetonitrile (5 mL) was added methyl iodide (0.58 mL, 9.30 mmol) followed by stirring at RT for 16 h. The mixture was concentrated under reduced pressure to affordthe title compound as white solid (0.35 g). LCMS: m/z 322.1 (M+H)$^+$.

Step-c: 7'-(1-(1-Methyl-1,2,5,6-tetrahydropyridin-3-yl)vinyl)-5'-nitrospiro[cyclobutane-1,3'-indolin]-2'-one To an ice cold suspension of 1-methyl-3-(1-(5'-nitro-2'-oxospiro [cyclobutane-1, 3'-indolin]-7'-yl)vinyl)pyridin-1-ium iodide (0.35 g, 0.75 mmol) in MeOH (8 mL) was added sodium borohydride (0.14 g, 3.75 mmol) portionwise over five min followed by stirring for 2 h at same condition. The reaction mixture was quenched with aqueous NH$_4$Cl and extracted with 10% MeOH in DCM. The organic layer was dried over sodium sulphate and concentrated under reduced pressure. The residue was purified by combi-flash to afford the title compound as brown solid (0.24 g). $^1$H NMR (400 MHz, DMSO-d$_6$): δ 10.75 (bs, 1H), 8.42 (d, J=2.0 Hz, 1H), 7.80 (d, J=2.5 Hz, 1H), 5.36 (s, 1H), 5.33-5.32 (m, 1H), 5.05 (s, 1H), 3.31-3.30 (m, 2H), 2.47-2.40 (m, 5H), 2.34 (s, 3H), 2.30-2.08 (m, 5H); LCMS: m/z 340.2 (M+H)$^+$.

Step-d: 5'-Amino-7'-(1-(1-methyl-1,2,5,6-tetrahydropyridin-3-yl)vinyl)spiro [cyclobutane-1,3'-indolin]-2'-one The compound was prepared according to the procedure of step-b of Intermediate-61. $^1$H NMR (400 MHz, DMSO-d$_6$): δ 9.85-9.80 (m, 1H), 6.68 (s, 1H), 6.26-6.24 (m, 1H), 4.75-4.65 (bs, 2H), 3.41-3.36 (m, 1H), 2.67-2.37 (m, 5H), 2.33-2.06 (m, 6H), 1.86-1.41 (m, 5H), 1.14-1.05 (m, 3H), 0.95-0.84 (m, 2H); LCMS: m/z 314.3 (M+H)$^+$.

Intermediate-63: 5'-Amino-1'-(4-methoxybenzyl)-2'-oxospiro [cyclobutane-1,3'-indolin]-7'-yl 4-methylpiperazine-1-carboxylate

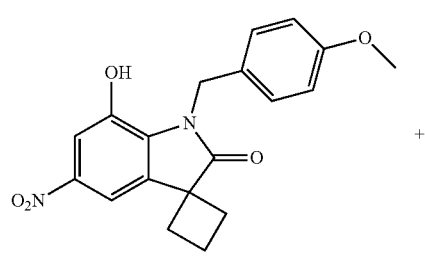

+

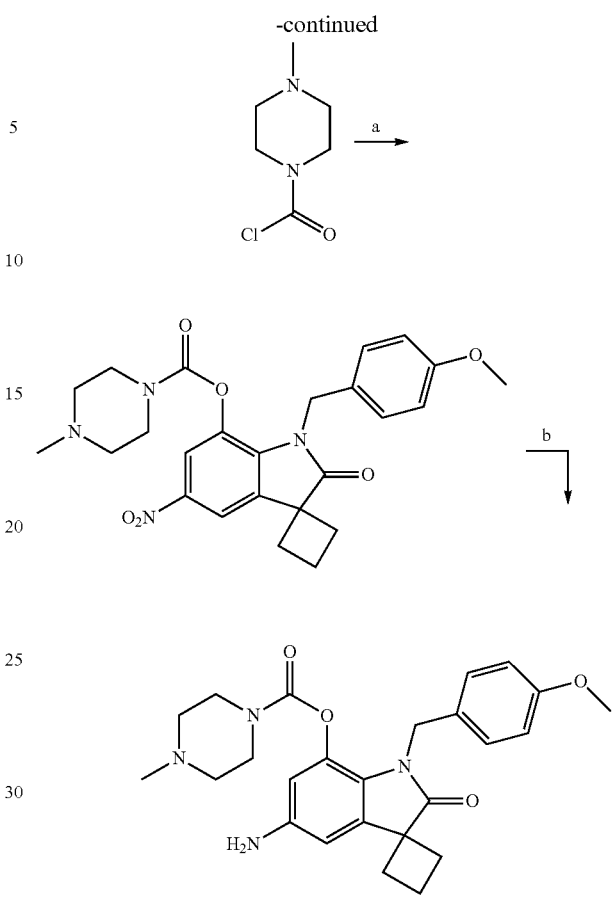

Step-a: 1'-(4-Methoxybenzyl)-5'-nitro-2'-oxospiro [cyclobutane-1,3'-indolin]-7'-yl 4-methylpiperazine-1-carboxylate To a cold solution of 7'-hydroxy-1'-(4-methoxybenzyl)-5'-nitrospiro[cyclobutane-1,3'-indolin]-2'-one (0.15 g, 0.42 mmol) in DMF (3 mL) was added potassium carbonate (0.14 g, 1.05 mmol) and DMAP (0.01 g, 0.08 mmol) followed by stirring for 10 min. 4-Methylpiperazine-1-carbonyl chloride (0.14 g, 0.84 mmol) was added followed by stirring at RT for 4 h. The mixture was poured into ice water, solids were filtered off, washed with water and dried under reduced pressure to give the title compound as brown solid (0.2 g). $^1$H NMR (400 MHz, DMSO-d$_6$): δ 8.46 (d, J=1.9 Hz, 1H), 7.99 (d, J=2.0 Hz, 1H), 6.98 (d, J=8.8 Hz, 2H), 6.86 (d, J=8.8 Hz, 2H), 4.95 (s, 2H), 3.70 (s, 3H), 3.33-3.28 (m, 8H), 2.33-2.20 (m, 6H), 2.16 (s, 3H); LC-MS: m/z 481.2 (M+H)$^+$.

Step-b: 5'-Amino-1'-(4-methoxybenzyl)-2'-oxospiro[cyclobutane-1,3'-indolin]-7'-yl 4-methylpiperazine-1-carboxylate The compound was prepared according to the procedure of step-d of Intermediate-18. $^1$H NMR (400 MHz, DMSO-d$_6$): δ 6.96 (d, J=8.4 Hz, 2H), 6.83 (d, J=8.8 Hz, 2H), 6.80 (d, J=1.9 Hz, 1H), 6.08 (d, J=1.9 Hz, 1H), 4.97 (s, 2H), 4.75 (s, 2H), 3.69 (s, 3H), 3.30-3.20 (m, 8H), 2.33-2.16 (m, 9H); LC-MS: m/z 451.2 (M+H)$^+$.

The below intermediate was prepared according to the protocol described in the synthesis of Intermediate-63 with appropriate variations in reactants, quantities of reagents, solvents and reaction conditions.

| No | Structure | Characterization Data |
|---|---|---|
| 64 | 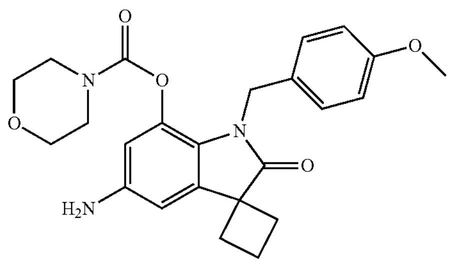 [SMILES: COc1ccc(CN2C(=O)C3(CCC3)c3cc(N)cc(OC(=O)N4CCOCC4)c32)cc1] | $^1$H NMR (400 MHz, DMSO-d$_6$): δ 6.97 (d, J = 8.3 Hz, 2H), 6.86-6.81 (m, 3H), 6.10 (d, J = 2.0 Hz, 1H), 4.77 (s, 2H), 3.69 (s, 3H), 3.51-3.46 (m, 4H), 3.23-3.21 (m, 4H), 2.49-2.48 (m, 2H), 2.33-2.18 (m, 4H); LCMS: m/z 438.2 (M + H)$^+$. |

The present invention is further exemplified, but not limited, by the following examples that illustrate the preparation of compounds according to the invention.

Example-I: 2,4-difluoro-N-(7'-(3-hydroxyphenyl)-2'-oxospiro[cyclobutane-1,3'-indolin]-5'-yl)benzenesulfonamide: (Compound-1)

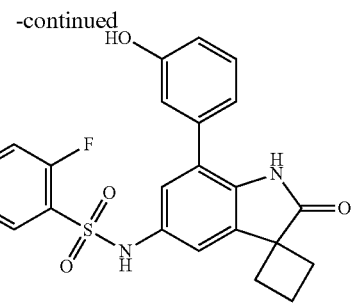

Compound-1

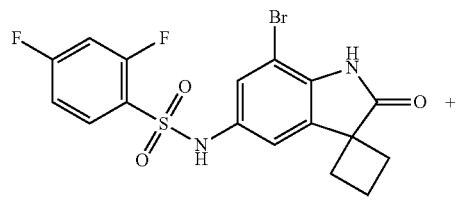

Intermediate-1

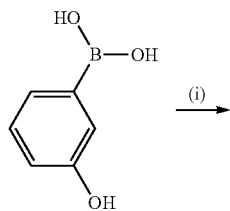

(i)

To a solution of N-(7'-bromo-2'-oxospiro[cyclobutane-1,3'-indolin]-5'-yl)-2,4-difluoro benzenesulfonamide (intermediate-1) (0.15 g, 0.34 mmol) in 1,4-dioxane (8 mL) and H$_2$O (2 mL) were added (3-hydroxyphenyl)boronic acid (0.057 g, 0.41 mmol), potassium phosphate (0.22 g, 1.02 mmol). The mixture was degassed with nitrogen purging for 20 min. Then Pd(Amphos)Cl$_2$(0.024 g, 0.034 mmol) was added and the mixture was heated at 100° C. for 16 h. The mixture was concentrated under reduced pressure and the residue was diluted with EtOAc (100 ml), washed with water (100 mL), brine (100 mL), dried over sodium sulphate and concentrated under reduced pressure and column purified to afford the title compound as white solid (0.07 g, 45%). $^1$H NMR (400 MHz, DMSO-d$_6$): δ 10.39 (s,1H), 10.04 (s, 1H), 9.51 (s, 1H), 7.88-7.82 (m, 1H), 7.58-7.53 (m, 1H), 7.27-7.19 (m, 3H), 6.82 (d, J=2.0 Hz, 1H), 6.75 (dd, J$_1$=7.8 Hz, J$_2$=1.5 Hz, 1H), 6.69-6.66 (m, 2H), 2.44-2.38 (m, 2H), 2.24-2.06 (m, 4H); LC-MS: m/z 457.1 (M+H)$^+$.

The below compounds were prepared by procedure similar to the one described in Example-I with appropriate variations in reactants, quantities of reagents and reaction conditions. The physiochemical characteristics of the compounds are also summarized.

| No | Reactant | Obtained Compound | Characterization Data $^1$H NMR (400 MHz, DMSO-d$_6$)/ LC-MS: |
|---|---|---|---|
| 2 | | | δ 10.47 (s, 1H), 10.29 (s, 1H), 8.20 (d, J = 5.4 Hz, 1H), 7.89-7.83 (m, 1H), 7.60-7.54 (m, 1H), 7.32 (d, J = 2.0 Hz, 1H), 7.28-7.23 (m, 1H), 6.87-6.86 (m, 2H), 6.68 (s, 1H), 3.88 (s, 3H), 2.46-2.38 (m, 2H), 2.24-2.09 (m, 4H); LC-MS: m/z 472.1 (M + H)$^+$. |

-continued

| No | Reactant | Obtained Compound | Characterization Data<br>¹H NMR (400 MHz, DMSO-d₆)/<br>LC-MS: |
|---|---|---|---|
| 3 | | | δ 10.44 (s, 1H), 10.25 (s, 1H), 8.06 (d, J = 1.9 Hz, 1H), 7.89-7.83 (m, 1H), 7.63-7.54 (m, 2H), 7.28-7.23 (m, 2H), 6.87 (d, J = 8.3 Hz, 1H), 6.81 (d, J = 2.0 Hz, 1H), 3.89 (s, 3H), 2.42-2.38 (m, 2H), 2.22-2.08 (m, 4H); LC-MS: m/z 472.1 (M + H)⁺. |
| 4 | | | δ 10.41 (s, 1H), 10.05 (s, 1H), 10.03 (s, 1H), 7.88-7.83 (m, 1H), 7.57-7.52 (m, 1H), 7.27-7.20 (m, 3H), 6.83-6.78 (m, 3H), 2.89 (t, J = 7.9 Hz, 2H), 2.46-2.32 (m, 4H), 2.23-2.07 (m, 4H); LC-MS: m/z 510.2 (M + H)⁺. |
| 5 | | | δ 10.40 (s, 1H), 10.17 (s, 1H), 8.21 (s, 1H), 7.88-7.86 (m, 1H), 7.69 (d, J = 8.4 Hz, 1H), 7.57 (t, J = 7.8 Hz, 1H), 7.48 (s, 1H), 7.26 (s, 2H), 7.06 (d, J = 8.3 Hz, 1H), 6.92 (d, J = 1.9 Hz, 1H), 3.86 (s, 3H), 2.45-2.41 (m, 2H), 2.20-2.08 (m, 4H); LCMS: m/z 495.2 (M + H)⁺. |
| 6 | | | δ 10.40 (s, 1H), 10.16 (s, 1H), 7.89-7.83 (m, 1H), 7.60-7.54 (m, 1H), 7.28-7.23 (m, 2H), 7.26 (s, 1H), 6.92 (s, 1H), 6.86 (d, J = 5.8 Hz, 1H), 6.84 (d, J = 1.9 Hz, 1H), 3.27 (s, 3H), 2.88 (t, J = 7.4 Hz, 2H), 2.56-2.53 (m, 2H), 2.43-2.39 (m, 2H), 2.23-2.08 (m, 4H); LC-MS: m/z 524.2 (M + H)⁺. |

| No | Reactant | Obtained Compound | Characterization Data<br>¹H NMR (400 MHz, DMSO-d₆)/<br>LC-MS: |
|---|---|---|---|
| 7 | 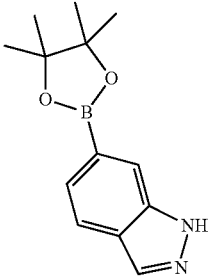 | 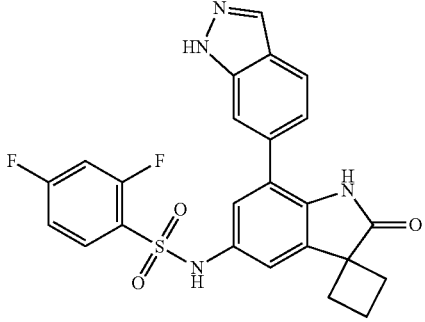 [SMILES: O=C1Nc2c(-c3ccc4cn[nH]c4c3)cc(NS(=O)(=O)c3ccc(F)cc3F)cc2C12CCC2] | δ 13.11 (s, 1H), 10.42 (brs, 1H), 10.19 (s, 1H), 8.09 (s, 1H), 7.91-7.84 (m, 1H), 7.81 (d, J = 8.3 Hz, 1H), 7.59-7.53 (m, 1H), 7.42 (s, 1H), 7.27-7.24 (m, 2H), 6.98 (d, J = 8.3 Hz, 1H), 6.92 (d, J = 1.9 Hz, 1H), 2.44-2.41 (m, 2H), 2.26-2.09 (m, 4H); LC-MS: m/z 481.1 (M + H)⁺. |
| 8 | 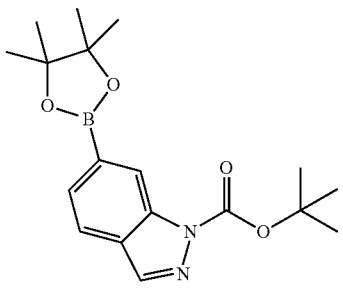 | 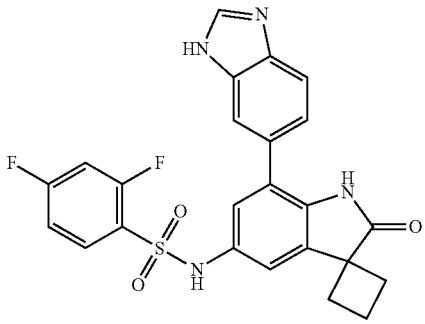 [SMILES: O=C1Nc2c(-c3ccc4nc[nH]c4c3)cc(NS(=O)(=O)c3ccc(F)cc3F)cc2C12CCC2] | δ 12.60 (bs, 1H), 11.39 (s, 1H), 10.11 (s, 1H), 8.28 (s, 1H), 7.89-7.83 (m, 1H), 7.63 (d, J = 8.4 Hz, 1H), 7.59-7.53 (m, 1H), 7.47 (s, 1H), 7.29-7.23 (m, 2H), 7.08 (d, J = 7.8 Hz, 1H), 6.89 (d, J = 2.0 Hz, 1H), 2.44-2.32 (m, 2H), 2.19-2.10 (m, 4H); LCMS: m/z 481.1 (M + H)⁺. |
| 9 | 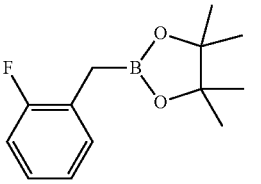 | 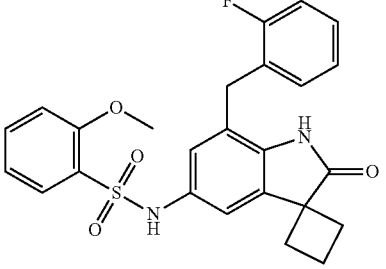 | δ 10.40 (s, 1H), 9.51 (s, 1H), 7.57-7.49 (m, 2H), 7.32-7.27 (m, 1H), 7.19-7.01 (m, 5H), 6.94 (t, J = 6.9 Hz, 1H), 6.49 (d, J = 1.4 Hz, 1H), 3.77 (s, 3H), 3.76 (s, 2H), 2.41-2.33 (m, 2H), 2.21-2.01 (m, 4H); LCMS: m/z 467.2 (M + H)⁺. |
| 10 | 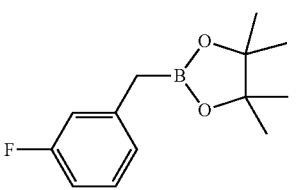 | 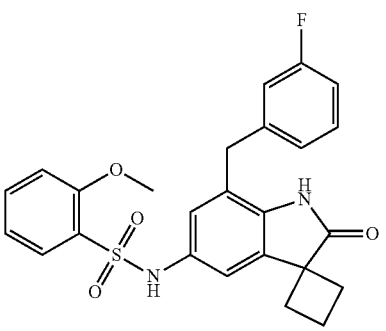 [SMILES: COc1ccccc1S(=O)(=O)Nc1cc(Cc2cccc(F)c2)c2c(c1)C1(CCC1)C(=O)N2] | δ 10.34 (s, 1H), 9.55 (s, 1H), 7.60 (dd, J = 7.8, 1.9 Hz, 1H), 7.55-7.50 (m, 1H), 7.30-7.26 (m, 1H), 7.11-7.08 (m, 2H), 7.04-6.99 (m, 1H), 6.95 (t, J = 7.4 Hz, 1H), 6.90-6.85 (m, 2H), 6.63 (d, J = 1.9 Hz, 1H), 3.82 (s, 3H), 3.77 (s, 2H), 2.40-2.32 (m, 2H), 2.20-2.06 (m, 4H); LCMS: m/z 467.2 (M + H)⁺. |
| 11 | 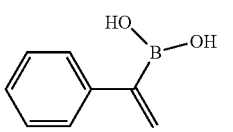 | 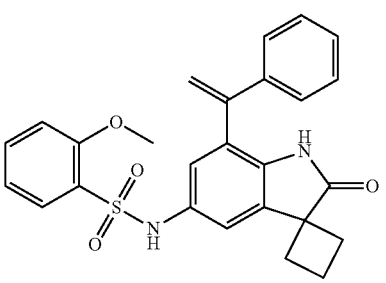 [SMILES: C=C(c1ccccc1)c1cc(NS(=O)(=O)c2ccccc2OC)cc2c1NC(=O)C21CCC1] | δ 9.82 (s, 1H), 9.62 (s, 1H), 7.64 (d, J = 7.9 Hz, 1H), 7.55 (t, J = 8.3 Hz, 1H), 7.32-7.30 (m, 3H), 7.26 (d, J = 1.4 Hz, 1H), 7.13 (d, J = 8.3 Hz, 1H), 7.07-7.05 (m, 2H), 7.00 (t, J = 7.3 Hz, 1H), 6.58 (d, J = 1.9 Hz, 1H), 5.74 (s, 1H), 5.16 (s, 1H), 3.78 (s, 3H), 2.39-2.32 (m, 2H), 2.19-2.11 (m, 4H); LCMS: m/z 461.2 (M + H)⁺. |

Example-II: N-(7'-amino-2'-oxospiro[cyclobutane-1,3'-indolin]-5'-yl)-2-methoxy-benzenesulfonamide: (Compound-12)

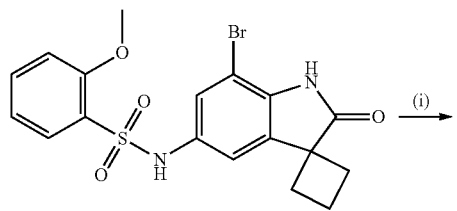

Intermediate-2

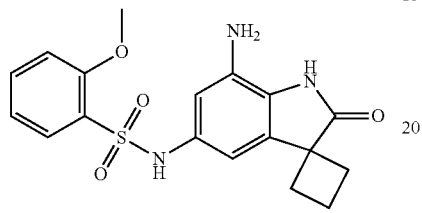

Compound-12

To a solution of N-(7'-bromo-2'-oxospiro[cyclobutane-1,3'-indolin]-5'-yl)-2-methoxybenzenesulfonamide (intermediate-2) (0.2 g, 0.46 mmol) in DMSO (1 mL) were added copper(1)iodide (0.009 g, 0.046), L-proline (0.01 g, 0.09 mmol), NaOH (0.03 g, 0.69 mmol) followed by aqueous ammonia (1 mL). The mixture was stirred at 100° C. in sealed tube for 16 h. The mixture was diluted with EtOAc (100 mL) and washed with water (100 mL) and brine (50 mL), dried over sodium sulphate and concentrated under reduced pressure and purified by preparative HPLC to afford the title compound as pale brown solid (0.03 g, 17%.). $^1$H NMR (400 MHz, DMSO-$d_6$): δ 9.56 (s, 1H), 9.44 (s, 1H), 7.66 (dd, J=1.5 Hz & 7.9 Hz, 1H), 7.54 (t, J=6.9 Hz, 1H), 7.17 (d, J=7.8 Hz, 1H), 6.98 (t, J=7.3 Hz, 1H), 6.55 (d, J=1.5 Hz, 1H), 6.35 (d, J=1.4 Hz, 1H), 5.0 (bs, 2H), 3.93 (s, 3H), 2.36-2.31 (m, 2H), 2.20-2.00 (m, 4H); LC-MS: m/z 374.1 (M+H)$^+$.

Example-III: N-(7'-((cyclopropylmethyl)amino)-2'-oxospiro[cyclobutane-1,3'-indolin]-5'-yl)-2-methoxybenzenesulfonamide (P1): (Compound-13) and N-(7'-(but-3-en-1-ylamino)-2'-oxospiro[cyclobutane-1,3'-indolin]-5'-yl)-2-methoxybenzenesulfonamide (P2): (Compound-14)

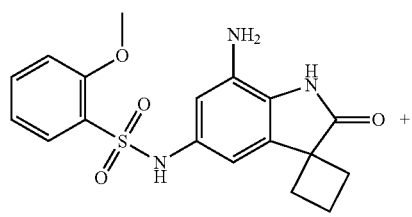

Compound-12

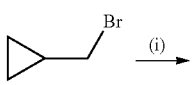

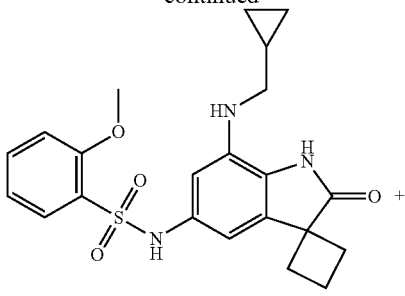

Compound-13

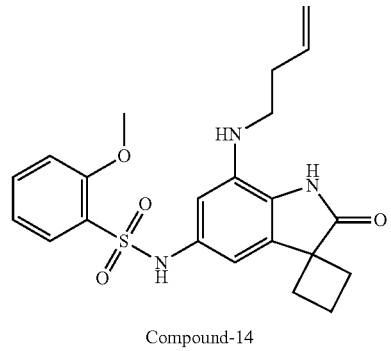

Compound-14

To a solution of N-(7'-amino-2'-oxospiro[cyclobutane-1,3'-indolin]-5'-yl)-2-methoxy benzenesulfonamide (Compound-12) (0.15 g, 0.4 mmol) in isopropyl alcohol (0.3 mL) was added(bromomethyl)cyclopropane (0.08 mL, 0.8 mmol). The mixture was stirred at 120° C. for 16 h. The mixture was diluted with EtOAc (100 mL), washed with water (100 mL) and brine (50 mL), dried over sodium sulphate and concentrated under reduced pressure and purified by preparative HPLC to afford the title compounds as off white solids P1(0.006 g, 4%.) & P2 (0.004 g, 2%). Compound-13 (P1): $^1$H NMR (400 MHz, DMSO-$d_6$): δ 9.71 (s, 1H), 9.41 (s, 1H), 7.68-7.66 (m, 1H), 7.53 (t, J=7.9 Hz, 1H), 7.16 (d, J=8.3 Hz, 1H), 6.97 (t, J=7.8 Hz, 1H), 6.55 (s, 1H), 6.20 (s, 1H), 4.95 (bs, 1H), 3.92 (s, 3H), 2.77-2.75 (m, 2H), 2.33-2.22 (m, 2H), 2.14-2.0 (m, 4H), 0.93-0.85 (m, 1H), 045 (d, J=7.3 Hz, 2H), 0.17 (d, J=4.4, 2H); ES-MS: m/z 426.5 (M−H)$^-$. Compound-14 (P2): $^1$H NMR (400 MHz, DMSO-$d_6$): δ 9.64 (s, 1H), 9.43 (s, 1H), 7.67 (dd, J=1.5 Hz & 7.8 Hz, 1H), 7.55-7.51 (m, 1H), 7.16 (d, J=7.8 Hz, 1H), 6.98 (t, J=7.4, 1H), 6.56 (d, J=1.4 Hz, 1H), 6.20 (d, J=1.4 Hz, 1H), 5.86-5.80 (m, 1H), 5.11-5.04 (m, 2H), 4.86-4.80 (m, 1H), 3.92 (s, 3H), 2.97-2.95 (m, 2H), 2.33-2.30 (m, 2H), 2.23-2.04 (m, 4H), 2.02-2.00 (m, 2H); ES-MS: m/z 428.3 (M+H)$^+$.

Example-IV: N-(7'-amino-2'-oxospiro[cyclobutane-1,3'-indolin]-5'-yl)-2,4-difluoro-benzenesulfonamide: (Compound-15)

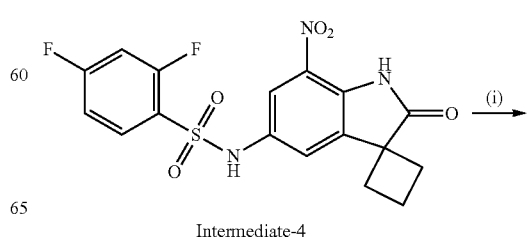

Intermediate-4

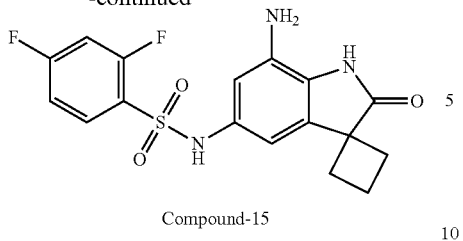

Compound-15

To a solution of 2,4-difluoro-N-(7'-nitro-2'-oxospiro[cyclobutane-1,3'-indolin]-5'-yl)benzenesulfonamide (intermediate-4) (6.7 g, 16.38 mmol) in EtOH (70 mL) and H₂O (35 mL) were added iron powder (4.6 g, 81.90 mmol) and NH₄Cl (2.6 g, 49.18 mmol). The mixture was heated to 100° C. for 2 h. The mixture was cooled to RT, filtered through celite and washed with EtOAc. The combined filtrate was concentrated, the residue was diluted with water and extracted with EtOAc (200 mL), washed with brine (200 mL), dried over sodium sulphate and concentrated under reduced pressure and purified to afford the title compound as brown solid (5.8 g, 93%). ¹H NMR (400 MHz, DMSO-d₆): δ 10.07 (s, 1H), 9.67 (s, 1H), 7.82-7.76 (m, 1H), 7.55-7.50 (m, 1H), 7.25-7.20 (m, 1H), 6.51 (d, J=1.5 Hz, 1H), 6.28 (d, J=2.0 Hz, 1H), 4.93 (s, 2H), 2.38-2.31 (m, 2H), 2.20-1.99 (m, 4H); ES-MS: m/z 378.1 (M−H)⁻.

Example-V: 2,4-difluoro-N-(7'-((1-methylpiperidin-3-yl)amino)-2'-oxospiro [cyclobutane-1,3'-indolin]-5'-yl)benzenesulfonamide (Compound-16)

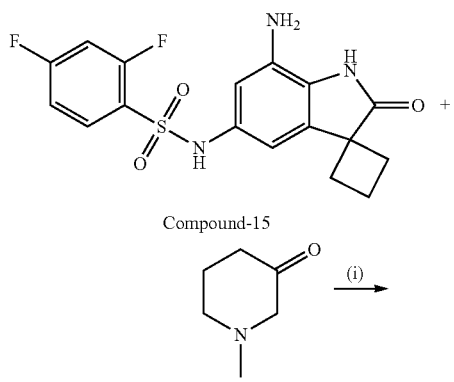

Compound-15

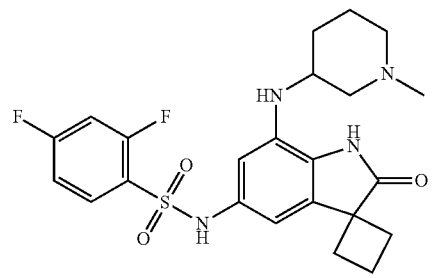

Compound-16

To a suspension of N-(7'-amino-2'-oxospiro[cyclobutane-1,3'-indolin]-5'-yl)-2,4-difluorobenzenesulfonamide (compound-15) (0.15 g, 0.39 mmol) in titanium isopropoxide (1.5 mL) was added 1-methylpiperidine-3-one (0.07 g, 0.59 mmol). The mixture was stirred at RT for 16 h. The mixture was cooled to 0° C., MeOH (3 mL) was added followed by NaBH4 (0.03 g, 0.78 mmol). The mixture was stirred at RT for 3 h. The mixture was diluted with EtOAc (100 mL), washed with aqueous ammonia (100 mL) and water (100 mL), dried over sodium sulphate and concentrated under reduced pressure and column purified to afford the title compound as off white solid (0.07 g, 37%). ¹H NMR (400 MHz, DMSO-d₆): δ 10.06 (bs, 1H), 9.81 (s, 1H), 7.82-7.76 (m, 1H), 7.53 (t, J=8.8 Hz, 1H), 7.22 (t, J=7.8 Hz, 1H), 6.55 (s, 1H), 6.17(s, 1H), 4.77 (d, J=7.8 Hz, 1H), 3.20-3.15 (m, 1H), 2.70-2.67 (m, 1H), 2.37-2.34 (m, 2H), 2.14 (s, 3H), 2.10-2.05 (m, 4H), 1.98-1.90 (m, 2H), 1.69-1.65 (m, 3H), 1.49-1.46 (m, 1H), 1.07-1.04 (m, 1H); LC-MS: m/z 477.2 (M+H)⁺.

The below compounds were prepared by procedure similar to the one described in Example-V with appropriate variations in reactants, quantities of reagents and reaction conditions. The physiochemical characteristics of the compounds are also summarized.

| No | Reactant | Obtained Compound | Characterization Data ¹H NMR (400 MHz, DMSO-d₆)/ LC-MS: |
|---|---|---|---|
| 17 | | | δ 10.06 (bs, 1H), 9.77 (s, 1H), 7.82-7.76 (m, 1H), 7.57-7.52 (m, 1H), 7.25-7.21 (m, 1H), 6.55 (s, 1H), 6.14 (s, 1H), 4.79 (d, J = 6.8 Hz, 1H), 3.07-2.95 (m, 1H), 2.89-2.78 (m, 2H), 2.38-2.20 (m, 5H), 2.17-2.00 (m, 6H), 1.80-1.76 (m, 2H), 1.34-1.23 (m, 2H); LC-MS: m/z 477.2 (M + H)⁺. |

| No | Reactant | Obtained Compound | Characterization Data<br>¹H NMR (400 MHz, DMSO-d₆)/<br>LC-MS: |
|---|---|---|---|
| 18 | 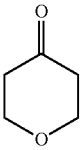 | 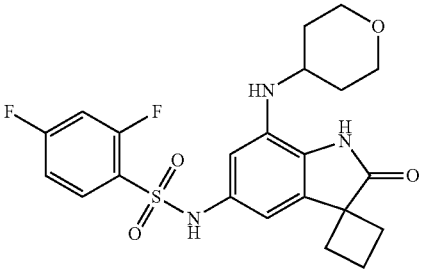 [SMILES: O=C1Nc2c(NC3CCOCC3)cc(NS(=O)(=O)c3ccc(F)cc3F)cc2C12CCC2] | δ 10.07 (s, 1H), 9.76 (s, 1H), 7.80-7.76 (m, 1H), 7.58-7.52 (m, 1H), 7.26-7.21 (m, 1H), 6.55 (s, 1H), 6.17 (s, 1H), 4.79 (d, J = 7.8 Hz, 1H), 3.84 (d, J = 11.7 Hz, 2H), 3.40-3.34 (m, 2H), 3.26-3.19 (m, 1H), 2.38-2.34 (m, 2H), 2.18-1.99 (m, 4H), 1.75 (d, J = 11.7 Hz, 2H), 1.31-1.16 (m, 2H); LC-MS: m/z 464.2 (M + H)⁺. |
| 19 | 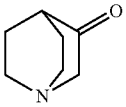 | 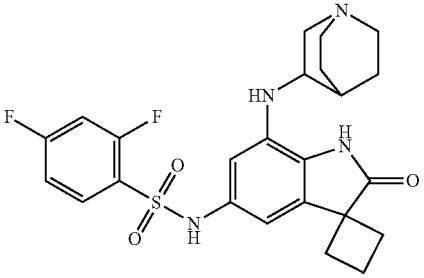 [SMILES: O=C1Nc2c(NC3CN4CCC3CC4)cc(NS(=O)(=O)c3ccc(F)cc3F)cc2C12CCC2] | δ 10.1 (bs, 1H), 9.87 (s, 1H), 7.81-7.76 (m, 1H), 7.57-7.53 (m, 1H), 7.25-7.21 (m, 1H), 6.56 (d, J = 1.0 Hz, 1H), 6.05 (s, 1H), 4.91 (d, J = 5.7 Hz, 1H), 3.22-3.15 (m, 2H), 2.75-2.71 (m, 4H), 2.36-2.34 (m, 4H), 2.19-2.01 (m, 2H), 1.66-1.60 (m, 4H), 1.50-1.45 (m, 1H), 1.35-1.33 (m, 1H); LC-MS: m/z 489.2 (M + H)⁺. |
| 20 | 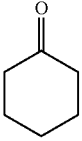 | 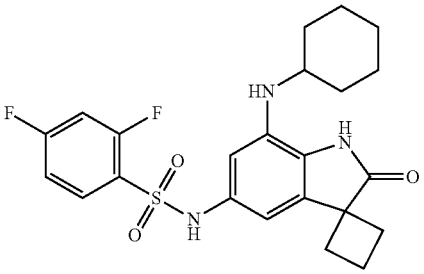 [SMILES: O=C1Nc2c(NC3CCCCC3)cc(NS(=O)(=O)c3ccc(F)cc3F)cc2C12CCC2] | δ 10.03 (s, 1H), 9.76 (s, 1H), 7.79-7.74 (m, 1H), 7.55-7.50 (m, 1H), 7.23-7.18 (m, 1H), 6.52 (d, J = 1.5 Hz, 1H), 6.07 (d, J = 1.5 Hz, 1H), 4.69 (d, J = 7.3 Hz, 1H), 2.94-2.90 (m, 1H), 2.36-2.30 (m, 2H), 2.16-1.99 (m, 4H), 1.77-1.56 (m, 5H), 1.30-1.14 (m, 3H), 1.05-0.85 (m, 2H); LC-MS: m/z 462.2 (M + H)⁺. |
| 21 | 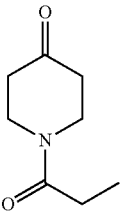 | 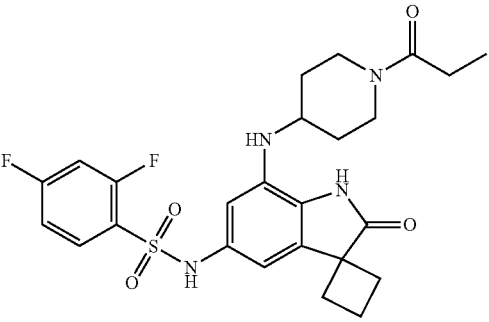 [SMILES: CCC(=O)N1CCC(Nc2cc(NS(=O)(=O)c3ccc(F)cc3F)cc3c2NC(=O)C32CCC2)CC1] | δ 10.09 (s, 1H), 9.76 (s, 1H), 7.83-7.78 (m, 1H), 7.58-7.54 (m, 1H), 7.26-7.23 (m, 1H), 6.55 (d, J = 1.0 Hz, 1H), 6.19 (d, J = 0.9 Hz, 1H), 4.77 (d, J = 7.4 Hz, 1H), 4.17 (d, J = 7.4 Hz, 1H), 3.78 (d, J = 13.7, 1H), 3.28-3.25 (m, 1H), 3.15-3.11 (m, 1H), 2.81 (t, J = 11.1 Hz, 1H), 2.37-2.31 (m, 4H), 2.18-2.02 (m, 4H), 1.83-1.75 (m, 2H), 1.23-1.08 (m, 2H), 0.99 (t, J = 7.3 Hz, 3H); LC-MS: m/z 517.2 (M − H)⁻. |
| 22 | 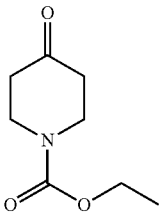 | 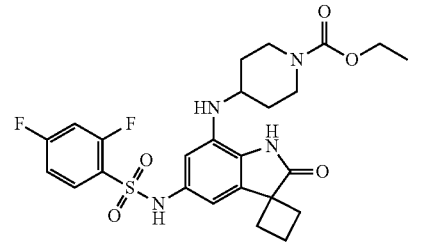 [SMILES: CCOC(=O)N1CCC(Nc2cc(NS(=O)(=O)c3ccc(F)cc3F)cc3c2NC(=O)C32CCC2)CC1] | δ 10.08 (s, 1H), 9.76 (s, 1H), 7.82-7.78 (m, 1H), 7.58-7.54 (m, 1H), 7.26-7.22 (m, 1H), 6.56 (d, J = 1.6 Hz, 1H), 6.17 (d, J = 1.6 Hz, 1H), 4.77 (d, J = 7.7 Hz, 1H), 4.04 (q, J = 7.2 Hz, 2H), 3.88-3.85 (m, 2H), 3.29-3.18 (m, 1H), 3.08-2.90 (m, 2H), 2.38-2.32 (m, 2H), 2.20-2.00 (m, 4H), 1.78-1.76 (m, 2H), 1.19 (t, J = 7.3 Hz, 3H); LC-MS: m/z 535.2 (M + H)⁺. |

-continued

| No | Reactant | Obtained Compound | Characterization Data<br>¹H NMR (400 MHz, DMSO-d₆)/<br>LC-MS: |
|---|---|---|---|
| 23 | 4-pyridinecarboxaldehyde | 2,4-difluoro-N-(7-((pyridin-4-ylmethyl)amino)-2-oxospiro[indoline-3,1'-cyclobutan]-5-yl)benzenesulfonamide | δ 10.07 (s, 1H), 9.72 (s, 1H), 8.51 (d, J = 5.9 Hz, 2H), 7.62-7.56 (m, 1H), 7.44-7.38 (m, 1H), 7.26 (d, J = 5.9 Hz, 2H), 7.15-7.10 (m, 1H), 6.56 (d, J = 1.4 Hz, 1H), 6.06 (d, J = 2.0 Hz, 1H), 5.70 (t, J = 5.9 Hz, 1H), 4.25 (d, J = 5.9 Hz, 2H), 2.39-2.33 (m, 2H), 2.18-2.04 (m, 4H); LC-MS: m/z 471.1 (M + H)⁺. |
| 24 | 1-ethylpiperidin-4-one | 2,4-difluoro-N-(7-((1-ethylpiperidin-4-yl)amino)-2-oxospiro[indoline-3,1'-cyclobutan]-5-yl)benzenesulfonamide | δ 10.02 (bs, 1H), 9.77 (s, 1H), 7.81-7.75 (m, 1H), 7.58-7.52 (m, 1H), 7.26-7.21 (m, 1H), 6.55 (s, 1H), 6.12 (s, 1H), 4.76 (d, J = 7.3 Hz, 1H), 2.97-2.82 (m, 2H), 2.73-2.67 (m, 2H), 2.38-2.34 (m, 4H), 2.19-1.91 (m, 5H), 1.76 (d, J = 11.7 Hz, 2H), 1.27-1.18 (m, 2H), 1.01 (t, J = 7.1 Hz, 3H),; LC-MS: m/z 491.1 (M + H)⁺. |
| 25 | 1H-imidazole-5-carbaldehyde | 2,4-difluoro-N-(7-((1H-imidazol-5-ylmethyl)amino)-2-oxospiro[indoline-3,1'-cyclobutan]-5-yl)benzenesulfonamide | δ 11.97 (bs, 1H), 10.12 (s, 1H), 9.76 (s, 1H), 7.78-7.76 (m, 1H), 7.61 (s, 1H), 7.52-7.50 (m, 1H), 7.21-7.19 (m, 1H), 6.96 (s, 1H), 6.55 (s, 1H), 6.31 (s, 1H), 5.26 (t, J = 4.9 Hz, 1H), 4.03 (d, J = 4.9 Hz, 2H), 2.36-2.23 (m, 2H), 2.16-2.03 (m, 4H); LC-MS: m/z 460.1 (M + H)⁺. |
| 26 | 6-fluoro-2,3-dihydro-1H-inden-1-one | 2,4-difluoro-N-(7-((6-fluoro-2,3-dihydro-1H-inden-1-yl)amino)-2-oxospiro[indoline-3,1'-cyclobutan]-5-yl)benzenesulfonamide | δ 10.15 (s, 1H), 9.70 (s, 1H), 7.83 (dd, J = 8.6 Hz & 15.0 Hz, 1H), 7.57-7.52 (m, 1H), 7.26-7.20 (m, 2H), 7.13-711 (m, 1H), 7.03-6.99 (m, 1H), 6.60 (s, 1H), 6.41 (s, 1H), 5.24 (d, J = 7.8 Hz, 1H), 4.72 (dd, J = 6.9 Hz & 13.3 Hz, 1H), 2.98-2.91 (m, 1H), 2.88-2.78 (m, 1H), 2.45-2.35 (m, 3H), 2.19-2.05 (m, 4H), 1.74-1.69 (m, 1H): LC-MS: m/z 512.2 (M − H)⁻. |

-continued

| No | Reactant | Obtained Compound | Characterization Data <br> ¹H NMR (400 MHz, DMSO-$d_6$)/ LC-MS: |
|---|---|---|---|
| 27 | 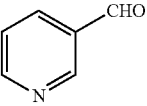 | 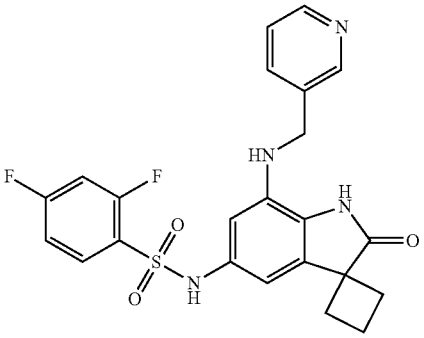 [SMILES: O=C1Nc2c(NCc3cccnc3)cc(NS(=O)(=O)c3ccc(F)cc3F)cc2C12CCC2] | δ 10.12 (s, 1H), 9.69 (s, 1H), 8.52-8.49 (m, 2H), 7.70-7.64 (m, 2H), 7.48-742 (m, 1H), 7.38-7.35 (m, 1H), 7.17-7.13 (m, 1H), 6.57 (s, 1H), 6.20 (s, 1H), 5.58 (t, J = 5.9 Hz, 1H), 4.22 (d, J = 5.9 Hz, 2H), 2.38-2.33 (m, 2H), 2.18-2.04 (m, 4H): LC-MS: m/z 471.1 (M + H)⁺. |
| 28 | 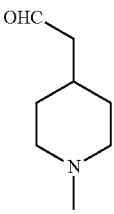 | 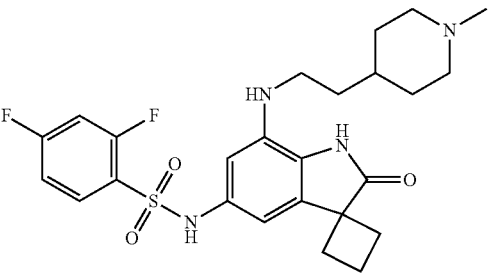 [SMILES: CN1CCC(CCNc2cc(NS(=O)(=O)c3ccc(F)cc3F)cc3c2NC(=O)C32CCC2)CC1] | δ 10.24 (bs, 1H), 9.68 (s, 1H), 7.79 (dd, J = 8.6 Hz, & 15.0 Hz, 1H), 7.51 (t, J = 8.6 Hz, 1H), 7.23-7.20 (m, 1H), 6.54 (s, 1H), 6.12 (s, 1H), 4.82 (t, J = 4.9 Hz, 1H), 2.93-2.88 (m, 2H), 2.73 (d, J = 11.2 Hz, 2H), 2.37-2.33 (m, 3H), 2.13 (s, 3H), 2.10-2.01 (m, 4H), 1.81 (t, J = 10.7 Hz, 2H), 1.58 (d, J = 12.3 Hz, 2H), 1.41-1.35 (m, 2H), 1.19-1.13 (m, 2H); LC-MS: m/z 505.2 (M + H)⁺. |
| 29 | 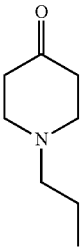 | 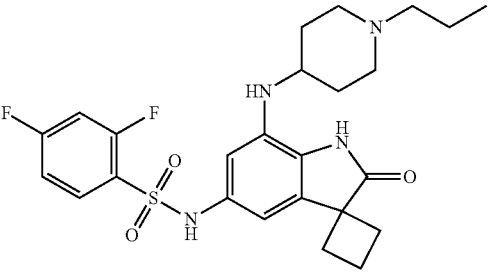 [SMILES: CCCN1CCC(Nc2cc(NS(=O)(=O)c3ccc(F)cc3F)cc3c2NC(=O)C32CCC2)CC1] | δ 10.03 (s, 1H), 9.77 (s, 1H), 7.81-7.75 (m, 1H), 7.55 (t, J = 9.0 Hz, 1H), 7.23 (t, J = 7.8 Hz, 1H), 6.55 (s, 1H), 6.13 (s, 1H), 4.76 (d, J = 6.4 Hz, 1H), 3.01-2.97 (m, 2H), 2.84-2.80 (m, 2H), 2.69-2.66 (m, 1H), 2.37-2.32 (m, 4H), 2.21-2.04 (m, 5H), 1.81-1.75 (m, 2H), 1.48-1.40 (m, 2H), 1.23-1.19 (m, 1H), 0.86 (t, J = 7.1 Hz, 3H); LC-MS: m/z 505.2 (M + H)⁺. |
| 30 | 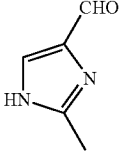 | 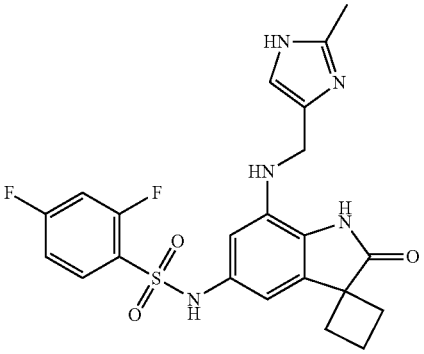 [SMILES: Cc1nc(CNc2cc(NS(=O)(=O)c3ccc(F)cc3F)cc3c2NC(=O)C32CCC2)c[nH]1] | δ 11.51 (bs, 1H), 10.12 (bs, 1H), 9.76 (s, 1H), 7.82-7.75 (m, 1H), 7.54-7.48 (m, 1H), 7.22-7.18 (m, 1H), 6.80 (bs, 1H), 6.55 (s, 1H), 6.29 (s, 1H), 5.22 (t, J = 4.9 Hz, 1H), 3.93 (s, 2H), 2.37-2.30 (m, 2H), 2.23 (s, 3H), 2.16-2.04 (m, 4H); LC-MS: m/z 474.1 (M + H)⁺. |

| No | Reactant | Obtained Compound | Characterization Data<br>¹H NMR (400 MHz, DMSO-d₆)/<br>LC-MS: |
|---|---|---|---|
| 31 | 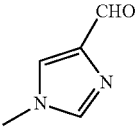 | 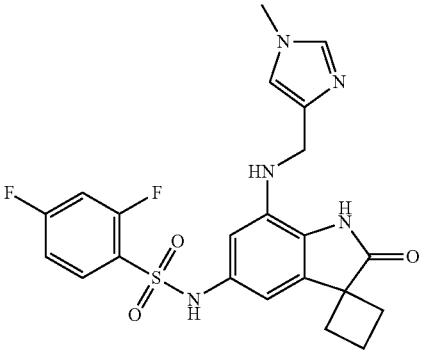 [SMILES: Cn1cnc(CNc2cc(NS(=O)(=O)c3ccc(F)cc3F)cc3c2NC(=O)C32CCC2)c1] | δ 10.11 (s, 1H), 9.75 (s, 1H), 7.82-7.76 (m, 1H), 7.55-7.49 (m, 2H), 7.23-7.18 (m, 1H), 6.96 (s, 1H), 6.54 (d, J = 1.9 Hz, 1H), 6.28 (d, J = 1.4 Hz, 1H), 5.27 (t, J = 5.4 Hz, 1H), 3.97 (d, J = 5.4 Hz, 2H), 3.60 (s, 3H), 2.37-2.32 (m, 2H), 2.18-1.99 (m, 4H); LC-MS: m/z 474.1 (M + H)⁺. |
| 32 | 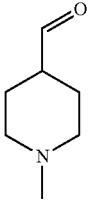 | 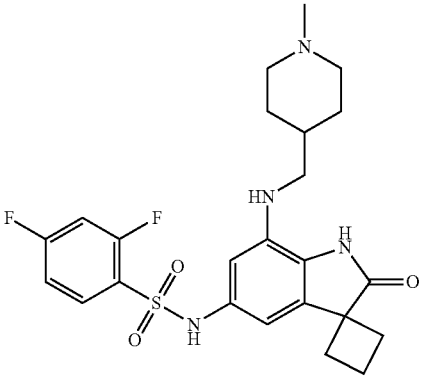 [SMILES: CN1CCC(CNc2cc(NS(=O)(=O)c3ccc(F)cc3F)cc3c2NC(=O)C32CCC2)CC1] | δ 10.05 (bs, 1H), 9.77 (s, 1H), 7.82-7.77 (m, 1H), 7.56-7.51 (m, 1H), 7.25-7.20 (m, 1H), 6.53 (d, J = 1.5 Hz, 1H), 6.17 (d, J = 1.5 Hz, 1H), 5.01 (bs, 1H), 2.85-2.77 (m, 4H), 2.38-2.23 (m, 2H), 2.18-2.11 (m, 4H), 2.10-1.94 (m, 5H), 1.68-1.66 (m, 2H), 1.39-1.34 (m, 1H), 1.24-1.16 (m, 2H); LC-MS: m/z 491.1 (M + H)⁺. |
| 33 | 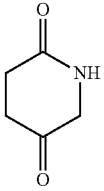 | 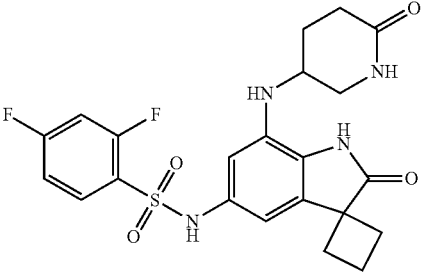 [SMILES: O=C1CCC(Nc2cc(NS(=O)(=O)c3ccc(F)cc3F)cc3c2NC(=O)C32CCC2)CN1] | δ 10.12 (s, 1H), 9.86 (s, 1H), 7.84-7.78 (m, 1H), 7.57-7.51 (m, 1H), 7.44 (s, 1H), 7.25-7.21 (m, 1H), 6.57 (d, J = 1.5 Hz, 1H), 6.26 (d, J = 1.5 Hz, 1H), 4.92 (d, J = 7.4 Hz, 1H), 3.50-3.48 (m, 1H), 2.93-2.98 (m, 1H), 2.37-2.31 (m, 4H), 2.29-2.07 (m, 2H), 2.06-1.98 (m, 3H), 1.93-1.89 (m, 1H), 1.71-1.62 (m, 1H); LC-MS: m/z 477.1 (M + H)⁺. |
| 34 & 35 | 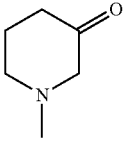 | 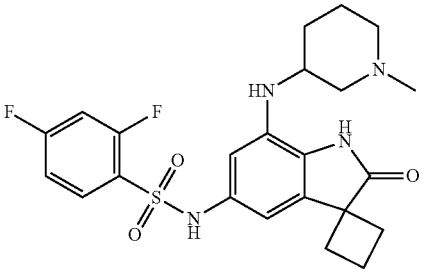 [SMILES: CN1CCCC(Nc2cc(NS(=O)(=O)c3ccc(F)cc3F)cc3c2NC(=O)C32CCC2)C1] | Isomer-I: δ 10.06 (bs, 1H), 9.81 (s, 1H), 7.82-7.76 (m, 1H), 7.54 (t, J = 8.8 Hz, 1H), 7.25-7.20 (m, 1H), 6.55 (d, J = 1.4 Hz, 1H), 6.18 (s, 1H), 4.78 (d, J = 7.8 Hz, 1H), 3.27-3.17 (m, 1H), 2.89-2.66 (m, 1H), 2.45-2.33 (m, 3H), 2.29-2.04 (m, 8H), 1.75-1.66 (m, 3H), 1.50-1.48 (m, 1H), 1.11-1.01 (m, 1H); LC-MS: m/z 477.2 (M + H)⁺.<br>Isomer-II: δ 10.06 (bs, 1H), 9.81 (s, 1H), 7.82-7.76 (m, 1H), 7.53 (t, J = 8.8 Hz, 1H), 7.22 (t, J = 7.9 Hz, 1H), 6.55 (s, 1H), 6.17 (s, 1H), 4.76 (d, J = 7.9 Hz, 1H), 3.17-3.15 (m, 1H), 2.70-2.67 (m, 1H), 2.38-2.34 (m, 3H), 2.15 (s, 3H), 2.10-2.05 (m, 4H), 1.96-1.90 (m, 1H), 1.72-1.64 (m, 3H), 1.52-1.43 (m, 1H), 1.09-1.01 (m, 1H); LC-MS: m/z 477.2 (M + H)⁺. |

-continued

| No | Reactant | Obtained Compound | Characterization Data<br>¹H NMR (400 MHz, DMSO-d₆)/<br>LC-MS: |
|---|---|---|---|
| 36 | | | δ 10.11 (s, 1H), 10.0 (s, 1H), 7.79-7.73 (m, 1H), 7.56-7.50 (m, 1H), 7.34-7.18 (m, 6H), 6.55 (d, J = 1.4 Hz, 1H), 6.13 (d, J = 1.0 Hz, 1H), 4.32 (d, J = 8.3 Hz, 1H), 3.53-3.50 (m, 1H), 3.41-3.38 (m, 1H), 2.80-2.67 (m, 2H), 2.43 (d, J = 11.2, 1H), 2.38-2.32 (m, 2H), 2.20-1.95 (m, 5H), 1.76 (d, J = 11.2 Hz, 1H), 1.52-1.41 (m, 2H), 0.98 (s, 3H), 0.73 (s, 3H); LCMS: m/z 581.3 (M + H)⁺. |
| 37 | | | δ 10.07 (s, 1H), 9.93 (s, 1H), 7.80 (dd, J = 14.6, 8.3 Hz, 1H), 7.59-7.53 (m, 1H), 7.27-7.22 (m, 1H), 6.55 (d, J = 0.9 Hz, 1H), 6.24 (s, 1H), 4.94 (d, J = 8.8 Hz, 1H), 4.64-4.52 (m, 1H), 4.21 (bs, 1H), 4.03 (bs, 1H), 3.49-3.38 (m, 1H), 3.15-2.80 (m, 2H), 2.37-2.30 (m, 2H), 2.19-2.11 (m, 1H), 2.09-1.99 (m, 3H), 1.63-1.60 (m, 1H), 1.56-1.45 (m, 1H), 1.40 (s, 9H); LCMS: m/z 579.2 (M − H)⁻. |
| 38 | | | δ 9.74 (s, 1H), 9.40 (s, 1H), 7.66 (dd, J = 1.5 Hz & 7.3 Hz, 1H), 7.55-7.53 (m, 1H), 7.17 (d, J = 8.3 Hz, 1H), 7.0-6.97 (m, 1H), 6.56 (s, 1H), 6.23 (s, 1H), 4.76-4.70 (m, 1H), 3.94 (s, 3H), 3.21-3.09 (m, 1H), 2.38-2.30 (m, 3H), 2.21-2.18 (m, 4H), 2.16-2.08 (m, 4H), 1.80-1.62 (m, 3H), 1.54-1.42 (m, 1H), 1.25-1.22 (m, 2H); LC-MS: m/z 471.2 (M + H)⁺. |
| 39. | | | δ 9.70 (s, 1H), 9.40 (s, 1H), 7.66 (dd, J = 1.9 Hz, & 7.8 Hz, 1H), 7.54 (t, J = 7.3 Hz, 1H), 7.17 (d, J = 8.3 Hz, 1H), 6.99 (t, J = 7.3 Hz, 1H), 6.50 (d, J = 1.5 Hz, 1H), 6.18 (d, J = 1.5 Hz, 1H), 4.73 (d, J = 6.9 Hz, 1H), 3.93 (s, 3H), 3.10-2.77 (m, 3H), 2.40-2.25 (m, 5H), 2.19-1.99 (m, 4H), 1.81-1.78 (m, 2H), 1.38-1.27 (m, 4H); LC-MS: m/z 471.2 (M + H)⁺. |

Example-VI: Methyl 5'-((2,4-difluorophenyl)sulfonamido)-2'-oxospiro[cyclobutane-1,3'-indoline]-7'-carboxylate (Compound-41) and 5'-((2,4-difluoro phenyl)sulfonamido)-2'-oxospiro[cyclobutane-1,3'-indoline]-7'-carboxylic acid (Compound-42)

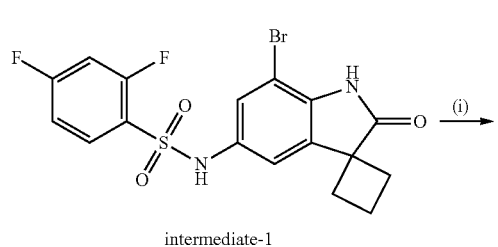

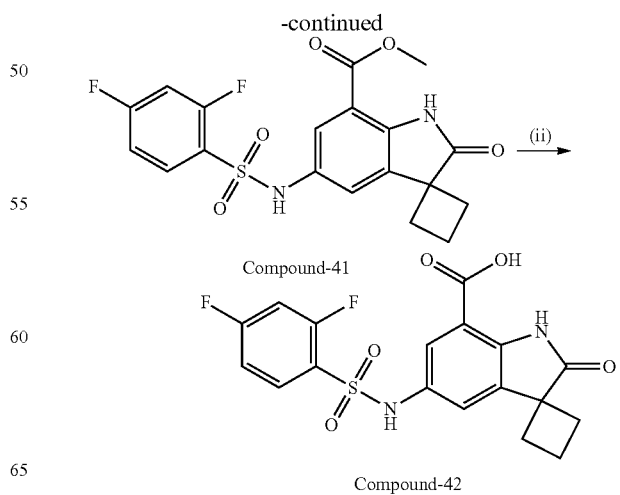

Step-(i): Methyl 5'-((2,4-difluorophenyl)sulfonamido)-2'-oxospiro[cyclobutane-1,3'-indoline]-7'-carboxylate (compound-41)

To a solution of N-(7'-bromo-2'-oxospiro[cyclobutane-1,3'-indolin]-5'-yl)-2,4-difluorobenzenesulfonamide (intermediate-1) (0.1 g, 0.23 mmol) in triethyl amine (5 mL) were added xantphos (0.013 g, 0.023 mmol), palladium(ll)acetate (0.01 g, 0.046 mmol) and methanol (0.09 mL, 2.3 mmol). The mixture was purged with carbon monoxide gas for 10 min and then heated to 70° C. for 4 h under carbon monoxide atmosphere. The mixture was diluted with EtOAc (50 mL) and washed with 1N HCl (50 mL), water (50 mL) and brine (50 mL). The mixture was dried over sodium sulphate, concentrated under reduced pressure and column purified to afford the title compound as off white solid (0.05 g, 52%). $^1$H NMR (400 MHz, DMSO-d$_6$): δ 10.52 (s, 1H), 10.14 (s, 1H), 7.85-7.81 (m, 1H), 7.57-7.52 (m, 1H), 7.51 (d, J=2.2 Hz, 1H), 7.38 (d, J=1.9 Hz, 1H), 7.26-7.23 (m, 1H), 3.81 (s, 3H), 2.42-2.36 (m, 2H), 2.24-2.08 (m, 4H); LC-MS: m/z 423.1 (M+H)$^+$.

Step-(ii): 5'-((2,4-difluorophenyl)sulfonamido)-2'-oxospiro[cyclobutane-1,3'-indoline]-7'-carboxylic acid (compound-42)

To a solution of methyl 5'-((2,4-difluorophenyl)sulfonamido)-2'-oxospiro[cyclobutane-1,3'-indoline]-7'-carboxylate (0.15 g, 0.35 mmol) in THF (4 mL) was added lithium hydroxide monohydrate (0.044 g, 1.05 mmol) in 1 mL of water. The mixture was stirred at RT for 16 h, concentrated, diluted with water, acidified with 1N HCl, extracted with EtOAc (50 mL) and washed with brine (50 mL). The product was dried over sodium sulphate and concentrated under reduced pressure to afford the title compound as off white solid (0.12 g, 82%). $^1$H NMR (400 MHz, DMSO-d$_6$): δ 13.32 (bs, 1H), 10.48 (s, 1H), 9.78 (s, 1H), 7.86-7.78 (m, 1H), 7.58-7.52 (m, 1H), 7.50 (d, J=2.4 Hz, 1H), 7.35 (d, J=2.0 Hz, 1H), 7.26-7.18 (m, 1H), 2.42-2.38 (m, 2H), 2.22-2.10 (m, 4H); LC-MS: m/z 407.1 (M−H)$^−$.

Example-VII (Method-A): N-(5'-((2,4-difluorophenyl)sulfonamido)-2'-oxospiro[cyclobutane-1,3'-indolin]-yl)-1-methylpiperidine-4-carboxamide (Compound-43)

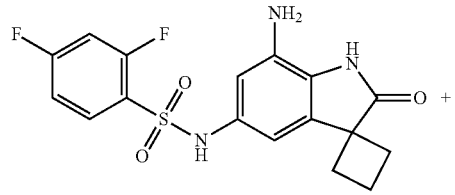

Compound-15

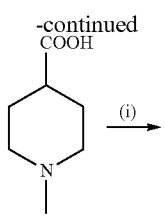

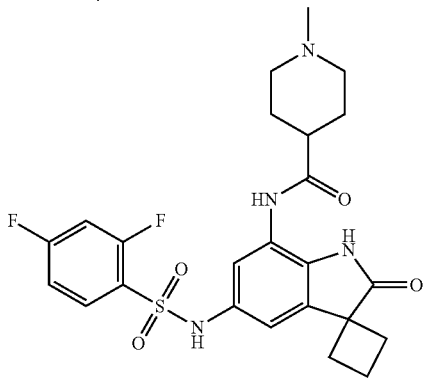

Compound-43

To a solution of N-(7'-amino-2'-oxospiro[cyclobutane-1,3'-indolin]-5'-yl)-2,4-difluorobenzenesulfonamide (compound-15) (0.1 g, 0.26 mmol) in DMF (2 mL) were added 1-methylpiperidine-4-carboxylic acid (0.074 g, 0.52 mmol), triethylamine (0.14 mL, 1.04 mmol) and PyBOP (0.27 g, 0.52 mmol). The mixture was stirred at RT for 16 h. The mixture was diluted with EtOAc (50 mL), washed with water (50 mL) and brine (50 mL), dried over sodium sulphate and concentrated under reduced pressure and column purified to afford the title compound as off white solid (0.01 g, 8%). $^1$H NMR (400 MHz, DMSO-d$_6$) δ 10.22 (bs, 1H), 9.81 (s, 1H), 9.19 (s, 1H), 7.84-7.79 (m, 1H), 7.53 (t, J=8.6 Hz, 1H), 7.27 (s, 1H), 7.24-7.20 (m, 1H), 7.03 (d, J=1.5 Hz, 1H), 3.17-3.16 (m, 1H), 2.88-2.85 (m, 2H), 2.41-2.35 (m, 2H), 2.29-1.91 (m, 9H), 1.79-1.76 (m, 2H), 1.68-1.60 (m, 2H): LC-MS: m/z 505.2 (M+H)$^+$.

The below compounds were prepared by procedure similar to the one described in Example-VII (method-A) with appropriate variations in reactants, quantities of reagents and reaction conditions. The physiochemical characteristics of the compounds are also summarized.

| No | Reactant | Obtained Compound | Characterization Data $^1$H NMR (400 MHz, DMSO-d$_6$)/ LC-MS: |
|---|---|---|---|
| 44 | ![nicotinic acid] | ![compound 44] | δ 10.42 (s, 1H), 10.14 (s, 1H), 10.01 (s, 1H), 9.08 (d, J = 2.0 Hz, 1H), 8.75-8.74 (m, 1H), 8.26 (d, J = 8.3 Hz, 1H), 7.88-7.82 (m, 1H), 7.58-7.53 (m, 2H), 7.27-7.22 (m, 1H), 7.15 (s, 1H), 7.12 (d, J = 1.4 Hz, 1H), 2.44-2.38 (m, 2H), 2.21-2.07 (m, 4H); LC-MS: m/z 485.1 (M + H)$^+$. |

| No | Reactant | Obtained Compound | Characterization Data<br>$^1$H NMR (400 MHz, DMSO-$d_6$)/<br>LC-MS: |
|---|---|---|---|
| 45 | COOH-pyridine | (structure) | δ 10.43 (s, 1H), 10.15 (s, 1H), 10.09 (s, 1H), 8.88-8.76 (m, 2H), 7.86-7.83 (m, 3H), 7.57-7.53 (m, 1H), 7.26-7.22 (m, 1H), 7.16 (d, J = 1.8 Hz, 1H), 7.10 (d, J = 1.9 Hz, 1H), 2.42-2.38 (m, 2H), 2.23-2.10 (m, 4H); LC-MS: m/z 485.1 (M + H)$^+$. |
| 46 | tetrahydropyran-4-carboxylic acid | (structure) | δ 10.33 (s, 1H), 9.82 (s, 1H), 9.19 (s, 1H), 7.85-7.79 (m, 1H), 7.56-7.51 (m, 1H), 7.26-7.21 (m, 2H), 7.05 (s, 1H), 3.96-3.88 (m, 2H), 3.41-3.33 (m, 3H), 2.39-2.32 (m, 2H), 2.21-2.04 (m, 4H), 1.73-1.59 (m, 4H); LC-MS: m/z 492.1 (M + H)$^+$. |

(Method-B): 2,4-Difluoro-N-(7'-(4-methylpiperazine-1-carbonyl)-2'-oxospiro[cyclobutane-1,3'-indolin]-5'-yl)benzenesulfonamide (Compound-47)

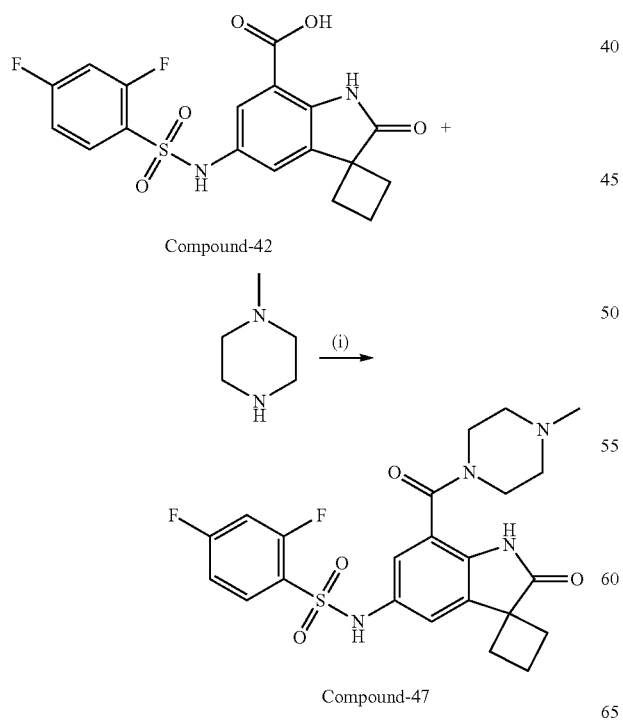

To a solution of 5'-((2,4-difluorophenyl)sulfonamido)-2'-oxospiro[cyclobutane-1,3'-indoline]-7'-carboxylic acid (compound-42) (0.1 g, 0.24 mmol) in DMF (3 mL) were added 1-methylpiperazine (0.032 mL, 0.29 mmol), HOBt (0.05 g, 0.36 mmol), EDC.HCl (0.07 g, 0.36 mmol) and diisopropylethylamine (0.13 mL, 0.72 mmol. The mixture was stirred at RT for 16 h, diluted with EtOAc (50 mL), washed with water (50 mL) and brine (50 mL), dried over sodium sulphate and concentrated under reduced pressure and column purified to afford the title compound as white solid (0.03 g, 25%); $^1$H NMR (400 MHz, DMSO-$d_6$): δ 10.37 (s, 1H), 10.32 (s, 1H), 7.80-7.78 (m, 1H), 7.57-7.52 (m, 1H), 7.32 (s, 1H), 7.23 (t, J=7.3 Hz, 1H), 6.67 (d, J=1.5 Hz, 1H), 3.60-3.54 (m, 2H), 3.15-3.04 (m, 2H), 2.44-2.30 (m, 4H), 2.17 (s, 3H), 2.20-2.12 (m, 6H); LC-MS: m/z 491.1 (M+H)$^+$.

The below compounds were prepared by procedure similar to the one described in Example-VII (method-B) with appropriate variations in reactants, quantities of reagents and reaction conditions. The physiochemical characteristics of the compounds are also summarized.

| No | Reactant | Obtained Compound | Characterization Data<br>¹H NMR (400 MHz, DMSO-d₆)/LC-MS: |
|---|---|---|---|
| 48 | morpholine | | δ 10.40 (s, 1H), 10.37 (s, 1H), 7.83-7.77 (m, 1H), 7.58-7.52 (m, 1H), 7.32 (d, J = 1.9 Hz, 1H), 7.26-7.21 (m, 1H), 6.72 (d, J = 2.0 Hz, 1H), 3.74-3.40 (m, 6H), 3.18-2.98 (m, 2H), 2.44-2.33 (m, 2H), 2.22-2.08 (m, 4H); LC-MS: m/z 478.1 (M + H)⁺. |
| 49 | 2-aminopyridine | | δ 10.82 (s, 1H), 10.47 (s, 1H), 10.17 (s, 1H), 8.37 (d, J = 4.4 Hz, 1H), 8.08 (d, J = 8.3 Hz, 1H), 7.87-7.81 (m, 2H), 7.59-7.55 (m, 1H), 7.39 (s, 1H), 7.36 (s, 1H), 7.26-7.22 (m, 1H), 7.16 (t, J = 6.8 Hz, 1H), 2.44-2.38 (m, 2H), 2.24-2.06 (m, 4H); LC-MS: m/z 485.0 (M + H)⁺. |
| 50 | 4-aminotetrahydropyran | | δ 10.34 (s, 1H), 9.81 (s, 1H), 8.39 (d, J = 7.4 Hz, 1H), 7.81-7.75 (m, 1H), 7.60-7.54 (m, 1H), 7.34 (d, J = 1.9 Hz, 1H), 7.25-7.20 (m, 1H), 7.18 (d, J = 1.5 Hz, 1H), 4.04-3.85 (m, 3H), 3.39-3.36 (m, 2H), 2.44-2.36 (m, 2H), 2.22-2.16 (m, 1H), 2.11-2.01 (m, 3H), 1.76-1.73 (m, 2H), 1.60-1.50 (m, 2H); LC-MS: m/z 492.0 (M + H)⁺. |
| 51 | 3-aminopyridine | | δ 10.51-10.49 (m, 2H), 10.27 (s, 1H), 8.82 (d, J= 2.4 Hz, 1H), 8.31-8.30 (m, 1H), 8.10-8.07 (m, 1H), 7.87-7.81 (m, 1H), 7.60-7.55 (m, 1H), 7.40-7.37 (m, 1H), 7.34 (s, 2H), 7.26-7.23 (m, 1H), 2.42-2.32 (m, 2H), 2.22-2.05 (m, 4H); LC-MS: m/z 485.2 (M + H)⁺. |

-continued
| No | Reactant | Obtained Compound | Characterization Data<br>¹H NMR (400 MHz, DMSO-d₆)/LC-MS: |
|---|---|---|---|
| 52 | 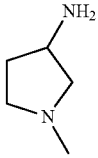 | 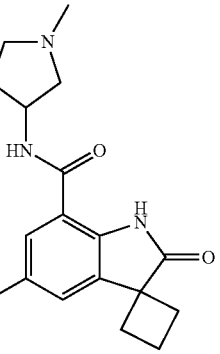 | δ 10.22 (bs, 1H), 9.84 (bs, 1H), 8.59 (d, J = 6.4 Hz, 1H), 7.81-7.75 (m, 1H), 7.60-7.55 (m, 1H), 7.35 (d, J = 1.5 Hz, 1H), 7.25-7.20 (m, 1H), 7.19 (d, J = 2.0 Hz, 1H), 4.35-4.31 (m, 1H), 2.87-2.67 (m, 1H), 2.60-2.50 (m, 1H), 2.40-2.11 (m, 6H), 2.18-2.03 (m, 6H), 1.84-1.81 (m, 1H); LC-MS: m/z 491.0 (M + H)⁺. |
| 53 | 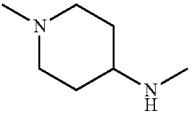 | 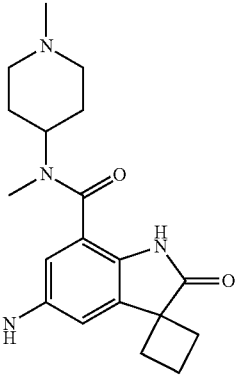 | δ 10.10 (bs, 1H), 9.99 (s, 1H), 7.83-7.78 (m, 1H), 7.43-7.38 (m, 1H), 7.27 (d, J = 1.9 Hz, 1H), 7.21-7.17 (m, 1H), 6.72 (d, J = 2.1 Hz, 1H), 3.62-3.44 (m, 1H), 2.78-2.69 (m, 2H), 2.63 (s, 3H), 2.45-2.34 (m, 2H), 2.25-2.07 (m, 7H), 1.73-1.64 (m, 4H), 1.56-1.48 (m, 2H); LC-MS: m/z 519.2 (M + H)⁺. |
| 54 | 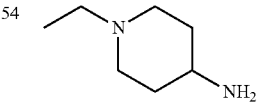 | 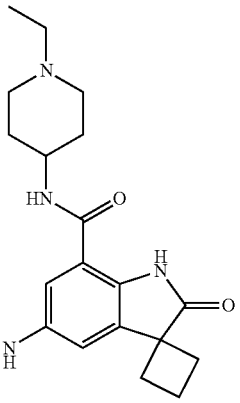 | δ 10.20 (bs, 1H), 9.78 (s, 1H), 8.34 (d, J = 7.9 Hz, 1H), 7.80-7.76 (m, 1H), 7.56-7.53 (m, 1H), 7.31 (d, J = 1.4 Hz, 1H), 7.24-7.18 (m, 2H), 3.76-3.66 (m, 1H), 2.94-2.90 (m, 2H), 2.44-2.33 (m, 4H), 2.22-1.98 (m, 6H), 1.80-1.77 (m, 2H), 1.59-1.53 (m, 2H), 1.01 (t, J = 7.4 Hz, 3H); LC-MS: m/z 519.3 (M + H)⁺. |
| 55 | 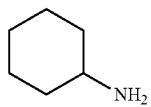 | 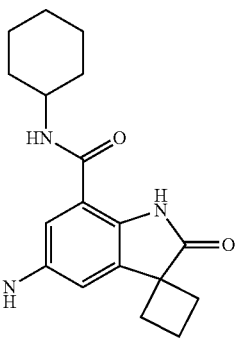 | δ 10.31 (s, 1H), 9.78 (s, 1H), 8.28 (d, J = 7.8 Hz, 1H), 7.80-7.74 (m, 1H), 7.60-7.54 (m, 1H), 7.35 (d, J = 2.0 Hz, 1H), 7.25-7.20 (m, 1H), 7.16 (d, J = 2.0 Hz, 1H), 3.71-3.68 (m, 1H), 2.41-2.32 (m, 2H), 2.21-2.00 (m, 4H), 1.78-1.73 (m, 4H), 1.61-1.58 (m, 1H), 1.31-1.19 (m, 5H); LC-MS: m/z 490.1 (M + H)⁺. |

| No | Reactant | Obtained Compound | Characterization Data<br>$^1$H NMR (400 MHz, DMSO-$d_6$)/LC-MS: |
|---|---|---|---|
| 56 | 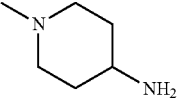 | 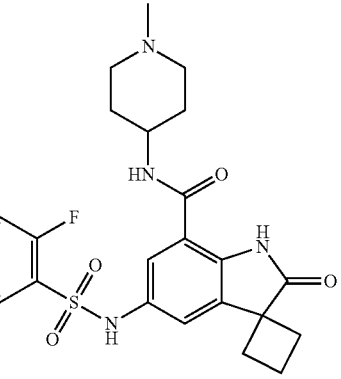 | δ 10.24 (bs, 1H), 9.76 (s, 1H), 8.32 (d, J = 7.3 Hz, 1H), 7.81-7.75 (m, 1H), 7.57-7.51 (m, 1H), 7.33 (s, 1H), 7.24-7.18 (m, 2H), 3.70-3.66 (m, 1H), 2.80 (d, J = 11.0 Hz, 2H), 2.45-2.33 (m, 2H), 2.20 (s, 3H), 2.16-1.97 (m, 6H), 1.77-1.74 (m, 2H), 1.61-1.53 (m, 2H); LC-MS: m/z 505.1 (M + H)$^+$. |
| 57 | 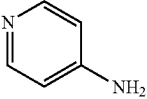 | 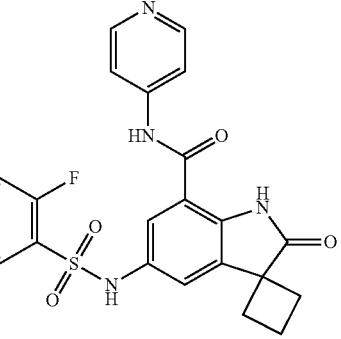 | δ 10.62 (s, 2H), 10.30 (bs, 1H), 8.46 (d, J = 6.9 Hz, 2H), 7.87-7.81 (m, 1H), 7.66 (d, J = 5.9 Hz, 2H), 7.58-7.53 (m, 1H), 7.35 (d, J = 2.0 Hz, 1H), 7.31 (d, J = 2.0 Hz, 1H), 7.26-7.21 (m, 1H), 2.45-2.42 (m, 2H), 2.33-2.06 (m, 4H); LC-MS: m/z 485.0 (M + H)$^+$. |
| 58 | 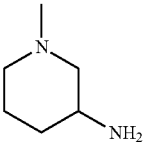 | 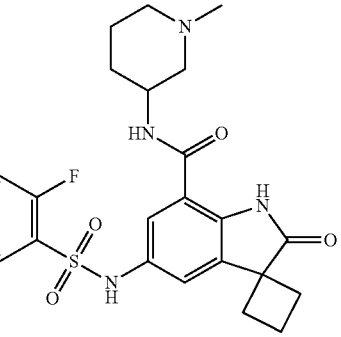 | δ 10.30 (bs, 1H), 9.87 (bs, 1H), 8.22 (d, J = 7.3 Hz, 1H), 7.79 (q, 1H), 7.56-7.53 (m, 1H), 7.28 (d, J = 1.9 Hz, 1H), 7.25-7.20 (m, 2H), 3.87 (d, J = 8.9 Hz, 1H), 3.88 (m, 1H), 2.74-2.54 (m, 1H), 2.41-2.32 (m, 2H), 2.19 (s, 3H), 2.16-2.00 (m, 4H), 1.99-1.91 (m, 2H), 1.75-1.66 (m, 2H), 1.53-1.40 (m, 1H), 1.34-1.14 (m, 1H); LC-MS: m/z 505.2 (M + H)$^+$. |
| 59 | 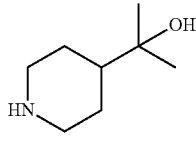 | 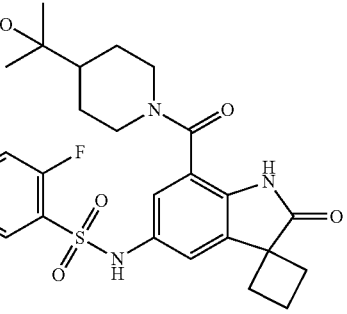 | δ 10.36 (s, 1H), 10.29 (s, 1H), 7.82-7.80 (m, 1H), 7.64-7.49 (m, 1H), 7.32 (d, J = 1.9 Hz, 1H), 7.25-7.20 (m, 1H), 6.67 (d, J = 1.9 Hz, 1H), 4.67-4.44 (m, 1H), 3.30-3.21 (m, 1H), 2.90-2.86 (m, 1H), 2.67-2.52 (m, 1H), 2.49-2.33 (m, 3H), 2.20-2.10 (m, 4H), 1.75-1.64 (m, 1H), 1.58-1.50 (m, 1H), 1.42-1.35 (m, 1H), 1.71-1.10 (m, 1H), 1.03 (s, 6H), 1.99-1.85 (m, 1H); LCMS: m/z 534.2 (M + H)$^+$. |

| No | Reactant | Obtained Compound | Characterization Data <br> $^1$H NMR (400 MHz, DMSO-$d_6$)/LC-MS: |
|---|---|---|---|
| 60 |  | 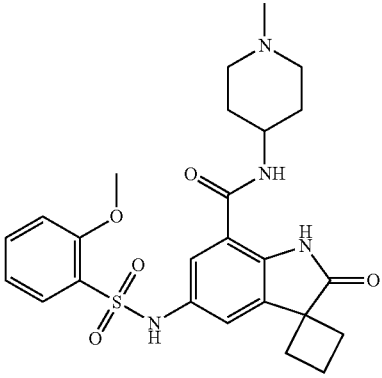 [SMILES: COc1ccccc1S(=O)(=O)Nc1cc(C(=O)NC2CCN(C)CC2)c2c(c1)C1(CCC1)C(=O)N2] | δ 9.72 (s, 1H), 9.65 (s, 1H), 8.29 (d, J = 7.3 Hz, 1H), 7.64 (dd, J = 1.4 Hz & 7.8 Hz, 1H), 7.59-7.55 (m, 1H), 7.34 (d, J = 2.0 Hz, 1H), 7.21 (d, J = 8.4 Hz, 1H), 7.12 (d, J = 1.5 Hz, 1H), 6.99 (t, J = 7.8 Hz, 1H), 3.93 (s, 3H), 3.70-3.64 (m, 1H), 2.80-2.77 (m, 2H), 2.39-2.33 (m, 2H), 2.19-2.10 (m, 4H), 2.08-1.94 (m, 5H), 1.77-1.74 (m, 2H), 1.60-1.55 (m, 2H); LC-MS: m/z 499.1 (M + H)$^+$. |

Example-VIII: 4-Fluoro-N-(7'-(morpholine-4-carbonyl)-2'-oxospiro[cyclobutane-1,3'-indolin]-5'-yl)-2-morpholinobenzenesulfonamide: (Compound-61)

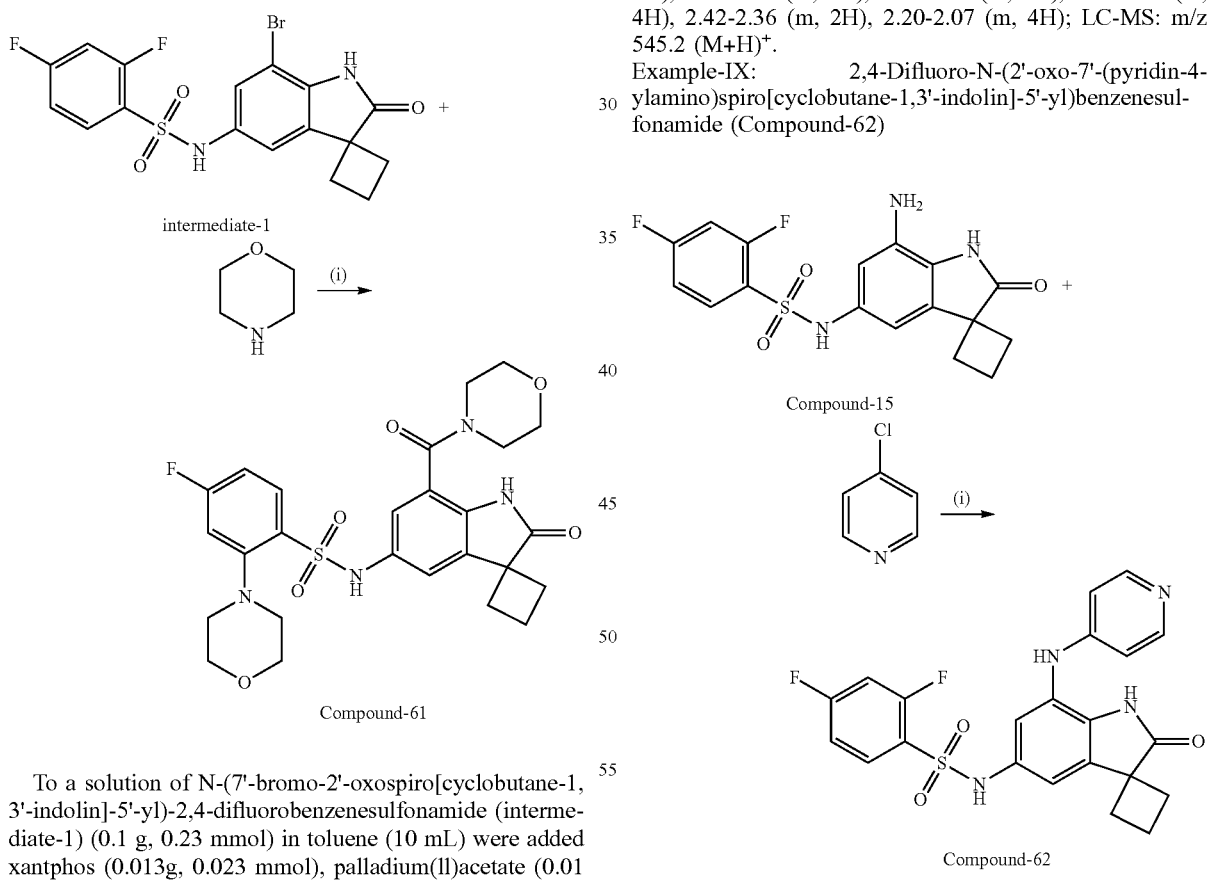

To a solution of N-(7'-bromo-2'-oxospiro[cyclobutane-1,3'-indolin]-5'-yl)-2,4-difluorobenzenesulfonamide (intermediate-1) (0.1 g, 0.23 mmol) in toluene (10 mL) were added xantphos (0.013g, 0.023 mmol), palladium(ll)acetate (0.01 g, 0.046 mmol), potassium phosphate (0.15 g, 0.69 mmol) and morpholine (0.024 mL, 0.28 mmol). The reaction mixture was purged with carbon monoxide gas for 10 min and then heated to 110° C. for 6 h under carbon monoxide atmosphere. The mixture was diluted with EtOAc (50 mL), washed with water (50 mL) and brine (50 mL), dried over sodium sulphate and concentrated under reduced pressure and purified by preparative HPLC to afford the title compound as brown solid (0.03 g, 27%). $^1$H NMR (400 MHz, DMSO-$d_6$): δ 10.30 (s, 1H), 9.58 (s, 1H), 7.94-7.91 (m, 1H), 7.29 (dd, J=2.6 Hz & 10.8 Hz, 1H), 7.20 (d, J=2.1 Hz, 1H), 7.12-7.08 (m, 1H), 6.67 (d, J=2.1 Hz, 1H), 3.82-3.80 (m, 4H), 3.65-3.37 (m, 6H), 3.10-3.03 (m, 2H), 2.90-2.88 (m, 4H), 2.42-2.36 (m, 2H), 2.20-2.07 (m, 4H); LC-MS: m/z 545.2 (M+H)$^+$.

Example-IX: 2,4-Difluoro-N-(2'-oxo-7'-(pyridin-4-ylamino)spiro[cyclobutane-1,3'-indolin]-5'-yl)benzenesulfonamide (Compound-62)

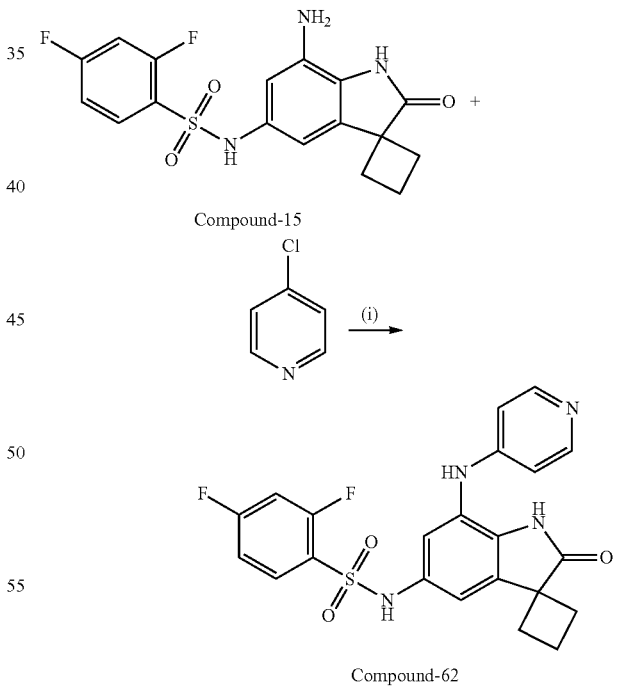

To a solution of N-(7'-amino-2'-oxospiro[cyclobutane-1,3'-indolin]-5'-yl)-2,4-difluorobenzenesulfonamide (compound-15) (0.1 g, 0.26 mmol) in HCl in 1,4-dioxane (10 mL) was added 4-chloropyridine (0.025 mL, 0.26 mmol) in a sealed tube. The mixture was heated to 110° C. for 16 h. The mixture was diluted with DCM (50 mL), washed with aqueous sodium bicarbonate (50 mL) and brine (50 mL), dried over sodium sulphate, concentrated under reduced pressure and purified by preparative HPLC to afford the title compound as white solid (0.025 g, 21%). $^1$H NMR (400 MHz, DMSO-d$_6$): δ 10.38 (bs, 1H), 10.01 (s, 1H), 8.13 (d, J=6.3 Hz, 2H), 8.08 (s, 1H), 7.85-7.79 (m, 1H), 7.61-7.55 (m, 1H), 7.29-7.25 (m, 1H), 7.10 (d, J=1.5 Hz, 1H), 6.77 (d, J=1.5 Hz, 1H), 6.47 (d, J=5.8 Hz, 2H), 2.45-2.33 (m, 2H), 2.20-2.08 (m, 4H); LC-MS: m/z 457.1 (M+H)$^+$.

Example-X: N-(5'-((2,4-difluorophenyl)sulfonamido)-2'-oxospiro[cyclobutane-1,3'-indolin]-7'-yl)acetamide (Compound-63)

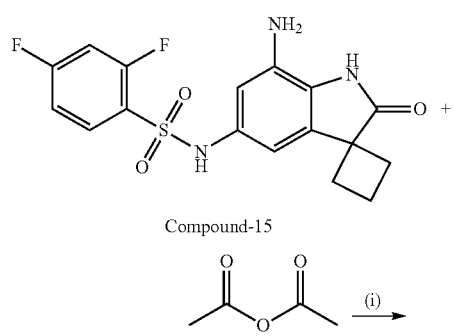

Compound-15

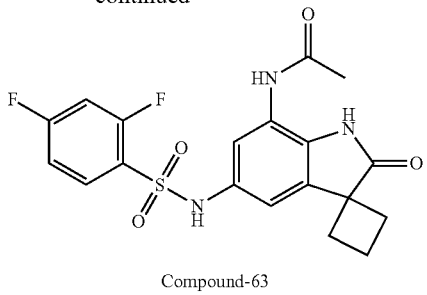

Compound-63

A solution of N-(7'-amino-2'-oxospiro[cyclobutane-1,3'-indolin]-5'-yl)-2,4-difluorobenzenesulfonamide (compound-15) (0.15 g, 0.39 mmol) in acetic anhydride (1 mL) was stirred at RT for 48 h. The mixture was poured into ice water and the solid formed was filtered off. The product was washed with water and dried under reduced pressure to afford the title compound as white solid (0.08 g, 48%). $^1$H NMR (400 MHz, DMSO-d$_6$): δ 10.35 (s, 1H), 9.78 (s, 1H), 9.32 (s, 1H), 7.85-7.78 (m, 1H), 7.56-7.50 (m, 1H), 7.25-7.20 (m, 1H), 7.14 (s, 1H), 7.05 (d, J=1.5 Hz, 1H), 2.43-2.33 (m, 2H), 2.17-2.00 (m, 4H), 1.98 (s, 3H); LC-MS: m/z 422.1 (M+H)$^+$.

Example-XI: 5'-((2-methoxyphenyl)sulfonamido)-2'-oxo-N-(piperidin-4-yl)spiro[cyclobutane-1,3'-indoline]-7'-carboxamide (Compound-64)

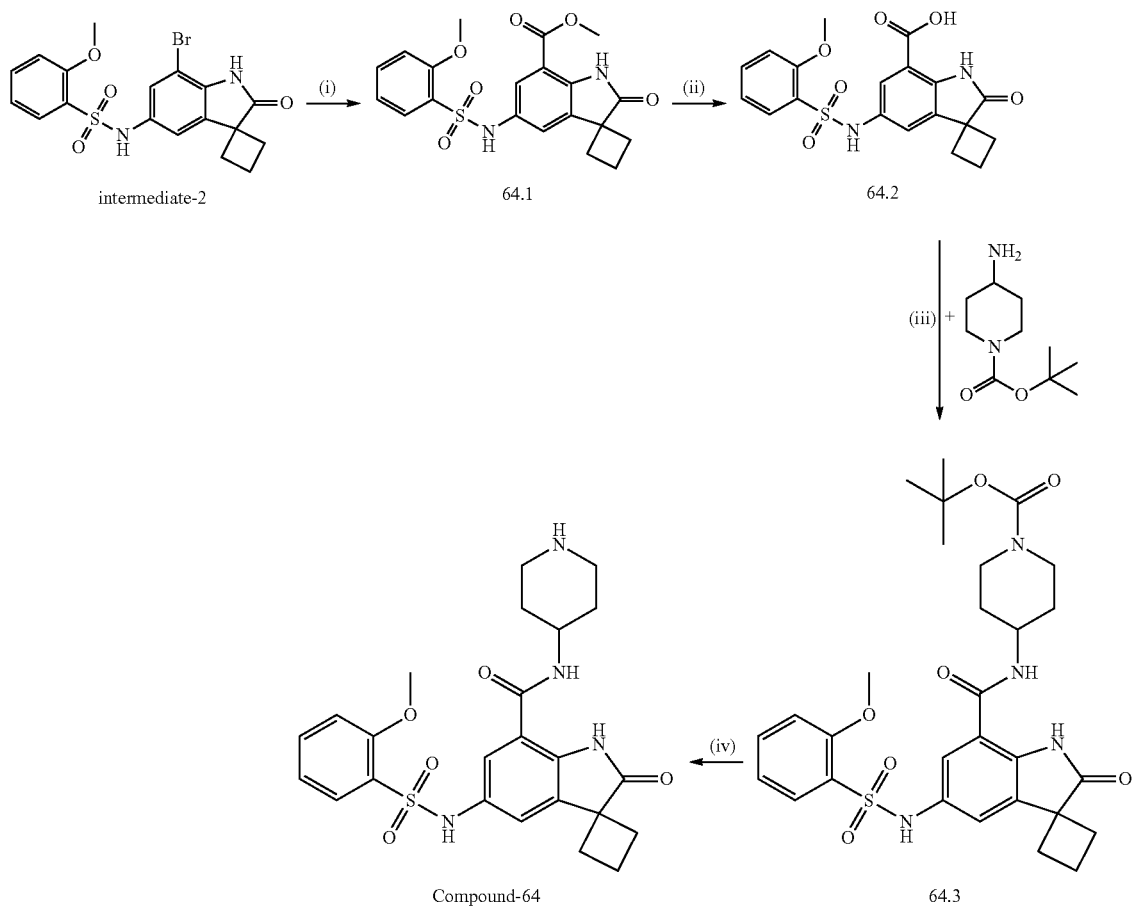 [SMILES: COc1ccccc1S(=O)(=O)Nc1cc(Br)c2c(c1)C1(CCC1)C(=O)N2 ; COC(=O)c1cc(NS(=O)(=O)c2ccccc2OC)cc2c1NC(=O)C21CCC1 ; COc1ccccc1S(=O)(=O)Nc1cc(C(=O)O)c2c(c1)C1(CCC1)C(=O)N2 ; CC(C)(C)OC(=O)N1CCC(N)CC1 ; COc1ccccc1S(=O)(=O)Nc1cc(C(=O)NC2CCNCC2)c2c(c1)C1(CCC1)C(=O)N2 ; COc1ccccc1S(=O)(=O)Nc1cc(C(=O)NC2CCN(C(=O)OC(C)(C)C)CC2)c2c(c1)C1(CCC1)C(=O)N2]

Step-(i): Methyl 5'-((2-methoxyphenyl)sulfonamido)-2'-oxospiro[cyclobutane-1,3'-indoline]-7'-carboxylate (64.1)

The process of this step was adopted from step-(i) of Example-VI. $^1$H NMR (400 MHz, DMSO-d$_6$): δ 10.05 (s, 1H), 9.90 (s, 1H), 7.72-7.69 (m, 1H), 7.55-7.48 (m, 1H), 7.42 (s, 1H), 7.40 (s, 1H), 7.16 (d, J=8.4 Hz, 1H), 7.01-6.98 (m, 1H), 3.90 (s, 3H), 3.79 (s, 3H), 2.39-2.32 (m, 2H), 2.19-2.11 (m, 4H); LC-MS: m/z 417.0 (M+H)$^+$.

Step-(ii): 5'-((2-Methoxyphenyl)sulfonamido)-2'-oxospiro[cyclobutane-1,3'-indoline]-7'-carboxylicacid (64.2)

The process of this step was adopted from step-(ii) of Example-VI. 1H NMR (400 MHz, DMSO-d$_6$): δ 12.02 (bs, 1H), 9.86 (s, 1H), 9.68 (s, 1H), 7.71-7.69 (m, 1H), 7.52-7.50 (m, 1H), 7.46 (d, J=1.9 Hz, 1H), 7.38 (d, J=2.5 Hz, 1H), 7.16 (d, J=8.3 Hz, 1H), 7.02-6.98 (m, 1H), 3.90 (s, 3H), 2.45-2.32 (m, 2H), 2.25-2.16 (m, 4H); LC-MS: m/z 403.0 (M+H)$^+$.

Step-(iii): tert-Butyl 4-(5'-((2-methoxyphenyl)sulfonamido)-2'-oxospiro [cyclobutane-1,3'-indoline]-7'-carboxamido)piperidine-1-carboxylate (64.3)

The process of this step was adopted from Example-VII (Method-B). $^1$H NMR (400 MHz, DMSO-d$_6$): δ 9.76 (s, 1H), 9.68 (s, 1H), 8.32 (d, J=7.9 Hz, 1H), 7.64 (dd, J=1.5 Hz & 7.8 Hz, 1H), 7.59-7.54 (m, 1H), 7.32 (d, J=2.0 Hz, 1H), 7.21 (d, J=8.3 Hz, 1H), 7.13 (d, J=1.5 Hz, 1H), 6.99 (t, J=7.6 Hz, 1H), 3.92 (s, 3H), 3.87-3.85 (m, 1H), 2.82-2.78 (m, 2H), 2.39-2.33 (m, 2H), 2.19-2.14 (m, 2H), 2.08-1.94 (m, 4H), 1.78-1.76 (m, 2H), 1.41 (s, 9H), 1.39-1.27 (m, 2H); LC-MS: m/z 583.2 (M–H)$^−$.

Step-(iv): 5'-((2-Methoxyphenyl)sulfonamido)-2'-oxo-N-(piperidin-4-yl)spiro[cyclobutane-1,3'-indoline]-7'-carboxamide (compound-64)

To a solution of tert-butyl 4-(5'-((2-methoxyphenyesulfonamido)-2'-oxo-spiro[cyclobutane-1,3'-indoline]-7'-carboxamido)piperidine-1-carboxylate (0.08 g, 0.136 mmol) in DCM (2 mL) was added TFA (0.05 mL, 0.68 mmol) at RT for 3 h. The mixture was diluted with DCM and washed with saturated NaHCO$_3$. The organic layer was dried over sodium sulphate, concentrated under reduced pressure and washed with diethyl ether to afford the title compound as pale yellow solid (0.03 g, 45%). $^1$H NMR (400 MHz, DMSO-d$_6$): δ 8.34 (d, J=7.3 Hz, 1H), 7.64 (dd, J=1.4 Hz & 7.8 Hz, 1H), 7.58-7.54 (m, 1H), 7.34 (d, J=2.0 Hz, 1H), 7.20 (d, J=8.3 Hz, 1H), 7.11 (d, J=2.0 Hz, 1H), 6.98 (t, J=7.9 Hz, 1H), 3.92 (s, 3H), 3.79-3.72 (m, 1H), 2.95 (d, J=12.2 Hz, 2H), 2.67-2.47 (m, 3H), 2.50-2.48 (m, 2H), 2.40-1.94 (m, 4H)1.72 (d, J=9.8 Hz, 2H), 1.44-1.24 (m, 2H); LC-MS: m/z 485.2 (M+H)$^+$.

The below compounds were prepared by procedure similar to the one described in Example-XI with appropriate variations in reactants, quantities of reagents and reaction conditions. The physiochemical characteristics of the compounds are also summarized.

| No | Reactant | Obtained Compound | Characterization Data $^1$H NMR (400 MHz, DMSO-d$_6$)/ LC-MS: |
|----|----------|-------------------|------------------|
| 65 | 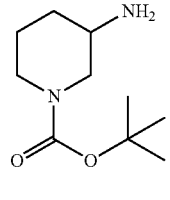 | 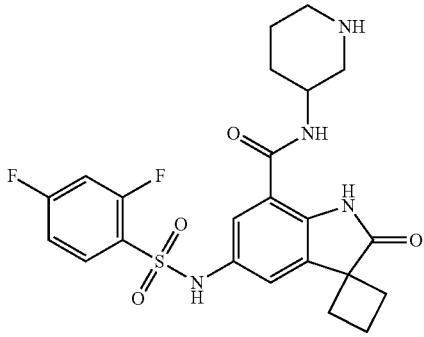 [SMILES: O=C(NC1CCCNC1)c1cc(NS(=O)(=O)c2ccc(F)cc2F)cc2c1NC(=O)C21CCC1] | δ 7.84-7.78 (m, 1H), 7.33 (d, J = 1.5 Hz, 1H), 7.30 (d, J = 2.0 Hz, 1H), 7.20-7.15 (m, 1H), 7.04 (t, J = 8.4 Hz, 1H), 4.03-4.00 (m, 1H), 3.20-3.16 (m, 1H), 3.09-2.97 (m, 1H), 2.67-2.49 (m, 4H), 2.31-2.14 (m, 4H), 2.00-1.97 (m, 1H), 1.84-1.80 (m, 1H), 1.65-1.57 (m, 2H); LC-MS: m/z 491.0 (M + H)$^+$. |
| 66 | 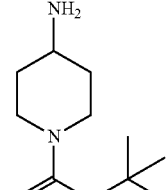 | 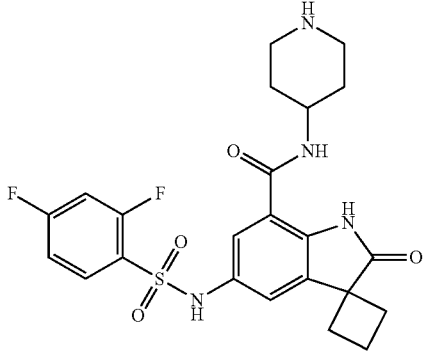 [SMILES: O=C(NC1CCNCC1)c1cc(NS(=O)(=O)c2ccc(F)cc2F)cc2c1NC(=O)C21CCC1] | δ 9.40 (bs, 1H), 8.31 (d, J = 7.3 Hz, 1H), 7.82-7.76 (m, 1H), 7.34-7.29 (m, 1H), 7.27 (d, J = 1.4 Hz, 1H), 7.17 (s, 1H), 7.12-7.08 (m, 1H), 3.90-3.88 (m, 1H), 3.40-3.35 (m, 1H), 3.15-3.12 (m, 2H), 2.78-2.73 (m, 2H), 2.39-2.32 (m, 2H), 2.18-2.04 (m, 4H), 1.83-1.81 (m, 2H), 1.60-1.52 (m, 2H); LC-MS: m/z 491.1 (M + H)$^+$. |

| No | Reactant | Obtained Compound | Characterization Data<br>$^1$H NMR (400 MHz, DMSO-$d_6$)/<br>LC-MS: |
|---|---|---|---|
| 67 | | Isomer-2* | δ 8.24-8.22 (m, 1H), 7.82-7.76 (m, 1H), 7.44 (t, J = 8.8 Hz, 1H), 7.24 (s, 1H), 7.22 (s, 1H), 7.16 (t, J = 8.8 Hz, 1H), 3.94-3.80 (m, 1H), 3.11-2.84 (m, 2H), 2.62-2.50 (m, 2H), 2.41-2.37 (m, 2H), 2.20-2.16 (m, 1H), 2.11-2.06 (m, 3H), 1.84-1.60 (m, 2H), 1.60-1.40 (m, 2H); LC-MS: m/z 491.2 (M + H)$^+$. |
| 68 | | Isomer-1* | δ 8.24-8.22 (m, 1H), 7.81-7.79 (m, 1H), 7.42 (t, J = 9.3 Hz, 1H), 7.25 (s, 1H), 7.20 (s, 1H), 7.18-7.14 (m, 1H), 3.94-3.80 (m, 1H), 3.12-2.98 (m, 1H), 2.97-2.84 (m, 1H), 2.62-2.50 (m, 2H), 2.40-2.26 (m, 2H), 2.25-1.98 (m, 4H), 1.86-1.58 (m, 2H), 1.58-1.38 (m, 2H); LC-MS: m/z 491.2 (M + H)$^+$. |

*Isomer-1 and 2 were separated by using Chiral HPLC under below conditions:
Column: Chiralpak-IA(250*4.6*5.0µ)
Mobile phase-A: 0.1% DEA in n-Hexane; Mobile phase-B: Ethanol
Isocratic: 70:30(A:B); Flow rate: 1.0 ml/min
Column temp: Ambient
Diluent: Mobile phase Example-XII: 2,4-Difluoro-N-(7'-(hydroxymethyl)-2'-oxospiro[cyclobutane-1,3'-indolin]-5'-yl)benzenesulfonamide (Compound-69)

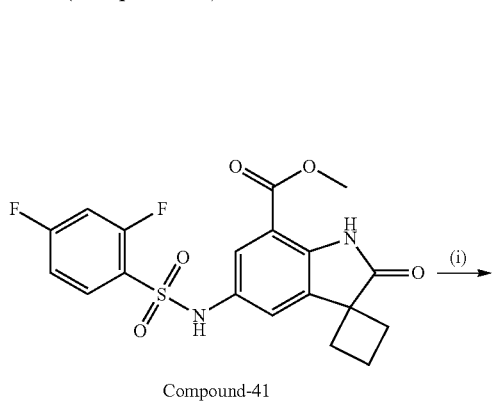

Compound-41

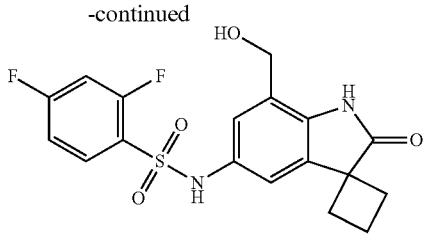

Compound-69

To a cooled solution of methyl 5'-((2,4-difluorophenyl)sulfonamido)-2'-oxo-spiro[cyclobutane-1,3'-indoline]-7'-carboxylate (compound-41) (0.15 g, 0.35 mmol) in THF (5 mL) was added Red-Al 60% in toluene (0.21 g, 1.05 mmol). The mixture was stirred at RT for 16 h. The reaction mixture was then quenched with rochelle salt, extracted with EtOAc (50 mL) and washed with water (50 mL) and brine (50 mL), dried over sodium sulphate, concentrated under reduced pressure and purified by preparative TLC to afford the title compound as off white solid (0.08 g, 57%). $^1$H NMR (400 MHz, DMSO-d$_6$): δ 10.28 (s, 1H), 10.14 (s, 1H), 7.83-7.77 (m, 1H), 7.56-7.51 (m, 1H), 7.25-7.19 (m, 1H), 7.12 (d, J=2.0 Hz, 1H), 6.95 (s, 1H), 5.10 (t, J=6.4 Hz, 1H), 4.33 (d, J=5.4 Hz, 2H), 2.41-2.33 (m, 2H), 2.22-2.05 (m, 4H); LC-MS: m/z 395.0 (M+H)$^+$.

Example-XIII: N-(7'-((1-ethylpiperidin-3-yl)amino)-2'-oxospiro[cyclo butane-1,3'-indolin]-5'-yl)-2,4-difluorobenzenesulfonamide: (Compound-70)

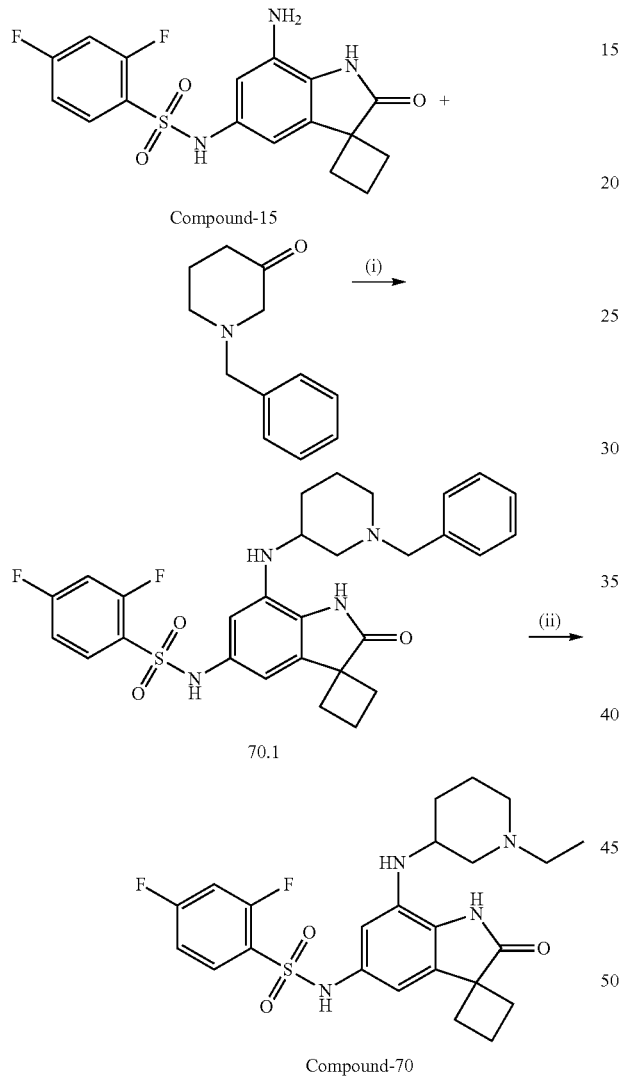

Step-(i): N-(7'-((1-benzylpiperidin-3-yl)amino)-2'-oxospiro[cyclobutane-1,3'-indolin]-5'-yl)-2,4-difluorobenzenesulfonamide (70.1)

The process of this step was adopted from Example-V. $^1$H NMR (400 MHz, DMSO-d$_6$): δ 10.07 (s, 1H), 9.80 (s, 1H), 7.79-7.75 (m, 1H), 7.53-7.49 (m, 1H), 7.33-7.18 (m, 6H), 6.54 (s, 1H), 6.19 (s, 1H), 4.75 (d, J=8.3 Hz, 1H), 4.55 (d, J=4.9 Hz, 1H), 3.50-3.35 (m, 2H), 3.21-3.18 (m, 1H), 2.81-2.78 (m, 2H), 2.68-2.62 (m, 1H), 2.40-2.35 (m, 2H), 2.19-1.98 (m, 4H), 1.96-1.88 (m, 2H), 1.66-1.60 (m, 2H); LC-MS: m/z 553.2 (M+H)$^+$.

Step-(ii): N-(7'-((1-ethylpiperidin-3-yl)amino)-2'-oxospiro[cyclobutane-1,3'-indolin]-5'-yl)-2,4-difluorobenzenesulfonamide (70).

To a solution of N-(7'-((1-benzylpiperidin-3-yeamino)-2'-oxospiro[cyclobutane-1,3'-indolin]-5'-yl)-2,4-difluorobenzenesulfonamide (0.08 g, 0.14 mmol) in EtOH (10 mL) was added palladium hydroxide (0.02 g, 0.014 mmol). The mixture was fitted with hydrogen gas bladder and stirred at RT for 4 h. Then mixture was filtered through celite bed and washed with EtOAc. The organic layer was concentrated under reduced pressure and column purified to afford the title compound as off white solid (0.005 g, 6%). $^1$H NMR (400 MHz, DMSO-d$_6$): δ 10.09 (bs, 1H), 9.80 (s, 1H), 7.82-7.76 (m, 1H), 7.55-7.50 (m, 1H), 7.25-7.20 (m, 1H), 6.55 (d, J=1.5 Hz, 1H), 6.19 (s, 1H), 4.75 (d, J=7.8 Hz, 1H), 3.18-3.16 (m, 1H), 2.85-2.82 (m, 1H), 2.38-2.29 (m, 4H), 2.18-2.01 (m, 4H), 1.91-1.89 (m, 2H), 1.78-1.74 (m, 1H), 1.68-1.65 (m, 2H), 1.48-1.40 (m, 1H), 1.07-1.04 (m, 1H), 0.98 (t, J=7.3 Hz, 3H); LC-MS: m/z 491.1 (M+H)$^+$.

Example-XIV: 2,4-Difluoro-N-(2'-oxo-7'-(piperidin-3-ylamino)spiro[cyclobutane-1,3'-indolin]-5'-yl)benzenesulfonamide hydrochloride (Compound-71)

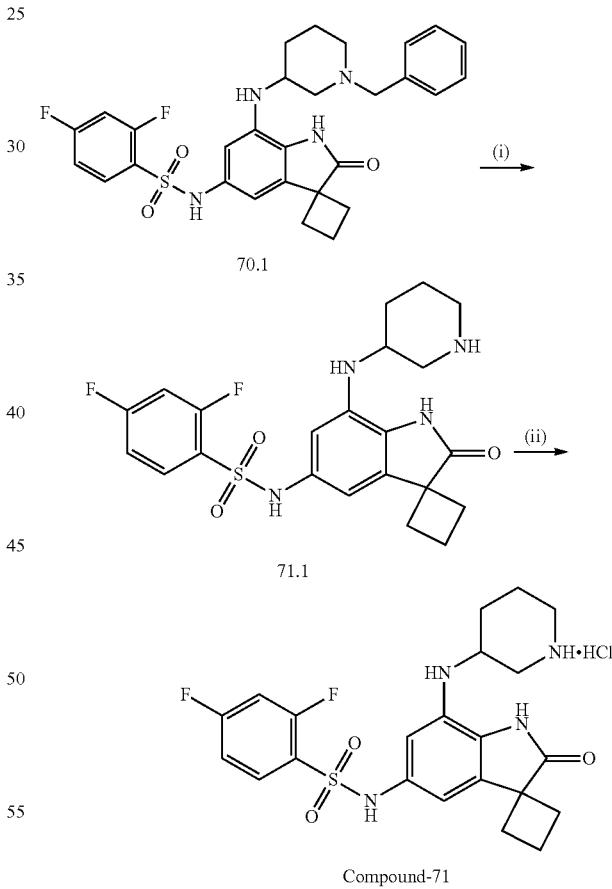

Step-(i): 2,4-Difluoro-N-(2'-oxo-7'-(piperidin-3-ylamino)spiro[cyclobutane-1,3'-indolin]-5'-yl)benzenesulfonamide (71.1)

To a solution of N-(7'-((1-benzylpiperidin-3-yeamino)-2'-oxospiro[cyclobutane-1,3'-indolin]-5'-yl)-2,4-difluorobenzenesulfonamide (70.1) (0.2 g, 0.36 mmol) in EtOAc (10 mL) was added 10% Pd—C (0.02 g). The mixture was stirred under H$_2$ bladder pressure at RT for 2 h. The mixture was filtered through celite bed and washed with EtOAc. The organic layer was concentrated under reduced pressure to afford the title compound as off white solid (0.05 g). ¹H NMR (400 MHz, DMSO-d₆): δ 9.77 (s, 1H), 7.79 (dd, J=8.6 Hz, 15.0 Hz, 1H), 7.55-7.50 (m, 1H), 7.25-7.20 (m, 1H), 6.51 (d, J=2.0 Hz, 1H), 6.19 (s, 1H), 4.73 (d, J=7.8 Hz, 1H), 4.15-4.12 (m, 1H), 3.17-3.05 (m, 1H), 2.99-2.84 (m, 2H), 2.81-1.79 (m, 1H), 2.46-2.33 (m, 2H), 2.24-2.01 (m, 6H), 1.90-1.81 (m, 1H), 1.64-1.61 (m, 1H), 1.45-1.40 (m, 2H); LC-MS: m/z 463.3 (M+H)⁺.

Step-(ii): 2,4-Difluoro-N-(2'-oxo-7'-(piperidin-3-ylamino)spiro[cyclobutane-1,3'-indolin]-5'-yl)benzenesulfonamide hydrochloride To a cooled solution of 2,4-difluoro-N-(2'-oxo-7'-(piperidin-3-ylamino)-spiro[cyclobutane-1,3'-indolin]-5'-yl)benzenesulfonamide (0.05 g, 0.11 mmol) in MeOH (1 mL) was added 6 N HCl (1 mL). The mixture was stirred at RT for 1 h. The mixture was concentrated under reduced pressure and washed with diethyl ether to afford the title compound as off white solid (0.03 g, 60%). ¹H NMR(400 MHz, DMSO-d₆): δ 10.16 (s, 1H), 9.99 (s, 1H), 9.11 (bs, 2H), 7.86-7.80 (m, 1H), 7.58-7.52 (m, 1H), 7.28-7.23 (m, 1H), 6.53 (s, 1H), 6.28 (s, 1H), 3.58-3.52 (m, 2H), 3.25-3.22 (m, 1H), 3.18-3.12 (m, 1H), 2.95-2.91 (m, 1H), 2.78-2.72 (m, 1H), 2.60-2.40 (m, 1H), 2.38-2.33 (m, 2H), 2.19-1.98 (m, 4H), 1.90-1.80 (m, 1H), 1.69-1.66 (m, 1H), 1.46-1.39 (m, 1H); LC-MS: m/z 463.2 (M+H)⁺.

Example-XV: 5'-((2,4-Difluoro-N-methylphenyl)sulfonamido)-N-(1-methyl piperidin-4-yl)-2'-oxospiro[cyclobutane-1,3'-indoline]-7'-carboxamide (Compound-72)

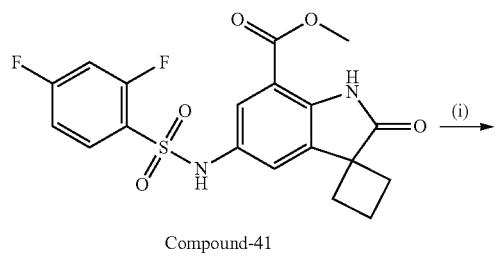

Compound-41

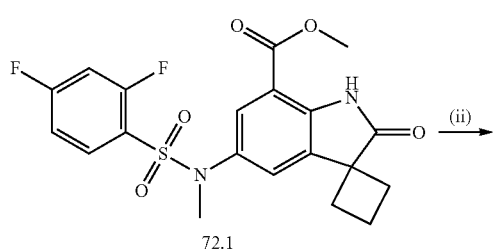

72.1

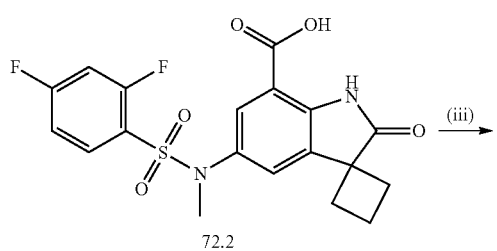

72.2

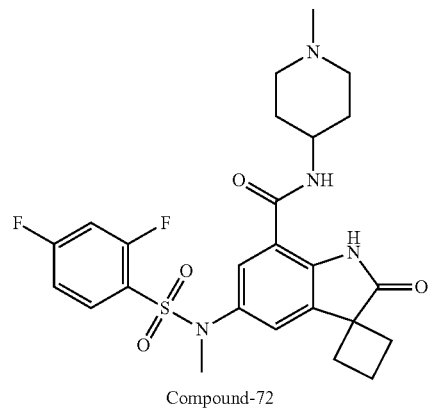

Compound-72

Step-(i): Methyl 5'-((2,4-difluoro—N-methylphenyl)sulfonamido)-2'-oxospiro[cyclobutane-1,3'-indoline]-7'-carboxylate (72.1)

To a solution of methyl 5'-((2,4-difluorophenyl)sulfonamido)-2'-oxospiro-[cyclobutane-1,3'-indoline]-7'-carboxylate (compound-41) (0.1 g, 0.245 mmol) in acetonitrile (5 mL) was added potassium carbonate (0.1 g, 0.73 mmol) followed by methyl iodide (0.02 mL, 0.29 mmol). The mixture was stirred at RT for 6 h. The mixture was diluted with EtOAc (50 mL), washed with water (50 mL) and brine (50 mL), dried over sodium sulphate, concentrated under reduced pressure and column purified to afford the title compound as off white solid (0.1 g, 94%). ¹H NMR (400 MHz, DMSO-d₆): δ 10.31 (s, 1H), 7.68-7.63 (m, 2H), 7.60 (d, J=1.9 Hz, 1H), 7.46 (d, J=2.0 Hz, 1H), 7.29-7.24 (m, 1H), 3.84 (s, 3H), 3.26 (s, 3H), 2.41-2.33 (m, 2H), 2.28-2.20 (m, 3H), 2.08-2.06 (m, 1H); LC-MS: m/z 437.1 (M+H)⁺.

Step-(ii): 5'-((2,4-Difluoro-N-methylphenyl)sulfonamido)-2'-oxospiro[cyclobutane-1,3'-indoline]-7'-carboxylic acid (72.2)

The process of this step was adopted from step-(ii) of Example-XI. ¹H NMR (400 MHz, DMSO-d₆): δ 13.19 (bs, 1H), 9.95 (s, 1H), 7.66-7.63 (m, 2H), 7.57 (s, 1H), 7.42 (d, J=1.9 Hz, 1H), 7.28-7.24 (m, 1H), 3.26 (s, 3H), 2.39-2.37 (m, 2H), 2.28-2.18 (m, 3H), 2.14-2.02 (m, 1H); LC-MS: m/z 423.0 (M+H)⁺.

Step-(iii): 5'-((2,4-Difluoro-N-methylphenyl)sulfonamido)-N-(1-methylpiperidin-4-yl)-2'-oxospiro[cyclobutane-1,3'-indoline]-7'-carboxamide The process of this step was adopted from Example-VII (Method-B). ¹H NMR (400 MHz, DMSO-d₆): δ 9.88 (s, 1H), 8.31 (d, J=7.8 Hz, 1H), 7.68-7.59 (m, 2H), 7.53 (d, J=2.0 Hz, 1H), 7.40 (d, J=1.4 Hz, 1H), 7.28-7.23 (m, 1H), 3.76-3.64 (m, 1H), 3.28 (s, 3H), 2.79-2.76 (m, 2H), 2.40-2.32 (m, 2H), 2.22-2.16 (m, 6H), 2.08-2.00 (m, 1H), 1.95-1.90 (m, 2H), 1.74-1.71 (m, 2H), 1.58-1.52 (m, 2H); LC-MS: m/z 519.0 (M+H)⁺.

The below compound was prepared by procedure similar to the one described in Example-XV step-(ii) & step-(iii) with appropriate variations in reactants, quantities of reagents and reaction conditions. The physiochemical characteristics of the compound is also summarized.

| No | Structure | Characterization data |
|---|---|---|
| 73* | 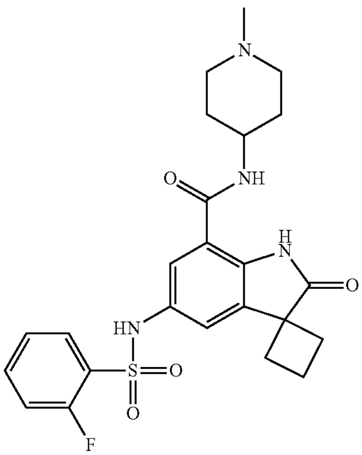 [SMILES: CN1CCC(NC(=O)c2cc(NS(=O)(=O)c3ccccc3F)cc3c2NC(=O)C32CCC2)CC1] | $^{1}$H NMR (400 MHz, DMSO-d$_6$): δ 10.14 (bs, 1H), 9.83 (s, 1H), 8.47 (d, J = 7.3 Hz, 1H), 7.75-7.68 (m, 2H), 7.48-7.43 (m, 1H), 7.37-7.31 (m, 2H), 7.16 (s, 1H), 3.86-3.84 (m, 1H), 3.15-3.13 (m, 2H), 2.67-2.60 (m, 2H), 2.55 (s, 3H), 2.44-2.33 (m, 2H), 2.18-2.16 (m, 1H), 2.15-1.99 (m, 3H), 1.91-1.88 (m, 2H), 1.75-1.70 (m, 2H); LC-MS: m/z 487.2 (M + H)$^+$. |

*The starting compound for this reaction is prepared by using intermediate-3 and further undergoing carboxylic ester formation as depicted in the preparation of compound-41

Example-XVI: 5'-((4-Bromo-2-fluorophenyl)sulfonamido)-N-(1-methylpiperidin-4-yl)-2'-oxospiro[cyclobutane-1,3'-indoline]-7'-carboxamide: (Compound-74)

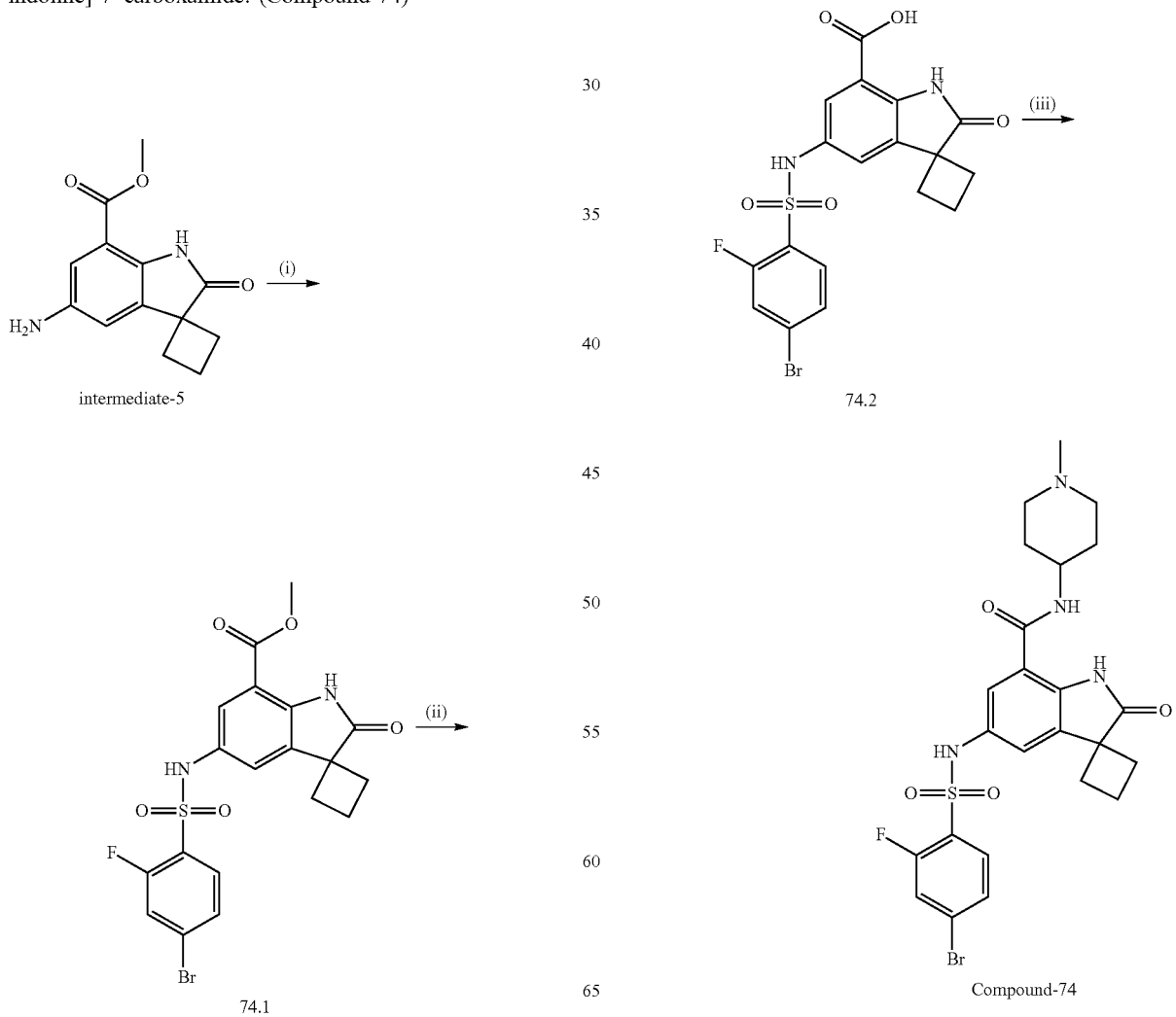

Step-(i): Methyl 5'-((4-bromo-2-fluorophenyl)sulfonamido)-2'-oxospiro[cyclobutane-1,3'-indoline]-7'-carboxylate (74.1)

The process of this step was adopted from step-f of intermediate-1. $^1$H NMR (400 MHz, DMSO-$d_6$): δ 10.59 (s, 1H), 10.17 (s, 1H), 7.88 (d, J=2.0 Hz, 1H), 7.85 (d, J=2.0 Hz, 1H), 7.59 (d, J=2.5 Hz, 1H), 7.50 (d, J=2.0 Hz, 1H), 7.38 (d, J=2.5 Hz, 1H), 3.81 (s, 3H), 2.42-2.21 (m, 2H), 2.20-2.07 (m, 4H); LC-MS: m/z 485.1 (M+H)$^+$.

Step-(ii): 5'-((4-Bromo-2-fluorophenyl)sulfonamido)-2'-oxospiro[cyclobutane-1,3'-indoline]-7'-carboxylic acid (70.2)

The process of this step was adopted from step-ii of Example-VI. $^1$H NMR (400 MHz, DMSO-$d_6$): δ 13.34 (bs, 1H), 10.54 (s, 1H), 9.81 (s, 1H), 7.87 (d, J=2.5 Hz, 1H), 7.85 (d, J=1.5 Hz, 1H), 7.59 (d, J=1.4 Hz, 1H), 7.48 (d, J=1.9 Hz, 1H), 7.35 (d, J=1.9 Hz, 1H), 2.42-2.33 (m, 2H), 2.25-2.11 (m, 4H); LC-MS: m/z 468.9 (M+H)$^+$.

Step-(iii): 5'-((4-Bromo-2-fluorophenyl)sulfonamido)-N-(1-methylpiperidin-4-yl)-2'-oxospiro[cyclobutane-1,3'-indoline]-7'-carboxamide (70)

The process of this step was adopted from method-B of Example-VII. $^1$H NMR (400 MHz, DMSO-$d_6$): δ 10.24 (bs, 1H), 9.76 (bs, 1H), 8.32 (d, J=7.8 Hz, 1H), 7.84 (dd, J=9.8 Hz & 1.5 Hz, 1H), 7.65-7.61 (m, 1H), 7.56-7.54 (m, 1H), 7.32 (d, J=2.0 Hz, 1H), 7.17 (d, J=2.0 Hz, 1H), 3.73-3.67 (m, 1H), 2.84 (d, J=11.2 Hz, 2H), 2.42-2.33 (m, 2H), 2.23 (s, 3H); 2.23-2.18 (m, 1H), 2.11-1.99 (m, 5H), 1.78-1.75 (m, 2H), 1.63-1.53 (m, 2H); LC-MS: m/z 564.9 (M+H)$^+$.

The below compounds were prepared by procedure similar to the one described in Example-XVI with appropriate variations in reactants, quantities of reagents and reaction conditions. The physiochemical characteristics of the compounds are also summarized.

Example-XVII: 2,4-Difluoro-N-(2'-oxo-7'-((6-oxo-1,2,3,6-tetrahydropyridin-4-yl)-amino)spiro[cyclobutane-1,3'-indolin]-5'-yl)benzenesulfonamide (Compound-76)

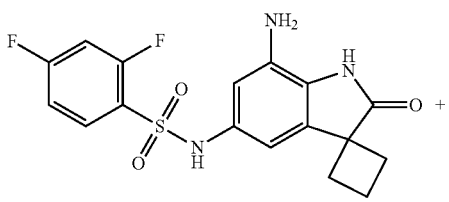

Compound-15

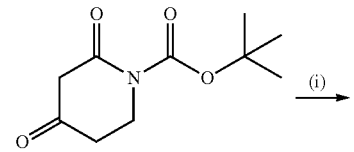

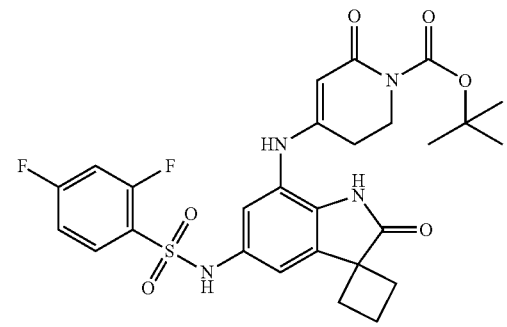

76.1

| No | Structure | Characterization data |
| --- | --- | --- |
| 75* | 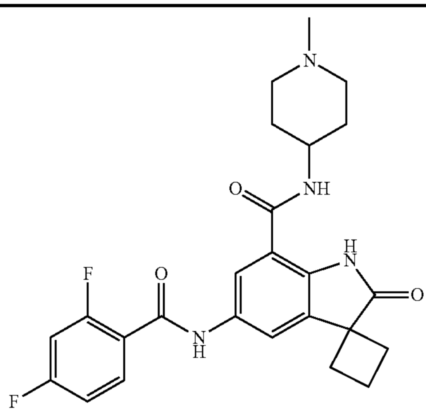 | 1H NMR (400 MHz, DMSO-$d_6$): δ 10.36 (s, 1H), 9.74 (s, 1H), 8.35 (d, J = 7.8 Hz, 1H), 8.35 (d, J = 7.8 Hz, 1H), 8.01 (s, 1H), 7.81-7.76 (m, 2H), 7.47-7.41 (m, 1H), 7.27-7.23 (m, 1H), 3.73-3.67 (m, 1H), 2.78-2.75 (m, 2H), 2.50-2.48 (m, 2H), 2.31-2.16 (m, 4H), 2.16 (s, 3H), 1.96-1.90 (m, 2H), 1.78-1.75 (m, 2H), 1.61-1.52 (m, 2H); LCMS: m/z 512.2 (M + H)$^+$. |
| 75a** | 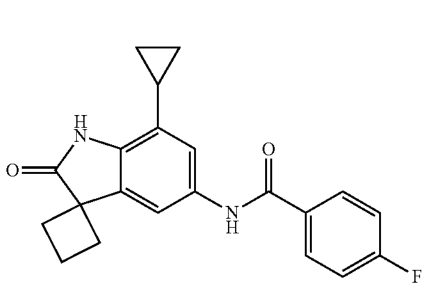 [SMILES: O=C(Nc1cc(C2CC2)c2c(c1)C1(CCC1)C(=O)N2)c1ccc(F)cc1] | $^1$H-NMR (400 MHz, CD$_3$OD): δ 7.98-7.95 (m, 2H), 7.73 (s, 1H), 7.21-7.16 (m, 2H), 7.07 (s, 1H), 2.64-2.57 (m, 2H), 2.39-2.26 (m, 5H), 1.87-1.83 (m, 1H), 0.97-0.92 (m, 2H), 0.69-0.65 (m, 2H); LC-MS: 351.2 [M + H]$^+$. |

*The step-(i) of compound 75 was carried out according to Example-VII method-A
**Compound 75a was prepared according to step-iii of example-IV -continued

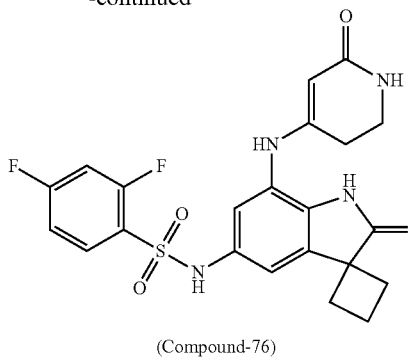

(Compound-76)

Step-(i): tert-Butyl 4-((5'-((2,4-difluorophenyl)sulfonamido)-2'-oxospiro[cyclobutane-1,3'-indolin]-7'-yl)amino)-6-oxo-3,6-dihydropyridine-1(2H)-carboxylate (76.1):

To a suspension of N-(7'-amino-2'-oxospiro[cyclobutane-1,3'-indolin]-5'-yl)-2,4-difluoro benzenesulfonamide (Compound-15) (0.05 g, 0.13 mmol) in DCE (2 mL) was added tert-butyl 2,4-dioxopiperidine-1-carboxylate (0.03 g, 0.16 mmol) followed by AcOH (0.045 mL, 0.78 mmol). The mixture was stirred at RT for 16 h. The mixture concentrated under reduced pressure and the residue was dissolved in MeOH (3 mL) at 0° C. Sodium borohydride (0.015 g, 0.39 mmol) was added followed by stirring at RT for 2 h. The mixture was diluted with EtOAc (50 mL), washed with water (50 mL), dried over sodium sulphate and concentrated under reduced pressure and column purified to afford the title compound as off white solid 0.021 g (28%). $^1$H NMR (400 MHz, DMSO-$d_6$): δ 10.43 (s, 1H), 10.15 (s, 1H), 8.41 (s, 1H), 7.86-7.80 (m, 1H), 7.56-7.51 (m, 1H), 7.24 (t, J=8.6 Hz, 1H), 7.17 (s, 1H), 6.70 (d, J=2.0 Hz, 1H), 4.15 (s, 1H), 3.71 (t, J=6.1 Hz, 2H), 2.44-2.33 (m, 4H), 2.18-2.08 (m, 4H), 1.43 (s, 9H); LC-MS: m/z 573.0 (M−H)⁻.

Step-(ii): 2,4-Difluoro-N-(2'-oxo-7'-((6-oxo-1,2,3,6-tetrahydropyridin-4-yl)amino) spiro[cyclobutane-1,3'-indolin]-5'-yl)benzenesulfonamide (76)

The process of this step was adopted from step-iv of Example-XI. $^1$H NMR (400 MHz, DMSO-$d_6$): δ 10.39 (s, 1H), 10.04 (s, 1H), 7.85-7.80 (m, 1H), 7.77 (s, 1H), 7.57-7.52 (m, 1H), 7.24 (t, J=8.6 Hz, 1H), 7.10 (d, J=1.4 Hz, 1H), 6.73 (d, J=1.4 Hz, 1H), 6.60 (s, 1H), 4.21 (s, 1H), 3.22-3.19 (m, 2H), 2.39-2.32 (m, 4H), 2.21-2.09 (m, 4H); LC-MS: m/z 475.0 (M+H)⁺.

The below compounds were prepared by a procedure similar to the one described in Example-XVII with appropriate variations in reactants, quantities of reagents and reaction conditions. The physiochemical characteristics of the compounds are also summarized.

| No | Structure | Characterization data $^1$H NMR (400 MHz, DMSO-$d_6$)/ LC-MS: |
|---|---|---|
| 77 | 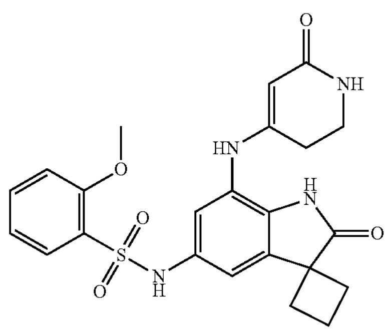 [SMILES: COc1ccccc1S(=O)(=O)Nc1cc(NC2=CC(=O)NCC2)c2c(c1)C1(CCC1)C(=O)N2] | δ 9.94 (s, 1H), 9.73 (s, 1H), 7.70 (d, J = 7.8 Hz, 1H), 7.67 (s, 1H), 7.53 (t, J = 7.1 Hz, 1H), 7.18 (d, J = 8.4 Hz, 1H), 7.07 (s, 1H), 6.99 (t, J = 7.6 Hz, 1H), 6.77 (s, 1H), 6.56 (s, 1H), 4.25 (s, 1H), 3.92 (s, 3H), 3.22-3.19 (m, 2H), 2.38-2.33 (m, 4H), 2.18-2.08 (m, 4H); LC-MS: m/z 469.2 (M + H)⁺. |
| 78* | 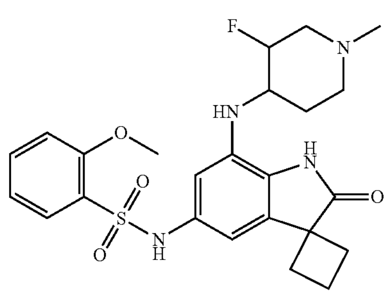 [SMILES: COc1ccccc1S(=O)(=O)Nc1cc(NC2CCN(C)CC2F)c2c(c1)C1(CCC1)C(=O)N2] | δ 9.89 (s, 1H), 9.38 (s, 1H), 7.66 (dd, J = 7.8, 1.5 Hz, 1H), 7.57-7.53 (m, 1H), 7.18 (d, J = 8.3 Hz, 1H), 7.02-6.97 (m, 1H), 6.58 (d, J = 1.5 Hz, 1H), 6.21 (d, J = 1.4 Hz, 1H), 4.84 (d, J = 8.8 Hz, 1H), 4.60-4.48 (m, 1H), 3.92 (s, 3H), 3.21-312 (m, 1H), 3.05-3.00 (m, 1H), 2.78-2.75 (m, 1H), 2.35-2.22 (m, 2H), 2.20 (s, 3H), 2.19-1.99 (m, 6H), 1.64-1.59 (m, 2H); ES-MS: m/z 489.2 (M + H)⁺. |
| 79* | 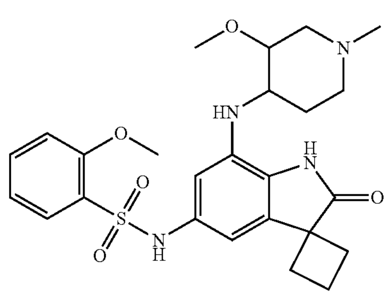 [SMILES: COc1ccccc1S(=O)(=O)Nc1cc(NC2CCN(C)CC2OC)c2c(c1)C1(CCC1)C(=O)N2] | δ 10.07 (s, 1H), 9.40 (s, 1H), 7.66-7.64 (m, 1H), 7.54 (t, J = 6.8 Hz, 1H), 7.17 (d, J = 8.3 Hz, 1H), 6.98 (t, J = 7.8 Hz, 1H), 6.57 (s, 1H), 6.17 (s, 1H), 4.65-4.62 (m, 1H), 3.92 (s, 3H), 3.29-3.21 (m, 2H), 3.10 (s, 3H), 2.35-2.25 (m, 3H), 2.17 (s, 3H), 2.13-1.99 (m, 5H), 1.91 (s, 2H), 1.65-1.59 (m, 1H), 1.55-1.45 (m, 1H); LCMS: m/z 501.3 (M + H)⁺. |

| No | Structure | Characterization data $^1$H NMR (400 MHz, DMSO-$d_6$)/LC-MS: |
|---|---|---|
| 79a | 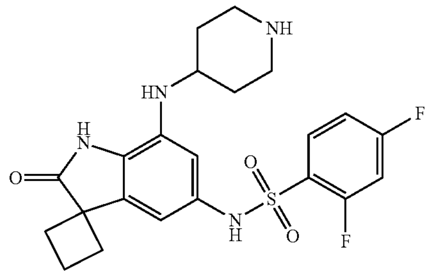 [SMILES: O=C1Nc2c(NC3CCNCC3)cc(NS(=O)(=O)c3ccc(F)cc3F)cc2C12CCC2] | δ 10.17 (s, 1H), 9.78 (s, 1H), 8.50 (m, 1H), 8.32 (m, 1H), 7.83-7.80 (m, 1H), 7.58-7.53 (t, 1H), 7.25 (t, 1H), 6.51 (s, 1H), 6.25 (s, 1H), 4.88 (d, 1H), 3.03-3.01 (m, 1H), 2.33 (m, 2H), 2.16-2.14 (m, 1H), 2.08-1.94 (m, 4H), 1.46-1.43 (m, 2H); LC-MS: 463.2 [M + H]$^+$. |

*Compounds 78 & 79 are obtained by addition alkylation reaction as depicted in step-(i) of example-XV Example-XVIII: Methyl 3-fluoro-4-(N-(7'-((1-methylpiperidin-4-yl) carbamoyl)-2'-oxospiro[cyclobutane-1,3'-indolin]-5'-yl)sulfamoyl)benzoate (Compound-80)

Example-XIX: 5'-((4—Cyano-2-fluorophenyl) sulfonamido)-N-(1-methylpiperidin-4-yl)-2'-oxospiro[cyclobutane-1,3'-indoline]-7'-carboxamide (Compound-81)

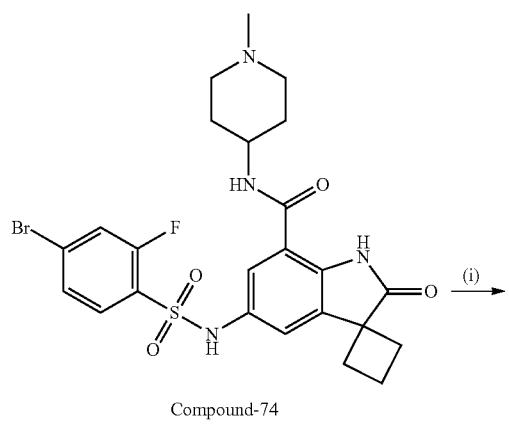

Compound-74

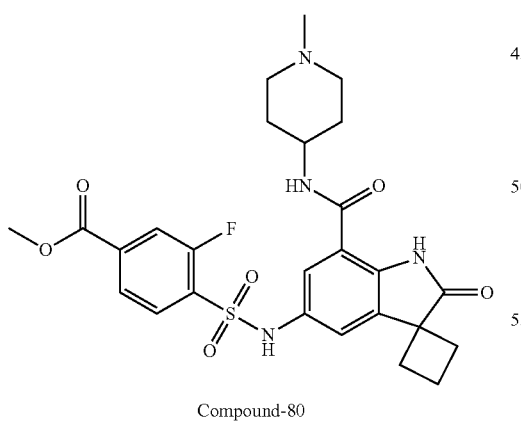

Compound-80

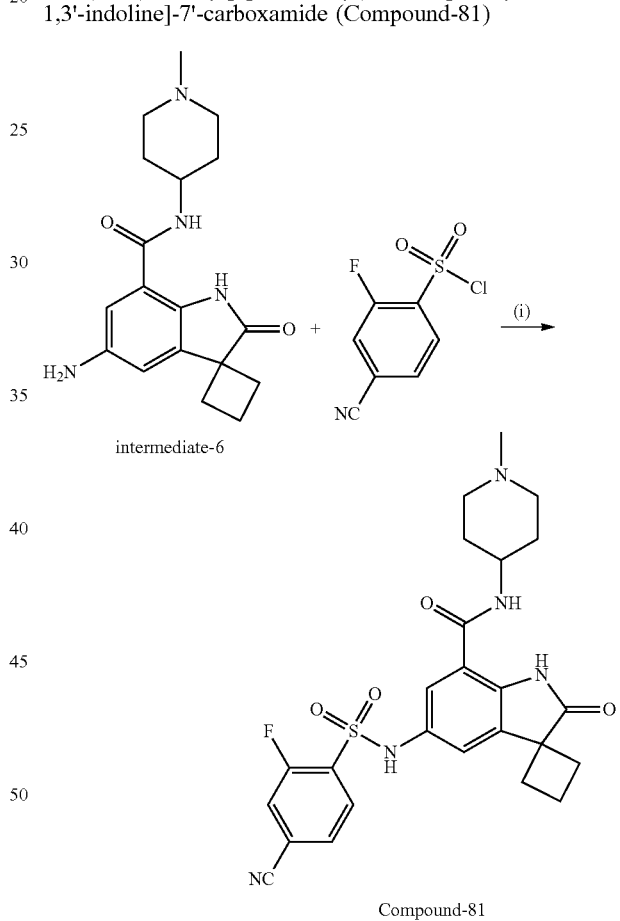

The process of this step was adopted from step-(i) of Example-XI. $^1$H NMR (400 MHz, DMSO-$d_6$): δ 10.25 (bs, 1H), 9.72 (s, 1H), 8.30 (d, J=7.9 Hz, 1H), 7.90-7.84 (m, 3H), 7.28 (s, 1H), 7.23 (s, 1H), 3.87 (s, 3H), 3.70-3.67 (m, 1H), 2.85-2.82 (m, 2H), 2.37-2.33 (m, 2H), 2.24 (s, 3H), 2.22-2.05 (m, 6H), 1.77-1.74 (m, 2H), 1.61-1.53 (m, 2H); LC-MS: m/z 545.2 (M+H)$^+$.

The process of this step was adopted from step-f of intermediate-1. $^1$H NMR (400 MHz, DMSO-$d_6$): δ 9.66 (bs, 1H), 8.30 (d, J=7.4 Hz, 1H), 8.05 (d, J=9.8 Hz, 1H), 7.90-7.86 (m, 1H), 7.78 (d, J=7.8 Hz, 1H), 7.25 (s, 2H), 3.78-3.68 (m, 1H), 2.91-2.88 (m, 2H), 2.40-2.29 (m, 2H), 2.29 (s, 3H), 2.18-2.02 (m, 6H), 1.80-1.76 (m, 2H), 1.64-1.55 (m, 2H); LCMS: m/z 512.2 (M+H)$^+$.

The below compounds were prepared by procedure similar to the one described in Example-XIX with appropriate variations in reactants, quantities of reagents and reaction conditions. The physiochemical characteristics of the compounds are also summarized.

| No | Reactant | Structure | Characterization data<br>¹H NMR (400 MHz, DMSO-d₆)/LC-MS |
|---|---|---|---|
| 83 | *cyclohexanesulfonyl chloride* | *structure* | δ 9.78 (bs, 1H), 9.53 (bs, 1H), 8.35 (d, J = 7.4 Hz, 1H), 7.50 (d, J = 1.4 Hz, 1H), 7.38 (d, J = 1.5 Hz, 1H), 3.79-3.62 (m, 1H), 2.96-2.88 (m, 1H), 2.82-2.78 (m, 2H), 2.47-2.40 (m, 2H), 2.32-2.01 (m, 1H), 1.94-1.85 (m, 4H), 1.76-1.55 (m, 3H), 1.45-1.37 (m, 2H), 1.27-1.07 (m, 3H); LCMS: m/z 475.3 (M + H)⁺. |
| 84 | *2-ethoxybenzenesulfonyl chloride* | *structure* | δ 9.72 (s, 1H), 9.47 (bs, 1H), 8.28 (d, J = 7.3 Hz, 1H), 7.66 (dd, J = 7.8, 1.5 Hz, 1H), 7.56-7.52 (m, 1H), 7.35 (d, J = 1.9 Hz, 1H), 7.20 (d, J = 8.3 Hz, 1H), 7.14 (d, J = 1.5 Hz, 1H), 6.97 (d, J = 7.9 Hz, 1H), 4.23 (q, J = 6.9 Hz, 1H), 3.78-3.64 (m, 1H), 2.84-2.75 (m, 2H), 2.41-2.32 (m, 2H), 2.20-2.10 (m, 5H), 2.09-1.94 (m, 5H), 1.79-1.72 (m, 2H), 1.62-1.53 (m, 2H), 1.36 (t, J = 6.9 Hz, 3H); LCMS: m/z 513.3 (M + H)⁺. |
| 85 | *piperidine-1-sulfonyl chloride* | *structure* | 7.54 (d, J= 1.9 Hz, 1H), 7.19 (d, J = 1.9 Hz, 1H), 3.89-3.84 (m, 1H), 3.16-3.13 (m, 4H), 2.90 (d, J = 12.2 Hz, 2H), 2.61-2.54 (m, 2H), 2.38-2.24 (m, 4H), 2.28 (s, 3H), 2.17 (t, J = 11.3 Hz, 2H), 1.96-1.92 (m, 2H), 1.74-1.65 (m, 2H), 1.57-1.48 (m, 6H); LCMS: m/z 476.3 (M + H)⁺. |
| 86 | *2,5-difluorobenzenesulfonyl chloride* | *structure* | δ 10.20 (bs, 1H), 9.79 (s, 1H), 8.38 (d, J = 7.4 Hz, 1H), 7.61-7.50 (m, 3H), 7.34 (d, J = 2.0 Hz, 1H), 7.20 (d, J = 2.0 Hz, 1H), 3.82-3.72 (m, 1H), 3.02-2.96 (m, 2H), 2.42-2.33 (m, 7H), 2.23-2.13 (m, 1H), 2.11-1.98 (m, 3H), 1.82-1.85 (m, 2H), 1.76-1.60 (m, 2H); LCMS: m/z 505.2 (M + H)⁺. |

| No | Reactant | Structure | Characterization data<br>¹H NMR (400 MHz, DMSO-d₆)/LC-MS |
|---|---|---|---|
| 87 | | 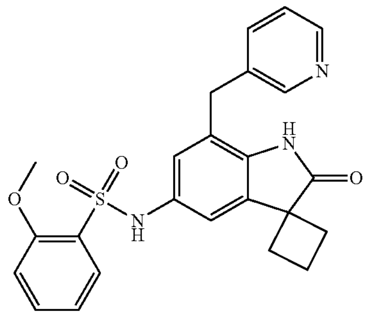 [SMILES: COc1ccccc1S(=O)(=O)Nc1cc(Cc2cccnc2)c2c(c1)C1(CCC1)C(=O)N2] | δ 10.39 (s, 1H), 9.56 (s, 1H), 8.41 (dd, J = 4.9, 2.0 Hz, 1H), 8.35 (d, J = 1.9 Hz, 1H), 7.60 (d, J = 1.4 Hz, 1H), 7.59-7.57 (m, 1H), 7.55-7.50 (m, 1H), 7.36-7.26 (m, 2H), 7.11-7.08 (m, 1H), 6.95 (t, J = 7.3 Hz, 1H), 6.61 (d, J = 2.0 Hz, 1H), 3.81 (s, 3H), 3.78 (s, 2H), 2.40-2.32 (m, 2H), 2.20-2.06 (m, 4H); LCMS: m/z 450.2 (M + H)⁺. |

Example-XX: 2,4-Difluoro-N-(2'-oxo-7'-(1,2,3,4-tetrahydroisoquinolin-7-yl) spiro-[cyclobutane-1,3'-indolin]-5'-yl) benzenesulfonamide (Compound-88)

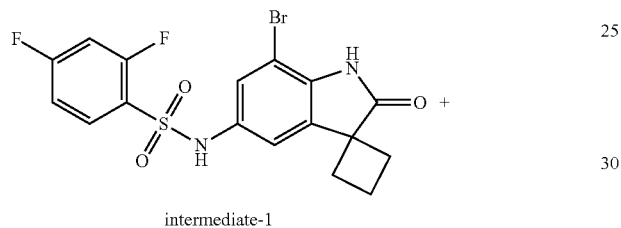

intermediate-1

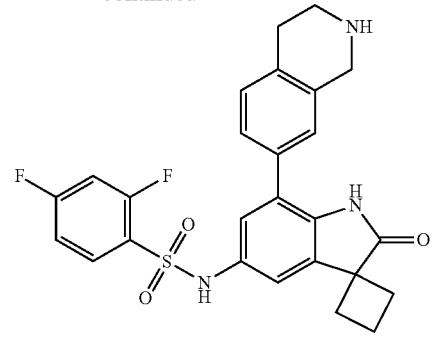

Compound-88

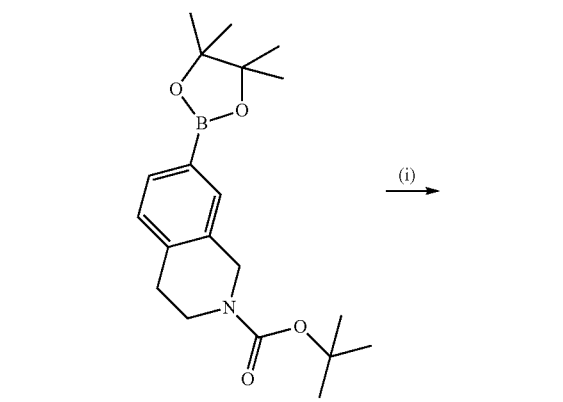

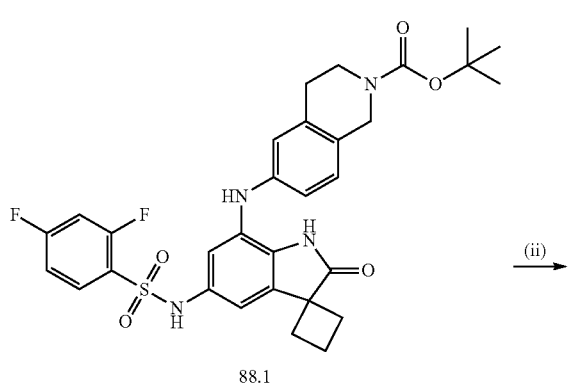

88.1

Step-(i): tert-Butyl 7-(5'-((2,4-difluorophenyl)sulfonamido)-2'-oxospiro[cyclo butane-1,3'-indolin]-7'-yl)-3,4-dihydroisoquinoline-2(1H)-carboxylate (88.1):

The process of this step was adopted from Example-I. ¹H NMR (400 MHz, DMSO-d₆): δ 10.38 (s, 1H), 10.16 (s, 1H), 7.86-7.82 (m, 1H), 7.59-7.53 (m, 1H), 7.27-7.21 (m, 3H), 7.08-7.02 (m, 2H), 6.83 (s, 1H), 4.54 (s, 2H), 3.56 (t, J=5.4 Hz, 2H), 2.79 (t, J=5.4 Hz, 2H), 2.43-2.33 (m, 2H), 2.23-2.06 (m, 4H), 1.44 (s, 9H).

Step-(ii): 2,4-Difluoro-N-(2'-oxo-7'-(1,2,3,4-tetrahydroisoquinolin-7-yl)spiro[cyclobutane-1,3'-indolin]-5'-yl) benzenesulfonamide (88):

To a solution of tert-butyl 7-(5'-((2,4-difluorophenyl)sulfonamido)-2'-oxospiro [cyclobutane-1,3'-indolin]-7'-yl)-3,4-dihydroisoquinoline-2(1H)-carboxylate (0.06 g, 0.1 mmol) in DCM (2 mL) was added TFA (0.04mL, 0.5 mmol). The mixture was stirred at RT for 2 h. The mixture was concentrated under reduced pressure, the residue was diluted with DCM and washed with aqueous sodium bi carbonate. The organic layer was dried over sodium sulphate, concentrated under reduced pressure to afford the title compound as brown solid which was washed with diethyl ether (0.025 g, 46%). ¹H NMR (400 MHz, DMSO-d₆): δ 10.04 (s, 1H), 7.87-7.81 (m, 1H), 7.51 (t, J=9.3 Hz, 1H), 7.24-7.23 (m, 1H), 7.20 (s, 1H), 7.12 (d, J=7.8 Hz, 1H), 6.99 (d, J=7.8 Hz, 1H), 6.93 (s, 1H), 6.78 (d, J=2.0 Hz, 1H), 3.91 (s, 2H), 2.99 (t, J=5.3 Hz, 2H), 2.73 (t, J=5.4 Hz, 2H) 2.44-2.40 (m, 2H), 2.33-2.06 (m, 4H); LC-MS: m/z 496.2 (M+H)⁺.

The below compound was prepared by a procedure similar to the one described in Example-XX with appropriate variations in reactants, quantities of reagents and reaction conditions. The physiochemical characteristics of the compound is also summarized.

| No | Structure | Characterization data |
|---|---|---|
| 89* | 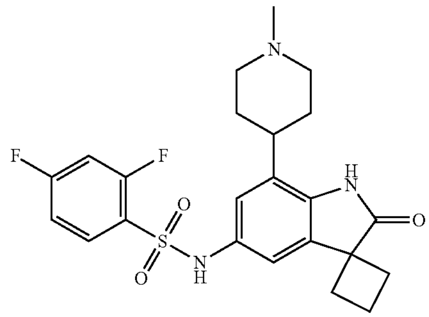 [SMILES: CN1CCC(c2cc(NS(=O)(=O)c3ccc(F)cc3F)cc3c2NC(=O)C32CCC2)CC1] | $^1$H NMR (400 MHz, DMSO-$d_6$): δ 10.34 (s, 1H), 10.18 (bs, 1H), 7.80-7.74 (m, 1H), 7.56-7.51 (m, 1H), 7.24-7.19 (m, 1H), 7.09 (d, J = 1.9 Hz, 1H), 6.68 (d, J = 1.5 Hz, 1H), 2.81 (d, J = 11.2 Hz, 2H), 2.56-2.53 (m, 1H), 2.40-2.35 (m, 2H), 2.19 (s, 3H), 2.15-2.06 (m, 4H), 1.97 (t, J = 10.8 Hz, 2H), 1.54-1.51 (m, 2H), 1.42-1.35 (m, 2H); LC-MS: m/z 462.2 (M + H)$^+$. |

*Compound 89 is obtained by additional alkylation as per the procedure depicted below.

Step-ii (Alkylation): To a solution of 2,4-difluoro-N-(2'-oxo-7'-(piperidin-4-yl)spiro[cyclobutane-1,3'-indolin]-5'-yl)benzenesulfonamide (0.3 g, 0.67 mmol) in MeOH (6 mL) and THF (6 m L) was added formaldehyde (0.16 mL, 2.01 mmol). The mixture was stirred at RT for 16 h and then cooled to 0° C. Sodium borohydride (0.051 g, 1.34 mmol) was added portion wise and the mixture was stirred at RT for 30 min The reaction mixture quenched with aqueous ammonium chloride, extracted with EtOAc (100 mL×2), dried over sodium sulphate, concentrated under reduced pressure and purified by combi-flash to afford compound 89 (0.12 g, 39%).

Example-XXI: 2,4-Dimethoxy-N-(2'-oxo-7'-(piperidin-4-yl)spiro[cyclobutane-1,3'-indolin]-5'-yl)benzenesulfonamide (Compound-92)

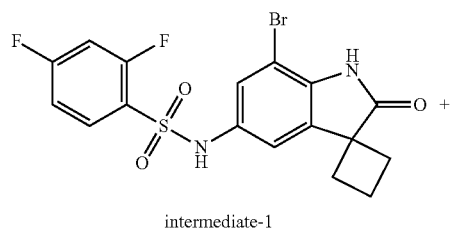

intermediate-1

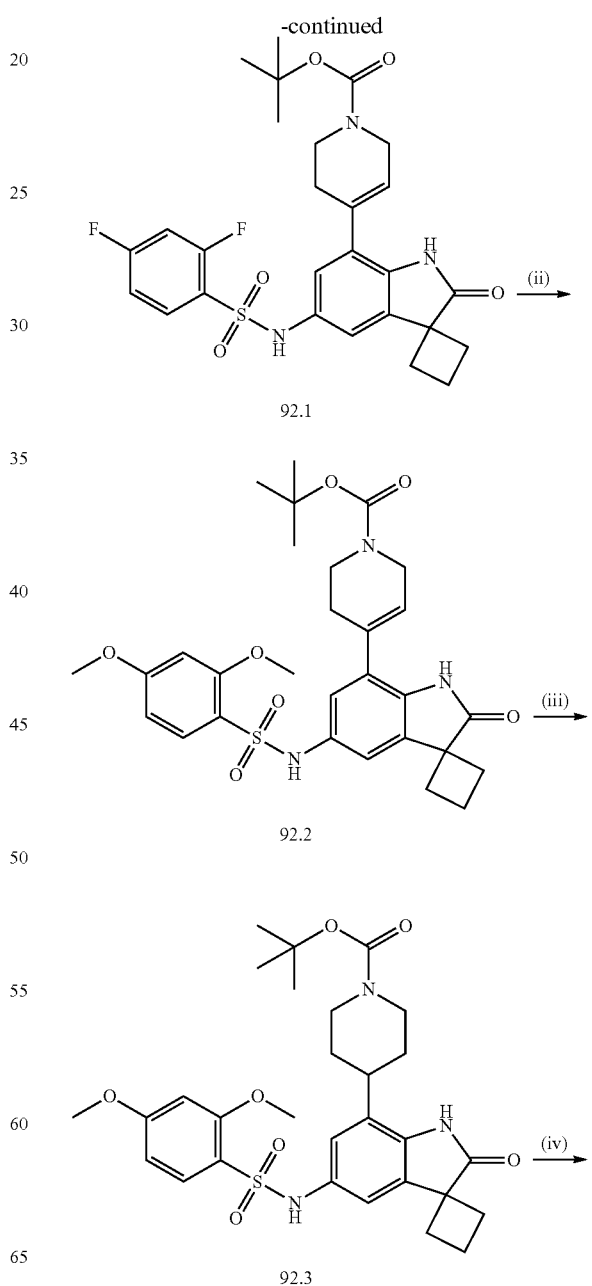

-continued

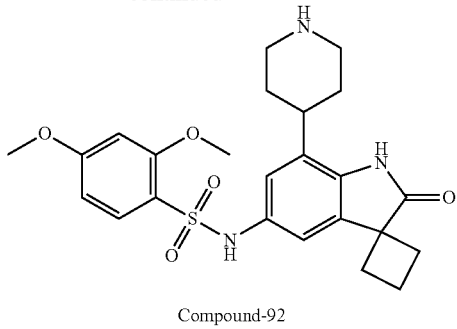

Compound-92

Step-i: tert-Butyl 4-(5'-(2,4-difluorophenylsulfonamido)-2'-oxospiro[cyclobutane-1,3'-indolin]-7'-yl)-5,6-dihydropyridine-1(2H)-carboxylate (92.1)

To a solution of N-(7'-bromo-2'-oxospiro[cyclobutane-1,3'-indolin]-5'-yl)-2,4-difluoro benzenesulfonamide (intermediate-1) (0.7 g, 1.58 mmol) in 1,4-dioxane (10 mL) and H$_2$O (2 mL) were added tert-butyl 4-(4,4,5,5-tetramethyl-1,3,2-dioxaborolan-2-yl)-3,6-dihydropyridine-1(2H)-carboxylate (0.98 g, 3.15 mmol) and potassium phosphate (1.0 g, 4.73 mmol). The mixture was degassed with nitrogen purging for 20 min. Then Pd(amphos)Cl$_2$ (0.11 g, 0.16 mmol) was added followed by heating at 100° C. for 16 h. The mixture was concentrated under reduced pressure and the residue was diluted with EtOAc (100 ml), washed with water (100 mL) and brine (100 mL), dried over sodium sulphate and concentrated under reduced pressure and purified by combi flash to afford the title compound as pale brown solid (0.7 g, 81%). $^1$H NMR (400 MHz, DMSO-d$_6$): δ 10.28 (s, 1H), 10.13 (s, 1H), 7.85-7.79 (m, 1H), 7.56-7.51 (m, 1H), 7.25-7.20 (m, 1H), 7.13 (d, J=1.9 Hz, 1H), 6.69 (d, J=1.9 Hz, 1H), 5.63 (s, 1H), 3.91 (s, 4H), 3.48 (t, J=5.4 Hz, 2H), 2.41-2.35 (m, 2H), 2.21-2.09 (m, 4H), 1.42 (s, 9H); LC-MS: m/z 544.2 (M−H)$^−$.

Step ii: tert-Butyl 4-(5'-((2,4-dimethoxyphenyl)sulfonamido)-2'-oxospiro [cyclobutane-1,3'-indolin]-7'-yl)-3,6-dihydropyridine-1(2H)-carboxylate (92.2)

To a solution of tert-butyl 4-(5'-(2,4-difluorophenylsulfonamido)-2'-oxospiro-[cyclobutane-1,3'-indolin]-7'-yl)-5,6-dihydropyridine-1(2H)-carboxylate (0.2 g, 0.36 mmol) in methanol (3 mL) was added sodium methoxide (0.1 g, 1.8 mmol) followed by stirring at 110° C. for 16 h. The reaction mixture was quenched with ice cooled water and extracted with EtOAc, dried over sodium sulphate, concentrated under reduced pressure and purified by combiflash to afford the title compound as off white solid (0.02 g, 10%). $^1$H NMR (400 MHz, DMSO-d$_6$): δ 10.05 (s, 1H), 9.52 (s, 1H), 7.61 (d, J=8.8 Hz, 1H), 7.13 (d, J=2 Hz, 1H), 6.64 (s, 1H), 6.63 (s, 1H), 6.54 (dd, J=8.8 Hz, 2.0 Hz, 1H), 5.61 (bs, 1H), 3.92 (bs, 2H), 3.89 (s, 3H), 3.77 (s, 3H), 3.48 (t, J=5.4 Hz,2H), 2.41-2.32 (m, 2H), 2.17-2.07 (m, 6H), 1.43 (s, 9H).

Step-iii: tert-Butyl 4-(5'-((2,4-dimethoxyphenyl)sulfonamido)-2'-oxospiro[cyclobutane-1,3'-indolin]-7'-yl)piperidine-1-carboxylate (92.3)

To a solution of tert-butyl 4-(5'-((2,4-dimethoxyphenyl)sulfonamido)-2'-oxospiro[cyclobutane-1,3'-indolin]-7'-yl)-3,6-dihydropyridine-1(2H)-carboxylate (0.018 g, 0.032 mmol) in MeOH (3 mL) was added 10% Pd—C (0.03 g) followed by stirring under H$_2$ bladder pressure at RT for 4 h. The mixture was filtered through celite and the bed was washed with EtOAc. The filtrate was concentrated under reduced pressure to afford the title compound as white solid (0.018 g). $^1$H NMR (400 MHz, DMSO-d$_6$): δ 10.30 (s, 1H), 9.42 (s, 1H), 7.58 (d, J=8.8 Hz, 1H), 7.08 (d, J=1.9 Hz, 1H), 6.67-6.61 (m, 2H), 6.52 (dd, J=8.8 Hz & 2.4 Hz, 1H), 4.04-3.90 (m, 2H), 3.87 (s, 3H), 3.77 (s, 3H), 2.73-2.66 (m, 2H), 2.52-2.50 (m, 1H), 2.39-2.32 (m, 2H), 2.20-2.06 (m, 4H), 1.56-1.53 (m, 2H), 1.43 (s, 9H), 1.27-1.41 (m, 2H).

Step-iv: 2,4-Dimethoxy-N-(2'-oxo-7'-(piperidin-4-yl)spiro[cyclobutane-1,3'-indolin]-5'-yl)benzenesulfonamide (92)

The process of this step was adopted from step-ii of Example-XX. $^1$H NMR (400 MHz, DMSO-d$_6$): δ 10.25 (s, 1H), 9.80-9.01 (bs, 1H), 7.59 (d, J=8.8 Hz, 1H), 7.07 (s, 1H), 6.75 (d, J=2.0 Hz, 1H), 6.62 (d, J=2.0 Hz, 1H), 6.52 (dd, J=8.8 Hz& 2.0 Hz, 1H), 3.89 (s, 3H), 3.77 (s, 3H), 3.23-3.20 (m, 2H), 2.77-2.67(m, 3H), 2.40-2.32 (m, 2H), 2.23-2.08 (m, 4H), 1.76-1.61 (m, 2H), 1.50-1.33 (m,2H); LC-MS: m/z 472.2 (M+H)$^+$.

Example-XXII: N-(7'-benzyl-2'-oxospiro[cyclobutane-1,3'-indolin]-5'-yl)-2-fluoro-4-methoxybenzenesulfonamide and N-(7'-benzyl-2'-oxospiro[cyclobutane-1,3'-indolin]-5'-yl)-4-fluoro-2-methoxybenzenesulfonamide: (Compounds 93 and 94)

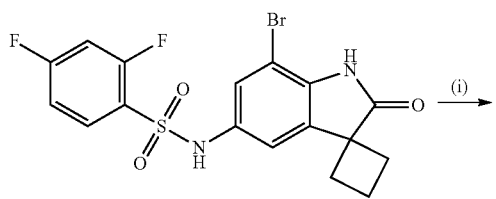

intermediate-1

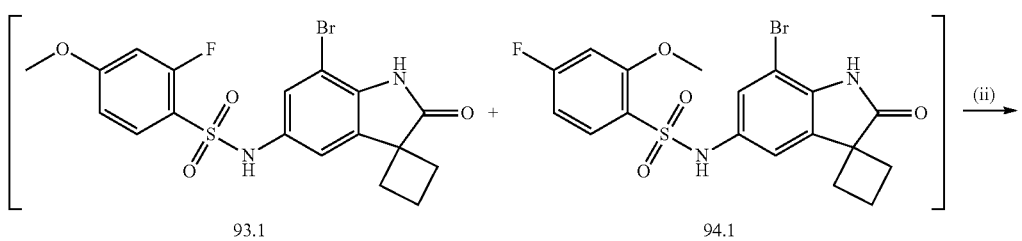

93.1      94.1

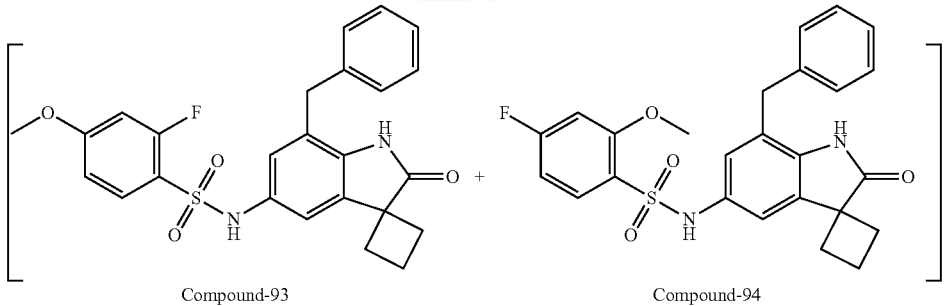

Compound-93 + Compound-94

Step-(i): N-(7'-bromo-2'-oxospiro[cyclobutane-1,3'-indolin]-5'-yl)-2-fluoro-4-methoxybenzenesulfonamide (93.1) and N-(7'-bromo-2'-oxospiro[cyclobutane-1,3'-indolin]-5'-yl)-4-fluoro-2-methoxybenzenesulfonamide (94.1):

The process of this step was adopted from step-(ii) of Example-XXI (mixture of two isomers). LC-MS: m/z 455.0 (M+H)$^+$.

Step-(ii): N-(7'-benzyl-2'-oxospiro[cyclobutane-1,3'-indolin]-5'-yl)-2-fluoro-4-methoxybenzenesulfonamide (Compound-93) and N-(7'-benzyl-2'-oxospiro[cyclobutane-1,3'-indolin]-5'-yl)-4-fluoro-2-methoxybenzenesulfonamide (Compound-94)

The process of this step was adopted from Example-I. Both the isomers were separated by preparative HPLC.
Compound-92: $^1$H NMR (400 MHz, DMSO-d$_6$): δ 10.38 (s, 1H), 9.91 (bs, 1H), 7.54 (t, J=8.8 Hz, 1H), 7.26-7.19 (m, 4H), 7.17-7.05 (m, 2H), 7.00-6.96 (m, 1H), 6.82-6.79 (m, 1H), 6.62 (d, J=1.9 Hz, 1H), 3.81 (s, 3H), 3.77 (s, 2H), 2.41-2.32 (m, 2H), 2.21-2.04 (m, 4H); LC-MS: m/z 467.2 (M+H)$^+$.
Compound-93: $^1$H NMR (400 MHz, DMSO-d$_6$): δ 10.36 (s, 1H), 9.60 (s, 1H), 7.63 (dd, J=8.8 Hz & 6.9 Hz, 1H), 7.27-7.18 (m, 3H), 7.10-7.09 (m, 1H), 7.05-7.01 (m, 3H), 6.82-6.77 (m, 1H), 6.57 (d, J=2.0 Hz, 1H), 3.81 (s, 3H), 3.74 (s, 2H), 2.41-2.37 (m, 2H), 2.33-2.09 (m, 4H); LC-MS: m/z 467.2 (M+H)$^+$.

The below compounds were prepared by a procedure similar to the one described in Example-XXII with appropriate variations in reactants, quantities of reagents and reaction conditions. The physiochemical characteristics of the compounds are also summarized.

| No | Reactant | Structure | Characterization data $^1$H NMR (400 MHz, DMSO-d$_6$)/ LCMS |
|---|---|---|---|
| 95 & 96 | (pinacol boronate of 3-fluorobenzyl) | Compound-95 | (compound-95): δ 10.37 (s, 1H), 9.60-9.58 (bs, 1H), 7.65-7.61 (m, 1H), 7.32-7.27 (m, 1H), 7.10 (d, J = 1.5 Hz, 1H), 7.05-6.99 (m, 2H), 6.90-6.85 (m, 2H), 6.80-6.75 (m, 1H), 6.58 (d, J = 1.9 Hz, 1H), 3.83 (s, 3H), 3.77 (s, 2H), 2.41-2.32 (m, 2H), 2.19-2.04 (m, 4H); LC-MS: m/z 485.2 (M + H)$^+$. |
| | | Compound-96 | (Compound-94): $^1$H NMR (400 MHz, DMSO-d$_6$): δ 10.39 (s, 1H), 9.85-9.80 (bs, 1H), 7.55 (t, J = 8.8 Hz, 1H), 7.30-7.26 (m, 1H), 7.10 (d, J = 2 Hz, 1H), 7.04-6.80 (m, 4H), 6.79 (d, J = 2 Hz, 1H), 6.64 (d, J = 1.9 Hz, 1H), 3.80 (s, 5H), 2.41-2.32 (m, 2H), 2.21-2.04 (m, 4H); LC-MS: m/z 485.1 (M + H)$^+$. |

| No | Reactant | Structure | Characterization data<br>¹H NMR (400 MHz, DMSO-d₆)/<br>LCMS |
|---|---|---|---|
| 97 | 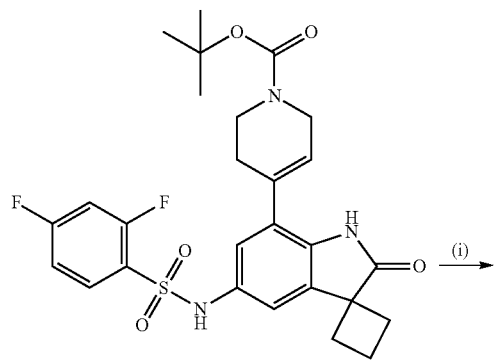 | 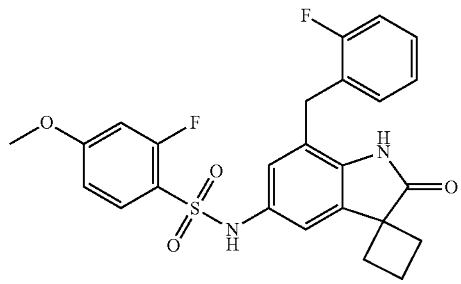 [SMILES: COc1ccc(S(=O)(=O)Nc2cc(Cc3ccccc3F)c3c(c2)C2(CCC2)C(=O)N3)c(F)c1] | δ 10.41 (s, 1H), 9.48 (bs, 1H), 7.48 (t, J = 8.8 Hz, 1H), 7.30-7.22 (m, 1H), 7.18-7.04 (m, 4H), 6.94 (dd, J = 2.4 Hz, 12.7 Hz, 1H), 6.79 (dd, J = 2.0 Hz, 8.8 Hz, 1H), 6.49 (d, J = 1.4 Hz, 1H), 3.80 (s, 3H), 3.78 (s, 2H), 2.42-2.39 (m, 2H), 2.16-2.11 (m, 4H),; LCMS: m/z 485.2 (M + H)⁺. |
Example-XXIII: 2-Fluoro-4-methoxy-N-(7'-(1-methylpiperidin-4-yl)-2'-oxospiro-[cyclobutane-1,3'-indolin]-5'-yl)benzenesulfonamide (Compound-98)
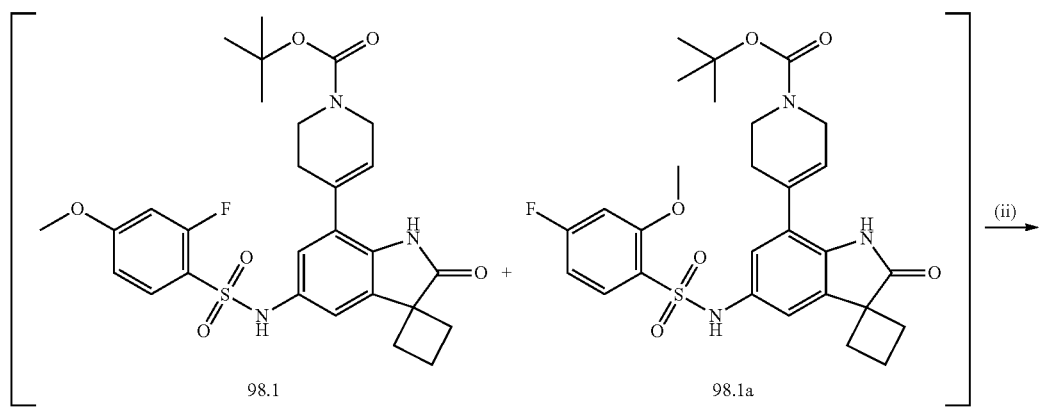

-continued
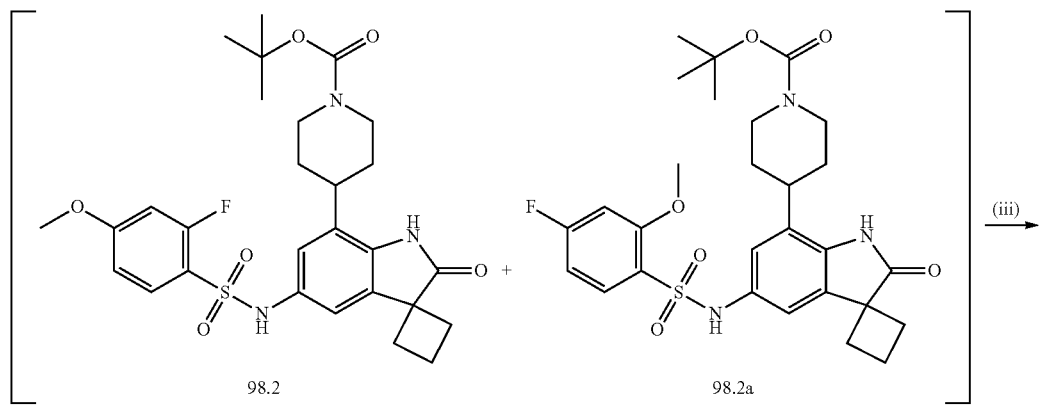
98.2 + 98.2a (iii) →
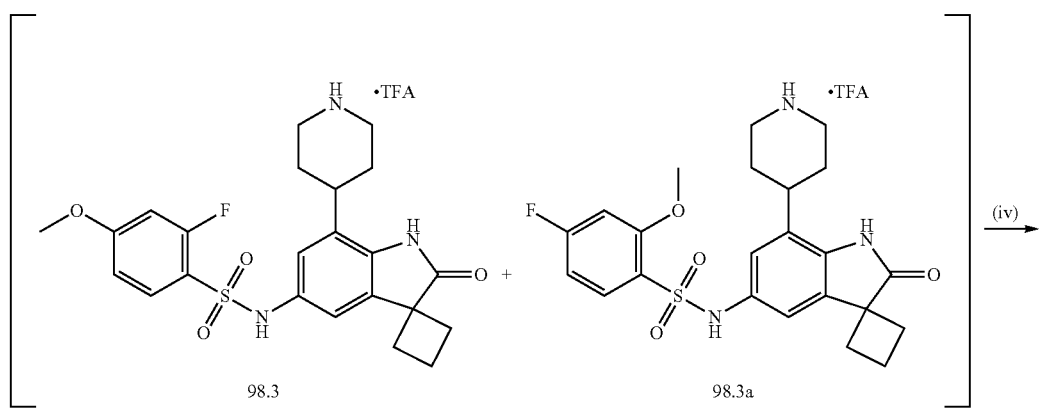
98.3 + 98.3a (iv) →
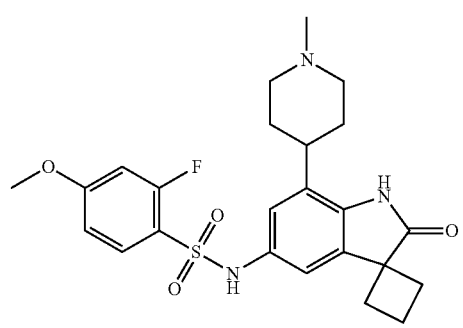
Compound-98

Step-i: tert-Butyl 4-(5'-((2-fluoro-4-methoxyphenyl)sulfonamido)-2'-oxospiro-[cyclobutane-1,3'-indolin]-7'-yl)-3,6-dihydropyridine-1(2H)-carboxylate (98.1) and tert-butyl 4-(5'-((4-fluoro-2-methoxyphenyl)sulfonamido)-2'-oxospiro[cyclobutane-1,3'-indolin]-7'-yl)-3,6-dihydropyridine-1(2H)-carboxylate 98.1a: (mixture)

The process of this step was adopted from step-(ii) of example-XXI; LC-MS: m/z 556.1 (M–H)⁻.

Step-ii: tert-Butyl 4-(5'-((2-fluoro-4-methoxyphenyl)sulfonamido)-2'-oxospiro-[cyclobutane-1,3'-indolin]-7'-yl)piperidine-1-carboxylate (98.2) and tert-Butyl 4-(5'-((4-fluoro-2-methoxyphenyl)sulfonamido)-2'-oxospiro [cyclobutane-1,3'-indolin]-7'-yl)piperidine-1-carboxylate (98.2a) (mixture)

The process of this step was adopted from step-(iii) of example-XXI; LC-MS: m/z 558.2 (M–H)⁻.

Step-iii: 2-Fluoro-4-methoxy-N-(2'-oxo-7'-(piperidin-4-yl)spiro[cyclobutane-1,3'-indolin]-5'-yl)benzenesulfonamide trifluoroacetate (98.3) and 4-fluoro-2-methoxy-N-(2'-oxo-7'-(piperidin-4-yl)spiro[cyclobutane-1,3'-indolin]-5'-yl) benzenesulfonamide trifluoroacetate (98.3a) (mixture)

The process of this step was adopted from step-ii of Example-XX. LC-MS: m/z 460.2 (M+H)⁺.

Step-iv: 2-Fluoro-4-methoxy-N-(7'-(1-methylpiperidin-4-yl)-2'-oxospiro [cyclobutane-1,3'-indolin]-5'-yl)benzenesulfonamide (98)

The process of this step was adopted from Example-XX (compound-89) alkylation. ¹H NMR (400 MHz, DMSO-d₆): δ 10.30 (s, 1H), 9.95 (bs, 1H), 7.61 (t, J=8.8 Hz, 1H), 7.08 (d, J=1.4 Hz, 1H), 7.02 (dd, J=12.5 Hz&2.1 Hz, 1H), 6.84 (dd, J=9.0 Hz, & 2.2 Hz, 1H), 6.68 (d, J=1.5 Hz, 1H), 3.79 (s, 3H), 2.79-2.76 (m, 2H), 2.49-2.41 (m, 1H), 2.40-2.32 (m, 2H), 2.16 (s,3H), 2.14-2.06 (m, 4H), 1.95-1.90 (m, 2H), 1.52-1.49 (m,2H), 1.40-1.33 (m,2H); LC-MS: m/z 474.2 (M+H)⁺.

Example-XXIV: 2,4-Difluoro-N-(7'-(6-hydroxypyridin-3-yl)-2'-oxospiro [cyclobutane-1,3'-indolin]-5'-yl)benzenesulfonamide (Compound-99)

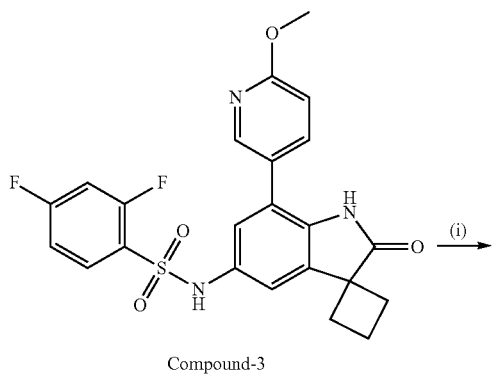

Compound-3

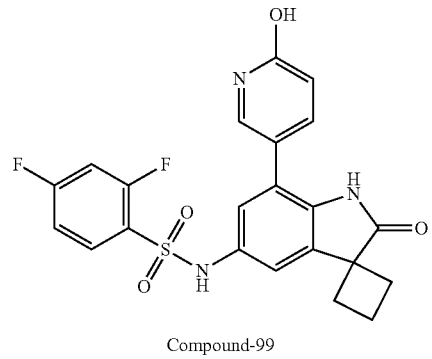

Compound-99

To a solution of N-(7'-bromo-2'-oxospiro[cyclobutane-1,3'-indolin]-5'-yl)-2,4-difluorobenzenesulfonamide (Compound-3) (0.2 g, 0.42 mmol) in 1,4-dioxane (10 mL) was added concentrated HCl (2 mL). The mixture was stirred at 90° C. for 16 h. The reaction mixture was neutralized with aqueous NaHCO₃, extracted with EtOAc (100 mL), dried over sodium sulphate, concentrated under reduced pressure and purified by combi flash to afford the title compound as white solid (0.18 g, 92%). ¹H NMR (400 MHz, DMSO-d₆): δ 11.77 (s,1H), 10.40 (s, 1H), 10.30 (s, 1H), 7.88-7.82 (m, 1H), 7.58-7.53 (m, 1H), 7.31-7.29 (m, 2H), 7.27-7.22 (m, 1H), 7.18 (d, J=1.9 Hz, 1H), 6.76 (d, J=2.0 Hz, 1H), 6.39-6.36 (m.1H), 2.42-2.33 (m, 2H), 2.21-2.05 (m, 4H); LC-MS: m/z 458.1 (M+H)⁺.

The below compound was prepared by a procedure similar to the one described in Example-XXIV with appropriate variations in reactants, quantities of reagents and reaction conditions. The physiochemical characteristics of the compound is also summarized.

| No | Structure | Characterization data |
|---|---|---|
| 100 | (structure shown) | ¹H NMR (400 MHz, DMSO-d₆): δ 11.62 (s, 1H), 10.46 (s, 1H), 10.28 (s, 1H), 7.88-7.82 (m, 1H), 7.59-7.53 (m, 1H), 7.40 (d, J = 6.9 Hz, 1H), 7.30 (d, J = 1.4 Hz, 1H), 7.27-7.23 (m, 1H), 6.83 (d, J = 1.9 Hz, 1H), 6.15 (s.1H), 6.03 (d, J = 6.8 Hz, 1H), 2.41-2.33 (m, 2H), 2.20-2.05 (m, 4H); LC-MS: m/z 458.1 (M + H)⁺. |

Example-XXV: 2,4-Difluoro-N-(7'-((3-fluoropiperidin-4-yl)amino)-2'-oxospiro[cyclobutane-1,3'-indolin]-5'-yl)benzenesulfonamide (Compound-102)

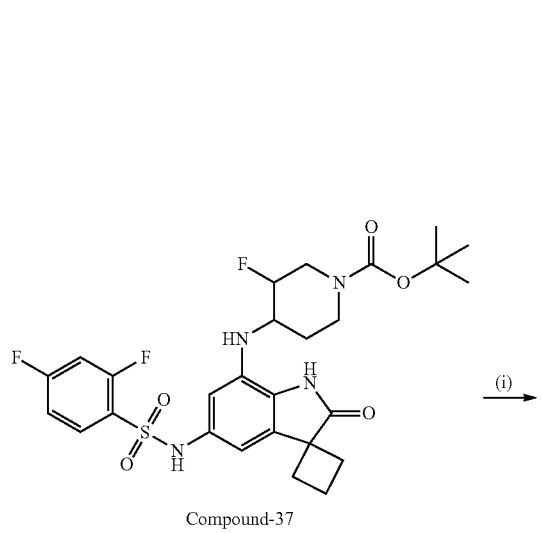

Compound-37

(i) →

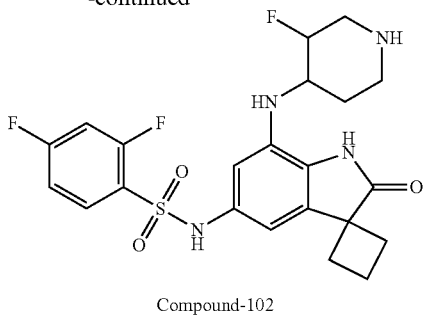

Compound-102

The process of this step was adopted from step-iv of Example-XI. $^1$H NMR (400 MHz, CD$_3$OD) δ: 7.82-7.76 (m, 1H), 7.22-7.16 (m, 1H), 7.08-7.03 (m, 1H), 6.68 (d, J=2.0 Hz, 1H), 6.36 (d, J=1.4 Hz, 1H), 4.64-4.52 (m, 1H), 3.52-3.41 (m, 1H), 3.30-3.23 (m, 2H), 3.09-3.05 (m, 1H), 2.87-2.73 (m, 1H), 2.72-2.65 (m, 1H), 2.52-2.44 (m, 2H), 2.29-2.12 (m, 4H), 1.75-1.60 (m, 2H); LCMS m/z 481.2 (M+H)$^+$.

The below compound was prepared by procedure similar to the one described in Example-XXV with appropriate variations in reactants, quantities of reagents and reaction conditions. The physiochemical characteristics of the compound is also summarized.

| No | Intermediate | Structure | Characterization Data $^1$H NMR (400 MHz, DMSO-d$_6$)/ LC-MS: |
|---|---|---|---|
| 103 | Compound-36 | 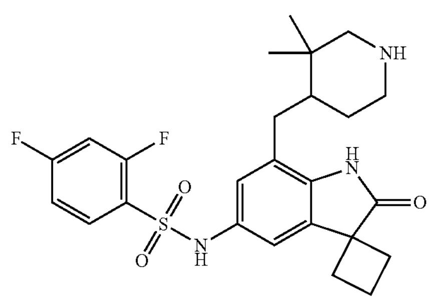 [SMILES: CC1(C)CNCCC1Cc1cc(NS(=O)(=O)c2ccc(F)cc2F)cc2c1NC(=O)C21CCC1] | δ 10.01 (s, 1H), 7.80-7.74 (m, 1H), 7.56-7.51 (m, 1H), 7.24-7.19 (m, 1H), 6.53 (d, J = 1.4 Hz, 1H), 6.17 (d, J = 1.0 Hz, 1H), 4.34 (d, J = 8.8 Hz, 1H), 2.98-2.94 (m, 1H), 2.88-2.82 (m, 1H), 2.65 (d, J = 12.2 Hz, 1H), 2.40-2.33 (m, 3H), 2.19-2.01 (m, 4H), 1.46-1.42 (m, 1H), 1.33-1.23 (m, 2H), 0.93 (s, 3H), 0.77 (s, 3H); LCMS: m/z 491.2 (M + H)$^+$. |

Example-XXVI: 2,4-Difluoro-N-(2'-oxo-7'-(2-oxopiperidin-4-yl)spiro[cyclobutane-1,3'-indolin]-5'-yl)benzenesulfonamide (Compound-104)

variations in reactants, quantities of reagents and reaction conditions. The physiochemical characteristics of the compound is also summarized.

| No. | Intermediate | Structure | Characterization data |
|---|---|---|---|
| 105 | (structure with OH-pyridine) | (structure with 2-oxopiperidine) | $^1$H NMR (400 MHz, DMSO-$d_6$): δ 10.40 (s, 1H), 10.24 (s, 1H), 7.82-7.60 (m, 1H), 7.55-7.50 (m, 2H), 7.24-7.19 (m, 1H) 7.10 (d, J = 1.9 Hz, 1H), 6.76 (d, J = 2.0 Hz, 1H), 3.16-3.14 (m, 1H), 3.03-2.95 (m, 2H), 2.41-2.37 (m, 2H), 2.36-2.04 (m, 6H), 1.80-1.75 (m, 2H); LC-MS: m/z 462.2 (M + H)$^+$. |

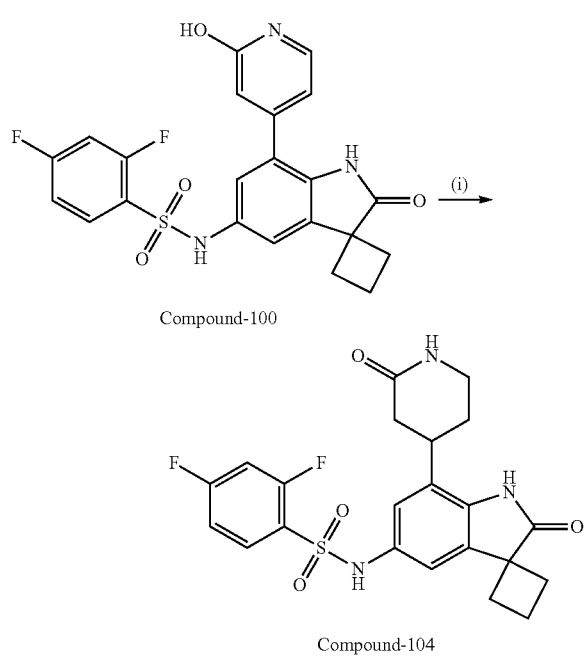

Compound-100

Compound-104

To a solution of 2,4-difluoro-N-(7'-(2-hydroxypyridin-4-yl)-2'-oxospiro[cyclobutane-1,3'-indolin]-5'-yl)benzenesulfonamide (Compound-100) (0.1 g, 0.22 mmol) in mixture of MeOH (3 mL) and THF (3 mL) was added platinum oxide (0.1 g) followed by stirring under H$_2$ bladder pressure at RT for 24 h. The mixture was filtered through celite and the bed was washed with EtOAc. The filtrate was concentrated under reduced pressure and purified by combi flash to afford the title compound as white solid (0.035 g, 34%). $^1$H NMR (400 MHz, DMSO-$d_6$): δ 10.36 (s, 1H), 10.25 (bs, 1H), 7.82-7.76 (m, 1H), 7.57-7.51 (m, 2H), 7.24-7.19 (m, 1H) 7.10 (d, J=1.5 Hz, 1H), 6.72 (d, J=1.5 Hz, 1H), 3.18-3.14 (m, 1H), 3.09-3.05 (m, 2H), 2.40-2.32 (m, 2H), 2.28-1.98 (m, 6H), 1.76-1.74 (m, 1H); 1.59-1.55 (m, 1H); LC-MS: m/z 462.1 (M+H)$^+$.

The below compound was prepared by a procedure similar to the one described in Example-XXVI with appropriate Example-XXVII: 2,4-Difluoro-N-(7'-(2-methyl-1,2,3,4-tetrahydroisoquinolin-7-yl)-2'-oxospiro[cyclobutane-1,3'-indolin]-5'-yl)benzenesulfonamide (Compound-106)

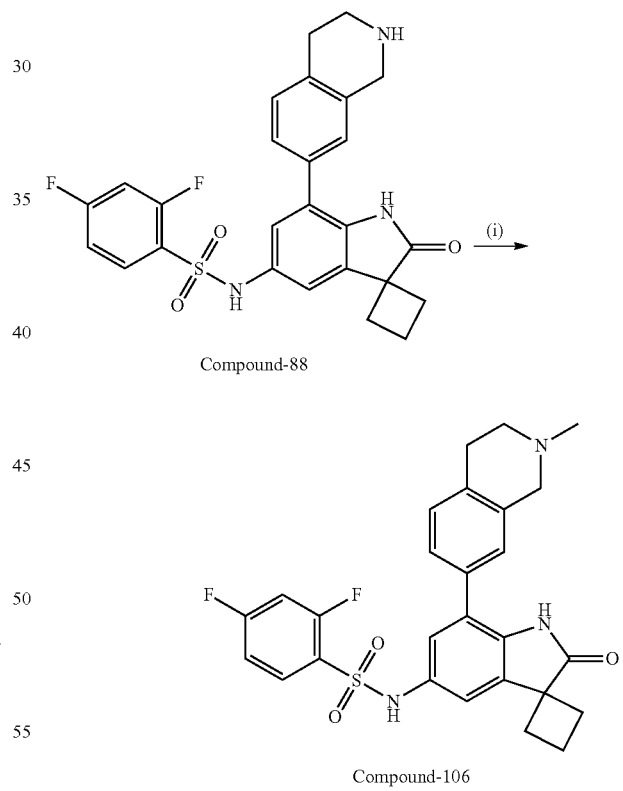

Compound-88

Compound-106

The process of this step was adopted from Example-XX (compound-89) alkylation step. $^1$H NMR (400 MHz, DMSO-$d_6$): δ 10.36 (s, 1H), 10.10 (s, 1H), 7.88-7.82 (m, 1H), 7.59-7.53 (m, 1H), 7.27-7.25 (m, 1H), 7.22 (d, J=2.0 Hz, 1H), 7.15 (d, J=8.3 Hz, 1H), 6.99 (d, J=7.8 Hz, 1H), 6.95 (s, 1H), 6.81 (d, J=1.9 Hz, 1H), 3.52 (s, 2H), 2.83 (t, J=5.4 Hz, 2H), 2.61 (t, J=5.4 Hz, 2H), 2.44-2.38 (m, 2H), 2.35 (s, 3H), 2.23-2.06 (m, 4H); LC-MS: m/z 510.2 (M+H)$^+$.

Example-XXVIII: 2-Methoxy-N-(2'-oxo-7'-(1-phenylethyl)spiro [cyclobutane-1,3'-indolin]-5'-yl)benzenesulfonamide (Compound-113)

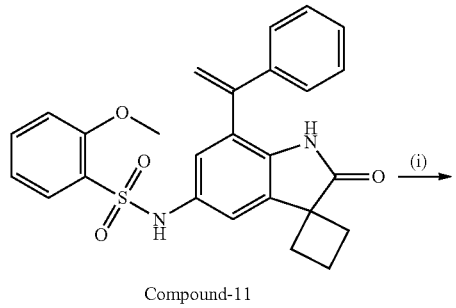

Compound-11

(i) →

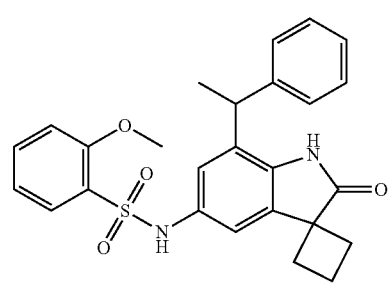

Compound-113

The process of this step was adopted from step-(iii) of Example-XXI. ¹H NMR (400 MHz, DMSO-d₆): δ 10.26 (s, 1H), 9.51 (s, 1H), 7.62 (dd, J=7.8, 1.4 Hz, 1H), 7.60-7.53 (m, 1H), 7.28-7.21 (m, 2H), 7.17-7.10 (m, 3H), 7.05 (d, J=7.3 Hz, 2H), 6.97 (t, J=7.8 Hz, 1H), 6.74 (d, J=1.5 Hz,1H), 4.15 (q, J=7.4 Hz, 1H), 3.83 (s, 3H), 2.39-2.31 (m, 2H), 2.19-2.05 (m, 4H), 1.33 (d, J=7.4 Hz, 3H); LCMS: m/z 463.2 (M+H)⁺.

The isomers wer separated by using chiral HPLC under below conditions: Column: Chiralpak-IA(250*4.6*5.0 μ)

Mobile phase-A: N-Hexane(0.1% DEA) ; Mobile phase-C: IPA:DCM(90:10)

Method-Isocratic: 50:50(A:C); Flow rate: 1.0 ml/min

Column temp: Ambient; Diluent: Mobile phase (Compound-114)

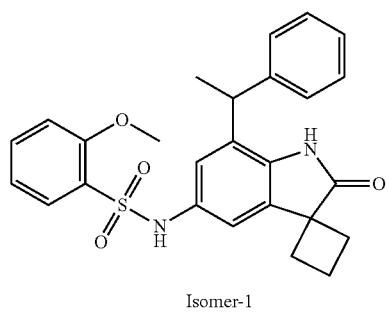

Isomer-1

(Compound-115)

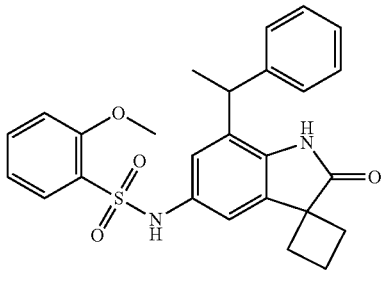

Isomer-II

Isomer-I: ¹H NMR (400 MHz, DMSO-d₆): δ 10.26 (s, 1H), 9.49 (bs, 1H), 7.62 (d, J=1.4 Hz, 1H), 7.60-7.53 (m, 1H), 7.25-7.21 (m, 2H), 7.17-7.10 (m, 3H), 7.05 (d, J=7.3 Hz, 2H), 6.97 (t, J=7.9 Hz, 1H), 6.75 (d, J=1.5Hz, 1H),4.15 (q, J=6.9 Hz, 1H), 3.83 (s, 3H), 2.39-2.33 (m, 2H), 2.19-2.05 (m, 4H), 1.33 (d, J=6.9 Hz, 3H); LCMS: m/z 463.2 (M+H)⁺.

Isomer-II: ¹H NMR (400 MHz, DMSO-d₆): δ 10.26 (s, 1H), 9.49 (bs, 1H), 7.62 (dd, J=1.5 Hz & 7.8 Hz, 1H), 7.60-7.53 (m, 1H), 7.25-7.21 (m, 2H), 7.17-7.10 (m, 3H), 7.05 (d, J=7.3 Hz, 2H), 6.97 (t, J=7.9 Hz, 1H), 6.75 (d, J=1.5 Hz, 1H), 4.15 (q, J=6.9 Hz, 1H), 3.83 (s, 3H), 2.39-2.33 (m, 2H), 2.19-2.05 (m, 4H), 1.33 (d, J=6.9 Hz, 3H); LCMS: m/z 463.2 (M+H)⁺.

Example-XXIX: 2,4-Difluoro-N-(7'-(2-(1-methylpiperidin-4-yl)ethyl)-2'-oxospiro-[cyclobutane-1,3'-indolin]-5'-yl)benzenesulfonamide (Compound-116)

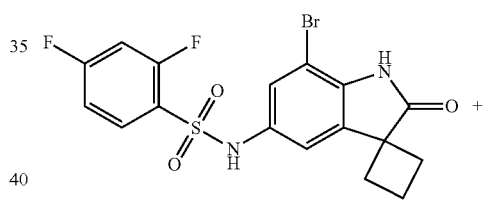

intermediate-1

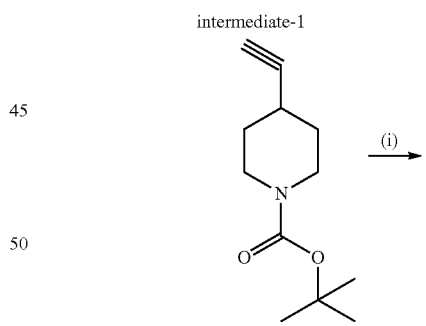

(i) →

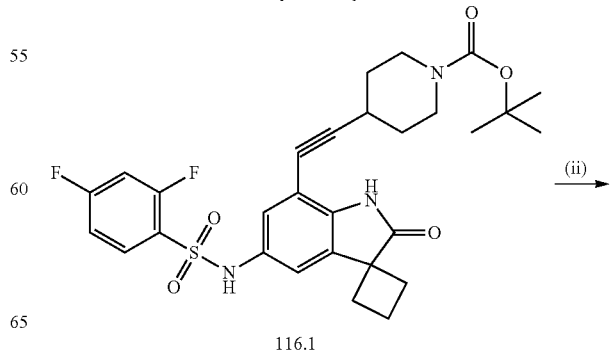

116.1

(ii) →

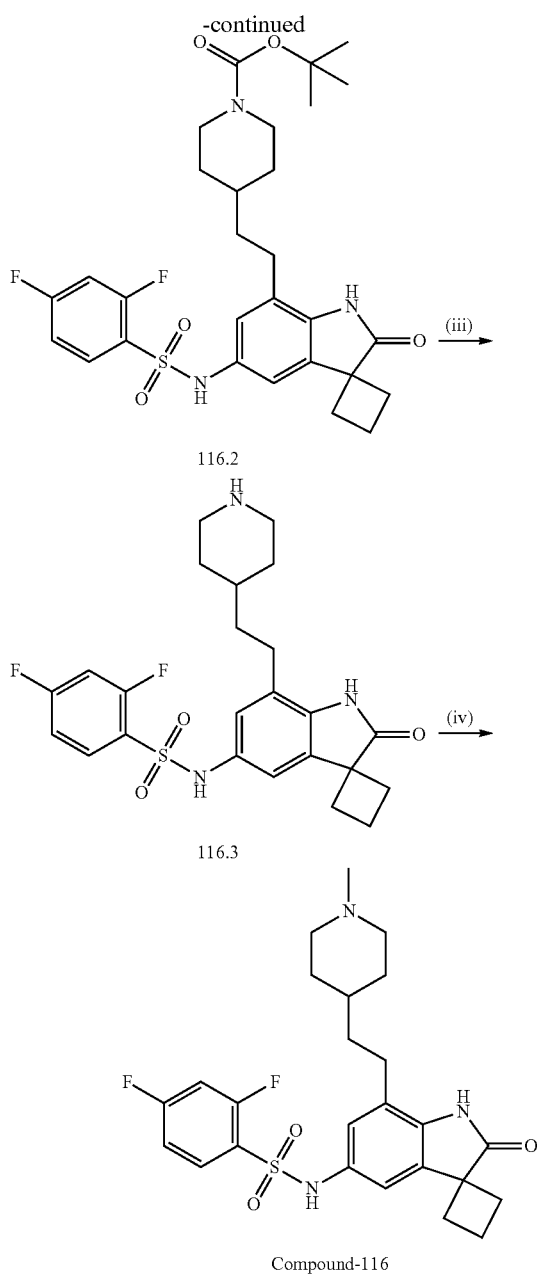

116.2

116.3

Compound-116

Step-i: tert-Butyl 4-((5'-((2,4-difluorophenyl)sulfonamido)-2'-oxospiro[cyclobutane-1,3'-indolin]-7'-yl)ethynyl)piperidine-1-carboxylate (116.1)

To a solution of N-(7'-bromo-2'-oxospiro[cyclobutane-1,3'-indolin]-5'-yl)-2,4-difluorobenzenesulfonamide (intermediate-1) (0.7 g, 1.58 mmol) was added tert-butyl 4-ethynylpiperidine-1-carboxylate (0.4 g, 1.89 mmol) in mixture of DMF (5 mL) and triethyl amine (5 mL). The mixture was degassed with nitrogen purging for 10 min. Then Pd(PPh$_3$)$_2$Cl$_2$ (0.11 g, 0.158 mmol) and copper iodide (0.06 g, 0.316 mmol) were added and the mixture again purged with nitrogen for 10 min and heated at 90° C. for 16 h. The mixture was filtered through celite bed and the bed was washed with EtOAc. The filtrate was washed with water, dried over sodium sulphate, concentrated under reduced pressure and purified by column chromatography to afford the title compound as yellow solid (0.12 g, 13%). $^1$H NMR (400 MHz, DMSO-d$_6$): δ 10.52 (s, 1H), 10.35 (s, 1H), 7.84-7.79 (m, 1H), 7.57-7.51 (m, 1H), 7.26-7.20 (m, 2H), 6.79 (d, J=2.0 Hz, 1H), 3.70-3.64 (m, 2H), 3.04-2.94 (m, 2H), 2.81-2.76 (m, 1H), 2.40-2.32 (m, 2H), 2.20-2.04 (m, 4H), 1.79-1.77 (m, 2H), 1.60-1.52 (m, 2H), 1.40 (s, 9H); LC-MS: m/z 570.2 (M−H)$^-$.

Step ii: tert-Butyl 4-(2-(5'-((2,4-difluorophenyl)sulfonamido)-2'-oxospiro [cyclobutane-1,3'-indolin]-7'-yl)ethyl)piperidine-1-carboxylate (116.2)

To a solution of tert-butyl 4-((5'-((2,4-difluorophenyl)sulfonamido)-2'-oxo-spiro[cyclobutane-1,3'-indolin]-7'-yl)ethynyl)piperidine-1-carboxylate (0.06 g, 0.1 mmol) in MeOH (20 mL) was added 10% Pd—C (0.05 g) followed by stirring under 60 psi hydrogen pressure using Parr shaker hydrogenation apparatus for 1 h. The mixture was filtered through celite bed and the bed was washed with EtOAc. The filtrate was concentrated under reduced pressure to afford the title compound as white solid (0.06 g). $^1$H NMR (400 MHz, DMSO-d$_6$): δ 10.28 (s, 1H), 10.17 (bs, 1H), 7.77 (dd, J$_1$=15.2 Hz, J$_2$=8.3 Hz, 1H), 7.55-7.50 (m, 1H), 7.23-7.19 (m, 1H), 7.05 (d, J=1.6 Hz, 1H), 6.63 (d, J=1.5 Hz, 1H), 3.91-3.88 (m, 2H), 2.67-2.63 (m, 2H), 2.43-2.33 (m, 4H), 2.21-2.03 (m, 4H), 1.63-1.59 (m, 2H), 1.39 (s, 9H), 1.37-1.24 (m, 3H), 0.99-0.91 (m, 2H); LC-MS: m/z 476.2 (M+1-Boc)$^+$.

Step-iii: 2,4-Difluoro-N-(2'-oxo-7'-(2-(piperidin-4-yl)ethyl)spiro[cyclobutane-1,3'-indolin]-5'-yl)benzenesulfonamide (116.3)

The process of this step was adopted from step-ii of Example-XX. $^1$H NMR (400 MHz, DMSO-d$_6$): δ 10.20 (s, 1H), 7.77 (dd, J$_1$=15.2 Hz, J$_2$=8.8 Hz, 1H), 7.48-7.42 (m, 1H), 7.19-7.15 (m, 1H), 7.00 (d, J=2.2 Hz, 1H), 6.60 (d, J=2.0 Hz, 1H), 3.09-3.06 (m, 2H), 2.67-2.56 (m, 2H), 2.42-2.32 (m, 4H), 2.19-2.03 (m, 4H), 1.70-1.67 (m, 2H), 1.35-1.23 (m, 3H), 1.13-1.01 (m, 2H); LC-MS: m/z 476.2 (M+H)$^+$.

Step-iv: 2,4-Difluoro-N-(7'-(2-(1-methylpiperidin-4-yl)ethyl)-2'-oxospiro [cyclobutane-1,3'-indolin]-5'-yl)benzenesulfonamide (116)

The process of this step was adopted from Example-XX (compound-89) alkylation. $^1$H NMR (400 MHz, DMSO-d$_6$): δ 10.27 (s, 1H), 10.10 (bs, 1H), 7.80-7.74 (m, 1H), 7.55-7.50 (m, 1H), 7.23-7.18 (m, 1H), 7.05 (d, J=2.0 Hz, 1H), 6.62 (d, J=1.9 Hz, 1H), 2.76-2.73 (m, 2H), 2.42-2.32 (m, 4H), 2.16 (s, 3H), 2.14-2.04 (m, 4H), 1.85-1.78 (m, 2H), 1.63-1.57 (m, 2H), 1.24-1.22 (m, 3H), 1.18-1.04 (m, 2H); LC-MS: m/z 490.2 (M+H)$^+$.

Example-XXX: N-(7'-benzoyl-2'-oxospiro[cyclobutane-1,3'-indolin]-5'-yl)-2-methoxybenzenesulfonamide (Compound-117)

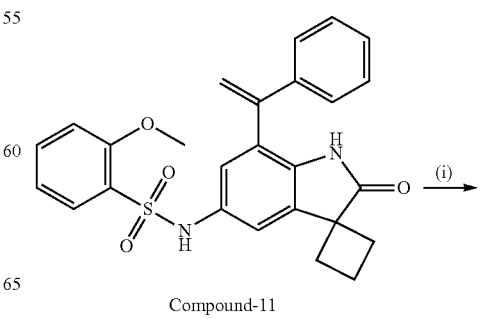

Compound-11

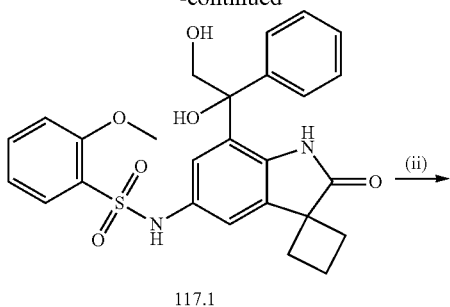

117.1

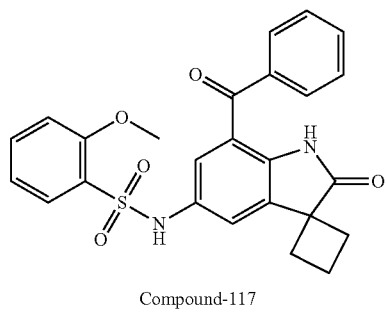

Compound-117

Step-i: N-(7'-(1,2-dihydroxy-1-phenylethyl)-2'-oxospiro[cyclobutane-1,3'-indolin]-5'-yl)-2-methoxybenzenesulfonamide (117.1)

To a solution of 2-methoxy-N-(2'-oxo-7'-(1-phenylvinyl)spiro[cyclobutane-1,3'-indolin]-5'-yl)benzenesulfonamide (0.6 g, 1.30 mmol) in acetone (6 mL) were added NMO (0.27 mL, 2.6 mmol) and osmium tetroxide 4% in water (0.03 mL) followed by stirring at RT for 16 h. The reaction mixture was quenched with aqueous sodium metabisulfite and extracted with EtOAc. The organic layer was dried over sodium sulphate, concentrated under reduced pressure and purified by combi flash to afford the title compound as off white solid (0.48 g, 75%).

Step-ii: N-(7'-benzoyl-2'-oxospiro[cyclobutane-1,3'-indolin]-5'-yl)-2-methoxy-benzenesulfonamide (117)

To a solution of N-(7'-(1,2-dihydroxy-1-phenylethyl)-2'-oxospiro[cyclobutane-1,3'-indolin]-5'-yl)-2-methoxybenzenesulfonamide (0.48 g, 0.97 mmol) in mixture of THF (8 mL) and water (1 mL) was added sodium meta periodate (2.06 g, 9.70 mmol) followed by stirring at 80° C. for 2 h. The mixture was diluted with water and extracted with EtOAc. The organic layer was dried over sodium sulphate, concentrated under reduced pressure and purified by combi flash to afford the title compound as white solid (0.24 g, 55%).

Example-XXXI: N-(7'-(hydroxy(phenyl)methyl)-2'-oxospiro[cyclobutane-1,3'-indolin]-5'-yl)-2-methoxybenzenesulfonamide (Compound-118)

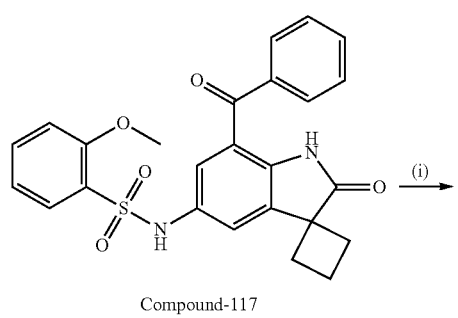

Compound-117

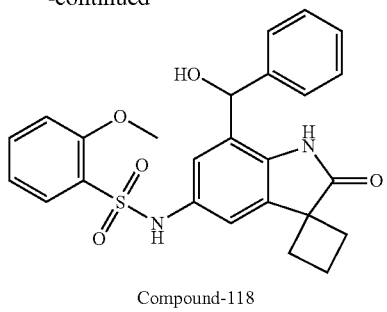

Compound-118

To a cold solution of N-(7'-benzoyl-2'-oxospiro[cyclobutane-1,3'-indolin]-5'-yl)-2-methoxybenzenesulfonamide (0.1 g, 0.216 mmol) in MeOH (4 mL) was added sodium borohydride (0.025 g, 0.65 mmol) followed by stirring at RT for 16 h. The mixture was concentrated under reduced pressure, diluted with water and extracted with EtOAc (50 ml×2). The organic layer was dried over sodium sulphate, concentrated under reduced pressure and purified by combi flash to afford the title compound as white solid (0.03 g, 30%); $^1$H NMR (400 MHz, DMSO-$d_6$): δ 10.15 (s, 1H), 9.57 (s, 1H), 7.62 (dd, J=1.5 Hz, 7.9 Hz, 1H), 7.55-7.51 (m, 1H), 7.26-7.21 (m, 5H), 7.19-7.09 (m, 2H), 7.00-6.94 (2H), 5.76 (d, J=3.4 Hz, 1H), 5.69 (d, J=3.4 Hz, 1H), 3.83 (s, 3H), 2.39-2.32 (m, 2H), 2.18-2.00 (m, 4H); LCMS: m/z 463.1 (M−H)⁻.

Example-XXXII: N-(7'-(1-hydroxy-1-phenylethyl)-2'-oxospiro[cyclobutane-1,3'-indolin]-5'-yl)-2-methoxybenzenesulfonamide (Compound-120)

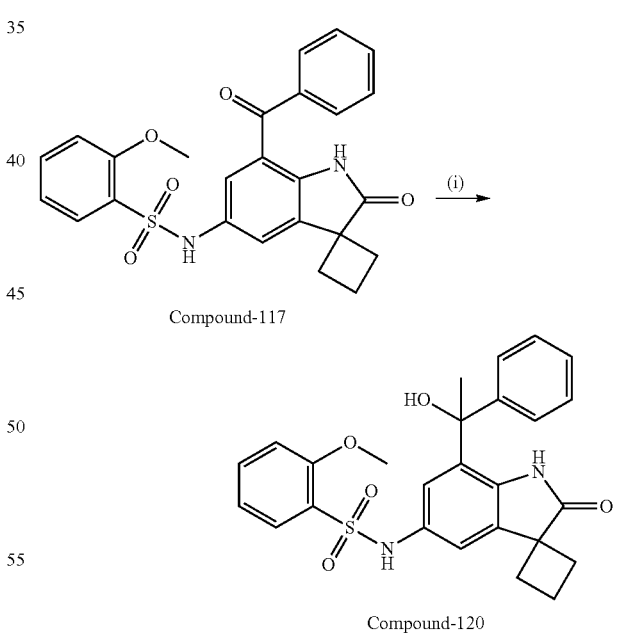

To a stirring suspension of ZnCl$_2$ (0.0003 g, 0.022 mmol) in THF was added methyl magnesium bromide (0.47 mL, 0.66 mmol) followed by stirring at RT for 1 h. The mixture was cooled to 0° C. and N-(7'-benzoyl-2'-oxospiro[cyclobutane-1,3'-indolin]-5'-yl)-2-methoxy benzenesulfonamide (0.1 g, 0.22) in THF was added followed by stirring at 0° C. for 2 h. The reaction mixture was quenched with saturated ammonium chloride and extracted with EtOAc. The organic layer was dried over sodium sulphate, concentrated under reduced pressure and purified by combi flash to afford the title compound as white solid (0.02 g, 20%). ¹H NMR (400 MHz, DMSO-d₆): δ 9.57 (s, 1H), 8.69 (s, 1H), 7.64 (d, J=7.9 Hz, 1H), 7.58 (t, J=6.8 Hz, 1H), 7.22 (d, J=6.9 Hz, 2H), 7.17-7.15 (m, 5H), 7.00 (t, J=7.8Hz, 1H), 6.83 (d, J=1.9 Hz, 1H), 6.09 (s, 1H), 3.88 (s, 3H), 2.37-2.31 (m, 2H), 2.15-2.05 (m, 4H), 1.64 (s, 3H); LCMS: m/z 477.1 (M−H)⁻.

Example-XXXIII: 1-(7'—Cyclopropyl-2'-oxospiro[cyclobutane-1,3'-indolin]-5'-yl)-3-(2-methoxyphenyl)urea (Compound-121)

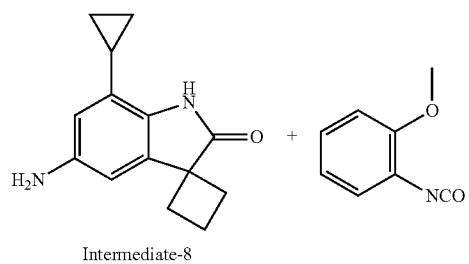

Intermediate-8

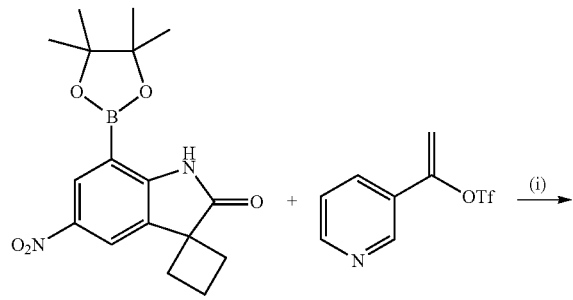

Compound-121

A mixture of intermediate-8 (0.1 g, 0.43 mmol) and pyridine (0.113 g, 1.31 mmol) in DCM (10 mL) was cooled to 0° C. 1-Isocyanato-2-methoxybenzene (0.0065 g, 0.43 mmol) was then added. The mixture was gradually warmed to RT and stirred for 2 h. The solid formed was filtered, washed with ether and hexanes to get the title compound (0.07 g, 42%). 1H-NMR (400MHz DMSO-d₆): 10.18 (s, 1H), 9.14 9s, 1H), 8.13-8.10 (m, 2H), 7.53 9s, 1H), 7.01 (d, 1H), 6.94-6.86 (m, 2H), 6.63 (s, 1H), 3.87 (s, 3H), 2.50-2.41 (m, 4H), 2.26-2.14 (m, 4H), 1.93-1.92 (m, 1H), 0.92 (d, 2H), 0.59 (d, 2H). LC-MS: m/z 378.1 (M+H)⁺.

Example-XXXIV: 2-Methoxy-N-(2'-oxo-7'-(1-(pyridin-3-yl)ethyl)spiro[cyclobutane-1,3'-indolin]-5'-yl)benzenesulfonamide (Compound 122)

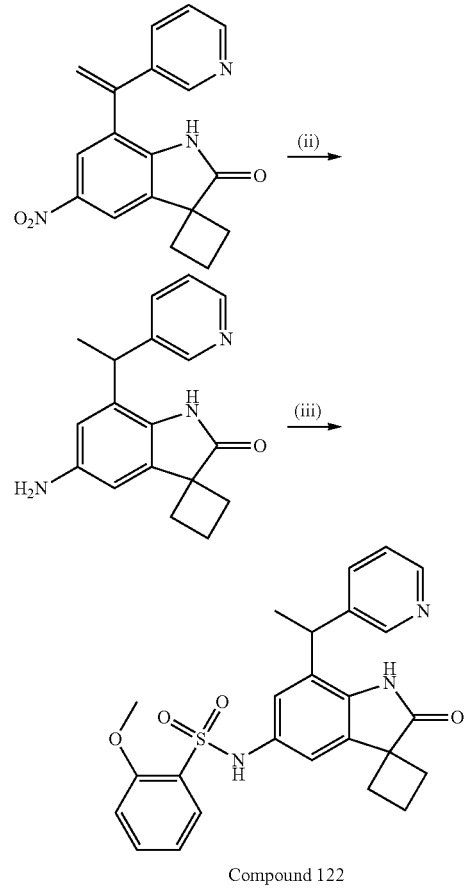

Compound 122

Step-i: 5'-Nitro-7'-(1-(pyridin-3-yl)vinyl)spiro[cyclobutane-1,3'-indolin]-2'-one To a solution of 5'-nitro-7'-(4,4,5,5-tetramethyl-1,3,2-dioxaborolan-2-yl)spiro-[cyclobutane-1,3'-indolin]-2'-one (intermediate-9) (0.5 g, 1.45 mmol) in 1,4-dioxane (10 mL) and H₂O (3 mL) in a sealed tube were added 1-(pyridin-3-yl) vinyl trifluoro methanesulfonate (intermediate-10) (0.73 g, 2.90 mmol) and sodium carbonate (0.38 g, 3.62 mmol). The mixture was degassed with nitrogen purging for 20 min. Then Pd (PPh₃)₄ (0.17 g, 0.145 mmol) was added followed by heating at 100° C. for 16 h. The mixture was concentrated under reduced pressure and the residue was diluted with EtOAc (100 ml), washed with water (100 mL) and brine (100 mL), dried over sodium sulphate, concentrated under reduced pressure and purified by combi flash to afford the title compound as yellow solid (0.4 g). ¹H NMR (400 MHz, DMSO-d₆): δ 10.72 (s, 1H), 8.57 (d, J=2.5 Hz, 1H), 8.54 (d, J=1.5 Hz, 1H), 8.53 (d, J=1.0 Hz, 1H), 7.90 (d, J=2.4 Hz, 1H), 7.68-7.53 (m, 1H), 7.40-7.36 (m, 1H), 6.10 (s, 1H), 5.56 (s, 1H), 2.48-2.41 (m, 4H), 2.28-2.22 (m, 2H); LCMS: m/z 322.2 (M+H).

Step-ii: 5'-Amino-7'-(1-(pyridin-3-yl)ethyl)spiro[cyclobutane-1,3'-indolin]-2'-one To a solution of 5'-nitro-7'-(1-(pyridin-3-yl)vinyl)spiro [cyclobutane-1,3'-indolin]-2'-one (0.4 g, 1.51 mmol) in MeOH (5 mL) was added Palladium hydroxide (0.2 g) followed by stirring under H₂ bladder pressure at RT for 6 h. The mixture was filtered through celite bed and washed with EtOAc. The organic layer was concentrated under reduced pressure and purified by combi flash to afford the title compound as white solid (0.18 g). ¹H NMR (400 MHz, DMSO-d$_6$): δ 10.01 (s, 1H), 8.52 (d, J=2.4 Hz, 1H), 8.38 (dd, J=1.4 Hz, 4.9 Hz, 1H), 7.64 (d, J=7.9 Hz, 1H), 7.32-7.29 (m, 1H), 6.69 (d, J=2.0 Hz, 1H), 6.32 (d, J=2.0 Hz, 1H), 4.69 (bs, 2H), 4.23 (q, J=7.4 Hz, 1H), 2.44-2.33 (m, 2H), 2.20-2.08 (m, 4H), 1.49 (d, J=7.4 Hz, 3H); LCMS: m/z 294.2 (M+H).

Step-iii: Synthesis of 2-methoxy-N-(2'-oxo-7'-(1-(pyridin-3-yl)ethyl)spiro[cyclobutane-1,3'-indolin]-5'-yl)benzenesulfonamide To an ice cooled solution of 5'-amino-7'-(1-(pyridin-3-yl)ethyl)spiro[cyclobutane-1,3'-indolin]-2'-one (0.15 g, 0.51 mmol) in DCM (6 mL) were added pyridine (0.2 mL, 2.55 mmol) and 2-methoxy benzenesulfonyl chloride (0.13 g, 0.61 mmol) folloed by stirring at RT for 3 h. The mixture was diluted with DCM (100 mL) and washed with water (100 mL) and brine (100 mL), dried over sodium sulphate and concentrated under reduced pressure and purified by preparative HPLC to afford the title compound as white solid (0.05 g, 21%). $^1$H NMR (400 MHz, DMSO-d$_6$): δ 10.33 (s, 1H), 9.55 (s, 1H), 8.40-8.37 (m, 2H), 7.61 (dd, J=1.5 Hz, 7.8 Hz, 1H), 7.56-7.52 (m, 1H), 7.35-7.32 (m, 1H), 7.29-7.26 (m, 1H), 7.13-7.11 (m, 2H), 6.97 (t, J=7.4 Hz, 1H), 6.74 (d, J=1.9 Hz, 1H), 4.20 (q, J=6.9 Hz, 1H), 3.84 (s, 3H), 2.40-2.32 (m, 2H), 2.20-2.05 (m, 4H), 1.38 (d, J=6.8 Hz, 3H); LCMS: m/z 464.2 (M+H)$^+$.

Example-XXXV: 2-Methoxy-N-(2'-oxo-7'-(1-(pyridin-2-yl)ethyl)spiro [cyclobutane-1,3'-indolin]-5'-yl)benzenesulfonamide (Compound 123)

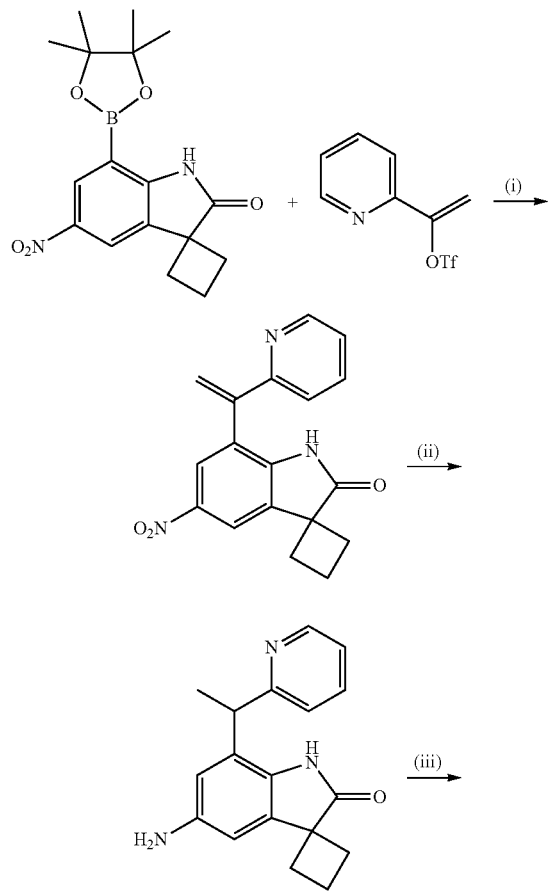

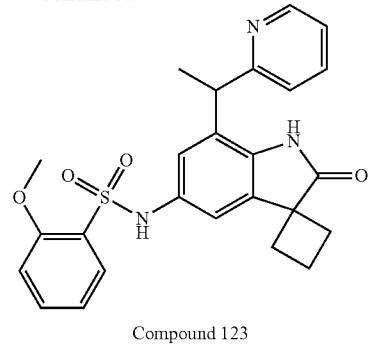

Compound 123

Step-i: 5'-Nitro-7'-(1-(pyridin-2-yl)vinyl)spiro[cyclobutane-1,3'-indolin]-2'-one The process of this step was adopted from step-i of Example-XXXIV. $^1$H NMR (400 MHz, DMSO-d$_6$): δ 10.73 (s, 1H), 8.53 (d, J=4.9 Hz, 1H), 8.47 (d, J=2.5 Hz, 1H), 7.90 (d, J=2.0 Hz, 1H), 7.83-7.79 (m, 1H), 7.53 (d, J=7.9 Hz, 1H), 7.35-7.32 (m, 1H), 6.43 (s, 1H), 5.65 (s, 1H), 2.46-2.41 (m, 2H), 2.28-2.19 (m, 4H); LCMS: m/z 322.1 (M+H)$^+$.

Step-ii: 5'-Amino-7'-(1-(pyridin-2-yl)ethyl)spiro[cyclobutane-1,3'-indolin]-2'-one The process of this step was adopted from step-ii of Example-XXXIV. $^1$H NMR (400 MHz, DMSO-d$_6$): δ 10.0 (s, 1H), 8.57 (d, J=3.9 Hz, 1H), 7.70-7.66 (m, 1H), 7.29 (d, J=7.8 Hz, 1H), 7.21-7.18 (m, 1H), 6.65 (d, J=2.4 Hz, 1H), 6.28 (d, J=1.9 Hz, 1H), 4.64 (bs, 2H), 4.31 (q, J=6.8 Hz, 1H), 2.42-2.33 (m, 2H), 2.17-2.06 (m, 4H), 1.50 (d, J=7.4 Hz, 3H); LCMS: m/z 294.0 (M+H)$^+$.

Step-iii: 2-Methoxy-N-(2'-oxo-7'-(1-(pyridin-2-yl)ethyl)spiro[cyclobutane-1,3'-indolin]-5'-yl)benzenesulfonamide The process of this step was adopted from step-iii of Example-XXXIV. $^1$H NMR (400 MHz, DMSO-d$_6$): δ 10.35 (s, 1H), 9.48 (s, 1H), 8.50 (d, J=3.9 Hz, 1H), 7.68-7.64 (m, 1H), 7.57-7.54 (m, 1H), 7.53-7.48 (m, 1H), 7.22-7.19 (m, 1H), 7.14-7.08 (m, 3H), 6.93 (t, J=7.8 Hz, 1H), 6.73 (d, J=2.0 Hz, 1H), 4.28 (q, J=6.9 Hz, 1H), 3.83 (s, 3H), 2.40-2.33 (m, 2H), 2.20-2.05 (m, 4H), 1.38 (d, J=6.8 Hz, 3H); LCMS: m/z 464.2 (M+H)$^+$.

Example-XXXVI: 2-Methoxy-N-(2'-oxo-7'-(pyridin-2-yloxy)spiro[cyclobutane-1,3'-indolin]-5'-yl)benzenesulfonamide (Compound 124)

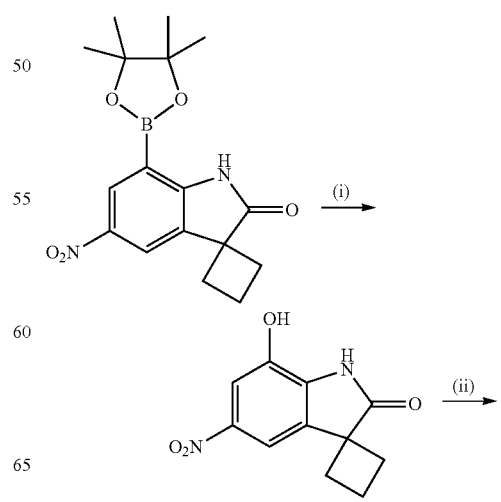

-continued

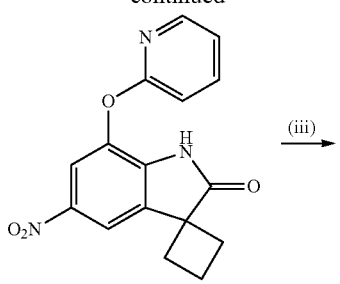

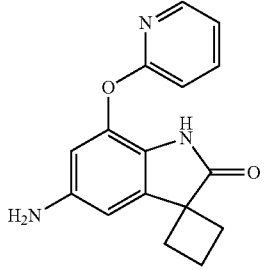

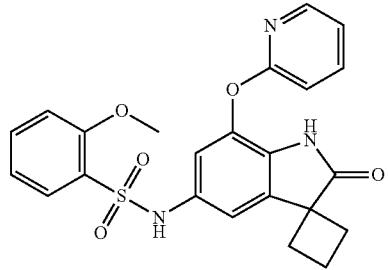

Compound 124

Step-i: 7'-Hydroxy-5'-nitrospiro[cyclobutane-1,3'-indolin]-2'-one

To a cold solution of 5'-nitro-7'-(4,4,5,5-tetramethyl-1,3,2-dioxaborolan-2-yl)-spiro[cyclobutane-1,3'-indolin]-2'-one (0.45 g, 1.31 mmol) in THF (10 mL) was added hydrogen peroxide 30% in water (2.5 mL) followed by stirring at RT for 6 h. The mixture was diluted with water and extracted with EtOAc. The organic layer was dried over sodium sulphate and concentrated under reduced pressure. The obtained solid was washed with diethyl ether to afford the title compound as yellow solid (0.35 g). $^1$H NMR (400 MHz, DMSO-d$_6$): δ 10.78 (s, 1H), 10.54 (s, 1H), 8.01 (d, J=2.0 Hz, 1H), 7.61 (d, J=1.9 Hz, 1H), 2.43-2.39 (m, 4H), 2.25-2.16 (m, 2H).

Step-ii: 5'-Nitro-7'-(pyridin-2-yloxy)spiro[cyclobutane-1,3'-indolin]-2'-one

To a solution of 7'-hydroxy-5'-nitrospiro[cyclobutane-1,3'-indolin]-2'-one (0.18 g, 0.72 mmol) in DMF (2 mL) was added potassium carbonate (0.3 g, 2.16 mmol) and 2-fluoro pyridine (0.14 g, 1.44 mmol) followed by heating to 150° C. for 16 h. The mixture was diluted with EtOAc and washed with water. The organic layer was dried over sodium sulphate, concentrated under reduced pressure and purified by combi flash to afford the title compound as yellow solid (0.11 g, 50%). $^1$H NMR (400 MHz, DMSO-d$_6$): δ 11.20 (s, 1H), 8.40 (d, J=1.9 Hz, 1H), 8.11 (dd, J=1.5 Hz, 4.9 Hz, 1H), 7.97 (d, J=1.9 Hz, 1H), 7.92-7.88 (m, 1H), 7.18-7.14 (m, 2H), 2.47-2.42 (m, 4H), 2.26-1.98 (m, 2H); LCMS: m/z 312.1 (M+H)$^+$.

Step-iii: 5'-Amino-7'-(pyridin-2-yloxy)spiro[cyclobutane-1,3'-indolin]-2'-one:

The process of this step was adopted from step-e of Intermediate-1. $^1$H NMR (400 MHz, DMSO-d$_6$): δ 9.95 (s, 1H), 8.11 (dd, J=1.4 Hz, 4.9 Hz, 1H), 7.82-7.78 (m, 1H), 7.09-7.06 (m, 1H), 6.94 (d, J=8.3 Hz, 1H), 6.72 (d, J=1.9 Hz, 1H), 6.14 (d, J=2.0, 1H), 4.89-4.88 (bs, 2H), 2.46-2.40 (m, 2H), 2.33-2.14 (m, 4H); LCMS: m/z 282.2 (M+H)$^+$.

Step-iv: 2-Methoxy-N-(2'-oxo-7'-(pyridin-2-yloxy)spiro[cyclobutane-1,3'-indolin]-5'-yl)benzenesulfonamide The process of this step was adopted from step-f of Intermediate-1. $^1$H NMR (400 MHz, DMSO-d$_6$): δ 10.32 (s, 1H), 9.75 (s, 1H), 8.06 (d, J=4.4 Hz, 1H), 7.81 (t, J=8.4 Hz, 1H), 7.69 (d, J=7.8 Hz, 1H), 7.56 (t, J=8.3 Hz, 1H), 7.17-7.09 (m, 3H), 7.01 (t, J=7.3 Hz, 1H), 6.92 (d, J=8.3 Hz, 1H), 6.63 (s, 1H), 3.85 (s, 3H), 2.42-2.32 (m, 2H), 2.19-2.07 (m, 4H); LCMS: m/z 452.2 (M+H)$^+$.

Example-XXXVII: N-(7'-(fluoro(phenyl)methyl)-2'-oxospiro[cyclobutane-1,3'-indolin]-5'-yl)-2-methoxybenzenesulfonamide (Compound 125)

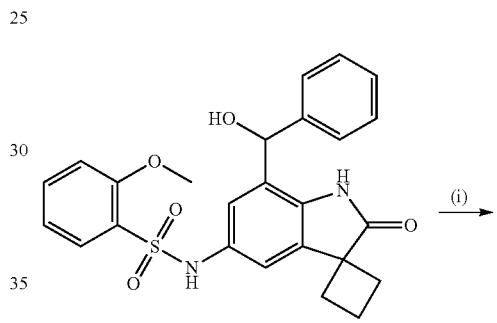

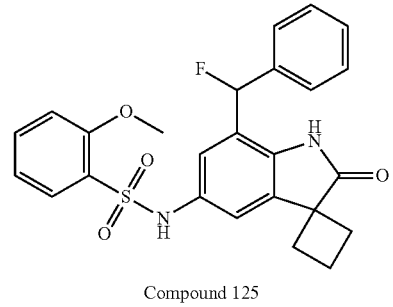

Compound 125

To a cold solution of N-(7'-(hydroxy(phenyl)methyl)-2'-oxospiro[cyclobutane-1,3'-indolin]-5'-yl)-2-methoxybenzenesulfonamide (0.09 g, 0.19 mmol) in DCM (4 mL) was added DAST (0.025 mL, 0.19 mmol) followed by stirring at RT for 30 min. The mixture was diluted with DCM and washed with saturated NaHCO$_3$. The organic layer was dried over sodium sulphate, concentrated and purified by combi flash to afford the title compound as brick red solid (0.03 g, 33%). $^1$H NMR (400 MHz, DMSO-d$_6$): δ 10.48 (s, 1H), 9.66 (s, 1H), 7.60 (d, J=7.8 Hz, 1H), 7.54 (t, J=7.3 Hz, 1H), 7.38-7.37 (m, 3H), 7.26 (s, 1H), 7.18 (d, J=6.4 Hz, 2H), 7.10 (d, J=8.3 Hz, 1H), 6.97 (t, J=7.4 Hz, 1H), 6.80 (s, 1H), 6.69-6.58 (m, 1H), 3.79 (s, 3H), 2.40-2.32 (m, 2H), 2.20-2.09 (m, 4H); LCMS: m/z 467.2 (M+H)$^+$.

Example-XXXVIII: 2,4-Difluoro-N-(2'-oxo-7'-(1-phenylethyl)spiro[cyclobutane-1,3'-indolin]-5'-yl)benzenesulfonamide (Compound 126)

Example- XXXIX: 2-Methoxy-N-(7'-((1-methylpiperidin-4-yl)oxy)-2'-oxospiro-[cyclobutane-1,3'-indolin]-5'-yl)benzenesulfonamide (Compound-127)

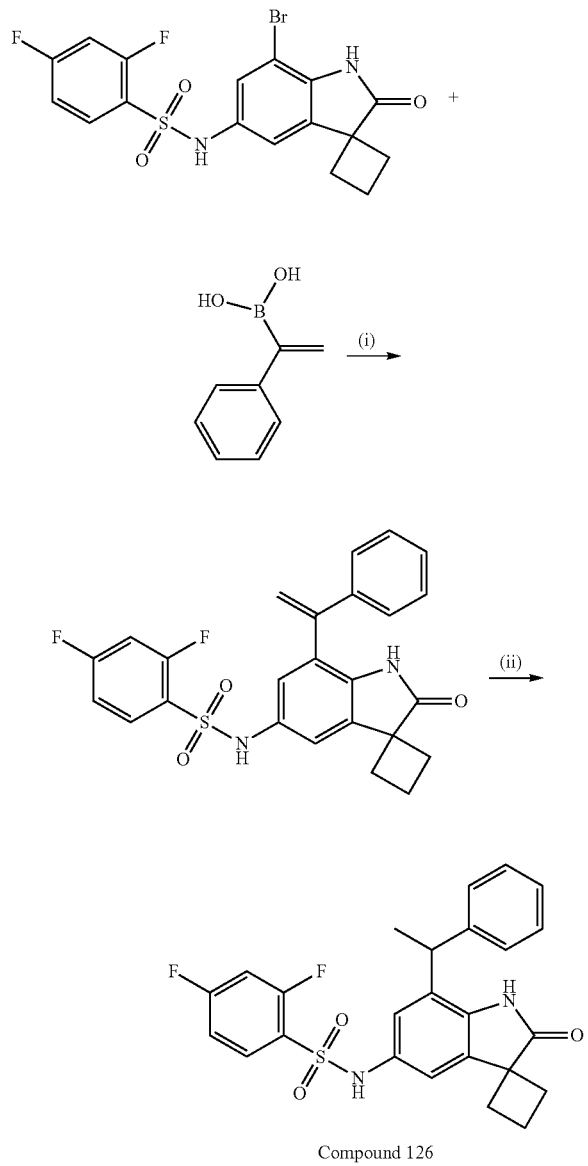

Compound 126

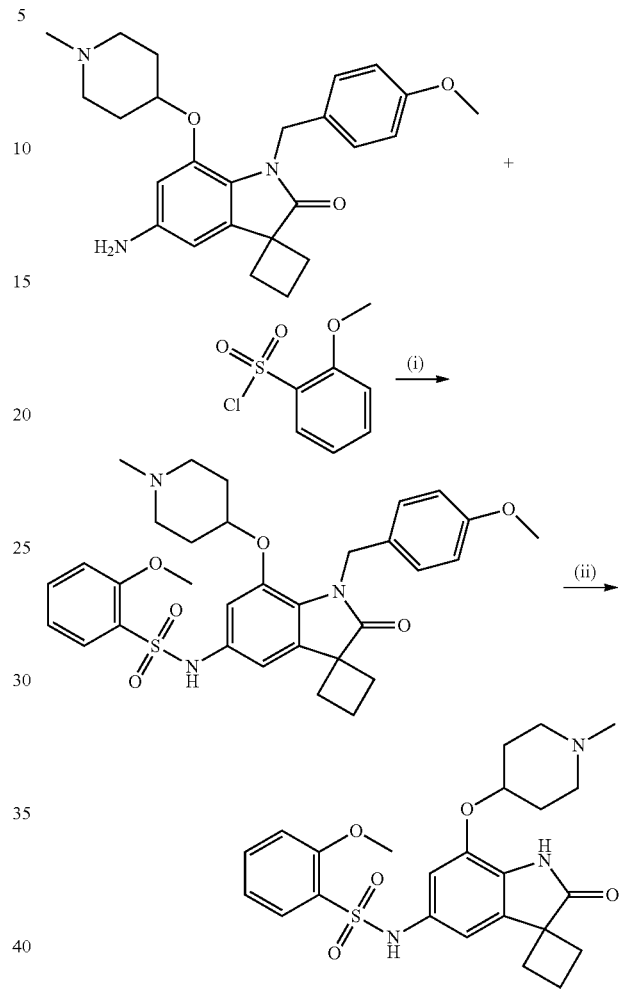

Step-i: 2,4-Difluoro-N-(2'-oxo-7'-(1-phenylvinyl)spiro[cyclobutane-1,3'-indolin]-5'-yl)benzenesulfonamide The process of this step was adopted from Example-I. $^1$H NMR (400 MHz, DMSO-$d_6$): δ 10.22 (s, 1H), 9.94 (s, 1H), 7.76-7.70 (m, 1H), 7.53-7.48 (m, 1H), 7.31-7.29 (m, 4H), 7.24-7.20 (m, 1H), 7.12-7.08 (m, 2H), 6.51 (d, J=2.0 Hz, 1H), 5.77 (s, 1H), 5.20 (s, 1H), 2.43-2.32 (m, 2H), 2.21-2.12 (m, 4H); LC-MS: m/z 467.1 (M+H)$^+$.

Step-ii: 2,4-Difluoro-N-(2'-oxo-7'-(1-phenylethyl)spiro[cyclobutane-1,3'-indolin]-5'-yl)benzenesulfonamide The process of this step was adopted from Example-XXVIII. $^1$H NMR (400 MHz, DMSO-$d_6$): δ 10.37 (s, 1H), 10.16 (s, 1H), 7.72-7.66 (m, 1H), 7.52-7.47 (m, 1H), 7.26-7.19 (m, 4H), 7.17-7.07 (m, 3H), 6.66 (d, J=1.9 Hz, 1H), 4.20 (q, J=6.8 Hz, 1H), 2.40-2.33 (m, 2H), 2.20-2.07 (m, 4H), 1.35 (d, J=7.4 Hz, 3H); LC-MS: m/z 469.1 (M+H)$^+$.

Step-(i): 2-Methoxy-N-(1'-(4-methoxybenzyl)-7'-((1-methylpiperidin-4-yl)oxy)-2'-oxospiro[cyclobutane-1,3'-indolin]-5'-yl)benzenesulfonamide To an ice cooled solution of 5'-amino-5'-(4-methoxybenzyl)-7'-((1-methylpiperidin-4-yl)oxy)spiro[cyclobutane-1,3'-indolin]-2'-one (4.0 g, 9.50 mmol) in DCM (40 mL) were added pyridine (2.3 mL, 28.5 mmol) and 2-methoxybenzenesulfonyl chloride (2.15 g, 10.45 mmol) followed by stirring at RT for 2 h. The mixture was diluted with DCM and washed with aqueous NaHCO$_3$ and brine, dried over sodium sulphate and concentrated under reduced pressure. The residue was purified by combi-flash to afford the title compound as an off white solid (4.0 g, 71%). $^1$H NMR (400 MHz, DMSO-$d_6$): δ 9.73 (bs, 1H), 7.73-7.72 (m, 1H), 7.59-7.54 (m, 1H), 7.18 (d, J=8.3 Hz, 1H), 7.03-6.98 (m, 3H), 6.92 (s, 1H), 6.82 (d, J=8.3 Hz, 2H), 6.60 (s, 1H), 4.92 (s, 2H), 4.18-4.12 (m, 1H), 3.90 (s, 3H), 3.68 (s, 3H), 2.44-2.10 (m, 13H), 1.79-1.76 (m, 2H), 1.58-1.49 (m, 2H); LC-MS: m/z 592.3 (M+H)$^+$.

Step-(ii): 2-Methoxy-N-(7'-((1-methylpiperidin-4-yl)oxy)-2'-oxospiro[cyclobutane-1,3'-indolin]-5'-yl)benzenesulfonamide To a cold solution of 2-methoxy-N-(1'-(4-methoxybenzyl)-7'-((1-methylpiperidin-4-yl)oxy)-2'-oxospiro[cyclobutane-1,3'-indolin]-5'-yl)benzenesulfonamide (4.0 g, 6.76 mmol) in DCM (40 mL) was added TFA (20 mL) followed by trifluoro methane sulfonic acid (4.0 mL) and the mixture was stirred at RT for 5 h. The mixture was slowly poured in aqueous NaHCO$_3$ and extracted with DCM. The organic layer was dried over Na$_2$SO$_4$, concentrated under reduced pressure and purified by combi-flash to afford the title compound as an off white solid (1.6 g, 50%). $^1$H NMR (400 MHz, DMSO-d$_6$): δ 10.16 (s, 1H), 9.62 (s, 1H), 7.66 (dd, J=7.9 Hz, & 1.5 Hz, 1H), 7.56-7.52 (m, 1H), 7.17 (d, J=8.3 Hz, 1H), 6.98 (t, J=7.3 Hz, 1H), 6.87 (d, J=1.5 Hz, 1H), 6.54 (d, J=1.5 Hz, 1H), 4.10-3.96 (m, 1H), 3.92 (s, 3H), 2.67-2.58 (m, 2H), 2.37-2.30 (m, 2H), 2.21-2.01 (m, 6H), 2.15 (s, 3H), 1.73-1.70 (m, 2H), 1.54-1.46 (m, 2H); LC-MS: m/z 472.2 (M+H)$^+$.

The below compounds were prepared by procedure similar to the one described in Example-XXXIX with appropriate variations in reactants, quantities of reagents and reaction conditions. The physiochemical characteristics of the compounds are also summarized.

| No. | Structure | Characterization data $^1$H NMR (400 MHz, DMSO-d$_6$)/LC-MS: |
|---|---|---|
| 128 | 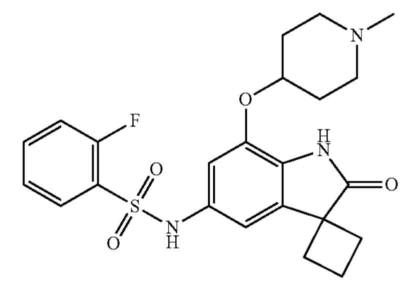 [SMILES: CN1CCC(Oc2cc(NS(=O)(=O)c3ccccc3F)cc3c2NC(=O)C32CCC2)CC1] | $^1$H NMR (400 MHz, DMSO-d$_6$): δ 10.23 (s, 1H), 10.16 (bs, 1H), 7.76-7.72 (m, 1H), 7.70-7.65 (m, 1H), 7.45-7.40 (m, 1H), 7.32 (t, J = 7.93 Hz, 1H), 6.85 (d, J = 1.4 Hz, 1H), 6.54 (d, J = 2.0 Hz, 1H), 4.05 (bs, 1H), 2.71-2.62 (m, 2H), 2.39-2.30 (m, 2H), 2.21-1.99 (m, 9H), 1.76-1.72 (m, 2H), 1.58-1.51 (m, 2H); LC-MS: m/z 460.2 (M + H)$^+$. |
| 129 | 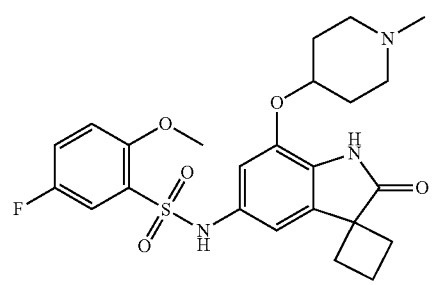 [SMILES: COc1ccc(F)cc1S(=O)(=O)Nc1cc(OC2CCN(C)CC2)c2c(c1)C1(CCC1)C(=O)N2] | $^1$H NMR (400 MHz, DMSO-d$_6$): δ 10.19 (s, 1H), 9.79-9.76 (bs, 1H), 7.46-7.41 (m, 2H), 7.24-7.20 (m, 1H), 6.88 (d, J = 1.9 Hz, 1H), 6.56 (d, J = 1.4 Hz, 1H), 4.10-4.07 (m, 1H), 3.90 (s, 3H), 2.70-2.67 (m, 2H), 2.40-1.91 (m, 11H), 1.75-1.74 (m, 2H), 1.58-1.55 (m, 2H); LC-MS: m/z 490.2 (M + H)$^+$. |
| 130 | 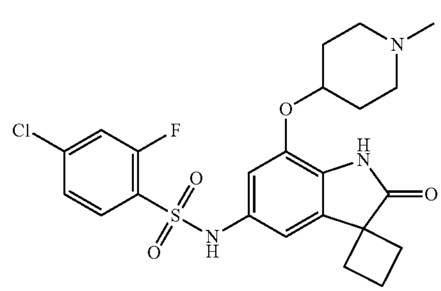 [SMILES: CN1CCC(Oc2cc(NS(=O)(=O)c3ccc(Cl)cc3F)cc3c2NC(=O)C32CCC2)CC1] | $^1$H NMR (400 MHz, DMSO-d$_6$): δ 10.22 (b,s 2H), 7.74-7.70 (m, 2H), 7.42 (d, J = 8.3 Hz, 1H), 6.87 (s, 1H), 6.50 (s, 1H), 4.05-4.03 (m, 1H), 2.65-2.63 (m, 2H), 2.38-2.36 (m, 2H), 2.20-2.26 (m, 9H), 1.74-1.72 (m, 2H), 1.56-1.54 (m, 2H); LC-MS: m/z 494.2 (M + H)$^+$. |
| 131 | 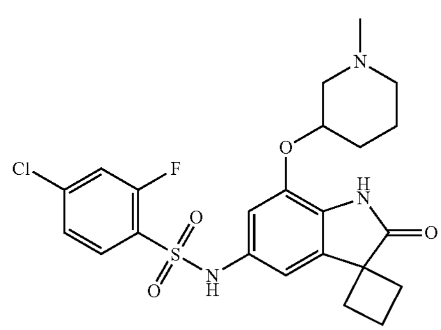 [SMILES: CN1CCCC(Oc2cc(NS(=O)(=O)c3ccc(Cl)cc3F)cc3c2NC(=O)C32CCC2)C1] | $^1$H NMR (400 MHz, DMSO-d$_6$): δ 10.27-10.18 (bs, 2H), 7.77-7.71 (m, 2H), 7.44-7.42 (m, 1H), 6.89-6.85 (m, 1H), 6.56-6.54 (m, 1H), 4.04-4.02 (m, 1H), 3.89-3.85 (m, 1H), 3.69-3.67 (m, 1H), 2.98-2.96 (m, 2H), 2.36-2.07 (m, 11H), 1.89-1.74 (m, 2H); LC-MS: m/z 494.2 (M + H)$^+$. |

| No. | Structure | Characterization data<br>¹H NMR (400 MHz, DMSO-d₆)/LC-MS: |
|---|---|---|
| 132 | 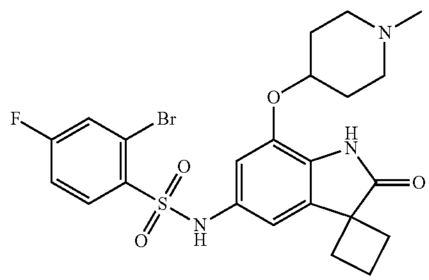 [SMILES: CN1CCC(Oc2cc(NS(=O)(=O)c3ccc(F)cc3Br)cc3c2NC(=O)C32CCC2)CC1] | ¹H NMR (400 MHz, DMSO-d₆): δ 10.21 (s, 1H), 10.20-10.10 (bs, 1H), 8.07-8.03 (m, 1H), 7.85 (dd, J = 8.8 Hz, & 2.9 Hz, 1H), 7.43-7.39 (m, 1H), 6.89 (d, J = 1.5 Hz, 1H), 6.54 (d, J = 1.5 Hz, 1H), 4.08-4.06 (m, 1H), 2.70-2.67 (m, 2H), 2.40-2.32 (m, 2H), 2.25-2.03 (m, 9H), 1.77-1.74 (m, 2H), 1.58-1.56 (m, 2H); LC-MS: m/z 538.1 (M + H)⁺. |
| 133 | 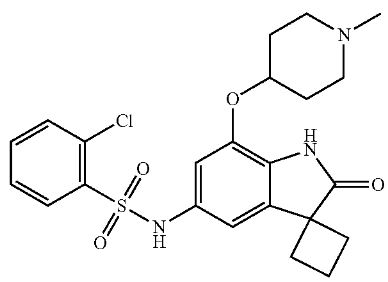 [SMILES: CN1CCC(Oc2cc(NS(=O)(=O)c3ccccc3Cl)cc3c2NC(=O)C32CCC2)CC1] | ¹H NMR (400 MHz, DMSO-d₆): δ 10.18 (bs, 1H), 10.14-10.12 (bs, 1H), 7.96 (dd, J = 7.9 Hz & 1.0 Hz, 1H), 7.65-7.58 (m, 2H), 7.49-7.45 (m, 1H), 6.88 (d, J = 1.5 Hz, 1H), 6.55 (d, J = 1.4 Hz, 1H), 4.05-4.03 (m, 1H), 2.67-2.66 (m, 2H), 2.38-2.32 (m, 2H), 2.23-2.06 (m, 9H), 1.75-1.72 (m, 2H), 1.57-1.53 (m, 2H); LC-MS: m/z 476.2 (M + H)⁺. |
| 134 | 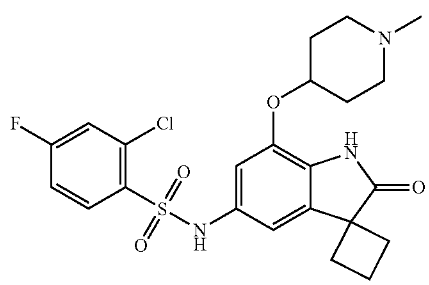 [SMILES: CN1CCC(Oc2cc(NS(=O)(=O)c3ccc(F)cc3Cl)cc3c2NC(=O)C32CCC2)CC1] | ¹H NMR (400 MHz, DMSO-d₆): δ 10.23 (s, 1H), 10.14 (bs, 1H), 8.03-7.99 (m, 1H), 7.72-7.69 (m, 1H), 7.38-7.34 (m, 1H), 6.89 (d, J = 1.4 Hz, 1H), 6.55 (d, J = 1.9 Hz, 1H), 4.11 (bs, 1H), 2.75-2.66 (m, 2H), 2.40-2.30 (m, 7H), 2.21-2.02 (m, 4H), 1.90-1.75 (m, 2H), 1.60-1.58 (m, 2H); LC-MS: m/z 494.1 (M + H)⁺. |
| 135 | 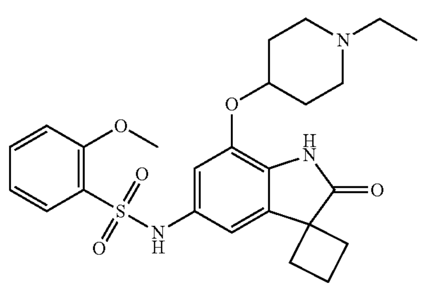 [SMILES: CCN1CCC(Oc2cc(NS(=O)(=O)c3ccccc3OC)cc3c2NC(=O)C32CCC2)CC1] | ¹H NMR (400 MHz, DMSO-d₆): δ 10.17 (bs, 1H), 9.63 (bs, 1H), 7.67 (dd, J = 7.8 Hz, & 1.4 Hz, 1H), 7.57-7.52 (m, 1H), 7.17 (d, J = 8.3 Hz, 1H), 6.99 (t, J = 7.9 Hz, 1H), 6.87 (d, J = 1.0 Hz, 1H), 6.55 (s, 1H), 4.10-3.99 (m, 1H), 3.92 (s, 3H), 2.68-2.66 (m, 2H), 2.36-2.21 (m, 4H), 2.19-2.05 (m, 6H), 1.74-1.72 (m, 2H), 1.52-1.50 (m, 2H), 1.09-1.07 (m, 3H); LC-MS: m/z 486.2 (M + H)⁺. |
| 136 | 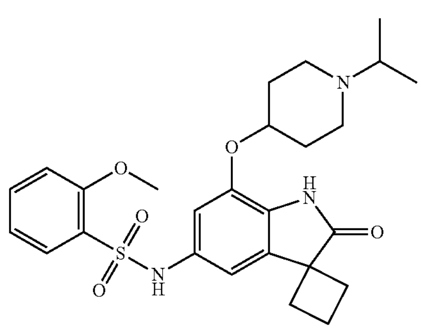 [SMILES: COc1ccccc1S(=O)(=O)Nc1cc(OC2CCN(C(C)C)CC2)c2c(c1)C1(CCC1)C(=O)N2] | ¹H NMR (400 MHz, DMSO-d₆): δ 10.11 (bs, 1H), 9.57 (bs, 1H), 7.67 (dd, J = 7.8 Hz, & 1.9 Hz, 1H), 7.56-7.52 (m, 1H), 7.17 (d, J = 8.3 Hz, 1H), 6.99 (t, J = 7.9 Hz, 1H), 6.86 (d, J = 1.4 Hz, 1H), 6.54 (d, J = 1.5 Hz, 1H), 3.97-3.95 (m, 1H), 3.92 (s, 3H), 2.67-2.54 (m, 3H), 2.37-2.33 (m, 2H), 2.20-2.04 (m, 6H), 1.74-1.72 (m, 2H), 1.49-1.46 (m, 2H), 0.97 (d, J = 6.4 Hz, 6H); LC-MS: m/z 500.2 (M + H)⁺. |

| No. | Structure | Characterization data<br>¹H NMR (400 MHz, DMSO-d₆)/LC-MS: |
|---|---|---|
| 137 | 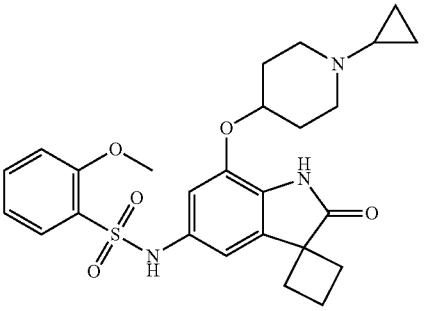 [SMILES: COc1ccccc1S(=O)(=O)Nc1cc(OC2CCN(C3CC3)CC2)c2c(c1)C1(CCC1)C(=O)N2] | ¹H NMR (400 MHz, DMSO-d₆): δ 10.11 (bs, 1H), 9.58 (bs, 1H), 7.69-7.66 (m, 1H), 7.57-7.52 (m, 1H), 7.17 (d, J = 8.3 Hz, 1H), 6.99 (t, J = 7.4 Hz, 1H), 6.87 (d, J = 1.5 Hz, 1H), 6.55 (d, J = 1.5 Hz, 1H), 4.02-4.00 (m, 1H), 3.92 (s, 3H), 2.81-2.78 (m, 2H), 2.67-2.27 (m, 7H), 2.19-2.05 (m, 5H), 1.68-1.61 (m, 2H), 1.49-1.41 (m, 2H), 0.42-0.38 (m, 2H), 0.27-0.26 (m, 2H); LC-MS: m/z 498.2 (M + H)⁺. |
| 138 | 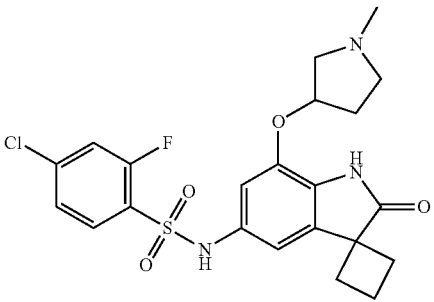 [SMILES: CN1CCC(Oc2cc(NS(=O)(=O)c3ccc(Cl)cc3F)cc3c2NC(=O)C32CCC2)C1] | ¹H NMR (400 MHz, DMSO-d₆): δ 10.25-10.19 (bs, 1H), 10.2 (bs, 1H), 7.76-7.72 (m, 2H), 7.44 (d, J = 8.3 Hz, 1H), 6.86 (s, 1H), 6.51 (s, 1H), 4.77-.475 (m, 1H), 2.96-2.72 (m, 4H), 2.54-2.20 (m, 4H), 2.19-2.02 (m, 6H), 1.84-1.81 (m, 1H); LC-MS: m/z 480. (M + H)⁺. |
| 139 | 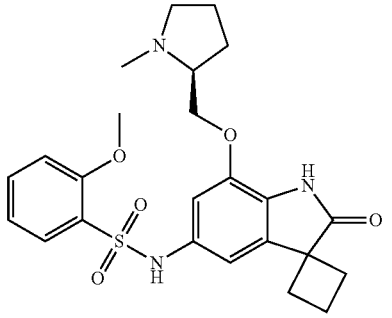 [SMILES: COc1ccccc1S(=O)(=O)Nc1cc(OC[C@@H]2CCCN2C)c2c(c1)C1(CCC1)C(=O)N2] | ¹H NMR (400 MHz, DMSO-d₆): δ 10.18 (bs, 1H), 9.65 (bs, 1H), 7.70 (d, J = 7.4 Hz, 1H), 7.55 (t, J = 7.4 Hz, 1H), 7.17 (d, J = 8.3 Hz, 1H), 7.01-6.89 (m, 1H), 6.85 (s, 1H), 6.62 (s, 1H), 3.92 (s, 3H), 3.75-3.66 (m, 2H), 2.67-2.33 (m, 6H), 2.16-2.01 (m, 6H), 1.91-1.50 (m, 4H); LC-MS: m/z 472.2 (M + H)⁺. |
| 140 | 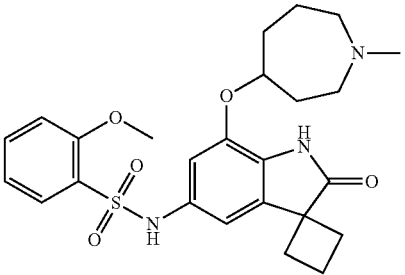 [SMILES: COc1ccccc1S(=O)(=O)Nc1cc(OC2CCCN(C)CC2)c2c(c1)C1(CCC1)C(=O)N2] | ¹H NMR (400 MHz, DMSO-d₆): δ 10.17 (bs, 1H), 9.62 (bs, 1H), 7.69-7.67 (m, 1H), 7.55 (t, J = 8.4 Hz, 1H), 7.16 (d, J = 8.4 Hz, 1H), 6.99 (t, J = 7.8 Hz, 1H), 6.84 (s, 1H), 6.57 (s, 1H), 4.39-4.37 (m, 1H), 3.92 (s, 3H), 2.67-2.43 (m, 4H), 2.40-1.91 (m, 7H), 1.85-1.83 (m, 4H), 1.69-1.60 (m, 4H); LCMS: m/z 486.2 (M + H)⁺. |
| 141 | 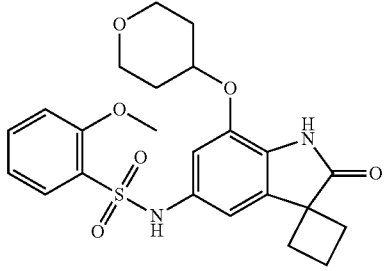 [SMILES: COc1ccccc1S(=O)(=O)Nc1cc(OC2CCOCC2)c2c(c1)C1(CCC1)C(=O)N2] | ¹H NMR (400 MHz, DMSO-d₆): δ 10.18 (s, 1H), 9.59 (s, 1H), 7.68-7.61 (m, 1H), 7.56-7.52 (m, 1H), 7.17 (d, J = 8.3 Hz, 1H), 6.98 (t, J = 7.3 Hz, 1H), 6.88 (d, J = 1.0 Hz, 1H), 6.56 (d, J = 1.4 Hz, 1H), 4.24-4.19 (m, 1H), 3.92 (s, 3H), 3.85-3.79 (m, 2H), 3.41-3.36 (m, 2H), 2.38-2.35 (m, 2H), 2.19-2.05 (m, 4H), 1.76-1.73 (m, 2H), 1.50-1.42 (m, 2H); LCMS: m/z 459.1 (M + H)⁺. |

| No. | Structure | Characterization data<br>¹H NMR (400 MHz, DMSO-d$_6$)/LC-MS: |
|---|---|---|
| 142 | 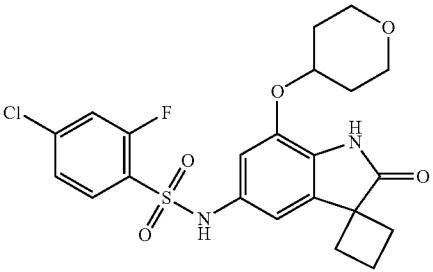 [SMILES: O=C1Nc2c(OC3CCOCC3)cc(NS(=O)(=O)c3ccc(Cl)cc3F)cc2C12CCC2] | ¹H NMR (400 MHz, DMSO-d$_6$): δ 10.28 (s, 1H), 10.27 (s, 1H), 7.75-7.70 (m, 2H), 7.44-7.42 (m, 1H), 6.88 (d, J = 1.5 Hz, 1H), 6.54 (d, J = 1.4 Hz, 1H), 4.28-4.24 (m, 1H), 3.86-3.81 (m, 2H), 3.42-3.36 (m, 2H), 2.40-2.34 (m, 2H), 2.20-2.04 (m, 4H), 1.79-1.75 (m, 2H), 1.53-1.45 (m, 2H); LC-MS: m/z 480.9 (M + H)⁺. |
| 143 | 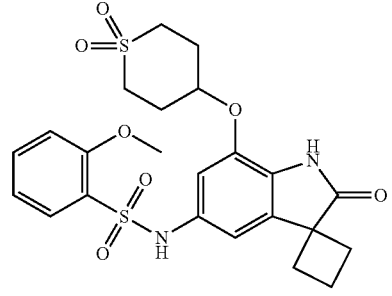 [SMILES: COc1ccccc1S(=O)(=O)Nc1cc(OC2CCS(=O)(=O)CC2)c2c(c1)C1(CCC1)C(=O)N2] | ¹H NMR (400 MHz, DMSO-d$_6$): δ 10.51 (s, 1H), 9.63 (s, 1H), 7.68 (dd, J = 7.8 & 1.5 Hz, 1H), 7.57-7.52 (m, 1H), 7.17 (d, J = 8.3 Hz, 1H), 6.99 (t, J = 7.8 Hz, 1H), 6.86 (d, J = 1.5 Hz, 1H), 6.16 (d, J = 1.5 Hz, 1H), 4.49-4.47 (m, 1H), 3.91 (s, 3H), 3.39-3.35 (m, 2H), 2.93-2.90 (m, 2H), 2.38-2.35 (m, 2H), 2.14-2.04 (m, 8H); LC-MS: m/z 507.1 (M + H)⁺. |
| 144 | 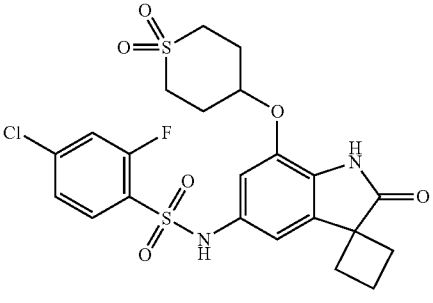 [SMILES: O=C1Nc2c(OC3CCS(=O)(=O)CC3)cc(NS(=O)(=O)c3ccc(Cl)cc3F)cc2C12CCC2] | ¹H NMR (400 MHz, DMSO-d$_6$): δ 10.60 (s, 1H), 10.33 (s, 1H), 7.76-7.72 (m, 2H), 7.45-7.43 (m, 1H), 6.85 (d, J = 1.6 Hz, 1H), 6.63 (d, J = 1.5 Hz, 1H), 4.58-4.55 (m, 1H), 3.47-3.41 (m, 2H), 2.95-2.92 (m, 2H), 2.41-2.32 (m, 2H), 2.21-2.01 (m, 8H); LCMS: m/z 529.1 (M + H)⁻. |
| 144.1 | 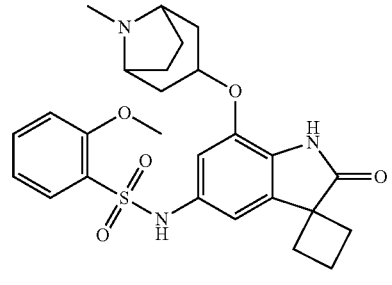 [SMILES: COc1ccccc1S(=O)(=O)Nc1cc(OC2CC3CCC(C2)N3C)c2c(c1)C1(CCC1)C(=O)N2] | ¹H NMR (400 MHz, DMSO-d$_6$): δ 10.05 (s, 1H), 9.59 (s, 1H), 7.71-7.68 (m, 1H), 7.57-7.53 (m, 1H), 7.17 (d, J = 8.3 Hz, 1H), 7.02-6.98 (m, 1H), 6.87 (d, J = 2.0 Hz, 1H), 6.60 (d, J = 1.5 Hz, 1H), 4.22-4.21 (m, 1H), 3.92 (s, 3H), 3.12-3.08 (m, 2H), 2.45-2.36 (m, 4H), 2.34-2.18 (m, 4H), 2.16-1.96 (m, 5H), 1.69-1.55 (m, 4H); LC-MS: m/z 498.0 (M + H)⁺. |
| 145 | 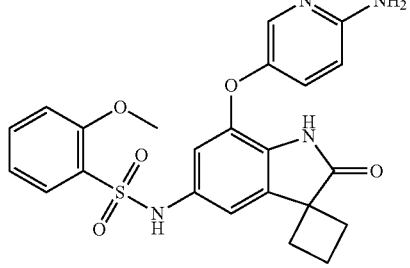 | ¹H NMR (400 MHz, DMSO-d$_6$): δ 10.39 (s, 1H), 9.60 (s, 1H), 7.60-7.53 (m, 3H), 7.10 (d, J = 8.4 Hz, 1H), 7.00-6.97 (m, 3H), 6.49 (d, J = 8.8 Hz, 1H), 6.28 (d, J = 2.0 Hz, 1H), 5.95 (bs, 2H), 3.79 (s, 3H), 2.41-2.37 (m, 2H), 2.19-1.98 (m, 4H); LC-MS: m/z 467.0 (M + H)⁺. |

| No. | Structure | Characterization data<br>¹H NMR (400 MHz, DMSO-d$_6$)/LC-MS: |
|---|---|---|
| 146 | 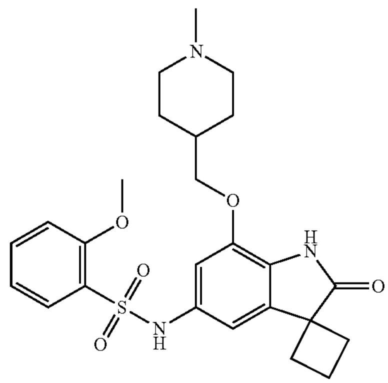 [SMILES: COc1ccccc1S(=O)(=O)Nc1cc(OCC2CCN(C)CC2)c2c(c1)C1(CCC1)C(=O)N2] | ¹H NMR (400 MHz, DMSO-d$_6$): δ 10.16 (s, 1H), 9.60 (s, 1H), 7.70-7.68 (m, 1H), 7.56-7.52 (m, 1H), 7.16 (d, J = 8.3 Hz, 1H), 6.99 (t, J = 7.3 Hz, 1H), 6.81 (d, J = 1.5 Hz, 1H), 6.56 (d, J = 1.0 Hz, 1H), 3.92 (s, 3H), 3.64 (d, J = 6.4 Hz, 2H), 2.85-2.79 (m, 2H), 2.48-2.32 (m, 2H), 2.19-2.14 (m, 4H), 2.10-2.00 (m, 3H), 1.89-1.82 (m, 2H), 1.75-1.72 (m, 2H), 1.67-1.62 (m, 1H), 1.29-1.23 (m, 2H); LC-MS: m/z 486.2 (M + H)⁺. |
| 147 | 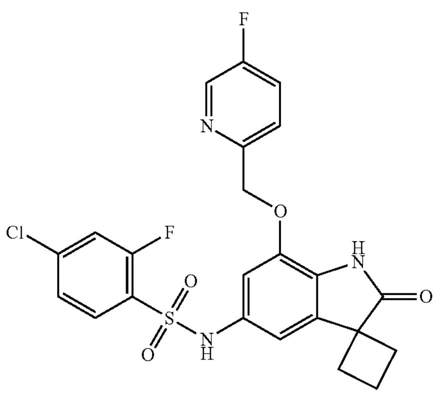 [SMILES: O=C1Nc2c(OCc3ccc(F)cn3)cc(NS(=O)(=O)c3ccc(Cl)cc3F)cc2C12CCC2] | ¹H NMR (400 MHz, DMSO-d$_6$): δ 10.46 (s, 1H), 10.35 (s, 1H), 8.56 (s, 1H), 7.79-7.67 (m, 4H), 7.40 (d, J = 8.3 Hz, 1H), 6.88 (s, 1H), 6.64 (s, 1H), 5.07 (s, 2H), 2.41-2.33 (m, 2H), 2.21-2.04 (m, 4H); LC-MS: m/z 506.1 (M + H)⁺. |
| 148 | 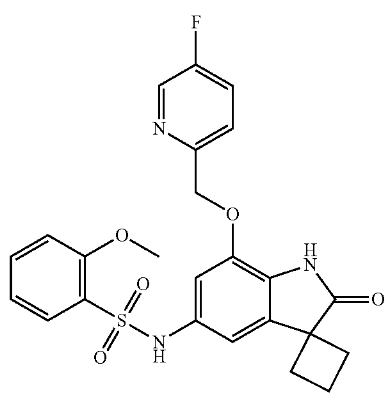 [SMILES: COc1ccccc1S(=O)(=O)Nc1cc(OCc2ccc(F)cn2)c2c(c1)C1(CCC1)C(=O)N2] | ¹H NMR (400 MHz, DMSO-d$_6$): δ 10.37 (s, 1H), 9.64 (s, 1H), 8.57 (s, 1H), 7.78-7.71 (m, 2H), 7.63 (d, J = 7.4 Hz, 1H), 7.52 (t, J = 7.8 Hz, 1H), 7.13 (d, J = 8.3 Hz, 1H), 6.96 (t, J = 7.2 Hz, 1H), 6.88 (s, 1H), 6.63 (s, 1H), 5.03 (s, 2H), 3.89 (s, 3H), 2.41-2.30 (m, 2H), 2.22-2.03 (m, 4H); LC-MS: m/z 484.2 (M + H)⁺. |
| 149 | 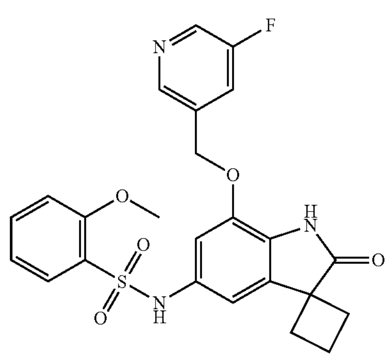 [SMILES: COc1ccccc1S(=O)(=O)Nc1cc(OCc2cncc(F)c2)c2c(c1)C1(CCC1)C(=O)N2] | ¹H NMR (400 MHz, DMSO-d$_6$): δ 10.38 (s, 1H), 9.68 (s, 1H), 8.56-8.53 (m, 2H), 7.94 (d, J = 9.7 Hz, 1H), 7.66 (d, J = 7.8 Hz, 1H), 7.53 (t, J = 7.8 Hz, 1H), 7.15 (d, J = 8.3 Hz, 1H), 6.97 (d, J = 7.8 Hz, 1H), 6.85 (s, 1H), 6.74 (s, 1H), 5.08 (s, 2H), 3.91 (s, 3H), 2.37-2.34 (m, 2H), 2.19-1.99 (m, 4H); ES-MS: m/z 482.4 (M − H)⁻. |

| No. | Structure | Characterization data<br>¹H NMR (400 MHz, DMSO-d₆)/LC-MS: |
|---|---|---|
| 150 & 151 | 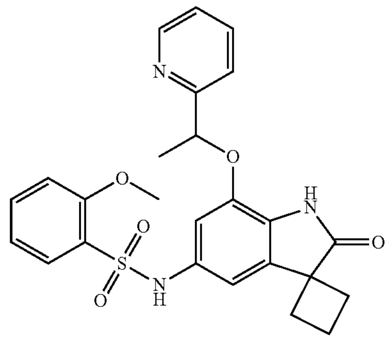 [SMILES: COc1ccccc1S(=O)(=O)Nc1cc(OC(C)c2ccccn2)c2c(c1)C1(CCC1)C(=O)N2] | Isomer-I: ¹H NMR (400 MHz, DMSO-d₆): δ 10.31 (s, 1H), 9.57 (s, 1H), 8.55 (d, J = 4.4 Hz, 1H), 7.77 (t, J = 7.8 Hz, 1H), 7.53-7.47 (m, 3H), 7.31 (t, J = 6.3 Hz, 1H), 7.08 (d, J = 8.4 Hz, 1H), 6.92 (t, J = 7.4 Hz, 1H), 6.82 (s, 1H), 6.48 (s, 1H), 5.21-5.16 (m, 1H), 3.82 (s, 3H), 2.40-2.30 (m, 2H), 2.16-2.12 (m, 1H), 2.08-2.03 (m, 3H), 1.47 (d, J = 6.4 Hz, 3H); LC-MS: m/z 480.2 (M + H)⁺.<br>Isomer-II: ¹H NMR (400 MHz, DMSO-d6): δ 10.31 (s, 1H), 9.58 (s, 1H), 8.55 (d, J = 4.4 Hz, 1H), 7.79-7.75 (m, 1H), 7.54-7.48 (m, 3H), 7.33-7.30 (m, 1H), 7.08 (d, J = 7.3 Hz, 1H), 6.94-6.91 (m, 1H), 6.82 (s, 1H), 6.48 (s, 1H), 5.21-5.17 (m, 1H), 3.82 (s, 3H), 2.36-2.34 (m, 2H), 2.18-2.16 (m, 1H), 2.08-2.03 (m, 3H), 1.47 (d, J = 6.4 Hz, 3H); LC-MS: m/z 480.2 (M + H)⁺. |
| 152, 153 & 154 | 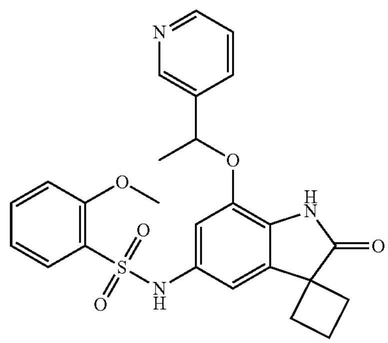 [SMILES: COc1ccccc1S(=O)(=O)Nc1cc(OC(C)c2cccnc2)c2c(c1)C1(CCC1)C(=O)N2] | Racemic mixture: ¹H NMR (400 MHz, DMSO-d₆): δ 10.28 (bs, 1H), 9.58 (bs, 1H), 8.63 (s, 1H), 8.50 (d, J = 3.9 Hz, 1H), 7.81 (d, J = 7.3 Hz, 1H), 7.56-7.49 (m, 2H), 7.38-7.35 (m, 1H), 7.10 (d, J = 8.3 Hz, 1H), 6.94 (d, J = 7.4 Hz, 1H), 6.78 (s, 1H), 6.61 (s, 1H), 5.32-5.30 (m, 1H), 3.84 (s, 3H), 2.36-2.33 (m, 2H), 2.15-2.01 (m, 4H), 1.48 (d, J = 5.9 Hz, 3H); LC-MS: m/z 480.1 (M + H)⁺.<br>Isomer-I: ¹H NMR (400 MHz, DMSO-d6): δ 10.30 (s, 1H), 9.60 (bs, 1H), 8.63 (s, 1H), 8.50 (d, J = 4.4 Hz, 1H), 7.81 (d, J = 7.8 Hz, 1H), 7.56-7.49 (m, 2H), 7.38-7.35 (m, 1H), 7.10 (d, J = 8.4 Hz, 1H), 6.94 (t, J = 7.4 Hz, 1H), 6.78 (s, 1H), 6.61 (s, 1H), 5.32-5.31 (m, 1H), 3.83 (s, 3H), 2.35-2.33 (m, 2H), 2.15-1.99 (m, 4H), 1.48 (d, J = 6.4 Hz, 3H);<br><br>LC-MS: m/z 480.2 (M + H)⁺.<br>Isomer-II: ¹H NMR (400 MHz, DMSO-d₆): δ 10.29 (s, 1H), 9.61 (bs, 1H), 8.63 (d, J = 1.5 Hz, 1H), 8.50 (d, J = 3.4 Hz, 1H), 7.81 (d, J = 7.8 Hz, 1H), 7.55 (d, J = 6.9 Hz, 1H), 7.50 (t, J = 8.3 Hz, 1H), 7.38-7.35 (m, 1H), 7.10 (d, J = 8.4 Hz, 1H), 6.93 (t, J = 7.4 Hz, 1H), 6.78 (s, 1H), 6.60 (s, 1H), 5.34-5.30 (m, 1H), 3.83 (s, 3H), 2.35-2.30 (m, 2H), 2.17-1.99 (m, 4H), 1.48 (d, J = 6.4 Hz, 3H); LC-MS: m/z 480.2 (M + H)⁺. |
| 155 & 156 | 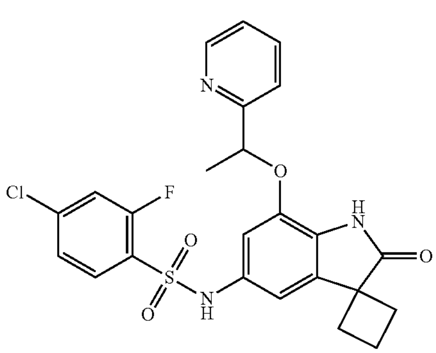 [SMILES: CC(Oc1cc(NS(=O)(=O)c2ccc(Cl)cc2F)cc2c1NC(=O)C21CCC1)c1ccccn1] | Isomer-I: ¹H NMR (400 MHz, DMSO-d₆): δ 10.37 (s, 1H), 10.24 (bs, 1H), 8.53 (d, J = 4.4 Hz, 1H), 7.71 (d, J = 6.9 Hz, 1H), 7.63 (d, J = 9.8 Hz, 1H), 7.55 (t, J = 8.3 Hz, 1H), 7.48 (d, J = 7.9 Hz, 1H), 7.36-7.29 (m, 2H), 6.82 (s, 1H), 6.45 (s, 1H), 5.24-5.20 (m, 1H), 2.37-2.31 (m, 2H), 2.20-2.01 (m, 4H), 1.50 (d, J = 6.4 Hz, 3H); LC-MS: m/z 502.1 (M + H)⁺.<br>Isomer-II: ¹H NMR (400 MHz, DMSO-d6): δ 10.39 (s, 1H), 10.29 (bs, 1H), 8.54 (d, J = 4.4 Hz, 1H), 7.79-7.75 (m, 1H), 7.65 (d, J = 1.4 Hz, 1H), 7.55 (t, J = 7.8 Hz, 1H), 7.48 (d, J = 7.9 Hz, 1H), 7.36-7.30 (m, 2H), 6.82 (s, 1H), 6.45 (s, 1H), 5.25-5.20 (m, 1H), 2.37-2.32 (m, 2H), 2.20-2.03 (m, 4H), 1.50 (d, J = 6.3 Hz, 3H); LC-MS: m/z 502.1 (M + H)⁺. |

| No. | Structure | Characterization data<br>¹H NMR (400 MHz, DMSO-d$_6$)/LC-MS: |
|---|---|---|
| 157 | 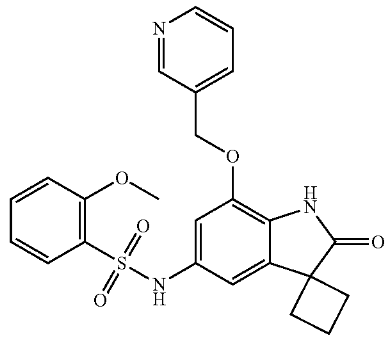 [SMILES: COc1ccccc1S(=O)(=O)Nc1cc(OCc2cccnc2)c2c(c1)C1(CCC1)C(=O)N2] | ¹H NMR (400 MHz, DMSO-d$_6$): δ 10.30 (s, 1H), 9.66 (s, 1H), 8.68 (s, 1H), 8.54 (d, J = 3.5 Hz, 1H), 7.87 (d, J = 7.9 Hz, 1H), 7.67 (d, J = 1.5 Hz, 1H), 7.55-7.51 (m, 1H), 7.41-7.38 (m, 1H), 7.14 (d, J = 8.3 Hz, 1H), 6.97 (t, J = 7.8 Hz, 1H), 6.84 (d, J = 1.0 Hz, 1H), 6.73 (d, J = 1.4 Hz, 1H), 5.04 (s, 2H), 3.89 (s, 3H), 2.36-2.32 (m, 2H), 2.18-2.14 (m, 1H), 2.08-2.00 (m, 3H); LC-MS: m/z 466.2 (M + H)⁺. |
| 158 | 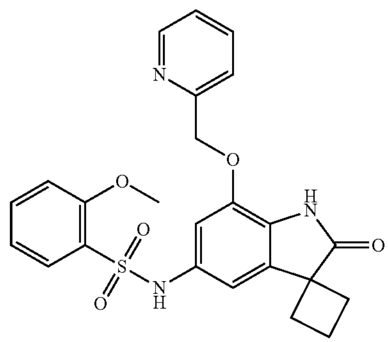 [SMILES: COc1ccccc1S(=O)(=O)Nc1cc(OCc2ccccn2)c2c(c1)C1(CCC1)C(=O)N2] | ¹H NMR (400 MHz, DMSO-d$_6$): δ 10.37 (s, 1H), 9.63 (s, 1H), 8.56 (d, J = 4.4 Hz, 1H), 7.83-7.79 (m, 1H), 7.64-7.61 (m, 2H), 7.54-7.49 (m, 1H), 7.36-7.34 (m, 1H), 7.11 (d, J = 8.3 Hz, 1H), 6.96 (t, J = 7.8 Hz, 1H), 6.88 (d, J = 1.5 Hz, 1H), 6.65 (d, J = 1.5 Hz, 1H), 5.03 (s, 2H), 3.87 (s, 3H), 2.38-2.32 (m, 2H), 2.19-2.03 (m, 4H); LC-MS: m/z 466.1 (M + H)⁺. |
| 159 | 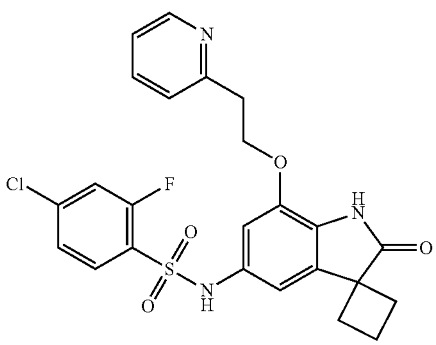 [SMILES: O=C1Nc2c(OCCc3ccccn3)cc(NS(=O)(=O)c3ccc(Cl)cc3F)cc2C12CCC2] | ¹H NMR (400 MHz, DMSO-d$_6$): δ 10.34 (s, 1H), 10.26 (s, 1H), 8.49 (d, J = 3.9 Hz, 1H), 7.76-7.69 (m, 1H), 7.41-7.35 (m, 3H), 7.25-7.21 (m, 2H), 6.82 (s, 1H), 6.60 (s, 1H), 4.20 (t, J = 6.8 Hz, 2H), 3.06 (t, J = 6.4 Hz, 2H), 2.38-2.33 (m, 2H), 2.21-2.04 (m, 4H); LCMS: m/z 501.9 (M + H)⁺. |
| 160 | 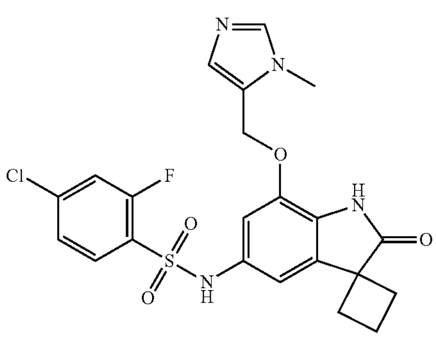 [SMILES: Cn1cncc1COc1cc(NS(=O)(=O)c2ccc(Cl)cc2F)cc2c1NC(=O)C21CCC1] | ¹H NMR (400 MHz, DMSO-d$_6$): δ 10.42 (s, 1H), 10.48 (s, 1H), 7.79-7.73 (m, 2H), 7.68 (s, 1H), 7.45-7.42 (m, 1H), 7.03 (s, 1H), 6.84 (d, J = 1.5 Hz, 1H), 6.78 (d, J = 1.5 Hz, 1H), 5.02 (s, 2H), 3.64 (s, 3H), 2.37-2.33 (m, 2H), 2.18-2.00 (m, 4H); LC-MS: m/z 490.9 (M + H)⁺. |

| No. | Structure | Characterization data<br>¹H NMR (400 MHz, DMSO-d$_6$)/LC-MS: |
|-----|-----------|------------------------------------------------|
| 161 | 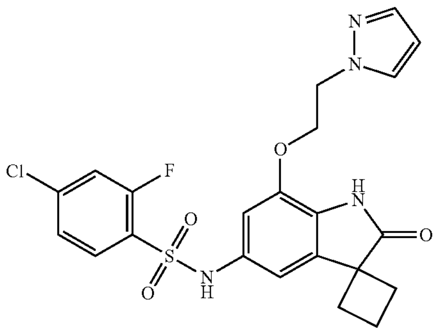 [SMILES: O=C1Nc2c(OCCn3cccn3)cc(NS(=O)(=O)c3ccc(Cl)cc3F)cc2C12CCC2] | ¹H NMR (400 MHz, DMSO-d$_6$): δ 10.83 (s, 1H), 10.32 (s, 1H), 7.95 (d, J = 1.9 Hz, 1H), 7.77-7.71 (m, 2H), 7.44-7.41 (m, 2H), 6.83 (d, J = 1.5 Hz, 1H), 6.56 (d, J = 1.5 Hz, 1H), 6.22 (d, J = 2.0 Hz, 1H), 4.43 (t, J = 4.9 Hz, 2H), 4.12 (t, J = 4.9 Hz, 2H), 2.37-2.33 (m, 2H), 2.18-2.03 (m, 4H); LC-MS: m/z 490.9 (M + H)⁺. |
| 162 | 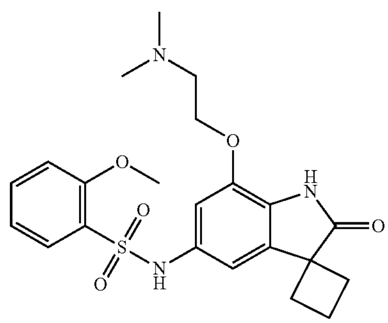 [SMILES: COc1ccccc1S(=O)(=O)Nc1cc(OCCN(C)C)c2c(c1)C1(CCC1)C(=O)N2] | ¹H NMR (400 MHz, DMSO-d$_6$): δ 10.14 (s, 1H), 9.62 (s, 1H), 7.70 (d, J = 7.8 Hz, 1H), 7.54 (t, J = 8.3 Hz, 1H), 7.16 (d, J = 8.3 Hz, 1H), 6.99 (t, J = 7.8 Hz, 1H), 6.85 (s, 1H), 6.59 (s, 1H), 3.92 (s, 3H), 3.91-3.90 (m, 2H), 2.57-2.54 (m, 2H), 2.39-2.32 (m, 2H), 2.19 (s, 6H), 2.16-2.10 (m, 1H), 2.08-1.99 (m, 3H); LC-MS: m/z 446.2 (M + H)⁺. |
| 163 | 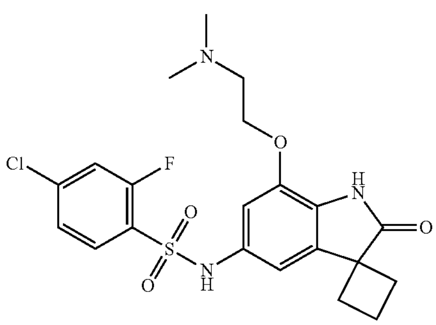 [SMILES: CN(C)CCOc1cc(NS(=O)(=O)c2ccc(Cl)cc2F)cc2c1NC(=O)C21CCC1] | ¹H NMR (400 MHz, DMSO-d$_6$): δ 10.23 (bs, 2H), 7.77-7.70 (m, 2H), 7.44-7.41 (m, 1H), 6.85 (d, J = 1.5 Hz, 1H), 6.57 (d, J = 1.4 Hz, 1H), 3.94 (t, J = 5.9 Hz, 2H), 2.56 (t, J = 5.8 Hz, 2H), 2.37-2.35 (m, 2H), 2.20 (s, 6H), 2.20-2.07 (m, 4H); LC-MS: m/z 467.9 (M + H)⁺. |
| 164 | 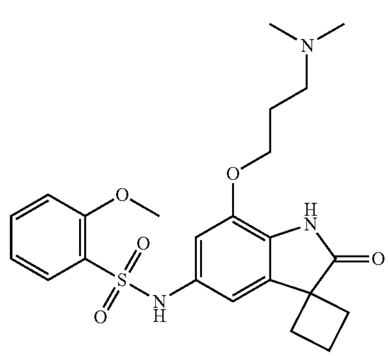 [SMILES: COc1ccccc1S(=O)(=O)Nc1cc(OCCCN(C)C)c2c(c1)C1(CCC1)C(=O)N2] | ¹H NMR (400 MHz, DMSO-d$_6$): δ 10.29 (bs, 1H), 9.66 (bs, 1H), 7.68 (d, J = 7.3 Hz, 1H), 7.55 (t, J = 7.4 Hz, 1H), 7.16 (d, J = 8.4 Hz, 1H), 6.99 (t, J = 7.3 Hz, 1H), 6.84 (s, 1H), 6.59 (s, 1H), 3.92 (s, 3H), 3.87-3.84 (m, 2H), 2.67-2.59 (m, 2H), 2.34-2.21 (m, 8H), 2.18-2.01 (m, 4H), 1.91-1.83 (m, 2H); LC-MS: m/z 460.2 (M + H)⁺. |

| No. | Structure | Characterization data<br>¹H NMR (400 MHz, DMSO-$d_6$)/LC-MS: |
|---|---|---|
| 165 | 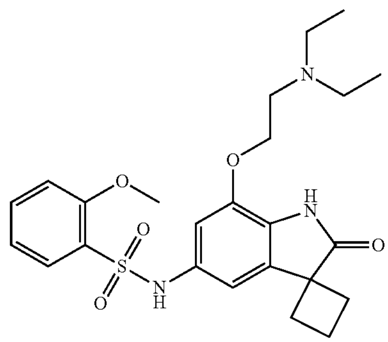 [SMILES: CCN(CC)CCOc1cc(NS(=O)(=O)c2ccccc2OC)cc2c1NC(=O)C21CCC1] | ¹H NMR (400 MHz, DMSO-$d_6$): δ 10.21 (bs, 1H), 9.66 (bs, 1H), 7.70 (d, J = 7.8 Hz, 1H), 7.55 (t, J = 7.9 Hz, 1H), 7.17 (d, J = 8.3 Hz, 1H), 6.99 (t, J = 7.8 Hz, 1H), 6.85 (s, 1H), 6.60 (bs, 1H), 3.92 (s, 3H), 3.86-3.84 (m, 2H), 2.67-2.56 (m, 6H), 2.35-2.33 (m, 2H), 2.18-2.01 (m, 4H), 1.09-1.08 (m, 6H); LC-MS: m/z 474.3 (M + H)⁺. |
| 166 | 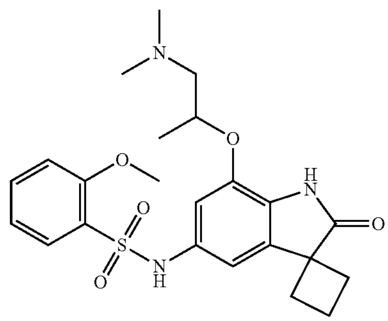 [SMILES: COc1ccccc1S(=O)(=O)Nc1cc(OC(C)CN(C)C)c2c(c1)C1(CCC1)C(=O)N2] | ¹H NMR (400 MHz, DMSO-$d_6$): δ 10.19 (s, 1H), 9.67 (s, 1H), 7.71-7.68 (m, 1H), 7.57-7.53 (m, 1H), 7.17 (d, J = 8.3 Hz, 1H), 7.00 (t, J = 7.3 Hz, 1H), 6.84 (d, J = 1.4 Hz, 1H), 6.60 (s, 1H), 3.92 (s, 3H), 3.78-3.75 (m, 1H), 2.48-2.19 (m, 10H), 2.17-1.99 (m, 4H), 1.10 (d, J = 5.9 Hz, 3H); LCMS: m/z 460.2 (M + H)⁺. |
| 166.1 | 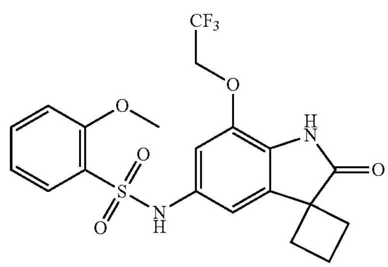 [SMILES: COc1ccccc1S(=O)(=O)Nc1cc(OCC(F)(F)F)c2c(c1)C1(CCC1)C(=O)N2] | ¹H NMR (400 MHz, DMSO-$d_6$): δ 10.34 (s, 1H), 9.71 (s, 1H), 7.72-7.69 (m, 1H), 7.57-7.53 (m, 1H), 7.17 (d, J = 7.9 Hz, 1H), 6.99 (t, J = 7.4 Hz, 1H), 6.93 (d, J = 1.4 Hz, 1H), 6.71 (d, J = 1.5 Hz, 1H), 4.56 (q, J = 8.8 Hz, 2H), 3.92 (s, 3H), 2.40-2.34 (m, 2H), 2.21-1.99 (m, 4H); LCMS: m/z 456.9 (M + H)⁺. |
| 166.2 | 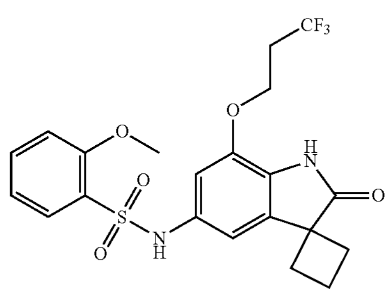 [SMILES: COc1ccccc1S(=O)(=O)Nc1cc(OCCC(F)(F)F)c2c(c1)C1(CCC1)C(=O)N2] | ¹H NMR (400 MHz, DMSO-$d_6$): δ 10.15 (s, 1H), 9.65 (s, 1H), 7.70 (dd, J = 7.8 Hz, & 1.5 Hz, 1H), 7.57-7.52 (m, 1H), 7.16 (d, J = 8.3 Hz, 1H), 6.99 (t, J = 7.8 Hz, 1H), 6.89 (d, J = 0.9 Hz, 1H), 6.62 (d, J = 1.4 Hz, 1H), 4.05 (t, J = 6.1 Hz, 2H), 3.92 (s, 3H), 2.69-2.63 (m, 2H), 2.37-2.33 (m, 2H), 2.17-2.02 (m, 4H); LC-MS: m/z 470.9 (M + H)⁺. |
| 167 | 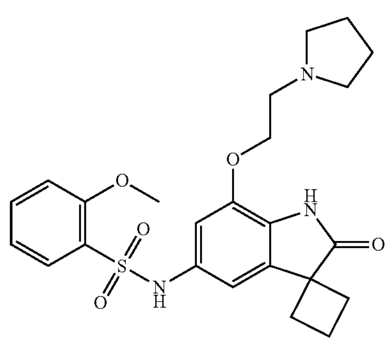 [SMILES: COc1ccccc1S(=O)(=O)Nc1cc(OCCN2CCCC2)c2c(c1)C1(CCC1)C(=O)N2] | ¹H NMR (400 MHz, DMSO-$d_6$): δ 10.18 (s, 1H), 9.68 (s, 1H), 7.70-7.68 (m, 1H), 7.56-7.51 (m, 1H), 7.15 (d, J = 8.3 Hz, 1H), 6.98 (t, J = 7.8 Hz, 1H), 6.84 (d, J = 1.5 Hz, 1H), 6.61 (s, 1H), 4.00-3.99 (m, 2H), 3.91 (s, 3H), 2.88-2.46 (m, 6H), 2.38-2.34 (m, 2H), 2.32-2.02 (m, 4H), 1.81-1.75 (m, 4H); LCMS: m/z 472.2 (M + H)⁺. |

-continued

| No. | Structure | Characterization data<br>$^1$H NMR (400 MHz, DMSO-$d_6$)/LC-MS: |
|---|---|---|
| 168 | 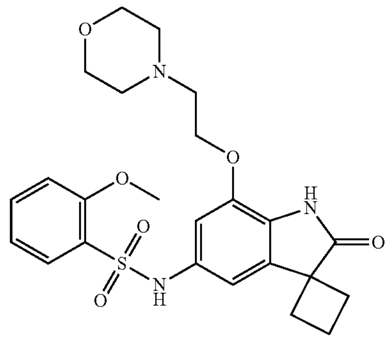 [SMILES: COc1ccccc1S(=O)(=O)Nc1cc(OCCN2CCOCC2)c2c(c1)C1(CCC1)C(=O)N2] | $^1$H NMR (400 MHz, DMSO-$d_6$): δ 10.15 (s, 1H), 9.63 (s, 1H), 7.71-7.69 (m, 1H), 7.56-7.52 (m, 1H), 7.17 (d, J = 7.6 Hz, 1H), 6.99 (t, J = 7.8 Hz, 1H), 6.85 (d, J = 1.4 Hz, 1H), 6.60 (d, J = 1.5 Hz, 1H), 3.96-3.94 (m, 2H), 3.92 (s, 3H), 3.53-3.51 (m, 4H), 2.60-2.57 (m, 2H), 2.40-2.32 (m, 6H), 2.18-2.13 (m, 1H), 2.08-1.99 (m, 3H); LC-MS: m/z 488.2 (M + H)$^+$. |
| 169 | 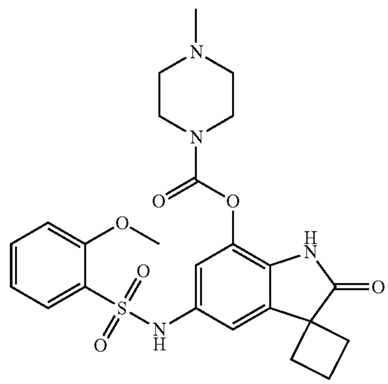 [SMILES: COc1ccccc1S(=O)(=O)Nc1cc(OC(=O)N2CCN(C)CC2)c2c(c1)C1(CCC1)C(=O)N2] | $^1$H NMR (400 MHz, DMSO-$d_6$): δ 10.49 (s, 1H), 9.79 (s, 1H), 7.72 (dd, J = 7.6 Hz, & 1.0 Hz, 1H), 7.66-7.53 (m, 1H), 7.16 (d, J = 8.8 Hz, 1H), 7.09 (d, J = 1.2 Hz, 1H), 7.03-6.99 (m, 1H), 6.67 (d, J = 1.2 Hz, 1H), 3.88 (s, 3H), 3.50-3.40 (m, 2H), 3.35-3.32 (m, 2H), 2.40-2.34 (m, 6H), 2.21 (s, 3H), 2.19-2.15 (m, 1H), 2.16-2.07 (m, 3H); LC-MS: m/z 501.2 (M + H)$^+$. |
| 170 | 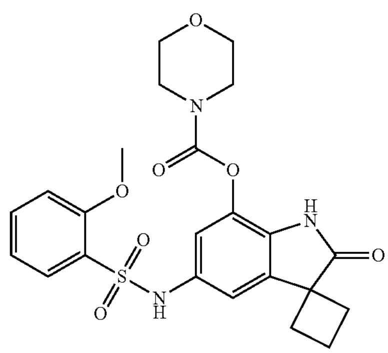 [SMILES: COc1ccccc1S(=O)(=O)Nc1cc(OC(=O)N2CCOCC2)c2c(c1)C1(CCC1)C(=O)N2] | $^1$H NMR (400 MHz, DMSO-$d_6$): δ 10.48 (s, 1H), 9.85-9.78 (bs, 1H), 7.73-7.71 (m, 1H), 7.55-7.53 (m, 1H), 7.16 (d, J = 8.3 Hz, 1H), 7.09 (d, J = 1.5 Hz, 1H), 7.00 (t, J = 7.3 Hz, 1H), 6.69 (d, J = 1.5 Hz, 1H), 3.88 (s, 3H), 3.64-3.62 (m, 4H), 3.48-3.51 (m, 2H), 2.45-2.7 (m, 8H); LCMS: m/z 486.1 (M − H)$^−$. |

Example-XL: 2,4-Difluoro-N-(1-methylpiperidin-4-yl)oxy-2'-oxospiro-[cyclobutane-1,3'-indolin]-5'-yl)benzenesulfonamide (Compound-171)

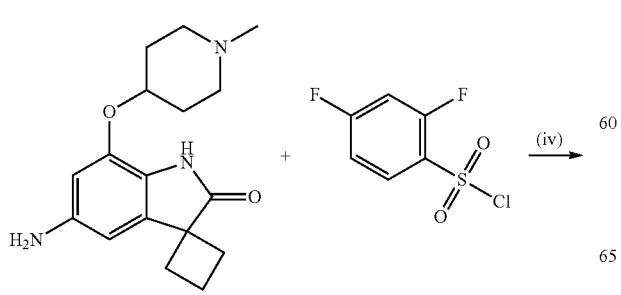

-continued

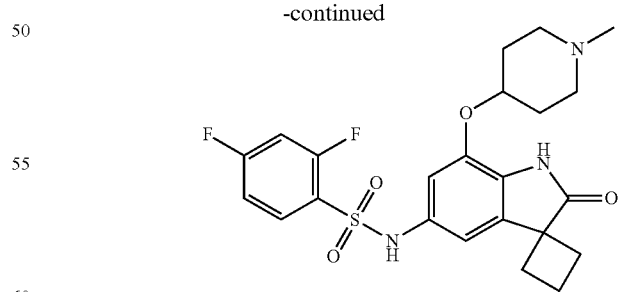

The process of this was adopted from step-i of Example-XXXIX. $^1$H NMR (400 MHz, DMSO-$d_6$): δ 10.41 (s, 1H), 10.32-10.31 (bs, 1H), 7.85-7.79 (m, 1H), 7.59-7.53 (m, 1H), 7.26-7.21 (m, 1H), 6.85 (d, J=0.9 Hz, 1H), 6.65 (s, 1H), 4.50-4.48 (m, 1H), 3.18-3.04 (m, 4H), 2.66 (s, 3H), 2.40-2.25 (m, 2H), 2.21-1.91 (m, 6H), 1.81-1.78 (m, 2H); LCMS: m/z 478.2 (M+H)$^+$.

The below compounds were prepared by procedure similar to the one described in Example-XL with appropriate variations in reactants, quantities of reagents and reaction conditions. The physiochemical characteristics of the compounds are also summarized.

Step-i: 4-Chloro-N-(7'-((4,4-difluorocyclohexyl)oxy)-1'-(4-methoxybenzyl)-2'-oxospiro[cyclobutane-1,3'-indolin]-5'-yl)-2-fluorobenzenesulfonamide The process of this was adopted from step-i of Example-XXXIX. LCMS: m/z 635.2 (M+H)+.

| No | Structure | Characterization Data<br>¹H NMR (400 MHz, DMSO-d₆)/LC-MS: |
|---|---|---|
| 172 | 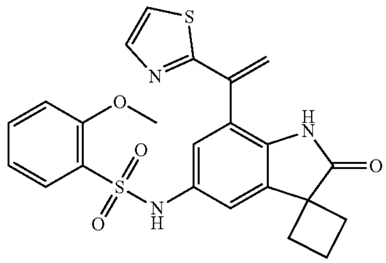 [SMILES: C=C(c1nccs1)c1cc(NS(=O)(=O)c2ccccc2OC)cc2c1NC(=O)C21CCC1] | ¹H NMR (400 MHz, DMSO-d₆): δ 10.03 (s, 1H), 9.71 (s, 1H), 7.82 (d, J = 2.8 Hz, 1H), 7.71-7.54 (m, 3H), 7.29 (d, J = 2.0 Hz, 1H), 7.16 (d, J = 8.4 Hz, 1H), 7.00 (t, J = 7.4 Hz, 1H), 6.77 (d, J = 2.0 Hz, 1H), 6.20 (s, 1H), 5.35 (s, 1H), 3.86 (s, 3H), 2.42-2.39 (m, 2H), 2.20-2.10 (m, 4H); LCMS: m/z 468.1 (M + H)+. |
| 173 & 174 | 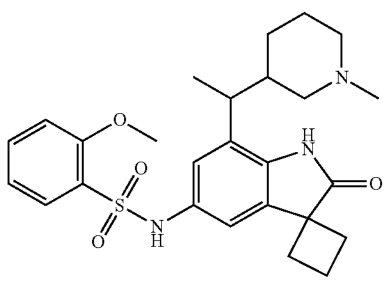 [SMILES: COc1ccccc1S(=O)(=O)Nc1cc(C(C)C2CCCN(C)C2)c2c(c1)C1(CCC1)C(=O)N2] | Isomer-I: ¹H NMR (400 MHz, DMSO-d₆): δ 10.12-10.10 (bs, 1H), 9.52-9.50 (bs, 1H), 7.65-7.63 (m, 1H), 7.54-7.49 (m, 1H), 7.15-7.09 (m, 1H), 7.07 (d, J = 1.4 Hz, 1H), 6.97-6.93 (m, 1H), 6.68 (d, J = 1.5 Hz, 1H), 3.92 (s, 3H), 2.60-1.97 (m, 12H), 1.67-1.23 (m, 7H), 0.96-0.94 (m, 3H); LCMS: m/z 484.2 (M + H)+.<br>Isomer-II: ¹H NMR (400 MHz, DMSO-d₆): δ 10.12-10.10 (bs, 1H), 9.52-9.50 (bs, 1H), 7.62 (d, J = 7.8 Hz, 1H), 7.51 (t, J = 6.8 Hz, 1H), 7.14 (d, J = 8.3 Hz, 1H), 7.08(s, 1H), 6.94 (t, J = 7.3 Hz, 1H), 6.65 (d, J = 1.4 Hz, 1H), 3.92 (s, 3H), 2.78-1.97 (m, 12H), 1.62-1.24 (m, 7H), 0.96 (d, J = 6.9 Hz, 3H); LCMS: m/z 484.3 (M + H)+. |

Example-XLI: 4-Chloro-N-(7'-((4,4-difluorocyclohexyl)oxy)-2'-oxospiro [cyclobutane-1,3'-indolin]-5'-yl)-2-fluorobenzenesulfonamide (Compound-175) & 4-chloro-2-fluoro-N-(2'-oxo-7'-((4-oxocyclohexyl)oxy)spiro [cyclobutane-1,3'-indolin]-5'-yl)benzenesulfonamide (Compound-176)

Step-ii: 4-Chloro-N-(7'-((4,4-difluorocyclohexyl)oxy)-2'-oxospiro[cyclobutane-1,3'-indolin]-5'-yl)-2-fluorobenzenesulfonamide The process of this was adopted from step-ii of Example-XXXIX.

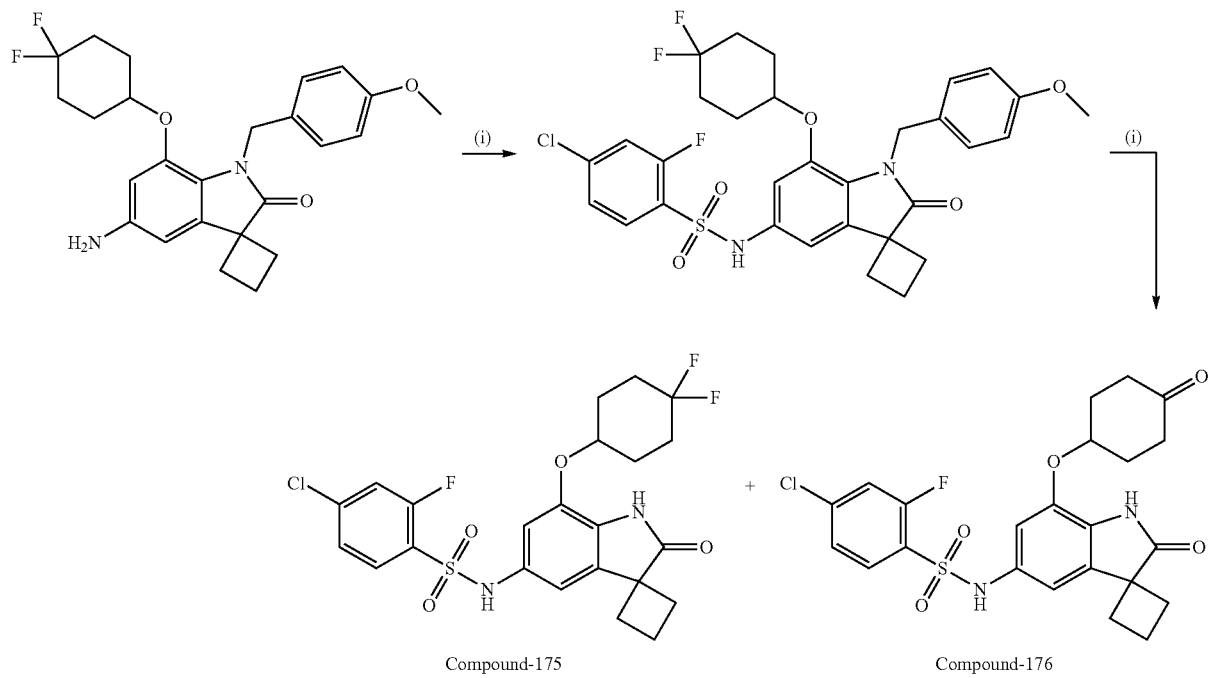

Compound-175          Compound-176

Compound-175: ¹H NMR (400 MHz, DMSO-d₆): δ 10.42 (s, 1H), 10.32 (s, 1H), 7.77-7.71 (m, 2H), 7.45-7.43 (m, 1H), 6.86 (s, 1H), 6.57 (s, 1H), 4.39-4.38 (m, 1H), 2.39-2.37 (m, 2H), 2.19-2.04 (m, 6H), 1.87-1.73 (m, 6H); LC-MS: m/z 515.1 (M+H)⁺.

Compound-176: ¹H NMR (400 MHz, DMSO-d₆): δ 10.39 (s, 1H), 10.33 (s, 1H), 7.75-7.71 (m, 2H), 7.45-7.43 (m, 1H), 6.87 (s, 1H), 6.64 (s, 1H), 4.56 (bs, 1H), 2.67-2.54 (m, 2H), 2.40-2.33 (m, 2H), 2.19-2.09 (m, 6H), 2.06-1.93 (m, 4H); LC-MS: m/z 493.1 (M+H)⁺.

Example-XLII: 2-Methoxy-N-(2'-oxo-7'-(1-(thiazol-2-yl)ethyl)spiro[cyclobutane-1,3'-indolin]-5'-yl)benzenesulfonamide (Compound-177)

To a solution of 2-methoxy-N-(2'-oxo-7'-(1-(thiazol-2-yl)vinyl)spiro[cyclobutane-1,3'-indolin]-5'-yl)benzenesulfonamide(0.05 g, 0.11 mmol) in MeOH (2 mL) was added Palladium hydroxide (0.02g) followed by stirring under hydrogen bladder pressure at RT for 16 h. The mixture was filtered through celite bed and washed with EtOAc. The organic layer was concentrated under reduced pressure and purified by combi-flash to afford the title compound as an off white solid (0.01 g, 20%). ¹H NMR (400 MHz, DMSO-d₆): δ 10.40 (s, 1H), 9.54 (s, 1H), 7.72 (d, J=3.2 Hz, 1H), 7.58-7.49 (m, 3H), 7.15 (s, 1H), 7.09 (d, J=8.4 Hz, 1H), 6.97 (t, J=7.6 Hz, 1H), 6.70 (s, 1H), 4.58-4.54 (m, 1H), 3.82 (s, 3H), 2.38-2.33 (m, 2H), 2.21-2.04 (m, 4H), 1.46 (d, J=6.8 Hz, 3H); LCMS: m/z 470.1 (M+H)⁺.

Example-XLIII: 2-Methoxy—N-methyl-N-(7'-((1-methylpipefidin-4-yl)oxy)-2'-oxospiro[cyclobutane-1,3'-indolin]-5'-yl)benzenesulfonamide (Compound-178)

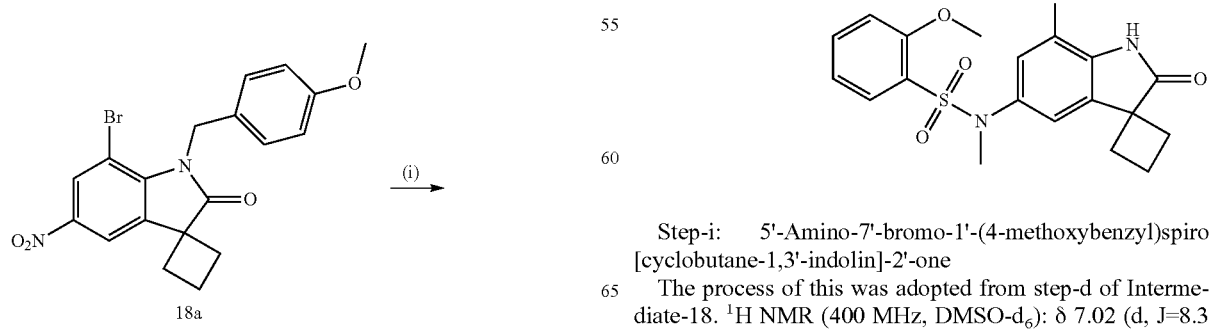

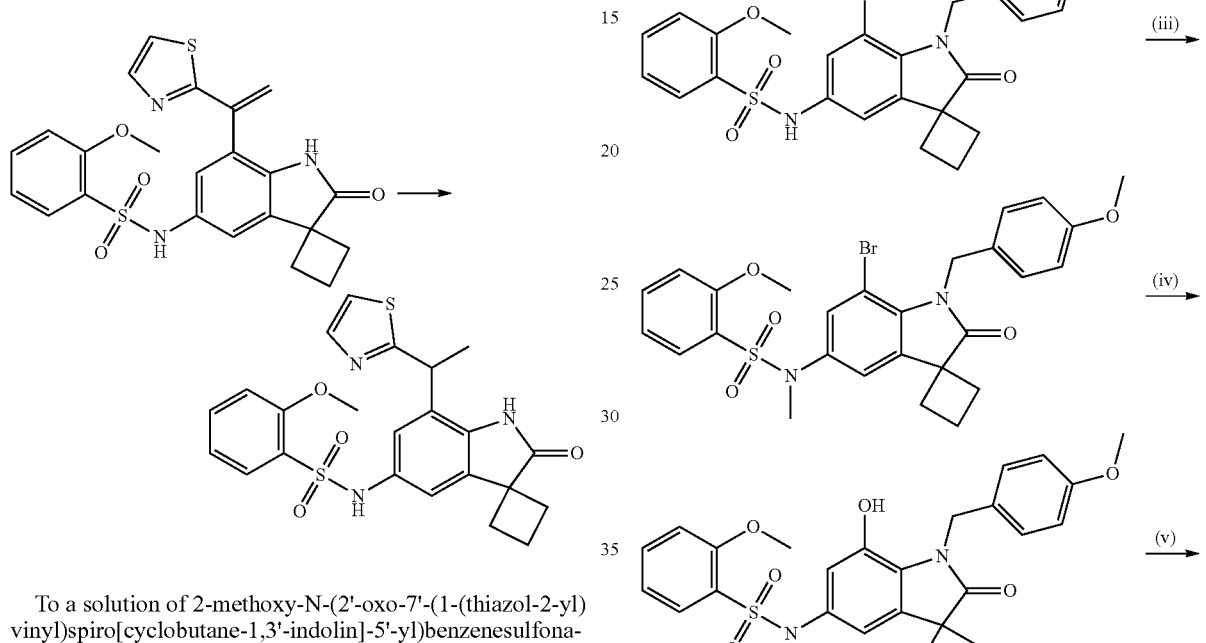

Step-i: 5'-Amino-7'-bromo-1'-(4-methoxybenzyl)spiro[cyclobutane-1,3'-indolin]-2'-one The process of this was adopted from step-d of Intermediate-18. ¹H NMR (400 MHz, DMSO-d₆): δ 7.02 (d, J=8.3 Hz, 2H), 6.93 (d, J=1.9 Hz, 1H), 6.85 (d, J=8.4 Hz, 2H), 6.55

(d, J=1.9 Hz, 1H), 5.10 (s, 2H), 5.08 (s, 2H), 3.70 (s, 3H), 2.53-2.46 (m, 2H), 2.33-2.12 (m, 4H); LC-MS: m/z 389.1 (M+2H)$^{2+}$.

Step-ii: N-(7'-bromo-1'-(4-methoxybenzyl)-2'-oxospiro[cyclobutane-1,3'-indolin]-5'-yl)-2-methoxybenzenesulfonamide The process of this was adopted from step-i of Example-XXXIX. $^1$H NMR (400 MHz, DMSO-d$_6$): δ 10.01 (s, 1H), 7.79-7.76 (m, 1H), 7.60-7.55 (m, 1H), 7.36 (d, J=2.0 Hz, 1H), 7.18 (d, J=8.4 Hz, 1H), 7.06-7.01 (m, 2H), 6.97 (d, J=8.8 Hz, 2H), 6.86 (d, J=8.8 Hz, 2H), 5.07 (s, 2H), 3.87 (s, 3H), 3.68 (s, 3H), 2.50-2.43 (m, 2H), 2.26-1.98 (m, 4H); LC-MS: m/z 559.1 (M+2H).

Step-iii: N-(7'-bromo-1'-(4-methoxybenzyl)-2'-oxospiro[cyclobutane-1,3'-indolin]-5'-yl)-2-methoxy—N-methylbenzenesulfonamide To a cold solution of N-(7'-bromo-1'-(4-methoxybenzyl)-2'-oxospiro[cyclobutane-1,3'-indolin]-5'-yl)-2-methoxybenzenesulfonamide (1.0 g, 1.79 mmol) in ACN (10 mL) was added K$_2$CO$_3$ (0.74 g, 5.38 mmol) and methyl iodide (0.22 mL, 3.58 mmol) followed by stirring at RT for 1 h. The mixture was poured into water and extracted with EtOAc. The organic layer dried over Na$_2$SO$_4$, concentrated under reduced pressure and purified by combi-flash to afford the title compound as an off white solid (1.0 g, 98%). $^1$H NMR (400 MHz, DMSO-d$_6$): δ 7.66-7.61 (m, 2H), 7.44 (d, J=1.9 Hz, 1H), 7.24 (d, J=7.8 Hz, 1H), 7.14 (d, J=1.9 Hz, 1H), 7.05 (t, J=7.3 Hz, 1H), 7.01 (d, J=8.3 Hz, 2H), 6.86 (d, J=8.8 Hz, 2H), 5.14 (s, 2H), 3.74 (s, 3H), 3.70 (s, 3H), 3.25 (s, 3H), 2.45-2.41 (m, 2H), 2.33-2.28 (m, 3H), 2.09-2.07 (m, 1H); LC-MS: m/z 571.1 (M+H)$^+$.

Step-iv: N-(7'-hydroxy-1'-(4-methoxybenzyl)-2'-oxospiro[cyclobutane-1,3'-indolin]-5'-yl)-2-methoxy—N-methylbenzenesulfonamide To a solution of N-(7'-bromo-1'-(4-methoxybenzyl)-2'-oxospiro[cyclobutane-1,3'-indolin]-5'-yl)-2-methoxy—N-methylbenzenesulfonamide (1.0 g, 1.74 mmol) in 1,4-dioxane (25 mL) and H$_2$O (10 mL) was added KOH (0.3 g, 5.24 mmol) followed by degassing with nitrogen purging for 20 min. Then $^t$BuXPhos (0.075 g, 0.17 mmol) and Pd$_2$(dba)$_3$ were added again followed by degassing with nitrogen purging for 20 min. Then the mixture was heated at 100° C. for 16 h. The mixture was concentrated under reduced pressure and the residue was diluted with EtOAc (100 ml), washed with water (100 mL) and brine (100 mL), dried over sodium sulphate and concentrated under reduced pressure and purified by combi-flash to afford the title compound as pale brown solid (0.7 g, 79%). $^1$H NMR (400 MHz, DMSO-d$_6$): δ 9.83 (s, 1H), 7.62-7.56 (m, 2H), 7.24 (d, J=8.3 Hz, 1H), 7.14 (d, J=8.8 Hz, 2H), 7.00 (t, J=7.9 Hz, 1H), 6.83 (d, J=8.8 Hz, 2H), 6.75 (d, J=1.9 Hz, 1H), 6.59 (d, J=1.9 Hz, 1H), 4.93 (s, 2H), 3.83 (s, 3H), 3.69 (s, 3H), 3.25 (s, 3H), 2.37-2.33 (m, 2H), 2.18-1.98 (m, 4H); LC-MS: m/z 509.2 (M+H)$^+$.

Step-v: 2-Methoxy-N-(1'-(4-methoxybenzyl)-7'-((1-methylpiperidin-4-yl)oxy)-2'-oxospiro[cyclobutane-1,3'-indolin]-5'-yl)—N-methylbenzenesulfonamide The process of this was adopted from step-c of Intermediate-18. $^1$H NMR (400 MHz, DMSO-d$_6$): δ 7.61-7.56 (m, 2H), 7.25 (d, J=7.9 Hz, 1H), 7.02-6.98 (m, 4H), 6.83 (d, J=8.3 Hz, 2H), 6.55 (d, J=1.5 Hz, 1H), 4.97 (s, 2H), 4.09 (bs, 1H), 3.85 (s, 3H), 3.68 (s, 3H), 3.31 (s, 3H), 2.41-2.37 (m, 4H), 2.22-2.18 (m, 3H), 2.11-2.03 (m, 6H), 1.64-1.61 (m, 2H), 1.36-1.31 (m, 2H); LC-MS: m/z 606.3 (M+H)$^+$.

Step-vi: 2-Methoxy—N-methyl-N-(7'-((1-methylpiperidin-4-yl)oxy)-2'-oxo spiro[cyclobutane-1,3'-indolin]-5'-yl)benzenesulfonamide The process of this was adopted from step-ii of Example-XXXIX. $^1$H NMR (400 MHz, DMSO-d$_6$): δ 10.27 (s, 1H), 7.62-7.58 (m, 1H), 7.55-7.52 (m, 1H), 7.26 (d, J=8.3 Hz, 1H), 6.98 (t, J=7.3 Hz, 1H), 6.91 (s, 1H), 6.56 (s, 1H), 4.11 (bs, 1H), 3.90 (s, 3H), 3.32 (s, 3H), 2.75-2.67 (m, 2H), 2.36-2.00 (m, 11H), 1.75-1.72 (m, 2H), 1.57-1.51 (m, 2H); LC-MS: m/z 486.2 (M+H)$^+$.

The below compounds were prepared by procedure similar to the one described in Example-XLIII with appropriate variations in reactants, quantities of reagents and reaction conditions. The physiochemical characteristics of the compounds are also summarized.

| No | Structure | Characterization Data $^1$H NMR (400 MHz, DMSO-d$_6$)/LC-MS: |
|---|---|---|
| 179 | 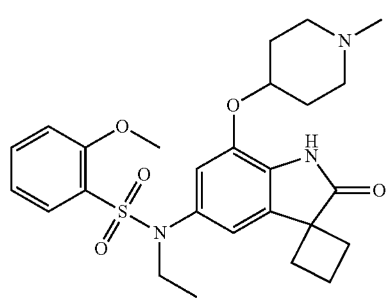 [SMILES: CCN(c1cc(OC2CCN(C)CC2)c2c(c1)C1(CCC1)C(=O)N2)S(=O)(=O)c1ccccc1OC] | $^1$H NMR (400 MHz, DMSO-d$_6$): δ 10.34 (s, 1H), 7.60 (t, J = 7.3 Hz, 1H), 7.48 (d, J = 7.9 Hz, 1H), 7.29 (d, J = 8.3 Hz, 1H), 6.95 (t, J = 7.3 Hz, 1H), 6.82 (s, 1H), 6.49 (s, 1H), 4.20 (bs, 1H), 3.96 (s, 3H), 3.83-3.78 (m, 2H), 2.86-2.78 (m, 2H), 2.42-2.32 (m, 6H), 2.16-1.99 (m, 5H), 1.81-1.73 (m, 2H), 1.63-1.57 (m, 2H), 1.05 (t, J = 7.3 Hz, 3H); LC-MS: m/z 500.3 (M + H)$^+$. |
| 180 | 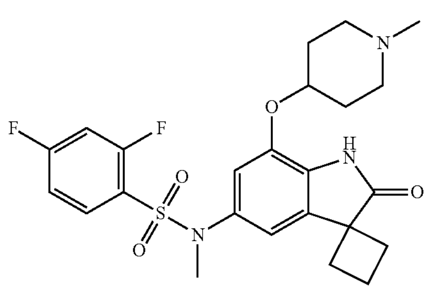 [SMILES: CN1CCC(Oc2cc(N(C)S(=O)(=O)c3ccc(F)cc3F)cc3c2NC(=O)C32CCC2)CC1] | $^1$H NMR (400 MHz, DMSO-d$_6$): δ 10.37 (s, 1H), 7.64-7.58 (m, 2H), 7.26-7.21 (m, 1H), 6.95 (d, J = 1.5 Hz, 1H), 6.64 (d, J = 1.5 Hz, 1H), 4.20 (bs, 1H), 3.25 (s, 3H), 2.69-2.55 (m, 2H), 2.39-2.32 (m, 2H), 2.23-1.99 (m, 9H), 1.77-1.74 (m, 2H), 1.59-1.57 (m, 2H); LC-MS: m/z 492.2 (M + H)$^+$. |

Example-XLIV: 5'-(((2-Methoxyphenyl)(methyl)(oxo)-l6-sulfanylidene) amino)-7'-nitrospiro[cyclobutane-1,3'-indolin]-2'-one (Compound-181)

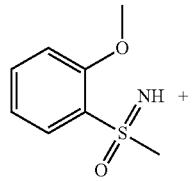

+

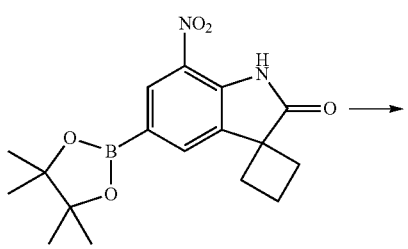

→

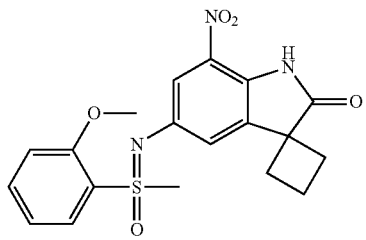

To a solution of imino(2-methoxyphenyl)(methyl)-l6-sulfanone (0.1 g, 0.54 mmol) and 7'-nitro-5'-(4,4,5,5-tetramethyl-1,3,2-dioxaborolan-2-yl)spiro[cyclobutane-1,3'-indolin]-2'-one (0.37 g, 1.08 mmol) in MeOH (3 mL) was added copper (II) acetate (0.01 g, 0.05 mmol) followed by stirring at RT for 16 h. The mixture was diluted with EtOAc and washed with water. The organic layer was dried over sodium sulphate and concentrated under reduced pressure. The residue was purified using combi-flash to afford the title compound as a yellow solid (0.15 g, 69%). $^1$H NMR (400 MHz, DMSO-d$_6$): δ 10.67 (s, 1H), 7.92 (d, J=7.3 Hz, 1H), 7.63 (t, J=7.5 Hz,1H), 7.39 (s, 1H), 7.26-7.22 (m, 2H), 7.16-7.12 (m, 1H), 3.92 (s, 3H), 3.49 (s, 3H), 2.48-2.32 (m, 2H), 2.21-2.16 (m, 4H); LCMS: m/z 402.1 (M+H)$^+$.

Example-XLV: 7'-Amino-5'-(((2-methoxyphenyl)(methyl)(oxo)-l6-sulfanylidene)amino)spiro[cyclobutane-1,3'-indolin]-2'-one (Compound-182)

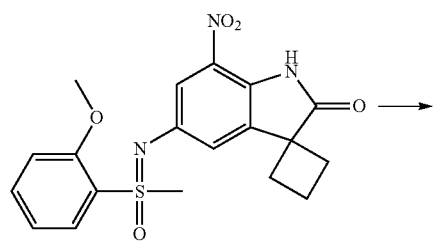

→

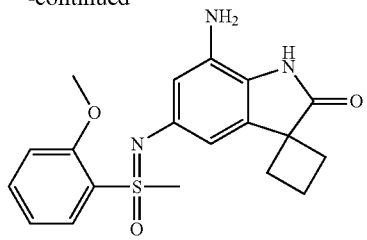

The process of this was adopted from step-d of Intermediate-18. $^1$H NMR (400 MHz, DMSO-d$_6$): δ 9.47 (s, 1H), 7.84 (dd, J=7.9, 1.4 Hz, 1H), 7.61-7.57 (m, 1H), 7.21 (d, J=8.3 Hz, 1H), 7.09 (t, J=7.6 Hz, 1H), 6.27 (d, J=1.9 Hz, 1H), 6.06 (d, J=1.9 Hz, 1H), 4.62 (s, 2H), 3.93 (s, 3H), 3.33 (s, 3H), 2.33-2.29 (m, 2H), 2.18-1.98 (m, 4H); LCMS: m/z 372.2 (M+H)$^+$.

Example-XLVI: 5'-(((2-Methoxyphenyl)(methyl)(oxo)-l6-sulfanylidene) amino)-7'-((1-methylpiperidin-4-yl)amino)spiro[cyclobutane-1,3'-indolin]-2'-one (Compound-183)

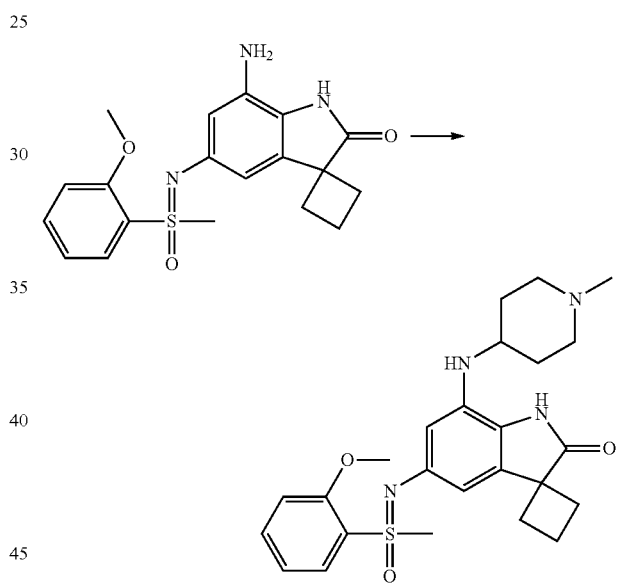

To a solution of 7'-amino-5'-(((2-methoxyphenyl)(methyl)(oxo)-l6-sulfanylidene) amino)spiro[cyclobutane-1,3'-indolin]-2'-one (0.1 g, 0.27 mmol) in THF (2 mL) was added 1-methylpiperidine-4-one (0.05 mL, 0.59 mmol) and titanium isopropoxide (1 mL) followed by stirring at RT for 16 h. The mixture was cooled to 0° C. and MeOH (3 mL) was added followed by sodium borohydride (0.02 g, 0.54 mmol). The mixture was stirred at RT for 1 h. The reaction mixture was quenched with aqueous ammonia and extracted with EtOAc. The organic layer was dried over sodium sulphate and concentrated under reduced pressure. The residue was purified by combi-flash to afford the title compound as an off white solid (0.02 g, 16%). $^1$H NMR (400 MHz, DMSO-d$_6$): δ 9.52 (s, 1H), 7.84 (dd, J=7.9, 1.4 Hz, 1H), 7.61-7.57 (m, 1H), 7.21 (d, J=8.3 Hz, 1H), 7.09 (t, J=7.6 Hz,1H), 6.30 (d, J=1.5 Hz, 1H), 5.90 (s, 1H), 4.44 (d, J=7.3, 1H), 3.91 (s, 3H), 3.36 (s, 3H), 2.98-2.95 (m, 1H), 2.78-2.62 (m, 2H), 2.45-1.98 (m, 13H), 1.78-1.65 (m, 2H); LCMS: m/z 469.2 (M+H)$^+$.

Example-XLVII: 2-Isopropoxy-N-(7'-((1-methylpiperidin-4-yl)oxy)-2'-oxo spiro[cyclobutane-1,3'-indolin]-5'-yl)benzenesulfonamide (Compound-184)

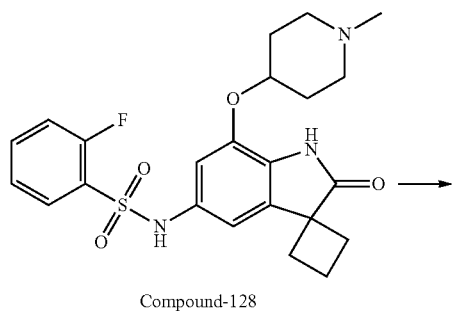

Compound-128

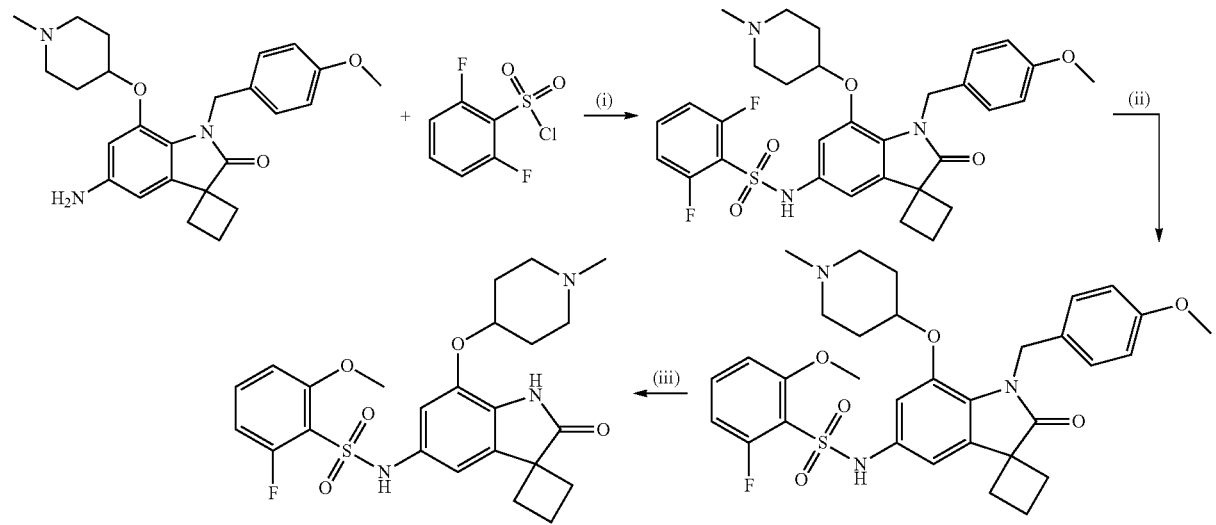

-continued

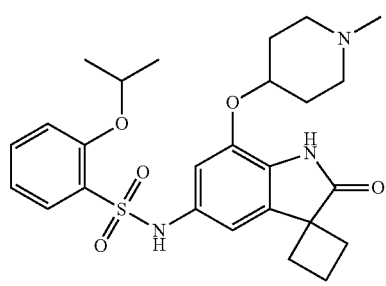

In a sealed tube, to a cold solution of 2-fluoro-N-(7'-((1-methylpiperidin-4-yl)oxy)-2'-oxospiro[cyclobutane-1,3'-indolin]-5'-yebenzenesulfonamide (0.075 g, 0.16 mmol, compound-128) in IPA (5 mL) was added sodium metal (0.04 g, 1.63 mmol). The mixture was slowly heated to 80° C. to dissolve sodium metal, the tube was sealed, and the mixture was heated to 130° C. for 16 h. The mixture was slowly poured into ice water and extracted with EtOAc. The organic layer was dried over sodium sulphate and concentrated under reduced pressure. The residue was purified by combiflash to afford the title compound as an off white solid (0.012 g, 15%). $^1$H NMR (400 MHz, DMSO-d$_6$): δ 10.17 (s, 1H), 9.29 (s, 1H), 7.73-7.71 (m, 1H), 7.53-7.49 (m, 1H), 7.18 (d, J=8.3 Hz, 1H), 6.95 (t, J=7.8 Hz, 1H), 6.88 (d, J=1.0 Hz, 1H), 6.59 (s, 1H), 4.83-4.77 (m, 1H), 4.13 (bs, 1H), 2.91-2.73 (m, 2H), 2.37-2.32 (m, 6H), 2.21-2.04 (m, 5H), 1.87-1.72 (m, 2H), 1.67-1.58 (m, 2H), 1.33 (d, J=5.9 Hz, 6H); LC-MS: m/z 500.2 (M+H)$^+$.

Example-XLVIII: 2-Fluoro-6-methoxy-N-(7'-((1-methylpiperidin-4-yl)oxy)-2'-oxospiro[cyclobutane-1,3'-indolin]-5'-yl)benzenesulfonamide (Compound-185)

Step-i: 2,6-Difluoro-N-(1'-(4-methoxybenzyl)-7'-((1-methylpiperidin-4-yl)oxy)-2'-oxospiro[cyclobutane-1,3'-indolin]-5'-yl)benzenesulfonamide The process of this was adopted from step-i of Example-XXXIX. $^1$H NMR (400 MHz, DMSO-d$_6$): δ 10.50-10.40 (bs, 1H), 7.71-7.67 (m, 1H), 7.26 (t, J=9.3 Hz, 2H), 7.02-6.97 (m, 2H), 6.83 (d, J=8.8 Hz, 2H), 6.63 (d, J=1.5 Hz, 1H), 4.95 (s, 2H), 4.10-4.08 (m, 1H), 3.68 (s, 3H), 2.67-2.40 (m, 5H), 2.33-2.06 (m, 9H), 1.73-1.71 (m, 2H), 1.45-1.38 (m, 2H); LC-MS: m/z 598.3 (M+H)$^+$.

Step-ii: 2-Fluoro-6-methoxy-N-(1'-(4-methoxybenzyl)-7'-((1-methylpiperidin-4-yl)oxy)-2'-oxospiro[cyclobutane-1,3'-indolin]-5'-yl)benzenesulfonamide In a sealed tube, to a solution of 2,6-difluoro-N-(1'-(4-methoxybenzyl)-7'-((1-methyl piperidin-4-yl)oxy)-2'-oxospiro[cyclobutane-1,3'-indolin]-5'-yl)benzenesulfonamide (0.1 g, 0.17 mmol) in MeOH (5 mL) was added sodium methoxide (0.09 g, 1.70 mmol). The tube was sealed and the mixture was slowly heated to 130° C. for 16 h. The mixture was slowly poured into ice water and extracted with EtOAc. The organic layer was dried over sodium sulphate and concentrated under reduced pressure to afford the title compound as pale brown sticky solid (0.1 g). $^1$H NMR (400 MHz, DMSO-d$_6$): δ 10.10-9.96 (bs, 1H), 7.57-7.51 (m, 1H), 7.42 (t, J=8.3 Hz, 1H), 7.01-6.94 (m, 2H), 6.86-6.81 (m, 3H), 6.71 (d, J=8.3 Hz, 1H), 6.66-6.64 (m, 1H), 4.99 (s, 2H), 4.27-4.02 (m, 1H), 3.91 (s, 3H), 3.82 (s, 3H), 2.67-2.02 (m, 13H), 1.90-1.68 (m, 2H), 1.39-1.30 (m, 2H); LC-MS: m/z 610.3 (M+H)$^+$.

Step-iii: 2-Fluoro-6-methoxy-N-(7'-((1-methylpiperidin-4-yl)oxy)-2'-oxo spiro[cyclobutane-1,3'-indolin]-5'-yl)benzenesulfonamide The process of this was adopted from step-ii of Example-XXXIX. $^1$H NMR (400 MHz, DMSO-d$_6$): δ 10.14 (s, 1H), 9.85 (bs, 1H), 7.53-7.52 (m, 1H), 6.98 (d, J=8.3 Hz, 1H), 6.92 (s, 1H), 6.86-6.82 (m, 1H), 6.18 (d, J=1.0 Hz, 1H), 4.10-3.96 (m, 1H), 3.92 (s, 3H), 2.67-2.33 (m, 6H), 2.16 (s, 3H), 2.06-2.02 (m, 4H), 1.73-1.70 (m, 2H), 1.56-1.52 (m, 2H); LC-MS: m/z 490.2 (M+H)$^+$.

The below compounds were prepared by procedure similar to the one described in Example-XLVIII with appropriate variations in reactants, quantities of reagents and reaction conditions. The physiochemical characteristics of the compounds are also summarized.

Example-XLIX: 4-Fluoro-2-methoxy-N-(7'-((1-methylpiperidin-4-yl)oxy)-2'-oxospiro[cyclobutane-1.3'-indolin]-5'-yl)benzenesulfonamide (Compound-189)

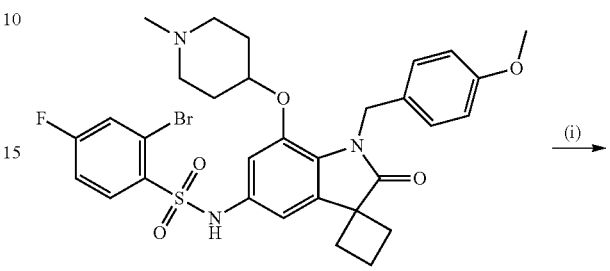

| No | Structure | Characterization Data $^1$H NMR (400 MHz, DMSO-d$_6$)/LC-MS: |
|---|---|---|
| 186 | 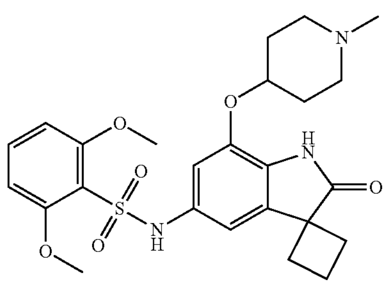 [SMILES: COc1cccc(OC)c1S(=O)(=O)Nc1cc(OC2CCN(C)CC2)c2c(c1)C1(CCC1)C(=O)N2] | $^1$H NMR (400 MHz, DMSO-d$_6$): δ 10.09 (s, 1H), 9.44 (bs, 1H), 7.41 (t, J = 8.8 Hz, 1H), 6.93 (d, J = 1.9 Hz, 1H), 6.70 (d, J = 8.8 Hz, 2H), 6.30 (d, J = 2.0 Hz, 1H), 4.01-3.98 (m, 1H), 3.81 (s, 6H), 2.67-2.61 (m, 2H), 2.39-2.33 (m, 2H), 2.17-2.00 (m, 9H), 1.77-1.74 (m, 2H), 1.57-1.51 (m, 2H); LC-MS: m/z 502.2 (M + H)$^+$. |
| 187 | 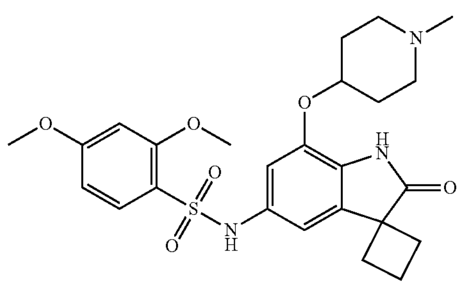 | $^1$H NMR (400 MHz, DMSO-d$_6$): δ 10.17 (bs, 1H), 9.49 (bs, 1H), 7.58 (d, J = 8.9 Hz, 1H), 6.87 (s, 1H), 6.64 (d, J = 1.9 Hz, 1H), 6.54-6.53 (m, 2H), 4.01-4.02 (m, 1H), 3.90 (s, 3H), 3.77 (s, 3H), 2.67-2.40 (m, 4H), 2.36-2.33 (m, 2H), 2.19-2.06 (m, 7H), 1.74-1.72 (m, 2H), 1.54-1.52 (m, 2H); LCMS: m/z 502.2 (M + H)$^+$. |
| 188 | 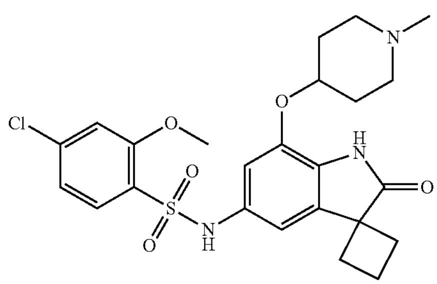 [SMILES: COc1cc(Cl)ccc1S(=O)(=O)Nc1cc(OC2CCN(C)CC2)c2c(c1)C1(CCC1)C(=O)N2] | $^1$H NMR (400 MHz, DMSO-d$_6$): δ 10.23 (bs, 1H), 9.75 (bs, 1H), 7.66 (d, J = 8.3 Hz, 1H), 7.31 (d, J = 1.4 Hz, 1H), 7.07 (dd, J = 8.3 Hz& 1.5 Hz, 1H), 6.87 (s, 1H), 6.52 (s, 1H), 4.06-4.04 (m, 1H), 3.95 (s, 3H), 2.67-2.07 (m, 13H), 1.78-1.76 (m, 2H), 1.60-1.57 (m, 2H); LCMS: m/z 507.2 (M + H)$^+$. |

-continued

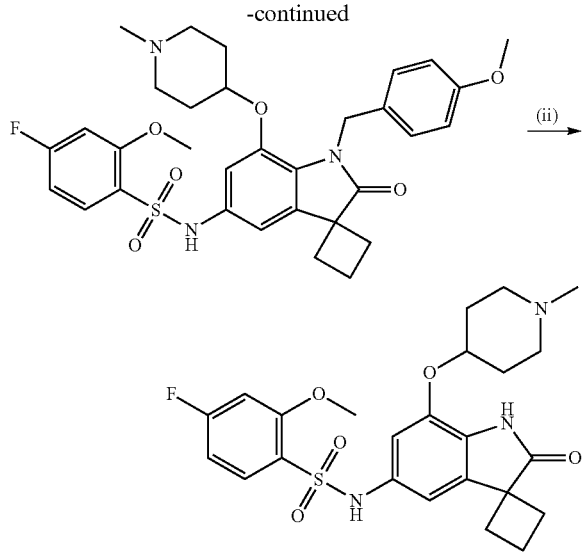

Step-i: 4-Fluoro-2-methoxy-N-(1'-(4-methoxybenzyl)-7'-((1-methylpiperidin-4-yl)oxy)-2'-oxospiro[cyclobutane-1,3'-indolin]-5'-yl)benzenesulfonamide To a solution of 2-bromo-4-fluoro-N-(1'-(4-methoxybenzyl)-7'-((1-methylpiperidin-4-yl)oxy)-2'-oxospiro[cyclobutane-1,3'-indolin]-5'-yl)benzenesulfonamide (0.4 g, 0.61 mmol) in 1,4-dioxane (3 mL) were added copper iodide (0.025 g, 0.12 mmol) and LiOMe (1 M in THF) (3 mL) followed by heating to 100° C. for 48 h. The mixture was poured into ice water and extracted with DCM. The organic layer was dried over sodium sulphate and concentrated under reduced pressure. The residue was purified by combi-flash to afford the title compound as pale brown solid (0.2 g, 54%). $^1$H NMR (400 MHz, DMSO-d$_6$): δ 9.70 (bs, 1H), 7.78-7.74 (m, 1H), 7.42-7.38 (m, 1H), 7.15-7.12 (m, 1H), 7.01-6.99 (m, 2H), 6.94-6.81 (m, 3H), 6.55 (d, J=1.4 Hz, 1H), 4.95 (s, 2H), 4.05-4.02 (s, 1H), 3.91 (s, 3H), 3.68 (s, 3H), 2.45-2.38 (m, 5H), 2.52-2.06 (m, 8H), 1.78-1.62 (m, 2H), 1.42-1.28 (m, 2H); LC-MS: m/z 610.3 (M+H)$^+$.

Step-ii: Synthesis of 4-fluoro-2-methoxy-N-(7'-((1-methylpiperidin-4-yl)oxy)-2'-oxospiro[cyclobutane-1,3'-indolin]-5'-yl)benzenesulfonamide The process of this was adopted from step-ii of Example-XXXIX. $^1$H NMR (400 MHz, DMSO-d$_6$): δ 10.18 (bs, 1H), 9.68 (bs, 1H), 7.73-7.69 (m, 1H), 7.15-7.13 (m, 1H), 6.87-6.81 (m, 2H), 6.51 (s, 1H), 4.01-3.99 (m, 1H), 3.93 (s, 3H), 2.67-2.36 (m, 4H), 2.16-2.07 (m, 9H), 1.72-1.70 (m, 2H), 1.55-1.48 (m, 2H); LC-MS: m/z 490.2 (M+H)$^+$.

Example-L: 2-Methoxy-N-(7'-(((1-methylazetidin-3-yl)methoxy)-2'-oxospiro [cyclobutane-1,3'-indolin]-5'-yl)benzenesulfonamide (Compound-190)

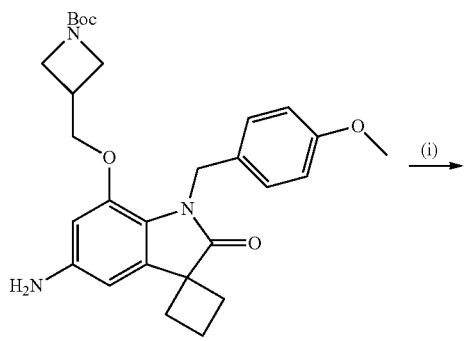

-continued

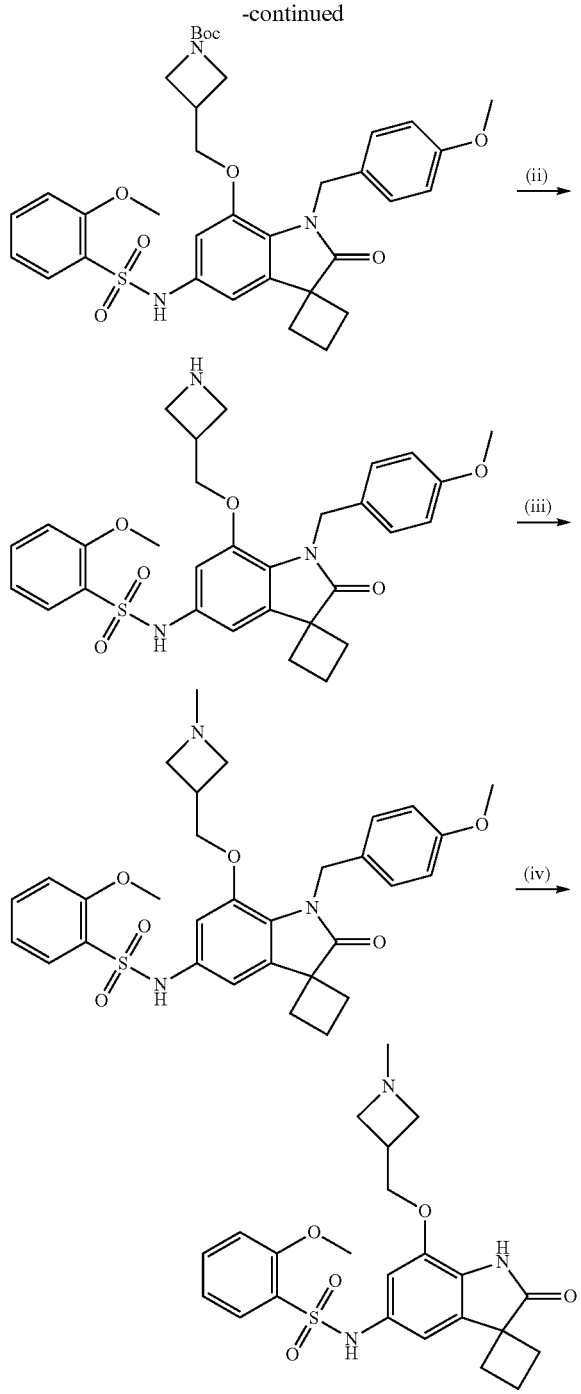

Step-i: tert-Butyl 3-(((1'-(4-methoxybenzyl)-5'-((2-methoxyphenyl)sulfonamido)-2'-oxospiro[cyclobutane-1,3'-indolin]-7'-yl)oxy)methyl)azetidine-1-carboxylate The process of this step was adopted from step-i of Example-XXXIX. $^1$H NMR (400 MHz, DMSO-d$_6$): δ 9.75 (s, 1H), 7.76-7.74 (m, 1H), 7.17 (d, J=8.3 Hz, 1H), 7.01 (t, J=7.4 Hz, 1H), 6.97 (d, J=8.8 Hz, 2H), 6.92 (d, J=1.4 Hz,1H), 6.82 (d, J=8.8 Hz, 2H), 6.64 (d, J=2.0 Hz, 1H), 4.86 (s, 2H), 3.90 (s, 3H), 3.87 (d, J=6.8 Hz, 2H), 3.81 (t, J=2.8 Hz, 2H), 3.68 (s, 3H), 3.48-3.44 (m, 2H), 2.76-2.71 (m, 1H), 2.67-2.38 (m, 3H), 2.22-2.19 (m, 1H), 2.08-2.04 (m, 3H), 1.36 (s, 9H); LCMS: m/z 662.2 (M−H)$^-$.

Step-ii: N-(7'-(azetidin-3-ylmethoxy)-1'-(4-methoxybenzyl)-2'-oxospiro[cyclobutane-1,3'-indolin]-5'-yl)-2-methoxybenzenesulfonamide To an ice cold solution of tert-butyl 3-(((1'-(4-methoxybenzyl)-5'-((2-methoxyphenyl)sulfonamido)-2'-oxospiro[cyclobutane-1,3'-indolin]-7'-yl)oxy)methyl)azetidine-1-carboxylate (0.29g, 0.44mmol) in DCM (6 mL) was added TFA (0.5 mL) followed by stirring for 2 h. The mixture was poured into aqueous NaHCO$_3$ and extracted with DCM. The organic layer was dried over sodium sulphate and concentrated under reduced pressure to afford the title compound as brown solid (0.18 g). $^1$H NMR (400 MHz, DMSO-d$_6$): δ 7.75 (d, J=7.8 Hz, 1H), 7.56 (t, J=6.8 Hz, 1H), 7.17 (d, J=8.3 Hz, 1H), 7.03-6.96 (m, 3H), 6.91 (d, J=1.4 Hz, 1H),6.83-6.80 (m, 2H), 6.63 (d, J=1.4 Hz, 1H), 4.87-4.85 (m, 2H), 3.90 (s, 3H), 3.90-3.88 (m, 2H), 3.67 (s, 3H), 3.51-3.48 (m, 2H), 3.18-3.05 (m, 2H), 2.82-2.78 (m, 1H), 2.47-2.40 (m, 2H), 2.31-2.06 (m, 4H); ESMS: m/z 564.4 (M+H)$^+$.

Step-iii: 2-Methoxy-N-(1'-(4-methoxybenzyl)-7'-((1-methylazetidin-3-yl)-methoxy)-2'-oxospiro[cyclobutane-1,3'-indolin]-5'-yl)benzenesulfonamide To a solution of N-(7'-(azetidin-3-ylmethoxy)-1'-(4-methoxybenzyl)-2'-oxo-spiro[cyclobutane-1,3'-indolin]-5'-yl)-2-methoxybenzenesulfonamide (0.18 g, 0.32 mmol) in a mixture of THF (5 mL) and MeOH (5 mL) was added aqueous formaldehyde 30% (0.3 mL) followed by stirring at RT for 16 h. The mixture was cooled to 0° C. and sodium borohydride (0.036 g, 0.96 mmol) was added followed by stirring at RT for 2 h. The reaction mixture quenched with aqueous NH$_4$Cl and extracted with DCM. The organic layer was dried over sodium sulphate and concentrated under reduced pressure. The residue was purified by combi-flash to afford the title compound as off white solid (0.12 g, 65%). $^1$H NMR (400 MHz, DMSO-d$_6$): δ 9.80-9.70 (bs, 1H), 7.76-7.73 (m, 1H), 7.58-7.54 (m, 1H), 7.18 (d, J=8.3 Hz, 1H), 7.02-6.99 (m, 3H), 6.91 (d, J=2.0 Hz, 1H),6.82 (d, J=8.8 Hz, 2H), 6.61 (d, J=1.5 Hz, 1H), 4.86 (s, 2H), 3.90 (s, 3H), 3.89 (d, J=6.8 Hz, 2H), 3.68 (s, 3H), 3.13 (t, J=7.3 Hz, 2H), 2.78 (t, J=5.8 Hz, 2H), 2.42-2.38 (m, 2H), 2.22-2.10 (m, 1H), 2.09 (s, 3H), 2.24-2.10 (m, 4H); LCMS: m/z 576.2 (M+H)$^+$.

Step-iv: 2-Methoxy-N-(7'-((1-methylazetidin-3-yl)methoxy)-2'-oxospiro[cyclobutane-1,3'-indolin]-5'-yl)benzenesulfonamide The process of this step was adopted from step-ii of Example-XXXIX. $^1$H NMR (400 MHz, DMSO-d$_6$): δ 10.20 (s, 1H), 9.75-9.70 (bs , 1H), 7.70 (dd, J=7.8 Hz & 1.5 Hz, 1H), 7.57-7.53 (m, 1H), 7.17 (d, J=8.3 Hz, 1H), 6.99 (t, J=7.3 Hz, 1H), 6.84 (d, J=1.4 Hz, 1H), 6.59 (d, J=1.4 Hz, 1H), 3.94-3.92 (m, 5H), 3.41-3.15 (m, 4H), 2.73-2.67 (m, 1H), 2.37-2.33 (m, 5H), 2.17-2.01 (m, 4H); LC-MS: m/z 458.2 (M+H)$^+$.

The below compounds were prepared by procedure similar to the one described in Example-L with appropriate variations in reactants, quantities of reagents and reaction conditions. The physiochemical characteristics of the compounds are also summarized.

| No | Structure | Characterization Data $^1$H NMR (400 MHz, DMSO-d$_6$)/LC-MS: |
|---|---|---|
| 191 & 192 | 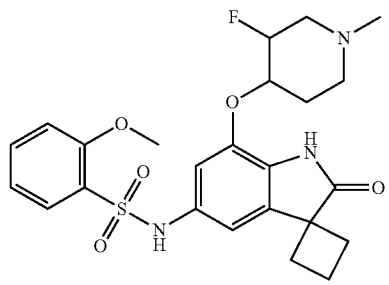 [SMILES: COc1ccccc1S(=O)(=O)Nc1cc(OC2CCN(C)CC2F)c2c(c1)C1(CCC1)C(=O)N2] | Isomer-I: $^1$H NMR (400 MHz, DMSO-d$_6$): δ 10.18 (bs, 1H), 9.59 (s, 1H), 7.67 (dd, J = 7.8 Hz, & 1.5 Hz, 1H), 7.57-7.52 (m, 1H), 7.17 (d, J = 7.8 Hz, 1H), 6.99 (t, J = 7.4 Hz, 1H), 6.88 (d, J = 1.4 Hz, 1H), 6.61 (d, J = 2.0 Hz, 1H), 4.63-4.50 (m, 1H), 4.00-3.98 (m, 1H), 3.91 (s, 3H), 2.99-2.96 (m, 1H), 2.67-2.57 (m, 1H), 2.38-2.01 (m, 11H), 1.79-1.74 (m, 1H), 1.49-1.45 (m, 1H); LC-MS: m/z 490.2 (M + H)$^+$. Isomer-II: $^1$H NMR (400 MHz, DMSO-d$_6$): δ 10.21 (bs, 1H), 9.61 (s, 1H), 7.67 (dd, J = 7.8 Hz, & 1.5 Hz, 1H), 7.57-7.52 (m, 1H), 7.17 (d, J = 7.8 Hz, 1H), 6.99 (t, J = 7.4 Hz, 1H), 6.91 (s, 1H), 6.12 (d, J = 1.5 Hz, 1H), 4.75-4.65 (m, 1H), 4.21-4.15 (m, 1H), 3.91 (s, 3H), 2.98-2.90 (m, 1H), 2.66-2.06 (m, 12H), 1.85-1.65 (m, 2H); LC-MS: m/z 490.2 (M + H)$^+$. |
| 193 | 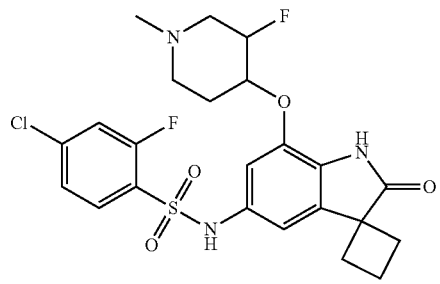 [SMILES: CN1CCC(Oc2cc(NS(=O)(=O)c3ccc(Cl)cc3F)cc3c2NC(=O)C32CCC2)C(F)C1] | $^1$H NMR (400 MHz, DMSO-d$_6$): δ 10.31 (s, 2H), 7.76-7.70 (m, 2H), 7.43 (dd, J = 8.4 Hz & 1.5 Hz, 1H), 6.89 (d, J = 1.4 Hz, 1H), 6.58 (d, J = 1.5 Hz, 1H), 4.64-4.51 (m, 1H), 4.04-4.02 (m, 1H), 3.02-2.97 (m, 1H), 2.67-2.32 (m, 3H), 2.22-2.03 (m, 9H), 1.82-1.79 (m, 1H), 1.51-1.48 (m, 1H); LC-MS: m/z 512.2 (M + H)$^+$. |

| No | Structure | Characterization Data<br>¹H NMR (400 MHz, DMSO-d₆)/LC-MS: |
|---|---|---|
| 194 | 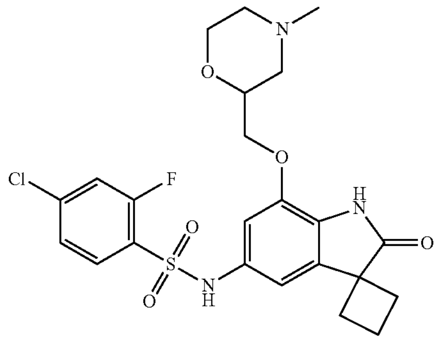 [SMILES: CN1CCOC(COc2cc(NS(=O)(=O)c3ccc(Cl)cc3F)cc3c2NC(=O)C32CCC2)C1] | ¹H NMR (400 MHz, DMSO-d₆): δ 10.36 (s, 1H), 10.30 (s, 1H), 7.78-7.72 (m, 2H), 7.45-7.42 (m, 1H), 6.85 (d, J = 1.5 Hz, 1H), 6.57 (d, J = 1.5 Hz, 1H), 3.90-3.86 (m, 2H), 3.79-3.69 (m, 3H), 3.51-3.49 (m, 1H), 2.87-2.84 (m, 1H), 2.61-2.58 (m, 2H), 2.39-2.33 (m, 1H), 2.20 (m, 3H), 2.017-2.01 (m, 4H), 1.85-1.83 (s, 1H); LCMS: m/z 510.0 (M + H)⁺. |
| 195 | 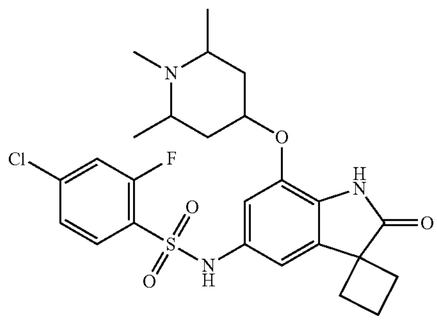 [SMILES: CC1CC(Oc2cc(NS(=O)(=O)c3ccc(Cl)cc3F)cc3c2NC(=O)C32CCC2)CC(C)N1C] | ¹H NMR (400 MHz, DMSO-d₆): δ 10.20 (bs, 2H), 7.75-7.71 (m, 2H), 7.43 (d, J = 8.8 Hz, 1H), 6.86 (s, 1H), 6.56 (s, 1H), 4.33-4.31 (m, 1H), 3.32-3.30 (m, 1H), 2.79-2.77 (m, 1H), 2.36-2.32 (m, 5H), 2.17-2.05 (m, 4H), 1.85-1.81 (m, 2H), 1.77-1.66 (m, 1H), 1.35-1.33 (m, 1H), 1.03 (d, J = 3.4 Hz, 6H); LC-MS: m/z 522.2 (M + H)⁺. |
| 196 | 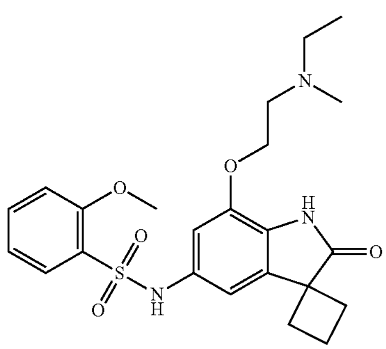 [SMILES: CCN(C)CCOc1cc(NS(=O)(=O)c2ccccc2OC)cc2c1NC(=O)C21CCC1] | ¹H NMR (400 MHz, DMSO-d₆): δ 10.17 (s, 1H), 9.62 (s, 1H), 7.69 (d, J = 7.8 Hz, 1H), 7.54 (t, J = 7.8 Hz, 1H), 7.16 (d, J = 8.3 Hz, 1H), 6.99 (t, J = 7.9 Hz, 1H), 6.85 (s, 1H), 6.59 (s, 1H), 3.92 (s, 3H), 3.90-3.89 (m, 2H), 2.62-2.60 (m, 2H), 2.44-2.32 (m, 4H), 2.18-2.10 (m, 4H), 2.03-2.01 (m, 3H), 0.96 (t, J = 6.8 Hz, 3H); LC-MS: m/z 460.2 (M + H)⁺. |

Example-LI: 4-Chloro-2-fluoro-N-(2'-oxo-7'-(piperidin-4-yloxy)spiro-[cyclobutane-1,3'-indolin]-5'-yl)benzene sulfonamide (Compound-197)

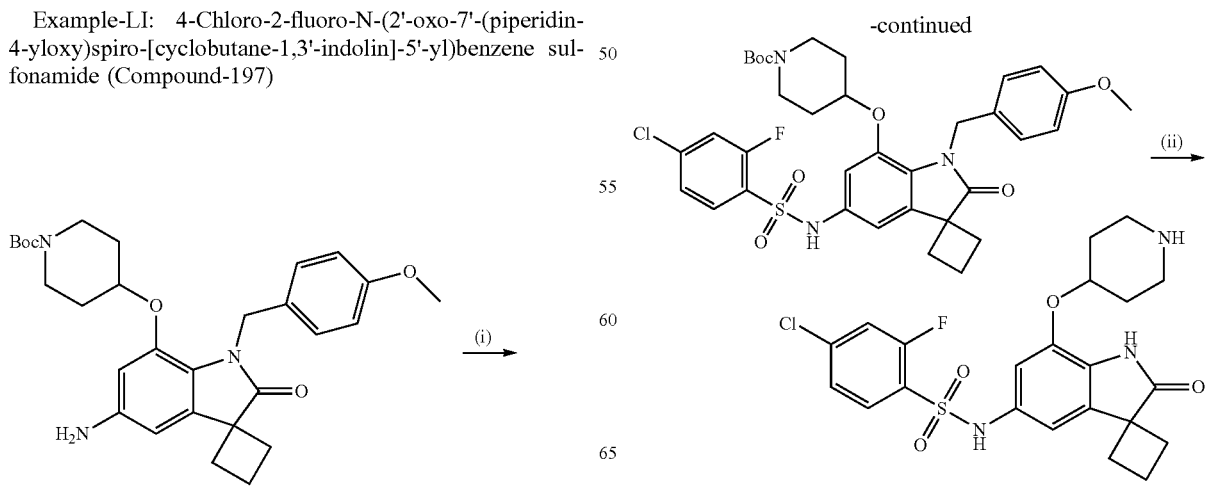

Step-i: tert-Butyl 4-((5'-((4-chloro-2-fluorophenyl)sulfonamido)-1'-(4-methoxybenzyl)-2'-oxospiro[cyclobutane-1,3'-indolin]-7'-yl)oxy)piperidine-1-carboxylate:

The process of this step was adopted from step-i of Example-XXXIX. $^1$H NMR (400 MHz, DMSO-d$_6$): δ 10.39 (s, 1H), 7.79-7.74 (m, 2H), 7.46 (d, J=8.3 Hz, 1H), 6.97-6.95 (m, 3H), 6.81(d, J=8.8 Hz, 2H), 6.54 (s, 1H), 4.94 (s, 2H), 4.25-4.21 (m, 1H), 3.67 (s, 3H), 3.46-3.43 (m, 2H), 3.25-2.98 (m, 2H), 2.46-2.33 (m, 2H), 2.29-2.06 (m, 4H), 1.63-1.58 (m, 2H), 1.39 (s, 9H), 1.23-1.17 (m, 2H); LC-MS: m/z 600.2 (M-Boc).

Step-ii: 4-Chloro-2-fluoro-N-(2'-oxo-7'-(piperidin-4-yloxy)spiro[cyclobutane-1,3'-indolin]-5'-yl)benzenesulfonamide The process of this step was adopted from step-ii of Example-XXXIX. $^1$H NMR (400 MHz, DMSO-d$_6$): δ 10.10 (bs, 1H), 7.72 (t, J=7.6 Hz, 1H), 7.65-7.57 (m, 1H), 7.36 (d, J=1.5 Hz, 1H), 6.79 (d, J=1.5 Hz, 1H), 6.45 (d, J=1.0 Hz, 1H), 4.19-4.17 (m, 1H), 3.40-3.20 (m, 1H), 3.17-3.04 (m, 2H), 2.69-2.65 (m, 2H), 2.39-2.23 (m, 2H), 2.19-2.02 (m, 4H), 1.79-1.75 (m, 2H), 1.53-1.49 (m, 2H); LC-MS: m/z 480.1 (M+H)$^+$.

The below compounds were prepared by procedure similar to the one described in Example-LI with appropriate variations in reactants, quantities of reagents and reaction conditions. The physiochemical characteristics of the compounds are also summarized.

| No | Structure | Characterization Data $^1$H NMR (400 MHz, DMSO-d$_6$)/LC-MS: |
|---|---|---|
| 198 | 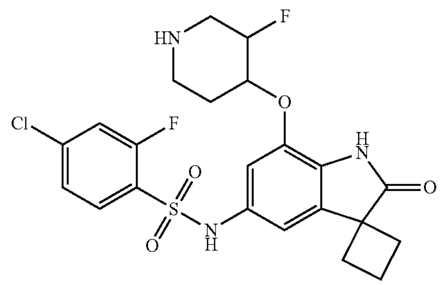 [SMILES: O=C1Nc2c(OC3CCNCC3F)cc(NS(=O)(=O)c3ccc(Cl)cc3F)cc2C12CCC2] | $^1$H NMR (400 MHz, DMSO-d$_6$): δ 10.26 (bs, 1H), 7.73-7.71 (m, 2H), 7.43-7.41 (m, 1H), 6.87 (s, 1H), 6.58 (s, 1H), 4.52-4.39 (m, 1H), 4.12-4.10 (m, 1H), 3.30-3.19 (m, 2H), 2.85-2.82 (m, 1H), 2.67-2.37 (m, 4H), 2.17-2.06 (m, 4H), 1.81-1.80 (m, 1H), 1.39-1.34 (m, 1H); LC-MS: m/z 498.2 (M + H)$^+$. |
| 199 | 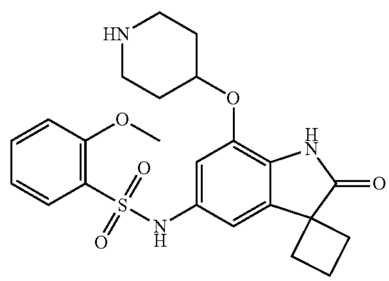 [SMILES: COc1ccccc1S(=O)(=O)Nc1cc(OC2CCNCC2)c2c(c1)C1(CCC1)C(=O)N2] | $^1$H NMR (400 MHz, DMSO-d$_6$): δ 10.11 (s, 1H), 7.68-7.66(m, 1H), 7.56-7.52 (m, 1H), 7.17 (d, J = 8.3 Hz, 1H), 6.98 (t, J = 7.3 Hz, 1H), 6.86 (d, J = 1.4 Hz, 1H), 6.54 (d, J = 1.0 Hz, 1H), 4.05-4.00 (m, 1H), 3.92 (s, 3H), 3.41-3.31 (m, 2H), 2.95-2.92 (m, 2H), 2.47-2.34 (m, 2H), 2.16-2.05 (m, 4H), 1.71-1.68 (m, 2H), 1.38-1.31 (m, 2H); LCMS: m/z 458.2 (M + H)$^+$. |
| 200 | 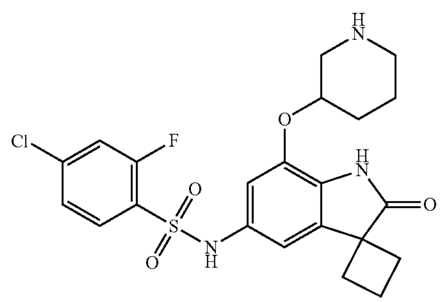 [SMILES: O=C1Nc2c(OC3CCCNC3)cc(NS(=O)(=O)c3ccc(Cl)cc3F)cc2C12CCC2] | $^1$H NMR (400 MHz, DMSO-d$_6$): δ 10.20 (bs, 1H), 7.74-7.65 (m, 2H), 7.40-7.38 (m, 1H), 6.81 (d, J = 1.5 Hz, 1H), 6.51 (d, J = 1.4 Hz, 1H), 4.19 (bs, 1H), 2.99-2.96 (m, 1H), 2.85-2.67 (m, 3H), 2.45-2.30 (m, 2H), 2.20-2.02 (m, 5H), 1.67-1.56 (m, 3H), 1.35-1.33 (m, 1H); LC-MS: m/z 479.9 (M + H)$^+$. |
| 201 | 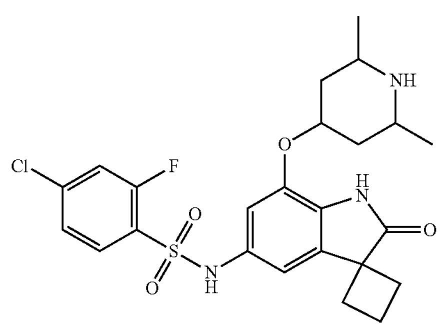 [SMILES: CC1CC(Oc2cc(NS(=O)(=O)c3ccc(Cl)cc3F)cc3c2NC(=O)C32CCC2)CC(C)N1] | $^1$H NMR (400 MHz, DMSO-d$_6$): δ 10.06 (s, 1H), 7.72 (t, J = 7.8 Hz, 1H), 7.61 (d, J = 8.3 Hz, 1H), 7.37 (d, J = 8.3 Hz, 1H), 6.80 (s, 1H), 6.48 (s, 1H), 4.32-4.30 (m, 1H), 3.51-3.49 (m, 1H), 3.11-3.09 (m, 1H), 2.38-2.33 (m, 2H), 2.17-2.05 (m, 4H), 1.86-1.83 (m, 1H), 1.75-1.72 (m, 1H), 1.57-1.55 (m, 1H), 1.20-1.17 (m, 1H), 1.14 (d, J = 6.8 Hz, 3H), 1.06 (d, J = 6.3 Hz, 3H); LC-MS: m/z 508.2 (M + H)$^+$. |

| No | Structure | Characterization Data<br>¹H NMR (400 MHz, DMSO-d₆)/LC-MS: |
|---|---|---|
| 202 | 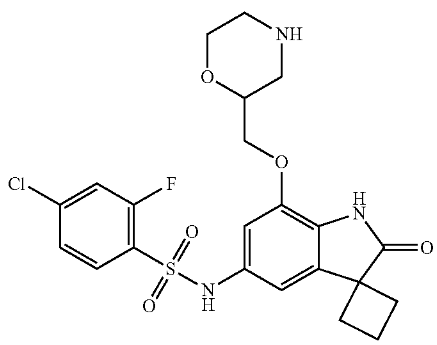 [SMILES: O=C1Nc2c(OCC3CNCCO3)cc(NS(=O)(=O)c3ccc(Cl)cc3F)cc2C12CCC2] | ¹H NMR (400 MHz, DMSO-d₆): δ 10.27 (s, 1H), 7.78-7.71 (m, 2H), 7.44-7.41 (m, 1H), 6.83 (d, J = 1.5 Hz, 1H), 6.56 (d, J = 1.5 Hz, 1H), 3.89-3.82 (m, 1H), 3.76-3.73 (m, 2H), 3.66-3.63 (m, 1H), 3.50-3.42 (m, 1H), 2.98-2.94 (m, 1H), 2.70-2.67 (m, 2H), 2.57-2.51 (m, 2H), 2.28-2.33 (m, 2H), 2.18-2.05 (m, 4H); LC-MS: m/z 495.9 (M + H)⁺. |
| 203 | 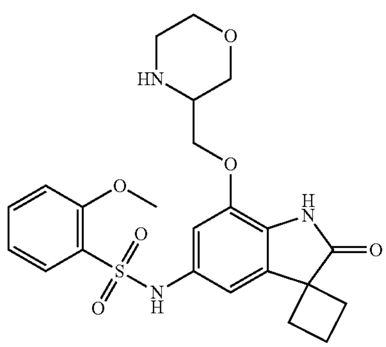 [SMILES: COc1ccccc1S(=O)(=O)Nc1cc(OCC2COCCN2)c2c(c1)C1(CCC1)C(=O)N2] | ¹H NMR (400 MHz, DMSO-d₆): δ 10.26 (s, 1H), 9.67 (s, 1H), 7.71-7.68 (m, 1H), 7.57-7.51 (m, 1H), 7.16 (d, J = 8.3 Hz, 1H), 6.99 (t, J = 7.4 Hz, 1H), 6.82 (d, J = 1.5 Hz, 1H), 6.56 (d, J = 1.5 Hz, 1H), 3.92 (s, 3H), 3.82-3.79 (m, 1H), 3.74-3.71 (m, 2H), 3.68-3.65 (m, 1H), 3.41-3.36 (m, 1H), 3.30-3.15 (m, 1H), 2.98-2.96 (m, 1H), 2.79-2.75 (m, 2H), 2.52-2.32 (m, 3H), 2.19-2.12 (m, 1H), 2.07-2.01 (m, 3H); LCMS: m/z 474.0 (M + H)⁺. |
| 204 | 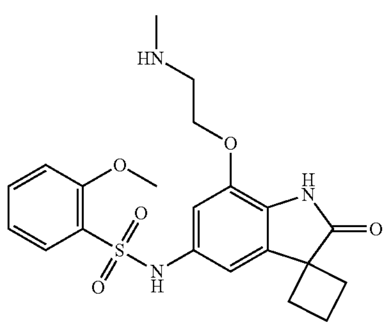 [SMILES: CNCCOc1cc(NS(=O)(=O)c2ccccc2OC)cc2c1NC(=O)C21CCC1] | ¹H NMR (400 MHz, DMSO-d₆): δ 10.15 (bs, 1H), 7.70-7.68 (m, 1H), 7.56-7.52 (m, 1H), 7.16 (d, J = 8.3 Hz, 1H), 7.00-6.99 (m, 1H), 6.83 (d, J = 1.0 Hz, 1H), 6.58 (s, 1H), 3.92 (s, 3H), 3.84 (t, J = 4.9 Hz, 2H), 2.75-2.73 (m, 2H), 2.37-2.29 (m, 5H), 2.19-2.01 (m, 4H); LC-MS: m/z 432.2 (M + H)⁺. |
| 205 | 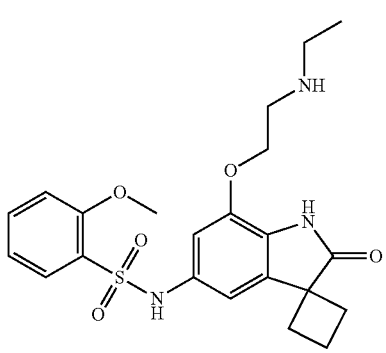 [SMILES: CCNCCOc1cc(NS(=O)(=O)c2ccccc2OC)cc2c1NC(=O)C21CCC1] | ¹H NMR (400 MHz, DMSO-d₆): δ 10.20 (bs, 1H), 7.70 (d, J = 7.8 Hz, 1H), 7.54 (t, J = 7.7 Hz, 1H), 7.16 (d, J = 8.3 Hz, 1H), 6.99 (t, J = 7.8 Hz, 1H), 6.85 (s, 1H), 6.61 (s, 1H), 3.95-3.93 (m, 2H), 3.92 (s, 3H), 3.09-3.04 (m, 2H), 2.80-2.79 (m, 2H), 2.36-2.33 (m, 2H), 2.16-2.02 (m, 4H), 1.11 (t, J = 7.3 Hz, 3H); LC-MS: m/z 446.2 (M + H)⁺. |

| No | Structure | Characterization Data<br>¹H NMR (400 MHz, DMSO-d₆)/LC-MS: |
|---|---|---|
| 206 | 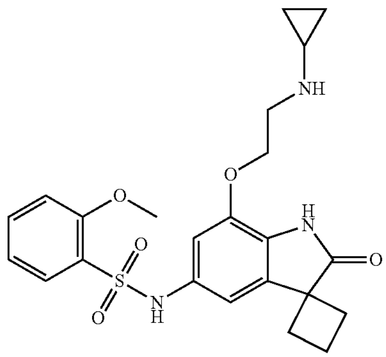 [SMILES: COc1ccccc1S(=O)(=O)Nc1cc(OCCNC2CC2)c2c(c1)C1(CCC1)C(=O)N2] | ¹H NMR (400 MHz, DMSO-d₆): δ 10.22 (s, 1H), 9.64-9.60 (bs, 1H), 7.69 (d, J = 7.0 Hz, 1H), 7.54 (t, J = 7.3 Hz, 1H), 7.16 (d, J = 8.3 Hz, 1H), 6.99 (t, J = 7.8 Hz, 1H), 6.84 (s, 1H), 6.58 (s, 1H), 3.92 (s, 3H), 3.84 (t, J = 4.4 Hz, 2H), 2.83 (d, J = 4.4 Hz, 2H), 2.67-2.33 (m, 3H), 2.20-2.02 (m, 5H), 0.37-0.35 (m, 2H), 0.22-0.21 (m, 2H); LC-MS: m/z 458.2 (M + H)⁺. |
| 207 | 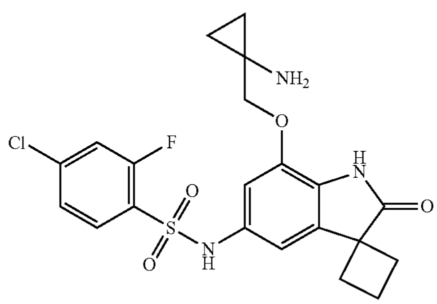 [SMILES: NC1(COc2cc(NS(=O)(=O)c3ccc(Cl)cc3F)cc3c2NC(=O)C32CCC2)CC1] | ¹H NMR (400 MHz, DMSO-d₆): δ 10.35 (bs, 1H), 7.76-7.68 (m, 2H), 7.43-7.40 (m, 1H), 6.80 (d, J = 1.5 Hz, 1H), 6.50 (d, J = 2.0 Hz, 1H), 5.12 (bs, 2H), 3.68 (s, 2H), 2.40-2.32 (m, 2H), 2.21-2.01 (m, 4H), 0.51 (s, 4H); LC-MS: m/z 465.9 (M + H)⁺. |
| 207.1 | 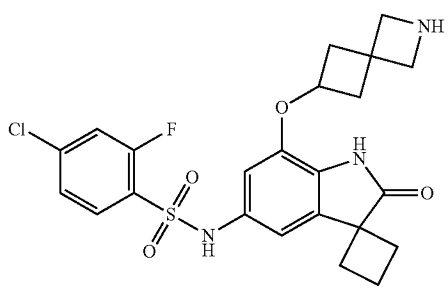 [SMILES: O=C1Nc2c(OC3CC4(CNC4)C3)cc(NS(=O)(=O)c3ccc(Cl)cc3F)cc2C12CCC2] | ¹H NMR (400 MHz, DMSO-d₆): δ 9.88 (bs, 1H), 7.74 (t, J = 8.3 Hz, 1H), 7.52-7.49 (m, 1H), 7.32 (d, J = 8.3 Hz, 1H), 6.71 (s, 1H), 6.27 (s, 1H), 4.39-4.35 (m, 1H), 3.78 (s, 2H), 3.72 (s, 2H), 2.66-2.54 (m, 2H), 2.36-2.33 (m, 2H), 2.14-2.04 (m, 6H); LCMS: m/z 492.0 (M + H)⁺. |

* Compound-203 was obtained by additional step of deprotection of benzyl group on morpholine ring by using Pd/C in methanol at H₂ atmosphere.

Example-LII: N-(7'-((4-Hydroxycyclohexyl)oxy)-2'-oxospiro[cyclobutane-1,3'-indolin]-5'-yl)-2-methoxybenzenesulfonamide (Compound-208)

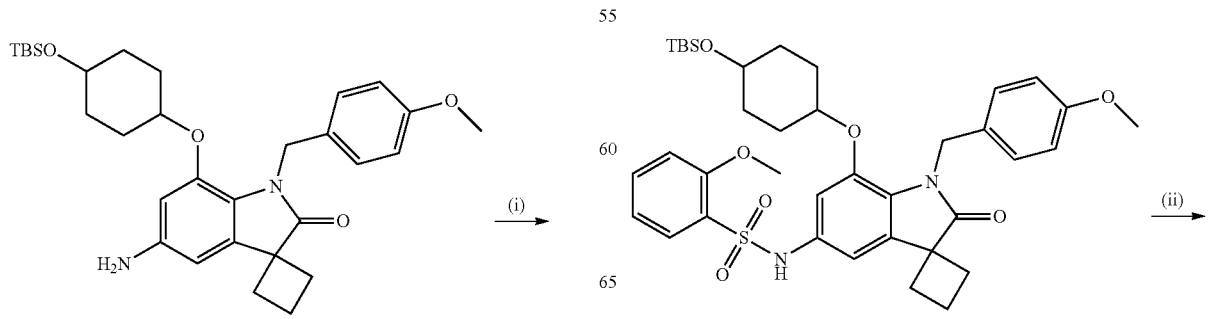

-continued

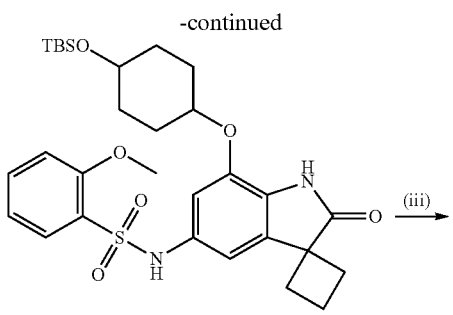

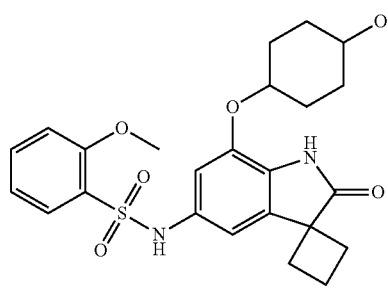

Step-i: N-(7'-((4-((tert-butyldimethylsilyl)oxy)cyclohexyl)oxy)-1'-(4-methoxybenzyl)-2'-oxospiro[cyclobutane-1,3'-indolin]-5'-yl)-2-methoxybenzenesulfonamide The process of this step was adopted from step-i of Example-XXXIX. ¹H NMR (400 MHz, DMSO-d₆): δ 9.69 (s, 1H), 7.72 (d, J=7.3 Hz, 1H), 7.57-7.53 (m, 1H), 7.17 (d, J=8.4 Hz, 1H), 7.04-6.90 (m, 4H), 6.82-6.76 (m, 2H), 6.58 (s, 1H), 4.91-4.88 (m, 2H), 4.03-4.01 (m, 1H), 3.91-3.84 (m, 4H), 3.70-3.67 (m, 3H), 2.42-2.39 (m, 2H), 2.23-2.09 (m, 4H), 1.71-1.50 (m, 4H), 1.33-1.11 (m, 4H), 0.86 (s, 9H), 0.03 (s, 6H); LC-MS: m/z 707.4 (M+H)⁺.

Step-ii: N-(7'-((4-((tert-butyldimethylsilyl)oxy)cyclohexyl)oxy)-2'-oxospiro-[cyclobutane-1,3'-indolin]-5'-yl)-2-methoxybenzenesulfonamide The process of this step was adopted from step-ii of Example-XXXIX. LC-MS: m/z 569.2 (M+H)⁺.

Step-iii: N-(7'-((4-hydroxycyclohexyl)oxy)-2'-oxospiro[cyclobutane-1,3'-indolin]-5'-yl)-2-methoxybenzenesulfonamide To an ice cold solution of N-(7'-((4-((tert-butyldimethylsilyl)oxy)cyclohexyl)-oxy)-2'-oxospiro[cyclobutane-1,3'-indolin]-5'-yl)-2-methoxybenzenesulfonamide (0.2 g, 0.34 mmol) in THF (10 mL) was added TBAF (1.0 M in THF) (0.5 mL, 0.51 mmol) followed by stirring at RT for 2 h. The reaction mixture was quenched with aqueous NH₄Cl and extracted with EtOAc. The organic layer was dried over sodium sulphate and concentrated under reduced pressure. The residue was purified by combi-flash to afford the title compound as off white solid (0.02 g). ¹H NMR (400 MHz, DMSO-d₆): δ 10.15 (s, 1H), 9.59 (s, 1H), 7.67 (d, J=7.8 Hz, 1H), 7.54 (t, J=7.8 Hz, 1H), 7.16 (d, J=8.3 Hz, 1H), 6.98 (t, J=7.8 Hz, 1H), 6.85 (s, 1H), 6.53 (s, 1H), 4.45 (d, J=2.9 Hz, 1H), 4.08-4.03 (m, 1H), 3.91 (s, 3H), 3.58-3.54 (m, 1H), 2.40-2.32 (m, 2H), 2.16-2.05 (m, 4H), 1.67-1.56 (m, 4H), 1.49-1.41 (m, 4H); LC-MS: m/z 473.2 (M+H)⁺.

Example-LIII: N-(7'-((1-(2-hydroxyethyl)piperidin-4-yl)oxy)-2'-oxospiro[cyclobutane-1,3'-indolin]-5'-yl)-2-methoxybenzenesulfonamide (Compound-209)

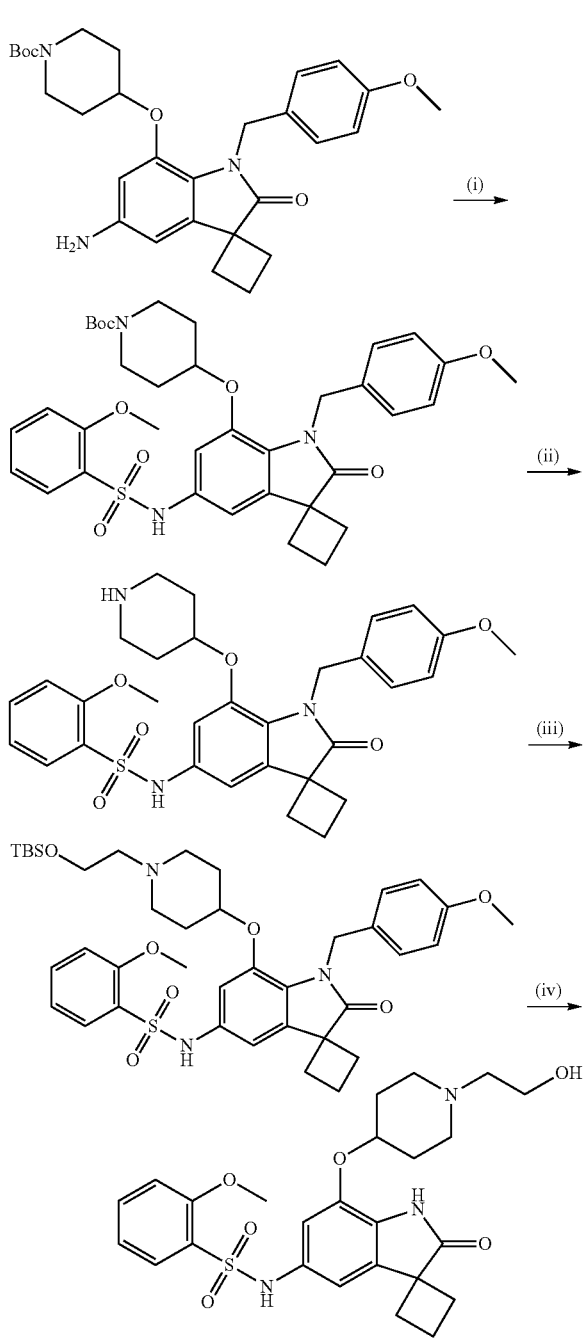

Step-i: tert-Butyl 4-((1'-(4-methoxybenzyl)-5'-((2-methoxyphenyl)sulfonamido)-2'-oxospiro[cyclobutane-1,3'-indolin]-7'-yl)oxy)piperidine-1-carboxylate The process of this step was adopted from step-i of Example-XXXIX. ¹H NMR (400 MHz, DMSO-d₆): δ 9.71 (s, 1H), 7.73(d, J=7.8 Hz, 1H), 7.57 (t, J=7.3 Hz, 1H), 7.18 (d, J=8.3 Hz, 1H), 7.02 (t, J=7.3 Hz, 1H), 6.96-6.93 (m, 3H), 6.94 (d, J=8.3 Hz, 2H), 6.59 (s, 1H), 4.91 (s, 2H), 4.21-4.19 (m, 1H), 3.90 (s, 3H), 3.67 (s, 3H), 3.46-3.43 (m, 2H), 3.04-2.98 (m, 2H), 2.44-2.09 (m, 6H), 1.62-1.60 (m, 2H), 1.40-1.38 (m, 11H); LCMS: m/z 676.4 (M+H)⁺.

Step-ii: 2-Methoxy-N-(1'-(4-methoxybenzyl)-2'-oxo-7'-(piperidin-4-yloxy)spiro-[cyclobutane-1,3'-indolin]-5'-yl)benzenesulfonamide The process of this step was adopted from step-ii of Example-L. ¹H NMR (400 MHz, DMSO-d₆): δ 9.77 (s, 1H), 7.74 (d, J=7.3 Hz, 1H), 7.57 (t, J=7.8 Hz, 1H), 7.18 (d, J=8.3 Hz, 1H), 7.03-6.97 (m, 3H), 6.90 (s, 1H), 6.82 (d, J=8.8 Hz, 2H), 6.66 (s, 1H), 4.91 (s, 2H), 4.36-4.34 (m, 1H), 3.90 (s, 3H), 3.69 (s, 3H), 3.10-3.00 (m, 4H), 2.49-2.40 (m, 3H), 2.23-2.09 (m, 4H), 1.90-1.87 (m, 2H), 1.57-1.55 (m, 2H); LCMS: m/z 578.3 (M+H)⁺.

Step-iii: N-(7'-((1-(2-((tert-butyldimethylsilyl)oxy)ethyl)piperidin-4-yl)oxy)-1'-(4-methoxybenzyl)-2'-oxospiro[cyclobutane-1,3'-indolin]-5'-yl)-2-methoxybenzene sulfonamide To a solution of 2-methoxy-N-(1'-(4-methoxybenzyl)-2'-oxo-7'-(piperidin-4-yloxy)spiro[cyclobutane-1,3'-indolin]-5'-yl)benzenesulfonamide (0.3 g, 0.52 mmol) in DCM (20 mL) were added triethyl amine (0.36 mL, 2.60 mmol) and (2-bromo-ethoxy)(tert-butyl)dimethylsilane (0.37 g, 1.56 mmol) followed by heating the mixture to 60° C. for 16 h. The mixture was diluted with DCM and washed with water The organic layer was dried over sodium sulphate and concentrated under reduced pressure.

The residue was purified by combi-flash to afford the title compound as yellow solid (0.18 g, 47%). ¹H NMR (400 MHz, DMSO-d₆): δ 9.77 (s, 1H), 7.79 (dd, J=7.4 Hz & 1.0 Hz, 1H), 7.65-7.61 (m, 1H), 7.25-7.21 (m, 1H), 7.10-7.06 (m, 2H), 7.00 (s, 1H), 6.88 (d, J=8.3 Hz, 2H), 6.65 (s, 1H), 4.99 (s, 2H), 4.13-4.10 (m, 1H), 3.97 (s, 3H), 3.75 (s, 3H), 3.73-3.71 (m, 2H), 2.65-2.40 (m, 8H), 2.31-2.18 (m, 5H), 1.74-1.70 (m, 2H), 1.45-1.42 (m, 2H), 0.94 (s, 9H), 0.12 (s, 6H); LCMS: m/z 736.4 (M+H)⁺.

Step-iv: N-(7'-((1-(2-hydroxyethyl)piperidin-4-yl)oxy)-2'-oxospiro[cyclobutane-1,3'-indolin]-5'-yl)-2-methoxybenzenesulfonamide The process of this step was adopted from step-ii of Example-XXXIX. ¹H NMR (400 MHz, DMSO-d₆): δ 10.14 (bs, 1H), 9.56-9.54 (bs, 1H), 7.67 (d, J=7.8 Hz, 1H), 7.54 (t, J=7.8 Hz, 1H), 7.17 (d, J=8.3 Hz, 1H), 6.99 (t, J=7.8 Hz, 1H), 6.87 (s, 1H), 6.55 (s, 1H), 4.45-4.43 (m, 1H), 4.04-3.99 (m, 1H), 3.92 (s, 3H), 3.49-3.51 (m, 2H), 2.76-2.67 (m, 2H), 2.67-2.05 (m, 10H), 1.74-1.70 (m, 2H), 1.53-1.49 (m, 2H); LC-MS: m/z 502.2 (M+H)⁺.

Example-LIV: 4-Chloro-2-fluoro-N-(7'-((1-(methylsulfonyl)piperidin-4-yl)-oxy)-2'-oxospiro[cyclobutane-1,3'-indolin]-5'-yl)benzenesulfonamide (Compound-210)

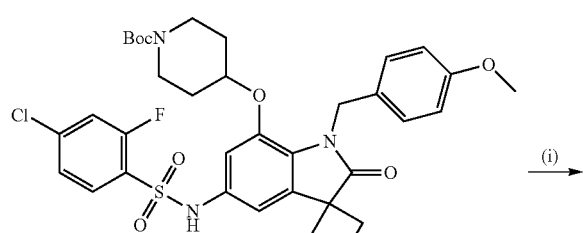

(i)

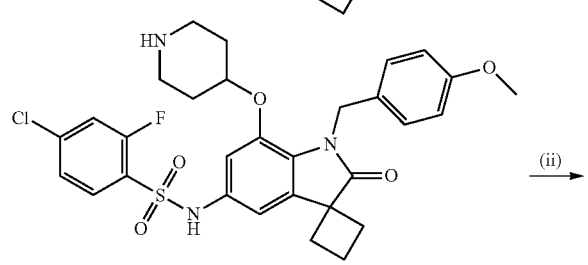

(ii)

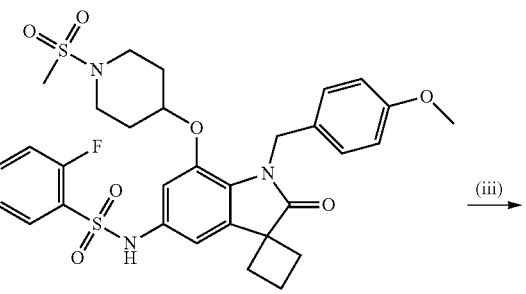

(iii)

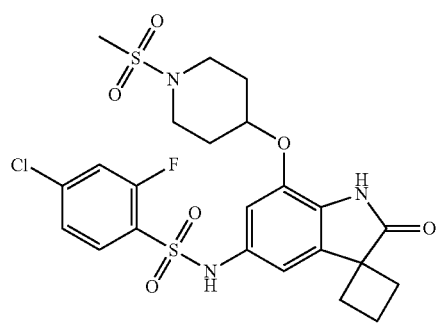

Step-i: 4-Chloro-2-fluoro-N-(1'-(4-methoxybenzyl)-2'-oxo-7'-(piperidin-4-yl-oxy)spiro[cyclobutane-1,3'-indolin]-5'-yl)benzenesulfonamide The process of this step was adopted from step-ii of Example-L. ¹H NMR (400 MHz, DMSO-d₆): δ 7.77 (t, J=7.9 Hz, 1H), 7.66-7.63 (m, 1H), 7.41 (d, J=1.5 Hz, 1H), 7.03 (d, J=8.3 Hz, 2H), 6.87 (d, J=1.5 Hz, 2H), 6.83 (d, J=8.8 Hz, 2H), 6.52 (s, 1H), 4.93 (s, 2H), 4.05-4.03 (m, 1H), 3.69 (s, 3H), 2.97-2.94 (m, 2H), 2.73-2.68 (m, 2H), 2.51-2.49 (m, 3H), 2.25-2.03 (m, 4H), 1.80-1.76 (m, 2H), 1.41-1.33 (m, 2H); LCMS: m/z 600.2 (M+H)⁺.

Step-ii: 4-Chloro-2-fluoro-N-(1'-(4-methoxybenzyl)-7'-((1-(methylsulfonyl)-piperidin-4-yl)oxy)-2'-oxospiro[cyclobutane-1,3'-indolin]-5'-yl)benzenesulfonamide:

The process of this step was adopted from step-i of Example-XXXIX. ¹H NMR (400 MHz, DMSO-d₆): δ 10.43 (s, 1H), 7.80-7.76 (m, 2H), 7.48-7.46 (m, 1H), 6.99 (d, J =8.3 Hz, 2H), 6.95 (d, J=1.4 Hz, 1H), 6.83 (d, J=8.4 Hz, 2H), 6.58 (d, J=1.4 Hz, 1H), 4.96 (s, 2H), 4.27-4.24 (m, 1H), 3.68 (s, 3H), 3.18-3.13 (m, 2H), 3.00-2.95 (m, 2H), 2.80 (s, 3H), 2.46-2.40 (m, 2H), 2.26-2.09 (m, 4H), 1.80-1.70 (m, 2H), 1.48-1.38 (m, 2H); LCMS: m/z 678.1 (M+H)⁺.

Step-iii: 4-Chloro-2-fluoro-N-(7'-((1-(methylsulfonyl)piperidin-4-yl)oxy)-2'-oxospiro[cyclobutane-1,3'-indolin]-5'-yl)benzenesulfonamide The process of this step was adopted from step-ii of Example-XXXIX. ¹H NMR (400 MHz, DMSO-d₆): δ 10.32 (s, 1H), 10.31 (s, 1H), 7.76-7.71 (m, 2H), 7.44 (dd, J=8.4 Hz & 1.5 Hz, 1H), 6.87 (s, 1H), 6.58 (s, 1H), 4.35-4.34 (m, 1H), 3.27-3.24 (m, 2H), 3.15-3.09 (m, 2H), 2.88 (s, 3H), 2.41-2.33 (m, 2H), 2.21-2.03 (m, 4H), 1.85-1.80 (m, 2H), 1.68-1.64 (m, 2H); LC-MS: m/z 558.1 (M+H)⁺.

213

Example-LV: 5'-((4-Chloro-2-fluorophenyl)sulfonamido)-N-(1-methylpiperidin-4-yl)-2'-oxospiro[cyclobutane-1,3'-indoline]-7'-carboxamide (Compound-211)

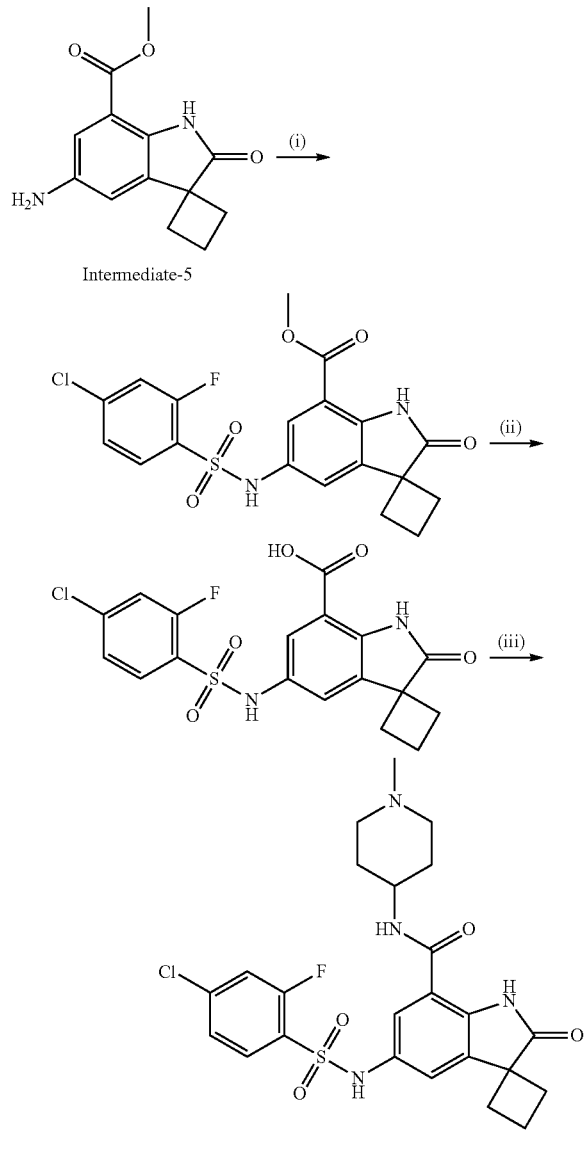

Intermediate-5

214

Step-i: Methyl 5'-((4-chloro-2-fluorophenyl)sulfonamido)-2'-oxospiro[cyclobutane-1,3'-indoline]-7'-carboxylate The process of this step was adopted from step-i of Example-XXXIX. $^1$H NMR (400 MHz, DMSO-$d_6$): δ 10.57 (s, 1H), 10.14 (s, 1H), 7.79-7.72 (m, 2H), 7.51 (d, J=2.0 Hz, 1H), 7.46-7.44 (m, 1H), 7.39 (d, J=2.0 Hz, 1H), 3.81 (s, 3H), 2.42-2.40 (m, 2H), 2.38-2.16 (m, 4H); LCMS: m/z 439.4 (M+H)$^+$.

Step-ii: 5'-((4-Chloro-2-fluorophenyl)sulfonamido)-2'-oxospiro[cyclobutane-1,3'-indoline]-7'-carboxylic acid To a solution of methyl 5'-((4-chloro-2-fluorophenyl)sulfonamido)-2'oxospiro-[cyclobutane-1,3'-indoline]-7'-carboxylate (0.22 g, 0.50 mmol) in a mixture of THF (4 mL) and water (1 mL) was added lithium hydroxide monohydrate (0.06 g, 1.50 mmol) followed by stirring at RT for 16 h. The mixture was concentrated, the residue was diluted with water and acidified with 1 N HCl and extracted with EtOAc. The organic layer was dried over sodium sulphate and concentrated under reduced pressure to afford the title compound as an off white solid (0.2 g). $^1$H NMR (400 MHz, DMSO-$d_6$): δ 13.28-13.21 (bs, 1H), 10.15 (s, 1H), 9.77 (s, 1H), 7.78-7.72 (m, 2H), 7.49-7.44 (m, 2H) 7.36 (d, J=1.9 Hz, 1H), 2.42-2.38 (m, 2H), 2.33-2.12 (m, 4H); LCMS: m/z 423.2 (M−H)$^-$.

Step-iii: 5'-((4-Chloro-2-fluorophenyl)sulfonamido)-N-(1-methylpiperidin-4-yl)-2'-oxospiro[cyclobutane-1,3'-indoline]-7'-carboxamide To a solution of 5'-((4-chloro-2-fluorophenyl)sulfonamido)-2'-oxospiro[cyclobutane-1,3'-indoline]-7'-carboxylic acid (0.08 g, 0.188 mmol) in DCM (3 mL) were added 1-methylpiperidin-4-amine (0.03 g, 0.28 mmol), DIPEA (0.1 mL, 0.57 mmol) and PyBOP (0.2 g, 0.38 mmol) followed by stirring at RT for 16 h. The mixture was diluted with EtOAc (50 mL), washed with water (50 mL) and brine (50 mL), dried over sodium sulphate and concentrated under reduced pressure. The residue was purified by combi-flash to afford the title compound as an off white solid (0.06 g, 50%). $^1$H NMR (400 MHz, DMSO-$d_6$): δ 10.24-10.1.8 (bs, 1H), 9.74 (bs, 1H), 8.31 (d, J=7.8 Hz, 1H), 7.73-7.69 (m, 2H), 7.41 (dd, J=8.3 Hz & 1.4 Hz, 1H), 7.31 (d, J=2.0 Hz, 1H), 7.18 (d, J=2.0 Hz, 1H), 3.74-3.65 (m, 1H), 2.90-2.80 (m, 2H), 2.40-2.35 (m, 2H), 2.17-1.99 (m, 9H), 1.77-1.75 (m, 2H), 1.59-1.55 (m, 2H); LC-MS: m/z 521.2 (M+H)$^+$.

The below compound was prepared by procedure similar to the one described in Example-LV with appropriate variations in reactants, quantities of reagents and reaction conditions. The physiochemical characteristics of the compounds are also summarized

| No | Structure | Characterization Data $^1$H NMR (400 MHz, DMSO-$d_6$)/LC-MS: |
|---|---|---|
| 211.1 | 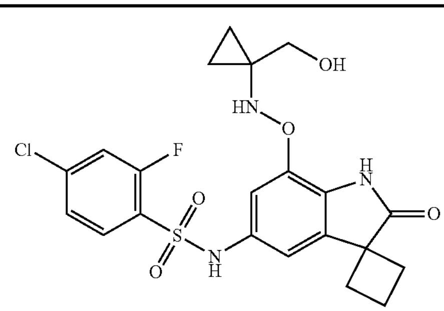 | $^1$H NMR (400 MHz, DMSO-$d_6$): δ 10.33 (s, 1H), 9.76 (s, 1H), 8.66 (s, 1H), 7.73-7.66 (m, 2H), 7.41-7.39 (m, 1H), 7.30 (d, J = 2.0 Hz, 1H), 7.18 (d, J = 2.0 Hz, 1H), 4.73 (t, J = 5.9 Hz, 1H), 3.47 (d, J = 5.9 Hz, 2H), 2.39-2.34 (m, 2H), 2.18-1.99 (m, 4H), 0.72-0.64 (m, 4H); LCMS: m/z 493.9 (M + H)$^+$. |

Example-LVI: 4-Chloro-2-fluoro-N-(2'-oxo-7'-((2-oxo-1,2-dihydropyridin-4-yl)oxy)spiro[cyclobutane-1,3'-indolin]-5'-yl)benzenesulfonamide (Compound-212)

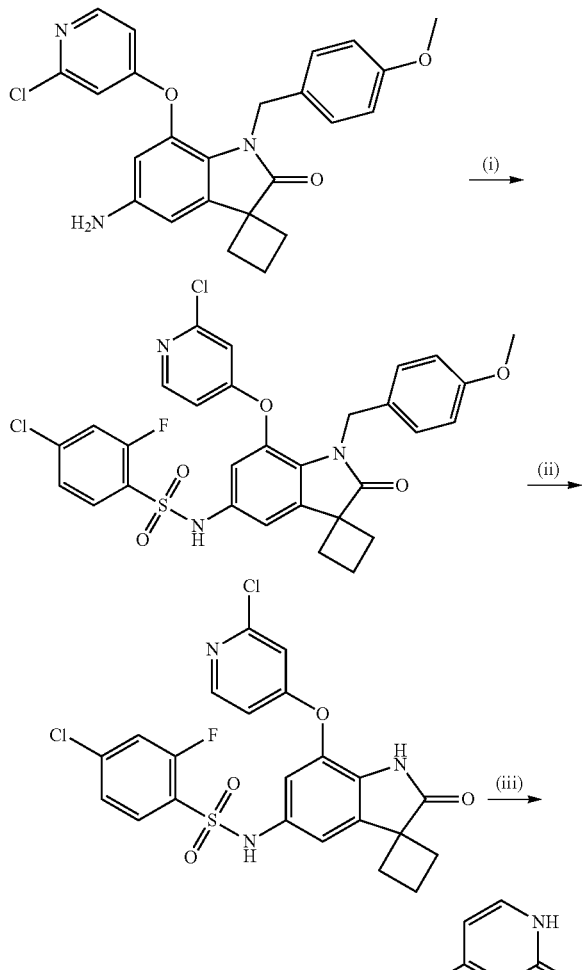

Step-i: 4-Chloro-N-(7'-((2-chloropyridin-4-yl)oxy)-1'-(4-methoxybenzyl)-2'oxo-spiro[cyclobutane-1,3'-indolin]-5'-yl)-2-fluorobenzenesulfonamide The process of this step was adopted from step-i of Example-XXXIX. LCMS: m/z 628.1 (M+H)$^+$.

Step-ii: 4-Chloro-N-(7'-((2-chloropyridin-4-yl)oxy)-2'-oxospiro[cyclobutane-1,3'-indolin]-5'-yl)-2-fluorobenzenesulfonamide:

The process of this step was adopted from step-ii of Example-XXXIX. $^1$H NMR (400 MHz, DMSO-d$_6$): δ 10.54 (s, 1H), 10.49 (s, 1H), 8.23 (d, J=5.4Hz, 1H), 7.74-7.68 (m, 2H), 7.43-7.41 (m, 1H), 7.22 (d, J=2.0 Hz, 1H), 6.85 (d, J=2.0Hz, 1H), 6.67-6.65 (m, 1H), 6.63 (d, J=1.5 Hz, 1H), 2.40-2.38 (m, 2H), 2.20-2.08 (m, 4H); LCMS: m/z 508.0 (M+H)$^+$.

Step-iii: 4-Chloro-2-fluoro-N-(2'-oxo-7'-((2-oxo-1,2-dihydropyridin-4-yl)oxy)-spiro[cyclobutane-L3'-indolin]-5'-yl)benzenesulfonamide A solution of 4-chloro-N-(7'-((2-chloropyridin-4-yl)oxy)-2'-oxospiro[cyclobutane-1,3'-indolin]-5'-yl)-2-fluorobenzenesulfonamide (0.1 g, 0.19 mmol) in TFA (3 mL) was heated to 140° C. for 16 h. The mixture was slowly poured into aqueous NaHCO$_3$, then acidified with aqueous citric acid solution and extracted with DCM. The organic layer was washed with water and brine, dried over sodium sulphate and concentrated under reduced pressure. The residue was purified by preparative HPLC to afford the title compound as white solid (0.015 g, 14%). $^1$H NMR (400 MHz, DMSO-d$_6$): δ 11.36 (bs, 1H), 10.57 (bs, 1H), 10.47 (s, 1H), 7.76-7.71 (m, 2H), 7.45 (d, J=8.3 Hz, 1H), 7.35 (d, J=7.4 Hz, 1H), 7.21 (d, J=1.0 Hz, 1H), 6.61 (d, J=1.5 Hz, 1H), 5.89-5.87 (m, 1H), 5.17 (d, J=2.4 Hz, 1H), 2.67-2.09 (m, 6H); LC-MS: m/z 490.1 (M+H)$^+$.

The below compound was prepared by a procedure similar to the one described in Example-LVI with appropriate variations in reactants, quantities of reagents and reaction conditions. The physiochemical characteristics of the compounds are also summarized.

| No | Structure | Characterization Data $^1$H NMR (400 MHz, DMSO-d$_6$)/LC-MS: |
|---|---|---|
| 213 | (structure shown) | $^1$H NMR (400 MHz, DMSO-d$_6$): δ 11.28 (bs, 1H), 10.31 (bs, 1H), 9.84 (bs, 1H), 7.69 (d, J = 7.9 Hz, 1H), 7.47-7.45 (m, 1H), 7.33 (d, J = 7.3 Hz, 1H), 7.13-7.09 (m, 2H), 6.98 (m, 1H), 6.56 (bs, 1H), 5.87-5.85 (m, 1H), 5.13 (bs, 1H), 3.82 (s, 3H), 2.38-2.32 (m, 2H), 2.18-2.10 (m, 4H); LC-MS: m/z 468.2 (M + H)$^+$. |

Example-LVII: Sodium ((2-methoxyphenyl)sulfonyl)(2'-oxo-7'-(1phenylethyl)-spiro[cyclobutane-1,3'-indolin]-5'-yl)amide (Compound-214)

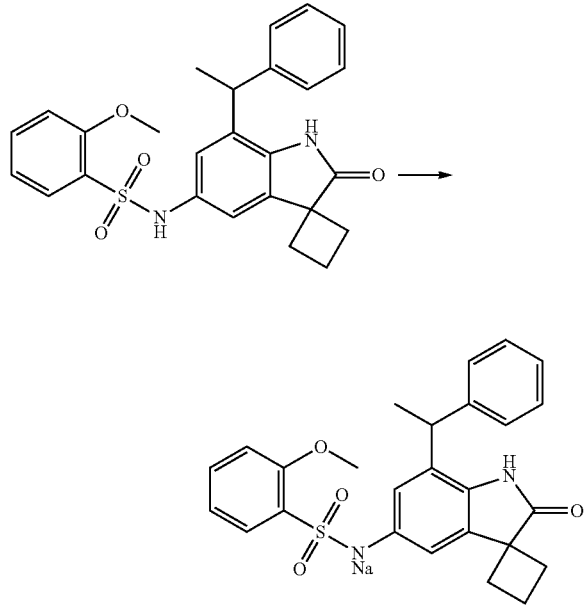

To a solution of 2-methoxy-N-(2'-oxo-7'-(1-phenylethyl)spiro[cyclobutane-1,3'-indolin]-5'-yl)benzenesulfonamide (0.025 g) in acetone (2 mL) was added sodium hydroxide followed by stirring at RT for 0.5 h. The resulted solids were filtered off, washed with hexane and dried under reduced pressure to afford the title compound as white solid (0.025 g, 96%). $^1$H NMR (400 MHz, DMSO-$d_6$): δ 9.80-9.78 (bs, 1H), 7.74 (d, J=7.6 Hz, 1H), 7.28-7.22 (m, 1H), 7.20-7.18 (m, 4H), 7.13-7.10 (m, 1H), 6.93 (d, J=8.3 Hz, 1H), 6.87-6.85 (m, 2H), 6.52 (s, 1H), 4.08-3.69 (m, 1H), 3.69 (s, 3H), 2.35-2.28 (m, 2H), 2.13-1.99 (m, 4H), 1.36 (d, J=7.6 Hz, 3H); LC-MS: m/z 463.5 (M+H)$^+$.

Example-LVIII: N-(4'-chloro-7'-((1-methylpiperidin-4-yl)oxy)-2'-oxospiro-[cyclobutane-1,3'-indolin]-5'-yl)-2-methoxybenzenesulfonamide (Compound-215)

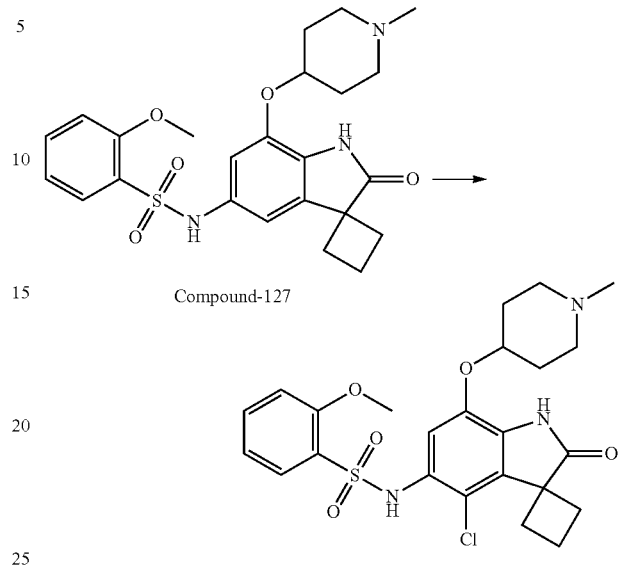

Compound-127

To an ice cold solution of 2-methoxy-N-(7'-((1-methylpiperidin-4-yl)oxy)-2'-oxospiro[cyclobutane-1,3'-indolin]-5'-yl)benzenesulfonamide (0.15 g, 0.32 mmol, Compound-127) in acetonitrile (2.0 mL) was added NCS (0.05 g, 0.35 mmol) followed by stirring at RT for 16 h. The mixture was poured into aqueous NaHCO$_3$ and extracted with DCM. The organic layer was dried over sodium sulphate and concentrated under reduced pressure. The residue was purified by combi-flash to afford the title compound as off white solid (0.06 g, 37%). $^1$H NMR (400 MHz, DMSO-$d_6$): δ 10.46 (s, 1H), 9.37 (bs, 1H), 7.60 (d, J=7.8 Hz, 2H), 7.24 (d, J=8.4 Hz, 1H), 7.00 (t, J=7.3 Hz, 1H), 6.51 (s, 1H), 3.95 (bs, 1H), 3.87 (s, 3H), 2.71-2.64 (m, 4H), 2.24-2.12 (m, 9H), 1.70-1.67 (m, 2H), 1.55-1.50 (m, 2H); LC-MS: m/z 506.2 (M+H)$^+$.

The below compound was prepared by procedure similar to the one described in Example-LVIII with appropriate variations in reactants, quantities of reagents and reaction conditions. The physiochemical characteristics of the compounds are also summarized.

| No | Structure | Characterization Data $^1$H NMR (400 MHz, DMSO-$d_6$)/LC-MS: |
|---|---|---|
| 216 | 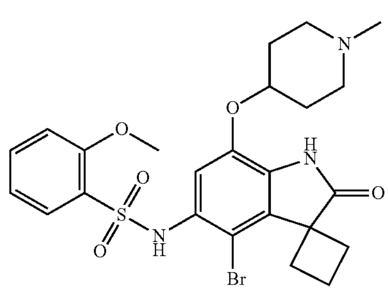 [SMILES: COc1ccccc1S(=O)(=O)Nc1cc(OC2CCN(C)CC2)c2c(c1Br)C1(CCC1)C(=O)N2] | $^1$H NMR (400 MHz, DMSO-$d_6$): δ 10.54 (s, 1H), 9.37 (bs, 1H), 7.65-7.59 (m, 2H), 7.25 (d, J = 8.3 Hz, 1H), 7.01 (t, J = 7.8 Hz, 1H), 6.49 (s, 1H), 4.07 (bs, 1H), 3.87 (s, 3H), 2.82-2.78 (m, 4H), 2.38-2.29 (m, 4H), 2.26-2.08 (m, 5H), 1.71-1.70 (m, 2H), 1.58-1.49 (m, 2H); LC-MS: m/z 550.1 (M + H)$^+$. |

Example-LIX: (5'-((2-Methoxyphenyl)sulfonamido)-2'oxospiro[cyclobutane-1,3'-indolin]-7'-yl)boronic acid (Compound-217)

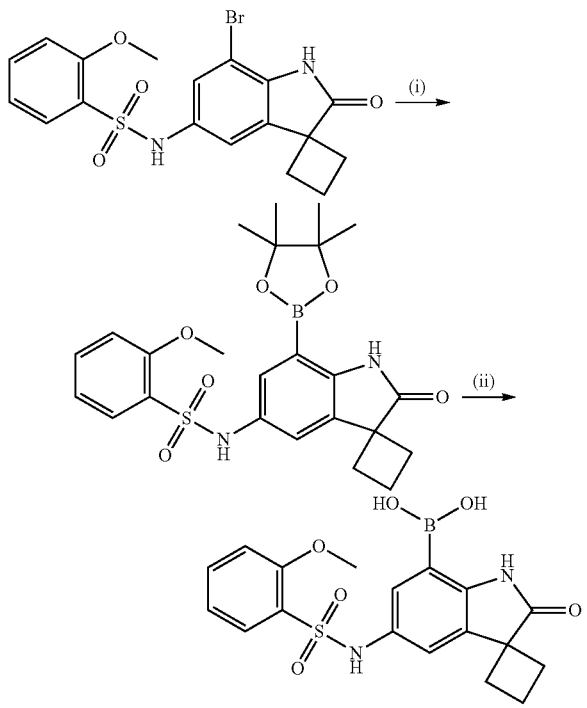

Step-i: 2-Methoxy-N-(2'-oxo-7'-(4,4,5,5-tetramethyl-1,3,2-dioxaborolan-2-yl)-spiro[cyclobutane-1,3'-indolin]-5'-yl) benzenesulfonamide To a solution of N-(7'-bromo-2'-oxospiro[cyclobutane-1,3'-indolin]-5'-yl)-2-methoxybenzenesulfonamide (0.5 g, 1.14 mmol, Intermediate-2) and 4,4,4',4',5,5,5',5'-octamethyl-2,2'-bi(1,3,2-dioxaborolane) (0.87 g, 3.42 mmol) in 1,4-dioxane (15 mL) was added potassium acetate (0.33 g, 3.42 mmol) followed by degassing with nitrogen purging for 15 min. Then Pd(dppf)$_2$Cl$_2$.DCM (0.093 g, 0.114 mmol) was added followed by degassing again with nitrogen purging for 15 min. The mixture was then heated to 100° C. for 16 h. The mixture was diluted with water and extracted with EtOAc. The organic layer was dried over sodium sulphate and concentrated under reduced pressure. The residue was purified by combi-flash to afford the title compound as white solid (0.25 g, 45%). $^1$H NMR (400 MHz, DMSO-d$_6$): δ 9.98 (s, 1H), 8.90 (s, 1H), 7.66 (d, J=7.8 Hz, 1H), 7.54 (t, J=7.4 Hz, 1H), 7.33 (d, J=1.5 Hz, 1H), 7.17 (d, J=8.3 Hz, 1H), 7.12 (d, J=1.5 Hz, 1H), 6.98 (t, J=7.3 Hz, 1H), 3.91 (s, 3H), 2.40-2.37 (m, 2H), 2.30-2.11 (m, 1H), 2.15-2.04 (m, 3H), 1.16 (s, 12H).

Step-ii: (5'-((2-Methoxyphenyl)sulfonamido)-2'-oxospiro[cyclobutane-1,3'-indolin]-7'-yl)boronic acid To an ice cold solution of 2-methoxy-N-(2'-oxo-7'-(4,4,5,5-tetramethyl-1,3,2-dioxaborolan-2-yl)spiro[cyclobutane-1,3'-indolin]-5'-yl)benzenesulfonamide (0.15 g, 0.31 mmol) in a mixture of acetone (1 mL) and water (0.5 mL) were added NH$_4$OAc (0.14 g, 1.86 mmol) and NaIO$_4$ (0.4 g, 1.86 mmol) followed by stirring at RT for 3 days. The reaction mixture was quenched with 2 N NaOH and then acidified with 1 N HCl followed by extraction with EtOAc. The organic layer was washed with brine, dried over sodium sulphate and concentrated under reduced pressure. The residue was purified by preparative HPLC to afford the title compound as white solid (0.05 g, 40%). $^1$H NMR (400 MHz, DMSO-d$_6$): δ 9.48 (bs, 1H), 8.85 (bs, 1H), 8.27-8.25 (bs, 2H), 7.63 (dd, J=7.8 Hz & 1.5 Hz, 1H), 7.56-7.51 (m, 1H), 7.29 (d, J=2.0 Hz, 1H), 7.19-7.16 (m, 2H), 6.96 (t, J=7.3 Hz, 1H), 3.93 (s, 3H), 2.38-2.34 (m, 3H), 2.17-2.00 (m, 3H); LC-MS: m/z 403.1 (M+H)$^+$.

Example-LX: N-(7'-((1-methylpiperidin-4-yl)oxy)2'-oxospiro[cyclobutane-1,3'-indolin]-5'-yl)-3-phenylpropanamide (Compound-218)

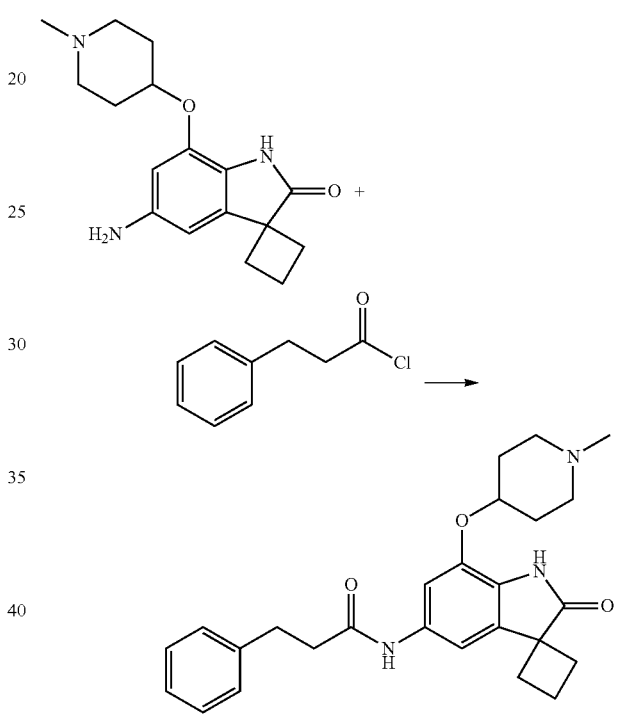

To an ice cold solution of 5'-amino-7'-((1-methylpiperidin-4-yl)oxy)spiro-[cyclobutane-1,3'-indolin]-2'-one (0.05 g, 0.16 mmol) in DCM (3 mL) was added pyridine (0.03 mL, 0.33 mmol) and 3-phenylpropanoyl chloride (0.03 mL, 0.19 mmol) followed by stirring at RT for 1 h. The mixture was diluted with DCM and washed with aqueous NaHCO$_3$. The organic layer was dried over sodium sulphate and concentrated under reduced pressure. The residue was purified by combi-flash to afford the title compound as an off white solid (0.03 g, 42%). $^1$H NMR (400 MHz, DMSO-d$_6$): δ 10.15 (s, 1H), 9.79 (s, 1H), 7.42 (s, 1H), 7.30-7.17 (m, 6H), 4.18 (bs, 1H), 2.90 (t, J=7.4 Hz, 2H), 2.74-2.62 (m, 2H), 2.61-2.57 (m, 2H), 2.42-2.40 (m, 2H), 2.23-2.04 (m, 9H), 1.97-1.82 (m, 2H), 1.69-1.67 (m, 2H); LC-MS: m/z 434.3 (M+H)$^+$.

The below compound was prepared by a procedure similar to the one described in Example-LX with appropriate variations in reactants, quantities of reagents and reaction conditions. The physiochemical characteristics of the compounds are also summarized.

| No | Structure | Characterization Data ¹H NMR (400 MHz, DMSO-d₆)/LC-MS: |
|---|---|---|
| 219 | 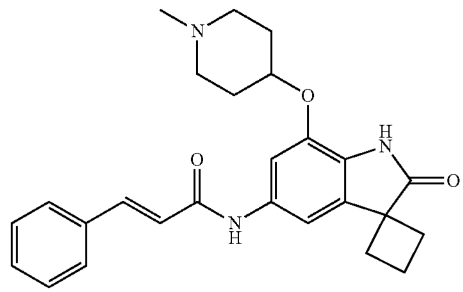 [SMILES: CN1CCC(Oc2cc(NC(=O)/C=C/c3ccccc3)cc3c2NC(=O)C32CCC2)CC1] | ¹H NMR (400 MHz, DMSO-d₆): δ 10.22 (s, 1H), 10.13 (s, 1H), 7.62-7.58 (m, 2H), 7.54-7.53 (m, 2H), 7.45-7.36 (m, 4H), 6.81-6.77 (m, 1H), 4.28 (bs, 1H), 2.81-2.76 (m, 2H), 2.50-2.44 (m, 2H), 2.28-2.20 (m, 9H), 1.97-1.87 (m, 2H), 1.80-1.61 (m, 2H); LC-MS: m/z 432.2 (M + H)⁺. |

Example-LXI: N-7'-((1-acetylpiperidin-4-yl)oxy)-2'-oxospiro[cyclobutane-1,3'-indolin]-5'-yl)-2-methoxybenzenesulfonamide (Compound-220)

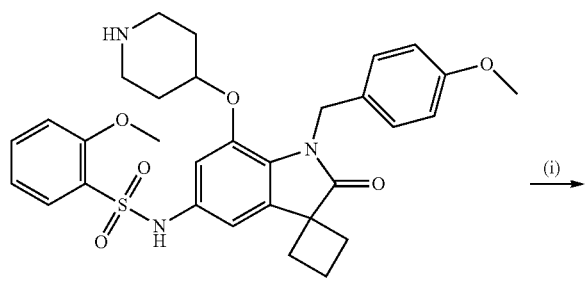

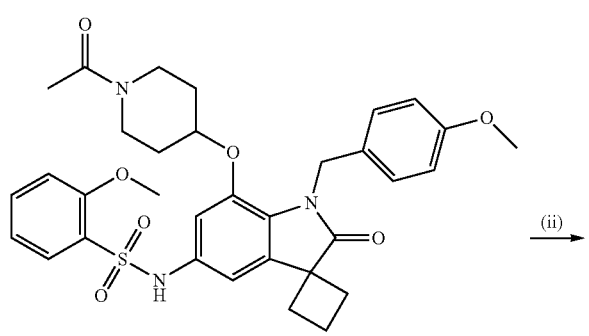

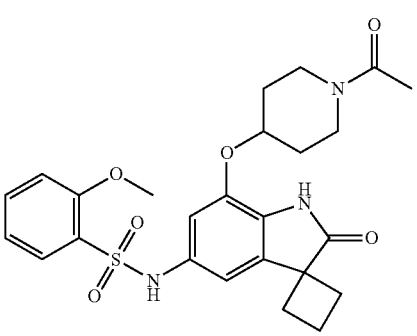

Step-i: N-(7'-((1-acetylpiperidin-4-yl)oxy)-1'-(4-methoxybenzyl)-2'-oxospiro-[cyclobutane-1,3'-indolin]-5'-yl)-2-methoxybenzenesulfonamide To an ice cold solution of 2-methoxy-N-(1'-(4-methoxybenzyl)-2'-oxo-7'-(piperidin-4-yloxy)spiro[cyclobutane-1,3'-indolin]-5'-yl)benzenesulfonamide (0.15 g, 0.26 mmol) and acetic acid (0.05 mL, 0.78 mmol) in DCM (3 mL) were added EDC.HCl (0.15 g, 0.78 mmol), HOBt (0.1 g, 0.72 mmol) and DIPEA (0.23 mL, 1.30 mmol) followed by stirring at RT for 16 h. The mixture was diluted with DCM and washed with water. The organic layer was dried over sodium sulphate and concentrated under reduced pressure. The residue was purified by combi-flash to afford the title compound as an off-white solid (0.13 g, 80%). ¹H NMR (400 MHz, DMSO-d₆): δ 10.51 (s, 1H), 9.75 (s, 1H), 7.74-7.72 (m, 1H), 7.60-7.55 (m, 1H), 7.19 (d, J=7.8 Hz, 1H), 7.03 (t, J=7.8 Hz, 1H), 7.00-6.93 (m, 3H), 6.79 (d, J=8.3 Hz, 2H), 6.61 (d, J=1.4 Hz, 1H), 4.90 (s, 2H), 4.25-4.23 (m, 1H), 3.90 (s, 3H), 3.69-3.67 (m, 1H), 3.67 (s, 3H), 3.44-2.41 (m, 1H), 3.17-3.13 (m, 1H), 3.01-2.97 (m, 1H), 2.49-2.40 (m, 2H), 2.24-2.06 (m, 4H), 1.96 (s, 3H), 1.66-1.59 (m, 2H), 1.19-1.13 (m, 2H); LCMS: m/z 620.0 (M+H)⁺.

Step-ii: N-(7'-((1-acetylpiperidin-4-yl)oxy)-2'-oxospiro[cyclobutane-1,3'-indolin]-5'-yl)-2-methoxybenzenesulfonamide The process of this step was adopted from step-ii of Example-XXXIX. ¹H NMR (400 MHz, DMSO-d₆): 610.24 (s, 1H), 9.65 (s, 1H), 7.70-7.67 (m, 1H), 7.58-7.54 (m, 1H), 7.18 (d, J=8.3 Hz, 1H), 7.00 (t, J=7.8 Hz, 1H), 6.87 (d, J=1.5 Hz, 1H), 6.59 (d, J=1.4 Hz, 1H), 4.32-4.29 (m, 1H), 3.92 (s, 3H), 3.63-3.55 (m, 2H), 3.40-3.28 (m, 2H), 2.38-2.33 (m, 2H), 2.16-2.05 (m, 4H), 2.00 (s, 3H) 1.76-1.61 (m, 2H), 1.53-1.41 (m, 2H); LCMS: m/z 500.0 (M+H)⁺.

The below compound was prepared by a procedure similar to the one described in Example-LXI with appropriate variations in reactants, quantities of reagents and reaction conditions. The physiochemical characteristics of the compounds are also summarized.

| No | Structure | Characterization Data<br>¹H NMR (400 MHz, DMSO-d₆)/LC-MS: |
|---|---|---|
| 221 | 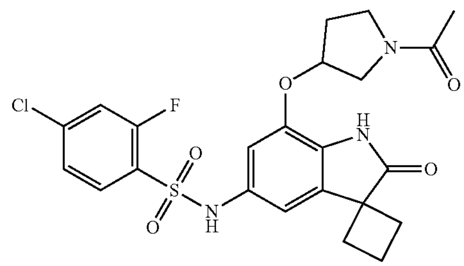 [SMILES: CC(=O)N1CCC(Oc2cc(NS(=O)(=O)c3ccc(Cl)cc3F)cc3c2NC(=O)C32CCC2)C1] | ¹H NMR (400 MHz, DMSO-d₆): δ 10.33 (s, 1H), 10.31-10.26 (m, 1H), 7.78-7.71 (m, 2H), 7.44 (d, J = 10.3 Hz, 1H), 6.87-6.85 (m, 1H), 6.59-6.57 (m, 1H), 4.85-4.80 (m, 1H), 3.71-3.32 (m, 4H), 2.40-2.34 (m, 2H), 2.20-1.98 (m, 6H), 1.96 (s, 3H); LCMS: m/z 507.9 (M + H)⁺. |

Example-LXII: N-(7'-bromo-2'-oxospiro[cyclobutane-1,3'-indolin]-5'-yl)-2-morpholinonicotinamide (Compound-222) & N-(7'-cyclopropyl-2'oxospiro[cyclobutane-1,3'-indolin]-5'-yl)-2-morpholinonicotinamide (Compound-223)

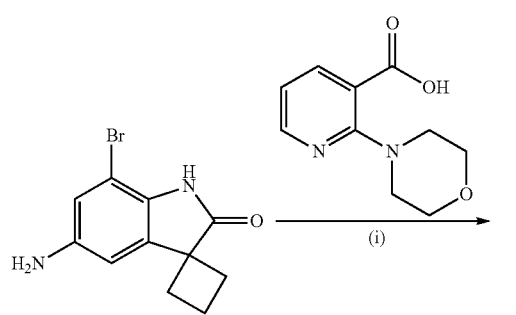

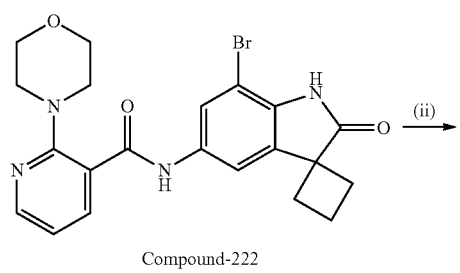

Compound-222

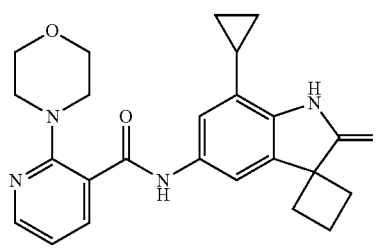

Compound-223

Step-i: N-(7'-bromo-2'-oxospiro[cyclobutane-1,3'-indolin]-5'-yl)-2-morpholino-nicotinamide To an ice cold solution of 5'-amino-7'-bromospiro[cyclobutane-1,3'-indolin]-2'-one (1.0 g, 3.74 mmol) and 2-morpholinonicotinic acid (0.93 g, 4.48 mmol) in DCM (20 mL) were added EDC.HCl (1.4 g, 7.48 mmol), HOBt (0.57 g, 3.74 mmol), DMAP (0.09 g, 0.75 mmol) and DIPEA (2.0 mL, 11.22 mmol) followed by stirring at RT for 16 h. The mixture was diluted with DCM and washed with water. The organic layer was dried over sodium sulphate and concentrated under reduced pressure. The residue was purified by combi-flash to afford the title compound as an off-white solid (0.6 g, 35%). ¹H NMR (400 MHz, DMSO-d₆): δ 10.52 (s, 1H), 10.48 (s, 1H), 8.32-8.31 (m, 1H), 7.91 (s, 1H), 7.83-7.81 (m, 1H), 7.79 (s, 1H), 7.00-6.97 (m, 1H), 3.65-3.64 (m, 4H), 3.30-3.28 (m, 4H), 2.50-2.45 (m, 2H), 2.31-2.11 (m, 4H); LC-MS: m/z 459.1 (M+H)⁺.

Step-ii: N-(7'-cyclopropyl-2'-oxospiro [cyclobutane-1,3'-indolin]-5'-yl)-2-morpholinonicotinamide The process of this step was adopted from Example-I. ¹H NMR (400 MHz, CDCl₃): δ 10.95 (s, 1H), 8.47-8.44 (m, 2H), 8.00 (s, 1H), 7.67 (s, 1H), 7.23-7.20 (m, 1H), 7.09 (s, 1H), 3.93-3.92 (m, 4H), 3.31-3.29 (m, 4H), 2.71-2.65 (m, 2H), 2.45-2.31 (m, 3H), 2.28-2.20 (m, 1H), 1.81-1.74 (m, 1H), 0.97 (d, J=8.4 Hz, 2H), 0.67 (d, J=4.9 Hz, 2H); LC-MS: m/z 419.2 (M+H)⁺.

The below compounds were prepared by a procedure similar to the one described in step-i of Example-LXII with appropriate variations in reactants, quantities of reagents and reaction conditions. The physiochemical characteristics of the compounds are also summarized.

| No | Structure | Characterization Data<br>¹H NMR (400 MHz, DMSO-$d_6$)/LC-MS: |
|---|---|---|
| 224 | 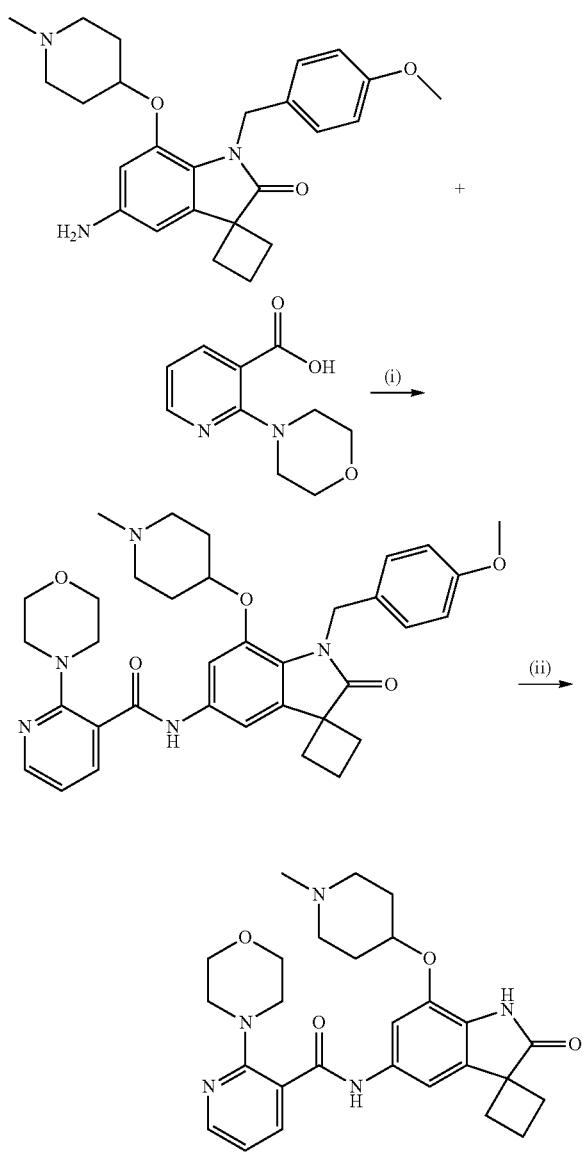 | ¹H NMR (400 MHz, DMSO-$d_6$): δ 10.29 (s, 1H), 10.24 (s, 1H), 7.71 (t, J = 8.3 Hz, 1H), 7.63-7.61 (m, 2H), 7.43 (d, J = 8.3 Hz, 1H), 7.28 (s, 1H), 4.24 (bs, 1H), 2.74-2.67 (m, 2H), 2.50-2.44 (m, 2H), 2.38-2.08 (m, 9H), 1.97-1.82 (m, 2H), 1.78-1.62 (m, 2H); LC-MS: m/z 458.2 (M + H)⁺. |

Example-LXIII: N-(7'-((1-methylpiperidin-4-yl)oxy)-2'oxospiro[cyclobutane-1,3'-indolin]-5'-yl)-2-morpholinonicotinamide (Compound-225)

Step-i: N-(1'-(4-methoxybenzyl)-7'-((1-methylpiperidin-4-yl)oxy)-2'-oxospiro-[cyclobutane-1,3'-indolin]-5'-yl)-2-morpholinonicotinamide The process of this step was adopted from step-i of Example-LXII. ¹H NMR (400 MHz, DMSO-$d_6$): δ 10.40 (s, 1H), 8.32-8.31 (m, 1H), 7.85-7.82 (m, 1H), 7.74 (d, J=1.9 Hz, 1H), 7.28-7.27 (m, 1H), 7.08 (d, J=8.8 Hz, 2H), 6.86 (d, J=8.8 Hz, 2H), 6.58 (d, J=4.9 Hz, 1H), 5.03 (s, 2H), 4.22-4.20 (m, 1H), 3.77 (s, 3H), 3.67-3.64 (m, 4H), 3.28-3.26 (m, 4H), 2.33-2.27 (m, 4H), 2.17-2.05 (m, 9H), 1.92-1.86 (m, 2H), 1.60-1.50 (m, 2H); LC-MS: m/z 612.1 (M+H)⁺.

Step-ii: N-(7'-((1-methylpiperidin-4-yl)oxy)-2'-oxospiro[cyclobutane-1,3'-indolin]-5'-yl)-2-morpholinonicotinamide The process of this step was adopted from step-ii of Example-XXXIX. ¹H NMR (400 MHz, DMSO-$d_6$): δ 10.35 (s, 1H), 10.21 (s, 1H), 8.32 (d, J=3.9 Hz, 1H), 7.84 (d, J=7.4 Hz, 1H), 7.66 (s, 1H), 7.28 (s, 1H), 7.01-6.98 (m, 1H), 4.22 (bs, 1H), 3.69-3.66 (m, 4H), 3.31-3.27 (m, 4H), 2.72-2.67 (m, 2H), 2.50-2.41 (m, 2H), 2.29-2.14 (m, 9H), 1.91-1.82 (m, 2H), 1.74-1.67 (m, 2H); LC-MS: m/z 492.1 (M+H)⁺.

Example-LXIV: 4-Fluoro-N-(2'-oxo-7'-((6-oxo-1,2,3,6-tetrahydropyridin-4-yl)-amino)spiro[cyclobutane-1,3'-indolin]-5'-yl)benzenesulfonamide (Compound-226)

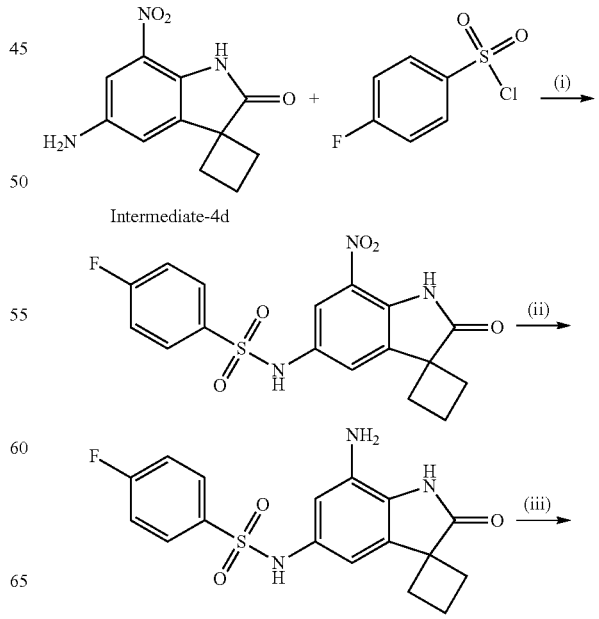

-continued

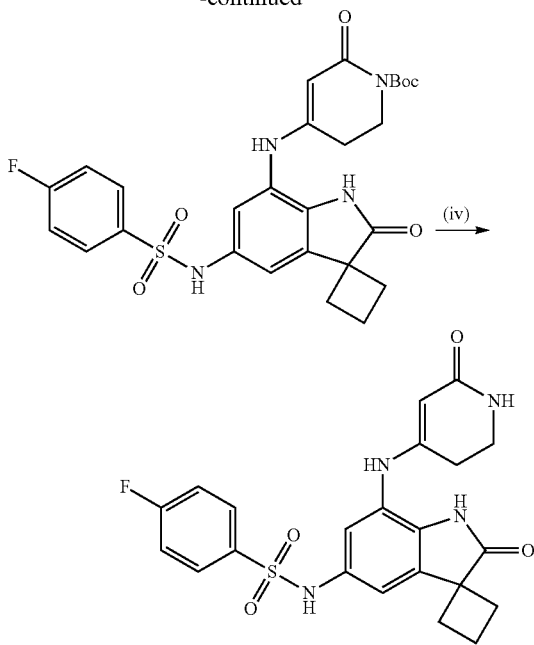

mmol) in DCE (2 mL) was added tert-butyl 2,4-dioxopiperidine-1-carboxylate (0.13 g, 0.61) and AcOH (0.05 mL) followed by stirring at RT for 16 h. The mixture concentrated under reduced pressure. The residue was purified by combi-flash to afford the title compound as white solid (0.1 g, 43%). $^1$H NMR (400 MHz, DMSO-$d_6$): δ 10.12 (s, 1H), 10.05 (s, 1H), 8.38 (bs, 1H), 7.76-7.73 (m, 2H), 7.42-7.37 (m, 2H), 7.11 (s, 1H), 6.67 (s, 1H), 4.22 (s, 1H), 3.71-3.70 (m, 2H), 2.42-2.39 (m, 3H), 2.17-2.08 (m, 5H), 1.43 (s, 9H); LCMS: m/z 555.0(M–H)$^-$.

Step-iv: 4-Fluoro-N-(2'-oxo-7'-((6-oxo-1,2,3,6-tetrahydropyridin-4-yl)amino)-spiro[cyclobutane-1,3'-indolin]-5'-yl)benzenesulfonamide The process of this step was adopted from step-ii of Example-L. $^1$H NMR (400 MHz, DMSO-$d_6$): δ 10.02-9.99 (bs, 2H), 7.76-7.73 (m, 3H), 7.40 (t, J=8.8 Hz, 2H), 7.04 (d, J=1.4 Hz, 1H), 6.71 (d, J=1.9 Hz, 1H), 6.56 (s, 1H), 4.24 (s, 1H), 3.22-3.18 (m, 2H), 2.41-2.33 (m, 4H), 2.18-2.08 (m, 4H); LCMS: m/z 457.1 (M+H)$^+$.

The below compounds were prepared by a procedure similar to the one described in Example-LXIV with appropriate variations in reactants, quantities of reagents and reaction conditions. The physiochemical characteristics of the compounds are also summarized.

| No | Structure | Characterization Data $^1$H NMR (400 MHz, DMSO-$d_6$)/LC-MS: |
|---|---|---|
| 227 | 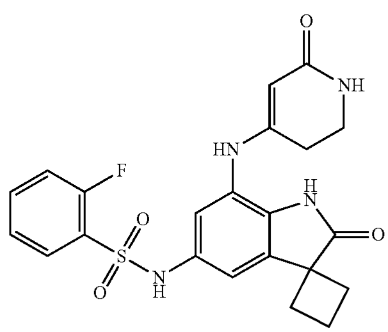 [SMILES: O=C1C=C(Nc2cc(NS(=O)(=O)c3ccccc3F)cc3c2NC(=O)C32CCC2)CCN1] | $^1$H NMR (400 MHz, DMSO-$d_6$): δ 10.32 (s, 1H), 9.99 (s, 1H), 7.79-7.73 (m, 2H), 7.67-7.65 (m, 1H), 7.46-7.40 (m, 1H), 7.33 (t, J = 7.9 Hz, 1H), 7.09 (d, J = 1.4 Hz, 1H), 6.76 (d, J = 2.0 Hz, 1H), 6.56 (s, 1H), 4.24 (s, 1H), 3.23-3.19 (m, 2H), 2.42-2.33 (m, 4H), 2.20-2.07 (m, 4H); LCMS: m/z 456.9 (M + H)$^+$. |

Step-i: 4-Fluoro-N-(7'-nitro-2'-oxospiro[cyclobutane-1,3'-indolin]-5'-yl)-benzenesulfonamide The process of this step was adopted from step-i of Example-XXXIX. $^1$H NMR (400 MHz, DMSO-$d_6$): δ 11.03 (s, 1H), 10.48 (s, 1H), 7.82-7.79 (m, 2H), 7.63 (d, J=2.0 Hz, 1H), 7.57 (d, J=1.9 Hz, 1H), 7.42 (t, J=8.8 Hz, 2H), 2.45-2.08 (m, 6H); LCMS: m/z 390.9 (M–H)$^-$.

Step-ii: N-(7'-amino-2'-oxospiro[cyclobutane-1,3'-indolin]-5'-yl)-4-fluoro-benzenesulfonamide The process of this step was adopted from step-d of intermediate-18. $^1$H NMR (400 MHz, DMSO-$d_6$): δ 9.71 (s, 1H), 9.66 (s, 1H), 7.77-7.73 (m, 2H), 7.38 (t, J=8.8 Hz, 2H), 6.45 (d, J=1.4 Hz, 1H), 6.27 (d, J=1.5 Hz, 1H), 4.90 (s, 2H), 2.38-2.33 (m, 2H), 2.16-2.00 (m, 4H); LCMS: m/z 361.9 (M+H)$^+$.

Step-iii: tert-Butyl 4-((5'-((4-fluorophenyl)sulfonamido)-2'-oxospiro[cyclobutane-1,3'-indolin]-7'-yl)amino)-6-oxo-3,6-dihydropyridine-1(2H)-carboxylate To a solution of N-(7'-amino-2'-oxospiro[cyclobutane-1,3'-indolin]-5'-yl)-4-fluorobenzenesulfonamide (0.15 g, 0.41

Example-LXV: 5'-(((2-Methoxyphenyl)(methyl)(oxo)-l6-sulfanylidene)amino)-7'-((1-methylpiperidin-4-yl)oxy)spiro[cyclobutane-1,3'-indolin]-2'-one (Compound-228)

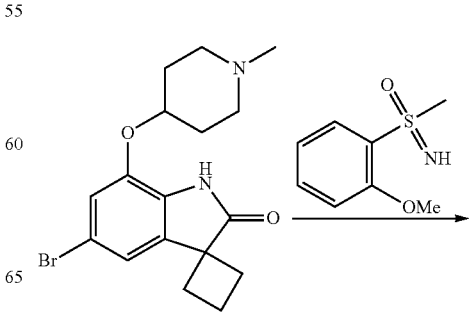

229

-continued

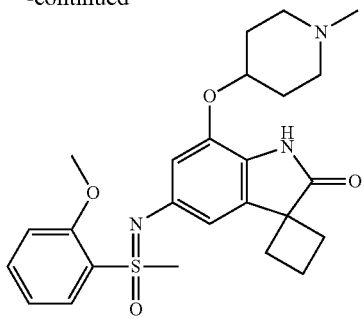

To a solution of 5'-bromo-7'-((1-methylpiperidin-4-yl) oxy)spiro[cyclobutane-1,3'-indolin]-2'-one (0.15 g, 0.41 mmol) and imino(2-methoxyphenyl)(methyl)-l6-sulfanone (0.075 g, 0.41 mmol) in 1,4-dioxane (3 mL) was added $K_3PO_4$ (0.26 g, 1.23 mmol) followed by degassing with nitrogen purging for 15 min. Then $Pd_2(dba)_3$ (0.04 g, 0.041 mmol) and XPhos (0.02 g, 0.041 mmol) were added followed by again degassing with nitrogen purging for 15 min. The mixture was heated to 100° C. for 16 h. The mixture diluted with EtOAc and washed with water. The organic layer was dried over sodium sulphate and concentrated under reduced pressure. The residue was purified by combi-flash to afford the title compound as pale brown solid (0.07 g, 22%). $^1$H NMR (400 MHz, DMSO-$d_6$): δ 9.93 (bs, 1H), 7.86 (d, J=7.9 Hz, 1H), 7.60-7.58 (m, 1H), 7.21 (d, J=8.3 Hz, 1H), 7.12-7.09 (m, 1H), 6.60 (s, 1H), 6.23 (s, 1H), 3.96-3.94 (m, 1H), 3.90 (s, 3H), 3.39 (s, 3H), 2.67-2.33 (m, 4H), 2.16-2.03 (m, 9H), 1.69-1.60 (m, 2H), 1.49-1.41 (m, 2H); LC-MS: m/z 470.0 (M+H)$^+$.

Example-LXVI: 2-Methoxy-N-(7'-((1-methyl-6-oxo-1,2,3,6-tetrahydropyridin-4-yl)amino)-2'-oxospiro[cyclobutane-1,3'-indolin]-5'-yl)benzenesulfonamide (Compound-229)

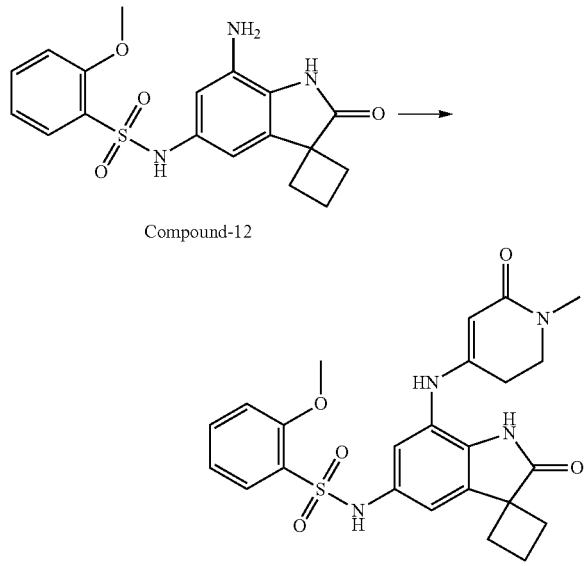

Compound-12

The process of this step was adopted from step-iii of Example-LXIV. $^1$H NMR (400 MHz, DMSO-$d_6$): δ 9.94 (s, 1H), 9.77 (s, 1H), 7.72-7.67 (m, 2H), 7.54-7.52 (m, 1H), 7.18 (d, J=8.3 Hz, 1H), 7.08 (d, J=1.9 Hz, 1H), 7.01-6.98 (m, 1H), 6.76 (d, J=1.9 Hz, 1H), 4.31 (s, 1H), 3.92 (s, 3H),

230

3.31-3.28 (m, 2H), 2.76 (s, 3H), 2.47-2.33 (m, 3H), 2.18-2.08 (m, 5H); LCMS: m/z 483.0 (M+H)$^+$.

Biological Data

In-Vitro biochemical data of spiro[cyclobutane-1,3'-indolin]-2'-one derivatives in time-resolved fluorescence resonance energy transfer (TR-FRET) assay.

The Bet bromodomain TR-FRET assay has been used to identify compounds that bind to Bet BRD4 bromodomain and prevent its interaction with acetylated histone peptides (Chung, C. et al., J. Med. Chem., 54, 3827-3838, 2011).

In the assay, optimized concentration of in-house Bet BRD4 full length bromo-domain protein and 300 nM of acetyl histone peptide substrate were diluted in assay buffer (50 mM HEPES, pH: 7.5, 50 mM NaCl, 500 μM CHAPS) and were added to the positive control and test control wells in a 384 well plate. Substrate control wells have 300 nM of acetyl histone peptide substrate diluted in assay buffer. Buffer blank wells were added with assay buffer. The reaction mixture was allowed for incubation at RT for 30 min. Stock solutions of test compounds at 20 mM DMSO were prepared. Compounds were serially diluted and added to the test wells in 384-well polypropylene plates. The reaction mixture was further incubated for 30 min at RT on a plate shaker. 2 nM of Europium labeled streptavidin and 10 nM of XL-665 labeled antibody diluted in detection buffer (50 mM HEPES, pH: 7.5, 50 mM NaCl, 500 μM CHAPS and 800 mM KF) were added to all the wells excluding the buffer blank wells. The reaction plate was incubated for additional 30 min at RT on plate shaker. The plate was read in Perkin Elmer WALLAC 1420 Multilabel Counter Victor 3 (Ex: 340 nm Em: 615 and 665 nm). The amount of displacement of the peptide was measured as ratio of specific 665 nm energy transfer signal to 615 nm signals. The $IC_{50}$ of the compounds was determined by fitting the dose response data to sigmoid curve fitting equation using Graph Pad Prism software V5.

The compounds were screened in the above mentioned assay and the results ($IC_{50}$) are summarized in the table below. The $IC_{50}$ values of the compounds are set forth in below Table 1 wherein "A" refers to an $ICs_{50}$ value of less than 600 nM, "B" refers to $IC_{50}$ value in range of 600.01 to 1000 nM and "C" refers to $IC_{50}$ value of greater than 1000 nM.

TABLE 1

| Group | Compound No. |
|---|---|
| A | 1, 4, 5, 9, 10, 11, 12, 13, 14, 15, 16, 17, 18, 19, 21, 23, 24, 25, 27, 28, 29, 30, 31, 32, 33, 34, 38, 39, 41, 50, 52, 54, 56, 57, 58, 60, 64, 65, 66, 68, 69, 70, 71, 73, 74, 76, 77, 78, 79a, 86, 87, 88, 89, 92, 93, 94, 95, 96, 98, 103, 104, 105, 106, 113, 114, 116, 121, 122, 123, 124, 125, 127-130, 132-149, 151-154, 156-172, 176-178, 180, 183-185, 187-192, 194-210, 212-214, 219, 220. |
| B | 2, 3, 6, 7, 8, 22, 35, 36, 42, 43, 49, 51, 55, 63, 67, 75a, 83, 84, 99, 102, 115, 126, 131, 150, 155, 175, 211, 215. |
| C | 20, 26, 37, 44, 45, 46, 47, 48, 53, 59, 61, 62, 72, 75, 80, 81, 85, 100, 173, 174, 179, 181, 182, 186, 216, 217, 222-224. |

Biochemical Assay Protocol for Studying Selectivity for BD1 Inhibition Over BD2 Inhibition The selectivity ratio of the compounds for BD1 inhibition over BD2 inhibition can be determined using the fluorescence resonance energy transfer (TR-FRET) assay protocol described above, but using BRD4 BD1 and BRD4 BD2 proteins instead of full length BRD4 protein.

The compounds were screened in the above mentioned assay for determining the selectivity for BRD4 BD1 inhibition over BRD4 BD2 inhibition. The results are summarized in the Table 2 below wherein "A" refers to a selectivity higher than 10 fold, "B" refers to selectivity between 2-10 fold. The selectivity ratios were calculated based on $IC_{50}$ values for BD1 and BD2 inhibition. The compounds appeared to exhibit substantial selectivity for inhibiting BD1 protein over BD2 protein.

TABLE 2

| Group | Compound No. |
|---|---|
| A | 9, 11, 17, 24, 35, 39, 43, 50-52, 54-58, 60, 63, 64, 65, 66-68, 70-74, 76, 78, 79a, 81, 83-85, 89, 92-96, 100, 103-105, 113-115, 127-130, 132-145, 149-154, 156-158, 160-162, 165-167, 169, 170, 172, 176-178, 180, 181, 183-185, 187-189, 191-202, 204, 205, 207.1-210, 211-215, 217, 222, 224-229 |
| B | 1, 3, 5, 7, 8, 10, 12, 15, 16, 19, 23, 25, 27, 29, 30-34, 36, 38, 41, 42, 49, 69, 75, 77, 86-88, 98, 99, 102, 106, 146-148, 159, 163, 164, 168, 171, 174, 175, 179, 182, 190, 203, 219, 221 |

The invention claimed is:
1. A compound of formula (I)

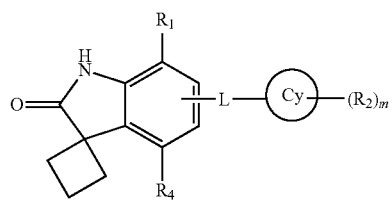

(I)

wherein
Cy is a 4-12 membered monocyclic or bicyclic ring containing 0-4 heteroatoms independently selected form N, O, or S;
L is a linker selected from —N($R_{3a}$)S(O)$_2$—, —S(O)$_2$N($R_{3b}$)—, —C($R_{3c}$)(O$R_{3d}$)—, —NS(O)(CH$_3$)—, —N($R_{3e}$)C(O)—, —N($R_{3f}$)C(O)N($R_{3g}$)—, —N($R_{3h}$)C(O)CH($R_{3i}$)—, —N($R_{3j}$)C(O)CH($R_{3k}$)CH($R_{3l}$)—, or —N($R_{3m}$)C(O)CHCH—;
$R_{3a}$, $R_{3b}$, $R_{3c}$, $R_{3d}$, $R_{3e}$, $R_{3f}$, $R_{3g}$, $R_{3h}$, $R_{3i}$, $R_{3j}$, $R_{3k}$, $R_{3l}$, and $R_{3m}$ are selected, independently, from hydrogen or $C_{1-7}$ alkyl;
$R_2$ is halogen, $C_{1-7}$ alkoxy, amino, cyano, oxo, —C(O)O—$C_{1-7}$ alkyl, optionally substituted aryl, or optionally substituted heterocyclyl; wherein the optional substitution at each occurrence is, independently, selected from 1, 2, or 3 substituents selected from halogen or $C_{1-7}$ alkoxy;
$R_4$ is hydrogen or halogen;
in cases wherein L is —S(O)$_2$N($R_{3b}$)—, —C($R_{3c}$)(O$R_{3d}$)—, —NS(O)(CH$_3$)—, —N($R_{3e}$)C(O)—, —N($R_{3f}$)C(O)N($R_{3g}$)—, —N($R_{3h}$)C(O)CH($R_{3i}$)—, —N($R_{3j}$)C(O)CH($R_{3k}$)CH($R_{3l}$)—, or —N($R_{3i}$)C(O)CHCH—;
then $R_1$ is hydrogen, $C_{1-7}$ alkyl, halogen, nitro, hydroxy $C_{1-7}$ alkyl, $C_{3-10}$ cycloalkyl, optionally substituted aryl, optionally substituted heterocyclyl, optionally substituted heterocyclyl $C_{1-7}$ alkyl, optionally substituted heterocyclyl $C_{2-7}$ alkenyl, optionally substituted aryl $C_{1-7}$ alkyl, optionally substituted aryl $C_{2-7}$ alkenyl, —NR$_a$R$_b$, —C(O)NR$_c$R$_d$, —C(O)OR$_e$, —C(O)R$_f$, —C(OR$_g$)-aryl, —C(OR$_h$)(R$_i$)-aryl, —OR$_j$, or —OC(O)R$_k$;

wherein the optional substitution at each occurrence is, independently, selected from 1, 2, or 3 substituents selected from halogen, hydroxy, $C_{1-7}$ alkyl, or $C_{1-7}$ alkoxy; except that $R_1$ is not hydrogen when L is —S(O)$_2$NH— or —CH(OH)—, and $R_1$ is not hydrogen or halogen when L is —NHC(O)CH(CH$_3$)—;
in cases wherein L is —N($R_{3a}$)S(O)$_2$—;
then $R_1$ is —NR$_a$R$_b$, —C(O)NR$_c$R$_d$, —C(O)OR$_e$, —C(O)R$_f$, —C(OR$_g$)-aryl, —B(OH)$_2$, —C(OR$_h$)(R$_i$)-aryl, —OR$_n$, or —OC(O)R$_k$, —CH(CH$_3$)—aryl, hydroxy $C_{1-7}$ alkyl, aryl halo $C_{1-7}$ alkyl, optionally substituted heterocyclyl $C_{1-7}$ alkyl, optionally substituted heterocyclyl $C_{2-7}$ alkenyl, optionally substituted aryl, optionally substituted aryl $C_{2-7}$ alkenyl, optionally substituted 9-12 membered heterocyclic ring having 1-3 heteroatoms selected from N or O, pyridinyl having 1-2 substituents selected from halogen, hydroxy or $C_{1-7}$ alkoxy, 2-oxopiperidinyl, fluorophenyl $C_{1-7}$ alkyl, 1-methylpiperidinyl (when at least one of $R_2$ is halogen), piperidinyl (when at least two of $R_2$ is $C_{1-7}$ alkoxy), or phenyl $C_{1-7}$ alkyl (when at least one of $R_2$ is halogen and at least one another of $R_2$ is $C_{1-7}$ alkoxy); wherein the optional substitution at each occurrence is, independently, selected from 1, 2, or 3 substituents selected from halogen, hydroxy, oxo, $C_{1-7}$ alkyl, or $C_{1-7}$ alkoxy;
$R_a$, $R_b$, $R_c$, and $R_d$ are, independently, selected from hydrogen, $C_{1-7}$ alkyl, $C_{2-7}$ alkenyl, —C(O)—$C_{1-7}$ alkyl, optionally substituted heterocyclyl, optionally substituted $C_{3-10}$ cycloalkyl, optionally substituted heterocyclyl $C_{1-7}$ alkyl, optionally substituted aryl, optionally substituted aryl $C_{1-7}$ alkyl, optionally substituted $C_{3-10}$ cycloalkyl $C_{1-7}$ alkyl, or optionally substituted —C(O)heterocyclyl; wherein the optional substitution at each occurrence is, independently, selected from 1, 2, or 3 substituents selected from $C_{1-7}$ alkyl, —C(O)—$C_{1-7}$ alkyl, —C(O)O—$C_{1-7}$ alkyl, halogen, aryl $C_{1-7}$ alkyl, $C_{1-7}$ alkoxy, oxo, or hydroxy $C_{1-7}$ alkyl;
$R_e$, $R_f$, $R_g$, $R_h$, $R_i$, and $R_j$ are, independently, selected from hydrogen, $C_{1-7}$ alkyl, halo $C_{1-7}$ alkyl, optionally substituted aryl, optionally substituted heterocyclyl, optionally substituted heterocyclyl $C_{1-7}$ alkyl, or optionally substituted heterocyclyl $C_{3-7}$ cycloalkyl;
wherein the optional substitution at each occurrence is, independently, selected from 1, 2, or 3 substituents selected from $C_{1-7}$ alkyl or hydroxy $C_{1-7}$ alkyl;
$R_k$ is selected from optionally substituted aryl, optionally substituted heterocyclyl, optionally substituted heterocyclyl $C_{1-7}$ alkyl; wherein the optional substitution at each occurrence is, independently, selected from 1, 2, or 3 substituents selected from $C_{1-7}$ alkyl or hydroxy $C_{1-7}$ alkyl;
$R_n$ is selected from optionally substituted aryl, halo $C_{1-7}$ alkyl, $C_{3-7}$ cycloalkyl substituted by 1-2 substituents selected from halogen, hydroxy or oxo, optionally substituted heterocyclyl, optionally substituted heterocyclyl $C_{1-7}$ alkyl, optionally substituted heterocyclyl $C_{3-7}$ cycloalkyl, or —Z—NR$_{a1}$R$_{b1}$; wherein the optional substitution at each occurrence is, independently, selected from 1, 2, or 3 substituents selected from hydroxy, $C_{1-7}$ alkyl, $C_{3-7}$ cycloalkyl, hydroxy $C_{1-7}$ alkyl, methylsulfonyl, halogen, amino, acetyl, or oxo;
$R_{a1}$ and $R_{b1}$ are, independently, hydrogen, $C_{1-7}$ alkyl, or $C_{3-7}$ cycloalkyl;

Z is C$_{1-7}$ alkyl, C$_{3-7}$ cycloalkyl or C$_{3-7}$ cycloalkyl C$_{1-7}$ alkyl;

m is selected from 0, 1, 2, or 3;

wherein heterocyclyl, at each occurrence is, independently, a non-aromatic, saturated or partially saturated, monocyclic or polycyclic ring with 3 to 10 ring atoms of which at least one is a heteroatom selected from the group consisting of O, N, and S; or a monocyclic, bicyclic, or polycyclic aromatic rings of 6-14 ring atoms containing at least one heteroatom selected from the group consisting of N, O, and S;

or a pharmaceutically acceptable salt thereof.

2. The compound according to claim 1, wherein the compound is represented by formula (IA):

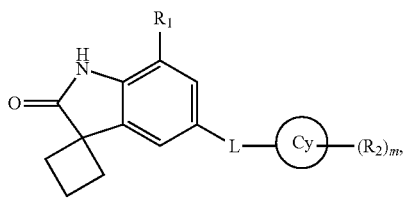

or a pharmaceutically acceptable salt thereof.

3. The compound according to claim 1, wherein the compound is represented by formula (IB):

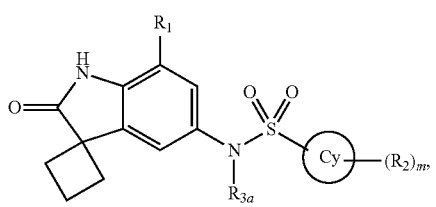

or a pharmaceutically acceptable salt thereof.

4. The compound according to claim 1, wherein the compound is represented by formula (IC):

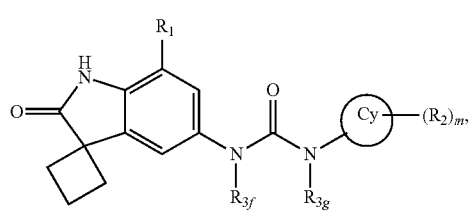

or a pharmaceutically acceptable salt thereof.

5. The compound according to claim 1, wherein the compound is represented by formula (ID):

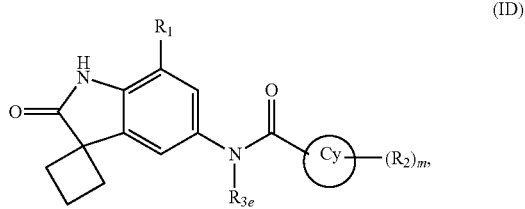

or a pharmaceutically acceptable salt thereof.

6. The compound according to claim 1, wherein Cy is an aromatic or a non-aromatic cyclic ring with 5-10 ring atoms of which 0-4 are heteroatoms selected from a group consisting of N, O, and S.

7. The compound according to claim 6, wherein Cy is phenyl, C$_{3-10}$ cycloalkyl, or a 5-6 membered heterocyclic ring having 1-3 heteroatoms selected from N or O.

8. The compound according to claim 1, wherein Cy is phenyl, C$_{3-10}$ cycloalkyl, or a 5-6 membered heterocyclic ring having 1-3 heteroatoms selected from N or O;

R$_4$ is hydrogen;

L is a linker selected from —N(R$_{3a}$)S(O)$_2$—, —N(R$_{3e}$)C(O)—, or —N(R$_{3f}$)C(O)N(R$_{3g}$)—;

R$_{3a}$, R$_{3e}$, R$_{3f}$ and R$_{3g}$ are selected, independently, from hydrogen or C$_{1-7}$ alkyl;

R$_2$ is halogen, C$_{1-7}$ alkoxy, cyano, —C(O)O—C$_{1-7}$ alkyl, or a 5-6 membered hetero-cyclic ring having 1-3 heteroatoms selected from N or O;

in cases wherein L is —N(R$_{3e}$)C(O)— or —N(R$_{3f}$)C(O)N(R$_{3g}$)—;

then R$_1$ is hydrogen, C$_{1-7}$ alkyl, halogen, hydroxy C$_{1-7}$ alkyl, C$_{3-10}$ cycloalkyl, optionally substituted aryl, optionally substituted heterocyclyl, optionally substituted heterocyclyl C$_{1-7}$ alkyl, optionally substituted aryl C$_{1-7}$ alkyl, optionally substituted aryl C$_{2-7}$ alkenyl, —NR$_a$R$_b$, —C(O)NR$_c$R$_d$, —C(O)OR$_e$, —C(O)R$_f$, —C(OR$_g$)-aryl, —C(OR$_h$)(R$_i$)-aryl, or —OR$_j$; wherein the optional substitution at each occurrence is, independently, selected from 1, 2, or 3 substituents selected from halogen, hydroxy, C$_{1-7}$ alkyl, or C$_{1-7}$ alkoxy;

in case wherein L is —N(R$_{3a}$)S(O)$_2$—;

then R$_1$ is —NR$_a$R$_b$, —C(O)NR$_c$R$_d$, —C(O)OR$_e$, —C(O)R$_f$, —C(OR$_g$)-aryl, —C(OR$_h$)(R$_i$)-aryl or —OR$_n$, —CH(CH$_3$)—aryl, hydroxy C$_{1-7}$ alkyl, aryl halo C$_{1-7}$ alkyl, optionally substituted heterocyclyl C$_{1-7}$ alkyl, optionally substituted aryl, optionally substituted aryl C$_{2-7}$ alkenyl, optionally substituted 9-12 membered heterocyclic ring having 1-3 heteroatoms selected from N or O, pyridinyl having 1-2 substituents selected from halogen, hydroxy or C$_{1-7}$ alkoxy, 2-oxopiperidinyl, fluorophenyl C$_{1-7}$ alkyl, 1-methylpiperidinyl (when at least one of R$_2$ is halogen), piperidinyl (when at least two of R$_2$ is C$_{1-7}$ alkoxy), phenyl C$_{1-7}$ alkyl (when at least one of R$_2$ is halogen and at least one another of R$_2$ is C$_{1-7}$ alkoxy); wherein the optional substitution at each occurrence is, independently, selected from 1, 2, or 3 substituents selected from halogen, hydroxy, oxo, C$_{1-7}$ alkyl, or C$_{1-7}$ alkoxy;

R$_a$, R$_b$, R$_c$, and R$_d$ are, independently, selected from hydrogen, C$_{1-7}$ alkyl, C$_{2-7}$ alkenyl, —C(O)—C$_{1-7}$ alkyl, optionally substituted heterocyclyl, optionally substituted C$_{3-10}$ cycloalkyl, optionally substituted heterocyclyl C$_{1-7}$ alkyl, optionally substituted aryl, optionally substituted aryl C$_{1-7}$ alkyl, or optionally substituted C$_{3-10}$ cycloalkyl C$_{1-7}$ alkyl, or optionally substituted —C(O)

heterocyclyl; wherein the optional substitution at each occurrence is, independently, selected from 1, 2, or 3 substituents selected from $C_{1-7}$ alkyl, —C(O)—$C_{1-7}$ alkyl, —C(O)O—$C_{1-7}$ alkyl, halogen, aryl $C_{1-7}$ alkyl, $C_{1-7}$ alkoxy, oxo, or hydroxy $C_{1-7}$ alkyl;

$R_e$, $R_f$, $R_g$, $R_h$, $R_i$, and $R_j$ are, independently, selected from hydrogen, $C_{1-7}$ alkyl, optionally substituted aryl or optionally substituted heterocyclyl; wherein the optional substitution at each occurrence is, independently, selected from 1, 2, or 3 substituents selected from $C_{1-7}$ alkyl or hydroxy $C_{1-7}$ alkyl;

$R_n$ is selected from optionally substituted aryl or optionally substituted heterocyclyl; wherein the optional substitution at each occurrence is, independently, selected from 1, 2, or 3 substituents selected from $C_{1-7}$ alkyl or hydroxy $C_{1-7}$ alkyl; and m is selected from 0, 1, 2, or 3;

wherein heterocyclyl, at each occurrence is, independently, a non-aromatic, saturated or partially saturated, monocyclic or polycyclic ring with 3 to 10 ring atoms of which at least one is a heteroatom selected from the group consisting of O, N, and S; or a monocyclic, bicyclic, or polycyclic aromatic rings of 6-14 ring atoms containing at least one heteroatom selected from the group consisting of N, O, and S;

or a pharmaceutically acceptable salt thereof.

9. The compound according to claim 1, wherein L is a linker selected from —NHS(O)$_2$—, —NHC(O)— or —NHC(O)NH—.

10. The compound according to claim 1, wherein L is —NHS(O)$_2$—.

11. The compound according to claim 1, wherein
Cy is phenyl;
L is —NHS(O)$_2$—;
$R_4$ is hydrogen;
$R_2$ is halogen or $C_{1-7}$ alkoxy;
$R_1$ is —NHR$_a$, —C(O)NHR$_c$, —C(O)OR$_e$, —C(O)R$_f$, —C(OH)phenyl, —C(OH)($C_{1-7}$ alkyl)phenyl or —OR, —CH(CH3)phenyl, hydroxy $C_{1-7}$ alkyl, aryl halo $C_{1-7}$ alkyl, optionally substituted heterocyclyl $C_{1-7}$ alkyl, optionally substituted phenyl, optionally substituted phenyl $C_{2-7}$ alkenyl, optionally substituted 9-12 membered heterocyclic ring having 1-3 heteroatoms selected from N or O, pyridinyl having 1-2 substituents selected from halogen, hydroxy or $C_{1-7}$ alkoxy, 2-oxopiperidinyl, fluorophenyl $C_{1-7}$ alkyl, 1-methylpiperidinyl (when at least one of $R_2$ is halogen), piperidinyl (when at least two of $R_2$ is $C_{1-7}$ alkoxy), or phenyl $C_{1-7}$ alkyl (when at least one of $R_2$ is halogen and at least one another of $R_2$ is $C_{1-7}$ alkoxy); wherein the optional substitution at each occurrence is, independently, selected from 1, 2, or 3 substituents selected from halogen, hydroxy, oxo, $C_{1-7}$ alkyl, or $C_{1-7}$ alkoxy;

$R_a$ and $R_c$ are, independently, selected from hydrogen, $C_{1-7}$ alkyl, $C_{2-7}$ alkenyl, —C(O)—$C_{1-7}$ alkyl, optionally substituted $C_{3-10}$ cycloalkyl, optionally substituted hetero-cyclyl, optionally substituted heterocyclyl $C_{1-7}$ alkyl, optionally substituted $C_{3-10}$ cycloalkyl $C_{1-7}$ alkyl, or optionally substituted —C(O)heterocyclyl; wherein the optional substitution at each occurrence is, independently, selected from 1, 2, or 3 substituents selected from $C_{1-7}$ alkyl, —C(O)—$C_{1-7}$ alkyl, —C(O)O—$C_{1-7}$ alkyl, halogen, phenyl $C_{1-7}$ alkyl, $C_{1-7}$ alkoxy, oxo, or hydroxy $C_{1-7}$ alkyl;

$R_e$ is hydrogen or $C_{1-7}$ alkyl;

$R_f$ and $R_j$ are independently optionally substituted phenyl or optionally substituted heterocyclyl; wherein the optional substitution at each occurrence is, independently, selected from 1, 2, or 3 substituents selected from $C_{1-7}$ alkyl or hydroxy $C_{1-7}$ alkyl;

wherein heterocyclyl at each occurrence is a 5-10 membered heterocyclic ring having 1-4 heteroatoms selected from O, N, or S; and m is selected from 0, 1, 2, or 3;

wherein heterocyclyl, at each occurrence is, independently, a non-aromatic, saturated or partially saturated, monocyclic or polycyclic ring with 3 to 10 ring atoms of which at least one is a heteroatom selected from the group consisting of O, N, and S; or a monocyclic, bicyclic, or polycyclic aromatic rings of 6-14 ring atoms containing at least one heteroatom selected from the group consisting of N, O, and S;

or a pharmaceutically acceptable salt thereof.

12. A compound according to claim 1, wherein Cy-(R$_2$)$_m$ is selected from the following groups or tautomers thereof:

and the * represents the point of attachment.

13. The compound according to claim 1, wherein $R_1$ is an optionally substituted heterocyclyl or optionally substituted heterocyclyl $C_{1-7}$ alkyl and is selected from the following groups or tautomers thereof:

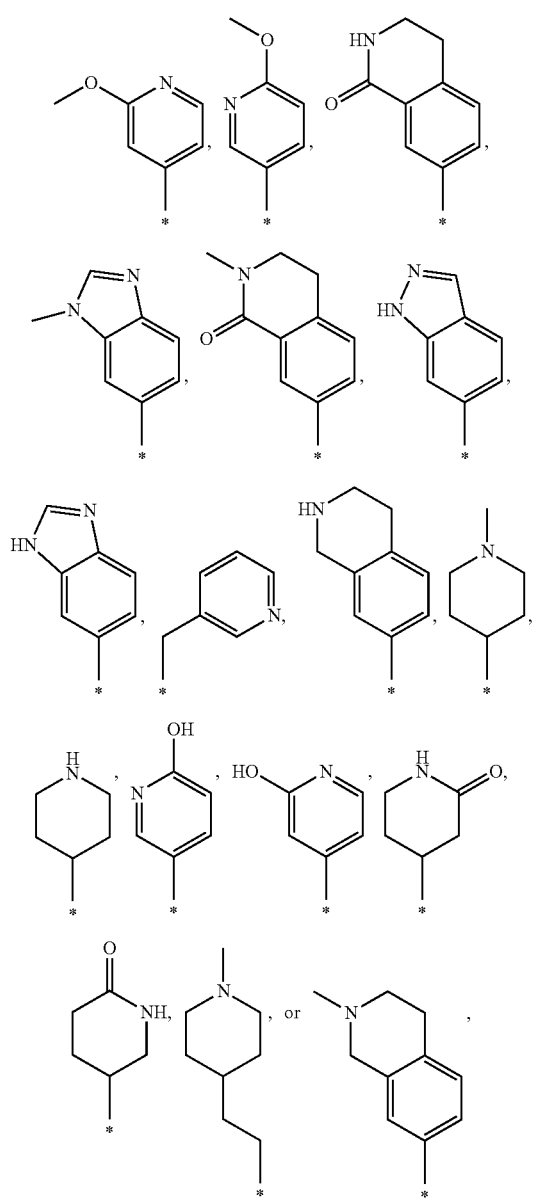
and the * represents the point of attachment.
14. The compound according to claim 1, wherein $R_1$ is —$NHR_a$ or —$C(O)NHR_c$, wherein $R_a$, and $R_c$ are, independently, selected from the following groups or tautomers thereof:
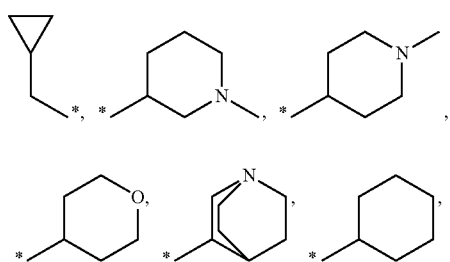
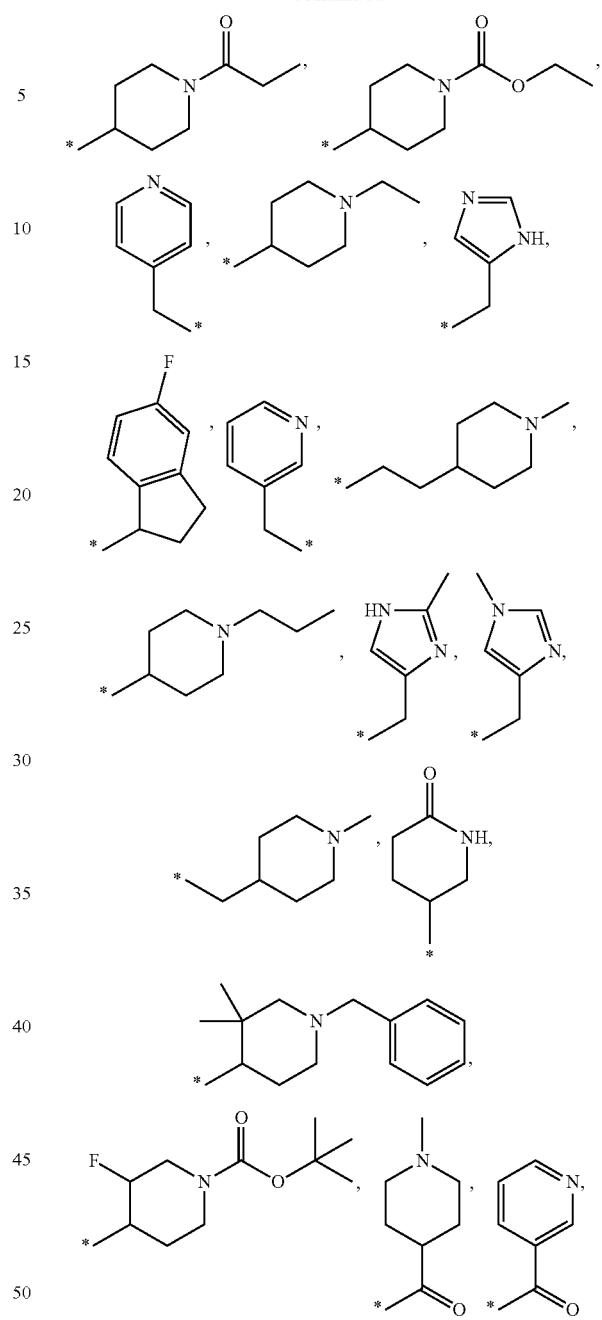

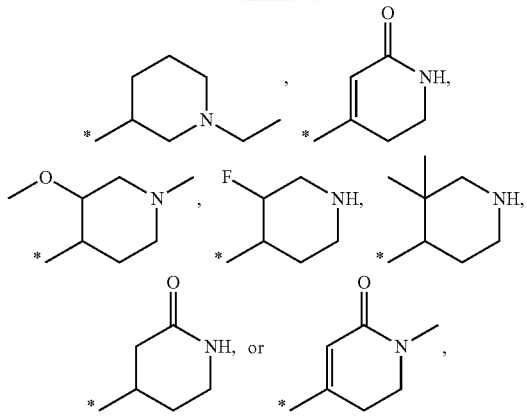

and the * represents the point of attachment.

15. The compound according to claim 1, wherein the compound is represented by formula (IE):

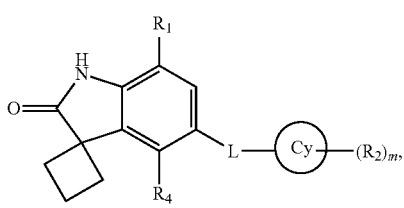

or a pharmaceutically acceptable salt thereof.

16. The compound according to claim 1, wherein Cy is a 4-12 membered monocyclic or bicyclic ring containing 0-4 heteroatoms independently selected form N, O, or S;

L is a linker selected from —N($R_{3a}$)S(O)$_2$—, —NS(O)(CH$_3$)—, —N($R_{3e}$)C(O)—, —N($R_{3f}$)C(O)N($R_{3g}$)—, —N($R_{3j}$)C(O)CH($R_{3k}$)CH($R_{3l}$)—, or —N($R_{3m}$)C(O)CHCH—;

$R_{3a}$, $R_{3e}$, $R_{3f}$, $R_{3g}$, $R_{3j}$, $R_{3k}$, $R_{3l}$, and $R_{3m}$ are selected, independently, from hydrogen or $C_{1-7}$ alkyl;

$R_2$ is halogen, $C_{1-7}$ alkoxy, amino, cyano, oxo, —C(O)O—$C_{1-7}$ alkyl, optionally substituted aryl, or optionally substituted heterocyclyl; wherein the optional substitution at each occurrence is, independently, selected from 1, 2, or 3 substituents selected from halogen or $C_{1-7}$ alkoxy;

$R_4$ is hydrogen or halogen;

in cases wherein L is —NS(O)(CH$_3$)—, —N($R_{3e}$)C(O)—, —N($R_{3f}$)C(O)N($R_{3g}$)—, —N($R_{3j}$)C(O)CH($R_{3k}$)CH($R_{3l}$)—, or —N($R_{3j}$)C(O)CHCH—;

then $R_1$ is hydrogen, $C_{1-7}$ alkyl, halo $C_{1-7}$ alkyl, halogen, nitro, hydroxy $C_{1-7}$ alkyl, $C_{3-10}$ cycloalkyl, optionally substituted aryl, optionally substituted heterocyclyl, optionally substituted heterocyclyl $C_{1-7}$ alkyl, optionally substituted heterocyclyl $C_{2-7}$ alkenyl, optionally substituted aryl $C_{1-7}$ alkyl, optionally substituted aryl $C_{2-7}$ alkenyl, —NR$_a$R$_b$, —C(O)NR$_c$R$_d$, —C(O)OR$_e$, —C(O)R$_f$ —C(OR$_g$)-aryl, —C(OR$_h$)(R$_i$)-aryl, —OR$_j$, or —OC(O)R$_k$;

wherein the optional substitution at each occurrence is, independently, selected from 1, 2, or 3 substituents selected from halogen, hydroxy, $C_{1-7}$ alkyl, or $C_{1-7}$ alkoxy;

in cases wherein L is —N($R_{3a}$)S(O)$_2$— then $R_1$ is —NR$_a$R$_b$, —C(O)NR$_c$R$_d$, —C(O)OR$_e$, —C(O)R$_f$, —C(OR$_g$)-aryl, —B(OH)$_2$, —C(OR$_h$)(R$_i$)-aryl, —OR$_n$, or —OC(O)R$_k$;

$R_a$, $R_b$, $R_c$, and $R_d$ are, independently, selected from hydrogen, $C_{1-7}$ alkyl, $C_{2-7}$ alkenyl, —C(O)—$C_{1-7}$ alkyl, optionally substituted heterocyclyl, optionally substituted $C_{3-10}$ cycloalkyl, optionally substituted heterocyclyl $C_{1-7}$ alkyl, optionally substituted aryl, optionally substituted aryl $C_{1-7}$ alkyl, optionally substituted $C_{3-10}$ cycloalkyl $C_{1-7}$ alkyl, or optionally substituted —C(O) heterocyclyl; wherein the optional substitution at each occurrence is, independently, selected from 1, 2, or 3 substituents selected from $C_{1-7}$ alkyl, —C(O)—$C_{1-7}$ alkyl, —C(O)O—$C_{1-7}$ alkyl, halogen, aryl $C_{1-7}$ alkyl, $C_{1-7}$ alkoxy, oxo, or hydroxy $C_{1-7}$ alkyl;

$R_e$, $R_f$, $R_g$, $R_h$, $R_i$, and $R_j$ are, independently, selected from hydrogen, $C_{1-7}$ alkyl, optionally substituted aryl, optionally substituted heterocyclyl, optionally substituted heterocyclyl $C_{1-7}$ alkyl, or optionally substituted heterocyclyl $C_{3-7}$ cycloalkyl; wherein the optional substitution at each occurrence is, independently, selected from 1, 2, or 3 substituents selected from $C_{1-7}$ alkyl or hydroxy $C_{1-7}$ alkyl;

$R_k$ is selected from optionally substituted aryl, optionally substituted heterocyclyl, or optionally substituted heterocyclyl $C_{1-7}$ alkyl; wherein the optional substitution at each occurrence is, independently, selected from 1, 2, or 3 substituents selected from $C_{1-7}$ alkyl or hydroxy $C_{1-7}$ alkyl;

$R_n$ is selected from optionally substituted aryl, optionally substituted heterocyclyl, optionally substituted heterocyclyl $C_{1-7}$ alkyl, optionally substituted heterocyclyl $C_{3-7}$ cycloalkyl, or —Z—NR$_{a1}$R$_{b1}$; wherein the optional substitution at each occurrence is, independently, selected from 1, 2, or 3 substituents selected from hydroxy, $C_{1-7}$ alkyl, $C_{3-7}$ cycloalkyl, hydroxy $C_{1-7}$ alkyl, methylsulfonyl, halogen, amino, acetyl; or oxo;

$R_{a1}$ and $R_{b1}$ are, independently, hydrogen, $C_{1-7}$ alkyl or $C_{3-7}$ cycloalkyl;

Z is $C_{1-7}$ alkyl, $C_{3-7}$ cycloalkyl, or $C_{3-7}$ cycloalkyl $C_{1-7}$ alkyl;

m is selected from 0, 1, 2, or 3;

wherein heterocyclyl, at each occurrence is, independently, a non-aromatic, saturated or partially saturated, monocyclic or polycyclic ring with 3 to 10 ring atoms of which at least one is a heteroatom selected from the group consisting of O, N, and S; or a monocyclic, bicyclic, or polycyclic aromatic rings of 6-14 ring atoms containing at least one heteroatom selected from the group consisting of N, O, and S;

or a pharmaceutically acceptable salt thereof.

17. The compound according to claim 15, wherein Cy is aromatic or non-aromatic cyclic ring with 5-10 ring atoms of which 0-4 are heteroatoms selected from a group consisting of N, O, and S.

18. The compound according to claim 17, wherein Cy is phenyl, $C_{3-10}$ cycloalkyl, or a 5-6 membered heterocyclic ring having 1-3 heteroatoms selected from N or O.

19. The compound according to claim 18, wherein Cy is phenyl, cyclohexyl, piperidinyl, or pyridyl.

20. The compound according to claim 15, wherein L is —N($R_{3a}$)S(O)$_2$—.

21. The compound according to claim 20, wherein L is —NHS(O)$_2$—.

22. The compound according to claim 1, wherein $R_4$ is hydrogen.

23. The compound according to claim 1, wherein $R_1$ is —$OR_n$ or —$OC(O)R_k$.

24. The compound according to claim 23, wherein $R_1$ is —$OR_n$.

25. The compound according to claim 24, wherein $R_n$ is an optionally substituted heterocyclyl, optionally substituted heterocyclyl $C_{1-7}$ alkyl, optionally substituted heterocyclyl $C_{3-7}$ cycloalkyl, or —Z—$NR_{a1}R_{b1}$; wherein the optional substitution at each occurrence is, independently, selected from 1, 2, or 3 substituents selected from $C_{1-7}$ alkyl, $C_{3-7}$ cycloalkyl, halogen, or oxo;

$R_{a1}$ and $R_{b1}$ are, independently, hydrogen, $C_{1-7}$ alkyl or $C_{3-7}$ cycloalkyl; and Z is $C_{1-7}$ alkyl, $C_{3-7}$ cycloalkyl, or $C_{3-7}$ cycloalkyl $C_{1-7}$ alkyl;

wherein the heterocyclyl, at each occurrence, is a 4-10 membered heterocyclic ring having 1-3 heteroatoms selected from N, O, or S.

26. The compound according to claim 24, wherein $R_n$ is an optionally substituted heterocyclyl or optionally substituted heterocyclyl $C_{1-7}$ alkyl or optionally substituted heterocyclyl $C_{3-7}$ cycloalkyl selected from the following groups or tautomers thereof:

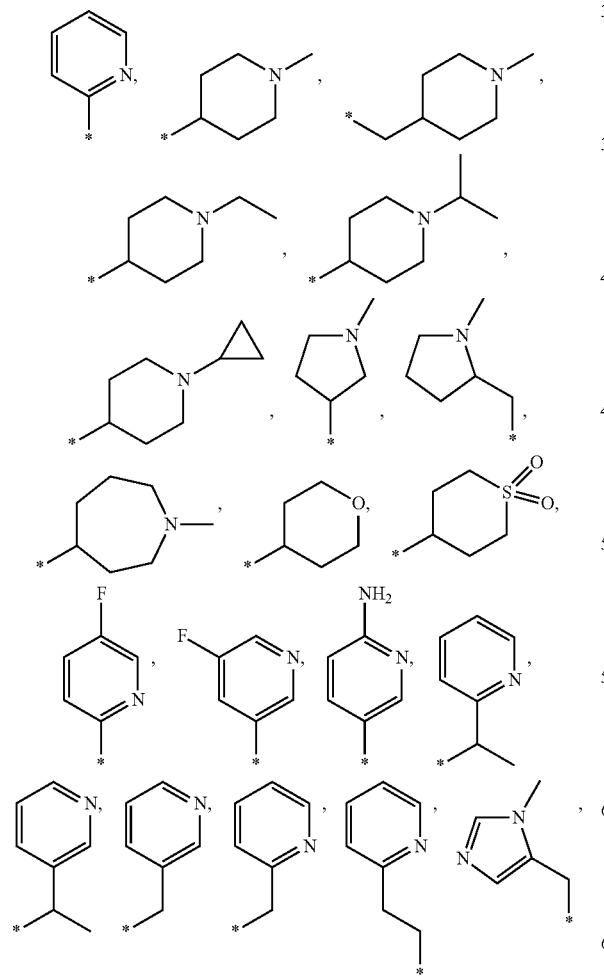

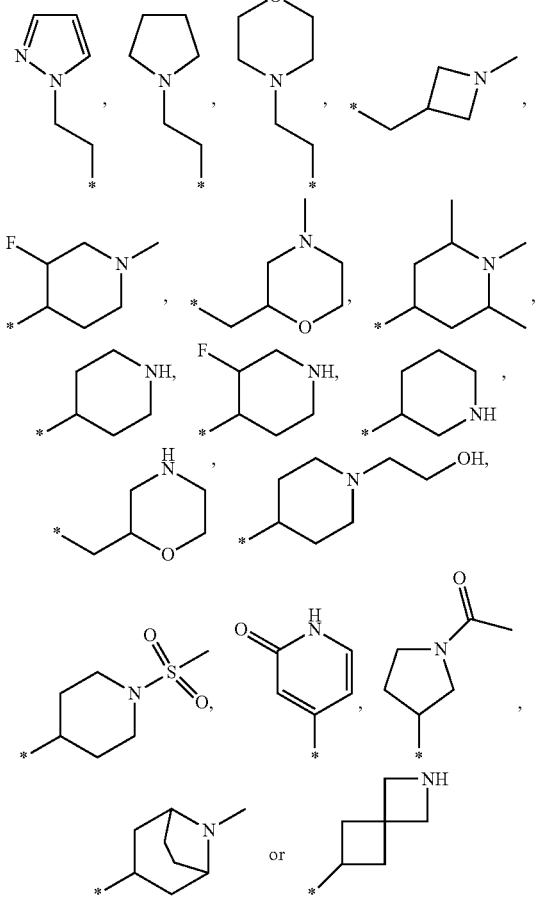

and the * represents the point of attachment.

27. The compound according to claim 15, wherein Cy-$(R_2)_m$ is selected from one of the following groups or tautomers thereof

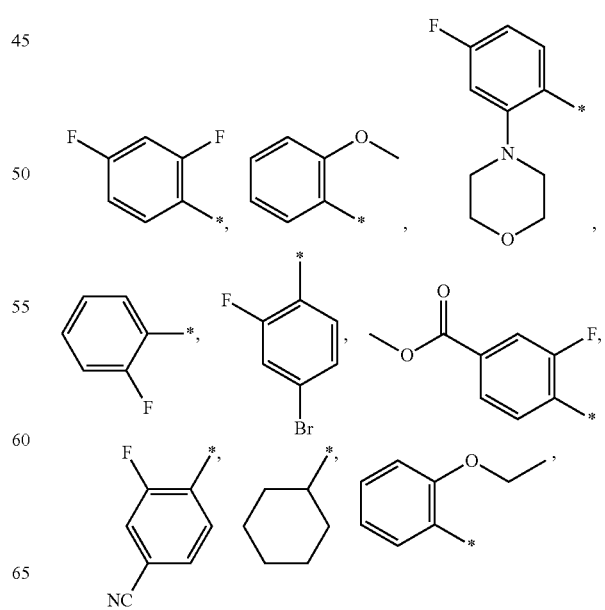

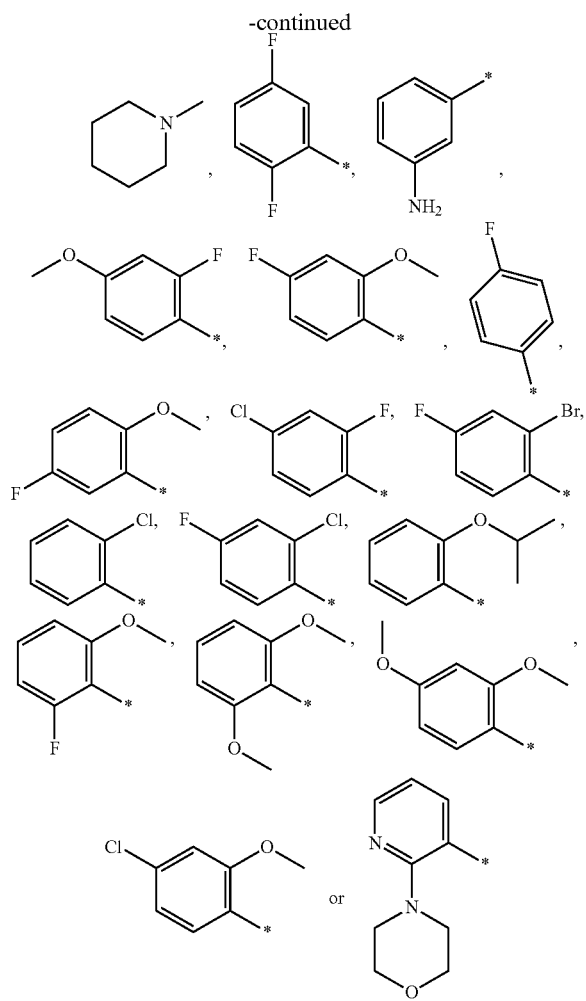

and the * represents the point of attachment.

28. The compound according to claim 1, wherein the heterocyclyl group, at each occurrence, independently, is a 4-10 membered heterocyclic ring having 1-4 heteroatoms selected from O, N, or S.

29. The compound according to claim 1 selected from the group consisting of:

2,4-Difluoro-N-(7'-(3-hydroxyphenyl)-2'-oxospiro[cyclobutane-1,3'-indolin]-5'-yl)benzenesulfonamide;

2,4-Difluoro-N-(7'-(2-methoxypyridin-4-yl)-2'-oxospiro[cyclobutane-1,3'-indolin]-5'-yl)benzenesulfonamide;

2,4-Difluoro-N-(7'-(6-methoxypyridin-3-yl)-2'-oxospiro[cyclobutane-1,3'-indolin]-5'-yl)benzenesulfonamide;

2,4-Difluoro-N-(2'-oxo-7'-(1-oxo-1,2,3,4-tetrahydro isoquinolin-7-yl)-spiro[cyclobutane-1,3'-indolin]-5'-yl) benzenesulfonamide;

2,4-Difluoro-N-(7'-(1-methyl-1H-benzo[d]imidazol-6-yl)-2'-oxospiro-[cyclobutane-1,3'-indolin]-5'-yl)benzene sulphonamide;

2,4-Difluoro-N-(7'-(2-methyl-1-oxo-1,2,3,4-tetrahydro isoquinolin-7-yl)-2'-oxospiro[cyclobutane-1,3'-indolin]-5'-yl)benzenesulfonamide;

N-(7'-(1H-indazol-6-yl)-2'-oxospiro[cyclobutane-1,3'-indolin]-5'-yl)-2,4-difluorobenzenesulfonamide;

N-(7'-(1H-benzo[d]imidazol-6-yl)-2'-oxospiro[cyclobutane-1,3'-indolin]-5'-yl)-2,4-difluorobenzenesulfonamide;

N-(7'-(2-fluorobenzyl)-2'-oxospiro[cyclobutane-1,3'-indolin]-5'-yl)-2-methoxybenzenesulfonamide;

N-(7'-(3-fluorobenzyl)-2'-oxospiro[cyclobutane-1,3'-indolin]-5'-yl)-2-methoxybenzenesulfonamide;

2-Methoxy-N-(2'-oxo-7'-(1-phenylvinyl)spiro[cyclobutane-1,3'-indolin]-5'-yl)benzenesulfonamide;

N-(7'-amino-2'-oxospiro[cyclobutane-1,3'-indolin]-5'-yl)-2-methoxy-benzenesulfonamide;

N-(7'-((cyclopropylmethyl)amino)-2'-oxospiro[cyclobutane-1,3'-indolin]-5'-yl)-2-methoxybenzenesulfonamide;

N-(7'-(but-3-en-1-ylamino)-2'-oxospiro[cyclobutane-1,3'-indolin]-5'-yl)-2-methoxybenzenesulfonamide;

N-(7'-amino-2'-oxospiro[cyclobutane-1,3'-indolin]-5'-yl)-2,4-difluoro-benzenesulfonamide;

2,4-Difluoro-N-(7'-(((1-methylpiperidin-3-yl)amino)-2'-oxo spiro[cyclobutane-1,3'-indolin]-5'-yl)benzenesulfonamide;

2,4-Difluoro-N-(7'-(((1-methylpiperidin-4-yl)amino)-2'-oxo spiro[cyclobutane-1,3'-indolin]-5'-yl)benzenesulfonamide;

2,4-Difluoro-N-(2'-oxo-7'-((tetrahydro-2H-pyran-4-yl)amino) spiro[cyclobutane-1,3'-indolin]-5'-yl)benzenesulfonamide;

2,4-Difluoro-N-(2'-oxo-7'-(quinuclidin-3-ylamino) spiro[cyclobutane-1,3'-indolin]-5'-yl)benzenesulfonamide;

N-(7'-(cyclohexylamino)-2'-oxospiro[cyclobutane-1,3'-indolin]-5'-yl)-2,4-difluorobenzenesulfonamide;

2,4-Difluoro-N-(2'-oxo-7'-((1-propionylpiperidin-4-yl) amino)spiro[cyclobutane-1,3'-indolin]-5'-yl)benzenesulfonamide;

Ethyl 4-((5'-(2,4-difluorophenylsulfonamido)-2'-oxospiro [cyclobutane-1,3'-indolin]-7'-yl)amino)piperidine-1-carboxylate;

2,4-Difluoro-N-(2'-oxo-7'-((pyridin-4-ylmethyl) amino) spiro[cyclobutane-1,3'-indolin]-5'-yl)benzenesulfonamide;

N-(7'-((1-ethylpiperidin-4-yl)amino)-2'-oxospiro[cyclo butane-1,3'-indolin]-5'-yl)-2,4-difluorobenzenesulfonamide;

N-(7'-(((1H-imidazol-5-yl)methyl)amino)-2'-oxospiro [cyclo butane-1,3'-indolin]-5'-yl)-2,4-difluorobenzene sulfonamide;

2,4-Difluoro-N-(7'-(((5-fluoro-2,3-dihydro-1H-inden-1-yl)amino)-2'-oxo-spiro[cyclobutane-1,3'-indolin]-5'-yl)benzenesulfonamide;

2,4-difluoro-N-(2'-oxo-7'-((pyridin-3-ylmethyl)amino) spiro[cyclobutane-1,3'-indolin]-5'-yl)benzenesulfonamide;

2,4-Difluoro-N-(7'-((2-(1-methylpiperidin-4-yl)ethyl) amino)-2'-oxospiro-[cyclobutane-1,3'-indolin]-5'-yl) benzenesulfonamide;

2,4-Difluoro-N-(2'-oxo-7'-((1-propylpiperidin-4-yl) amino) spiro[cyclobutane-1,3'-indolin]-5'-yl)benzenesulfonamide;

2,4-Difluoro-N-(7'-(((2-methyl-1H-imidazol-4-yl) methyl)amino)-2'-oxo-spiro[cyclobutane-1,3'-indolin]-5'-yl)benzenesulfonamide;

2,4-Difluoro-N-(7'-(((1-methyl-1H-imidazol-4-yl) methyl) amino)-2'-oxo-spiro[cyclobutane-1,3'-indolin]-5'-yl)benzenesulfonamide;

2,4-Difluoro-N-(7'-(((1-methylpiperidin-4-yl)methyl) amino)-2'-oxo-spiro[cyclobutane-1,3'-indolin]-5'-yl) benzenesulfonamide;

2,4-Difluoro-N-(2'-oxo-7'-((6-oxopiperidin-3-yl)amino) spiro[cyclobutane-1,3'-indolin]-5'-yl)benzenesulfonamide;

2,4-Difluoro-N-(7'-((1-methylpiperidin-3-yl)amino)-2'-oxospiro[cyclobutane-1,3'-indolin]-5'-yl)benzenesulfonamide;

2,4-Difluoro-N-(7'-((1-methylpiperidin-3-yl)amino)-2'-oxospiro[cyclobutane-1,3'-indolin]-5'-yl)benzenesulfonamide;

N-(7'-((1-benzyl-3,3-dimethylpiperidin-4-yl)amino)-2'-oxospiro[cyclobutane-1,3'-indolin]-5'-yl)-2,4-difluorobenzenesulfonamide;

tert-Butyl 4-((5'-(2,4-difluorophenylsulfonamido)-2'-oxospiro[cyclobutane-1,3'-indolin]-7'-yl)amino)-3-fluoro piperidine-1-carboxylate;

2-Methoxy-N-(7'-((1-methylpiperidin-3-yl)amino)-2'-oxo spiro[cyclobutane-1,3'-indolin]-5'-yl)benzenesulfonamide;

2-Methoxy-N-(7'-((1-methylpiperidin-4-yl)amino)-2'-oxo spiro[cyclobutane-1,3'-indolin]-5'-yl)benzenesulfonamide;

Methyl 5'-(2,4-difluorophenylsulfonamido)-2'-oxospiro[cyclobutane-1,3'-indoline]-7'-carboxylate;

5'-(2,4-Difluorophenylsulfonamido)-2'-oxospiro[cyclobutane-1,3'-indoline]-7'-carboxylic acid;

N-(5'-(2,4-difluorophenylsulfonamido)-2'-oxospiro[cyclo butane-1,3'-indolin]-7'-yl)-l-methylpiperidine-4-carboxamide;

N-(5'-(2,4-Difluorophenylsulfonamido)-2'-oxospiro[cyclobutane-1,3'-indolin]-7'-yl)nicotinamide;

N-(5'-(2,4-Difluorophenylsulfonamido)-2'-oxospiro[cyclobutane-1,3'-indolin]-7'-yl)isonicotinamide;

N-(5'-(2,4-Difluorophenylsulfonamido)-2'-oxospiro[cyclo butane-1,3'-indolin]-7'-yl)tetrahydro-2H-pyran-4-carboxamide;

2,4-Difluoro-N-(7'-(4-methylpiperazine-1-carbonyl)-2'-oxo spiro[cyclobutane-1,3'-indolin]-5'-yl)benzenesulfonamide;

2,4-Difluoro-N-(7'-(morpholine-4-carbonyl)-2'-oxospiro[cyclobutane-1,3'-indolin]-5'-yl)benzenesulfonamide;

5'-(2,4-Difluorophenylsulfonamido)-2'-oxo-N-(pyridin-2-yl)spiro[cyclobutane-1,3'-indoline]-7'-carboxamide;

5'-(2,4-Difluorophenylsulfonamido)-2'-oxo-N-(tetrahydro-2H-pyran-4-yl)spiro[cyclobutane-1,3'-indoline]-7'-carboxamide;

5'-(2,4-Difluorophenylsulfonamido)-2'-oxo-N-(pyridin-3-yl)spiro[cyclobutane-1,3'-indoline]-7'-carboxamide;

5'-(2,4-Difluorophenylsulfonamido)-N-(1-methylpyrrolidin-3-yl)-2'-oxo-spiro[cyclobutane-1,3'-indoline]-7'-carboxamide;

5'-(2,4-Difluorophenylsulfonamido)—N-methyl-N-(1-methyl piperidin-4-yl)-2'-oxospiro[cyclobutane-1,3'-indoline]-7'-carboxamide;

5'-(2,4-Difluorophenylsulfonamido)-N-(1-ethylpiperidin-4-yl)-2'-oxo-spiro[cyclobutane-1,3'-indoline]-7'-carboxamide;

N-cyclohexyl-5'-(2,4-difluorophenylsulfonamido)-2'-oxospiro[cyclobutane-1,3'-indoline]-7'-carboxamide;

5'-(2,4-Difluorophenylsulfonamido)-N-(1-methylpiperidin-4-yl)-2'-oxo-spiro[cyclobutane-1,3'-indoline]-7'-carboxamide;

5'-(2,4-Difluorophenylsulfonamido)-2'-oxo-N-(pyridin-4-yl)spiro[cyclobutane-1,3'-indoline]-7'-carboxamide;

5'-(2,4-Difluorophenylsulfonamido)-N-(1-methylpiperidin-3-yl)-2'-oxo-spiro[cyclobutane-1,3'-indoline]-7'-carboxamide;

2,4-Difluoro-N-(7'-(4-(2-hydroxypropan-2-yl)piperidine-1-carbonyl)-2'-oxospiro[cyclobutane-1,3'-indolin]-5'-yl)benzenesulfonamide;

5'-(2-Methoxyphenylsulfonamido)-N-(1-methylpiperidin-4-yl)-2'-oxo-spiro[cyclobutane-1,3'-indoline]-7'-carboxamide;

4-Fluoro-N-(7'-(morpholine-4-carbonyl)-2'-oxospiro[cyclo butane-1,3'-indolin]-5'-yl)-2-morpholinobenzenesulfonamide;

2,4-Difluoro-N-(2'-oxo-7'-(pyridin-4-ylamino)spiro [cyclobutane-1,3'-indolin]-5'-yl)benzenesulfonamide;

N-(5'-(2,4-difluorophenylsulfonamido)-2'-oxospiro[cyclobutane-1,3'-indolin]-7'-yl)acetamide;

5'-(2-Methoxyphenylsulfonamido)-2'-oxo-N-(piperidin-4-yl)spiro[cyclobutane-1,3'-indoline]-7'-carboxamide;

5'-(2,4-Difluorophenylsulfonamido)-2'-oxo-N-(piperidin-3-yl)spiro[cyclobutane-1,3'-indoline]-7'-carboxamide;

5'-(2,4-Difluorophenylsulfonamido)-2'-oxo-N-(piperidin-4-yl)spiro[cyclobutane-1,3'-indoline]-7'-carboxamide;

5'-(2,4-Difluorophenylsulfonamido)-2'-oxo-N-(piperidin-3-yl)spiro[cyclobutane-1,3'-indoline]-7'-carboxamide, isomer 2;

5'-(2,4-Difluorophenylsulfonamido)-2'-oxo-N-(piperidin-3-yl)spiro[cyclobutane-1,3'-indoline]-7'-carboxamide, isomer 1;

2,4-Difluoro-N-(7'-(hydroxymethyl)-2'-oxospiro[cyclobutane-1,3'-indolin]-5'-yl)benzenesulfonamide;

N-(7'-((1-ethylpiperidin-3-yl)amino)-2'-oxospiro[cyclobutane-1,3'-indolin]-5'-yl)-2,4-difluorobenzenesulfonamide;

2,4-difluoro-N-(2'-oxo-7'-(piperidin-3-ylamino)spiro[cyclo butane-1,3'-indolin-5'-yl)benzenesulfonamide hydrochloride;

5'-(2,4-Difluoro-N-methylphenylsulfonamido)-N-(1-methyl piperidin-4-yl)-2'-oxospiro[cyclobutane-1,3'-indoline]-7'-carboxamide;

5'-(2-Fluorophenylsulfonamido)-N-(1-methylpiperidin-4-yl)-2'-oxospiro[cyclobutane-1,3'-indoline]-7'-carboxamide;

5'-(4-bromo-2-fluorophenylsulfonamido)-N-(1-methyl piperidin-4-yl)-2'-oxospiro[cyclobutane-1,3'-indoline]-7'-carboxamide;

5'-(2,4-Difluorobenzamido)-N-(1-methylpiperidin-4-yl)-2'-oxospiro-[cyclobutane-1,3'-indoline]-7'-carboxamide;

N-(7'—Cyclopropyl-2'-oxospiro[cyclobutane-1,3'-indolin]-5'-yl)-4-fluoro-benzamide;

2,4-Difluoro-N-(2'-oxo-7'-((6-oxo-1,2,3,6-tetrahydropyridin-4-yl)amino)spiro[cyclobutane-1,3'-indolin]-5'-yl)benzenesulfonamide;

2-Methoxy-N-(2'-oxo-7'-((6-oxo-1,2,3,6-tetrahydropyridin-4-yl)amino)-spiro[cyclobutane-1,3'-indolin]-5'-yl)benzenesulfonamide;

N-(7'-((3-fluoro-1-methylpiperidin-4-yl)amino)-2'-oxospiro [cyclobutane-1,3'-indolin]-5'-yl)-2-methoxy benzenesulfonamide;

2-Methoxy-N-(7'-((3-methoxy-1-methylpiperidin-4-yl) amino) -2'-oxo-spiro[cyclobutane-1,3'-indolin]-5'-yl) benzenesulfonamide;

2,4-Difluoro-N-(2'-oxo-7'-(piperidin-4-ylamino)spiro [cyclobutane-1,3'-indolin]-5'-yl)benzenesulfonamide;

Methyl 3-fluoro-4-(N-(7'-((1-methylpiperidin-4-yl) carbamoyl)-2'-oxo-spiro[cyclobutane-1,3'-indolin]-5'-yl) sulfamoyl)benzoate;

5'-(4—Cyano-2-fluorophenylsulfonamido)-N-(1-methyl piperidin-4-yl)-2'-oxospiro[cyclobutane-1,3'-indoline]-7'-carboxamide;

5'-(Cyclohexanesulfonamido)-N-(1-methylpiperidin-4-yl)-2'-oxospiro-[cyclobutane-1,3'-indoline]-7'-carboxamide;

5'-(2-Ethoxyphenylsulfonamido)-N-(1-methylpiperidin-4-yl)-2'-oxospiro[cyclobutane-1,3'-indoline]-7'-carboxamide;

N-(1-methylpiperidin-4-yl)-2'-oxo-5'-(piperidine-1-sulfon amido)spiro-[cyclobutane-1,3'-indoline]-7'-carboxamide;

5'-(2,5-Difluorophenylsulfonamido)-N-(1-methylpiperidin-4-yl)-2'-oxo-spiro[cyclobutane-1,3'-indoline]-7'-carboxamide;

2-Methoxy-N-(2'-oxo-7'-(pyridin-3-ylmethyl) spiro[cyclobutane-1,3'-indolin]-5'-yl)benzenesulfonamide;

2,4-Difluoro-N-(2'-oxo-7'-(1,2,3,4-tetrahydroisoquinolin-7-yl)spiro[cyclobutane-1,3'-indolin]-5'-yl)benzenesulfonamide;

2,4-Difluoro-N-(7'-(1-methylpiperidin-4-yl)-2'-oxo spiro[cyclobutane-1,3'-indolin]-5'-yl)benzenesulfonamide;

2,4-Dimethoxy-N-(2'-oxo-7'-(piperidin-4-yl)spiro[cyclobutane-1,3'-indolin]-5'-yl)benzenesulfonamide;

N-(7'-Benzyl-2'-oxospiro[cyclobutane-1,3'-indolin]-5'-yl)-2-fluoro-4-methoxybenzenesulfonamide;

N-(7'-Benzyl-2'-oxospiro[cyclobutane-1,3'-indolin]-5'-yl)-4-fluoro-2-methoxybenzenesulfonamide;

2-Fluoro-N-(7'-(3-fluorobenzyl)-2'-oxospiro[cyclobutane-1,3'-indolin]-5'-yl)-4-methoxybenzenesulfonamide;

4-Fluoro-N-(7'-(3-fluorobenzyl)-2'-oxospiro[cyclobutane-1,3'-indolin]-5'-yl)-2-methoxybenzenesulfonamide;

2-Fluoro-N-(7'-(2-fluorobenzyl)-2'-oxospiro[cyclobutane-1,3'-indolin]-5'-yl)-4-methoxybenzenesulfonamide;

2-Fluoro-4-methoxy-N-(7'-(1-methylpiperidin-4-yl)-2'-oxospiro[cyclobutane-1,3'-indolin]-5'-yl)benzenesulfonamide;

2,4-Difluoro-N-(7'-(6-hydroxypyridin-3-yl)-2'-oxo spiro[cyclobutane-1,3'-indolin]-5'-yl)benzenesulfonamide;

2,4-Difluoro-N-(7'-(2-hydroxypyridin-4-yl)-2'-oxo spiro[cyclobutane-1,3'-indolin]-5'-yl)benzenesulfonamide;

2,4-Difluoro-N-(7'-((3-fluoropiperidin-4-yl)amino)-2'-oxo spiro[cyclobutane-1,3'-indolin]-5'-yl)benzenesulfonamide;

N-(7'-((3,3-dimethylpiperidin-4-yl)amino)-2'-oxospiro[cyclobutane-1,3'-indolin]-5'-yl)-2,4-difluorobenzenesulfonamide;

2,4-Difluoro-N-(2'-oxo-7'-(2-oxopiperidin-4-yl)spiro [cyclobutane-1,3'-indolin]-5'-yl)benzenesulfonamide;

2,4-Difluoro-N-(2'-oxo-7'-(6-oxopiperidin-3-yl)spiro [cyclobutane-1,3'-indolin]-5'-yl)benzenesulfonamide;

2,4-Difluoro-N-(7'-(2-methyl-1,2,3,4-tetrahydroisoquinolin-7-yl)-2'-oxo-spiro[cyclobutane-1,3'-indolin]-5'-yl)benzene sulfonamide;

2-Methoxy-N-(2'-oxo-7'-(1-phenylethyl)spiro[cyclobutane-1,3'-indolin]-5'-yl)benzenesulfonamide;

2-Methoxy-N-(2'-oxo-7'-(1-phenylethyl)spiro[cyclobutane-1,3'-indolin]-5'-yl)benzenesulfonamide, isomer 1;

2-Methoxy-N-(2'-oxo-7'-(1-phenylethyl)spiro[cyclobutane-1,3'-indolin]-5'-yl)benzenesulfonamide, isomer 2;

2,4-Difluoro-N-(7'-(2-(1-methylpiperidin-4-yl)ethyl)-2'-oxo spiro[cyclobutane-1,3'-indolin]-5'-yl)benzenesulfonamide;

N-(7'-benzoyl-2'-oxospiro[cyclobutane-1,3'-indolin]-5'-yl)-2-methoxy-benzenesulfonamide;

N-(7'-(hydroxy(phenyl)methyl)-2'-oxospiro[cyclobutane-1,3'-indolin]-5'-yl)-2-methoxybenzenesulfonamide;

N-(7'-(1-hydroxy-1-phenylethyl)-2'-oxospiro[cyclobutane-1,3'-indolin]-5'-yl)-2-methoxybenzenesulfonamide;

1-(7'—Cyclopropyl-2'-oxospiro[cyclobutane-1,3'-indolin]-5'-yl)-3-(2-methoxyphenyl)urea;

2-Methoxy-N-(2'-oxo-7'-(1-(pyridin-3-yl)ethyl)spiro[cyclobutane-1,3'-indolin]-5'-yl)benzenesulfonamide;

2-Methoxy-N-(2'-oxo-7'-(1-(pyridin-2-yl)ethyl)spiro [cyclobutane-1,3'-indolin]-5'-yl)benzenesulfonamide;

2-Methoxy-N-(2'-oxo-7'-(pyridin-2-yloxy)spiro[cyclobutane-1,3'-indolin]-5'-yl)benzenesulfonamide;

N-(7'-(fluoro(phenyl)methyl)-2'-oxospiro[cyclobutane-1,3'-indolin]-5'-yl)-2-methoxybenzenesulfonamide;

2,4-Difluoro-N-(2'-oxo-7'-(1-phenylethyl)spiro[cyclobutane-1,3'-indolin]-5'-yl)benzenesulfonamide;

2-Methoxy-N-(7'-((1-methylpiperidin-4-yl)oxy)-2'-oxospiro[cyclobutane-1,3'-indolin]-5'-yl)benzenesulfonamide;

2-Fluoro-N-(7'-((1-methylpiperidin-4-yl)oxy)-2'-oxospiro[cyclobutane-1,3'-indolin]-5'-yl)benzenesulfonamide;

5-Fluoro-2-methoxy-N-(7'-((1-methylpiperidin-4-yl)oxy)-2'-oxospiro-[cyclobutane-1,3'-indolin]-5'-yl)benzenesulfonamide;

4-Chloro-2-fluoro-N-(7'-((1-methylpiperidin-4-yl)oxy)-2'-oxospiro[cyclobutane-1,3'-indolin]-5'-yl)benzenesulfonamide;

4-Chloro-2-fluoro-N-(7'-((1-methylpiperidin-3-yl)oxy)-2'-oxospiro[cyclobutane-1,3'-indolin]-5'-yl)benzenesulfonamide;

2-Bromo-4-fluoro-N-(7'-((1-methylpiperidin-4-yl)oxy)-2'-oxospiro[cyclobutane-1,3'-indolin]-5'-yl)benzenesulfonamide;

2-Chloro-N-(7'-((1-methylpiperidin-4-yl)oxy)-2'-oxospiro[cyclobutane-1,3'-indolin]-5'-yl)benzenesulfonamide;

2-Chloro-4-fluoro-N-(7'-((1-methylpiperidin-4-yl)oxy)-2'-oxospiro[cyclobutane-1,3'-indolin]-5'-yl)benzenesulfonamide;

N-(7'-((1-ethylpiperidin-4-yl)oxy)-2'-oxospiro[cyclobutane-1,3'-indolin]-5'-yl)-2-methoxybenzenesulfonamide;

N-(7'-((1-isopropylpiperidin-4-yl)oxy)-2'-oxospiro[cyclobutane-1,3'-indolin]-5'-yl)-2-methoxybenzenesulfonamide;

N-(7'-((1-cyclopropylpiperidin-4-yl)oxy)-2'-oxospiro[cyclobutane-1,3'-indolin]-5'-yl)-2-methoxybenzenesulfonamide;

4-Chloro-2-fluoro-N-(7'-((1-methylpyrrolidin-3-yl)oxy)-2'-oxospiro[cyclobutane-1,3'-indolin]-5'-yl)benzenesulfonamide;

(S)-2-methoxy-N-(7'-((1-methylpyrrolidin-2-yl)methoxy)-2'-oxospiro[cyclobutane-1,3'-indolin]-5'-yl)benzenesulfonamide;

2-Methoxy-N-(7'-((1-methylazepan-4-yl)oxy)-2'-oxospiro[cyclobutane-1,3'-indolin]-5'-yl)benzenesulfonamide;

2-Methoxy-N-(2'-oxo-7'-((tetrahydro-2H-pyran-4-yl)oxy)spiro[cyclobutane-1,3'-indolin]-5'-yl)benzenesulfonamide;

4-Chloro-2-fluoro-N-(2'-oxo-7'-((tetrahydro-2H-pyran-4-yl)oxy)spiro-[cyclobutane-1,3'-indolin]-5'-yl)benzenesulfonamide;

N-(7'-((1,1-dioxidotetrahydro-2H-thiopyran-4-yl)oxy)-2'-oxospiro[cyclobutane-1,3'-indolin]-5'-yl)-2-methoxybenzenesulfonamide;

4-Chloro-N-(7'-((1,1-dioxidotetrahydro-2H-thiopyran-4-yl)oxy)-2'-oxospiro[cyclobutane-1,3'-indolin]-5'-yl)-2-fluorobenzenesulfonamide;

N-(7'-((6-aminopyridin-3-yl)oxy)-2'-oxospiro[cyclobutane-1,3'-indolin]-5'-yl)-2-methoxybenzenesulfonamide;

2-Methoxy-N-(7'-((1-methylpiperidin-4-yl)methoxy)-2'-oxospiro[cyclobutane-1,3'-indolin]-5'-yl)benzenesulfonamide;

4-Chloro-2-fluoro-N-(7'-((5-fluoropyridin-2-yl)methoxy)-2'-oxospiro[cyclobutane-1,3'-indolin]-5'-yl)benzenesulfonamide;

N-(7'-((5-fluoropyridin-2-yl)methoxy)-2'-oxospiro[cyclobutane-1,3'-indolin]-5'-yl)-2-methoxybenzenesulfonamide;

N-(7'-((5-fluoropyridin-3-yl)methoxy)-2'-oxospiro[cyclobutane-1,3'-indolin]-5'-yl)-2-methoxybenzenesulfonamide;

2-Methoxy-N-(2'-oxo-7'-(1-(pyridin-2-yl)ethoxy)spiro[cyclobutane-1,3'-indolin]-5'-yl)benzenesulfonamide, Isomer I;

2-Methoxy-N-(2'-oxo-7'-(1-(pyridin-2-yl)ethoxy)spiro[cyclobutane-1,3'-indolin]-5'-yl)benzenesulfonamide, Isomer II;

2-methoxy-N-(2'-oxo-7'-(1-(pyridin-3-yl)ethoxy)spiro[cyclobutane-1,3'-indolin]-5'-yl)benzenesulfonamide, racemic;

2-methoxy-N-(2'-oxo-7'-(1-(pyridin-3-yl)ethoxy)spiro[cyclobutane-1,3'-indolin]-5'-yl)benzenesulfonamide, Isomer I;

2-methoxy-N-(2'-oxo-7'-(1-(pyridin-3-yl)ethoxy)spiro[cyclobutane-1,3'-indolin]-5'-yl)benzenesulfonamide, Isomer II;

4-Chloro-2-fluoro-N-(2'-oxo-7'-(1-(pyridin-2-yl)ethoxy)spiro[cyclobutane-1,3'-indolin]-5'-yl)benzenesulfonamide, Isomer I 4-Chloro-2-fluoro-N-(2'-oxo-7'-(1-(pyridin-2-yl)ethoxy)spiro[cyclobutane-1,3'-indolin]-5'-yl)benzenesulfonamide, Isomer II:

2-Methoxy-N-(2'-oxo-7'-(pyridin-3-ylmethoxy)spiro[cyclobutane-1,3'-indolin]-5'-yl)benzenesulfonamide;

2-Methoxy-N-(2'-oxo-7'-(pyridin-2-ylmethoxy)spiro[cyclobutane-1,3'-indolin]-5'-yl)benzenesulfonamide;

4-Chloro-2-fluoro-N-(2'-oxo-7'-(2-(pyridin-2-yl)ethoxy)spiro[cyclobutane-1,3'-indolin]-5'-yl)benzenesulfonamide;

4-Chloro-2-fluoro-N-(7'-((1-methyl-1H-imidazol-5-yl)methoxy)-2'-oxospiro[cyclobutane-1,3'-indolin]-5'-yl)benzenesulfonamide;

N-(7'-(2-(1H-pyrazol-1-yl)ethoxy)-2'-oxospiro[cyclobutane-1,3'-indolin]-5'-yl)-4-chloro-2-fluorobenzenesulfonamide;

N-(7'-(2-(dimethylamino)ethoxy)-2'-oxospiro[cyclobutane-1,3'-indolin]-5'-yl)-2-methoxybenzenesulfonamide;

4-Chloro-N-(7'-(2-(dimethylamino)ethoxy)-2'-oxospiro[cyclobutane-1,3'-indolin]-5'-yl)-2-fluorobenzenesulfonamide;

N-(7'-(3-(dimethylamino)propoxy)-2'-oxospiro[cyclobutane-1,3'-indolin]-5'-yl)-2-methoxybenzenesulfonamide;

N-(7'-(2-(diethylamino)ethoxy)-2'-oxospiro[cyclobutane-1,3'-indolin]-5'-yl)-2-methoxybenzenesulfonamide;

N-(7'-((1-(dimethylamino)propan-2-yl)oxy)-2'-oxospiro[cyclobutane-1,3'-indolin]-5'-yl)-2-methoxybenzenesulfonamide;

2-Methoxy-N-(2'-oxo-7'-(2-(pyrrolidin-1-yl)ethoxy)spiro[cyclobutane-1,3'-indolin]-5'-yl)benzenesulfonamide;

2-Methoxy-N-(7'-(2-morpholinoethoxy)-2'-oxospiro[cyclobutane-1,3'-indolin]-5'-yl)benzenesulfonamide;

5'-((2-Methoxyphenyl)sulfonamido)-2'-oxospiro[cyclobutane-1,3'-indolin]-7'-yl 4-methylpiperazine-1-carboxylate;

5'-((2-Methoxyphenyl)sulfonamido)-2'-oxospiro[cyclobutane-1,3'-indolin]-7'-yl morpholine-4-carboxylate;

2,4-Difluoro-N-(7'-((1-methylpiperidin-4-yl)oxy)-2'-oxospiro[cyclobutane-1,3'-indolin]-5'-yl)benzenesulfonamide;

2-Methoxy-N-(2'-oxo-7'-(1-(thiazol-2-yl)vinyl)spiro[cyclobutane-1,3'-indolin]-5'-yl)benzenesulfonamide;

2-Methoxy-N-(7'-(1-(1-methylpiperidin-3-yl)ethyl)-2'-oxospiro[cyclobutane-1,3'-indolin]-5'-yl)benzenesulfonamide, Isomer I;

2-Methoxy-N-(7'-(1-(1-methylpiperidin-3-yl)ethyl)-2'-oxospiro[cyclobutane-1,3'-indolin]-5'-yl)benzenesulfonamide, Isomer II;

4-Chloro-N-(7'-((4,4-difluorocyclohexyl)oxy)-2'-oxospiro[cyclobutane-1,3'-indolin]-5'-yl)-2-fluorobenzenesulfonamide;

4-Chloro-2-fluoro-N-(2'-oxo-7'-((4-oxocyclohexyl)oxy)spiro[cyclobutane-1,3'-indolin]-5'-yl)benzenesulfonamide;

2-Methoxy-N-(2'-oxo-7'-(1-(thiazol-2-yl)ethyl)spiro[cyclobutane-1,3'-indolin]-5'-yl)benzenesulfonamide;

2-Methoxy—N-methyl-N-(7'-((1-methylpiperidin-4-yl)oxy)-2'-oxospiro[cyclobutane-1,3'-indolin]-5'-yl)benzenesulfonamide;

N-ethyl-2-methoxy-N-(7'-((1-methylpiperidin-4-yl)oxy)-2'-oxospiro[cyclobutane-1,3'-indolin]-5'-yl)benzenesulfonamide;

2,4-Difluoro-N-methyl-N-(7'-((1-methylpiperidin-4-yl)oxy)-2'-oxospiro-[cyclobutane-1,3'-indolin]-5'-yl)benzenesulfonamide;

5'-(((2-Methoxyphenyl)(methyl)(oxo)-l6-sulfanylidene)amino)-7'-nitrospiro[cyclobutane-1,3'-indolin]-2'-one;

7'-Amino-5'-(((2-methoxyphenyl)(methyl)(oxo)-l6-sulfanylidene)amino)spiro[cyclobutane-1,3'-indolin]-2'-one;

5'-(((2-Methoxyphenyl)(methyl)(oxo)-l6-sulfanylidene)amino)-7'-((1-methylpiperidin-4-yl)amino)spiro[cyclobutane-1,3'-indolin]-2'-one;

2-Isopropoxy-N-(7'-((1-methylpiperidin-4-yl)oxy)-2'-oxospiro[cyclobutane-1,3'-indolin]-5'-yl)benzenesulfonamide;

2-Fluoro-6-methoxy-N-(7'-((1-methylpiperidin-4-yl)oxy)-2'-oxospiro[cyclobutane-1,3'-indolin]-5'-yl)benzenesulfonamide;

2,6-Dimethoxy-N-(7'-((1-methylpiperidin-4-yl)oxy)-2'-oxospiro[cyclobutane-1,3'-indolin]-5'-yl)benzenesulfonamide;

2,4-Dimethoxy-N-(7'-((1-methylpiperidin-4-yl)oxy)-2'-oxospiro[cyclobutane-1,3'-indolin]-5'-yl)benzenesulfonamide;

4-Chloro-2-methoxy-N-(7'-((1-methylpiperidin-4-yl)oxy)-2'-oxospiro[cyclobutane-1,3'-indolin]-5'-yl)benzenesulfonamide;

4-Fluoro-2-methoxy-N-(7'-((1-methylpiperidin-4-yl)oxy)-2'-oxospiro[cyclobutane-1,3'-indolin]-5'-yl)benzenesulfonamide;

2-Methoxy-N-(7'-((1-methylazetidin-3-yl)methoxy)-2'-oxospiro[cyclobutane-1,3'-indolin]-5'-yl)benzenesulfonamide;

N-(7'-((3-fluoro-1-methylpiperidin-4-yl)oxy)-2'-oxospiro[cyclobutane-1,3'-indolin]-5'-yl)-2-methoxybenzenesulfonamide, Isomer I;

N-(7'-((3-fluoro-1-methylpiperidin-4-yl)oxy)-2'-oxospiro[cyclobutane-1,3'-indolin]-5'-yl)-2-methoxybenzenesulfonamide, Isomer II;
4-Chloro-2-fluoro-N-(7'-((3-fluoro-1-methylpiperidin-4-yl)oxy)-2'-oxospiro[cyclobutane-1,3'-indolin]-5'-yl)benzenesulfonamide;
4-Chloro-2-fluoro-N-(7'-((4-methylmorpholin-2-yl)methoxy)-2'-oxospiro[cyclobutane-1,3'-indolin]-5'-yl)benzenesulfonamide;
4-Chloro-2-fluoro-N-(2'-oxo-7'-((1,2,6-trimethylpiperidin-4-yl)oxy)spiro-[cyclobutane-1,3'-indolin]-5'-yl)benzenesulfonamide;
N-(7'-(2-(ethyl(methyl)amino)ethoxy)-2'-oxospiro[cyclobutane-1,3'-indolin]-5'-yl)-2-methoxybenzenesulfonamide;
4-Chloro-2-fluoro-N-(2'-oxo-7'-(piperidin-4-yloxy)spiro[cyclobutane-1,3'-indolin]-5'-yl)benzenesulfonamide;
4-Chloro-2-fluoro-N-(7'-((3-fluoropiperidin-4-yl)oxy)-2'-oxospiro[cyclobutane-1,3'-indolin]-5'-yl)benzenesulfonamide;
2-Methoxy-N-(2'-oxo-7'-(piperidin-4-yloxy)spiro[cyclobutane-1,3'-indolin]-5'-yl)benzenesulfonamide;
4-Chloro-2-fluoro-N-(2'-oxo-7'-(piperidin-3-yloxy)spiro[cyclobutane-1,3'-indolin]-5'-yl)benzenesulfonamide;
4-Chloro-N-(7'-((2,6-dimethylpiperidin-4-yl)oxy)-2'-oxospiro[cyclobutane-1,3'-indolin]-5'-yl)-2-fluorobenzenesulfonamide;
4-Chloro-2-fluoro-N-(7'-(morpholin-2-ylmethoxy)-2'-oxospiro[cyclobutane-1,3'-indolin]-5'-yl)benzenesulfonamide;
2-Methoxy-N-(7'-(morpholin-3-ylmethoxy)-2'-oxospiro[cyclobutane-1,3'-indolin]-5'-yl)benzenesulfonamide;
2-Methoxy-N-(7'-(2-(methylamino)ethoxy)-2'-oxospiro[cyclobutane-1,3'-indolin]-5'-yl)benzenesulfonamide;
N-(7'-(2-(ethylamino)ethoxy)-2'-oxospiro[cyclobutane-1,3'-indolin]-5'-yl)-2-methoxybenzenesulfonamide;
N-(7'-(2-(cyclopropylamino)ethoxy)-2'-oxospiro[cyclobutane-1,3'-indolin]-5'-yl)-2-methoxybenzenesulfonamide;
N-(7'-((1-aminocyclopropyl)methoxy)-2'-oxospiro[cyclobutane-1,3'-indolin]-5'-yl)-4-chloro-2-fluorobenzenesulfonamide;
N-(7'-((4-hydroxycyclohexyl)oxy)-2'-oxospiro[cyclobutane-1,3'-indolin]-5'-yl)-2-methoxybenzenesulfonamide;
N-(7'-((1-(2-hydroxyethyl)piperidin-4-yl)oxy)-2'-oxospiro[cyclobutane-1,3'-indolin]-5'-yl)-2-methoxybenzenesulfonamide;
4-Chloro-2-fluoro-N-(7'-((1-(methylsulfonyl)piperidin-4-yl)oxy)-2'-oxospiro[cyclobutane-1,3'-indolin]-5'-yl)benzenesulfonamide;
5'-((4-Chloro-2-fluorophenyl)sulfonamido)-N-(1-methylpiperidin-4-yl)-2'-oxospiro[cyclobutane-1,3'-indoline]-7'-carboxamide;
4-Chloro-2-fluoro-N-(2'-oxo-7'-((2-oxo-1,2-dihydropyridin-4-yl)oxy)spiro[cyclobutane-1,3'-indolin]-5'-yl)benzenesulfonamide;
2-Methoxy-N-(2'-oxo-7'-((2-oxo-1,2-dihydropyridin-4-yl)oxy)spiro-[cyclobutane-1,3'-indolin]-5'-yl)benzenesulfonamide;
Sodium ((2-methoxyphenyl)sulfonyl)(2'-oxo-7'-(1-phenylethyl)spiro[cyclobutane-1,3'-indolin]-5'-yl)amide;
N-(4'-chloro-7'-((1-methylpiperidin-4-yl)oxy)-2'-oxospiro[cyclobutane-1,3'-indolin]-5'-yl)-2-methoxybenzenesulfonamide;
N-(4'-bromo-7'-((1-methylpiperidin-4-yl)oxy)-2'-oxospiro[cyclobutane-1,3'-indolin]-5'-yl)-2-methoxybenzenesulfonamide;
(5'-((2-Methoxyphenyl)sulfonamido)-2'-oxospiro[cyclobutane-1,3'-indolin]-7'-yl)boronic acid;
N-(7'-((1-methylpiperidin-4-yl)oxy)-2'-oxospiro[cyclobutane-1,3'-indolin]-5'-yl)-3-phenylpropanamide;
N-(7'-((1-methylpiperidin-4-yl)oxy)-2'-oxospiro[cyclobutane-1,3'-indolin]-5'-yl)cinnamamide;
N-(7'-((1-acetylpiperidin-4-yl)oxy)-2'-oxospiro[cyclobutane-1,3'-indolin]-5'-yl)-2-methoxybenzenesulfonamide;
N-(7'-((1-acetylpyrrolidin-3-yl)oxy)-2'-oxospiro[cyclobutane-1,3'-indolin]-5'-yl)-4-chloro-2-fluorobenzenesulfonamide;
N-(7'-bromo-2'-oxospiro[cyclobutane-1,3'-indolin]-5'-yl)-2-morpholino-nicotinamide;
N-(7'-cyclopropyl-2'-oxospiro[cyclobutane-1,3'-indolin]-5'-yl)-2-morpholinonicotinamide;
4-Chloro-2-fluoro-N-(7'-((1-methylpiperidin-4-yl)oxy)-2'-oxospiro[cyclobutane-1,3'-indolin]-5'-yl)benzamide;
N-(7'-((1-methylpiperidin-4-yl)oxy)-2'-oxospiro[cyclobutane-1,3'-indolin]-5'-yl)-2-morpholinonicotinamide;
4-Fluoro-N-(2'-oxo-7'-((6-oxo-1,2,3,6-tetrahydropyridin-4-yl)amino)spiro[cyclobutane-1,3'-indolin]-5'-yl)benzenesulfonamide;
2-Fluoro-N-(2'-oxo-7'-((6-oxo-1,2,3,6-tetrahydropyridin-4-yl)amino)spiro[cyclobutane-1,3'-indolin]-5'-yl)benzenesulfonamide;
5'-(((2-Methoxyphenyl)(methyl)(oxo)-l6-sulfanylidene)amino)-7'-((1-methylpiperidin-4-yl)oxy)spiro[cyclobutane-1,3'-indolin]-2'-one; and
2-Methoxy-N-(7'-((1-methyl-6-oxo-1,2,3,6-tetrahydropyridin-4-yl)amino)-2'-oxospiro[cyclobutane-1,3'-indolin]-5'-yl)benzenesulfonamide;
or a pharmaceutically acceptable salt thereof.

30. A pharmaceutical composition comprising a compound according to claim 1 together with a pharmaceutically acceptable carrier.

* * * * *

UNITED STATES PATENT AND TRADEMARK OFFICE
CERTIFICATE OF CORRECTION

PATENT NO. : 10,336,697 B2
APPLICATION NO. : 15/736450
DATED : July 2, 2019
INVENTOR(S) : Ravi K. Ujjinamatada et al.

Page 1 of 1

It is certified that error appears in the above-identified patent and that said Letters Patent is hereby corrected as shown below:

In the Claims

Claim 8, Column 234, Line 43, "in case wherein" should read -- in cases wherein --.

Claim 11, Column 235, Line 38, "-C(OH)( $C_{1-7}$ alkyl)phenyl or -OR," should read -- -C(OH)($C_{1-7}$ alkyl)phenyl or -OR$_j$, --.

Claim 11, Column 235, Line 39, "CH(CH3)" should read -- CH(CH$_3$) --.

Claim 11, Column 235, Lines 56-57, "hetero-cyclyl" should read -- heterocyclyl --.

Claim 29, Column 249, Line 34, "Isomer I" should read -- Isomer I; --.

Claim 29, Column 249, Line 36, "Isomer II:" should read -- Isomer II; --.

Signed and Sealed this
Twenty-sixth Day of November, 2019

Andrei Iancu
*Director of the United States Patent and Trademark Office*